(12) United States Patent
Yasuma

(10) Patent No.: US 7,652,133 B2
(45) Date of Patent: Jan. 26, 2010

(54) INDOLE COMPOUND

(75) Inventor: Tsuneo Yasuma, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 106 days.

(21) Appl. No.: 11/907,929

(22) Filed: Oct. 18, 2007

(65) Prior Publication Data

US 2008/0096877 A1     Apr. 24, 2008

(30) Foreign Application Priority Data

Oct. 19, 2006  (JP)  ............... 2006-285551

(51) Int. Cl.
    C07D 417/04     (2006.01)
(52) U.S. Cl. .................................... 544/62
(58) Field of Classification Search ............... None
    See application file for complete search history.

(56) References Cited

U.S. PATENT DOCUMENTS

2009/0118304 A1    5/2009    Takahashi et al.

FOREIGN PATENT DOCUMENTS

| EP | 0 673 937 | 9/1995 |
|---|---|---|
| EP | 1 873 144 | 1/2008 |
| JP | 2000-309534 | 11/2000 |
| JP | 2000 309534 | 11/2000 |
| WO | 95/07276 | 3/1995 |
| WO | 2004/031179 | 4/2004 |
| WO | 2005/049019 | 6/2005 |
| WO | 2006/112549 | 10/2006 |
| WO | 2007/037534 | 4/2007 |
| WO | 2007/037543 | 4/2007 |

OTHER PUBLICATIONS

International Search Report issued Feb. 28, 2008 in the International (PCT) Application of which the present application is the U.S. National Stage.

Primary Examiner—Kamal A Saeed
(74) Attorney, Agent, or Firm—Wenderoth, Lind & Ponack, L.L.P.

(57) ABSTRACT

The purpose of the present invention is to provide a glucokinase activator useful as a pharmaceutical agent such as an agent for the prophylaxis or treatment of diabetes, obesity and the like.

The present invention provides a glucokinase activator containing a compound represented by the formula (I):

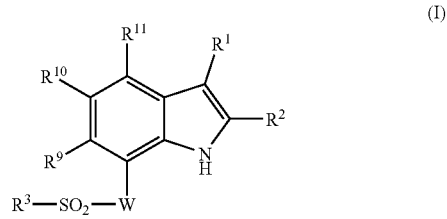

wherein
$R^1$ is a hydrogen atom or a halogen atom;
$R^2$ is a group represented by

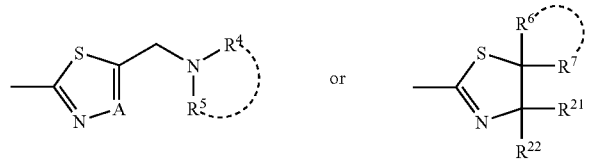

wherein each symbol is defined in the specification, or a salt thereof or a prodrug thereof.

1 Claim, No Drawings

INDOLE COMPOUND

TECHNICAL FIELD

The present invention relates to a indole compound having a glucokinase activating action and useful as a therapeutic agent for diabetes and the like.

BACKGROUND ART

Glucokinase (sometimes to be abbreviated to as GK in the present specification) (EC2.7.1.1) is one of the four kinds of hexokinases found in mammals, and is also called hexokinase IV. GK is an enzyme that catalyzes the conversion of glucose to glucose-6-phosphate, which is the first step of glycolysis. GK is mainly present in the pancreatic β cell and the liver, and acts in the pancreatic β cell as a sensor of extracellular glucose concentration that defines the glucose-stimulated insulin secretion. In the liver, the enzyme reaction of GK becomes a rate determining factor and regulates glycogen synthesis and glycolysis. The three hexokinases (I, II, III) other than GK reach the maximum enzyme activity at a glucose concentration of 1 mM or below. In contrast, GK shows low affinity for glucose and has a Km value of 8-15 mM which is close to a physiological blood glucose level. Accordingly, GK-mediated promotion of intracellular glucose metabolism occurs, which corresponds to blood glucose changes from normal blood glucose (5 mM) to postprandial hyperglycemia (10-15 mM).

The hypothesis proposed by Matschinsky et al. in 1984 that GK acts as a glucose sensor in the pancreatic β cell and hepatocytes has been demonstrated by the analysis of glucokinase transgenic mouse in recent years (see The Journal of Biological Chemistry (J. Biol. Chem.), 1995, vol. 270, page 30253-30256; The Journal of Biological Chemistry (J. Biol. Chem.), 1997, vol. 272, page 22564-22569; The Journal of Biological Chemistry (J. Biol. Chem.), 1997, vol. 272, page 22570-22575; NIHONRINSHO, 2002, vol. 60, page 523-534; and Cell, 1995, vol. 83, page 69-78). That is, GK heterozygous deficient mouse showed a hyperglycemic condition, and further, a disordered glucose-stimulated insulin secretion response. GK homozygous deficient mouse dies shortly after birth with manifestations of marked hyperglycemia and urinary sugar. On the other hand, GK overexpressed mouse (hetero type) showed decreased blood glucose level, increased blood glucose clearance rate, increased liver glycogen content and the like. From these findings, it has been clarified that GK plays an important role in the systemic glucose homeostasis. In other words, decreased GK activity causes insulin secretion failure and lower liver glucose metabolism, which develops impaired glucose tolerance and diabetes. Conversely, GK activation or increased GK activity due to overexpression causes promoted insulin secretion and promoted liver glucose metabolism, which in turn increases the systemic use of glucose to improve glucose tolerance.

In addition, it has been clarified from the analysis of a report on GK gene abnormality mainly in the family of MODY2 (Maturity Onset Diabetes of the Young) that GK also acts as a glucose sensor in human, and plays a key role in glucose homeostasis (see Nature, 1992, vol. 356, page 721-722). In GK gene abnormality, due to the decreased affinity of GK for glucose (increased Km value) and decreased Vmax, the blood glucose threshold value of insulin secretion increases and the insulin secretory capacity decreases. In the liver, due to the decreased GK activity, decreased glucose uptake, promoted gluconeogenesis, decreased glycogen synthesis and liver insulin resistance are observed. On the other hand, a family with a mutation increasing the GK activity has also been found. In such family, fasting hypoglycemia associated with increased plasma insulin concentration is observed (see New England Journal Medicine, 1998, vol. 338, page 226-230).

As mentioned above, GK acts as a glucose sensor in mammals including human, and plays an important role in blood glucose regulation. On the other hand, control of blood glucose utilizing the glucose sensor system of GK is considered to open a new way to treat diabetes in many type 2 diabetes patients. Particularly, since a GK activating substance is expected to show insulin secretagogue action in the pancreatic β cell and glucose uptake promotion and glucose release suppressive action in the liver, it will be useful as a prophylactic or therapeutic drug for type 2 diabetes.

In recent years, it has been clarified that pancreatic β cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, different from pancreatic β cell and the liver, a pharmaceutical agent capable of activating glucokinase of VHM has a possibility of providing not only a blood glucose corrective effect but also improvement of obesity.

As mentioned above, a pharmaceutical agent capable of activating GK is useful as a prophylactic or therapeutic drug for diabetes, diabetic complications, and obesity.

As the indole compound, the following compound has been reported.

(1) It has been reported that a compound represented by the formula:

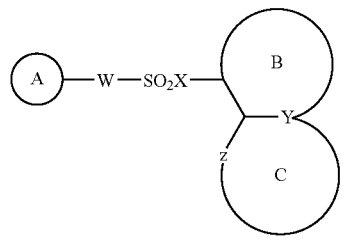

wherein ring A is an optionally substituted monocyclic or bicyclic aromatic ring;

ring B is an optionally substituted 6-membered unsaturated hydrocarbon ring or an optionally substituted 6-membered unsaturated heterocycle containing one nitrogen atom;

ring C is an optionally substituted 5-membered heterocycle containing one or two nitrogen atomsatoms;

W is a single bond or —CH=CH—;

X is —N(R$^1$)— or an oxygen atom;

Y is a carbon atom or a nitrogen atom;

Z is —N(R²)— or a nitrogen atom; and
R¹ and R² are the same or different and each is a hydrogen atom or lower alkyl
is useful as an antitumor agent or an angiogenesis inhibitor (see WO 95/07276 and JP-A-2000-309534).
(2) It has been reported that a compound represented by the formula:

$$A-\underset{H}{N}-\overset{O}{\underset{\|}{C}}-B$$

$$B: \left( \begin{array}{c} \text{[indole structure with } R^1, R^2, R^3, R^4, R^5, R^6 \text{]} \end{array} \right. , \left. \begin{array}{c} \text{[indole structure with } R^1, R^2, R^3, R^4, R^6, R^7 \text{]} \end{array} \right.$$

$$\left. \begin{array}{c} \text{[indole structure with } R^1, R^2, R^3, R^4, R^5, R^7 \text{]} \end{array} \right)$$

wherein
$R^1$, $R^2$, $R^3$, $R^4$, $R^6$ and $R^7$ are each independently a hydrogen atom, a halogen atom, a nitro group, —CN, —OH, —COOH, —CF$_3$, —NR$^{10}$R$^{11}$ (wherein R$^{10}$ and R$^{11}$ are each independently a hydrogen atom, a C$_{1-6}$ alkyl group, —SO$_2$CH$_3$ etc.), a C$_{1-6}$ alkyl group, a C$_{3-8}$ cycloalkyl group, a heteroaryl group and the like;
$R^5$ is a C$_{1-6}$ alkyl group and the like; and
A is an optionally substituted thiazolyl and the like, is useful as a glucokinase activator (see WO2005/049019).

However, none of the above-mentioned prior articles discloses the following formula (I).

DISCLOSURE OF THE INVENTION

The purpose of the present invention is to provide a glucokinase activator which is useful as a pharmaceutical agent such as agents for the prophylaxis or treatment of diabetes, obesity and the like, and the like.

The present inventors have conducted intensive studies and found that a compound represented by the formula (I):

[formula (I): indole with substituents R¹, R², R⁹, R¹⁰, R¹¹, and R³—SO₂—W]

wherein
R¹ is a hydrogen atom or a halogen atom;
R² is a group represented by

[thiazole structure with R⁴, R⁵] or [thiazoline structure with R⁶, R⁷, R²¹, R²²]

wherein
A is CH or N;
R⁴ and R⁵ are each independently an optionally substituted C$_{1-6}$ alkyl group or an optionally substituted C$_{3-10}$ cycloalkyl group, or R⁴ and R⁵ in combination form an optionally substituted ring wherein the ring should not be morpholine; and
R⁶, R⁷, R²¹ and R²² are each independently a hydrogen atom, an optionally substituted hydrocarbon group, a cyano group or an acyl group, or R⁶ and R⁷ in combination form an optionally substituted ring;
W is O or NR⁸ wherein R⁸ is a hydrogen atom, an optionally substituted C$_{1-6}$ alkyl group or an optionally substituted C$_{3-10}$ cycloalkyl group;
R³ is an optionally substituted heterocyclic group or an optionally substituted C$_{6-14}$ aryl group; and
R⁹, R¹⁰ and R¹¹ are each independently a hydrogen atom, a halogen atom, an optionally substituted C$_{1-6}$ alkyl group or an optionally substituted C$_{1-6}$ alkoxy group,
provided that
a compound wherein R²¹ is a hydrogen atom or a C$_{1-6}$ alkoxy-carbonyl group, R²² is a hydrogen atom, and R⁶ and R⁷ are both hydrogen atomsatoms, and
a compound wherein R²¹ is a hydrogen atom or a C$_{1-6}$ alkoxy-carbonyl group, R²² is a hydrogen atom, and R⁶ and R⁷ are both methyl groups
are excluded,
or a salt thereof [hereinafter to be abbreviated as compound (I)]
unexpectedly has a superior glucokinase activating action as well as superior properties as a pharmaceutical product such as stability and the like, and can be a safe and useful as a pharmaceutical agent, which resulted in the completion of the present invention.

Accordingly, the present invention relates to
[1] compound (I);
[2] the compound of the above-mentioned [1], which is a compound represented by the formula (I):

[formula (I): indole with substituents R¹, R², R⁹, R¹⁰, R¹¹, and R³—SO₂—W]

wherein
R$^1$ is a hydrogen atom or a halogen atom;
R$^2$ is a group represented by

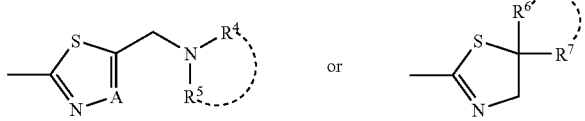

wherein
A is CH or N;
R$^4$ and R$^5$ are each independently an optionally substituted C$_{1-6}$ alkyl group or an optionally substituted C$_{3-10}$ cycloalkyl group, or R$^4$ and R$^5$ in combination form an optionally substituted ring wherein the ring should not be morpholine; and
R$^6$ and R$^7$ are each independently a hydrogen atom, an optionally substituted hydrocarbon group, a cyano group or an acyl group, or R$^6$ and R$^7$ in combination form an optionally substituted ring;
W is O or NR$^8$ wherein R$^8$ is a hydrogen atom or an optionally substituted C$_{1-6}$ alkyl group;
R$^3$ is an optionally substituted heterocyclic group; and
R$^9$, R$^{10}$ and R$^{11}$ are each independently a hydrogen atom, a halogen atom, an optionally substituted C$_{1-6}$ alkyl group or an optionally substituted C$_{1-6}$ alkoxy group,
provided that
a compound wherein R$^6$ and R$^7$ are both hydrogen atoms, and
a compound wherein R$^6$ and R$^7$ are both methyl groups
are excluded,
or a salt thereof;
[3] the compound of the above-mentioned [1], wherein R$^2$ is a group represented by

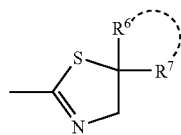

wherein R$^6$ and R$^7$ are as defined in the above-mentioned [1];
[4] the compound of the above-mentioned [3], wherein R$^6$ is a C$_{1-6}$ alkyl group substituted by an optionally substituted heterocyclic group;
[5] the compound of the above-mentioned [3], wherein R$^7$ is a hydrogen atom;
[6] the compound of the above-mentioned [3], wherein R$^6$ and R$^7$ in combination form an optionally substituted ring;
[7] the compound of the above-mentioned [3], wherein W is NR$^8$ wherein R$^8$ is as defined in the above-mentioned [1];
[8] the compound of the above-mentioned [3], wherein R$^3$ is a 5- or 6-membered monocyclic aromatic heterocyclic group;
[9] the compound of the above-mentioned [3], wherein R$^9$ is a hydrogen atom or a halogen atom;
[10] the compound of the above-mentioned [3], wherein R$^{10}$ is a hydrogen atom, a halogen atom, a C$_{1-6}$ alkyl group or an optionally substituted C$_{1-6}$ alkoxy group;
[11] the compound of the above-mentioned [3], wherein R$^{11}$ is a hydrogen atom, a halogen atom or a C$_{1-6}$ alkyl group;
[12] N,N-dimethyl-2-{4-[(2-{7-[methyl(2-thienylsulfonyl)amino]-1H-indol-2-yl}-1,3-thiazol-5-yl)methyl]piperazin-1-yl}acetamide;
N-methyl-N-[2-(8-oxa-1-thia-3-azaspiro[4.5]dec-2-en-2-yl)-1H-indol-7-yl]thiophene-2-sulfonamide;
N-[2-[4-(hydroxymethyl)-4,5-dihydro-1,3-thiazol-2-yl]-5-(2-methoxyethoxy)-1H-indol-7-yl]-N-methylpyridine-2-sulfonamide;
N-methyl-N-{2-[5-(morpholinomethyl)-4,5-dihydro-1,3-thiazol-2-yl]-1H-indol-7-yl}thiophene-2-sulfonamide;
2-(2-{7-[methyl(pyridin-2-ylsulfonyl)amino]-1H-indol-2-yl}-4,5-dihydro-1,3-thiazol-5-yl)acetamide;
N-(difluoromethyl)-N-{2-[5-(morpholinomethyl)-4,5-dihydro-1,3-thiazol-2-yl]-1H-indol-7-yl}thiophene-2-sulfonamide;
2-{2-[7-[methyl(2-thienylsulfonyl)amino]-5-(trifluoromethoxy)-1H-indol-2-yl]-4,5-dihydro-1,3-thiazol-5-yl}acetamide;
N-(5-(2-methoxyethoxy)-2-{5-[(1-oxidothiomorpholino)methyl]-4,5-dihydro-1,3-thiazol-2-yl}-1H-indol-7-yl)-N-methylpyridine-2-sulfonamide;
2-(2-{7-[methyl(2-thienylsulfonyl)amino]-1H-indol-2-yl}-1-thia-3,8-diazaspiro[4.5]dec-2-en-8-yl)acetamide; or
N-[2-{5-[(1,1-dioxidothiomorpholino)methyl]-4,5-dihydro-1,3-thiazol-2-yl}-5-(2-methoxyethoxy)-1H-indol-7-yl]-N-methylpyridine-2-sulfonamide;
or a salt thereof;
[13] a prodrug of compound (I);
[14] a glucokinase activator comprising compound (I) or a prodrug thereof;
[15] a pharmaceutical agent comprising compound (I) or a prodrug thereof;
[16] the pharmaceutical agent of the above-mentioned [15], which is an agent for the prophylaxis or treatment of diabetes or obesity;
[17] a method of activating a glucokinase in a mammal, which comprises administering compound (I) or a prodrug thereof to the mammal;
[18] a method for the prophylaxis or treatment of diabetes or obesity in a mammal, which comprises administering compound (I) or a prodrug thereof to the mammal;
[19] use of compound (I) or a prodrug thereof for the production of a glucokinase activator;
[20] use of compound (I) or a prodrug thereof for the production of an agent for the prophylaxis or treatment of diabetes or obesity;
and the like.

Since compound (I) has a superior glucokinase activating action, compound (I) is useful as a pharmaceutical agent such as an agent for the prophylaxis or treatment of diabetes, obesity and the like, and the like.

DETAILED DESCRIPTION OF THE INVENTION

Unless otherwise specified, as the "halogen atom" in the present specification, fluorine atom, chlorine atom, bromine atom or iodine atom can be mentioned.

Unless otherwise specified, as the "C$_{1-3}$ alkylenedioxy group" in the present specification, methylenedioxy, ethylenedioxy or the like.

Unless otherwise specified, as the "C$_{1-6}$ alkyl group" in the present specification, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

Unless otherwise specified, as the "$C_{1-6}$ alkoxy group" in the present specification, methoxy, ethoxy, propoxy, isopropoxy, butoxy, isobutoxy, sec-butoxy, tert-butoxy or the like.

Unless otherwise specified, as the "$C_{1-6}$ alkoxy-carbonyl group" in the present specification, methoxycarbonyl, ethoxycarbonyl, propoxycarbonyl, tert-butoxycarbonyl or the like.

Unless otherwise specified, as the "$C_{1-6}$ alkyl-carbonyl group" in the present specification, acetyl, propanoyl, butanoyl, isobutanoyl, pentanoyl, isopentanoyl, hexanoyl or the like.

Each symbol in the formulas is described in detail in the following.

$R^1$ is a hydrogen atom or a halogen atom.

$R^1$ is preferably a hydrogen atom or a fluorine atom, more preferably a hydrogen atom.

$R^2$ is a group represented by

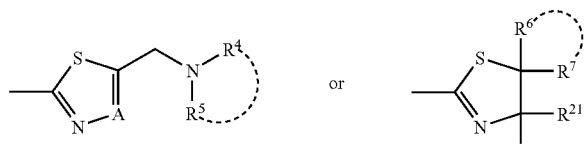

wherein each symbol is as defined above.

$R^2$ is preferably a group represented by

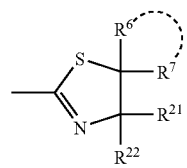

wherein each symbol is as defined above,
more preferably a group represented by

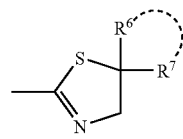

wherein each symbol is as defined above.

In the embodiment wherein $R^2$ is a group represented by

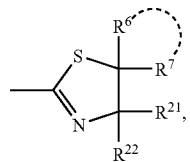

$R^6$, $R^7$, $R^{21}$ and $R^{22}$ are each independently a hydrogen atom, an optionally substituted hydrocarbon group, a cyano group or an acyl group, or $R^6$ and $R^7$ in combination form an optionally substituted ring.

As the "hydrocarbon group" of the "optionally substituted hydrocarbon group" for $R^6$, $R^7$, $R^{21}$ or $R^{22}$, for example, a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group, a $C_{3-10}$ cycloalkyl-$C_{1-6}$ alkyl group and the like can be mentioned.

As used herein, as the $C_{1-10}$ alkyl group, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As the $C_{2-10}$ alkenyl group, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As the $C_{2-10}$ alkynyl group, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the $C_{3-10}$ cycloalkyl group, for example, cyclopropyl, cyclobutyl, cyclopentyl, cyclohexyl, cycloheptyl, cyclooctyl and the like can be mentioned.

As the $C_{3-10}$ cycloalkenyl group, for example, 2-cyclopenten-1-yl, 3-cyclopenten-1-yl, 2-cyclohexen-1-yl, 3-cyclohexen-1-yl and the like can be mentioned.

As the $C_{4-10}$ cycloalkadienyl group, for example, 2,4-cyclopentadien-1-yl, 2,4-cyclohexadien-1-yl, 2,5-cyclohexadien-1-yl and the like can be mentioned.

The above-mentioned $C_{3-10}$ cycloalkyl group, $C_{3-10}$ cycloalkenyl group and $C_{4-10}$ cycloalkadienyl are each optionally condensed with a benzene ring to form a fused cyclic group, and as the fused cyclic group, for example, indanyl, dihydronaphthyl, tetrahydronaphthyl, fluorenyl and the like can be mentioned. In addition, as the aforementioned hydrocarbon group, a cross-linked hydrocarbon group such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl, norbornanyl and the like, and the like can also be mentioned.

As the $C_{6-14}$ aryl group, for example, phenyl, naphthyl, anthryl, phenanthryl, acenaphthylenyl, biphenylyl and the like can be mentioned. Of these, phenyl, 1-naphthyl, 2-naphthyl and the like are preferable.

As the $C_{7-13}$ aralkyl group, for example, benzyl, phenethyl, naphthylmethyl, biphenylmethyl and the like can be mentioned.

As the $C_{8-13}$ arylalkenyl group, for example, styryl and the like can be mentioned.

As the $C_{3-10}$ cycloalkyl-$C_{1-6}$ alkyl group, for example, cyclohexylmethyl and the like can be mentioned.

The $C_{1-10}$ alkyl group, $C_{2-10}$ alkenyl group and $C_{2-10}$ alkynyl group exemplified as the aforementioned "hydrocarbon group" optionally have 1 to 3 substituents at substitutable positions.

As such substituents, for example,
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group, (c) a $C_{1-6}$ alkoxy group, and
(d) a halogen atom;
(3) an optionally substituted heterocyclic group (those similar to the below-mentioned "optionally substituted heterocyclic group" for $R^3$ can be mentioned);
(4) an amino group optionally mono- or di-substituted by substituent(s) selected from
  (a) a $C_{1-6}$ alkyl group optionally substituted by 1 to 3 substituents selected from a hydroxy group and a $C_{1-6}$ alkylsulfonyl group (e.g., methylsulfonyl),
  (b) a $C_{1-6}$ alkyl-carbonyl group,
  (c) a $C_{1-6}$ alkoxy-carbonyl group optionally substituted by 1 to 3 $C_{6-14}$ aryl groups (e.g., phenyl),
  (d) a $C_{6-14}$ aryl-carbonyl group (e.g., benzoyl),
  (e) a $C_{7-13}$ aralkyl-carbonyl group (e.g., benzylcarbonyl, phenethylcarbonyl),
  (f) a carbamoyl group optionally mono- or di-substituted by substituent(s) selected from a $C_{1-6}$ alkyl group, a $C_{6-14}$ aryl group (e.g., phenyl) and a $C_{7-13}$ aralkyl group (e.g., benzyl),
  (g) a $C_{1-6}$ alkylsulfonyl group (e.g., methylsulfonyl, ethylsulfonyl, isopropylsulfonyl),
  (h) a $C_{6-14}$ arylsulfonyl group (e.g., benzenesulfonyl, 1-naphthalenesulfonyl, 2-naphthalenesulfonyl) optionally substituted by 1 to 3 $C_{1-6}$ alkyl groups,
  (i) a $C_{7-13}$ aralkylsulfonyl group (e.g., benzylsulfonyl)
  (j) a $C_{3-10}$ cycloalkyl group (e.g., cyclohexyl) optionally substituted by 1 to 3 substituents selected from a hydroxy group and a $C_{1-6}$ alkyl group,
  (k) an aromatic heterocyclic group (e.g., triazolyl), and
  (l) a non-aromatic heterocyclic group (e.g., tetrahydrothiopyranyl, 1-oxidotetrahydrothiopyranyl, 1,1-dioxidotetrahydrothiopyranyl);
(5) an amidino group;
(6) a $C_{1-6}$ alkyl-carbonyl group optionally substituted by 1 to 3 halogen atoms;
(7) a $C_{1-6}$ alkoxy-carbonyl group optionally substituted by 1 to 3 halogen atoms;
(8) an aromatic heterocyclyl-carbonyl group (e.g., thienylcarbonyl, indolylcarbonyl) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(9) a non-aromatic heterocyclyl-carbonyl group (e.g., piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
  (a) a hydroxy group,
  (b) a $C_{1-6}$ alkyl group optionally substituted by 1 to 3 hydroxy groups,
  (c) a halogen atom, and
  (d) a carboxy group;
(10) a $C_{1-6}$ alkylsulfonyl group (e.g., methylsulfonyl, ethylsulfonyl) optionally substituted by 1 to 3 halogen atoms;
(11) a carbamoyl group optionally mono- or di-substituted by substituent(s) selected from
  (a) a $C_{1-6}$ alkyl group optionally substituted by 1 to 3 substituents selected from a hydroxy group, a $C_{1-6}$ alkoxy group, a $C_{1-6}$ alkylsulfonyl group (e.g., methylsulfonyl) and an aromatic heterocyclic group (e.g., furyl),
  (b) a $C_{6-14}$ aryl group (e.g., phenyl),
  (c) a $C_{7-13}$ aralkyl group (e.g., benzyl),
  (d) a $C_{1-6}$ alkoxy group,
  (e) a $C_{3-10}$ cycloalkyl group (e.g., cyclopropyl),
  (f) a $C_{1-6}$ alkylsulfonyl group (e.g., methylsulfonyl),
  (g) an aromatic heterocyclic group (e.g., triazolyl, tetrazolyl), and
  (h) a non-aromatic heterocyclic group (e.g., tetrahydropyranyl);
(12) a thiocarbamoyl group optionally mono- or di-substituted by $C_{1-6}$ alkyl group(s) optionally substituted by 1 to 3 halogen atoms;
(13) a sulfamoyl group optionally mono- or di-substituted by $C_{1-6}$ alkyl group(s) optionally substituted by 1 to 3 halogen atoms;
(14) a carboxy group;
(15) a hydroxy group;
(16) a $C_{1-6}$ alkoxy group optionally substituted by 1 to 3 substituents selected from
  (a) a halogen atom,
  (b) a carboxy group,
  (c) a $C_{1-6}$ alkoxy group, and
  (d) a $C_{1-6}$ alkoxy-carbonyl group;
(17) a $C_{2-6}$ alkenyloxy group (e.g., ethenyloxy) optionally substituted by 1 to 3 halogen atoms;
(18) a $C_{3-10}$ cycloalkyloxy group (e.g., cyclohexyloxy);
(19) a $C_{7-13}$ aralkyloxy group (e.g., benzyloxy) optionally substituted by 1 to 3 halogen atoms;
(20) a $C_{6-14}$ aryloxy group (e.g., phenyloxy, naphthyloxy);
(21) a $C_{1-6}$ alkyl-carbonyloxy group (e.g., acetyloxy, tert-butylcarbonyloxy);
(22) a mercapto group;
(23) a $C_{1-6}$ alkylthio group (e.g., methylthio, ethylthio) optionally substituted by 1 to 3 substituents selected from
  (a) a halogen atom,
  (b) a $C_{6-14}$ aryl group, and
  (c) a carboxy group;
(24) a $C_{6-14}$ arylthio group (e.g., phenylthio, naphthylthio);
(25) an aromatic heterocyclyl-thio group (e.g., tetrazolylthio) optionally substituted by 1 to 3 $C_{1-6}$ alkyl groups;
(26) a sulfo group;
(27) a cyano group;
(28) an azido group;
(29) a nitro group;
(30) a nitroso group;
(31) a halogen atom;
(32) a $C_{1-6}$ alkylsulfinyl group (e.g., methylsulfinyl);
(33) an oxo group;
(34) a $C_{3-10}$ cycloalkyl-$C_{1-6}$ alkyloxy group (e.g., cyclopropylmethyloxy);
(35) a $C_{1-3}$ alkylenedioxy group;
(36) an aromatic heterocyclyl-carbonylthio group (e.g., indolylcarbonylthio) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(37) a formyl group;
(38) an aromatic heterocyclyl-oxy group (e.g., pyrimidyloxy, pyrazinyloxy);
(39) a $C_{1-6}$ alkylsulfonyloxy group (e.g., methylsulfonyloxy);
(40) a $C_{2-6}$ alkenyl-carbonyl group (e.g., vinylcarbonyl);
(41) a non-aromatic heterocyclyl-carbonyloxy group (e.g., morpholinylcarbonyloxy) optionally substituted by 1 to 3 $C_{1-6}$ alkyl groups;
and the like can be mentioned.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group, $C_{8-13}$ arylalkenyl group and $C_{3-10}$ cycloalkyl-$C_{1-6}$ alkyl group exemplified as the aforementioned "hydrocarbon group" optionally have 1 to 3 substituents at substitutable positions.

As such substituents, for example, (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;
(3) an aromatic heterocyclic group (e.g., thienyl, furyl, pyridyl, pyrimidinyl, pyridazinyl, oxazolyl, thiazolyl, tetrazolyl, oxadiazolyl, pyrazinyl, quinolyl, indolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;
(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, thiazolinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group,
   (d) a $C_{1-6}$ alkyl-carbonyl group,
   (e) a $C_{1-6}$ alkylsulfonyl group,
   (f) an oxo group, and
   (g) a halogen atom;
(5) an amino group optionally mono- or di-substituted by substituent(s) selected from
   (a) a $C_{1-6}$ alkyl group optionally substituted by 1 to 3 substituents selected from a hydroxy group and a $C_{1-6}$ alkylsulfonyl group (e.g., methylsulfonyl),
   (b) a $C_{1-6}$ alkyl-carbonyl group,
   (c) a $C_{1-6}$ alkoxy-carbonyl group optionally substituted by 1 to 3 $C_{6-14}$ aryl groups (e.g., phenyl),
   (d) a $C_{6-14}$ aryl-carbonyl group (e.g., benzoyl),
   (e) a $C_{7-13}$ aralkyl-carbonyl group (e.g., benzylcarbonyl, phenethylcarbonyl),
   (f) a carbamoyl group optionally mono- or di-substituted by substituent(s) selected from a $C_{1-6}$ alkyl group, a $C_{6-14}$ aryl group (e.g., phenyl) and a $C_{7-13}$ aralkyl group (e.g., benzyl),
   (g) a $C_{1-6}$ alkylsulfonyl group (e.g., methylsulfonyl, ethylsulfonyl, isopropylsulfonyl),
   (h) a $C_{6-14}$ arylsulfonyl group (e.g., benzenesulfonyl, 1-naphthalenesulfonyl, 2-naphthalenesulfonyl) optionally substituted by 1 to 3 $C_{1-6}$ alkyl groups,
   (i) a $C_{7-13}$ aralkylsulfonyl group (e.g., benzylsulfonyl)
   (j) a $C_{3-10}$ cycloalkyl group (e.g., cyclohexyl) optionally substituted by 1 to 3 substituents selected from a hydroxy group and a $C_{1-6}$ alkyl group,
   (k) an aromatic heterocyclic group (e.g., triazolyl), and
   (l) a non-aromatic heterocyclic group (e.g., tetrahydrothiopyranyl, 1-oxidotetrahydrothiopyranyl, 1,1-dioxidotetrahydrothiopyranyl);
(6) an amidino group;
(7) a $C_{1-6}$ alkyl-carbonyl group optionally substituted by 1 to 3 halogen atoms;
(8) a $C_{1-6}$ alkoxy-carbonyl group optionally substituted by 1 to 3 halogen atoms;
(9) an aromatic heterocyclyl-carbonyl group (e.g., thienylcarbonyl, indolylcarbonyl) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(10) a non-aromatic heterocyclyl-carbonyl group (e.g., piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
   (a) a hydroxy group,
   (b) a $C_{1-6}$ alkyl group optionally substituted by 1 to 3 hydroxy groups,
   (c) a halogen atom, and
   (d) a carboxy group;
(11) a $C_{1-6}$ alkylsulfonyl group (e.g., methylsulfonyl, ethylsulfonyl) optionally substituted by 1 to 3 halogen atoms;
(12) a carbamoyl group optionally mono- or di-substituted by substituent(s) selected from
   (a) a $C_{1-6}$ alkyl group optionally substituted by 1 to 3 substituents selected from a hydroxy group, a $C_{1-6}$ alkoxy group, a $C_{1-6}$ alkylsulfonyl group (e.g., methylsulfonyl) and an aromatic heterocyclic group (e.g., furyl),
   (b) a $C_{6-14}$ aryl group (e.g., phenyl),
   (c) a $C_{7-13}$ aralkyl group (e.g., benzyl),
   (d) a $C_{1-6}$ alkoxy group,
   (e) a $C_{3-10}$ cycloalkyl group (e.g., cyclopropyl),
   (f) a $C_{1-6}$ alkylsulfonyl group (e.g., methylsulfonyl),
   (g) an aromatic heterocyclic group (e.g., triazolyl, tetrazolyl), and
   (h) a non-aromatic heterocyclic group (e.g., tetrahydropyranyl);
(13) a thiocarbamoyl group optionally mono- or di-substituted by $C_{1-6}$ alkyl group(s) optionally substituted by 1 to 3 halogen atoms;
(14) a sulfamoyl group optionally mono- or di-substituted by $C_{1-6}$ alkyl group(s) optionally substituted by 1 to 3 halogen atoms;
(15) a carboxy group;
(16) a hydroxy group;
(17) a $C_{1-6}$ alkoxy group optionally substituted by 1 to 3 substituents selected from
   (a) a halogen atom,
   (b) a carboxy group,
   (c) a $C_{1-6}$ alkoxy group, and
   (d) a $C_{1-6}$ alkoxy-carbonyl group;
(18) a $C_{2-6}$ alkenyloxy group (e.g., ethenyloxy) optionally substituted by 1 to 3 halogen atoms;
(19) a $C_{3-10}$ cycloalkyloxy group (e.g., cyclohexyloxy);
(20) a $C_{7-13}$ aralkyloxy group (e.g., benzyloxy) optionally substituted by 1 to 3 halogen atoms;
(21) a $C_{6-14}$ aryloxy group (e.g., phenyloxy, naphthyloxy);
(22) a $C_{1-6}$ alkyl-carbonyloxy group (e.g., acetyloxy, tert-butylcarbonyloxy);
(23) a mercapto group;
(24) a $C_{1-6}$ alkylthio group (e.g., methylthio, ethylthio) optionally substituted by 1 to 3 substituents selected from
   (a) a halogen atom,
   (b) a $C_{6-14}$ aryl group, and
   (c) a carboxy group;
(25) a $C_{6-14}$ arylthio group (e.g., phenylthio, naphthylthio);
(26) an aromatic heterocyclyl-thio group (e.g., tetrazolylthio) optionally substituted by 1 to 3 $C_{1-6}$ alkyl groups;
(27) a sulfo group;

(28) a cyano group;
(29) an azido group;
(30) a nitro group;
(31) a nitroso group;
(33) a halogen atom;
(33) a $C_{1-6}$ alkylsulfinyl group (e.g., methylsulfinyl);
(34) an oxo group;
(35) a $C_{3-10}$ cycloalkyl-$C_{1-6}$ alkyloxy group (e.g., cyclopropylmethyloxy);
(36) a $C_{1-3}$ alkylenedioxy group;
(37) an aromatic heterocyclyl-carbonylthio group (e.g., indolylcarbonylthio) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(38) a formyl group;
(39) an aromatic heterocyclyl-oxy group (e.g., pyrimidyloxy, pyrazinyloxy);
(40) a $C_{1-6}$ alkylsulfonyloxy group (e.g., methylsulfonyloxy);
(41) a $C_{2-6}$ alkenyl-carbonyl group (e.g., vinylcarbonyl);
(42) a non-aromatic heterocyclyl-carbonyloxy group (e.g., morpholinylcarbonyloxy) optionally substituted by 1 to 3 $C_{1-6}$ alkyl groups;
(43) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy group optionally substituted by 1 to 3 substituents selected from a carboxy group and a $C_{1-6}$ alkoxy-carbonyl group,
  (e) a $C_{1-6}$ alkyl-carbonyl group,
  (f) a $C_{1-6}$ alkoxy-carbonyl group,
  (g) a $C_{1-6}$ alkyl-carbonyloxy group (e.g., acetyloxy, tert-butylcarbonyloxy),
  (h) a carbamoyl group optionally mono- or di-substituted by substituent(s) selected from a $C_{1-6}$ alkyl, a $C_{1-6}$ alkylsulfonyl group and an amino group,
  (i) an aromatic heterocyclic group (e.g., thienyl, tetrazolyl, imidazolyl, furyl, pyridyl) optionally substituted by 1 to 3 $C_{1-6}$ alkyl groups,
  (j) a non-aromatic heterocyclic group (e.g., tetrahydrofuranyl, piperidino, piperazinyl, morpholinyl, dihydrooxadiazolyl, hexahydropyrazinooxazinyl (e.g., hexahydropyrazino[2,1-c][1,4]oxazinyl)) optionally substituted by 1 to 3 substituents selected from a $C_{1-6}$ alkyl-carbonyl group and an oxo group,
  (k) an amino group optionally mono- or di-substituted by $C_{1-6}$ alkyl group(s) (the $C_{1-6}$ alkyl group is optionally substituted by 1 to 3 substituents selected from a non-aromatic heterocyclic group (e.g., morpholinyl), a $C_{1-6}$ alkoxy group and a $C_{1-6}$ alkylsulfonyl group),
  (l) a $C_{1-6}$ alkylsulfonyl group optionally substituted by 1 to 3 carboxy groups,
  (m) a $C_{1-6}$ alkylthio group optionally substituted by 1 to 3 substituents selected from a carboxy group, a $C_{1-6}$ alkoxy-carbonyl group, a hydroxy group and a carbamoyl group,
  (n) a phosphono group optionally mono- or di-substituted by $C_{1-6}$ alkyl group(s),
  (o) a non-aromatic heterocyclyl-carbonyl group (e.g., morpholinylcarbonyl),
  (p) a cyano group, and
  (q) a $C_{6-14}$ aryloxy group optionally substituted by 1 to 3 substituents selected from a carboxy group and a $C_{1-6}$ alkoxy-carbonyl group;
(44) a $C_{2-6}$ alkenyl group (e.g., ethenyl, 1-propenyl) optionally substituted by 1 to 3 substituents selected from
  (a) a halogen atom,
  (b) a carboxy group,
  (c) a $C_{1-6}$ alkoxy-carbonyl group, and
  (d) a carbamoyl group;
(45) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
and the like can be mentioned.

As the "acyl group" for $R^6$, $R^7$, $R^{21}$ or $R^{22}$, for example, groups represented by the formulas: —$COR^a$, —CO—$OR^a$, —$SO_2R^a$, —$SOR^a$, —CO—$NR^{a'}R^{b'}$, —CS—$NR^{a'}R^{b'}$ and —$SO_2$—$NR^{a'}R^{b'}$ wherein $R^a$ is a hydrogen atom, an optionally substituted hydrocarbon group or an optionally substituted heterocyclic group, and $R^{a'}$ and $R^{b'}$ are the same or different and each is a hydrogen atom, an optionally substituted hydrocarbon group or an optionally substituted heterocyclic group, or $R^{a'}$ and $R^{b'}$ form, together with the adjacent nitrogen atom, an optionally substituted nitrogen-containing heterocycle, and the like can be mentioned.

As the "optionally substituted hydrocarbon group" for $R^a$, $R^{a'}$ or $R^{b'}$, those similar to the "optionally substituted hydrocarbon group" for $R^6$, $R^7$, $R^{21}$ or $R^{22}$ can be mentioned. As the "optionally substituted heterocyclic group" for $R^a$, $R^{a'}$ or $R^{b'}$, those similar to the below-mentioned "optionally substituted heterocyclic group" for $R^3$ can be mentioned.

As the "nitrogen-containing heterocycle" of the "optionally substituted nitrogen-containing heterocycle" formed by $R^{a'}$ and $R^{b'}$ together with the adjacent nitrogen atom, for example, a 5- to 7-membered nitrogen-containing heterocycle containing, as a ring-constituting atom besides carbon atoms, at least one nitrogen atom and optionally further containing one or two heteroatoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, oxopiperazine and the like can be mentioned.

The nitrogen-containing heterocycle optionally has 1 to 3 (preferably 1 or 2) substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned.

As preferable examples of the "acyl group",
(1) a formyl group;
(2) a carboxy group;
(3) a carbamoyl group;
(4) a $C_{1-6}$ alkyl-carbonyl group;
(5) a $C_{1-6}$ alkoxy-carbonyl group optionally substituted by 1 to 3 substituents selected from
  (a) a carboxy group,
  (b) a carbamoyl group,
  (c) a thiocarbamoyl group,
  (d) a $C_{1-6}$ alkoxy-carbonyl group, and
  (e) a $C_{1-6}$ alkyl-carbonyloxy group
(e.g., methoxycarbonyl, ethoxycarbonyl, propoxycarbonyl, tert-butoxycarbonyl; carboxyethoxycarbonyl, carboxyethoxycarbonyl, carboxybutoxycarbonyl; carbamoylmethoxycarbonyl; thiocarbamoylmethoxycarbonyl; ethoxycarbonylmethoxycarbonyl, ethoxycarbonylethoxycarbonyl, methoxycarbonylbutoxycarbonyl, ethoxycarbonylbutoxycarbonyl; tert-butylcarbonyloxymethoxycarbonyl);
(6) a $C_{3-10}$ cycloalkyl-carbonyl group (e.g., cyclopentylcarbonyl, cyclohexylcarbonyl);
(7) a $C_{6-14}$ aryl-carbonyl group (e.g., benzoyl, 1-naphthoyl, 2-naphthoyl) optionally substituted by 1 to 3 substituents selected from
 (a) a halogen atom,
 (b) a cyano group,
 (c) a $C_{1-6}$ alkyl group optionally substituted by 1 to 3 halogen atoms,
 (d) a $C_{1-6}$ alkoxy group,
 (e) a carboxy group,
 (f) a $C_{1-6}$ alkoxy-carbonyl group, and
 (g) a carbamoyl group;
(8) a $C_{6-14}$ aryloxy-carbonyl group (e.g., phenyloxycarbonyl, naphthyloxycarbonyl) optionally substituted by 1 to 3 substituents selected from
 (a) a carboxy group,
 (b) a $C_{1-6}$ alkoxy-carbonyl group, and
 (c) a carbamoyl group;
(9) a $C_{7-13}$ aralkyloxy-carbonyl group optionally substituted by 1 to 3 substituents selected from
 (a) a carboxy group,
 (b) a carbamoyl group,
 (c) a thiocarbamoyl group,
 (d) a $C_{1-6}$ alkoxy-carbonyl group,
 (e) a halogen atom,
 (f) a cyano group,
 (g) a nitro group,
 (h) a $C_{1-6}$ alkoxy group,
 (i) a $C_{1-6}$ alkylsulfonyl group, and
 (j) a $C_{1-6}$ alkyl group
(e.g., benzyloxycarbonyl, phenethyloxycarbonyl; carboxybenzyloxycarbonyl; methoxycarbonylbenzyloxycarbonyl; biphenylylmethoxycarbonyl);
(10) a carbamoyl group mono- or di-substituted by $C_{1-6}$ alkyl group(s) optionally substituted by 1 to 3 substituents selected from a halogen atom and a $C_{1-6}$ alkoxy group (e.g., methylcarbamoyl, ethylcarbamoyl, dimethylcarbamoyl, diethylcarbamoyl, ethylmethylcarbamoyl, propylcarbamoyl, isopropylcarbamoyl, butylcarbamoyl, isobutylcarbamoyl, trifluoroethylcarbamoyl, N-methoxyethyl-N-methylcarbamoyl);
(11) a $C_{1-6}$ alkylsulfonyl group optionally substituted by 1 to 3 substituents selected from
 (a) a carboxy group,
 (b) a carbamoyl group, and
 (c) a $C_{1-6}$ alkoxy-carbonyl group
(e.g., methylsulfonyl, carboxymethylsulfonyl);
(12) a $C_{1-6}$ alkylsulfinyl group (e.g., methylsulfinyl);
(13) a thiocarbamoyl group;
(14) a $C_{7-13}$ aralkyl-carbonyl group (e.g., benzylcarbonyl, phenethylcarbonyl);
(15) an aromatic heterocyclyl-carbonyl group (e.g., furylcarbonyl, thienylcarbonyl, thiazolylcarbonyl, pyrazolylcarbonyl, pyridylcarbonyl, pyrazinylcarbonyl, benzofurylcarbonyl, benzothienylcarbonyl, quinoxalinylcarbonyl) optionally substituted by 1 to 3 substituents selected from
 (a) a $C_{1-6}$ alkyl group,
 (b) a $C_{6-14}$ aryl group,
 (c) a $C_{7-13}$ aralkyl group,
 (d) a $C_{1-6}$ alkoxy group,
 (e) a carboxy group,
 (f) a $C_{1-6}$ alkoxy-carbonyl group, and
 (g) a carbamoyl group;
(16) a non-aromatic heterocyclyl-carbonyl group (e.g., tetrahydrofurylcarbonyl, morpholinylcarbonyl, thiomorpholinylcarbonyl, piperidinylcarbonyl, pyrrolidinylcarbonyl, piperazinylcarbonyl, dioxolylcarbonyl, dioxolanylcarbonyl, 1,3-dihydro-2-benzofuranylcarbonyl, thiazolidinylcarbonyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group, and
 (d) a halogen atom;
(17) a sulfamoyl group;
(18) a sulfamoyl group mono- or di-substituted by $C_{1-6}$ alkyl group(s) optionally substituted by 1 to 3 substituents selected from a halogen atom and a $C_{1-6}$ alkoxy group (e.g., methylsulfamoyl, ethylsulfamoyl, dimethylsulfamoyl);
and the like can be mentioned.

When $R^6$ and $R^7$ are independent, $R^6$ is preferably an optionally substituted $C_{1-6}$ alkyl group, a cyano group or an acyl group, more preferably a $C_{1-6}$ alkyl group substituted by an optionally substituted heterocyclic group.

As preferable specific examples for $R^6$,
(1) a $C_{1-6}$ alkyl group (preferably methyl, ethyl, isopropyl) optionally substituted by 1 to 3 substituents selected from
 (a) a non-aromatic heterocyclic group (preferably piperidinyl, pyrrolidinyl, morpholinyl, piperazinyl) optionally substituted by 1 to 3 substituents selected from
  (i) a hydroxy group,
  (ii) a $C_{1-6}$ alkyl-carbonyl group (preferably acetyl),
  (iii) a $C_{1-6}$ alkylsulfonyl group (preferably methylsulfonyl), and
  (iv) a halogen atom (preferably fluorine atom),
 (b) an amino group,
 (c) a hydroxy group, and
 (d) a $C_{1-6}$ alkoxy group (preferably methoxy);
(2) a cyano group;
(3) a carboxy group;
(4) a $C_{1-6}$ alkoxy-carbonyl group (preferably methoxycarbonyl);
(5) a carbamoyl group; and
(6) a non-aromatic heterocyclyl-carbonyl group (preferably pyrrolidinylcarbonyl);
[preferably a $C_{1-6}$ alkyl group (preferably methyl, ethyl, isopropyl) substituted by 1 to 3 substituents selected from
 (a) a non-aromatic heterocyclic group (preferably piperidinyl, pyrrolidinyl, morpholinyl, piperazinyl) optionally substituted by 1 to 3 substituents selected from
  (i) a hydroxy group,
  (ii) a $C_{1-6}$ alkyl-carbonyl group (preferably acetyl),
  (iii) a $C_{1-6}$ alkylsulfonyl group (preferably methylsulfonyl), and
  (iv) a halogen atom (preferably fluorine atom)]
can be mentioned.

As another preferable specific examples for $R^6$,
(1) a $C_{1-6}$ alkyl group (preferably methyl, ethyl, isopropyl, isobutyl) optionally substituted by 1 to 3 substituents selected from
 (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
  (i) a hydroxy group,
  (ii) a $C_{1-6}$ alkyl-carbonyl group (preferably acetyl), (iii) a $C_{1-6}$ alkylsulfonyl group (preferably methylsulfonyl),
(iv) a halogen atom (preferably fluorine atom),
(v) an oxo group,
(vi) a $C_{1-6}$ alkyl group (preferably methyl, ethyl) optionally substituted by 1 to 3 hydroxy groups, and
(vii) a $C_{1-3}$ alkylenedioxy group (preferably ethylenedioxy), (b) an amino group optionally mono- or di-substituted by substituent(s) selected from
(i) a $C_{1-6}$ alkyl group (preferably methyl, ethyl, isobutyl) optionally substituted by 1 to 3 substituents selected from a hydroxy group and a $C_{1-6}$ alkylsulfonyl group (preferably methylsulfonyl),
(ii) a $C_{1-6}$ alkyl-carbonyl group (preferably acetyl),
(iii) a $C_{1-6}$ alkoxy-carbonyl group (preferably methoxycarbonyl) optionally substituted by 1 to 3 $C_{6-14}$ aryl groups (preferably phenyl),
(iv) a $C_{3-10}$ cycloalkyl group (preferably cyclohexyl) optionally substituted by 1 to 3 substituents selected from a hydroxy group and a $C_{1-6}$ alkyl group (preferably methyl),
(v) an aromatic heterocyclic group (preferably triazolyl), and
(vi) a non-aromatic heterocyclic group (preferably tetrahydrothiopyranyl, 1-oxidotetrahydrothiopyranyl, 1,1-dioxidotetrahydrothiopyranyl), (c) a hydroxy group,
(d) a $C_{1-6}$ alkoxy group (preferably methoxy),
(e) a $C_{1-6}$ alkylsulfonyloxy group (preferably methylsulfonyloxy),
(f) a $C_{1-6}$ alkyl-carbonyl group (preferably acetyl),
(g) a $C_{2-6}$ alkenyl-carbonyl group (preferably vinylcarbonyl),
(h) a $C_{1-6}$ alkoxy-carbonyl group (preferably ethoxycarbonyl),
(i) a carboxy group,
(j) a non-aromatic heterocyclyl-carbonyl group (preferably piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
(i) a hydroxy group,
(ii) a $C_{1-6}$ alkyl group (preferably methyl, ethyl) optionally substituted by 1 to 3 hydroxy groups,
(iii) a halogen atom (preferably fluorine atom), and
(iv) a carboxy group,
(k) a non-aromatic heterocyclyl-carbonyloxy group (preferably morpholinylcarbonyloxy) optionally substituted by 1 to 3 $C_{1-6}$ alkyl groups (preferably methyl),
(l) a carbamoyl group optionally mono- or di-substituted by substituent(s) selected from
(i) a $C_{1-6}$ alkyl group (preferably methyl, ethyl) optionally substituted by 1 to 3 substituents selected from a hydroxy group, a $C_{1-6}$ alkoxy group (preferably methoxy) and a $C_{1-6}$ alkylsulfonyl group (preferably methylsulfonyl),
(ii) a $C_{1-6}$ alkoxy group (preferably methoxy),
(iii) a $C_{3-10}$ cycloalkyl group (preferably cyclopropyl),
(iv) a $C_{1-6}$ alkylsulfonyl group (preferably methylsulfonyl),
(v) an aromatic heterocyclic group (preferably triazolyl, tetrazolyl), and
(vi) a non-aromatic heterocyclic group (preferably tetrahydropyranyl),
(m) a $C_{1-6}$ alkylthio group (preferably methylthio) optionally substituted by 1 to 3 carboxy groups, and
(n) a formyl group;
(2) a cyano group;
(3) a carboxy group;
(4) a $C_{1-6}$ alkoxy-carbonyl group (preferably methoxycarbonyl);
(5) a carbamoyl group optionally mono- or di-substituted by $C_{1-6}$ alkyl group(s) (preferably ethyl); and
(6) a non-aromatic heterocyclyl-carbonyl group (preferably pyrrolidinylcarbonyl, morpholinylcarbonyl, piperazinylcarbonyl) optionally substituted by 1 to 3 $C_{1-6}$ alkyl groups (preferably methyl);

[preferably a $C_{1-6}$ alkyl group (preferably methyl, ethyl, isopropyl, isobutyl) substituted by 1 to 3 substituents selected from
(a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
(i) a hydroxy group,
(ii) a $C_{1-6}$ alkyl-carbonyl group (preferably acetyl),
(iii) a $C_{1-6}$ alkylsulfonyl group (preferably methylsulfonyl),
(iv) a halogen atom (preferably fluorine atom),
(v) an oxo group,
(vi) a $C_{1-6}$ alkyl group (preferably methyl, ethyl) optionally substituted by 1 to 3 hydroxy groups, and
(vii) a $C_{1-3}$ alkylenedioxy group (preferably ethylenedioxy)]
can be mentioned.

When $R^6$ and $R^7$ are independent, $R^7$ is preferably a hydrogen atom or an optionally substituted $C_{1-6}$ alkyl group, more preferably a hydrogen atom.

As preferable specific examples for $R^7$,
(1) a hydrogen atom; and
(2) a $C_{1-6}$ alkyl group (preferably methyl);
can be mentioned.

When $R^6$ and $R^7$ in combination form an optionally substituted ring, as the "ring" of the "optionally substituted ring", for example, a $C_{3-10}$ cycloalkane, a $C_{3-10}$ cycloalkene, a $C_{3-10}$ cycloalkadiene, a monocyclic non-aromatic heterocycle and the like can be mentioned.

As the $C_{3-10}$ cycloalkane, $C_{3-10}$ cycloalkene and $C_{4-10}$ cycloalkadiene, rings corresponding to the $C_{3-10}$ cycloalkyl group, $C_{3-10}$ cycloalkenyl group and $C_{4-10}$ cycloalkadienyl group exemplified as the "hydrocarbon group" of the "optionally substituted hydrocarbon group" for $R^6$, $R^7$, $R^{21}$ or $R^{22}$ can be mentioned. As the monocyclic non-aromatic heterocycle, a ring corresponding to the monocyclic non-aromatic heterocyclic group exemplified as the below-mentioned "optionally substituted heterocyclic group" for $R^3$, can be mentioned.

The "ring" of the "optionally substituted ring" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned.

When $R^6$ and $R^7$ in combination form an optionally substituted ring, the "optionally substituted ring" is preferably an optionally substituted monocyclic non-aromatic heterocycle (preferably piperidine, tetrahydropyran, 1-oxidotetrahydrothiopyran) or an optionally substituted $C_{3-10}$ cycloalkane (preferably cyclohexane), more preferably an optionally substituted monocyclic non-aromatic heterocycle (preferably piperidine, tetrahydropyran, 1-oxidotetrahydrothiopyran).

As preferable specific examples, a monocyclic non-aromatic heterocycle (preferably piperidine, tetrahydropyran) optionally substituted by 1 to 3 substituents selected from (a) a $C_{1-6}$ alkyl group (preferably methyl, ethyl) optionally substituted by aromatic heterocyclic group(s) (preferably imidazolyl) optionally substituted by 1 to 3 $C_{1-6}$ alkyl groups (preferably methyl), (b) a $C_{7-13}$ aralkyl group (preferably benzyl), (c) a $C_{1-6}$ alkyl-carbonyl group (preferably acetyl), (d) a $C_{1-6}$ alkylsulfonyl group (preferably methylsulfonyl), and (e) a carbamoyl group optionally mono- or di-substituted by $C_{1-6}$ alkyl group(s) (preferably methyl);

can be mentioned.

As another preferable specific examples, (1) a monocyclic non-aromatic heterocycle (preferably piperidine, tetrahydropyran, 1-oxidotetrahydrothiopyran) optionally substituted by 1 to 3 substituents selected from (a) a $C_{1-6}$ alkyl group (preferably methyl, ethyl, isobutyl) optionally substituted by 1 to 3 substituents selected from
  (i) an aromatic heterocyclic group (preferably imidazolyl, furyl, pyridyl) optionally substituted by 1 to 3 $C_{1-6}$ alkyl groups (preferably methyl),
  (ii) a cyano group,
  (iii) a hydroxy group,
  (iv) a carboxy group,
  (v) a $C_{1-6}$ alkoxy group (preferably methoxy),
  (vi) a $C_{1-6}$ alkyl-carbonyl group (preferably acetyl),
  (vii) a $C_{1-6}$ alkoxy-carbonyl group (preferably methoxycarbonyl), and
  (viii) a carbamoyl group optionally mono- or di-substituted by $C_{1-6}$ alkyl group(s) (preferably ethyl), (b) a $C_{7-13}$ aralkyl group (preferably benzyl), (c) a $C_{1-6}$ alkyl-carbonyl group (preferably acetyl), (d) a $C_{1-6}$ alkylsulfonyl group (preferably methylsulfonyl), (e) a carbamoyl group optionally mono- or di-substituted by $C_{1-6}$ alkyl group(s) (preferably methyl), and (f) a non-aromatic heterocyclic group (preferably tetrahydropyranyl); and (2) a $C_{3-10}$ cycloalkane (preferably cyclohexane) optionally substituted by 1 to 3 substituents selected from an oxo group and a $C_{1-3}$ alkylenedioxy group (preferably ethylenedioxy);

can be mentioned.

$R^{21}$ is preferably a hydrogen atom or an optionally substituted $C_{1-6}$ alkyl group.

As preferable specific examples for $R^{21}$,
(1) a hydrogen atom; and
(2) a $C_{1-6}$ alkyl group (preferably methyl) optionally substituted by 1 to 3 substituents selected from a hydroxy group and a non-aromatic heterocyclic group (preferably morpholinyl);
can be mentioned.

$R^{22}$ is preferably a hydrogen atom.

In the embodiment wherein $R^2$ is a group represented by

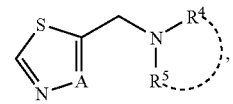

A is CH or N;

$R^4$ and $R^5$ are each independently an optionally substituted $C_{1-6}$ alkyl group or an optionally substituted $C_{3-10}$ cycloalkyl group, or $R^4$ and $R^5$ in combination form an optionally substituted ring (the ring should not be morpholine).

In this embodiment, A is preferably CH.

The "$C_{1-6}$ alkyl group" of the "optionally substituted $C_{1-6}$ alkyl group" for $R^4$ or $R^5$ optionally has 1 to 3 substituents at substitutable positions. As such substituents, those exemplified as the substituents which the $C_{1-10}$ alkyl group and the like exemplified as the "hydrocarbon group" of the "optionally substituted hydrocarbon group" for $R^6$, $R^7$, $R^{21}$ or $R^{22}$ optionally has, can be mentioned.

As the "$C_{3-10}$ cycloalkyl group" of the "optionally substituted $C_{3-10}$ cycloalkyl group" for $R^4$ or $R^5$, those similar to the "$C_{3-10}$ cycloalkyl group" exemplified as the "hydrocarbon group" of the "optionally substituted hydrocarbon group" for $R^6$, $R^7$, $R^{21}$ or $R^{22}$ can be mentioned.

The "$C_{3-10}$ cycloalkyl group" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned.

When $R^4$ and $R^5$ are independent, $R^4$ and $R^5$ are preferably each independently
(1) a $C_{1-6}$ alkyl group (preferably methyl, ethyl, propyl, isopropyl, butyl, isobutyl, neopentyl) optionally substituted by 1 to 3 substituents selected from
  (a) a $C_{1-6}$ alkoxy group (preferably methoxy, ethoxy),
  (b) a $C_{1-6}$ alkylsulfonyl group (preferably methylsulfonyl, ethylsulfonyl),
  (c) a $C_{1-6}$ alkoxy-carbonyl group (preferably methoxycarbonyl, ethoxycarbonyl), and
  (d) an aromatic heterocyclic group (preferably pyridyl); or
(2) a $C_{3-10}$ cycloalkyl group (preferably cyclopropyl).

When $R^4$ and $R^5$ in combination form an optionally substituted ring, as the "ring" of the "optionally substituted ring", an optionally substituted nitrogen-containing non-aromatic heterocycle can be mentioned. As the "nitrogen-containing non-aromatic heterocycle" of the "optionally substituted nitrogen-containing non-aromatic heterocycle", for example, a monocyclic nitrogen-containing non-aromatic heterocycle (the ring should not be morpholine), a fused nitrogen-containing non-aromatic heterocycle, a nitrogen-containing spiro ring and the like can be mentioned.

As the "monocyclic nitrogen-containing non-aromatic heterocycle", for example, a 5- to 7-membered monocyclic nitrogen-containing non-aromatic heterocycle (the ring should not be morpholine) containing, as a ring-constituting atom besides carbon atoms, at least one nitrogen atom and optionally further containing 1 to 3 heteroatoms selected from an oxygen atom, a sulfur atom and a nitrogen atom can be mentioned. As preferable specific examples of the 5- to 7-membered monocyclic nitrogen-containing non-aromatic heterocycle, pyrrolidine, oxopyrrolidine, dioxopyrrolidine, piperidine, thiomorpholine, 1,1-dioxidothiomorpholine, piperazine, oxopiperazine and the like can be mentioned.

As the "fused nitrogen-containing non-aromatic heterocycle", for example, a ring wherein the above-mentioned 5- to 7-membered monocyclic nitrogen-containing non-aromatic heterocycle and 1 or 2 rings selected from a 5 or 6-membered aromatic heterocycle, a 5 or 6-membered non-aromatic heterocycle and a benzene ring are condensed, and a ring wherein the above-mentioned ring is partially saturated, can be mentioned. As the 5 or 6-membered aromatic heterocycle and 5 or 6-membered non-aromatic heterocycle, for example, a ring corresponding to a 5- or 6-membered ring group, from among the aromatic heterocyclic group and non-aromatic heterocyclic group exemplified as the "heterocyclic group" of the below-mentioned "optionally substituted heterocyclic group" for $R^3$, can be mentioned.

As preferable specific examples of the fused nitrogen-containing non-aromatic heterocycle, tetrahydropyrrolo[3,4-c]pyrrole-1,3(2H,3aH)-dione, hexahydropyrazino[2,1-c][1,4]oxazin-4(3H)-one, hexahydro[1,3]oxazolo[3,4-a]pyrazin-3-one, 5,6,7,8-tetrahydro[1,2,4]triazolo[4,3-a]pyrazine and the like can be mentioned.

As the "nitrogen-containing spiro heterocycle", for example, a ring formed by the above-mentioned 5- to 7-membered monocyclic nitrogen-containing non-aromatic heterocycle and 1 or 2 rings selected from a $C_{3-10}$ cycloalkane, a $C_{3-10}$ cycloalkene, a $C_{4-10}$ cycloalkadiene and a 5 or 6-membered non-aromatic heterocycle can be mentioned.

As the $C_{3-10}$ cycloalkane, $C_{3-10}$ cycloalkene and $C_{4-10}$ cycloalkadiene, a ring corresponding to the $C_{3-10}$ cycloalkyl group, $C_{3-10}$ cycloalkenyl group and $C_{4-10}$ cycloalkadienyl group exemplified as the "hydrocarbon group" of the "optionally substituted hydrocarbon group" for $R^6$, $R^7$, $R^{21}$ or $R^{22}$ can be mentioned. As the 5 or 6-membered non-aromatic heterocycle, a ring corresponding to a 5- or 6-membered ring group, from among the monocyclic non-aromatic heterocyclic group exemplified as the "heterocyclic group" of the below-mentioned "optionally substituted heterocyclic group" for $R^3$, can be mentioned.

As preferable specific examples of the nitrogen-containing spiro heterocycle, 1-oxa-3,8-diazaspiro[4.5]decan-2-one and the like can be mentioned.

The "ring" of the "optionally substituted ring" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned.

When $R^4$ and $R^5$ in combination form an optionally substituted ring, the "optionally substituted ring" is preferably an "optionally substituted nitrogen-containing non-aromatic heterocycle (the ring should not be morpholine)", more preferably a nitrogen-containing non-aromatic heterocycle (the ring should not be morpholine)

[preferably a monocyclic nitrogen-containing non-aromatic heterocycle (the ring should not be morpholine) (preferably pyrrolidine, oxopyrrolidine, piperidine, thiomorpholine, 1,1-dioxidothiomorpholine, piperazine, oxopiperazine);

a fused nitrogen-containing non-aromatic heterocycle (preferably tetrahydropyrrolo[3,4-c]pyrrole-1,3(2H,3aH)-dione, hexahydropyrazino[2,1-c][1,4]oxazin-4(3H)-one, hexahydro[1,3]oxazolo[3,4-a]pyrazin-3-one, 5,6,7,8-tetrahydro[1,2,4]triazolo[4,3-a]pyrazine); or a nitrogen-containing spiro heterocycle (preferably 1-oxa-3,8-diazaspiro[4.5]decan-2-one)] optionally substituted by 1 to 3 substituents selected from (1) a $C_{1-6}$ alkyl group (preferably methyl, ethyl, propyl, isopropyl, butyl, isobutyl, tert-butyl) optionally substituted by 1 to 3 substituents selected from
   (a) a halogen atom (preferably fluorine atom),
   (b) a carboxy group,
   (c) a hydroxy group,
   (d) a $C_{1-6}$ alkoxy group (preferably methoxy, ethoxy),
   (e) a $C_{1-6}$ alkoxy-carbonyl group (preferably methoxycarbonyl, ethoxycarbonyl),
   (f) a carbamoyl group optionally mono- or di-substituted by $C_{1-6}$ alkyl group(s) (preferably methyl), and
   (g) a non-aromatic heterocyclic group (preferably tetrahydrofuranyl);

(2) an aromatic heterocyclic group (preferably pyridyl, pyrimidinyl) optionally substituted by 1 to 3 $C_{1-6}$ alkyl groups;

(3) an amino group optionally mono- or di-substituted by $C_{1-6}$ alkyl-carbonyl group(s) (preferably acetylamino);

(4) a $C_{1-6}$ alkyl-carbonyl group (preferably acetyl);

(5) a $C_{1-6}$ alkoxy-carbonyl group (preferably methoxycarbonyl, ethoxycarbonyl);

(6) a non-aromatic heterocyclyl-carbonyl group (preferably pyrrolidinylcarbonyl);

(7) a $C_{1-6}$ alkylsulfonyl group (preferably methylsulfonyl, ethylsulfonyl);

(8) a carbamoyl group;

(9) a hydroxy group; and

(10) an aromatic heterocyclyl-oxy group (preferably pyrimidyloxy, pyrazinyloxy).

Preferably, $R^4$ and $R^5$ in combination form an optionally substituted ring (the ring should not be morpholine).

W is O or $NR^8$ wherein $R^8$ is a hydrogen atom, an optionally substituted $C_{1-6}$ alkyl group or an optionally substituted $C_{3-10}$ cycloalkyl group.

W is preferably $NR^8$ wherein $R^8$ is defined above.

The "$C_{1-6}$ alkyl group" of the "optionally substituted $C_{1-6}$ alkyl group" for $R^8$ optionally has 1 to 3 substituents at substitutable positions. As such substituents, those exemplified as the substituents which the $C_{1-10}$ alkyl group and the like exemplified as the "hydrocarbon group" of the "optionally substituted hydrocarbon group" for $R^6$, $R^7$, $R^{21}$ or $R^{22}$ optionally has, can be mentioned.

As the "optionally substituted $C_{3-10}$ cycloalkyl" for $R^8$, those similar to the "optionally substituted $C_{3-10}$ cycloalkyl" for $R^4$ or $R^5$ can be mentioned.

As preferable specific examples for $R^8$
(1) a hydrogen atom; and
(2) a $C_{1-6}$ alkyl group (preferably methyl, ethyl, propyl, isopropyl) optionally substituted by 1 to 3 substituents selected from
   (a) a $C_{3-10}$ cycloalkyl group (preferably cyclopropyl), and
   (b) a $C_{1-6}$ alkoxy group (preferably methoxy, ethoxy);
can be mentioned.

As another preferable specific examples for $R^8$
(1) a hydrogen atom; and
(2) a $C_{1-6}$ alkyl group (preferably methyl, ethyl, propyl, isopropyl, isobutyl) optionally substituted by 1 to 3 substituents selected from
   (a) a $C_{3-10}$ cycloalkyl group (preferably cyclopropyl),
   (b) a $C_{1-6}$ alkoxy group (preferably methoxy, ethoxy), (c) a halogen atom (preferably fluorine atom),
(d) a cyano group,
(e) a hydroxy group,
(f) a carboxy group,
(g) a carbamoyl group, and
(h) a $C_{1-6}$ alkoxy-carbonyl group (preferably ethoxycarbonyl);

can be mentioned.

$R^3$ is an optionally substituted heterocyclic group or an optionally substituted $C_{6-14}$ aryl group.

As the "heterocyclic group" of the "optionally substituted heterocyclic group" for $R^3$, an aromatic heterocyclic group and a non-aromatic heterocyclic group can be mentioned.

As used herein, as the aromatic heterocyclic group, for example, a 4- to 7-membered (preferably 5- or 6-membered) monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group can be mentioned. As the fused aromatic heterocyclic group, for example, a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like can be mentioned.

As preferable examples of the aromatic heterocyclic group, monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

fused heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), imidazothiazolyl (e.g., imidazo[2,1-b]thiazol-5-yl)pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like can be mentioned.

As the non-aromatic heterocyclic group, for example, a 4- to 7-membered (preferably 5- or 6-membered) monocyclic non-aromatic heterocyclic group containing, as a ring-constituting atom besides carbon atoms, 1 to 4 heteroatoms selected from an oxygen atom, a sulfur atom and a nitrogen atom, and a fused non-aromatic heterocyclic group can be mentioned. As the fused non-aromatic heterocyclic group, for example, a group derived from a fused ring wherein a ring corresponding to the 4- to 7-membered monocyclic non-aromatic heterocyclic group and 1 or 2 rings selected from a 5- or 6-membered aromatic or non-aromatic heterocycle containing 1 or 2 nitrogen atoms (e.g., pyrrole, imidazole, pyrazole, pyrazine, pyridine, pyrimidine, pyrrolidine, imidazolidine, pyrazolidine, piperidine, piperazine), a 5-membered aromatic or non-aromatic heterocycle containing one sulfur atom (e.g., thiophene, tetrahydrothiophene) and a benzene ring are fused, a group wherein the above-mentioned group is partially saturated, and the like can be mentioned.

As preferable examples of the non-aromatic heterocyclic group, monocyclic non-aromatic heterocyclic groups such as tetrahydrofuranyl (e.g., 2-tetrahydrofuranyl), pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), thioxooxazolidinyl (e.g., 2-thioxo-1,3-oxazolidin-5-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), pyrazolidinyl (e.g., pyrazolidin-1-yl), tetrahydropyrimidinyl, dioxanyl (e.g., 1,3-dioxan-2-yl, 1,3-dioxan-4-yl, 1,3-dioxan-5-yl, 1,4-dioxan-2-yl), dioxenyl (e.g., 4H-1,3-dioxin-2-yl, 4H-1,3-dioxin-4-yl, 4H-1,3-dioxin-5-yl, 4H-1,3-dioxin-6-yl, 2,3-dihydro-1,4-dioxin-2-yl, 2,3-dihydro-1,4-dioxin-5-yl) and the like;

fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), hexahydropyrazinooxazinyl (e.g., hexahydropyrazino[2,1-c][1,4]oxazinyl) and the like;

and the like can be mentioned.

The "heterocyclic group" of the aforementioned "optionally substituted heterocyclic group" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned.

As the "$C_{6-14}$ aryl group" of the "optionally substituted $C_{6-14}$ aryl group" for $R^3$, those similar to the "$C_{6-14}$ aryl group" exemplified as the "hydrocarbon group" of the "optionally substituted hydrocarbon group" for $R^6$, $R^7$, $R^{21}$ or $R^{22}$ can be mentioned.

The "$C_{6-14}$ aryl group" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned.

$R^3$ is preferably an optionally substituted 5- or 6-membered monocyclic aromatic heterocyclic group (preferably thienyl, pyridyl, furyl, thiazolyl, imidazolyl) or an optionally substituted $C_{6-14}$ aryl group (e.g., phenyl), more preferably an optionally substituted 5- or 6-membered monocyclic aromatic heterocyclic group (preferably thienyl, pyridyl, furyl, thiazolyl, imidazolyl), particularly preferably a 5- or 6-membered monocyclic aromatic heterocyclic group (preferably thienyl, pyridyl, furyl, thiazolyl, imidazolyl).

As preferable specific examples for $R^3$,
(1) a 5- or 6-membered monocyclic aromatic heterocyclic group (preferably thienyl, pyridyl, furyl, thiazolyl, imidazolyl) optionally substituted by 1 to 3 substituents selected from
  (a) a halogen atom (preferably chlorine atom), and
  (b) a $C_{1-6}$ alkyl group (preferably methyl); and
(2) a $C_{6-14}$ aryl group (e.g., phenyl) optionally substituted by 1 to 3 substituents selected from
  (a) a $C_{1-6}$ alkyl group (preferably methyl) optionally substituted by 1 to 3 halogen atoms (preferably fluorine atom), and
  (b) a $C_{1-6}$ alkoxy group (preferably methoxy);
can be mentioned.

$R^9$, $R^{10}$ and $R^{11}$ are each independently a hydrogen atom, a halogen atom, an optionally substituted $C_{1-6}$ alkyl group or an optionally substituted $C_{1-6}$ alkoxy group.

The "$C_{1-6}$ alkyl group" of the "optionally substituted $C_{1-6}$ alkyl group" for $R^9$, $R^{10}$ or $R^{11}$ optionally has 1 to 3 substituents at substitutable positions. As such substituents, those exemplified as the substituents which the $C_{1-10}$ alkyl group and the like exemplified as the "hydrocarbon group" of the "optionally substituted hydrocarbon group" for $R^6$, $R^7$, $R^{21}$ or $R^{22}$ optionally has, can be mentioned.

The "$C_{1-6}$ alkoxy group" of the "optionally substituted $C_{1-6}$ alkoxy group" for $R^9$, $R^{10}$ or $R^{11}$ optionally has 1 to 3 substituents at substitutable positions. As such substituents, those exemplified as the substituents which the $C_{1-10}$ alkyl group and the like exemplified as the "hydrocarbon group" of the "optionally substituted hydrocarbon group" for $R^6$, $R^7$, $R^{21}$ or $R^{22}$ optionally has, can be mentioned.

$R^9$ is preferably a hydrogen atom or a halogen atom (preferably chlorine atom).

$R^{10}$ is preferably a hydrogen atom, a halogen atom, a $C_{1-6}$ alkyl group or an optionally substituted $C_{1-6}$ alkoxy group, more preferably a hydrogen atom, a $C_{1-6}$ alkyl group or an optionally substituted $C_{1-6}$ alkoxy group.

As preferable specific examples for $R^{10}$,
(1) a hydrogen atom;
(2) a halogen atom (preferably bromine atom);
(3) a $C_{1-6}$ alkyl group (preferably methyl); and
(4) a $C_{1-6}$ alkoxy group (preferably methoxy, ethoxy, propoxy, isopropoxy) optionally substituted by 1 to 3 substituents selected from
  (a) a halogen atom (preferably fluorine atom),
  (b) a hydroxy group,
  (c) a carboxy group,
  (d) a carbamoyl group,
  (e) a $C_{1-6}$ alkoxy group (preferably methoxy),
  (f) a $C_{1-6}$ alkyl-carbonyl group (preferably acetyl),
  (g) a $C_{1-6}$ alkoxy-carbonyl group (preferably ethoxycarbonyl), and
  (h) a $C_{1-6}$ alkylsulfonyl group (preferably methylsulfonyl);
can be mentioned.

$R^{11}$ is preferably a hydrogen atom, a halogen atom (preferably chlorine atom) or a $C_{1-6}$ alkyl group (preferably methyl).

Compound (I) does not contain
a compound wherein $R^{21}$ is a hydrogen atom or a $C_{1-6}$ alkoxy-carbonyl group, $R^{22}$ is a hydrogen atom, and $R^6$ and $R^7$ are both hydrogen atoms, and
a compound wherein $R^{21}$ is a hydrogen atom or a $C_{1-6}$ alkoxy-carbonyl group, $R^{22}$ is a hydrogen atom, and $R^6$ and $R^7$ are both methyl groups.

Preferable examples of compound (I) is as follow.
[Compound (A)]
Compound (I) wherein
$R^1$ is a hydrogen atom;
$R^2$ is a group represented by

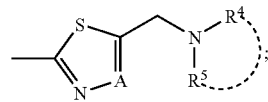

A is CH or N;
$R^4$ and $R^5$ are each independently
(1) a $C_{1-6}$ alkyl group (preferably methyl, ethyl, propyl, isopropyl, butyl, isobutyl, neopentyl) optionally substituted by 1 to 3 substituents selected from
  (a) a $C_{1-6}$ alkoxy group (preferably methoxy, ethoxy),
  (b) a $C_{1-6}$ alkylsulfonyl group (preferably methylsulfonyl, ethylsulfonyl),
  (c) a $C_{1-6}$ alkoxy-carbonyl group (preferably methoxycarbonyl, ethoxycarbonyl), and
  (d) an aromatic heterocyclic group (preferably pyridyl); or
(2) a $C_{3-10}$ cycloalkyl group (preferably cyclopropyl); or
$R^4$ and $R^5$ in combination form a nitrogen-containing non-aromatic heterocycle (the ring should not be morpholine)
[preferably a monocyclic nitrogen-containing non-aromatic heterocycle (the ring should not be morpholine) (preferably pyrrolidine, oxopyrrolidine, piperidine, thiomorpholine, 1,1-dioxidothiomorpholine, piperazine, oxopiperazine);
a fused nitrogen-containing non-aromatic heterocycle (preferably tetrahydropyrrolo[3,4-c]pyrrole-1,3(2H,3aH)-dione, hexahydropyrazino[2,1-c][1,4]oxazin-4(3H)-one, hexahydro[1,3]oxazolo[3,4-a]pyrazin-3-one, 5,6,7,8-tetrahydro[1,2,4]triazolo[4,3-a]pyrazine); or
a nitrogen-containing spiro heterocycle (preferably 1-oxa-3,8-diazaspiro[4.5]decan-2-one)] optionally substituted by 1 to 3 substituents selected from
(1) a $C_{1-6}$ alkyl group (preferably methyl, ethyl, propyl, isopropyl, butyl, isobutyl, tert-butyl) optionally substituted by 1 to 3 substituents selected from
(a) a halogen atom (preferably fluorine atom),
(b) a carboxy group,
(c) a hydroxy group,
(d) a $C_{1-6}$ alkoxy group (preferably methoxy, ethoxy),
(e) a $C_{1-6}$ alkoxy-carbonyl group (preferably methoxycarbonyl, ethoxycarbonyl),
(f) a carbamoyl group optionally mono- or di-substituted by $C_{1-6}$ alkyl group(s) (preferably methyl), and
(g) a non-aromatic heterocyclic group (preferably tetrahydrofuranyl),
(2) an aromatic heterocyclic group (preferably pyridyl, pyrimidinyl) optionally substituted by 1 to 3 $C_{1-6}$ alkyl groups,
(3) an amino group optionally mono- or di-substituted by $C_{1-6}$ alkyl-carbonyl group(s) (preferably acetylamino),
(4) a $C_{1-6}$ alkyl-carbonyl group (preferably acetyl),
(5) a $C_{1-6}$ alkoxy-carbonyl group (preferably methoxycarbonyl, ethoxycarbonyl),
(6) a non-aromatic heterocyclyl-carbonyl group (preferably pyrrolidinylcarbonyl),
(7) a $C_{1-6}$ alkylsulfonyl group (preferably methylsulfonyl, ethylsulfonyl),
(8) a carbamoyl group,
(9) a hydroxy group, and
(10) an aromatic heterocyclyl-oxy group (preferably pyrimidyloxy, pyrazinyloxy),
W is $NR^8$;
$R^1$ is
(1) a hydrogen atom, or
(2) a $C_{1-6}$ alkyl group (preferably methyl, ethyl, propyl, isopropyl) optionally substituted by 1 to 3 substituents selected from
(a) a $C_{3-10}$ cycloalkyl group (preferably cyclopropyl), and
(b) a $C_{1-6}$ alkoxy group (preferably methoxy, ethoxy);
$R^3$ is a 5- or 6-membered monocyclic aromatic heterocyclic group (preferably thienyl);
$R^9$ is a hydrogen atom or a halogen atom (preferably chlorine atom);
$R^{10}$ is a hydrogen atom; and
$R^{11}$ is a hydrogen atom, halogen atom (preferably chlorine atom) or a $C_{1-6}$ alkyl group (preferably methyl).
[Compound (A1)]
Compound (A) wherein A is N.
[Compound (A2)]
Compound (A) wherein A is CH.
[Compound (B)]
Compound (I) wherein
$R^1$ is a hydrogen atom;
$R^2$ is a group represented by

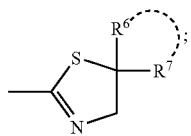

$R^6$ is
(1) a $C_{1-6}$ alkyl group (preferably methyl, ethyl, isopropyl) optionally substituted by 1 to 3 substituents selected from
(a) a non-aromatic heterocyclic group (preferably piperidinyl, pyrrolidinyl, morpholinyl, piperazinyl) optionally substituted by 1 to 3 substituents selected from
(i) a hydroxy group,
(ii) a $C_{1-6}$ alkyl-carbonyl group (preferably acetyl),
(iii) a $C_{1-6}$ alkylsulfonyl group (preferably methylsulfonyl), and
(iv) a halogen atom (preferably fluorine atom),
(b) an amino group,
(c) a hydroxy group, and
(d) a $C_{1-6}$ alkoxy group (preferably methoxy),
(2) a cyano group,
(3) a carboxy group,
(4) a $C_{1-6}$ alkoxy-carbonyl group (preferably methoxycarbonyl),
(5) a carbamoyl group, or
(6) a non-aromatic heterocyclyl-carbonyl group (preferably pyrrolidinylcarbonyl),
[preferably a $C_{1-6}$ alkyl group (preferably methyl, ethyl, isopropyl) substituted by 1 to 3 substituents selected from
(a) a non-aromatic heterocyclic group (preferably piperidinyl, pyrrolidinyl, morpholinyl, piperazinyl) optionally substituted by 1 to 3 substituents selected from
(i) a hydroxy group,
(ii) a $C_{1-6}$ alkyl-carbonyl group (preferably acetyl),
(iii) a $C_{1-6}$ alkylsulfonyl group (preferably methylsulfonyl), and
(iv) a halogen atom (preferably fluorine atom)], and
$R^7$ is
(1) a hydrogen atom, or
(2) a $C_{1-6}$ alkyl group (preferably methyl); or
$R^6$ and $R^7$ in combination form a monocyclic non-aromatic heterocycle (preferably piperidine, tetrahydropyran) optionally substituted by 1 to 3 substituents selected from
(a) a $C_{1-6}$ alkyl group (preferably methyl, ethyl) optionally substituted by aromatic heterocyclic group(s) (preferably imidazolyl) optionally substituted by 1 to 3 $C_{1-6}$ alkyl groups (preferably methyl),
(b) a $C_{7-13}$ aralkyl group (preferably benzyl),
(c) a $C_{1-6}$ alkyl-carbonyl group (preferably acetyl),
(d) a $C_{1-6}$ alkylsulfonyl group (preferably methylsulfonyl), and
(e) a carbamoyl group optionally mono- or di-substituted by $C_{1-6}$ alkyl group(s) (preferably methyl);
W is $NR^8$;
$R^8$ is
(1) a hydrogen atom, or
(2) a $C_{1-6}$ alkyl group (preferably methyl, ethyl, propyl, isopropyl) optionally substituted by 1 to 3 substituents selected from
(a) a $C_{3-10}$ cycloalkyl group (preferably cyclopropyl), and
(b) a $C_{1-6}$ alkoxy group (preferably methoxy, ethoxy);
$R^3$ is a 5- or 6-membered monocyclic aromatic heterocyclic group (preferably thienyl);
$R^9$ is a hydrogen atom or a halogen atom (preferably chlorine atom);

$R^{10}$ is a hydrogen atom; and
$R^{11}$ is a hydrogen atom, halogen atom (preferably chlorine atom) or a $C_{1-6}$ alkyl group (preferably methyl).
[Compound (C)]
Compound (I) wherein
$R^1$ is a hydrogen atom or a halogen atom (preferably fluorine atom);
$R^2$ is a group represented by

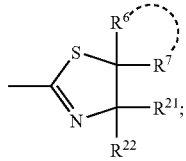

$R^6$ is
(1) a $C_{1-6}$ alkyl group (preferably methyl, ethyl, isopropyl, isobutyl) optionally substituted by 1 to 3 substituents selected from
  (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
    (i) a hydroxy group,
    (ii) a $C_{1-6}$ alkyl-carbonyl group (preferably acetyl),
    (iii) a $C_{1-6}$ alkylsulfonyl group (preferably methylsulfonyl),
    (iv) a halogen atom (preferably fluorine atom),
    (v) an oxo group,
    (vi) a $C_{1-6}$ alkyl group (preferably methyl, ethyl) optionally substituted by 1 to 3 hydroxy groups, and
    (vii) a $C_{1-3}$ alkylenedioxy group (preferably ethylenedioxy),
  (b) an amino group optionally mono- or di-substituted by substituent(s) selected from
    (i) a $C_{1-6}$ alkyl group (preferably methyl, ethyl, isobutyl) optionally substituted by 1 to 3 substituents selected from a hydroxy group and a $C_{1-6}$ alkylsulfonyl group (preferably methylsulfonyl),
    (ii) a $C_{1-6}$ alkyl-carbonyl group (preferably acetyl),
    (iii) a $C_{1-6}$ alkoxy-carbonyl group (preferably methoxycarbonyl) optionally substituted by 1 to 3 $C_{6-14}$ aryl groups (preferably phenyl),
    (iv) a $C_{3-10}$ cycloalkyl group (preferably cyclohexyl) optionally substituted by 1 to 3 substituents selected from a hydroxy group and a $C_{1-6}$ alkyl group (preferably methyl),
    (v) an aromatic heterocyclic group (preferably triazolyl), and
    (vi) a non-aromatic heterocyclic group (preferably tetrahydrothiopyranyl, 1-oxidotetrahydrothiopyranyl, 1,1-dioxidotetrahydrothiopyranyl),
  (c) a hydroxy group,
  (d) a $C_{1-6}$ alkoxy group (preferably methoxy),
  (e) a $C_{1-6}$ alkylsulfonyloxy group (preferably methylsulfonyloxy),
  (f) a $C_{1-6}$ alkyl-carbonyl group (preferably acetyl),
  (g) a $C_{2-6}$ alkenyl-carbonyl group (preferably vinylcarbonyl),
  (h) a $C_{1-6}$ alkoxy-carbonyl group (preferably ethoxycarbonyl),
  (i) a carboxy group,
  (j) a non-aromatic heterocyclyl-carbonyl group (preferably piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
    (i) a hydroxy group,
    (ii) a $C_{1-6}$ alkyl group (preferably methyl, ethyl) optionally substituted by 1 to 3 hydroxy groups,
    (iii) a halogen atom (preferably fluorine atom), and
    (iv) a carboxy group,
  (k) a non-aromatic heterocyclyl-carbonyloxy group (preferably morpholinylcarbonyloxy) optionally substituted by 1 to 3 $C_{1-6}$ alkyl groups (preferably methyl),
  (l) a carbamoyl group optionally mono- or di-substituted by substituent(s) selected from
    (i) a $C_{1-6}$ alkyl group (preferably methyl, ethyl) optionally substituted by 1 to 3 substituents selected from a hydroxy group, a $C_{1-6}$ alkoxy group (preferably methoxy) and a $C_{1-6}$ alkylsulfonyl group (preferably methylsulfonyl),
    (ii) a $C_{1-6}$ alkoxy group (preferably methoxy),
    (iii) a $C_{3-10}$ cycloalkyl group (preferably cyclopropyl),
    (iv) a $C_{1-6}$ alkylsulfonyl group (preferably methylsulfonyl),
    (v) an aromatic heterocyclic group (preferably triazolyl, tetrazolyl), and
    (vi) a non-aromatic heterocyclic group (preferably tetrahydropyranyl),
  (m) a $C_{1-6}$ alkylthio group (preferably methylthio) optionally substituted by 1 to 3 carboxy groups, and
  (n) a formyl group,
(2) a cyano group,
(3) a carboxy group,
(4) a $C_{1-6}$ alkoxy-carbonyl group (preferably methoxycarbonyl),
(5) a carbamoyl group optionally mono- or di-substituted by $C_{1-6}$ alkyl group(s) (preferably ethyl), or
(6) a non-aromatic heterocyclyl-carbonyl group (preferably pyrrolidinylcarbonyl, morpholinylcarbonyl, piperazinylcarbonyl) optionally substituted by 1 to 3 $C_{1-6}$ alkyl groups (preferably methyl),
[preferably a $C_{1-6}$ alkyl group (preferably methyl, ethyl, isopropyl, isobutyl) substituted by 1 to 3 substituents selected from
  (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
    (i) a hydroxy group,
    (ii) a $C_{1-6}$ alkyl-carbonyl group (preferably acetyl),
    (iii) a $C_{1-6}$ alkylsulfonyl group (preferably methylsulfonyl),
    (iv) a halogen atom (preferably fluorine atom),
    (v) an oxo group,
    (vi) a $C_{1-6}$ alkyl group (preferably methyl, ethyl) optionally substituted by 1 to 3 hydroxy groups, and
    (vii) a $C_{1-3}$ alkylenedioxy group (preferably ethylenedioxy)], and
$R^7$ is
(1) a hydrogen atom, or
(2) a $C_{1-6}$ alkyl group (preferably methyl); or
$R^6$ and $R^7$ in combination form (1) a monocyclic non-aromatic heterocycle (preferably piperidine, tetrahydropyran, 1-oxidotetrahydrothiopyran) optionally substituted by 1 to 3 substituents selected from
  (a) a $C_{1-6}$ alkyl group (preferably methyl, ethyl, isobutyl) optionally substituted by 1 to 3 substituents selected from
    (i) an aromatic heterocyclic group (preferably imidazolyl, furyl, pyridyl) optionally substituted by 1 to 3 $C_{1-6}$ alkyl groups (preferably methyl),
    (ii) a cyano group,
    (iii) a hydroxy group,
    (iv) a carboxy group,
    (v) a $C_{1-6}$ alkoxy group (preferably methoxy),
    (vi) a $C_{1-6}$ alkyl-carbonyl group (preferably acetyl),
    (vii) a $C_{1-6}$ alkoxy-carbonyl group (preferably methoxy-carbonyl), and
    (viii) a carbamoyl group optionally mono- or di-substituted by $C_{1-6}$ alkyl group(s) (preferably ethyl),
  (b) a $C_{7-13}$ aralkyl group (preferably benzyl),
  (c) a $C_{1-6}$ alkyl-carbonyl group (preferably acetyl),
  (d) a $C_{1-6}$ alkylsulfonyl group (preferably methylsulfonyl),
  (e) a carbamoyl group optionally mono- or di-substituted by $C_{1-6}$ alkyl group(s) (preferably methyl), and
  (f) a non-aromatic heterocyclic group (preferably tetrahydropyranyl), or
(2) a $C_{3-10}$ cycloalkane (preferably cyclohexane) optionally substituted by 1 to 3 substituents selected from an oxo group and a $C_{1-3}$ alkylenedioxy group (preferably ethylenedioxy);

$R^{21}$ is
(1) a hydrogen atom, or
(2) a $C_{1-6}$ alkyl group (preferably methyl) optionally substituted by 1 to 3 substituents selected from a hydroxy group and a non-aromatic heterocyclic group (preferably morpholinyl);

$R^{22}$ is a hydrogen atom;
W is $NR^8$;
$R^8$ is
(1) a hydrogen atom, or
(2) a $C_{1-6}$ alkyl group (preferably methyl, ethyl, propyl, isopropyl, isobutyl) optionally substituted by 1 to 3 substituents selected from
  (a) a $C_{3-10}$ cycloalkyl group (preferably cyclopropyl),
  (b) a $C_{1-6}$ alkoxy group (preferably methoxy, ethoxy),
  (c) a halogen atom (preferably fluorine atom),
  (d) a cyano group,
  (e) a hydroxy group,
  (f) a carboxy group,
  (g) a carbamoyl group, and
  (h) a $C_{1-6}$ alkoxy-carbonyl group (preferably ethoxycarbonyl);

$R^3$ is
(1) a 5- or 6-membered monocyclic aromatic heterocyclic group (preferably thienyl, pyridyl, furyl, thiazolyl, imidazolyl) optionally substituted by 1 to 3 substituents selected from
  (a) a halogen atom (preferably chlorine atom), and
  (b) a $C_{1-6}$ alkyl group (preferably methyl), or
(2) a $C_{6-14}$ aryl group (e.g., phenyl) optionally substituted by 1 to 3 substituents selected from
  (a) a $C_{1-6}$ alkyl group (preferably methyl) optionally substituted by 1 to 3 halogen atoms (preferably fluorine atom), and
  (b) a $C_{1-6}$ alkoxy group (preferably methoxy);

$R^9$ is a hydrogen atom or a halogen atom (preferably chlorine atom);

$R^{10}$ is
(1) a hydrogen atom,
(2) a halogen atom (preferably bromine atom),
(3) a $C_{1-6}$ alkyl group (preferably methyl), or
(4) a $C_{1-6}$ alkoxy group (preferably methoxy, ethoxy, propoxy, isopropoxy) optionally substituted by 1 to 3 substituents selected from
  (a) a halogen atom (preferably fluorine atom),
  (b) a hydroxy group,
  (c) a carboxy group,
  (d) a carbamoyl group,
  (e) a $C_{1-6}$ alkoxy group (preferably methoxy),
  (f) a $C_{1-6}$ alkyl-carbonyl group (preferably acetyl),
  (g) a $C_{1-6}$ alkoxy-carbonyl group (preferably ethoxycarbonyl), and
  (h) a $C_{1-6}$ alkylsulfonyl group (preferably methylsulfonyl); and $R^{11}$ is a hydrogen atom, a halogen atom (preferably chlorine atom) or a $C_{1-6}$ alkyl group (preferably methyl).

[Compound (D)]
Compound (I) wherein
$R^1$ is a hydrogen atom or a halogen atom (preferably fluorine atom);
$R^2$ is a group represented by

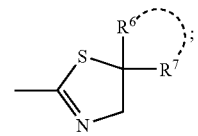

$R^6$ is
(1) a $C_{1-6}$ alkyl group (preferably methyl, ethyl, isopropyl, isobutyl) optionally substituted by 1 to 3 substituents selected from
  (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
    (i) a hydroxy group,
    (ii) a $C_{1-6}$ alkyl-carbonyl group (preferably acetyl),
    (iii) a $C_{1-6}$ alkylsulfonyl group (preferably methylsulfonyl),
    (iv) a halogen atom (preferably fluorine atom),
    (v) an oxo group,
    (vi) a $C_{1-6}$ alkyl group (preferably methyl, ethyl) optionally substituted by 1 to 3 hydroxy groups, and
    (vii) a $C_{1-3}$ alkylenedioxy group (preferably ethylenedioxy),
  (b) an amino group optionally mono- or di-substituted by substituent(s) selected from
    (i) a $C_{1-6}$ alkyl group (preferably methyl, ethyl, isobutyl) optionally substituted by 1 to 3 substituents selected from a hydroxy group and a $C_{1-6}$ alkylsulfonyl group (preferably methylsulfonyl),
    (ii) a $C_{1-6}$ alkyl-carbonyl group (preferably acetyl),
    (iii) a $C_{1-6}$ alkoxy-carbonyl group (preferably methoxycarbonyl) optionally substituted by 1 to 3 $C_{6-14}$ aryl groups (preferably phenyl), (iv) a $C_{3-10}$ cycloalkyl group (preferably cyclohexyl) optionally substituted by 1 to 3 substituents selected from a hydroxy group and a $C_{1-6}$ alkyl group (preferably methyl),
(v) an aromatic heterocyclic group (preferably triazolyl), and
(vi) a non-aromatic heterocyclic group (preferably tetrahydrothiopyranyl, 1-oxidotetrahydrothiopyranyl, 1,1-dioxidotetrahydrothiopyranyl),
(c) a hydroxy group,
(d) a $C_{1-6}$ alkoxy group (preferably methoxy),
(e) a $C_{1-6}$ alkylsulfonyloxy group (preferably methylsulfonyloxy),
(f) a $C_{1-6}$ alkyl-carbonyl group (preferably acetyl),
(g) a $C_{2-6}$ alkenyl-carbonyl group (preferably vinylcarbonyl),
(h) a $C_{1-6}$ alkoxy-carbonyl group (preferably ethoxycarbonyl),
(i) a carboxy group,
(j) a non-aromatic heterocyclyl-carbonyl group (preferably piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
(i) a hydroxy group,
(ii) a $C_{1-6}$ alkyl group (preferably methyl, ethyl) optionally substituted by 1 to 3 hydroxy groups,
(iii) a halogen atom (preferably fluorine atom), and
(iv) a carboxy group,
(k) a non-aromatic heterocyclyl-carbonyloxy group (preferably morpholinylcarbonyloxy) optionally substituted by 1 to 3 $C_{1-6}$ alkyl groups (preferably methyl),
(l) a carbamoyl group optionally mono- or di-substituted by substituent(s) selected from
(i) a $C_{1-6}$ alkyl group (preferably methyl, ethyl) optionally substituted by 1 to 3 substituents selected from a hydroxy group, a $C_{1-6}$ alkoxy group (preferably methoxy) and a $C_{1-6}$ alkylsulfonyl group (preferably methylsulfonyl),
(ii) a $C_{1-6}$ alkoxy group (preferably methoxy),
(iii) a $C_{3-10}$ cycloalkyl group (preferably cyclopropyl),
(iv) a $C_{1-6}$ alkylsulfonyl group (preferably methylsulfonyl),
(v) an aromatic heterocyclic group (preferably triazolyl, tetrazolyl), and
(vi) a non-aromatic heterocyclic group (preferably tetrahydropyranyl),
(m) a $C_{1-6}$ alkylthio group (preferably methylthio) optionally substituted by 1 to 3 carboxy groups, and
(n) a formyl group,
(2) a cyano group,
(3) a carboxy group,
(4) a $C_{1-6}$ alkoxy-carbonyl group (preferably methoxycarbonyl),
(5) a carbamoyl group optionally mono- or di-substituted by $C_{1-6}$ alkyl group(s) (preferably ethyl), or
(6) a non-aromatic heterocyclyl-carbonyl group (preferably pyrrolidinylcarbonyl, morpholinylcarbonyl, piperazinylcarbonyl) optionally substituted by 1 to 3 $C_{1-6}$ alkyl groups (preferably methyl),
[preferably a $C_{1-6}$ alkyl group (preferably methyl, ethyl, isopropyl, isobutyl) substituted by 1 to 3 substituents selected from (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
(i) a hydroxy group,
(ii) a $C_{1-6}$ alkyl-carbonyl group (preferably acetyl),
(iii) a $C_{1-6}$ alkylsulfonyl group (preferably methylsulfonyl),
(iv) a halogen atom (preferably fluorine atom),
(v) an oxo group,
(vi) a $C_{1-6}$ alkyl group (preferably methyl, ethyl) optionally substituted by 1 to 3 hydroxy groups, and
(vii) a $C_{1-3}$ alkylenedioxy group (preferably ethylenedioxy)], and
$R^7$ is
(1) a hydrogen atom, or
(2) a $C_{1-6}$ alkyl group (preferably methyl); or
$R^6$ and $R^7$ in combination form
(1) a monocyclic non-aromatic heterocycle (preferably piperidine, tetrahydropyran, 1-oxidotetrahydrothiopyran) optionally substituted by 1 to 3 substituents selected from
(a) a $C_{1-6}$ alkyl group (preferably methyl, ethyl, isobutyl) optionally substituted by 1 to 3 substituents selected from
(i) an aromatic heterocyclic group (preferably imidazolyl, furyl, pyridyl) optionally substituted by 1 to 3 $C_{1-6}$ alkyl groups (preferably methyl),
(ii) a cyano group,
(iii) a hydroxy group,
(iv) a carboxy group,
(v) a $C_{1-6}$ alkoxy group (preferably methoxy),
(vi) a $C_{1-6}$ alkyl-carbonyl group (preferably acetyl),
(vii) a $C_{1-6}$ alkoxy-carbonyl group (preferably methoxycarbonyl), and
(viii) a carbamoyl group optionally mono- or di-substituted by $C_{1-6}$ alkyl group(s) (preferably ethyl),
(b) a $C_{7-13}$ aralkyl group (preferably benzyl),
(c) a $C_{1-6}$ alkyl-carbonyl group (preferably acetyl),
(d) a $C_{1-6}$ alkylsulfonyl group (preferably methylsulfonyl),
(e) a carbamoyl group optionally mono- or di-substituted by $C_{1-6}$ alkyl group(s) (preferably methyl), and
(f) a non-aromatic heterocyclic group (preferably tetrahydropyranyl), or
(2) a $C_{3-10}$ cycloalkane (preferably cyclohexane) optionally substituted by 1 to 3 substituents selected from an oxo group and a $C_{1-3}$ alkylenedioxy group (preferably ethylenedioxy);
W is $NR^8$;
$R^8$ is
(1) a hydrogen atom, or
(2) a $C_{1-6}$ alkyl group (preferably methyl, ethyl, propyl, isopropyl, isobutyl) optionally substituted by 1 to 3 substituents selected from
(a) a $C_{3-10}$ cycloalkyl group (preferably cyclopropyl),
(b) a $C_{1-6}$ alkoxy group (preferably methoxy, ethoxy),
(c) a halogen atom (preferably fluorine atom),
(d) a cyano group,
(e) a hydroxy group, (f) a carboxy group,
(g) a carbamoyl group, and
(h) a $C_{1-6}$ alkoxy-carbonyl group (preferably ethoxycarbonyl);
$R^3$ is
(1) a 5- or 6-membered monocyclic aromatic heterocyclic group (preferably thienyl, pyridyl, furyl, thiazolyl, imidazolyl) optionally substituted by 1 to 3 substituents selected from
   (a) a halogen atom (preferably chlorine atom), and
   (b) a $C_{1-6}$ alkyl group (preferably methyl), or
(2) a $C_{6-14}$ aryl group (e.g., phenyl) optionally substituted by 1 to 3 substituents selected from
   (a) a $C_{1-6}$ alkyl group (preferably methyl) optionally substituted by 1 to 3 halogen atoms (preferably fluorine atom), and
   (b) a $C_{1-6}$ alkoxy group (preferably methoxy);
$R^9$ is a hydrogen atom or a halogen atom (preferably chlorine atom);
$R^{10}$ is
(1) a hydrogen atom,
(2) a halogen atom (preferably bromine atom),
(3) a $C_{1-6}$ alkyl group (preferably methyl), or
(4) a $C_{1-6}$ alkoxy group (preferably methoxy, ethoxy, propoxy, isopropoxy) optionally substituted by 1 to 3 substituents selected from
   (a) a halogen atom (preferably fluorine atom),
   (b) a hydroxy group,
   (c) a carboxy group,
   (d) a carbamoyl group,
   (e) a $C_{1-6}$ alkoxy group (preferably methoxy),
   (f) a $C_{1-6}$ alkyl-carbonyl group (preferably acetyl),
   (g) a $C_{1-6}$ alkoxy-carbonyl group (preferably ethoxycarbonyl), and
   (h) a $C_{1-6}$ alkylsulfonyl group (preferably methylsulfonyl); and
$R^{11}$ is a hydrogen atom, a halogen atom (preferably chlorine atom) or a $C_{1-6}$ alkyl group (preferably methyl).
[Compound (E)]
Compound (I) wherein
$R^1$ is a hydrogen atom or a halogen atom (preferably fluorine atom);
$R^2$ is a group represented by

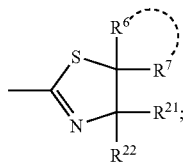

$R^6$ is
(1) a $C_{1-6}$ alkyl group (preferably methyl, ethyl, isopropyl, isobutyl) optionally substituted by 1 to 3 substituents selected from
   (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from
      (i) a hydroxy group,
      (ii) a $C_{1-6}$ alkyl-carbonyl group (preferably acetyl),
      (iii) a $C_{1-6}$ alkylsulfonyl group (preferably methylsulfonyl),
      (iv) a halogen atom (preferably fluorine atom),
      (v) an oxo group,
      (vi) a $C_{1-6}$ alkyl group (preferably methyl, ethyl) optionally substituted by 1 to 3 hydroxy groups, and
      (vii) a $C_{1-3}$ alkylenedioxy group (preferably ethylenedioxy),
   (b) an amino group optionally mono- or di-substituted by substituent(s) selected from
      (i) a $C_{1-6}$ alkyl group (preferably methyl, ethyl, isobutyl) optionally substituted by 1 to 3 substituents selected from a hydroxy group and a $C_{1-6}$ alkylsulfonyl group (preferably methylsulfonyl),
      (ii) a $C_{1-6}$ alkyl-carbonyl group (preferably acetyl),
      (iii) a $C_{1-6}$ alkoxy-carbonyl group (preferably methoxycarbonyl) optionally substituted by 1 to 3 $C_{6-14}$ aryl groups (preferably phenyl),
      (iv) a $C_{3-10}$ cycloalkyl group (preferably cyclohexyl) optionally substituted by 1 to 3 substituents selected from a hydroxy group and a $C_{1-6}$ alkyl group (preferably methyl),
      (v) an aromatic heterocyclic group (preferably triazolyl), and
      (vi) a non-aromatic heterocyclic group (preferably tetrahydrothiopyranyl, 1-oxidotetrahydrothiopyranyl, 1,1-dioxidotetrahydrothiopyranyl),
   (c) a hydroxy group,
   (d) a $C_{1-6}$ alkoxy group (preferably methoxy),
   (e) a $C_{1-6}$ alkylsulfonyloxy group (preferably methylsulfonyloxy),
   (f) a $C_{1-6}$ alkyl-carbonyl group (preferably acetyl),
   (g) a $C_{2-6}$ alkenyl-carbonyl group (preferably vinylcarbonyl),
   (h) a $C_{1-6}$ alkoxy-carbonyl group (preferably ethoxycarbonyl),
   (i) a carboxy group,
   (j) a non-aromatic heterocyclyl-carbonyl group (preferably piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
      (i) a hydroxy group,
      (ii) a $C_{1-6}$ alkyl group (preferably methyl, ethyl) optionally substituted by 1 to 3 hydroxy groups,
      (iii) a halogen atom (preferably fluorine atom), and
      (iv) a carboxy group,
   (k) a non-aromatic heterocyclyl-carbonyloxy group (preferably morpholinylcarbonyloxy) optionally substituted by 1 to 3 $C_{1-6}$ alkyl groups (preferably methyl),
   (l) a carbamoyl group optionally mono- or di-substituted by substituent(s) selected from
      (i) a $C_{1-6}$ alkyl group (preferably methyl, ethyl) optionally substituted by 1 to 3 substituents selected from a hydroxy group, a $C_{1-6}$ alkoxy group (preferably methoxy) and a $C_{1-6}$ alkylsulfonyl group (preferably methylsulfonyl),
      (ii) a $C_{1-6}$ alkoxy group (preferably methoxy),
      (iii) a $C_{3-10}$ cycloalkyl group (preferably cyclopropyl),
      (iv) a $C_{1-6}$ alkylsulfonyl group (preferably methylsulfonyl),
      (v) an aromatic heterocyclic group (preferably triazolyl, tetrazolyl), and
      (vi) a non-aromatic heterocyclic group (preferably tetrahydropyranyl), (m) a $C_{1-6}$ alkylthio group (preferably methylthio) optionally substituted by 1 to 3 carboxy groups, and (n) a formyl group, (2) a cyano group, (3) a carboxy group, (4) a $C_{1-6}$ alkoxy-carbonyl group (preferably methoxycarbonyl), (5) a carbamoyl group optionally mono- or di-substituted by $C_{1-6}$ alkyl group(s) (preferably ethyl), or (6) a non-aromatic heterocyclyl-carbonyl group (preferably pyrrolidinylcarbonyl, morpholinylcarbonyl, piperazinylcarbonyl) optionally substituted by 1 to 3 $C_{1-6}$ alkyl groups (preferably methyl),

[preferably a $C_{1-6}$ alkyl group (preferably methyl, ethyl, isopropyl, isobutyl) substituted by 1 to 3 substituents selected from (a) a heterocyclic group (preferably piperidinyl, pyrrolidinyl, morpholinyl, piperazinyl, thiomorpholinyl, 1-oxidothiomorpholinyl, 1,1-dioxidothiomorpholinyl, pyrazolinyl, pyrazolidinyl, azetidinyl, imidazolyl, triazolyl) optionally substituted by 1 to 3 substituents selected from (i) a hydroxy group, (ii) a $C_{1-6}$ alkyl-carbonyl group (preferably acetyl), (iii) a $C_{1-6}$ alkylsulfonyl group (preferably methylsulfonyl), (iv) a halogen atom (preferably fluorine atom), (v) an oxo group, (vi) a $C_{1-6}$ alkyl group (preferably methyl, ethyl) optionally substituted by 1 to 3 hydroxy groups, and (vii) a $C_{1-3}$ alkylenedioxy group (preferably ethylenedioxy)], and $R^7$ is (1) a hydrogen atom, or (2) a $C_{1-6}$ alkyl group (preferably methyl); or $R^6$ and $R^7$ in combination form (1) a monocyclic non-aromatic heterocycle (preferably piperidine, tetrahydropyran, 1-oxidotetrahydrothiopyran) optionally substituted by 1 to 3 substituents selected from (a) a $C_{1-6}$ alkyl group (preferably methyl, ethyl, isobutyl) optionally substituted by 1 to 3 substituents selected from (i) an aromatic heterocyclic group (preferably imidazolyl, furyl, pyridyl) optionally substituted by 1 to 3 $C_{1-6}$ alkyl groups (preferably methyl), (ii) a cyano group, (iii) a hydroxy group, (iv) a carboxy group, (v) a $C_{1-6}$ alkoxy group (preferably methoxy), (vi) a $C_{1-6}$ alkyl-carbonyl group (preferably acetyl), (vii) a $C_{1-6}$ alkoxy-carbonyl group (preferably methoxycarbonyl), and (viii) a carbamoyl group optionally mono- or di-substituted by $C_{1-6}$ alkyl group(s) (preferably ethyl), (b) a $C_{7-13}$ aralkyl group (preferably benzyl), (c) a $C_{1-6}$ alkyl-carbonyl group (preferably acetyl), (d) a $C_{1-6}$ alkylsulfonyl group (preferably methylsulfonyl), (e) a carbamoyl group optionally mono- or di-substituted by $C_{1-6}$ alkyl group(s) (preferably methyl), and (f) a non-aromatic heterocyclic group (preferably tetrahydropyranyl), or (2) a $C_{3-10}$ cycloalkane (preferably cyclohexane) optionally substituted by 1 to 3 substituents selected from an oxo group and a $C_{1-3}$ alkylenedioxy group (preferably ethylenedioxy);

$R^{21}$ is a $C_{1-6}$ alkyl group (preferably methyl) optionally substituted by 1 to 3 substituents selected from a hydroxy group and a non-aromatic heterocyclic group (preferably morpholinyl);

$R^{22}$ is a hydrogen atom;

W is $NR^8$;

$R^8$ is (1) a hydrogen atom, or (2) a $C_{1-6}$ alkyl group (preferably methyl, ethyl, propyl, isopropyl, isobutyl) optionally substituted by 1 to 3 substituents selected from (a) a $C_{3-10}$ cycloalkyl group (preferably cyclopropyl), (b) a $C_{1-6}$ alkoxy group (preferably methoxy, ethoxy), (c) a halogen atom (preferably fluorine atom), (d) a cyano group, (e) a hydroxy group, (f) a carboxy group, (g) a carbamoyl group, and (h) a $C_{1-6}$ alkoxy-carbonyl group (preferably ethoxycarbonyl);

$R^3$ is (1) a 5- or 6-membered monocyclic aromatic heterocyclic group (preferably thienyl, pyridyl, furyl, thiazolyl, imidazolyl) optionally substituted by 1 to 3 substituents selected from (a) a halogen atom (preferably chlorine atom), and (b) a $C_{1-6}$ alkyl group (preferably methyl), or (2) a $C_{6-14}$ aryl group (e.g., phenyl) optionally substituted by 1 to 3 substituents selected from (a) a $C_{1-6}$ alkyl group (preferably methyl) optionally substituted by 1 to 3 halogen atoms (preferably fluorine atom), and (b) a $C_{1-6}$ alkoxy group (preferably methoxy);

$R^9$ is a hydrogen atom or a halogen atom (preferably chlorine atom);

$R^{10}$ is (1) a hydrogen atom, (2) a halogen atom (preferably bromine atom), (3) a $C_{1-6}$ alkyl group (preferably methyl), or (4) a $C_{1-6}$ alkoxy group (preferably methoxy, ethoxy, propoxy, isopropoxy) optionally substituted by 1 to 3 substituents selected from (a) a halogen atom (preferably fluorine atom), (b) a hydroxy group, (c) a carboxy group, (d) a carbamoyl group, (e) a $C_{1-6}$ alkoxy group (preferably methoxy), (f) a $C_{1-6}$ alkyl-carbonyl group (preferably acetyl), (g) a $C_{1-6}$ alkoxy-carbonyl group (preferably ethoxycarbonyl), and (h) a $C_{1-6}$ alkylsulfonyl group (preferably methylsulfonyl); and $R^{11}$ is a hydrogen atom, a halogen atom (preferably chlorine atom) or a $C_{1-6}$ alkyl group (preferably methyl).

[Compound (F)]

N,N-dimethyl-2-{4-[(2-{7-[methyl(2-thienylsulfonyl)amino]-1H-indol-2-yl}-1,3-thiazol-5-yl)methyl]piperazin-1-yl}acetamide;

N-methyl-N-[2-(8-oxa-1-thia-3-azaspiro[4.5]dec-2-en-2-yl)-1H-indol-7-yl]thiophene-2-sulfonamide;

N-[2-[4-(hydroxymethyl)-4,5-dihydro-1,3-thiazol-2-yl]-5-(2-methoxyethoxy)-1H-indol-7-yl]-N-methylpyridine-2-sulfonamide;

N-methyl-N-{2-[5-(morpholinomethyl)-4,5-dihydro-1,3-thiazol-2-yl]-1H-indol-7-yl}thiophene-2-sulfonamide;

2-(2-{7-[methyl(pyridin-2-ylsulfonyl)amino]-1H-indol-2-yl}-4,5-dihydro-1,3-thiazol-5-yl)acetamide;

N-(difluoromethyl)-N-{2-[5-(morpholinomethyl)-4,5-dihydro-1,3-thiazol-2-yl]-1H-indol-7-yl}thiophene-2-sulfonamide;

2-{2-[7-[methyl(2-thienylsulfonyl)amino]-5-(trifluoromethoxy)-1H-indol-2-yl]-4,5-dihydro-1,3-thiazol-5-yl}acetamide;

N-(5-(2-methoxyethoxy)-2-{5-[(1-oxidothiomorpholino)methyl]-4,5-dihydro-1,3-thiazol-2-yl}-1H-indol-7-yl)-N-methylpyridine-2-sulfonamide;

2-(2-{7-[methyl(2-thienylsulfonyl)amino]-1H-indol-2-yl}-1-thia-3,8-diazaspiro[4.5]dec-2-en-8-yl)acetamide; or N-[2-{5-[(1,1-dioxidothiomorpholino)methyl]-4,5-dihydro-1,3-thiazol-2-yl}-5-(2-methoxyethoxy)-1H-indol-7-yl]-N-methylpyridine-2-sulfonamide;

or a salt thereof.

When compound (I) is in the form of a salt, as such salts, for example, a salt with inorganic base, a salt with organic base, a salt with inorganic acid, a salt with organic acid, a salt with basic or acidic amino acid and the like can be mentioned.

As preferable examples of the salt with inorganic base, alkali metal salts such as sodium salt, potassium salt and the like; alkaline earth metal salts such as calcium salt, magnesium salt and the like; and aluminum salts; ammonium salts and the like can be mentioned.

As preferable examples of the salt with organic base, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salt with inorganic acid, salt with hydrochloric acid, hydrobromic acid, nitric acid, sulfuric acid, phosphoric acid and the like can be mentioned.

As preferable examples of the salt with organic acid, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salt with basic amino acid, salts with arginine, lysine, ornithine and the like can be mentioned.

As preferable examples of the salt with acidic amino acid, salts with aspartic acid, glutamic acid and the like can be mentioned.

A prodrug of the compound (I) means a compound which is converted to the compound (I) with a reaction due to an enzyme, an gastric acid, etc. under the physiological condition in the living body, that is, a compound which is converted to the compound (I) with enzymatic oxidation, reduction, hydrolysis and the like; a compound which is converted to the compound (I) by hydrolysis and the like due to gastric acid and the like. A prodrug of the compound (I) may be a compound obtained by subjecting an amino group in the compound (I) to an acylation, alkylation or phosphorylation (e.g., a compound obtained by subjecting an amino group in the compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in the compound (I) to an acylation, alkylation, phosphorylation or boration (e.g., a compound obtained by subjecting an hydroxy group in the compound (I) to an acetylation, palmitoylation, propanoylation, pivaloylation, succinylation, fumarylation, alanylation or dimethylaminomethylcarbonylation); a compound obtained by subjecting a carboxyl group in the compound (I) to an esterification or amidation (e.g., a compound obtained by subjecting a carboxyl group in the compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from the compound (I) according to a method known per se.

A prodrug of the compound (I) may also be one which is converted into the compound (I) under a physiological condition, such as those described in *IYAKUHIN NO KAIHATSU* (*Development of Pharmaceuticals*), Vol. 7, Design of Molecules, p. 163-198, Published by HIROKAWA SHOTEN (1990).

The compound (I) may be labeled with an isotope (e.g., $^3$H, $^{14}$C, $^{35}$S, $^{125}$I etc.) and the like.

Furthermore, the compound (I) may be a non-hydrate or hydrate.

Deuterium-converted compound wherein $^1$H has been converted to $^2$H(D) are also encompassed in the compound (I).

The compound (I) or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys etc.) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; or solvent, solubilizing agent, suspending agent, isotonicity agent, buffer and soothing agent for liquid preparations, and the like. Where necessary, an additive for pharmaceutical preparations such as preservative, antioxidant, coloring agent, sweetening agent and the like can be used.

Preferable examples of the excipient include lactose, sucrose, D-mannitol, D-sorbitol, starch, α-starch, dextrin, crystalline cellulose, low-substituted hydroxypropylcellulose, sodium carboxymethylcellulose, gum acacia, pullulan, light anhydrous silicic acid, synthetic aluminum silicate, magnesium aluminate metasilicate and the like.

Preferred examples of the lubricant include magnesium stearate, calcium stearate, talc, colloidal silica and the like.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethylstarch, light anhydrous silicic acid, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferred examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferred examples of the isotonicity agent include sodium chloride, glycerol, D-mannitol, D-sorbitol, glucose and the like.

Preferred examples of the buffer include buffers such as phosphate, acetate, carbonate, citrate and the like.

Preferred examples of the soothing agent include benzyl alcohol and the like.

Preferred examples of the preservative include p-oxybenzoates, chlorobutanol, benzyl alcohol, phenethyl alcohol, dehydroacetic acid, sorbic acid and the like.

Preferred examples of the antioxidant include sulfite, ascorbate and the like.

Preferable examples of the coloring agent include water-soluble edible tar pigments (e.g., food colors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., beta carotene, chlorophil, red iron oxide) and the like.

Preferable examples of the sweetening agent include saccharin sodium, dipotassium glycyrrhizinate, aspartame, stevia and the like.

The dosage form of the aforementioned pharmaceutical composition is, for example, an oral agent such as tablets (inclusive of sugar-coated tablets, film-coated tablets, sublingual tablets and orally disintegrable tablets), capsules (inclusive of soft capsules and microcapsules), granules, powders, troches, syrups, emulsions, suspensions, films (e.g., orally disintegrable film) and the like; a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like, and the like. These may be administered safely via an oral or parenteral (e.g., topical, rectal, intravenous administrations etc.) route.

These agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. Concrete production methods of preparations are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used as an agent for the prophylaxis or treatment of diabetes (e.g., type-1 diabetes, type-2 diabetes, gestational diabetes, obese diabetes etc.); an agent for the prophylaxis or treatment of obesity; an agent for the prophylaxis or treatment of hyperlipidemia (e.g., hypertriglyceridemia, hypercholesterolemia, hypo-HDL-emia, postprandial hyperlipidemia etc.); an agent for the prophylaxis or treatment of arteriosclerosis; an agent for the prophylaxis or treatment of impaired glucose tolerance (IGT); and an agent for preventing progression of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic foot lesion (e.g., gangrene, ulcer), xerostomia, hypacusis, cerebrovascular disorder, peripheral blood circulation disorder, diabetic diarrhea], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease, pyelonephritis, hydronephrosis), muscular dystrophy, myocardial infarction, angina pectoris, cerebrovascular accident (e.g., cerebral infarction, cerebral apoplexy), abnormal sugar metabolism, abnormal lipid metabolism, insulin resistance syndrome, Syndrome X, metabolic syndrome (according to the above-mentioned report by WHO, state concurrently associated with at least one of type 2 diabetes, impaired glucose tolerance and insulin resistance, and at least two from obesity, abnormal lipid metabolism, hypertension and trace albumin urine), Cushing's syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of non-alcoholic steatohepatitis), pneumonia, pancreatitis, inflammatory bowel disease, ulcerative colitis, stomach mucous membrane injury (including stomach mucous membrane injury caused by aspirin)), visceral fat syndrome, Alzheimer's disease, cerebrovascular dementia, depression and the like.

The compound of the present invention can also be used for improvement of insulin resistance, promotion or increase of insulin secretion, decrease of visceral fat, suppression of accumulation of visceral fat, improvement of sugar metabolism, improvement of lipid metabolism (including suppression of oxidative LDL production, improvement of lipoprotein metabolism, lowering of blood remnant), improvement of coronary metabolism, prophylaxis or treatment of cardiovascular complication, prophylaxis or treatment of heart failure complication, prophylaxis or treatment of anovulation, prophylaxis or treatment of hirsutism, prophylaxis or treatment of hyperandrogenism, improvement of pancreatic ($\beta$ cell) function, regeneration of pancreas ($\beta$ cell), promotion of regeneration of pancreas ($\beta$ cell) and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type-2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent, an antithrombotic agent, a therapeutic agent for osteoporosis, a antidementia agent, an erectile dysfunction improver, a therapeutic agent for pollakiuria or urinary incontinence, a therapeutic agent for dysuria and the like (hereinafter to be referred to as a combination drug). In this case, the timing of administration of the compound of the present invention and a combination drug is not limited. These may be simultaneously administered to an administration subject or administered in a staggered manner. Moreover, the compound of the present invention and a combination drug may be administered as two kinds of preparations each containing an active ingredient, or may be administered as a single preparation containing both active ingredients.

The dose of the combination drug can be determined as appropriate based on the dose clinically employed. The proportion of the compound of the present invention and the combination drug can be appropriately determined depending on the administration subject, administration route, target disease, condition, combination and the like. When, for example, the administration subject is human, the combination drug is used in an amount of 0.01-100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), $\alpha$-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Vildagliptin, Sitagliptin, Saxagliptin, T-6666, TS-021), $\beta$3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11$\beta$-hydroxysteroid dehydrogenase inhibitors (e.g., BVT-3498), adiponectin or agonists thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., Tolrestat, Epalrestat, Zenarestat, Zopolrestat, Minalrestat, Fidarestat, CT-112, ranirestat (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), stimulators (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The combination drug is preferably insulin preparation, insulin sensitizer, α-glucosidase inhibitor, biguanide, insulin secretagogue (preferably sulfonylurea) and the like.

Two or more kinds of the above-mentioned combination drugs may be used in an appropriate combination.

When the compound of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent for diabetic complications, therapeutic agent for hyperlipidemia and antihypertensive agent can be reduced whereby an adverse effect which may be caused by these agents can be prevented effectively.

Compound (I) can be produced, for example, according to methods shown in the following Schemes 1 and 2.

Scheme 1

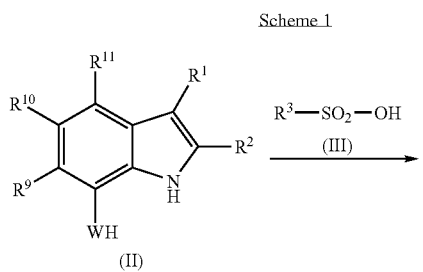

wherein each symbol is as defined above.

In this scheme, compound (I) can be produced by reacting compound (II) with compound (III) or a reactive derivative thereof.

As preferable reactive derivative of compound (III), for example, a reactive derivative generally used such as a sulfonyl halide, a sulfonic anhydride, N-sulfonylimidazolide and the like can be mentioned, and a sulfonyl halide is particularly preferable.

This reaction can be carried out in the presence of a base. As the base, for example, alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogencarbonates such as sodium hydrogencarbonate, potassium hydrogencarbonate and the like; alkali metal $C_{1-6}$ alkoxides such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithium such as methyllithium, n-butyllithium, sec-butyllithium, tert-butyllithium and the like; lithium amides such as lithium diisopropylamide and the like, and the like can be mentioned.

This reaction is preferably carried out in a solvent inert to the reaction. As such solvent, while the solvent is not particularly limited as long as the reaction proceeds, for example, alcohols such as methanol, ethanol, propanol, isopropanol, butanol, tert-butylalcohol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide; water and the like can be mentioned. These solvents may be used in a mixture at an appropriate ratio.

The amount of compound (III) or a reactive derivative thereof to be used is generally 1 to 10 mol, preferably 1 to 3 mol, per 1 mol of compound (II). The amount of the base to be used is generally 1 to 10 mol, preferably 1 to 3 mol, per 1 mol of compound (III) or a reactive derivative thereof.

The reaction temperature is generally −30° C. to 100° C. The reaction time is generally 0.5 to 20 hr.

Compound (III) can be produced according to a method known per se.

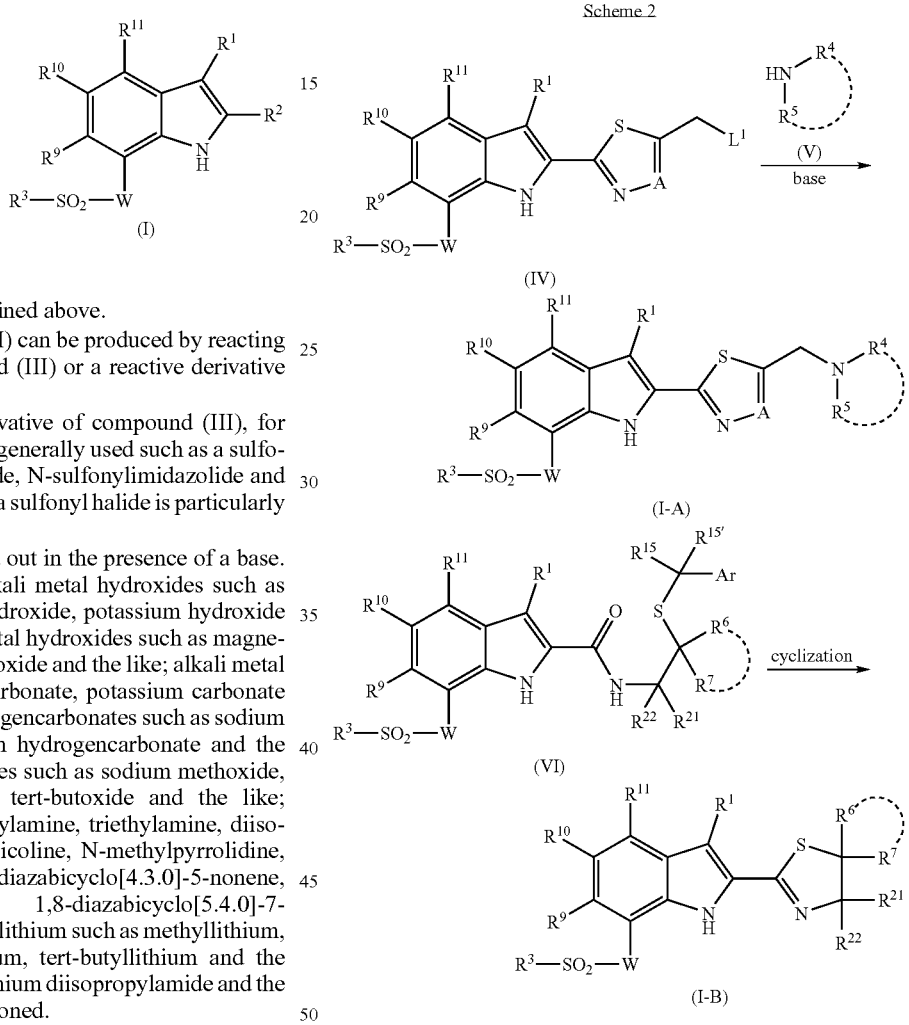

wherein $L^1$ is a leaving group, $R^{15}$ and $R^{15'}$ are each independently a hydrogen atom, an optionally substituted $C_{1-6}$ alkyl group or an optionally substituted $C_{6-14}$ aryl group, Ar is a phenyl group or a 4-methoxyphenyl group, and the other symbols are as defined above.

As the "optionally substituted $C_{1-6}$ alkyl group" for $R^{15}$ or $R^{15'}$, those similar to the "optionally substituted $C_{1-6}$ alkyl group" for $R^4$ or $R^5$ can be mentioned, and methyl group and ethyl group are preferable.

As the "$C_{6-14}$ aryl group" of "optionally substituted $C_{6-14}$ aryl group" for $R^{15}$ or $R^{15'}$, those similar to the "$C_{6-14}$ aryl group" exemplified as the "hydrocarbon group" of the "optionally substituted hydrocarbon group" for $R^6$, $R^7$, $R^{21}$ or $R^{22}$ can be mentioned. The $C_{6-14}$ aryl group optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^6$, $R^7$, $R^{21}$ or $R^{22}$ optionally has, can be mentioned. The "optionally substituted $C_{6-14}$ aryl group" is preferably a phenyl group or a 4-methoxyphenyl group.

As the "leaving group" for $L^1$, for example, a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); a $C_{6-10}$ arylsulfonyloxy group optionally substituted by 1 to 3 substituents selected from a $C_{1-6}$ alkyl group, a $C_{1-6}$ alkoxy group and a nitro group (e.g., phenylsulfonyloxy, m-nitrophenylsulfonyloxy, p-toluenesulfonyloxy); a $C_{1-6}$ alkoxysulfonyloxy group; a $C_{6-10}$ aryloxysulfonyloxy group; a $C_{1-6}$ alkoxy group; a di-$C_{1-6}$ alkylamino group and the like can be mentioned.

Compound (I-A) can be produced by reacting compound (IV) with compound (V) in the presence of a base.

The amount of compound (V) to be used is generally 1 to 10 mol, preferably 1 to 3 mol, per 1 mol of compound (IV).

As the base, those exemplified for the reaction of compound (II) with compound (III) or a reactive derivative thereof as shown in Scheme 1 can be mentioned.

This reaction is preferably carried out in a solvent inert to the reaction. As such solvent, those exemplified for the reaction of compound (II) with compound (III) or a reactive derivative thereof as shown in Scheme 1 can be mentioned.

The amount of the base to be used is generally 1 to 10 mol, preferably 1 to 3 mol, per 1 mol of compound (IV).

The reaction temperature is generally −100° C. to 100° C. The reaction time is generally 0.5 to 20 hr.

Compound (I-B) can be produced from compound (VI) according to methods described in Angew. Chem., Int. Ed., 2003, vol. 42, page 83, Tetrahedron, 1999, vol. 55, page 10271, and the like.

In this reaction, compound (VI) is reacted with triphenylphosphine oxide and trifluoromethanesulfonic anhydride or phosphorus pentachloride.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; nitriles such as acetonitrile, propionitrile and the like; aromatic hydrocarbons such as benzene, toluene and the like; saturated hydrocarbons such as cyclohexane, hexane and the like, and the like can be mentioned. These solvents may be used in a mixture at an appropriate ratio.

The amount of the triphenylphosphine oxide and trifluoromethanesulfonic anhydride or phosphorus pentachloride to be used is generally 1 to 10 mol, preferably 1 to 6 mol, per 1 mol of compound (VI), respectively.

The reaction temperature is generally −70° C. to 100° C. The reaction time is generally 0.5 to 20 hr.

Compound (II), (IV) and (VI) used as starting materials in the aforementioned Schemes 1 and 2 can be produced, for example, according to the following Scheme 3 to 7 or a method analogous thereto.

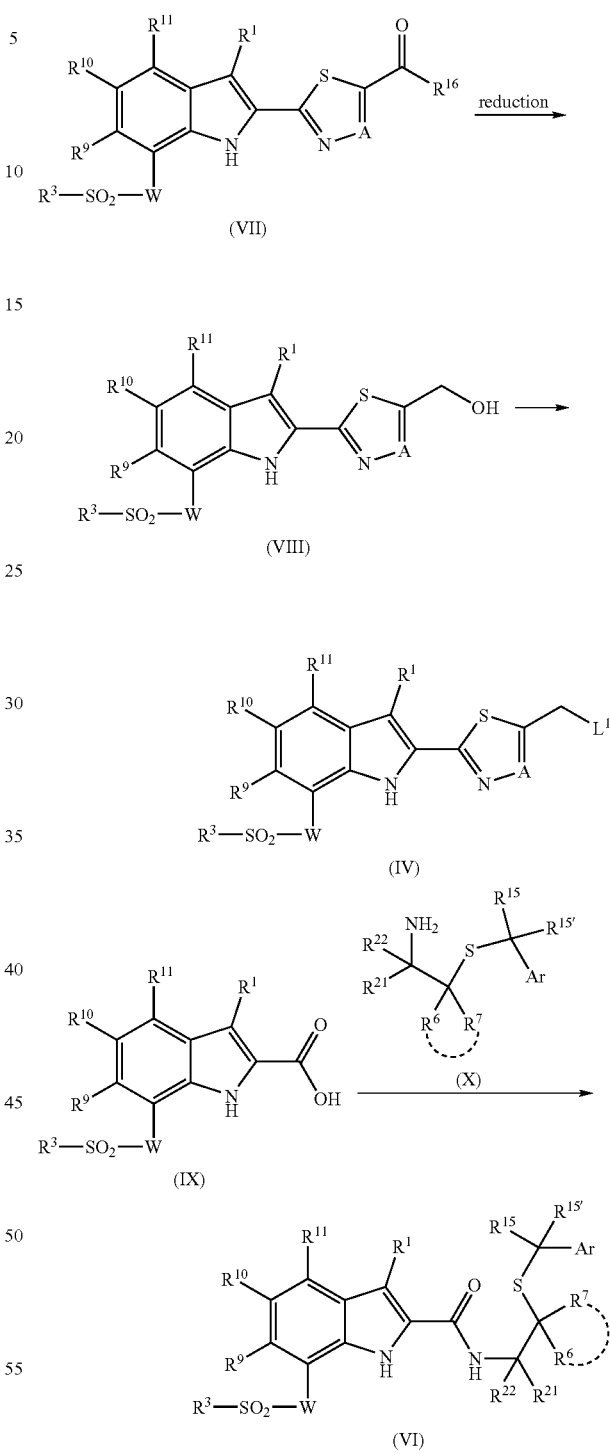

wherein $R^{16}$ is a hydrogen atom or a $C_{1-6}$ alkoxy group, and the other symbols are as defined above.

Compound (VIII) can be produced by subjecting compound (VII) to a reduction reaction.

The reduction reaction is carried out, for example, using a reducing agent. As the reducing agent, for example, metal hydrides such as aluminum hydride, diisobutylaluminum hydride, tributyltin hydride and the like; metal hydrogen complex compounds such as lithium aluminum hydride, sodium borohydride and the like; borane complexes such as borane-tetrahydrofuran complex, borane-dimethylsulfide complex and the like; alkylboranes such as thexylborane, disiamylborane and the like; diborane; metals such as zinc, aluminum, tin, iron and the like; alkali metal (e.g., sodium, lithium etc.)/liquid ammonia (Birch reduction) and the like can be mentioned.

The amount of the reducing agent to be used is appropriately determined according to the kind of the reducing agent. For example, the amount of the metal hydride or metal hydrogen complex compound to be used is generally about 0.25 to about 10 mol, preferably about 0.5 to about 5 mol, per 1 mol of compound (VII), the amount of the borane complex, alkylborane or diborane to be used is generally about 1 to about 10 mol, preferably about 1 to about 5 mol, per 1 mol of compound (VII), and the amount of the metal (including alkali metal used for Birch reduction) to be used is generally about 1 to about 20 equivalents, preferably about 1 to about 5 equivalents, per 1 equivalent of compound (VII).

The reduction reaction is preferably carried out in a solvent inert to the reaction. As such solvent, while the solvent is not particularly limited as long as the reaction proceeds, for example, alcohols such as methanol, ethanol, 1-propanol, 2-propanol, tert-butylalcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like, and the like can be mentioned. These solvents may be used in a mixture at an appropriate ratio.

While the reaction time varies depending on the kind and amount of the reducing agent to be used, it is generally about 1 hr to about 100 hr, preferably about 1 hr to about 50 hr. The reaction temperature is generally about −20 to about 120° C., preferably about 0 to about 80° C.

Compound (IV) can be produced by converting the hydroxy group of compound (VIII) to a leaving group for $L^1$ according to a method known per se.

Compound (VI) can be produced by reacting compound (IX) or a reactive derivative of the carboxy group or a salt thereof with compound (X).

As the reactive derivative of the carboxy group of compound (IX), for example, 1) an acid chloride
2) an acid azide;
3) a mixed acid anhydride with an acid (e.g., substituted phosphates such as dialkylphosphate, phenylphosphate, diphenylphosphate, dibenzylphosphate, halogenated phosphate and the like; dialkylphosphorous acid; sulfurous acid; thiosulfuric acid; sulfuric acid; sulfonic acids such as methanesulfonic acid and the like; aliphatic carboxylic acids such as formic acid, acetic acid, propionic acid, butyric acid, isobutyric acid, pivalic acid, pentanoic acid, isopentanoic acid, trichloroacetic acid and the like; aromatic carboxylic acids such as benzoic acid and the like);
4) a symmetric acid anhydride;
5) an activated amide with imidazole, 4-substituted imidazole, dimethylpyrazole, triazole or tetrazole;
6) an activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthioester, p-nitrophenyl ester, p-cresyl thioester, carboxymethyl thioester, pyranyl ester, pyridyl ester, piperidyl ester, 8-quinolylthio ester and the like;
7) a ester with a N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole);

and the like can be mentioned. These reactive derivatives are appropriately determined according to the kind of compound (IX) to be used.

As preferable salt of compound (IX) or a reactive derivative of the carboxy group, for example, salts with a base, such as alkali metal salts (e.g., sodium salt, potassium salt and the like), alkaline earth metal salts (e.g., calcium salt, magnesium salt and the like), ammonium salts, organic base salts (e.g., trimethylamine salt, triethylamine salt, pyridine salt, picoline salt, dicyclohexylamine salt, N,N-dibenzylethylenediamine salt and the like) and the like can be mentioned.

This reaction is preferably carried out in a solvent inert to the reaction. As such solvent, those exemplified for the reaction of compound (II) with compound (III) or a reactive derivative thereof as shown in Scheme 1 can be mentioned.

In this reaction, when compound (IX) is used in the form of a free acid or a salt thereof, the reaction is preferably carried out in the presence of a conventional condensing agent such as a carbodiimide (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like), N,N'-carbonylbis(2-methylimidazole), a trialkyl phosphate, a polyphosphate (e.g., ethyl polyphosphate, isopropyl polyphosphate and the like), phosphorus oxychloride, diphenylphosphorylazide, thionyl chloride, oxalyl chloride, a lower alkyl haloformate (e.g., ethyl chloroformate, isopropyl chloroformate and the like), triphenylphosphine, N-hydroxybenzotriazole, 1-(p-chlorobenzenesulfonyloxy)-6-chloro-1H-benzotriazole, Vilsmeier-reagent (prepared by the reaction of N,N'-dimethylformamide and thionyl chloride, phosgene, chloroformic acid trichloromethyl, phosphorus oxychloride and the like), and the like.

This reaction can be carried out in the presence of a base, as necessary. As such base, those exemplified for the reaction of compound (II) with compound (III) or a reactive derivative thereof as shown in Scheme 1 can be mentioned.

The amount of compound (X) to be used is generally 1 to 10 mol, preferably 1 to 3 mol, per 1 mol of compound (IX). The amount of the base to be used is generally 1 to 10 mol, preferably 1 to 3 mol, per 1 mol of compound (IX).

The reaction temperature is generally −30° C. to 100° C. The reaction time is generally 0.5 to 20 hr.

When an mixed acid anhydride is used as a reactive derivative of compound (IX), compound (IX) can be reacted with a chloroformate (e.g., methyl chloroformate, ethyl chloroformate, isobutyl chloroformate) in the presence of a base (e.g., triethylamine, N-methylmorpholine, N,N-dimethylaniline, sodium hydrogencarbonate, sodium carbonate, potassium carbonate), and then reacted with compound (X).

This reaction is preferably carried out in a solvent inert to the reaction. As such solvent, while the solvent is not particularly limited as long as the reaction proceeds, for example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, 1,2-dichloroethane, carbon tetrachloride, trichloroethylene and the like; hydrocarbons such as n-hexane, benzene, toluene and the like; amides such as formamide, N,N-dimethylformamide, N,N-dimethylacetamide and the like; nitrites such as acetonitrile, propionitrile and the like; sulfoxides such as dimethylsulfoxide and the like; sulfolane; hexamethylphosphoramide and the like can be mentioned. These solvents may be used in a mixture at an appropriate ratio.

The amount of compound (X) to be used is generally 1 to 10 mol, preferably 1 to 3 mol, per 1 mol of compound (IX).

The reaction temperature is generally −30° C. to 100° C. The reaction time is generally 0.5 to 20 hr.

Compound (VII) can be produced, for example, according to the following method.

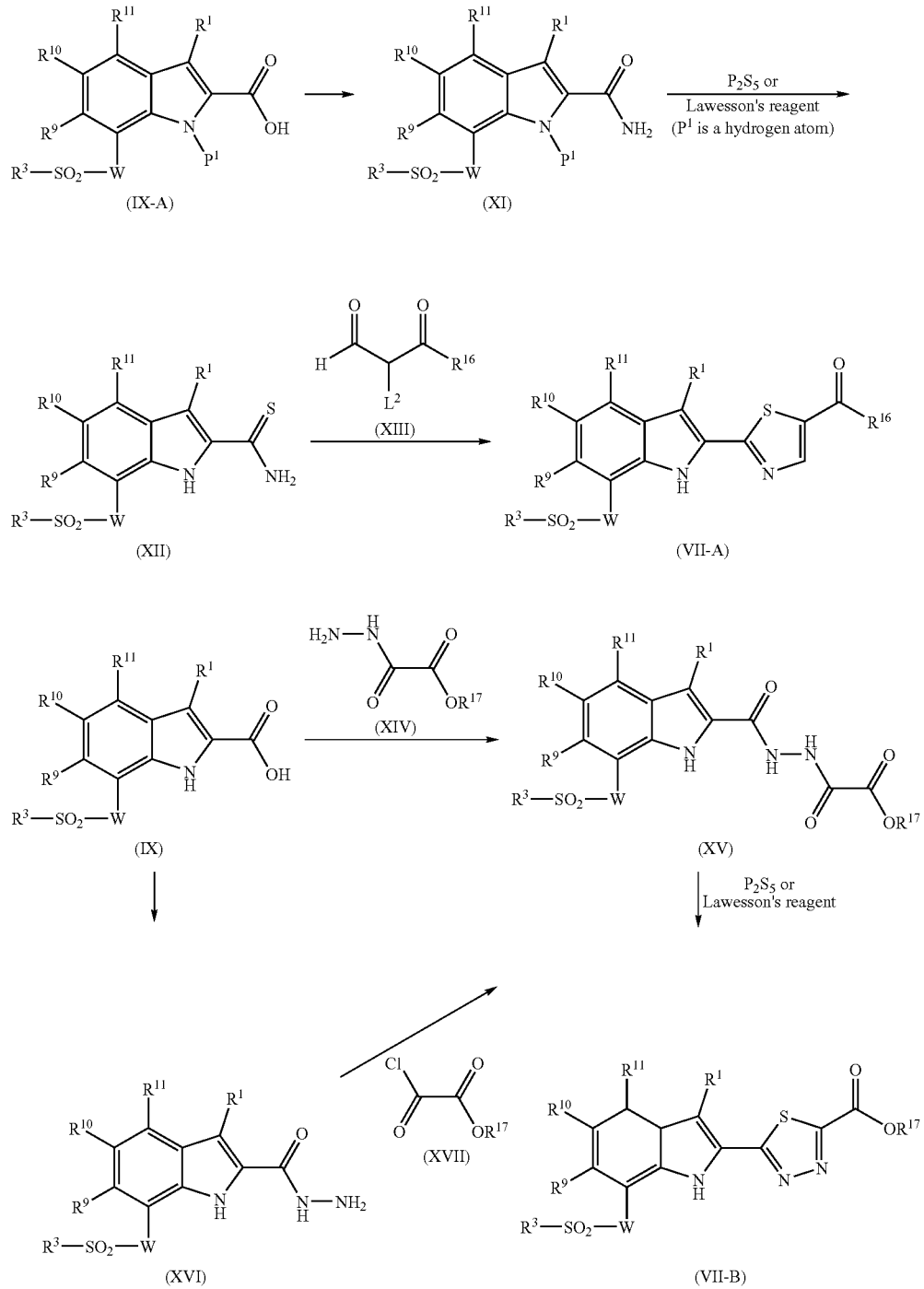

Scheme 4 wherein $R^{17}$ is a $C_{1-6}$ alkyl group, $L^2$ is a leaving group, $P^1$ is a hydrogen atom or a protecting group, and the other symbols are as defined above.

As the "leaving group" for $L^2$, those exemplified as the aforementioned $L^1$ can be mentioned.

As the "protecting group" for $P^1$, for example, a formyl group; a $C_{1-6}$ alkyl-carbonyl group, a phenylcarbonyl group, a $C_{1-6}$ alkoxy-carbonyl group, an allyloxycarbonyl group, a phenyloxycarbonyl group, a fluorenylmethyloxycarbonyl group, a $C_{7-10}$ aralkyl-carbonyl group (e.g., benzylcarbonyl), a $C_{7-10}$ aralkyloxy-carbonyl group (e.g., benzyloxycarbonyl), a $C_{7-20}$ aralkyl group (e.g., benzyl, trityl) and a methoxymethyl group, each of which has optionally substituent(s), and the like can be mentioned. As the substituents, for example, a phenyl group, a halogen atom, a $C_{1-6}$ alkyl-carbonyl group, a $C_{1-6}$ alkoxy group optionally substituted by halogen atom(s), a nitro group and the like can be mentioned. The number of the substituents is 1 to 3.

Compound (XI) can be produced by reacting compound (IX-A) or a reactive derivative of the carboxy group or a salt thereof with ammonia or a salt thereof.

As the reactive derivative of the carboxy group of compound (IX-A), those exemplified as the reactive derivative of the carboxy group of compound (IX) in Scheme 3 can be mentioned.

As the salt of compound (IX-A) or a reactive derivative of the carboxy group, those exemplified as the preferable salt of compound (IX) or a reactive derivative of the carboxy group in Scheme 3 can be mentioned.

As the ammonia or a salt thereof, aqueous ammonia, ammonium acetate, ammonium chloride and the like can be mentioned.

This reaction is carried out in the same manner as in the reaction of compound (IX) or a reactive derivative of the carboxy group or a salt thereof with compound (X) in Scheme 3, and using ammonia or a salt thereof instead of compound (X).

In compound (IX-A), when $P^1$ is a protecting group, the protecting group can be removed according to a conventional deprotection such as an acid treatment, an alkali treatment, a catalytic reduction and the like, as necessary.

Compound (XII) wherein $P^1$ is a hydrogen atom can be produced by reacting compound (XI) with diphosphorus pentasulfide or a Lawesson's reagent.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like, and the like can be mentioned. These solvents may be used in a mixture at an appropriate ratio.

The amount of the diphosphorus pentasulfide or Lawesson's reagent to be used is generally 0.5 to 10 mol, preferably 0.5 to 3 mol, per 1 mol of compound (XI).

The reaction temperature is generally −30° C. to 200° C. The reaction time is generally 0.5 to 20 hr.

Compound (VII-A) can be produced by reacting compound (XII) with compound (XIII).

This reaction is carried out in the presence of a acid catalyst or a base, as necessary.

As the acid catalyst, for example, mineral acids such as hydrochloric acid, sulfuric acid and the like; Lewis acids such as a boron trihalide (e.g., boron trichloride, boron trifluoride), a titanium tetrahalide (e.g., titanium tetrachloride, titanium tetrabromide), an aluminum halide (e.g., aluminum chloride, aluminum bromide) and the like; organic acids such as acetic acid, formic acid, trifluoroacetic acid and the like, and the like can be mentioned.

As the base, for example, organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like can be mentioned.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like can be mentioned. These solvents may be used in a mixture at an appropriate ratio.

When an acid catalyst is used, the amount of compound (XIII) and the acid catalyst to be used is generally 1 to 10 mol, preferably 1 to 3 mol, per 1 mol of compound (XII), respectively.

While the reaction time varies depending on the kind and amount of compound (XII), compound (XIII) and the acid catalyst to be used, it is generally about 1 hr to about 100 hr, preferably about 1 hr to about 50 hr. The reaction temperature is generally about −20 to about 120° C., preferably about 0 to about 80° C.

When a base is used, the amount of the compound (XIII) and the base to be used is generally 1 to 10 mol, preferably 1 to 3 mol, per 1 mol of compound (XII), respectively.

While the reaction time varies depending on the kind and amount of compound (XII), compound (XIII) and the base to be used, it is generally about 1 hr to about 100 hr, preferably about 1 hr to about 50 hr. The reaction temperature is generally about −20 to about 120° C., preferably about 0 to about 80° C.

Compound (XIII) can be produced according to a method known per se.

Compound (XV) can be produced by reacting compound (IX) or a reactive derivative of the carboxy group or a salt thereof with compound (XIV).

As the reactive derivative of the carboxy group of compound (IX) or a salt thereof, those exemplified in Scheme 3 can be mentioned.

This reaction is carried out in the same manner as in the reaction of compound (IX) or a reactive derivative of the carboxy group or a salt thereof with compound (X) in Scheme 3, and using compound (XIV) instead of compound (X).

Compound (XV) can also be produced from compound (IX) or a reactive derivative of the carboxy group or a salt thereof in two steps.

In the first step, compound (XVI) can be produced by reacting compound (IX) or a reactive derivative of the carboxy group or a salt thereof with hydrazine.

As the solvent to be used in this reaction, those exemplified for the aforementioned reaction of compound (IX) with compound (XIV) can be mentioned.

This reaction is carried out in the same manner as in the reaction of compound (IX) or a reactive derivative of the carboxy group or a salt thereof with compound (X) in Scheme 3, and using hydrazine instead of compound (X).

In the second step, compound (XV) can be produced by reacting compound (XVI) with compound (XVII).

As the solvent to be used in this reaction, those exemplified for the aforementioned reaction of compound (IX) with compound (XIV) can be mentioned.

This reaction can be carried out in the presence of a base, as necessary. As such base, for example, organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like can be mentioned.

The amount of compound (XVII) and the base to be used is generally 1 to 10 mol, preferably 1 to 3 mol, per 1 mol of compound (XVI), respectively.

The reaction temperature is generally −30° C. to 200° C. The reaction time is generally 0.5 to 20 hr.

Compound (VII-B) can be produced by reacting compound (XV) with diphosphorus pentasulfide or a Lawesson's reagent.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like, and the like can be mentioned. These solvents may be used in a mixture at an appropriate ratio.

The amount of the diphosphorus pentasulfide or Lawesson's reagent to be used is generally 0.5 to 10 mol, preferably 0.5 to 3 mol, per 1 mol of compound (XV).

The reaction temperature is generally −30° C. to 200° C. The reaction time is generally 0.5 to 20 hr.

Compounds (XIII), (XIV) and (XVII) can be produced according to a method known per se.

Compound (IX) can be produced, for example, according to the following method.

Scheme 5

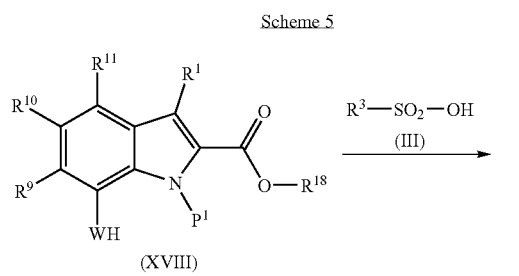

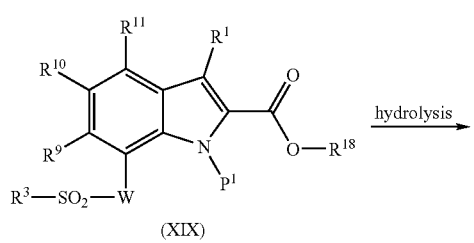

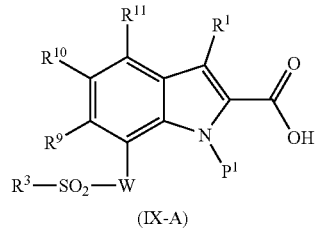

(IX-A)

wherein $R^{18}$ is a $C_{1-6}$ alkyl group, and the other symbols are as defined above.

Compound (XIX) can be produced by reacting compound (XVIII) with compound (III) or a reactive derivative thereof.

This reaction is carried out in the same manner as in the reaction of the compound (II) with compound (III) or a reactive derivative thereof in Scheme 1.

Compound (IX-A) can be produced by subjecting compound (XIX) to a hydrolysis. The hydrolysis is carried out using an acid or a base according to a conventional method.

As the acid, for example, mineral acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. The Lewis acid can be used together with a thiol or a sulfide.

As the base, for example, alkali metal hydroxides such as lithium hydroxide, sodium hydroxide, potassium hydroxide, barium hydroxide and the like; alkali metal carbonates such as sodium carbonate, potassium carbonate and the like; alkali metal $C_{1-6}$ alkoxides such as sodium methoxide, sodium ethoxide, potassium tert-butoxide and the like; organic bases such as triethylamine, imidazole, formamidine and the like, and the like can be mentioned.

The amount of the acid or base to be used is generally about 0.5 to 10 mol, preferably about 0.5 to 6 mol, per 1 mol of compound (XIX).

The hydrolysis is carried out without a solvent or in a solvent inert to the reaction. As such solvent, while the solvent is not particularly limited as long as the reaction proceeds, for example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitrites such as acetonitrile, propionitrile and the like; ketones such as acetone, methyl ethyl ketone and the like; sulfoxides such as dimethylsulfoxide and the like; water and the like can be mentioned. These solvents may be used in a mixture at an appropriate ratio.

The reaction time is generally 10 min to 60 hr, preferably 10 min to 12 hr. The reaction temperature is generally −10 to 200° C., preferably 0 to 120° C.

In compound (XVIII), compound (XIX) and compound (IX-A), when $P^1$ is a protecting group, the protecting group can be removed according to a conventional deprotection such as an acid treatment, an alkali treatment, a catalytic reduction and the like, as necessary.

Compound (XVIII) can be produced, for example, according to the following method.

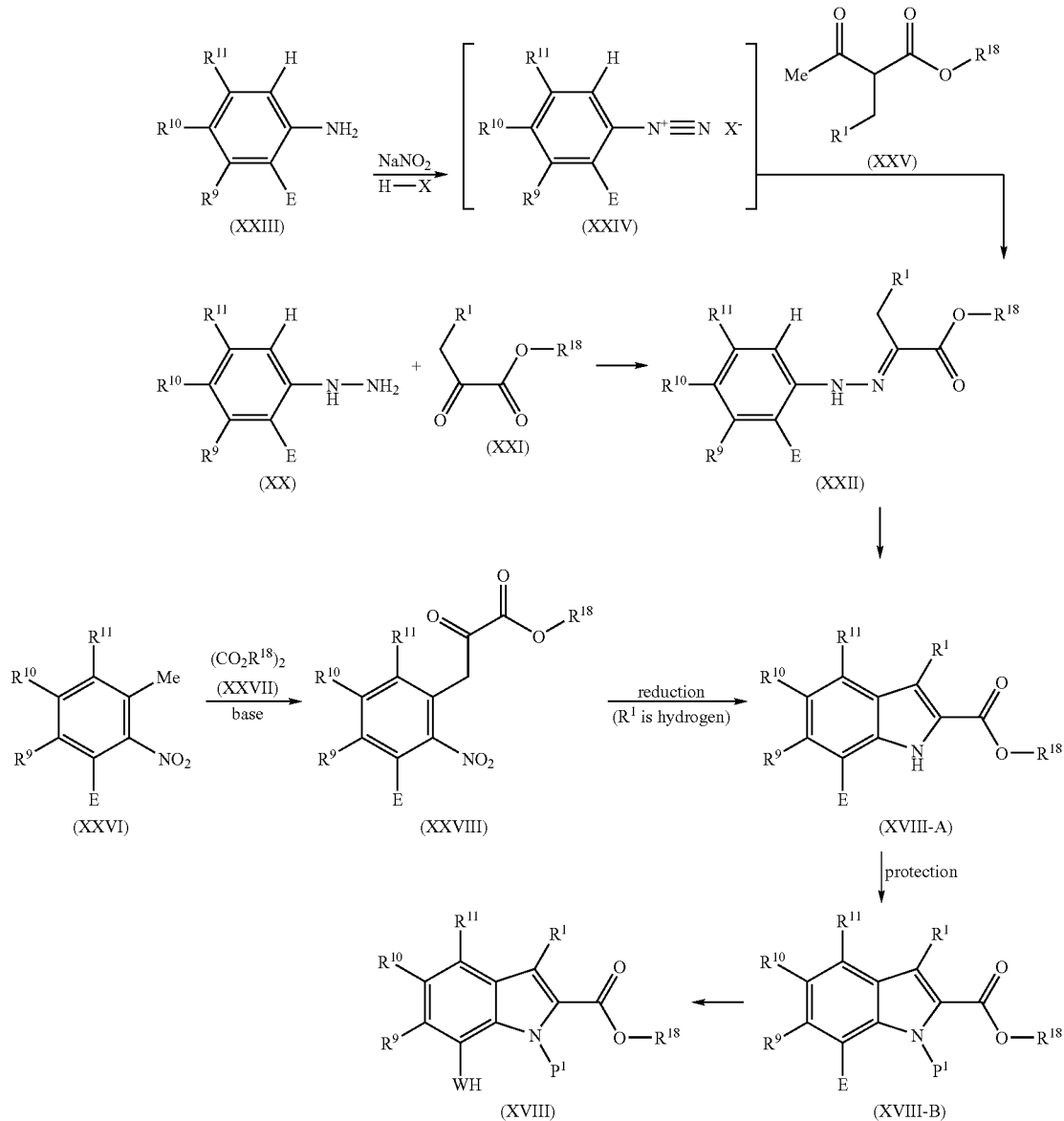

wherein E is a nitro group, an optionally protected amino group or an optionally protected hydroxy group, H—X is a mineral acid such as hydrochloric acid, sulfuric acid and the like; or a organic acid such as acetic acid, formic acid, trifluoroacetic acid and the like, and the other symbols are as defined above.

In the "optionally protected amino group" for E, as the amino-protecting group, for example, a formyl group; a $C_{1-6}$ alkyl-carbonyl group, a phenylcarbonyl group, a $C_{1-6}$ alkoxycarbonyl group, an allyloxycarbonyl group, a phenyloxycarbonyl group, a fluorenylmethyloxycarbonyl group, a $C_{7-10}$ aralkyl-carbonyl group (e.g., benzylcarbonyl), a $C_{7-10}$ aralkyloxy-carbonyl group (e.g., benzyloxycarbonyl), a $C_{7-20}$ aralkyl group (e.g., benzyl, trityl), a phthaloyl group, a dithi-asuccinoyl group and a N,N-dimethylaminomethylene group, each of which optionally has substituent(s), and the like can be mentioned. As the substituents, for example, a phenyl group, a halogen atom, a $C_{1-6}$ alkyl-carbonyl group, a $C_{1-6}$ alkoxy group optionally substituted by halogen atom(s), a nitro group and the like can be mentioned. The number of the substituents is 1 to 3.

In the "optionally protected hydroxy group" for E, As the hydroxy-protecting group, for example, a $C_{1-6}$ alkyl group, a $C_{7-20}$ aralkyl group (e.g., benzyl, trityl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a tetrahydrofuranyl group and a trialkylsilyl group (e.g., trimethylsilyl, tert-butyldimethylsilyl, diisopropylethylsilyl), each of which optionally has substituent(s), and the like can be mentioned. As the substituents, for example, a halogen atom, a $C_{1-6}$ alkyl group, a phenyl group, a $C_{7-10}$ aralkyl group (e.g., benzyl etc.), a $C_{1-6}$ alkoxy group, a nitro group and the like can be mentioned. The number of the substituents is 1 to 4.

Compound (XXII) can be produced by reacting compound (XX) with compound (XXI).

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; alcohols such as methanol, ethanol, 1-propanol, 2-propanol, tert-butylalcohol and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like can be mentioned. These solvents may be used in a mixture at an appropriate ratio.

In this reaction, the reaction can generally be promoted using an acid catalyst. As the acid catalyst, for example, mineral acids such as hydrochloric acid, sulfuric acid and the like; Lewis acids such as a boron trihalide (e.g., boron trichloride, boron trifluoride), a titanium tetrahalide (e.g., titanium tetrachloride, titanium tetrabromide), an aluminum halide (e.g., aluminum chloride, aluminum bromide) and the like; organic acids such as acetic acid, formic acid, trifluoroacetic acid and the like, and the like can be mentioned.

The amount of compound (XXI) and the acid catalyst to be used is generally 1 to 10 mol, preferably 1 to 3 mol, per 1 mol of compound (XX), respectively.

While the reaction time varies depending on the kind and amount of compound (XX), compound (XXI) and the acid catalyst to be used, it is generally about 1 hr to about 100 hr, preferably about 1 hr to about 50 hr. The reaction temperature is generally about −20 to about 120° C., preferably about 0 to about 80° C.

Compound (XXII) can also be produced by subjecting compound (XXIIII) to the Japp-Klingemann reaction [Org. Reactions, 1959, vol. 10, page 143; J. Chem. Soc., 1927, page 1].

In this reaction, compound (XXIV) which is produced using compound (XXIII), an acid (H—X) and sodium nitrite according to a method known per se, is reacted with compound (XXV) in the presence of a base.

As the base, for example, alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogencarbonates such as sodium hydrogencarbonate, potassium hydrogencarbonate and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, and the like can be mentioned.

This reaction is preferably carried out in a solvent inert to the reaction. As such solvent, while the solvent is not particularly limited as long as the reaction proceeds, for example, alcohols such as methanol, ethanol, propanol, isopropanol, butanol, tert-butylalcohol and the like; ethers such as 1,4-dioxane, tetrahydrofuran, diethyl ether, tert-butyl methyl ether, diisopropyl ether, 1,2-dimethoxyethane and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; water and the like can be mentioned. These solvents may be used in a mixture at an appropriate ratio.

The amount of compound (XXV) to be used is generally 1 to 10 mol, preferably 1 to 3 mol, per 1 mol of compound (XXIV). The amount of the base to be used is generally 1 to 10 mol, preferably 1 to 3 mol, per 1 mol of compound (XXIV).

The reaction time is generally about 1 hr to about 100 hr, preferably about 1 hr to about 50 hr. The reaction temperature is generally about −20 to about 120° C., preferably about 0 to about 80° C.

Compound (XVIII-A) can be produced by subjecting compound (XXII) to the Fischer method [Berichte, 1883, vol. 16, page 2241]. In this reaction, compound (XXII) is reacted with an acidic catalyst under heating.

As the acidic catalyst, for example, zinc chloride (without a solvent or in a solvent such as naphthalene, ethanol and the like), hydrogen chloride/ethanol, sulfuric acid/ethanol, concentrated sulfuric acid, hydrogen chloride/acetic acid, acetic acid, boron fluoride, polyphosphoric acid, methanesulfonic acid, phosphorous pentoxide and the like can be mentioned. These acidic catalysts may be used in a mixture at an appropriate ratio.

The amount of the acidic catalyst to be used is generally 1 to 10 mol, preferably 1 to 3 mol, per 1 mol of compound (XXII).

While the reaction time varies depending on the kind and amount of the acidic catalyst to be used, it is generally about 1 hr to about 100 hr, preferably about 1 hr to about 50 hr. The reaction temperature is generally about 0 to about 200° C., preferably about 80 to about 190° C.

Compound (XVIII-A) can also be produced by subjecting compound (XXVI) to the Reissert method [Berichte, 1897, vol. 30, page 1030] in two steps.

In the first step, compound (XXVIII) can be produced by reacting compound (XXVI) with compound (XXVII) in the presence of a base. In the second step, compound (XVIII-A) can be produced by subjecting compound (XXVIII) to a reduction reaction.

As the base to be used in the first step, for example, alkali metal $C_{1-6}$ alkoxides such as sodium methoxide, sodium ethoxide, potassium ethoxide, potassium tert-butoxide and the like, and the like can be mentioned.

The amount of compound (XXVII) and the base to be used is generally 1 to 10 mol, preferably 1 to 3 mol, per 1 mol of compound (XXVI), respectively.

The reaction temperature is generally −30° C. to 100° C. The reaction time is generally 0.5 to 20 hr.

The reduction reaction in the second step is carried out, for example, using a reducing agent. As the reducing agent, for example, metals such as iron, zinc, tin and the like; sulfides such as sodium dithionite and the like; and the like can be mentioned. The amount of the reducing agent to be used is appropriately determined according to the kind of the reducing agent. For example, the amount of the metal to be used is generally about 1 to about 20 equivalents, preferably about 1 to about 5 equivalents, per 1 equivalent of compound (XXVIII), and the amount of the sulfide to be used is generally about 1 to about 20 equivalents, preferably about 1 to about 5 equivalents, per 1 equivalent of compound (XXVIII).

The reduction reaction can also be carried out by a hydrogenation reaction. In this case, for example, catalysts such as palladium carbon, palladium black, platinum dioxide, Raney-nickel, Raney-cobalt, iron trichloride and the like can be used.

The amount of the catalyst to be used is generally about 5 to 1000 wt %, preferably about 10 to 300 wt %, relative to compound (XXVIII). The hydrogenation reaction can also be carried out using various hydrogen sources instead of hydrogen gas. As such hydrogen source, for example, formic acid, ammonium formate, triethylammonium formate, sodium phosphinate, hydrazine and the like can be mentioned. The amount of the hydrogen source to be used is generally about 1 to 100 mol, preferably about 1 to 5 mol, per 1 mol of compound (XXVIII).

The reduction reaction is preferably carried out in a solvent inert to the reaction. As such solvent, while the solvent is not particularly limited as long as the reaction proceeds, for example, alcohols such as methanol, ethanol, 1-propanol, 2-propanol, tert-butylalcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like, and the like can be mentioned. These solvents may be used in a mixture at an appropriate ratio.

While the reaction time varies depending on the kind and amount of the reducing agent to be used, it is generally about 1 hr to about 100 hr, preferably about 1 hr to about 50 hr. The reaction temperature is generally about −20 to about 120° C., preferably about 0 to about 80° C.

Compound (XVIII-B) can be produced by subjecting compound (XVIII-A) to a protection reaction known per se, as necessary.

Compound (XVIII) can be produced by subjecting compound (XVIII-B) wherein E is a protected amino group or a protected hydroxy group to a conventional deprotection reaction such as an acid treatment, an alkali treatment, a catalytic reduction and the like, as necessary.

Compound (XVIII) wherein W is an amino group can be produced by subjecting compound (XVIII-B) wherein E is a nitro group to a reduction reaction.

The reduction reaction is carried out, for example, using a reducing agent. As the reducing agent, for example, metals such as iron, zinc, tin and the like; sulfides such as sodium dithionite and the like can be mentioned. The amount of the reducing agent to be used is appropriately determined according to the kind of the reducing agent. For example, the amount of the metal to be used is generally about 1 to about 20 equivalents, preferably about 1 to about 5 equivalents, per 1 equivalent of compound (XVIII-B), and the amount of the sulfide to be used is generally about 1 to about 20 equivalents, preferably about 1 to about 5 equivalents, per 1 equivalent of compound (XVIII-B).

The reduction reaction can also be carried out by a hydrogenation reaction. In this case, for example, catalysts such as palladium carbon, palladium black, platinum dioxide, Raney-nickel, Raney-cobalt, iron trichloride and the like can be used. The amount of the catalyst to be used is generally about 5 to 1000 wt %, preferably about 10 to 300 wt %, per 1 mol of compound (XVIII-B). The hydrogenation reaction can also be carried out using various hydrogen sources instead of hydrogen gas. As such hydrogen source, for example, formic acid, ammonium formate, triethylammonium formate, sodium phosphinate, hydrazine and the like can be mentioned. The amount of the hydrogen source to be used is generally about 1 to 10 mol, preferably about 1 to 5 mol, per 1 mol of compound (XVIII-B).

This reaction is preferably carried out in a solvent inert to the reaction. As such solvent, while the solvent is not particularly limited as long as the reaction proceeds, for example, alcohols such as methanol, ethanol, propanol, isopropanol, butanol, tert-butylalcohol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; hydrocarbons such as n-hexane, benzene, toluene and the like; amides such as formamide, N,N-dimethylformamide, N,N-dimethylacetamide and the like; organic acids such as formic acid, acetic acid, propionic acid, trifluoroacetic acid, methanesulfonic acid and the like; water and the like can be mentioned. These solvents may be used in a mixture at an appropriate ratio.

While the reaction time varies depending on the kind and amount of the reducing agent to be used and the activity and amount of the catalyst to be used, it is generally about 1 hr to about 100 hr, preferably about 1 hr to about 50 hr. The reaction temperature is generally about −20 to about 120° C., preferably about 0 to about 80° C.

Compounds (XX), (XXI), (XXIII), (XXV), (XXVI) and (XXVII) used as starting materials in Scheme 6 can be produced according to a method known per se.

Compound (X) used as a starting material in Scheme 3 can be produced, for example, according to the following method.

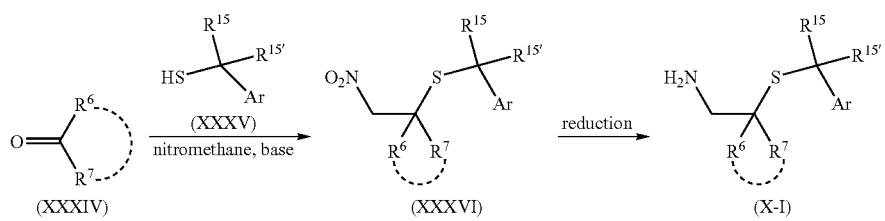

Scheme 7

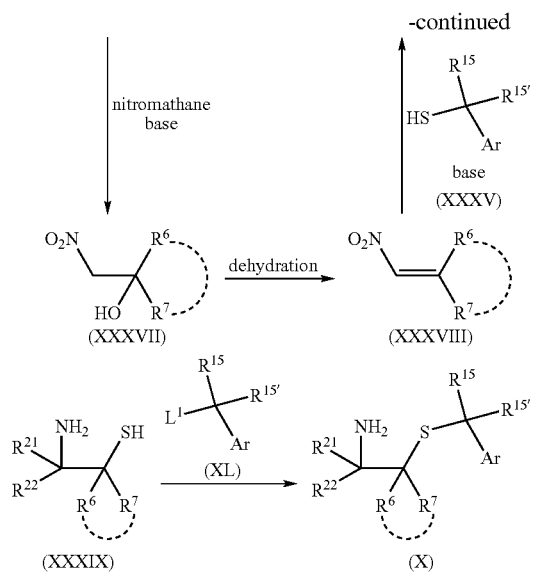

wherein each symbol is as defined above.

Compound (XXXVI) can be produced from compound (XXXIV) according to a known method [J. Org. Chem. Soc., 1963, vol. 28, page 1240; Tetrahedron, 2003, vol. 59, page 4979].

In this reaction, compound (XXXIV) is reacted with compound (XXXV), nitromethane and a base.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; halogenated hydrocarbons such as dichloromethane, chloroform, 1,2-dichloroethane, carbon tetrachloride, trichloroethylene and the like, and the like can be mentioned. These solvents may be used in a mixture at an appropriate ratio.

As the base, for example, amines such as pyrrolidine, piperazine, morpholine, ethylenediamine and the like, and the like can be mentioned.

The amount of the base to be used is generally 0.01 to 10 mol, preferably 0.05 to 2 mol, per 1 mol of compound (XXXIV).

The amount of compound (XXXV) to be used is generally 1 to 10 mol, preferably 1 to 3 mol, per 1 mol of compound (XXXIV).

The amount of the nitromethane to be used is generally 1 to 50 mol, preferably 1 to 10 mol, per 1 mol of compound (XXXIV).

While the reaction time varies depending on the kind and amount of compound (XXXIV), compound (XXXV), the nitromethane and base to be used, it is generally about 1 hr to about 100 hr, preferably about 1 hr to about 50 hr. The reaction temperature is generally about 0 to about 200° C., preferably about 25 to about 100° C.

Compound (XXXVI) can also be produced from compound (XXXIV) in three steps.

In the first step, compound (XXXVII) can be produced by subjecting compound (XXXIV) and nitromethane to the Henry reaction [J. Org. Chem. Soc., 1963, vol. 28, page 1240; Synthesis, 1994, page 190; J. Am. Chem. Soc., 2003, vol. 125, page 3700] in the presence of a base.

This reaction is carried out without a solvent or in a solvent inert to the reaction. As such solvent, while the solvent is not particularly limited as long as the reaction proceeds, for example, alcohols such as methanol, ethanol, tert-butylalcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; halogenated hydrocarbons such as dichloromethane, chloroform, 1,2-dichloroethane, carbon tetrachloride, trichloroethylene and the like, and the like can be mentioned. These solvents may be used in a mixture at an appropriate ratio.

As the base to be used in the first step, for example, alkali metal $C_{1-6}$ alkoxides such as sodium methoxide, sodium ethoxide, potassium ethoxide, potassium tert-butoxide and the like, and the like can be mentioned.

The amount of the base to be used is generally 0.01 to 10 mol, preferably 0.05 to 2 mol, per 1 mol of compound (XXXIV).

The amount of the nitromethane to be used is generally 1 to 50 mol, preferably 1 to 10 mol, per 1 mol of compound (XXXIV).

While the reaction time varies depending on the kind and amount of compound (XXXIV), the nitromethane and base to be used, it is generally about 1 hr to about 100 hr, preferably about 1 hr to about 50 hr. The reaction temperature is generally about 0 to about 200° C., preferably about 25 to about 100° C.

In the second step, compound (XXXVIII) can be produced by subjecting compound (XXXVII) to a dehydration reaction.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitrites such as acetonitrile, propionitrile and the like; halogenated hydrocarbons such as dichloromethane, chloroform, 1,2-dichloroethane, carbon tetrachloride, trichloroethylene and the like; pyridine and the like, and the like can be mentioned. These solvents may be used in a mixture at an appropriate ratio.

The dehydration reaction is generally carried out using a dehydrating agent. As the dehydrating agent, chlorinating agents such as thionyl chloride, phosphoryl chloride and the like; sulfonylating agents such as methanesulfonyl chloride, methanesulfonic anhydride and the like; acylating agents such as acetyl chloride, acetic anhydride, trifluoroacetic anhydride and the like, and the like can be mentioned.

The amount of the dehydrating agent to be used is generally 1 to 10 mol, preferably 1 to 3 mol, per 1 mol of compound (XXXVII).

This reaction can be carried out in the presence of a base, as necessary. As such base, those exemplified for the reaction of compound (II) with compound (III) or a reactive derivative thereof as shown in Scheme 1 can be mentioned.

When a base is used, the amount of the base to be used is generally 1 to 10 mol, preferably 1 to 3 mol, per 1 mol of compound (XXXVII).

The reaction temperature is generally −30° C. to 200° C. The reaction time is generally 0.5 to 20 hr.

In the third step, compound (XXXVI) can be produced by reacting compound (XXXVIII) with compound (XXXV) in the presence of a base.

This reaction is carried out without a solvent or in a solvent inert to the reaction. As such solvent, those exemplified for the reaction of compound (II) with compound (III) or a reactive derivative thereof as shown in Scheme 1 can be mentioned.

The base to be used in this reaction, those exemplified for the reaction of compound (II) with compound (III) or a reactive derivative thereof as shown in Scheme 1 can be mentioned.

The amount of compound (XXXV) to be used is generally 1 to 10 mol, preferably 1 to 2 mol, per 1 mol of compound (XXXVIII).

The amount of the base to be used is generally 0.05 to 10 mol, preferably 0.1 to 3 mol, per 1 mol of compound (XXXVIII).

The reaction temperature is generally −30° C. to 100° C. The reaction time is generally 0.5 to 20 hr.

Compound (X-1) can be produced by subjecting compound (XXXVI) to a reduction reaction.

The reduction reaction is carried out, for example, using a reducing agent. As the reducing agent, for example, metal hydrides such as aluminum hydride, diisobutylaluminum hydride, tributyltin hydride and the like; metal hydrogen complex compounds such as lithium aluminum hydride, sodium borohydride and the like; borane complexes such as borane-tetrahydrofuran complex, borane-dimethylsulfide complex and the like; alkylboranes such as thexylborane, disiamylborane and the like; diborane; metals such as zinc, aluminum, tin, iron and the like, and the like can be mentioned.

The amount of the reducing agent to be used is appropriately determined according to the kind of the reducing agent. For example, the amount of the metal hydride or metal hydrogen complex compound to be used is generally about 0.25 to about 10 mol, preferably about 0.5 to about 5 mol, per 1 mol of compound (XXXVI), and the amount of the borane complex, alkylborane or diborane to be used is generally about 1 to about 10 mol, preferably about 1 to about 5 mol, per 1 mol of compound (XXXVI).

The reduction reaction is preferably carried out in a solvent inert to the reaction. As such solvent, while the solvent is not particularly limited as long as the reaction proceeds, for example, alcohols such as methanol, ethanol, 1-propanol, 2-propanol, tert-butylalcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like, and the like can be mentioned. These solvents may be used in a mixture at an appropriate ratio.

While the reaction time varies depending on the kind and amount of the reducing agent to be used, it is generally about 1 hr to about 100 hr, preferably about 1 hr to about 50 hr. The reaction temperature is generally about −20 to about 120° C., preferably about 0 to about 80° C.

Compound (X) can be produced by reacting compound (XXXIX) with compound (XL) in the presence of an acid catalyst or a base, as necessary.

As the acid catalyst, for example, mineral acids such as hydrochloric acid, sulfuric acid and the like; organic acids such as acetic acid, formic acid, trifluoroacetic acid and the like, and the like can be mentioned.

As the base, for example, organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like can be mentioned.

This reaction is carried out without a solvent or in a solvent inert to the reaction. As such solvent, while the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; esters such as ethyl formate, ethyl acetate, n-butyl acetate and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like can be mentioned. These solvents may be used in a mixture at an appropriate ratio.

When an acid catalyst is used, the amount of the compound (XL) and the acid catalyst to be used is generally 1 to 10 mol, preferably 1 to 3 mol, per 1 mol of compound (XXXIX), respectively.

While the reaction time varies depending on the kind and amount of compound (XXXIX), compound (XL) and the acid catalyst to be used, it is generally about 1 hr to about 100 hr, preferably about 1 hr to about 50 hr. The reaction temperature is generally about −20 to about 120° C., preferably about 0 to about 80° C.

When a base is used, the amount of compound (XL) and the base to be used is generally 1 to 10 mol, preferably 1 to 3 mol, per 1 mol of compound (XXXIX), respectively.

While the reaction time varies depending on the kind and amount of compound (XXXIX), compound (XL) and the base to be used, it is generally about 1 hr to about 100 hr, preferably about 1 hr to about 50 hr. The reaction temperature is generally about −20 to about 120° C., preferably about 0 to about 80° C.

Compound (I) can also be produced, for example, according to methods shown in the following Schemes 8 and 9.

Scheme 8

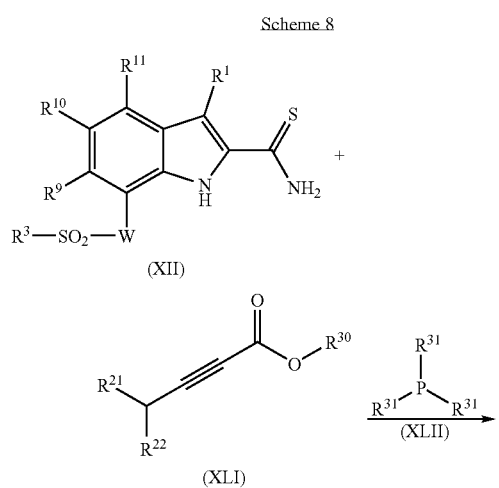

-continued

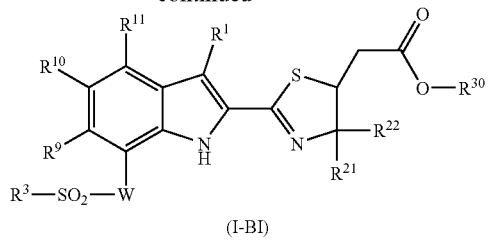

wherein $R^{30}$ is an optionally substituted $C_{1-6}$ alkyl group, $R^{31}$ is an optionally substituted $C_{1-6}$ alkyl group or an optionally substituted aryl group, and the other symbols are as defined above.

Compound (I-B1) can be produced from compound (XII) according to a method described in J. Org. Chem., 2002, vol. 67, page 4595.

In this reaction, compound (XII) and compound (XLI) are reacted with in the presence of compound (XLII).

This reaction is carried out without a solvent or in a solvent inert to the reaction. As such solvent, those exemplified for the reaction of compound (II) with compound (III) or a reactive derivative thereof as shown in Scheme 1 can be mentioned.

The amount of compound (XLI) to be used is generally 1 to 10 mol, preferably 1 to 4 mol, per 1 mol of compound (XII).

The amount of compound (XLII) to be used is generally 0.1 to 10 mol, preferably 0.1 to 2 mol, per 1 mol of compound (XII).

The reaction temperature is generally −30° C. to 200° C. The reaction time is generally 0.5 to 20 hr.

Scheme 9

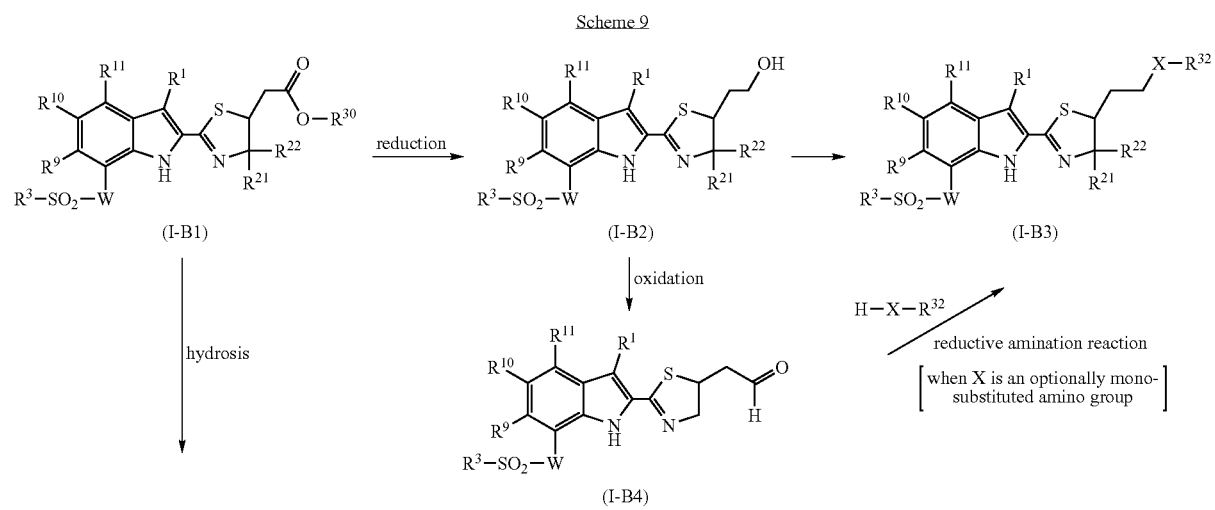

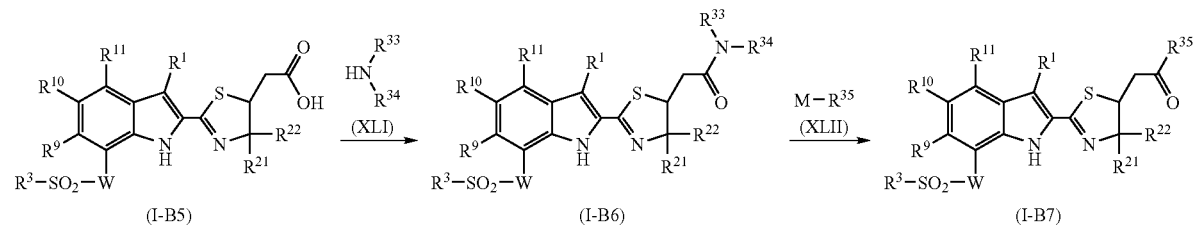

-continued

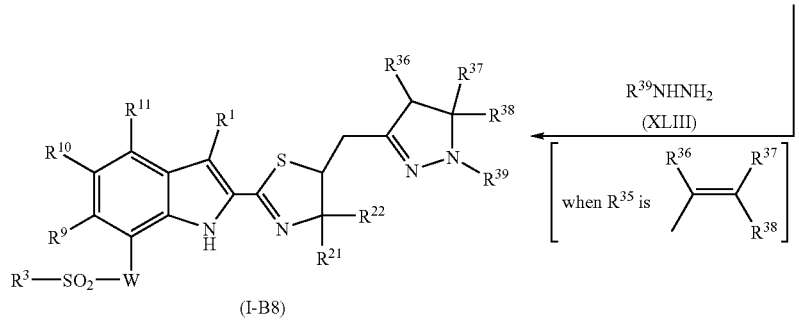

(I-B8)

wherein X is an oxygen atom, an optionally oxidized sulfur atom or an optionally mono-substituted amino group, M is a metal (e.g., potassium, sodium, lithium, magnesium, copper, mercury, zinc, thallium, boron, tin and the like, each of which is optionally complexed), $R^{32}$ is a hydrogen atom, an optionally substituted hydroxy group, an optionally mono- or di-substituted amino group, an optionally substituted acyl group, an optionally substituted hydrocarbon group or an optionally substituted heterocyclic group, X and $R^{32}$ in combination optionally form an optionally substituted ring, $R^{33}$ and $R^{34}$ are each independently a hydrogen atom, an optionally substituted hydrocarbon group, an optionally substituted heterocyclic group, an optionally substituted hydroxy group, an optionally mono- or di-substituted amino group or an optionally substituted acyl group, $R^{33}$ and $R^{34}$ in combination optionally form an optionally substituted ring, $R^{35}$ is an optionally substituted hydrocarbon group or an optionally substituted heterocyclic group, $R^{36}$, $R^{37}$ and $R^{38}$ are each independently, a hydrogen atom or an optionally substituted hydrocarbon group, $R^{39}$ is a hydrogen atom, an optionally substituted hydrocarbon group or an optionally substituted heterocyclic group, and the other symbols are as defined above.

Compound (I-B2) can be produced by subjecting compound (I-B1) to a reduction reaction.

As the reducing agent to be used in this reaction, for example, metal hydrides such as aluminum hydride, diisobutylaluminum hydride, tributyltin hydride and the like; metal hydrogen complex compounds such as lithium aluminum hydride, sodium borohydride, lithium borohydride, calcium borohydride and the like; borane complexes such as borane-tetrahydrofuran complex, borane-dimethylsulfide complex and the like; alkylboranes such as thexylborane, disiamylborane and the like; diborane and the like can be mentioned.

The amount of the reducing agent to be used is appropriately determined according to the kind of the reducing agent. For example, the amount of the metal hydride or metal hydrogen complex compound to be used is about 0.25 to about 10 mol, preferably about 0.5 to about 5 mol, per 1 mol of compound (I-B1), and the amount of the borane complex, alkylborane or diborane to be used is about 1 to about 10 mol, preferably about 1 to about 5 mol, per 1 mol of compound (I-B1).

The reduction reaction is advantageously carried out using a solvent inert to the reaction. As such solvent, while the solvent is not particularly limited as long as the reaction proceeds, for example, alcohols such as methanol, ethanol, 1-propanol, 2-propanol, tert-butylalcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propionic acid, trifluoroacetic acid, methanesulfonic acid and the like, and the like can be mentioned. These solvents may be used in a mixture at an appropriate ratio.

While the reaction time varies depending on the kind and amount of the reducing agent to be used, it is generally about 1 hr to about 100 hr, preferably about 1 hr to about 50 hr. The reaction temperature is generally about −20 to about 120° C., preferably about 0 to about 80° C.

Compound (I-B3) can be produced by subjecting compound (I-B2) to a substituent-conversion reaction known per se.

For example, compound (I-B3) can be produced by introducing the leaving group for $L^1$ to compound (I-B2) according to the method shown in Scheme 3, and by subjecting the resulting compound to a nucleophilic substitution reaction known per se. Alternatively, compound (I-B3) can also be produced by subjecting compound (I-B2) to the Mitsunobu reaction known per se.

Compound (I-B3) wherein X is a optionally mono-substituted amino group can also be produced from compound (I-B4).

For example, compound (I-B3) can be produced by subjecting compound (I-B4) to a reductive amination reaction known per se.

This reaction can be carried out by a catalytic reduction, or using, as a reducing agent, a metal hydrogen complex compound such as sodium borohydride, sodium tri(acetoxy)borohydride, sodium cyanoborohydride and the like.

The amount of the reducing agent to be used is appropriately determined according to the kind of the reducing agent. For example, the amount of the metal hydride or metal hydrogen complex compound to be used is about 0.25 to about 10 mol, preferably about 0.5 to about 5 mol, per 1 mol of compound (I-B4).

The reduction reaction is advantageously carried out using a solvent inert to the reaction. As such solvent, while the solvent is not particularly limited as long as the reaction proceeds, for example, alcohols such as methanol, ethanol, 1-propanol, 2-propanol, tert-butylalcohol and the like; ethers such as diethyl ether, diisopropyl ether, diphenyl ether, tetrahydrofuran, 1,4-dioxane, 1,2-dimethoxyethane and the like; halogenated hydrocarbons such as dichloromethane, chloroform, 1,2-dichloroethane, carbon tetrachloride, trichloroethylene and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like, and the like can be mentioned. These solvents may be used in a mixture at an appropriate ratio.

While the reaction time varies depending on the kind and amount of the reducing agent to be used and the activity and amount of the catalyst to be used, it is generally about 1 hr to about 100 hr, preferably about 1 hr to about 50 hr. The reaction temperature is generally about −20 to about 120° C., preferably about 0 to about 80° C.

Compound (I-B4) can be produced by subjecting compound (I-B2) to an oxidization reaction.

The oxidation reaction is carried out using an oxidant according to a conventional method. As the oxidant, activated manganese dioxide, pyridinium chlorochromate (PCC), pyridinium dichromate (PDC), 1,1,1-tris(acetyloxy)-1,1-dihydro-1,2-benziodoxol-3-(1H)-one (Dess-Martin Periodinane), dimethyl sulfoxide-acid anhydride (acetic anhydride, trifluoroacetic anhydride and the like), dimethyl sulfoxide-thionyl chloride, dimethyl sulfoxide-sulfuryl chloride, dimethyl sulfoxide-oxalyl chloride, dimethyl sulfoxide-chlorine, and dimethylsulfoxide-dicyclohexylcarbodiimide (DCC) in the presence of an acid (phosphoric acid, trifluoroacetic acid, dichloroacetic acid and the like), and the like can be mentioned.

The amount of the oxidant to be used is about 0.25 to about 10 mol, preferably about 0.5 to about 5 mol, per 1 mol of compound (I-B2).

The oxidation reaction is advantageously carried out using a solvent inert to the reaction. As such solvent, while the solvent is not particularly limited as long as the reaction proceeds, for example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; aromatic hydrocarbons such as benzene, toluene and the like; saturated hydrocarbons such as cyclohexane, hexane and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide; organic acids such as formic acid, acetic acid, propionic acid, trifluoroacetic acid, methanesulfonic acid and the like, and the like can be mentioned. These solvents may be used in a mixture at an appropriate ratio.

While the reaction time varies depending on the kind and amount of the oxidant to be used, it is generally about 1 hr to about 100 hr, preferably about 1 hr to about 50 hr. The reaction temperature is generally about −70 to about 120° C., preferably about −70 to about 80° C.

Compound (I-B5) can be produced by subjecting compound (I-B1) to a hydrolysis.

This reaction is carried out in the same manner as in the hydrolysis of compound (XIX) in Scheme 5.

Compound (I-B6) can be produced by reacting compound (I-B5) or a reactive derivative of the carboxy group or a salt thereof with compound (XLI).

This reaction is carried out in the same manner as in the reaction of compound (IX) or a reactive derivative of the carboxy group or a salt thereof with compound (X) in Scheme 3.

Compound (I-B7) can be produced by reacting compound (I-B6) with compound (XLII).

As preferable of compound (XLII), organic lithium such as methyllithium, n-butyllithium, vinyllithium, phenyllithium and the like; Grignard reagents such as methylmagnesium bromide, methylmagnesium chloride, vinylmagnesium bromide, phenylmagnesium bromide and the like can be mentioned.

The reaction of compound (I-B6) with compound (XLII) is advantageously carried out using a solvent inert to the reaction. As such solvent, while the solvent is not particularly limited as long as the reaction proceeds, for example, ethers such as dioxane, tetrahydrofuran, diethyl ether, tert-butyl methyl ether, diisopropyl ether, ethylene glycol dimethyl ether and the like; aromatic hydrocarbons such as benzene, toluene and the like; saturated hydrocarbons such as cyclohexane, hexane and the like, and the like can be mentioned. These solvents may be used in a mixture at an appropriate ratio.

The amount of compound (XLII) to be used is 1 to 10 mol equivalents, preferably 1 to 3 mol equivalents, relative to compound (I-B6).

The reaction temperature is generally −30° C. to 100° C. The reaction time is generally 0.5 to 20 hr.

Compound (I-B8) can be produced by reacting compound (I-B7) wherein $R^{35}$ is [—$CR^{36}$=$CR^{37}R^{38}$] with compound (XLIII) in the presence of an acid catalyst, as necessary.

As the acid catalyst to be used in this reaction, for example, mineral acids such as hydrochloric acid, sulfuric acid and the like; Lewis acids such as a boron trihalide (e.g., boron trichloride, boron trifluoride and the like), a titanium tetrahalide (e.g., titanium tetrachloride, titanium tetrabromide and the like), an aluminum halide (e.g., aluminum chloride, aluminum bromide and the like) and the like; organic acids such as acetic acid, formic acid, trifluoroacetic acid and the like can be mentioned.

This reaction is advantageously without a solvent or in a solvent inert to the reaction. As such solvent, while the solvent is not particularly limited as long as the reaction proceeds, for example, alcohols such as methanol, ethanol, 1-propanol, 2-propanol, tert-butylalcohol and the like; ethers such as diethyl ether, diisopropyl ether, diphenyl ether, tetrahydrofuran, 1,4-dioxane, 1,2-dimethoxyethane and the like; halogenated hydrocarbons such as dichloromethane, chloroform, 1,2-dichloroethane, carbon tetrachloride, trichloroethylene and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like, and the like can be mentioned. These solvents may be used in a mixture at an appropriate ratio.

The amount of compound (XLIII) to be used is 1 to 10 mol equivalents, preferably 1 to 3 mol equivalents, relative to compound (I-B7).

The reaction temperature is generally −30° C. to 100° C. The reaction time is generally 0.5 to 20 hr.

In the above-mentioned production method, when the starting compound or the compound of the present invention has an amino group, a carboxyl group, a hydroxy group or a carbonyl group as a substituent, a protecting group generally used in peptide chemistry and the like may be introduced into these groups. The protecting group can be removed according to a conventional method in any step in each scheme.

Compound (I) can also be produced by subjecting the compound obtained in each of the above-mentioned production methods to a substituent-conversion reaction.

The compound of the present invention obtained according to the above-mentioned production method can be isolated and purified by a known means, for example, concentration, concentration under reduced pressure, solvent extraction, crystallization, recrystallization, phase transfer, chromatography and the like. In addition, various starting material compounds used in each of the above-mentioned production methods can be isolated and purified by a known means such as those mentioned above and the like. Alternatively, the starting material compounds may be directly used in the form of a reaction mixture without isolation as the starting materials of the next step.

For the production of the compound of the present invention, when the starting material compound can form a salt, the compound may also be used in the form of a salt. As such salt, those similar to the salts of the aforementioned compound of the present invention can be mentioned.

When the compound of the present invention contains an optical isomer, a stereoisomer, a positional isomer or a rotational isomer, these are encompassed in the compound of the present invention, and obtained as a single product according to a synthetic method and separation method known per se. For example, an optical isomer and an optical isomer resolved from this compound are also encompassed in the compound of the present invention.

The compound of the present invention may be in the form of a crystal.

The crystal of the compound of the present invention (hereinafter sometimes to be abbreviated as the crystal of the present invention) can be produced by crystallization of the compound of the present invention according to a crystallization method known per se.

In the present specification, the melting point refers to that measured using, for example, micromelting point measuring apparatus (Yanako, MP-500D or Buchi, B-545) or DSC (differential scanning calorimetry) device (SEIKO, EXSTAR6000) and the like.

In general, melting points vary depending on measurement apparatuses, measurement conditions and the like. The crystal in the present specification may show a different melting point described in the present specification, as long as it is within general error range.

The crystal of the present invention is superior in physicochemical properties (e.g., melting point, solubility, stability and the like) and biological properties (e.g., pharmacokinetics (absorption, distribution, metabolism, excretion), efficacy expression and the like), and is extremely useful as a pharmaceutical agent.

EXAMPLES

The present invention is explained in detail in the following by referring to the following Reference Examples, Examples, Experimental Examples and Formulation Examples, which are not to be construed as limitative. In addition, the present invention may be modified without departing from the scope of invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

The other symbols used herein mean the following:
s: singlet
d: doublet
t: triplet
q: quartet
m: multiplet
br: broad
J: coupling constant
Hz: Hertz
$CDCl_3$: deuterated chloroform
$DMSO-d_6$: dimethyl sulfoxide-$d_6$
$^1$H-NMR: proton nuclear magnetic resonance
TFA: trifluoroacetic acid In the following Reference Examples and Examples, nuclear magnetic resonance spectrum (NMR) were measured under the following conditions.

NMR measurement tools: Varian Inc. Varian Gemini 200 (200 MHz), Varian Gemini 300 (300 MHz), Bruker BioSpin Corp. AVANCE 300.

In the following Examples, high performance liquid chromatography (HPLC)—mass spectrum (LC-MS) was measured under the following conditions.

measurement tools: Micromass Ltd., Quattro Micro and Agilent Technologies, Inc. HP1100, or Waters Corporation, MUX system (Micromass Ltd., Zq)

Column: Shiseido Co., Ltd., Capcelpak C18 UG-120, 1.5×35 mm solvent: SOLUTION A; 5 mM ammonium acetate/2% acetonitrile/water, SOLUTION B; 5 mM ammonium acetate/95% acetonitrile/water gradient cycle: 0.00 min (SOLUTION A 100%), 2.00 min (SOLUTION B 100%), 3.00 min (SOLUTION B 100%), 3.01 min (SOLUTION A 100%), 3.80 min (SOLUTION A 100%)

flow rate: 0.5 ml/min, detection: UV 220 nm ionization method: Electron Spray Ionization: ESI In the following Reference Examples and Examples, purification by preparative high performance liquid chromatography (HPLC) was performed under the following conditions. In the case of a compound having a basic functional group, however, when trifluoroacetic acid is used in this operation, neutralization and the like may be necessary to obtain a free compound.

tools: Gilson, Inc., high through-put purification system

Column: Shiseido Co., Ltd., Capcelpak C18 UG-120, S-5 µM, 20×50 mm solvent: SOLUTION A; 0.1% trifluoroacetic acid-containing water, SOLUTION B; 0.1% trifluoroacetic acid-containing acetonitrile gradient cycle: 0.00 min (SOLUTION A/SOLUTION B=95/5), 1.10 min (SOLUTION A/SOLUTION B=95/5), 5.00 min (SOLUTION A/SOLUTION B=0/100), 6.40 min (SOLUTION A/SOLUTION B=0/100), 6.50 min (SOLUTION A/SOLUTION B=95/5).

flow rate: 20 ml/min, detection: UV 220 nm

Alternatively, tools: Waters mass preparative system (UV Purification System)

Column: Develosil ODS-UG-10 solvent: SOLUTION A; 0.1% trifluoroacetic acid-containing water, SOLUTION B; 0.1% trifluoroacetic acid-containing acetonitrile gradient cycle: 0.00 min (SOLUTION A/SOLUTION B=95/5), 1.00 min (SOLUTION A/SOLUTION B=95/5), 2.00 min (SOLUTION A/SOLUTION B=80/20), 5.00 min (SOLUTION A/SOLUTION B=5/95), 5.10 min (SOLUTION A/SOLUTION B=0/100), 7.00 min (SOLUTION A/SOLUTION B 100/0)

flow rate: 150 ml/min detection: UV 220 nm

In the following Reference Examples and Examples, preparative high performance liquid chromatography (HPLC) for chiral resolution was performed using K-Prep manufactured by YMC Co., Ltd. and preparative supercritical fluid chromatography (SFC) was performed using Multigram II manufactured by METTLER-TOLEDO K.K.

Reference Example 1 ethyl 1-(methoxymethyl)-7-nitro-1H-indole-2-carboxylate

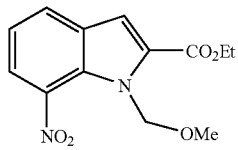

To a suspension of sodium hydride (60%, in oil, 0.51 g) in N,N-dimethylformamide (15 ml) was slowly added ethyl 7-nitro-1H-indole-2-carboxylate (2.50 g) at 0° C., and the mixture was stirred for 30 min. Chloromethyl methyl ether (1.00 ml) was added to the reaction mixture over 20 min at 0° C., and the mixture was stirred at room temperature for 1 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (2.29 g, yield 77%) as pale-yellow crystals from a fraction eluted with ethyl acetate-hexane (1:3, volume ratio). melting point 62-63° C.

Reference Example 2 ethyl 7-amino-1-(methoxymethyl)-1H-indole-2-carboxylate

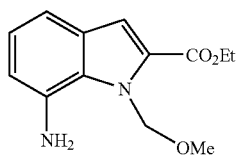

A mixture of ethyl 1-(methoxymethyl)-7-nitro-1H-indole-2-carboxylate (2.35 g), 10% palladium-carbon (0.24 g), ethanol (4 ml) and tetrahydrofuran (10 ml) was stirred overnight at room temperature under hydrogen atmosphere. The palladium-carbon was removed by filtration, and the filtrate was concentrated. The residue was subjected to silica gel column chromatography to give the title compound (1.92 g, yield 91%) as a yellow oil from a fraction eluted with ethyl acetate-hexane (1:3, volume ratio).

$^1$H-NMR (CDCl$_3$)δ: 1.41 (3H, t, J=7.2 Hz), 3.44 (3H, s), 4.36 (2H, q, J=7.2 Hz), 4.53 (2H, brs), 6.16 (2H, s), 6.61 (1H, dd, J=7.7, 0.9 Hz), 6.97 (1H, t, J=7.7 Hz), 7.10 (1H, dd, J=7.7, 0.9 Hz), 7.28 (1H, s).

Reference Example 3 ethyl 1-(methoxymethyl)-7-[(2-thienylsulfonyl)amino]-1H-indole-2-carboxylate

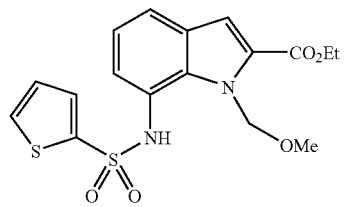

To a mixture of ethyl 7-amino-1-(methoxymethyl)-1H-indole-2-carboxylate (0.70 g) and pyridine (8 ml) was added thiophene-2-sulfonyl chloride (0.57 g) at 0° C., and the mixture was stirred at room temperature for 2 hr. The reaction mixture was concentrated, 10% aqueous citric acid solution was added, and the mixture was extracted with ethyl acetate. The ethyl acetate layer was washed with saturated brine, dried (MgSO$_4$), and concentrated. The obtained residue was subjected to silica gel column chromatography to give the title compound (1.03 g, yield 93%) as a yellow oil from a fraction eluted with ethyl acetate-hexane (1:2, volume ratio).

$^1$H-NMR (CDCl$_3$)δ: 1.40 (3H, t, J=7.2 Hz), 3.45 (3H, s), 4.35 (2H, q, J=7.2 Hz), 5.70 (2H, s), 7.00 (1H, dd, J=5.1, 3.7 Hz), 7.19 (1H, t, J=7.8 Hz), 7.32 (1H, s), 7.46-7.64 (4H, m), 8.87 (1H, brs).

Reference Example 4 ethyl 1-(methoxymethyl)-7-[methyl(2-thienylsulfonyl)amino]-1H-indole-2-carboxylate A mixture of ethyl 1-(methoxymethyl)-7-[(2-thienylsulfonyl)amino]-1H-indole-2-carboxylate (1.03 g), methyl iodide (0.24 ml), potassium carbonate (0.36 g) and N,N-dimethylformamide (10 ml) was stirred overnight at room temperature. Water was added to the reaction mixture, and the resulting crystals were collected by filtration, washed with water, and dried to give the title compound (1.06 g, yield 99%) as colorless crystals. melting point 143-145° C.

Reference Example 5 ethyl 7-[methyl(2-thienylsulfonyl)amino]-1H-indole-2-carboxylate

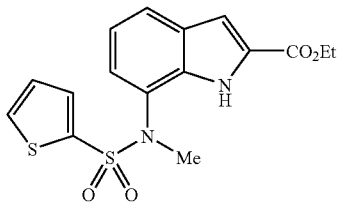

A mixture of ethyl 1-(methoxymethyl)-7-[methyl(2-thienylsulfonyl)amino]-1H-indole-2-carboxylate (1.06 g), concentrated hydrochloric acid (1 ml) and ethanol (5 ml) was heated overnight under reflux. Water was added to the reaction mixture, and the resulting crystals were collected by filtration, washed with water, and dried. The obtained crystals were subjected to silica gel column chromatography to give the title compound (0.43 g, yield 46%) as colorless crystals from a fraction eluted with ethyl acetate-hexane (2:1, volume ratio). The crystals were recrystallized from ethyl acetate-hexane. melting point 164-165° C.

Reference Example 6

7-[methyl(2-thienylsulfonyl)amino]-1H-indole-2-carboxylic acid

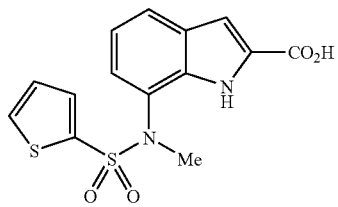

A mixture of ethyl 7-[methyl(2-thienylsulfonyl)amino]-1H-indole-2-carboxylate (0.40 g), 8N aqueous sodium hydroxide solution (0.40 ml), tetrahydrofuran (5 ml) and methanol (5 ml) was stirred at 60° C. for 1 hr. The reaction mixture was concentrated, and water was added to the residue. The mixture was acidified with 10% aqueous citric acid solution, and the resulting crystals were collected by filtration, washed with water, and dried to give the title compound (0.35 g, yield 91%) as colorless crystals. melting point >240° C. (decomposition).

Reference Example 7

7-[methyl(2-thienylsulfonyl)amino]-1H-indole-2-carboxamide

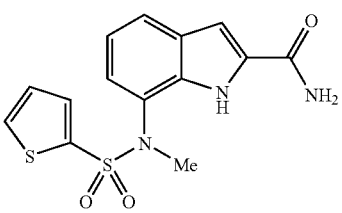

To a mixture of 7-[methyl(2-thienylsulfonyl)amino]-1H-indole-2-carboxylic acid (17.20 g), 1H-1,2,3-benzotriazol-1-ol (8.29 g) and N,N-dimethylformamide (150 ml) was added N-[3-(dimethylamino)propyl]-N'-ethylcarbodiimide hydrochloride (11.8 g) at room temperature, and the mixture was stirred at 50° C. for 20 min. The mixture was allowed to cool to room temperature, and 28% aqueous ammonia (3.4 ml) was added. The reaction mixture was stirred at room temperature for 2 hr, and water was added. The mixture was acidified with 10% aqueous citric acid solution, and the resulting crystals were filtrated, washed with water, washed with cooled ethyl acetate, and dried to give the title compound (11.47 g, yield 67%) as colorless crystals. melting point 244-245° C.

Reference Example 8

1-(methoxymethyl)-7-[(2-thienylsulfonyl)amino]-1H-indole-2-carboxamide

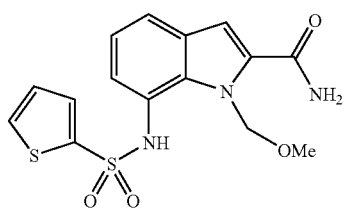

In the same manner as in Reference Example 7, the title compound (26.9 g, yield 88%) was obtained as colorless crystals from 1-(methoxymethyl)-7-[(2-thienylsulfonyl)amino]-1H-indole-2-carboxylic acid (29.4 g). melting point 142-144° C.

Reference Example 9

7-[(cyclopropylmethyl)(2-thienylsulfonyl)amino]-1-(methoxymethyl)-1H-indole-2-carboxamide

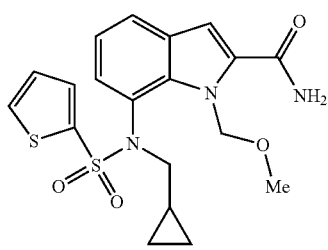

A mixture of 1-(methoxymethyl)-7-[(2-thienylsulfonyl)amino]-1H-indole-2-carboxamide (1.0 g), (bromomethyl)cyclopropane (456 mg), potassium carbonate (1.13 g) and N,N-dimethylformamide (5 ml) was stirred at 85° C. for 20 hr. The reaction mixture was diluted with ethyl acetate and saturated brine. The organic layer was washed with aqueous sodium bicarbonate and saturated brine, dried over magnesium sulfate, and filtrated, and the filtrate was concentrated. The residue was subjected to basic silica gel column chromatography, and eluted with ethyl acetate-hexane mixture (2:1) to give the title compound (820 mg, yield 72%) as an amorphous form.

$^1$H-NMR (CDCl$_3$) δ: 0.16-0.05 (1H, m), 0.08-0.19 (1H, m), 0.37-0.47 (1H, m), 0.86-1.08 (1H, m), 3.43 (1H, dd, J=13.5, 7.3 Hz), 3.45 (3H, s), 3.79 (1H, dd, J=13.5, 7.3 Hz), 6.20 (2H, s), 6.68 (1H, d, J=7.7 Hz), 7.01 (1H, t, J=7.7 Hz), 7.08-7.18 (2H, m), 7.44-7.51 (1H, m), 7.59-7.72 (2H, m).

Reference Example 10

7-[(cyclopropylmethyl)(2-thienylsulfonyl)amino]-1H-indole-2-carboxamide

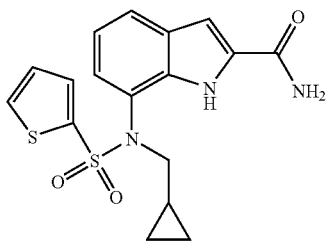

A mixture of 1-(methoxymethyl)-7-[(cyclopropylmethyl)(2-thienylsulfonyl)amino]-1H-indole-2-carboxamide (390 mg), oxalic acid dihydrate (351 mg), methanol (15 ml) and water (15 ml) was stirred at 70° C. for 1 hr, and then at 90° C. for 14 hr. The reaction mixture was allowed to cool to room temperature, and the resulting crystals were collected by filtration, washed successively with water and diethyl ether-hexane mixture, and dried to give the title compound (286 mg, yield 81%) as crystals. melting point 229-231° C.

Reference Example 11

7-[isopropyl(2-thienylsulfonyl)amino]-1H-indole-2-carboxamide

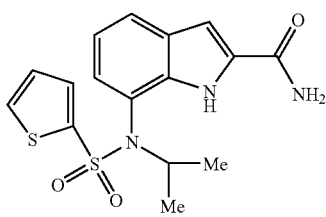

A mixture of 1-(methoxymethyl)-7-[(2-thienylsulfonyl)amino]-1H-indole-2-carboxamide (1.0 g), 2-iodopropane (574 mg), potassium carbonate (1.13 g) and N,N-dimethylacetamide (5 ml) was stirred at room temperature for a week. The reaction mixture was diluted with ethyl acetate and saturated brine, and the organic layer was washed with aqueous sodium bicarbonate and saturated brine, dried over magnesium sulfate, and filtrated. The filtrate was concentrated, and the residue was subjected to basic silica gel column chromatography, and eluted with ethyl acetate-hexane (2:1) mixture to give a solid. A mixture of this solid, oxalic acid dihydrate (605 mg), methanol (15 ml) and water (15 ml) was stirred at 100° C. for 3.5 days. The reaction mixture was allowed to cool to room temperature, and the obtained solid was collected by filtration, washed successively with water, hexane-diisopropyl ether mixture and hexane. The obtained solid was subjected to basic silica gel column chromatography, and eluted with ethyl acetate-hexane mixture (2:1) to give the title compound (340 mg, yield 34%) as an amorphous solid.

$^1$H-NMR (CDCl$_3$) δ: 1.04-1.21 (6H, m), 4.79-4.96 (1H, m), 6.79-6.94 (2H, m), 7.01-7.11 (2H, m), 7.47-7.55 (1H, m), 7.59 (1H, dd, J=5.1, 1.3 Hz), 7.66 (1H, d, J=7.9 Hz), 9.98 (1H, s).

Reference Example 12

7-[(2-ethoxyethyl)(2-thienylsulfonyl)amino]-1H-indole-2-carboxamide

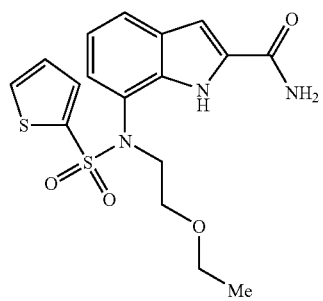

A mixture of 1-(methoxymethyl)-7-[(2-thienylsulfonyl)amino]-1H-indole-2-carboxamide (6.25 g), 1-bromo-2-ethoxyethane (3.41 g), potassium carbonate (7.09 g) and N,N-dimethylformamide (30 ml) was stirred at 75° C. for 6 hr. The reaction mixture was diluted with ethyl acetate and saturated brine. The organic layer was washed with aqueous sodium bicarbonate and saturated brine, dried over magnesium sulfate, and filtrated, and the filtrate was concentrated. The obtained residue was subjected to basic silica gel column chromatography, and eluted with ethyl acetate-hexane (2:1) mixture to give a solid. A mixture of this solid (5.50 g), oxalic acid dihydrate (4.77 g), methanol (50 ml) and water (50 ml) was stirred at 90° C. for 14 hr. The reaction mixture was allowed to cool to room temperature, and diluted with water, and the obtained solid was crystallized, and washed with water to give the title compound (4.70 g, yield 95%) as crystals. melting point 135° C.

Reference Example 13

7-[methyl(2-thienylsulfonyl)amino]-1H-indole-2-carbothioamide

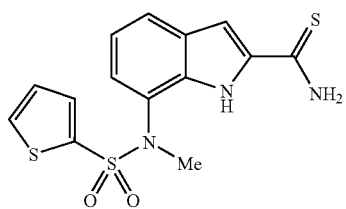

A mixture of 7-[methyl(2-thienylsulfonyl)amino]-1H-indole-2-carboxamide (11.47 g), Lawesson's reagent (15.2 g) and tetrahydrofuran (150 ml) was stirred at 50° C. for 4 hr. The reaction mixture was concentrated, and the resulting crystals were filtrated, washed with toluene, and dried to give the title compound (11.16 g, yield 93%) as yellow crystals. melting point 239-240° C.

Reference Example 14

7-[(cyclopropylmethyl)(2-thienylsulfonyl)amino]-1H-indole-2-carbothioamide

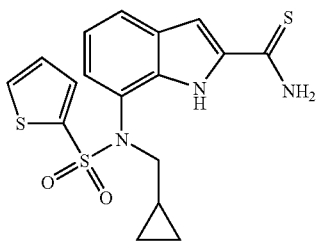

A mixture of 7-[(cyclopropylmethyl)(2-thienylsulfonyl)amino]-1H-indole-2-carboxamide (264 mg), Lawesson's reagent (339 mg) and tetrahydrofuran (5 ml) was stirred at 60° C. for 2 hr. The reaction mixture was concentrated under reduced pressure, and the residue was subjected to silica gel column chromatography, and eluted with a mixed solvent of ethyl acetate-hexane (1:1) to give the title compound (243 mg, yield 88%) as an amorphous solid.
MS m/z 392 (M+H$^+$).

Reference Example 15

7-[ethyl(2-thienylsulfonyl)amino]-1H-indole-2-carbothioamide

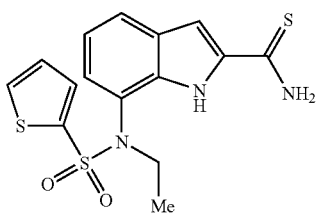

A mixture of 1-(methoxymethyl)-7-[(2-thienylsulfonyl)amino]-1H-indole-2-carboxamide (6.0 g), ethyl iodide (1.6 ml), potassium carbonate (6.78 g) and N,N-dimethylformamide (30 ml) was stirred at room temperature for 20 hr. The reaction mixture was diluted with ethyl acetate and saturated brine, and the organic layer was washed with aqueous sodium bicarbonate and saturated brine, dried over magnesium sulfate, and filtrated. The filtrate was concentrated, and the residue was subjected to basic silica gel column chromatography, and eluted with ethyl acetate-hexane (1:1) mixture to give a solid. A mixture of this solid, oxalic acid dihydrate (5.84 g), methanol (50 ml) and water (50 ml) was stirred at 95° C. for 7 hr. The reaction mixture was concentrated, diluted with ethyl acetate-tetrahydrofuran mixture, and washed with water, and the aqueous layer was extracted with ethyl acetate-tetrahydrofuran mixture. The combined organic layer was dried over magnesium sulfate, and filtrated. The filtrate was concentrated, and the obtained solid was washed with water. A mixture of this solid, Lawesson's reagent (3.76 g) and tetrahydrofuran (50 ml) was stirred at 65° C. for 2.5 hr. The reaction mixture was concentrated, and the residue was crystallized from methylene chloride-toluene mixture to give the title compound (3.5 g, yield 62%) as crystals. melting point 163° C.

Reference Example 16

7-[isopropyl(2-thienylsulfonyl)amino]-1H-indole-2-carbothioamide

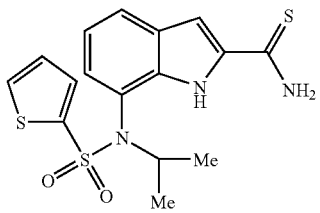

A mixture of 7-[isopropyl(2-thienylsulfonyl)amino]-1H-indole-2-carboxamide (320 mg), Lawesson's reagent (213 mg) and tetrahydrofuran (5 ml) was stirred at 70° C. for 1 hr. The reaction mixture was concentrated under reduced pressure, and the residue was crystallized from methylene chloride-toluene mixture, and washed with hexane to give the title compound (148 mg, yield 44%) as crystals. melting point 204-205° C.

Reference Example 17

7-[(2-ethoxyethyl)(2-thienylsulfonyl)amino]-1H-indole-2-carbothioamide

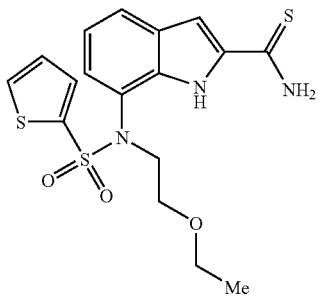

A mixture of 7-[(2-ethoxyethyl)(2-thienylsulfonyl)amino]-1H-indole-2-carboxamide (4.70 g), Lawesson's reagent (3.06 g) and tetrahydrofuran (30 ml) was stirred at 70° C. for 3 hr. The reaction mixture was concentrated, and toluene was added to the residue. The obtained solid was washed with toluene to give the title compound (2.99 g, yield 58%) as crystals. melting point 182° C.

Reference Example 18

N-{2-[5-(hydroxymethyl)-1,3-thiazol-2-yl]-1H-indol-7-yl}-N-methylthiophene-2-sulfonamide

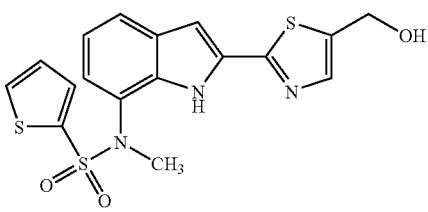

A mixture of 7-[methyl(2-thienylsulfonyl)amino]-1H-indole-2-carbothioamide (1.00 g), bromomalonaldehyde (0.86 g) and N,N-dimethylacetamide (8 ml) was stirred at 80° C. for 3 hr. Water was added to the reaction mixture, and the resulting crystals were collected by filtration, washed with water, and dried. The obtained crystals were dissolved in tetrahydrofuran (8 ml) and methanol (8 ml), sodium borohydride (63 mg) was added at 0° C., and the mixture was stirred at 0° C. for 1 hr. The reaction mixture was concentrated, 10% aqueous citric acid solution was added, and the resulting crystals were collected by filtration, washed with water, and dried. The crystals were subjected to silica gel column chromatography to give the title compound (0.43 g, yield 39%) as colorless crystals from a fraction eluted with ethyl acetate-hexane (3:1, volume ratio). melting point 201-202° C.

Reference Example 19

N-ethyl-N-{2-[5-(hydroxymethyl)-1,3-thiazol-2-yl]-1H-indol-7-yl}thiophene-2-sulfonamide

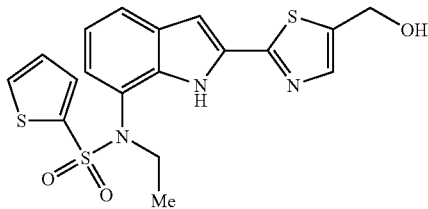

A mixture of 7-[ethyl(2-thienylsulfonyl)amino]-1H-indole-2-carbothioamide (4.10 g), bromomalonaldehyde (3.55 g) and N,N-dimethylacetamide (30 ml) was stirred at 95° C. for 1.5 hr. Water was added to the reaction mixture, and the obtained precipitate was collected by filtration and dissolved in tetrahydrofuran (30 ml) and methanol (30 ml). After cooling with an ice bath, sodium borohydride (508 mg) was added, and the mixture was stirred at room temperature for 16 hr. The reaction mixture was concentrated, and diluted with ethyl acetate-tetrahydrofuran mixture. The organic layer was washed successively with aqueous sodium bicarbonate and saturated brine, dried over magnesium sulfate, and filtrated, and the filtrate was concentrated. The residue was subjected to silica gel column chromatography, and eluted with ethyl acetate-hexane (2:1) mixture to give the title compound (800 mg, yield 17%) as a solid.

MS m/z 420 (M+H$^+$).

Reference Example 20

N-(cyclopropylmethyl)-N-{2-[5-(hydroxymethyl)-1,3-thiazol-2-yl]-1H-indol-7-yl}thiophene-2-sulfonamide

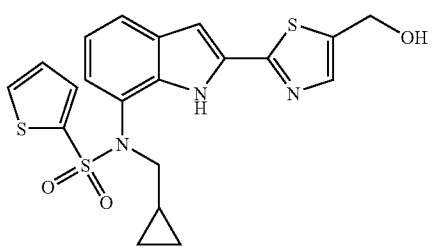

In the same manner as in Reference Example 19, the title compound (100 mg, yield 50%) was obtained as crystals from 7-[(cyclopropylmethyl)(2-thienylsulfonyl)amino]-1H-indole-2-carbothioamide (225 mg) and bromomalonaldehyde (182 mg). melting point 174° C.

Reference Example 21

N-(2-[5-(hydroxymethyl)-1,3-thiazol-2-yl]-1H-indol-7-yl)-N-isopropylthiophene-2-sulfonamide

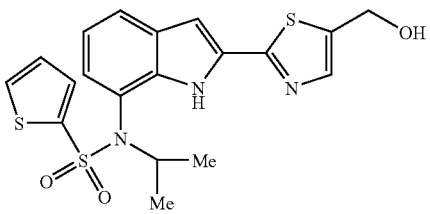

In the same manner as in Reference Example 19, the title compound (124 mg, yield 88%) was obtained as crystals from 7-[isopropyl(2-thienylsulfonyl)amino]-1H-indole-2-carbothioamide (123 mg) and bromomalonaldehyde (103 mg). melting point 209° C.

Reference Example 22

N-(2-ethoxyethyl)-N-{2-[5-(hydroxymethyl)-1,3-thiazol-2-yl]-1H-indol-7-yl}thiophene-2-sulfonamide

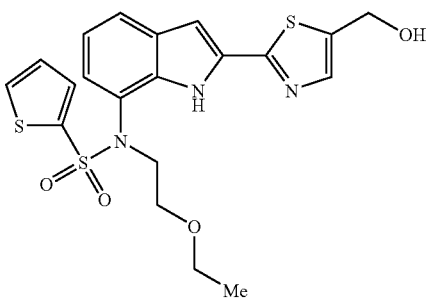

In the same manner as in Reference Example 19, the title compound (1.00 g, yield 29%) was obtained as a amorphous form from 7-[(2-ethoxyethyl)(2-thienylsulfonyl)amino]-1H-indole-2-carbothioamide (3.00 g) and bromomalonaldehyde (2.32 g).

MS m/z 464 (M+H$^+$).

Reference Example 23

N-{2-[5-(chloromethyl)-1,3-thiazol-2-yl]-1H-indol-7-yl}-N-methylthiophene-2-sulfonamide

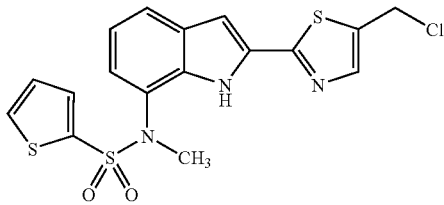

A mixture of N-{2-[5-(hydroxymethyl)-1,3-thiazol-2-yl]-1H-indol-7-yl}-N-methylthiophene-2-sulfonamide (0.10 g), thionyl chloride (0.03 ml), N,N-dimethylformamide (one drop) and tetrahydrofuran (6 ml) was stirred overnight at room temperature. Water was added to the reaction mixture, and the mixture was extracted with ethyl acetate. The ethyl acetate layer was washed successively with saturated brine, aqueous sodium bicarbonate and saturated brine, dried (MgSO$_4$), and concentrated to give the title compound (0.08 g, yield 76%) as yellow crystals. melting point 204-205° C.

Reference Example 24

N-{2-[5-(chloromethyl)-1,3-thiazol-2-yl]-1H-indol-7-yl}-N-isopropylthiophene-2-sulfonamide

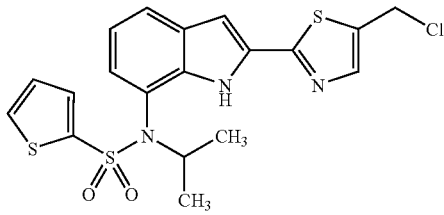

A mixture of N-{2-[5-(hydroxymethyl)-1,3-thiazol-2-yl]-1H-indol-7-yl}-N-isopropylthiophene-2-sulfonamide (2.12 g), thionyl chloride (0.70 ml), N,N-dimethylformamide (two drop) and tetrahydrofuran (30 ml) was stirred overnight at room temperature. Water was added to the reaction mixture, and the mixture was extracted with ethyl acetate. The ethyl acetate layer was washed successively with saturated brine, aqueous sodium bicarbonate and saturated brine, dried (MgSO$_4$), and concentrated. The residue was crystallized from diethyl ether, and the crystals were collected by filtration, washed with diethyl ether, and dried to give the title compound (2.00 g, yield 90%) as yellow crystals. melting point 184-185° C.

Reference Example 25

N-{2-[5-(chloromethyl)-1,3-thiazol-2-yl]-1H-indol-7-yl}-N-ethylthiophene-2-sulfonamide

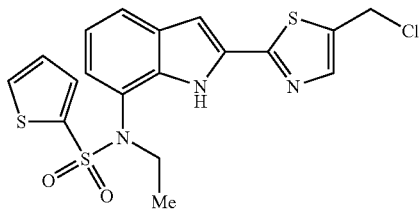

To a mixture of N-ethyl-N-{2-[5-(hydroxymethyl)-1,3-thiazol-2-yl]-1H-indol-7-yl}thiophene-2-sulfonamide (3.43 g), N,N-dimethylformamide (0.05 ml) and tetrahydrofuran (50 ml) was added thionyl chloride (1.56 g), and the mixture was stirred overnight at room temperature. The reaction mixture was diluted with ethyl acetate and saturated brine, and the organic layer was washed with saturated brine, and dried over magnesium sulfate, and filtrated. The filtrate was concentrated, and the obtained solid was washed with ether-hexane (1:1) to give the title compound (3.27 g, yield 91%) as a pale-yellow solid.

$^1$H-NMR (CDCl$_3$) δ: 1.12 (3H, t, J=7.1 Hz), 3.77 (2H, q, J=7.1 Hz), 4.85 (2H, d, J=0.8 Hz), 6.57 (1H, dd, J=7.6, 0.9 Hz), 6.96-7.03 (2H, m), 7.09 (1H, dd, J=4.9, 3.8 Hz), 7.39 (1H, dd, J=3.8, 1.3 Hz), 7.56-7.64 (2H, m), 7.74 (1H, s), 9.48 (1H, s).

Reference Example 26

N-{2-[5-(chloromethyl)-1,3-thiazol-2-yl]-1H-indol-7-yl}-N-(cyclopropylmethyl)thiophene-2-sulfonamide

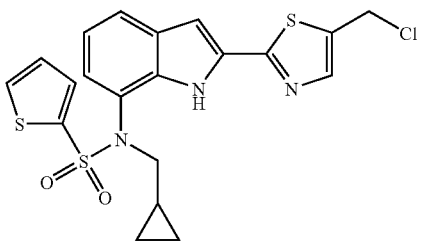

In the same manner as in Reference Example 25, the title compound (2.05 g, yield 97%) was obtained as a pale-yellow solid from N-(cyclopropylmethyl)-N-{2-[5-(hydroxymethyl)-1,3-thiazol-2-yl]-1H-indol-7-yl}thiophene-2-sulfonamide (2.15 g). melting point 135° C.

Reference Example 27

N-{2-[5-(chloromethyl)-1,3-thiazol-2-yl]-1H-indol-7-yl}-N-(2-ethoxyethyl)thiophene-2-sulfonamide

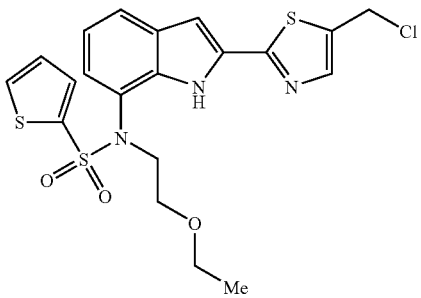

In the same manner as in Reference Example 25, the title compound (970 mg, yield 93%) was obtained as a pale-yellow solid from N-(2-ethoxyethyl)-N-{2-[5-(hydroxymethyl)-1,3-thiazol-2-yl]-1H-indol-7-yl}thiophene-2-sulfonamide (1.00 g).

$^1$H-NMR (CDCl$_3$) δ: 1.14 (3H, t, J=7.0 Hz), 3.38-3.55 (4H, m), 3.91 (2H, s), 4.85 (2H, s), 6.69 (1H, d, J=7.5 Hz), 6.95-7.03 (2H, m), 7.05-7.10 (1H, m), 7.42-7.46 (1H, m), 7.57-7.62 (2H, m), 7.73 (1H, s), 9.75 (1H, s).

Reference Example 28 ethyl [2-({7-[methyl(2-thienylsulfonyl)amino]-1H-indol-2-yl}carbonyl)hydrazino](oxo)acetate

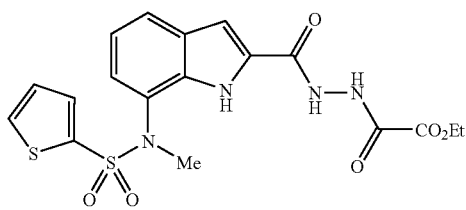

To a mixture of 7-[methyl(2-thienylsulfonyl)amino]-1H-indole-2-carboxylic acid (0.50 g), 1H-1,2,3-benzotriazol-1-ol (0.24 g) and N,N-dimethylformamide (10 ml) was added N-[3-(dimethylamino)propyl]-N'-ethylcarbodiimide hydrochloride (0.30 g) at room temperature, and the mixture was stirred for 10 min. Ethyl hydrazino(oxo)acetate (0.33 g) was added, and the reaction mixture was stirred at room temperature for 2 hr. Water was added, and the mixture was extracted with ethyl acetate. The ethyl acetate layer was washed with saturated brine, dried (MgSO$_4$), and concentrated. The obtained residue was subjected to silica gel column chromatography to give the title compound (0.43 g, yield 63%) as colorless crystals from a fraction eluted with ethyl acetate. melting point 133-134° C.

Reference Example 29 ethyl 5-{7-[methyl(2-thienylsulfonyl)amino]-1H-indol-2-yl}-1,3,4-thiadiazole-2-carboxylate

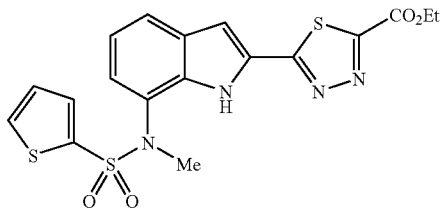

A mixture of ethyl [2-({7-[methyl(2-thienylsulfonyl)amino]-1H-indol-2-yl}carbonyl)hydrazino](oxo)acetate (0.43 g), Lawesson's reagent (0.42 g) and tetrahydrofuran (10 ml) was stirred overnight at 50° C. The reaction mixture was concentrated, and the residue was subjected to silica gel column chromatography to give the title compound (0.29 g, yield 68%) as colorless crystals from a fraction eluted with ethyl acetate-hexane (2:3, volume ratio). The crystals were recrystallized from ethyl acetate-hexane. melting point 176-177° C.

Reference Example 30

N-{2-[5-(hydroxymethyl)-1,3,4-thiadiazol-2-yl]-1H-indol-7-yl}-N-methylthiophene-2-sulfonamide

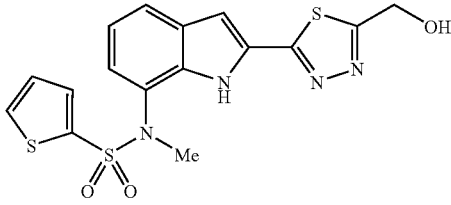

To a mixture of ethyl 5-{7-[methyl(2-thienylsulfonyl)amino]-1H-indol-2-yl}-1,3,4-thiadiazole-2-carboxylate (1.38 g), tetrahydrofuran (20 ml) and methanol (4 ml) was added sodium borohydride (0.26 g), and the mixture was stirred at room temperature for 30 min. The reaction mixture was concentrated, and water was added to the residue. The resulting crystals were collected by filtration, washed with water, and dried to give the title compound (1.18 g, yield 94%) as colorless crystals. melting point 259-260° C. (decomposition).

Reference Example 31

3-(benzylthio)-3-methyl-4-nitrobutan-1-ol

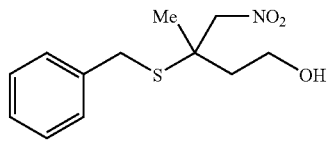

A mixture of 4-hydroxy-2-butanone (5.00 g), benzylmercaptan (6.65 ml), nitromethane (30.7 ml), ethylenediamine (3.80 ml) and acetonitrile (30 ml) was stirred at room temperature for 4 hr. The reaction mixture was concentrated, and the obtained residue was subjected to silica gel column chromatography to give the title compound (5.70 g, yield 39%) as a colorless oil from a fraction eluted with ethyl acetate-hexane (1:1, volume ratio).

$^1$H-NMR (CDCl$_3$) δ: 1.53 (3H, s), 1.77 (1H, t, J=5.6 Hz), 1.94-2.12 (4H, m), 3.78-4.01 (4H, m), 4.52 (1H, d, J=11.1 Hz), 4.61 (1H, d, J=11.1 Hz), 7.22-7.35 (5H, m).

Reference Example 32

4-amino-3-(benzylthio)-3-methylbutan-1-ol

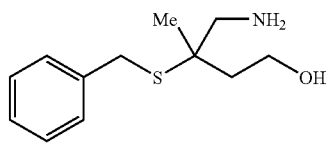

To a mixture of lithium aluminum hydride (1.67 g) and tetrahydrofuran (30 ml) was added a solution of 3-(benzylthio)-3-methyl-4-nitrobutan-1-ol (3.00 g) in tetrahydrofuran (10 ml) over 1 hr at room temperature. The reaction mixture was stirred at room temperature for 1 hr, ethanol (10 ml) and water (6.4 ml) were added in this order, and the resulting inorganic salt was removed by filtration. The filtrate was concentrated, and the residue was dissolved in ethyl acetate, dried (MgSO$_4$), and concentrated to give the title compound (2.62 g, yield 99%) as a yellow oil.

$^1$H-NMR (CDCl$_3$) δ: 1.37 (3H, s), 1.78-1.98 (2H, m), 2.66 (1H, d, J=12.6 Hz), 2.78 (1H, d, J=12.6 Hz), 3.55-3.86 (4H, m), 7.20-7.38 (5H, m).

Reference Example 33

N-[2-(benzylthio)-4-hydroxy-2-methylbutyl]-7-[methyl(2-thienylsulfonyl)amino]-1H-indole-2-carboxamide

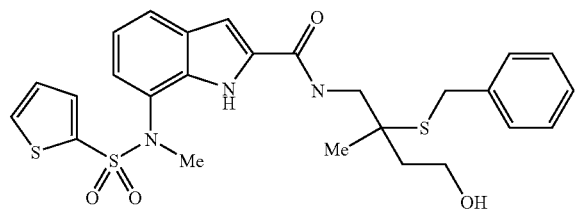

To a mixture of 7-[methyl(2-thienylsulfonyl)amino]-1H-indole-2-carboxylic acid (2.00 g), 4-amino-3-(benzylthio)-3-methylbutan-1-ol (1.61 g), 1H-1,2,3-benzotriazol-1-ol (0.96 g) and N,N-dimethylformamide (20 ml) was added N-[3-(dimethylamino)propyl]-N'-ethylcarbodiimide hydrochloride (1.37 g) at room temperature, and the mixture was stirred at room temperature for 5 hr. Water was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (2.10 g, yield 65%) as colorless crystals from a fraction eluted with ethyl acetate. melting point 132-133° C.

Reference Example 34

4-[3-(benzylthio)-3-methyl-4-nitrobutyl]morpholine

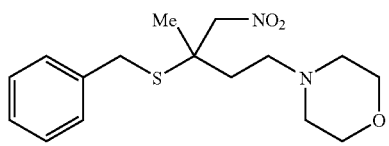

A mixture of 3-buten-2-one (2.00 ml) and morpholine (2.35 ml) was stirred at room temperature for 30 min (exothermic reaction). Benzylmercaptan (3.20 ml), nitromethane (13.2 ml), ethylenediamine (1.8 ml) and acetonitrile (10 ml) were added to the reaction mixture, and the mixture was stirred overnight at room temperature. The reaction mixture was concentrated, and the obtained residue was subjected to silica gel column chromatography to give the title compound (3.27 g, yield 41%) as a yellow oil from a fraction eluted with ethyl acetate.

$^1$H-NMR (CDCl$_3$) δ: 1.50 (3H, s), 1.82-2.20 (2H, m), 2.38-2.70 (6H, m), 3.69 (4H, t, J=4.7 Hz), 3.75 (1H, d, J=12.2 Hz), 3.80 (1H, d, J=12.2 Hz), 4.48 (1H, d, J=11.1 Hz), 4.61 (1H, d, J=11.1 Hz), 7.22-7.35 (5H, m).

Reference Example 35

2-(benzylthio)-2-methyl-4-(morpholino)butan-1-amine

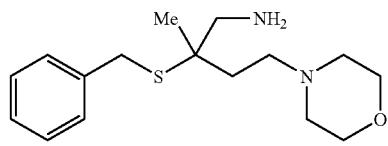

In the same manner as in Reference Example 32, the title compound (2.90 g, yield 98%) was obtained as a yellow oil from 4-[3-(benzylthio)-3-methyl-4-nitrobutyl]morpholine (3.27 g).

$^1$H-NMR (CDCl$_3$) δ: 1.26 (3H, s), 1.58-1.82 (2H, m), 2.37-2.59 (6H, m), 2.62 (1H, d, J=13.8 Hz), 2.68 (1H, d, J=13.8 Hz), 3.60-3.80 (6H, m), 7.18-7.38 (5H, m).

Reference Example 36

N-[2-(benzylthio)-2-methyl-4-(morpholino)butyl]-7-[methyl(2-thienylsulfonyl)amino]-1H-indole-2-carboxamide

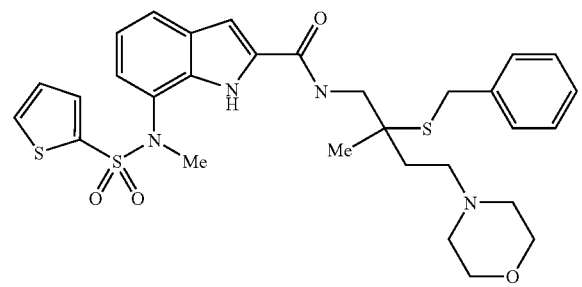

In the same manner as in Reference Example 33, the title compound (1.39 g, yield 76%) was obtained as yellow amorphous crystals from 7-[methyl(2-thienylsulfonyl)amino]-1H-indole-2-carboxylic acid (1.00 g) and 2-(benzylthio)-2-methyl-4-(morpholino)butan-1-amine (1.00 g). MS: 613 (MH$^+$).

Reference Example 37

({[2,2-dimethoxy-1-methyl-1-(nitromethyl)ethyl]thio}methyl)benzene

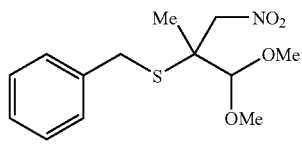

A mixture of 1,1-dimethoxyacetone (5.00 ml), benzylmercaptan (5.50 ml), nitromethane (23 ml), ethylenediamine (3.00 ml) and acetonitrile (15 ml) was stirred at room temperature, and then overnight at 80° C. The reaction mixture was concentrated, and the obtained residue was subjected to silica gel column chromatography to give the title compound (5.81 g, yield 48%) as a colorless oil from a fraction eluted with ethyl acetate-hexane (1:6, volume ratio).

$^1$H-NMR (CDCl$_3$) δ: 1.46 (3H, s), 3.57 (3H, s), 3.58 (3H, s), 3.91 (1H, d, J=11.4 Hz), 3.96 (1H, d, J=11.4 Hz), 4.39 (1H, s), 4.64 (1H, d, J=11.4 Hz), 4.69 (1H, d, J=11.4 Hz), 7.19-7.35 (5H, m).

Reference Example 38

2-(benzylthio)-3,3-dimethoxy-2-methylpropan-1-amine

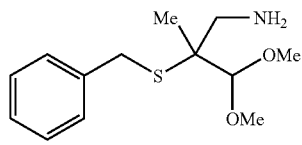

In the same manner as in Reference Example 32, the title compound (4.69 g, yield 90%) was obtained as a yellow oil from ({[2,2-dimethoxy-1-methyl-1-(nitromethyl)ethyl]thio}methyl)benzene (5.81 g).

$^1$H-NMR (CDCl$_3$) δ: 1.46 (3H, s), 2.77 (1H, d, J=13.6 Hz), 2.88 (1H, d, J=13.6 Hz), 3.54 (3H, s), 3.56 (3H, s), 3.80 (1H, d, J=12.2 Hz), 3.85 (1H, d, J=12.2 Hz), 4.27 (1H, s), 7.18-7.37 (5H, m).

Reference Example 39

N-[2-(benzylthio)-3,3-dimethoxy-2-methylpropyl]-7-[methyl(2-thienylsulfonyl)amino]-1H-indole-2-carboxamide

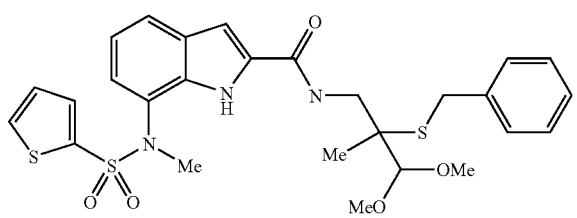

In the same manner as in Reference Example 33, the title compound (3.87 g, yield 76%) was obtained as a yellow oil from 7-[methyl(2-thienylsulfonyl)amino]-1H-indole-2-carboxylic acid (3.00 g) and 2-(benzylthio)-3,3-dimethoxy-2-methylpropan-1-amine (2.73 g).

$^1$H-NMR (CDCl$_3$) δ: 1.35 (3H, s), 3.33 (3H, s), 3.60 (3H, s), 3.61 (3H, s), 3.69 (1H, dd, J=13.8, 5.4 Hz), 3.79 (1H, dd, J=13.8, 5.4 Hz), 3.86 (1H, d, J=12.3 Hz), 4.25 (1H, s), 6.61 (1H, d, J=7.8 Hz), 6.74 (1H, d, J=2.1 Hz), 6.89 (1H, t, J=5.4 Hz), 6.99 (1H, t, J=7.8 Hz), 7.11 (1H, dd, J=5.1, 3.9 Hz), 7.18-7.43 (6H, m), 7.59 (1H, d, J=7.8 Hz), 7.63 (1H, dd, J=5.1, 1.5 Hz), 9.49 (1H, brs).

Reference Example 40

N-[2-(benzylthio)-2-methyl-3-oxopropyl]-7-[methyl(2-thienylsulfonyl)amino]-1H-indole-2-carboxamide

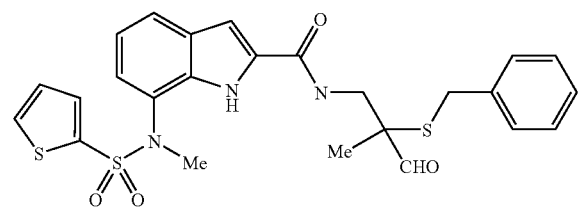

A mixture of N-[2-(benzylthio)-3,3-dimethoxy-2-methylpropyl]-7-[methyl(2-thienylsulfonyl)amino]-1H-indole-2-carboxamide (1.00 g), Amberlyst (registered trade mark) 15 ion exchange resin (0.20 g), water (0.1 ml) and acetone (10 ml) was stirred overnight at room temperature. The insoluble substance was removed by filtration, and the filtrate was concentrated to give the title compound (0.83 g, yield 92%) as colorless crystals. melting point 149-150° C.

Reference Example 41

N-[2-(benzylthio)-2-methyl-3-morpholinopropyl]-7-[methyl(2-thienylsulfonyl)amino]-1H-indole-2-carboxamide To a mixture of N-[2-(benzylthio)-2-methyl-3-oxopropyl]-7-[methyl(2-thienylsulfonyl)amino]-1H-indole-2-carboxamide (0.40 g), morpholine (0.13 ml) and 1,2-dichloroethane (4 ml) was added sodium triacetoxyborohydride (0.36 g) at 0° C., and the mixture was stirred at room temperature for 4 hr. Saturated aqueous sodium hydrogencarbonate was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (0.25 g, yield 55%) as colorless crystals from a fraction eluted with ethyl acetate-hexane (2:1, volume ratio). melting point 150-152° C.

Reference Example 42 tert-butyl 4-{2-(benzylthio)-2-methyl-3-[({7-[methyl (2-thienylsulfonyl)amino]-1H-indol-2-yl}carbonyl) amino]propyl}piperazine-1-carboxylate

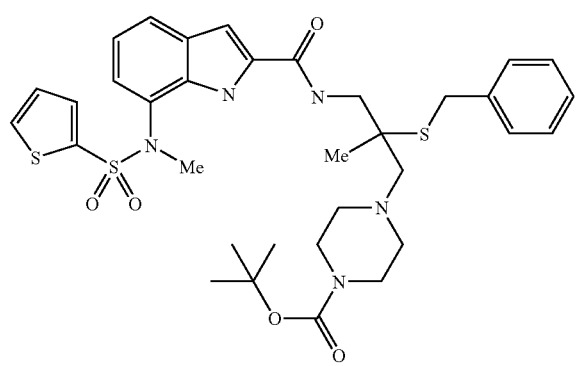

In the same manner as in Reference Example 41, the title compound (1.55 g, yield 64%) was obtained as colorless crystals from N-[2-(benzylthio)-2-methyl-3-oxopropyl]-7-[methyl(2-thienylsulfonyl)amino]-1H-indole-2-carboxamide (1.83 g) and tert-butyl piperazine-1-carboxylate (1.30 g). melting point 180-181° C.

Reference Example 43

N-[2-(benzylthio)-3-(hydroxyimino)-2-methylpropyl]-7-[methyl(2-thienylsulfonyl)amino]-1H-indole-2-carboxamide

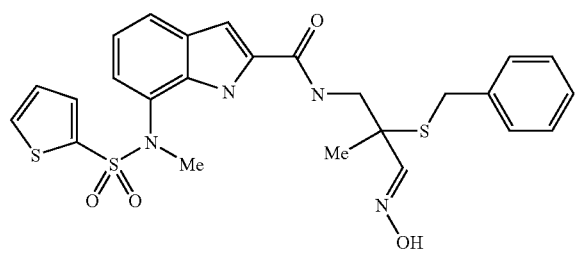

A mixture of N-[2-(benzylthio)-2-methyl-3-oxopropyl]-7-[methyl(2-thienylsulfonyl)amino]-1H-indole-2-carboxamide (1.00 g), hydroxylamine hydrochloride (0.26 g), potassium carbonate (0.52 g) and methanol (8 ml) was stirred at room temperature for 2 hr. Water was added to the reaction mixture, and the mixture was extracted with ethyl acetate. The ethyl acetate layer was washed with saturated brine, dried (MgSO$_4$), and concentrated to give the title compound (0.25 g, yield 55%) as colorless amorphous crystals. MS: 543 (MH$^+$).

Reference Example 44

N-[2-(benzylthio)-2-cyanopropyl]-7-[methyl(2-thienylsulfonyl)amino]-1H-indole-2-carboxamide

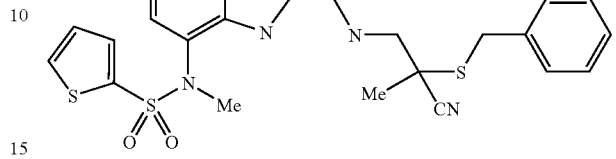

To a mixture of N-[2-(benzylthio)-3-(hydroxyimino)-2-methylpropyl]-7-[methyl(2-thienylsulfonyl)amino]-1H-indole-2-carboxamide (1.00 g) and pyridine (6 ml) was added trifluoromethanesulfonic anhydride (0.40 ml) at 0° C., and the mixture was stirred overnight at room temperature. The reaction mixture was concentrated, 10% aqueous citric acid solution was added to the residue, and the mixture was extracted with ethyl acetate. The ethyl acetate layer was washed with saturated brine, dried (MgSO$_4$), and concentrated. The residue was subjected to basic silica gel column chromatography to give the title compound (0.43 g, yield 45%) as colorless crystals from a fraction eluted with ethyl acetate-hexane (1:2, volume ratio). melting point 181-182° C.

Reference Example 45

N-[(1-benzyl-4-hydroxypiperidin-4-yl)methyl]-7-[methyl(2-thienylsulfonyl)amino]-1H-indole-2-carboxamide

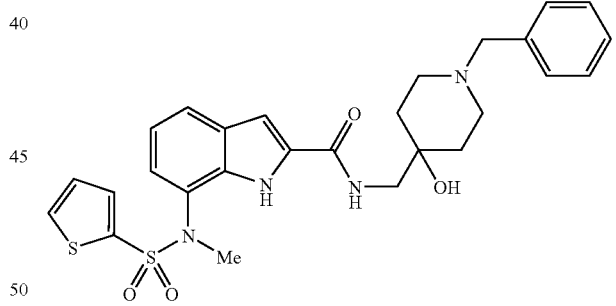

To a solution of 7-[methyl(2-thienylsulfonyl)amino]-1H-indole-2-carboxylic acid in N,N-dimethylformamide (30 ml) were added 1H-1,2,3-benzotriazol-1-ol (0.738 g), N-[3-(dimethylamino)propyl]-N'-ethylcarbodiimide hydrochloride (0.520 g) and 4-(aminomethyl)-1-benzylpiperidin-4-ol (1.06 g), and the mixture was stirred at room temperature for 24 hr. Saturated aqueous sodium hydrogencarbonate solution was added to the reaction solution, and the mixture was extracted with ethyl acetate. The extract was washed with saturated brine, dried over anhydrous magnesium sulfate, and concentrated under reduced pressure. The residue was purified by silica gel column chromatography (ethyl acetate:methanol=100:0-95:5) to give the title compound (1.32 g, yield 76%) as a colorless amorphous solid.

MS m/z 539 (M+H$^+$).

Reference Example 46

({[2,2-dimethoxy-1-(nitromethyl)ethyl]thio}methyl)benzene

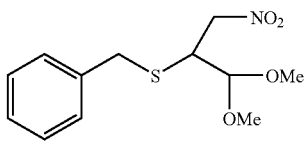

A solution of (1E)-3,3-dimethoxy-1-nitroprop-1-ene (3.03 g, prepared according to Terahedron 2002, 58, 5773-5778), benzylmercaptan (2.54 ml) and piperidine (0.25 ml) in toluene (20 ml) was stirred at room temperature for 48 hr. Water was added to the reaction solution, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=0:100-20:80) to give the title compound (4.78 g, yield 86%) as a yellow oil.

$^1$H-NMR (CDCl$_3$) δ: 3.27 (3H, s), 3.37 (3H, s), 3.39-3.47 (1H, m), 3.74-3.87 (2H, m), 4.19 (1H, d, J=3.8 Hz), 4.38 (1H, dd, J=13.8, 7.9 Hz), 4.68 (1H, dd, J=13.8, 5.7 Hz), 7.24-7.37 (5H, m)

Reference Example 47

2-(benzylthio)-3,3-dimethoxypropan-1-amine

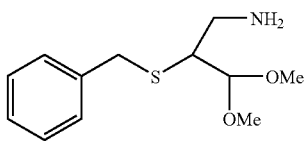

To a suspension of lithium aluminum hydride (13.0 g) in tetrahydrofuran (60 ml) was added dropwise a solution (76 ml) of ({[2,2-dimethoxy-1-(nitromethyl)ethyl]thio}methyl)benzene (18.6 g) in tetrahydrofuran at 0° C. The reaction mixture was allowed to warm to room temperature, and stirred at room temperature for 1 hr. Water and 2N aqueous sodium hydroxide solution were added to the reaction solution, and the mixture was diluted with ethyl acetate. The mixture was filtrated through celite, and the filtrate was concentrated under reduced pressure. The residue was purified by basic silica gel column chromatography (ethyl acetate:hexane=30:70-100:0) to give the title compound (12.6 g, yield 76%) as a yellow oil.

$^1$H-NMR (CDCl$_3$) δ: 2.63-2.78 (2H, m), 2.86-2.94 (1H, m), 3.37 (3H, s), 3.38 (3H, s), 3.75-3.87 (2H, m), 4.31 (1H, d, J=5.5 Hz), 7.20-7.40 (5H, m).

Reference Example 48

N-[2-(benzylthio)-3,3-dimethoxypropyl]-7-[methyl(2-thienylsulfonyl)amino]-1H-indole-2-carboxamide

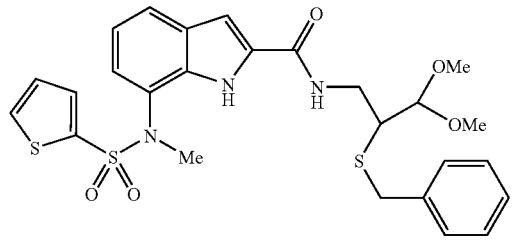

To a solution of 7-[methyl(2-thienylsulfonyl)amino]-1H-indole-2-carboxylic acid (0.662 g) in N,N-dimethylformamide (20 ml) were added 1H-1,2,3-benzotriazol-1-ol (0.414 g), N-[3-(dimethylamino)propyl]-N'-ethylcarbodiimide hydrochloride (0.292 g) and 2-(benzylthio)-3,3-dimethoxypropan-1-amine (0.500 g), and the mixture was stirred at room temperature for 15 hr. Water was added to the reaction solution, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=10:90-60:40) to give the title compound (0.776 g, yield 70%) as a colorless amorphous solid.

$^1$H-NMR (CDCl$_3$) δ: 2.87-2.97 (1H, m), 3.33 (3H, s), 3.39 (3H, s), 3.47 (3H, s), 3.54-3.64 (1H, m), 3.78-3.89 (3H, m), 4.35 (1H, d, J=4.3 Hz), 6.59-6.64 (1H, m), 6.72-6.82 (2H, m), 6.96-7.03 (1H, m), 7.09-7.14 (1H, m), 7.16-7.22 (1H, m), 7.24-7.31 (2H, m), 7.32-7.38 (2H, m), 7.39-7.42 (1H, m), 7.56-7.67 (2H, m), 9.48 (1H, s).

Reference Example 49

N-[2-(benzylthio)-3-oxopropyl]-7-[methyl(2-thienylsulfonyl)amino]-1H-indole-2-carboxamide

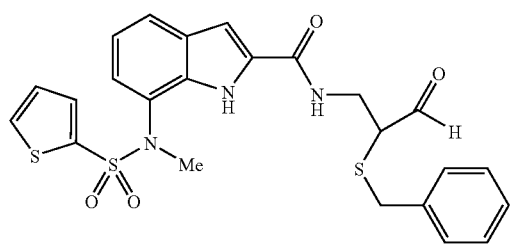

In the same manner as in Reference Example 40, the title compound (0.490 g, yield 95%) was obtained as a colorless amorphous solid from N-[2-(benzylthio)-3,3-dimethoxypropyl]-7-[methyl(2-thienylsulfonyl)amino]-1H-indole-2-carboxamide (0.560 g).

MS m/z 514 (M+H$^+$).

Reference Example 50

N-[2-(benzylthio)-3-(morpholino)propyl]-7-[methyl(2-thienylsulfonyl)amino]-1H-indole-2-carboxamide

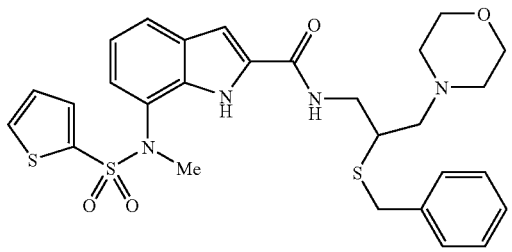

In the same manner as in Reference Example 41, the title compound (0.218 g, yield 81%) was obtained as a colorless amorphous solid from N-[2-(benzylthio)-3-oxopropyl]-7-[methyl(2-thienylsulfonyl)amino]-1H-indole-2-carboxamide (0.235 g) and morpholine (0.08 ml).
MS m/z 585 (M+H$^+$).

Reference Example 51

N-[2-(benzylthio)-3-(3,3-difluoropiperidino)propyl]-7-[methyl(2-thienylsulfonyl)amino]-1H-indole-2-carboxamide

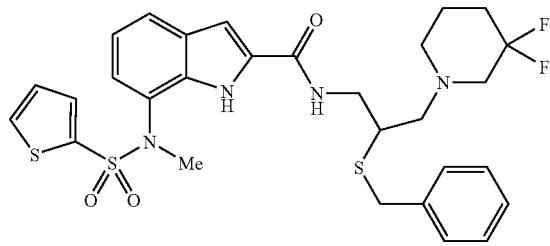

In the same manner as in Reference Example 41, the title compound (0.160 g, yield 66%) was obtained as a colorless amorphous solid from N-[2-(benzylthio)-3-oxopropyl]-7-[methyl(2-thienylsulfonyl)amino]-1H-indole-2-carboxamide (0.200 g) and 3,3-difluoropiperidine (0.122 g).
MS m/z 619 (M+H$^+$).

Reference Example 52 tert-butyl 4-{2-(benzylthio)-3-[({7-[methyl(2-thienylsulfonyl)amino]-1H-indol-2-yl}carbonyl)amino]propyl}piperazine-1-carboxylate

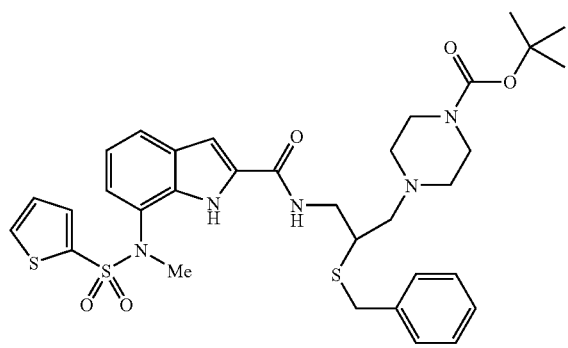

In the same manner as in Reference Example 41, the title compound (0.330 g, yield 100%) was obtained as a colorless amorphous solid from N-[2-(benzylthio)-3-oxopropyl]-7-[methyl(2-thienylsulfonyl)amino]-1H-indole-2-carboxamide (0.250 g) and tert-butyl piperazine-1-carboxylate (0.181 g).
MS m/z 684 (M+H$^+$).

Reference Example 53

N-[2-(benzylthio)-2-cyanoethyl]-7-[methyl(2-thienylsulfonyl)amino]-1H-indole-2-carboxamide

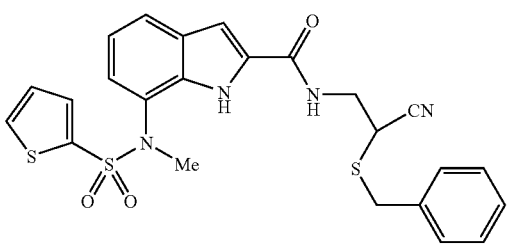

In the same manners as in Reference Example 43 and Reference Example 44, the title compound (3.60 g, yield in two steps 48%) was obtained as a colorless amorphous solid from N-[2-(benzylthio)-3-oxopropyl]-7-[methyl(2-thienylsulfonyl)amino]-1H-indole-2-carboxamide (7.50 g) and hydroxylamine hydrochloride (2.08 g).
MS m/z 511 (M+H$^+$).

Reference Example 54

8-benzylhexahydropyrazino[2,1-c][1,4]oxazin-4(3H)-one

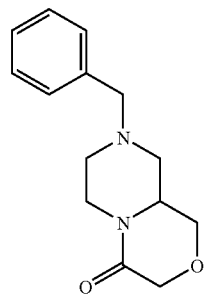

To a mixture of (4-benzylpiperazin-2-yl)methanol (6.4 g, 30 mmol) prepared according to J. Med. Chem. 1993, 36, 2075-2083, water (100 ml) and tetrahydrofuran (100 ml) were successively added potassium carbonate (8.3 g, 60 mmol) with chloroacetyl chloride (3.6 mL, 45 mmol), and the mixture was stirred at room temperature for 12 hr. The reaction mixture was concentrated under reduced pressure, and the residue was partitioned between ethyl acetate and water. The organic layer was washed with saturated brine, dried over anhydrous magnesium sulfate, and concentrated under reduced pressure. The residue was dissolved in ethanol (100 ml), potassium hydroxide (2 g) was added, and the mixture was stirred at 50° C. for 3 hr. The reaction mixture was concentrated under reduced pressure, and the residue was partitioned between ethyl acetate and water. The organic layer was washed with saturated brine, dried over anhydrous magnesium sulfate, and concentrated under reduced pressure to give the title compound (2.6 g, yield 35%) as a yellow oil. MS 247 (M+1).

Reference Example 55 hexahydropyrazino[2,1-c][1,4]oxazin-4(3H)-one hydrochloride

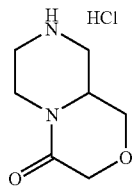

To a solution of 8-benzylhexahydropyrazino[2,1-c][1,4]oxazin-4(3H)-one (2.6 g, 10.5 mmol) in methanol (50 ml) were added ammonium formate (3.0 g) and 10% palladium-carbon (50% containing water, 1.5 g), and the mixture was stirred at 80° C. for 15 min. The reaction mixture was allowed to cool to room temperature, and the palladium-carbon was removed by filtration. The filtrate was concentrated under reduced pressure, and 4N hydrogen chloride-ethyl acetate solution was added to the residue. The precipitated crystals were collected by filtration, washed with ethyl acetate, and dried under reduced pressure to give the title compound (1.8 g, yield 93%) as a pale-yellow powder. MS 157 (M+1).

Reference Example 56

7-benzylhexahydro[1,3]oxazolo[3,4-a]pyrazin-3-one

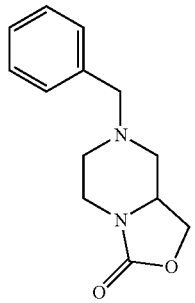

A mixture of (4-benzylpiperazin-2-yl)methanol (2.8 g, 10 mmol) prepared according to J. Med. Chem. 1993, 36, 2075-2083 and 1,1'-carbonylbis(1H-imidazole) (3.2 g), triethylamine (2.8 ml) and tetrahydrofuran (30 ml) was stirred at 80° C. for 1 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (1.5 g, yield 65%) as a colorless oil from a fraction eluted with ethyl acetate. MS 233 (M+1).

Reference Example 57 hexahydro[1,3]oxazolo[3,4-a]pyrazin-3-one hydrochloride

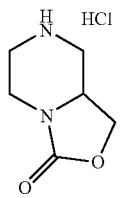

To a solution of 7-benzylhexahydro[1,3]oxazolo[3,4-a]pyrazin-3-one (1.5 g) in methanol (25 ml) were added ammonium formate (2.0 g) and 10% palladium-carbon (50% containing water, 1.0 g), and the mixture was stirred at 80° C. for 10 min. The reaction mixture was allowed to cool to room temperature, and the palladium-carbon was removed by filtration. The filtrate was concentrated under reduced pressure, and 4N hydrogen chloride-ethyl acetate solution was added to the residue. The precipitated crystals were collected by filtration, washed with ethyl acetate, and dried under reduced pressure to give the title compound (1.0 g, yield 87%) as a pale-yellow powder. MS 143 (M+1).

Reference Example 58

4-(benzylthio)-4-(nitromethyl)tetrahydro-2H-pyran

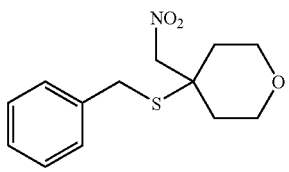

A mixture of tetrahydro-4H-pyran-4-one (10.3 g), benzylmercaptan (25.6 g), nitromethane (62.8 g), ethylenediamine (6.18 g) and acetonitrile (150 ml) was heated overnight under reflux. The reaction mixture was concentrated, and the obtained residue was subjected to silica gel column chromatography to give the title compound (17.6 g, yield 67%) as colorless crystals from a fraction eluted with ethyl acetate-hexane (3:1, volume ratio).

$^1$H-NMR (CDCl$_3$) δ: 1.63-2.05 (4H, m), 3.70-4.03 (6H, m), 4.51 (2H, s), 7.20-7.45 (5H, m).

Reference Example 59 tert-butyl 4-(benzylthio)-4-(nitromethyl)piperidine-1-carboxylate

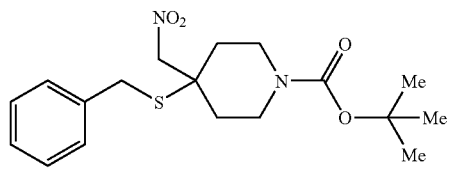

In the same manner as in Reference Example 58, the title compound (1.3 g, yield 71%) was obtained as colorless crystals from tert-butyl 4-oxopiperidine-1-carboxylate (1.00 g), benzylmercaptan (2.48 g), nitromethane (3.05 g) and ethylenediamine (0.3 g).

$^1$H-NMR (CDCl$_3$) δ: 1.45 (9H, s), 1.79 (4H, q, J=3.7 Hz), 3.13-3.37 (2H, m), 3.72 (2H, m), 3.80-4.00 (2H, m), 4.51 (2H, s), 7.20-7.45 (5H, m).

Reference Example 60

1-[4-(benzylthio)tetrahydro-2H-pyran-4-yl]methanamine

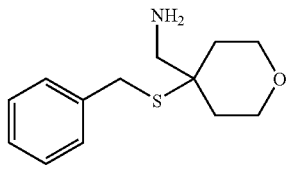

To a mixture of lithium aluminum hydride (2.23 g) and diethyl ether (120 ml) was added a solution of 4-(benzylthio)-4-(nitromethyl)tetrahydro-2H-pyran (5.35 g) in diethyl ether (30 ml) and tetrahydrofuran (15 ml) at 0° C., and the reaction mixture was stirred at 50° C. for 2 hr. The reaction mixture was ice-cooled, sodium sulfate 10 hydrate (19.33 g) was added, and the mixture was stirred overnight at room temperature. The reaction mixture was dried (MgSO$_4$), and the inorganic salt was removed by filtration. The filtrate was concentrated, and the obtained residue was subjected to silica gel column chromatography to give the title compound (3.20 g, yield 67%) as a yellow oil from a fraction eluted with ethyl acetate-methanol (3:1, volume ratio).

$^1$H-NMR (CDCl$_3$) δ: 1.40-1.80 (4H, m), 2.68 (2H, s), 3.60 (2H, s), 3.66-4.00 (4H, m), 7.18-7.45 (5H, m).

Reference Example 61 tert-butyl 4-(aminomethyl)-4-(benzylthio)piperidine-1-carboxylate

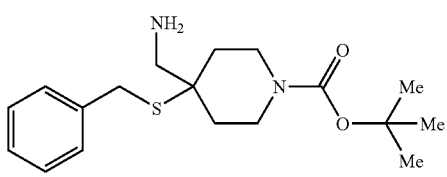

To a mixture of lithium aluminum hydride (0.4 g) and diethyl ether (20 ml) was added a solution of tert-butyl 4-(benzylthio)-4-(nitromethyl)piperidine-1-carboxylate (1.28 g) in diethyl ether (5 ml) at 0° C. The reaction mixture was heated under reflux for 1 hr. The excess lithium aluminum hydride was decomposed with ethyl acetate, and water was added. The reaction mixture was diluted with a mixed solvent of tetrahydrofuran and ethyl acetate, and the inorganic salt was removed by filtration. The filtrate was washed with saturated brine, dried (MgSO$_4$), and concentrated, and the obtained residue was subjected to silica gel column chromatography to give the title compound (0.33 g, yield 28%) as a colorless oil from a fraction eluted with ethyl acetate-methanol (2:1, volume ratio).

$^1$H-NMR (CDCl$_3$) δ: 1.35-1.80 (13H, s), 2.66 (2H, s), 3.17-3.37 (2H, m), 3.60 (2H, s), 3.65-3.92 (2H, m), 7.16-7.45 (5H, m).

Reference Example 62

N-{[4-(benzylthio)tetrahydro-2H-pyran-4-yl]methyl}-7-[methyl(2-thienylsulfonyl)amino]-1H-indole-2-carboxamide

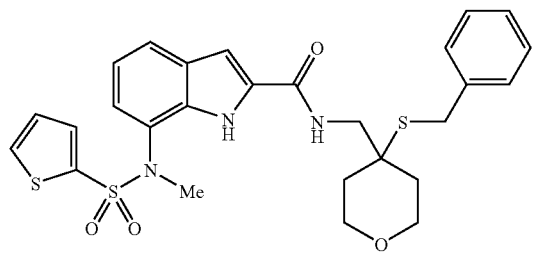

A mixture of 7-[methyl(2-thienylsulfonyl)amino]-1H-indole-2-carboxylic acid (0.50 g), 1-[4-(benzylthio)tetrahydro-2H-pyran-4-yl]methanamine (0.39 g), 1H-1,2,3-benzotriazol-1-ol (0.20 g), N-[3-(dimethylamino)propyl]-N'-ethylcarbodiimide hydrochloride (0.34 g), tetrahydrofuran (10 ml) and acetonitrile (3 ml) was stirred overnight at room temperature. Saturated aqueous sodium hydrogencarbonate was added to the reaction mixture, and the mixture was extracted with ethyl acetate. The ethyl acetate layer was washed with saturated brine, dried (NaSO$_4$), and concentrated. The residue was subjected to silica gel column chromatography to give the title compound (764 mg, yield 92%) as colorless crystals from a fraction eluted with ethyl acetate.

$^1$H-NMR (CDCl$_3$) δ: 1.73-1.86 (4H, m), 3.33 (3H, s), 3.56 (2H, d, J=5.9 Hz), 3.71-3.81 (4H, s), 3.83-3.92 (2H, m), 6.55-6.63 (2H, m), 6.80 (1H, d, J=2.0 Hz), 7.01 (1H, t, J=7.78 Hz), 7.10-7.14 (1H, m), 7.23-7.43 (6H, m), 7.61 (1H, d, J=7.8 Hz), 7.64 (1H, d, J=4.9 Hz), 9.50 (1H, s).

Reference Example 63 tert-butyl 4-(benzylthio)-4-{[({7-[methyl(2-thienylsulfonyl)amino]-1H-indol-2-yl}carbonyl)amino]methyl}piperidine-1-carboxylate

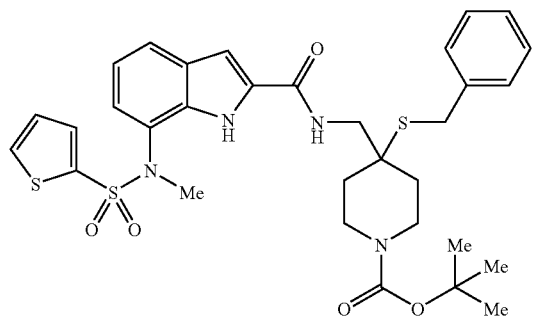

A mixture of 7-[methyl(2-thienylsulfonyl)amino]-1H-indole-2-carboxylic acid (0.30 g), tert-butyl 4-(aminomethyl)-4-(benzylthio)piperidine-1-carboxylate (0.33 g), 1H-1,2,3-benzotriazol-1-ol (0.13 g), N-[3-(dimethylamino)propyl]-N'-ethylcarbodiimide hydrochloride (0.22 g) and tetrahydrofuran (6 ml) was stirred overnight at room temperature. Saturated aqueous sodium hydrogencarbonate was added to the reaction mixture, and the mixture was extracted

Reference Example 64 ethyl 1-(methoxymethyl)-4-methyl-7-nitro-1H-indole-2-carboxylate

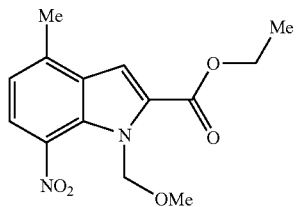

A mixture of ethyl 4-methyl-7-nitro-1H-indole-2-carboxylate (7.0 g), 60% sodium hydride (1.35 g) and N,N-dimethylformamide (40 ml) was stirred at room temperature for 30 min. This solution was ice-cooled, and a solution of chloromethyl methyl ether (2.6 ml) in tetrahydrofuran (15 ml) was added dropwise. The mixture was stirred at 4° C. for 4 hr, and the reaction solution was diluted with ethyl acetate, washed with saturated brine, aqueous citric acid solution and water, dried over anhydrous magnesium sulfate, and concentrated under reduced pressure. The obtained residue was subjected to silica gel column chromatography (ethyl acetate:hexane=5:95-1:5) to give the title compound (5.6 g, yield 68%) as pale-yellow needle crystals.

$^1$H-NMR (CDCl$_3$) δ: 1.44 (3H, t, J=7.2 Hz), 2.65 (3H, s), 2.92 (3H, s), 4.42 (2H, q, J=7.2 Hz), 6.04 (2H, s), 7.05 (1H, dd, J=8.0, 0.8 Hz), 7.49 (1H, s), 7.82 (1H, d, J=8.0 Hz).

Reference Example 65 ethyl 1-(methoxymethyl)-4-methyl-7-[(2-thienylsulfonyl)amino]-1H-indole-2-carboxylate

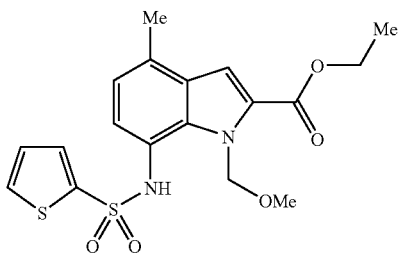

Ethyl 1-(methoxymethyl)-4-methyl-7-nitro-1H-indole-2-carboxylate (5.6 g) and 10% palladium-carbon (50% containing water, 1.25 g) were added to a mixed solvent of tetrahydrofuran (70 ml) and ethanol (70 ml), and the mixture was stirred at room temperature for 5 hr under hydrogen atmosphere. The catalyst was filtered off, and the filtrate was concentrated under reduced pressure.

The obtained residue was dissolved in pyridine (50 ml), and thiophene-2-sulfonyl chloride (4.0 g) was added under ice-cooling, and the mixture was stirred at room temperature for 18 hr. The reaction solution was concentrated under reduced pressure, and the residue was diluted with ethyl acetate. The mixture was washed with aqueous citric acid solution and brine, dried over anhydrous magnesium sulfate, and concentrated under reduced pressure. The obtained residue was subjected to silica gel column chromatography (ethyl acetate:hexane=1:9-1:3) to give the title compound (8.4 g, yield 100%) as a pale-yellow oil.

$^1$H-NMR (CDCl$_3$) δ: 1.41 (3H, t, J=7.0 Hz), 2.52 (3H, s), 3.41 (3H, s), 4.35 (2H, q, J=7.0 Hz), 5.69 (2H, s), 6.92-7.02 (2H, m), 7.34 (1H, s), 7.44-7.52 (3H, m), 8.65 (1H, brs).

Reference Example 66 ethyl 1-(methoxymethyl)-4-methyl-7-[methyl(2-thienylsulfonyl)amino]-1H-indole-2-carboxylate

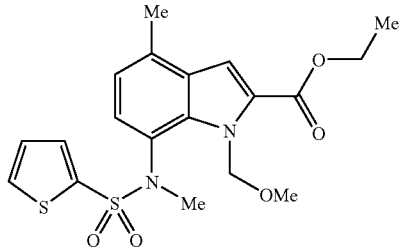

A mixture of ethyl 1-(methoxymethyl)-4-methyl-7-[(2-thienylsulfonyl)amino]-1H-indole-2-carboxylate (7.8 g), methyl iodide (1.7 ml), potassium carbonate (2.9 g) and N,N-dimethylformamide (14 ml) was stirred at room temperature for 18 hr. The reaction solution was concentrated under reduced pressure, and the obtained residue was diluted with ethyl acetate. The mixture was washed with aqueous citric acid solution, water and saturated brine, dried over anhydrous magnesium sulfate, and concentrated under reduced pressure. The obtained colorless crystals were washed with diethyl ether-hexane to give the title compound (6.85 g, yield 85%) as colorless needle crystals.

$^1$H-NMR (CDCl$_3$) δ: 1.42 (3H, t, J=7.0 Hz), 2.54 (3H, s), 3.29 (3H, s), 3.35 (3H, s), 4.40 (2H, q, J=7.0 Hz), 6.33 (1H, d, J=9.8 Hz), 6.43 (1H, d, J=9.8 Hz), 6.45 (1H, d, J=7.8 Hz), 6.78 (1H, dd, J=7.8, 0.8 Hz), 7.16 (1H, dd, J=5.0, 4.0 Hz), 7.40 (1H, s), 7.47 (1H, dd, J=4.0, 1.4 Hz), 7.67 (1H, dd, J=5.0, 1.4 Hz).

Reference Example 67 4-methyl-7-[methyl(2-thienylsulfonyl)amino]-1H-indole-2-carboxylic acid

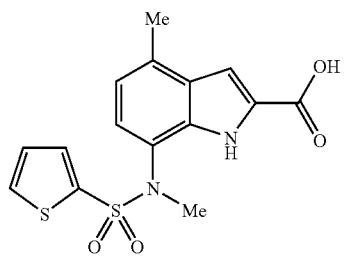

A solution of ethyl 1-(methoxymethyl)-4-methyl-7-[methyl(2-thienylsulfonyl)amino]-1H-indole-2-carboxylate (4.0 g), 6N hydrochloric acid (20 ml), tetrahydrofuran (20 ml) and ethanol (60 ml) was stirred at 80° C. for 4 hr. The reaction solution was concentrated under reduced pressure, and the obtained residue was diluted with ethyl acetate. The mixture was washed with saturated brine, dried over anhydrous magnesium sulfate, and concentrated under reduced pressure. The obtained solid was dissolved in a mixed solvent of tetrahydrofuran (40 ml) and methanol (40 ml), an aqueous solution (20 ml) of 85% potassium hydroxide (2.2 g) was added to this solution, and the mixture was stirred at room temperature for 18 hr. The reaction solution was concentrated under reduced pressure, and the obtained residue was acidified with aqueous citric acid solution. The precipitated crystals were collected by filtration, washed with water, and dried to give the title compound (3.3 g, yield 99%) as colorless crystals. MS: 351 (MH$^+$). melting point 223-225° C.

Reference Example 68

4-methyl-7-[methyl(2-thienylsulfonyl)amino]-1H-indole-2-carboxamide

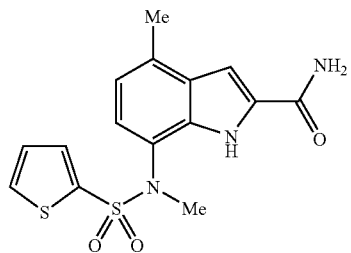

A mixture of 4-methyl-7-[methyl(2-thienylsulfonyl)amino]-1H-indole-2-carboxylic acid (2.2 g), 1H-1,2,3-benzotriazol-1-ol (1.2 g), N-[3-(dimethylamino)propyl]-N'-ethylcarbodiimide hydrochloride (1.5 g) and N,N-dimethylformamide (30 ml) was stirred at room temperature for 1 hr, and then at 60° C. for 1 hr. 28% Aqueous ammonia (2.0 ml) was added to the reaction solution, and the mixture was stirred at room temperature for 3 hr. The reaction solution was concentrated under reduced pressure, and the obtained residue was diluted with ethyl acetate. The mixture was washed with water, aqueous sodium hydrogencarbonate solution and saturated brine, dried over anhydrous magnesium sulfate, and concentrated under reduced pressure. The obtained oil was crystallized from ethyl acetate-hexane to give the title compound (1.84 g, yield 84%) as colorless prism crystals. melting point 221-222° C.

Reference Example 69 4-methyl-7-[methyl(2-thienylsulfonyl)amino]-1H-indole-2-carbothioamide

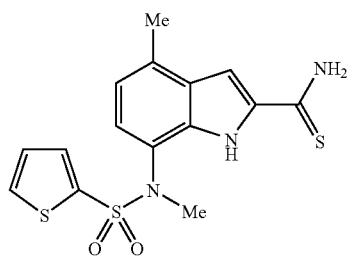

A mixture of 4-methyl-7-[methyl(2-thienylsulfonyl)amino]-1H-indole-2-carboxamide (1.78 g), Lawesson's reagent (2.26 g) and tetrahydrofuran (120 ml) was stirred at 60° C. for 2 hr. The reaction solution was concentrated under reduced pressure, and the obtained oil was crystallized from dichloromethane-toluene to give the title compound (1.56 g, yield 84%) as pale-yellow crystals. MS: 366 (MH$^+$).

Reference Example 70

N-{2-[5-(hydroxymethyl)-1,3-thiazol-2-yl]-4-methyl-1H-indol-7-yl}-N-methylthiophene-2-sulfonamide

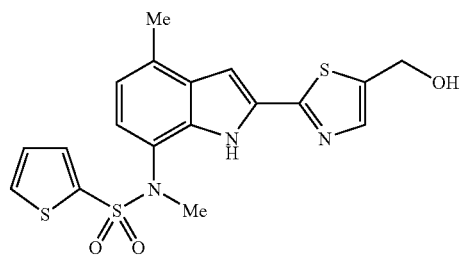

A solution of 4-methyl-7-[methyl(2-thienylsulfonyl)amino]-1H-indole-2-carbothioamide (0.95 g), bromomalonaldehyde (0.78 g) and N,N-dimethylacetamide (15 ml) was stirred at 80° C. for 3 hr. The reaction solution was diluted with ethyl acetate, washed twice with water, and concentrated under reduced pressure. The obtained residue was washed with toluene to give yellow crystals (857 mg). The mother liquor was concentrated, and the residue was subjected to silica gel column chromatography (ethyl acetate:hexane=1:2-1:1) to give yellow crystals (80 mg). The above-mentioned crystals were combined, dissolved in a mixed solvent of tetrahydrofuran (20 ml) and methanol (20 ml), and the solution was ice-cooled. Sodium borohydride (0.10 g) was added to this solution, and the mixture was stirred under ice-cooling for 2 hr. Aqueous citric acid solution was added to the reaction solution, and the organic solvent was evaporated under reduced pressure. The obtained residue was extracted with ethyl acetate, and the extract was washed with saturated brine, dried over anhydrous sodium sulfate, and concentrated under reduced pressure. The obtained residue was subjected to silica gel column chromatography (ethyl acetate:hexane=1:2-2:1-1:0), and washed with ethyl acetate-hexane to give the title compound (0.56 g, yield 60%) as pale-yellow crystals. melting point 184-185° C.

MS: 420 (MH$^+$).

Reference Example 71

N-{2-[5-(chloromethyl)-1,3-thiazol-2-yl]-4-methyl-1H-indol-7-yl}-N-methylthiophene-2-sulfonamide

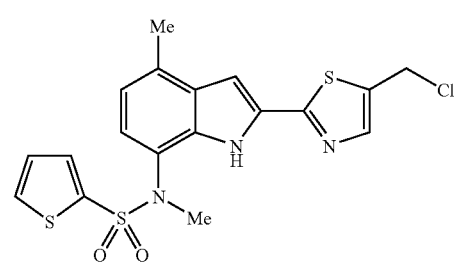

N-{2-[5-(Hydroxymethyl)-1,3-thiazol-2-yl]-4-methyl-1H-indol-7-yl}-N-methylthiophene-2-sulfonamide (0.55 g) was dissolved in absolute tetrahydrofuran (25 ml), and this solution was ice-cooled. Thionyl chloride (0.15 ml) and N,N-dimethylformamide (one drop) were added, and the mixture was stirred for 1 hr under ice-cooling, and then at room temperature for 7 hr. The reaction solution was diluted with ethyl acetate, washed with water and saturated brine, dried over anhydrous magnesium sulfate, and concentrated under reduced pressure. The obtained residue was subjected to silica gel column chromatography (ethyl acetate:hexane=1:1), and the obtained crystals were washed with ethyl acetate-hexane to give the title compound (0.427 g, yield 74%) as pale-yellow crystals. melting point 194-195° C.

Reference Example 72 ethyl 7-[ethyl(2-thienylsulfonyl)amino]-4-methyl-1H-indole-2-carboxylate

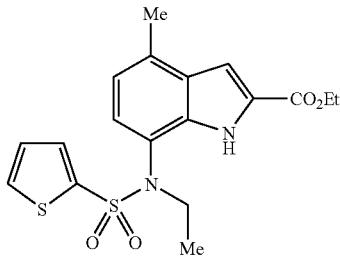

To a mixture of ethyl 7-[(2-thienylsulfonyl)amino]-4-methyl-1H-indole-2-carboxylate (2.89 g), potassium carbonate (1.2 g) and N,N-dimethylformamide (25 ml) was added dropwise a solution of ethyl iodide (0.67 ml) in N,N-dimethylformamide (2 ml) under ice-cooling. The mixture was stirred at room temperature for 2 days. The reaction solution was diluted with ethyl acetate, washed successively with aqueous citric acid solution, water and saturated brine, dried over anhydrous magnesium sulfate, and concentrated under reduced pressure. The obtained yellow oil was crystallized from ethyl acetate-hexane, and the obtained crystals were washed with ethyl acetate-hexane to give the title compound (2.16 g, yield 70%) as colorless prism crystals. melting point 148-149° C.
MS: 393 (MH$^+$).

Reference Example 73

7-[ethyl(2-thienylsulfonyl)amino]-4-methyl-1H-indole-2-carboxamide

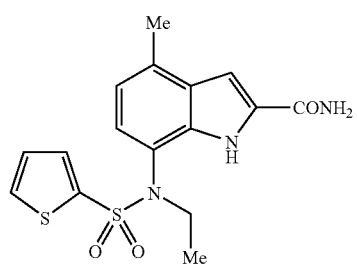

To a solution of ethyl 7-[ethyl(2-thienylsulfonyl)amino]-4-methyl-1H-indole-2-carboxylate (2.12 g) in tetrahydrofuran (15 ml)-methanol (15 ml) was added an aqueous solution (5 ml) of 85% potassium hydroxide (1.0 g), and the mixture was stirred at room temperature for 15 hr. The reaction solution was acidified with aqueous citric acid solution, and extracted with ethyl acetate. The extract was washed with water and saturated brine, dried over anhydrous magnesium sulfate, and concentrated under reduced pressure to give 7-[ethyl(2-thienylsulfonyl)amino]-4-methyl-1H-indole-2-carboxylic acid (2.0 g, yield quantitative) as a colorless amorphous solid. To a mixture of the obtained solid (2.0 g), 1H-1,2,3-benzotriazol-1-ol-ammonia complex (1.0 g) and N,N-dimethylformamide (20 ml) was added N-[3-(dimethylamino)propyl]-N'-ethylcarbodiimide hydrochloride (1.3 g) under ice-cooling, and the mixture was stirred at room temperature for 2 days. The reaction solution was diluted with ethyl acetate, and washed successively with aqueous sodium hydrogencarbonate solution, water and saturated brine, dried over anhydrous magnesium sulfate, and concentrated under reduced pressure. The obtained residue was subjected to silica gel column chromatography (ethyl acetate:hexane=1:1-3:1) to give the title compound (2.0 g, yield quantitative) as a colorless amorphous solid.
MS: 364 (MH$^+$).

Reference Example 74

N-ethyl-N-[2-(5-formyl-1,3-thiazol-2-yl)-4-methyl-1H-indol-7-yl]thiophene-2-sulfonamide

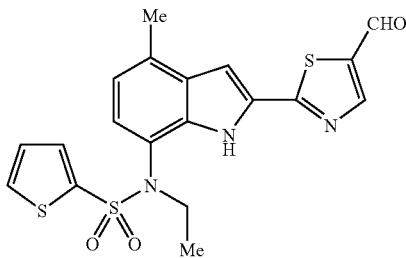

A mixture of 7-[ethyl(2-thienylsulfonyl)amino]-4-methyl-1H-indole-2-carboxamide (1.9 g), Lawesson's reagent (2.1 g) and tetrahydrofuran (100 ml) was stirred at 40° C. for 4 hr. The reaction solution was concentrated under reduced pressure, and the obtained oil was crystallized from dichloromethane-toluene, and washed with toluene to give 7-[ethyl (2-thienylsulfonyl)amino]-4-methyl-1H-indole-2-carbothioamide (2.0 g, yield quantitative) as pale-yellow crystals. A solution of the obtained crystals (2.0 g) and bromomalonaldehyde (2.4 g) in N,N-dimethylacetamide (50 ml) was stirred at 70° C. for 3 hr. The reaction solution was diluted with ethyl acetate, washed successively with water and saturated brine, dried over anhydrous magnesium sulfate, and concentrated under reduced pressure. The obtained oil was crystallized from dichloromethane-toluene to give the title compound (1.6 g, yield 70%) as pale-yellow crystals.
MS: 432 (MH$^+$).

Reference Example 75

N-ethyl-N-{2-[5-(hydroxymethyl)-1,3-thiazol-2-yl]-4-methyl-1H-indol-7-yl}thiophene-2-sulfonamide

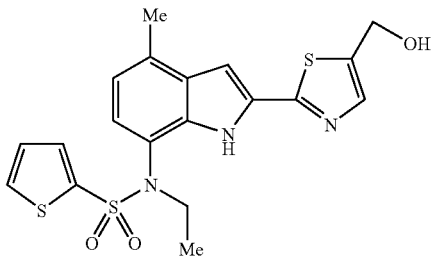

To a solution of N-ethyl-N-[2-(5-formyl-1,3-thiazol-2-yl)-4-methyl-1H-indol-7-yl]thiophene-2-sulfonamide (1.3 g) in a mixed solvent of methanol (15 ml) and tetrahydrofuran (40 ml) was added sodium borohydride (0.14 g) under ice-cooling, and the mixture was stirred at the same temperature for 2 hr. Aqueous citric acid solution was added to the reaction mixture, and the mixture was extracted with ethyl acetate. The extract was washed with saturated brine, dried over anhydrous magnesium sulfate, and concentrated under reduced pressure. The obtained crystals were washed with ethyl acetate-hexane to give the title compound (0.74 g) as pale-yellow crystals. The mother liquor was concentrated, and the residue was subjected to silica gel column chromatography (ethyl acetate:hexane=3:7-6:4) to give the title compound (0.20 g) as pale-yellow crystals. total yield 0.94 g (yield 72%). melting point 166-167° C.

MS: 434 (MH$^+$).

Reference Example 76

N-ethyl-N-{2-[5-(chloromethyl)-1,3-thiazol-2-yl]-4-methyl-1H-indol-7-yl}thiophene-2-sulfonamide

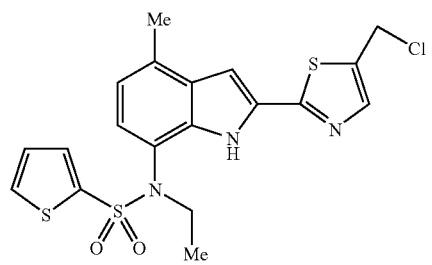

N-Ethyl-N-{2-[5-(hydroxymethyl)-1,3-thiazol-2-yl]-4-methyl-1H-indol-7-yl}thiophene-2-sulfonamide (0.27 g) was dissolved in absolute tetrahydrofuran (10 ml). This solution was ice-cooled, thionyl chloride (0.080 ml) and N,N-dimethylformamide (one drop) were added, and the mixture was stirred for 1 hr under ice-cooling, and then at room temperature for 2 hr. The reaction solution was diluted with ethyl acetate, washed with water and saturated brine, dried over anhydrous magnesium sulfate, and concentrated under reduced pressure. The obtained yellow oil was crystallized from ethyl acetate-hexane to give the title compound (0.26 g, yield 93%) as pale-yellow prism crystals. melting point 177-178° C.

Reference Example 77 ethyl 7-amino-4-chloro-1-(methoxymethyl)-1H-indole-2-carboxylate

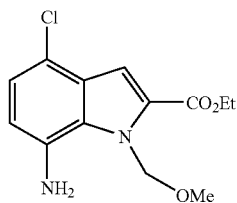

A mixture of ethyl 7-amino-1-(methoxymethyl)-1H-indole-2-carboxylate (3.18 g), N-chlorosuccinimide (1.74 g) and N,N-dimethylformamide (20 ml) was stirred overnight at room temperature. Water was added to the reaction mixture, and the mixture was extracted with ethyl acetate. The ethyl acetate layer was washed with saturated brine, dried (MgSO$_4$), and concentrated. The residue was subjected to silica gel column chromatography to give the title compound (0.91 g, yield 25%) as a yellow oil from a fraction eluted with ethyl acetate-hexane (1:4, volume ratio).

$^1$H-NMR (CDCl$_3$) δ: 1.42 (3H, t, J=7.2 Hz), 3.44 (3H, s), 4.37 (2H, q, J=7.2 Hz), 4.51 (2H, brs), 6.16 (2H, s), 6.50 (1H, d, J=8.1 Hz), 6.94 (1H, d, J=8.1 Hz), 7.36 (1H, s).

Reference Example 78 ethyl 4-chloro-1-(methoxymethyl)-7-[(2-thienylsulfonyl)amino]-1H-indole-2-carboxylate

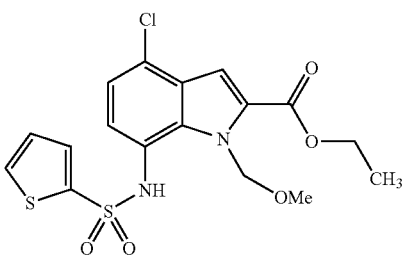

To a mixture of ethyl 7-amino-4-chloro-1-(methoxymethyl)-1H-indole-2-carboxylate (0.91 g) and pyridine (10 ml) was added thiophene-2-sulfonyl chloride (0.50 g) at 0° C., and the mixture was stirred overnight at room temperature. The reaction mixture was concentrated, 10% aqueous citric acid solution was added, and the mixture was extracted with ethyl acetate. The ethyl acetate layer was washed with saturated brine, dried (MgSO$_4$), and concentrated. The obtained residue was subjected to silica gel column chromatography to give the title compound (1.14 g, yield 83%) as a yellow oil from a fraction eluted with ethyl acetate-hexane (1:2, volume ratio).

$^1$H-NMR (CDCl$_3$) δ: 1.41 (3H, t, J=7.1 Hz), 3.44 (3H, s), 4.36 (2H, q, J=7.1 Hz), 5.69 (2H, s), 6.99-7.03 (1H, m), 7.18 (1H, t, J=8.4 Hz), 7.40 (1H, s), 7.48-7.54 (3H, m), 8.77 (1H, brs).

Reference Example 79 ethyl 4-chloro-1-(methoxymethyl)-7-[methyl(2-thienylsulfonyl)amino]-1H-indole-2-carboxylate

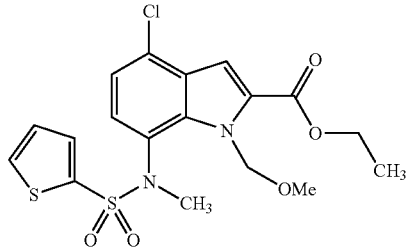

A mixture of ethyl 4-chloro-1-(methoxymethyl)-7-[(2-thienylsulfonyl)amino]-1H-indole-2-carboxylate (1.14 g), methyl iodide (0.33 ml), potassium carbonate (0.37 g) and N,N-dimethylformamide (10 ml) was stirred overnight at room temperature. Water was added to the reaction mixture, and the resulting crystals were collected by filtration, washed with water, and dried to give the title compound (1.10 g, yield 93%) as colorless crystals. melting point 137-138° C.

Reference Example 80

4-chloro-7-[methyl(2-thienylsulfonyl)amino]-1H-indole-2-carboxamide

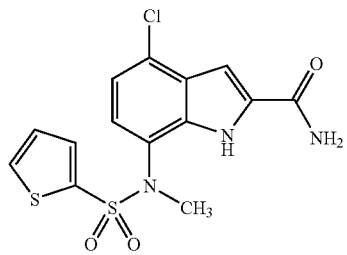

A mixture of ethyl 4-chloro-1-(methoxymethyl)-7-[(2-thienylsulfonyl)amino]-1H-indole-2-carboxylate (1.10 g), 6N hydrochloric acid (5 ml), tetrahydrofuran (20 ml) and ethanol (10 ml) was heated overnight under reflux. Water was added to the reaction mixture, and the mixture was extracted with ethyl acetate. The ethyl acetate layer was washed with saturated brine, and concentrated. A mixture of the obtained residue, 4N aqueous sodium hydroxide solution (1.2 ml), tetrahydrofuran (10 ml) and methanol (10 ml) was stirred at 60° C. for 1 hr. The reaction mixture was acidified with 10% aqueous citric acid solution, and extracted with ethyl acetate. The ethyl acetate layer was washed with saturated brine, dried (MgSO$_4$), and concentrated. To a mixture of the obtained residue, 1H-1,2,3-benzotriazol-1-ol (0.40 g) and N,N-dimethylformamide (10 ml) was added N-[3-(dimethylamino)propyl]-N'-ethylcarbodiimide hydrochloride (0.57 g) at room temperature, and the mixture was stirred at 50° C. for 30 min. The mixture was allowed to cool to room temperature, and 28% aqueous ammonia (0.75 ml) was added. The reaction mixture was stirred at room temperature for 2 hr, followed by an addition of water. The mixture was acidified with 10% aqueous citric acid solution, and extracted with ethyl acetate, and the ethyl acetate layer was washed with saturated brine, dried (MgSO$_4$), and concentrated. The residue was subjected to silica gel column chromatography to give the title compound (0.25 g, yield 78%) as pale-yellow crystals from a fraction eluted with tetrahydrofuran-hexane (2:1, volume ratio). melting point 252-254° C.

Reference Example 81

4-chloro-7-[methyl(2-thienylsulfonyl)amino]-1H-indole-2-carbothioamide

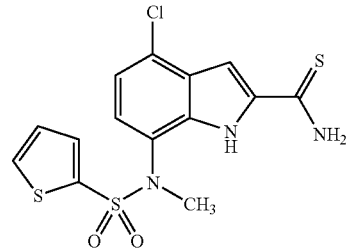

A mixture of 4-chloro-7-[methyl(2-thienylsulfonyl)amino]-1H-indole-2-carboxamide (0.54 g), Lawesson's reagent (0.59 g) and tetrahydrofuran (20 ml) was stirred at 60° C. for 3 hr. The reaction mixture was concentrated, toluene was added, and the resulting crystals were filtrated, washed with toluene, and dried to give the title compound (0.51 g, yield 87%) as yellow crystals. melting point >248° C. (decomposition).

Reference Example 82

N-{4-chloro-2-[5-(hydroxymethyl)-1,3-thiazol-2-yl]-1H-indol-7-yl}-N-methylthiophene-2-sulfonamide

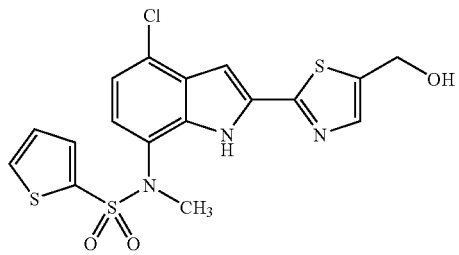

A mixture of 4-chloro-7-[methyl(2-thienylsulfonyl)amino]-1H-indole-2-carbothioamide (0.51 g), bromomalonaldehyde (0.30 g) and N,N-dimethylacetamide (15 ml) was stirred at 90° C. for 4 hr. Water was added to the reaction mixture, and the resulting crystals were collected by filtration, washed with water, and dried. To a mixture of the obtained crystals, tetrahydrofuran (5 ml) and methanol (5 ml) was added sodium borohydride (55 mg) at 0° C., and the mixture was stirred at the same temperature for 1 hr. 10% Aqueous citric acid solution was added to the reaction mixture, and the mixture was extracted with ethyl acetate. The ethyl acetate layer was washed with saturated brine, dried (MgSO₄), and concentrated. The residue was subjected to silica gel column chromatography to give the title compound (0.30 g, yield 52%) as pale-yellow crystals from a fraction eluted with tetrahydrofuran-hexane (2:1, volume ratio). melting point 225-226° C.

Reference Example 83 ethyl 7-amino-6-chloro-1H-indole-2-carboxylate

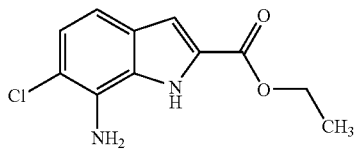

A mixture of ethyl 7-amino-1H-indole-2-carboxylate (2.30 g), N-chlorosuccinimide (1.40 g) and N,N-dimethylformamide (10 ml) was stirred overnight at room temperature. Water was added to the reaction mixture, and the resulting crystals were collected by filtration, washed with water, and dried. The obtained crystals were subjected to silica gel column chromatography to give the title compound (1.59 g, yield 63%) as pale-yellow crystals from a fraction eluted with ethyl acetate-hexane (2:3, volume ratio). melting point 217-218° C. (decomposition).

Reference Example 84 ethyl 6-chloro-7-[(2-thienylsulfonyl)amino]-1H-indole-2-carboxylate

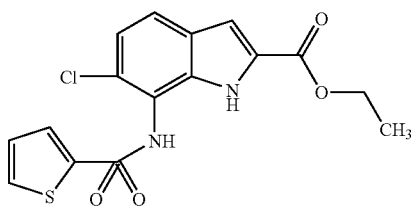

To a mixture of ethyl 7-amino-6-chloro-1H-indole-2-carboxylate (1.59 g) and pyridine (10 ml) was added thiophene-2-sulfonyl chloride (1.46 g), and the mixture was stirred at 50° C. for 3 hr. The reaction mixture was concentrated, 10% aqueous citric acid solution was added, and the mixture was extracted with ethyl acetate. The ethyl acetate layer was washed with saturated brine, dried (MgSO₄), and concentrated. The obtained residue was subjected to silica gel column chromatography to give the title compound (2.17 g, yield 85%) as colorless crystals from a fraction eluted with tetrahydrofuran-hexane (1:2, volume ratio). The crystals were recrystallized from ethyl acetate. melting point 191-192° C.

Reference Example 85

6-chloro-7-[(2-thienylsulfonyl)amino]-1H-indole-2-carboxylic acid

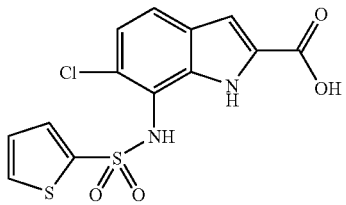

A mixture of ethyl 6-chloro-7-[(2-thienylsulfonyl)amino]-1H-indole-2-carboxylate (1.00 g), 4N aqueous sodium hydroxide solution (2.3 ml), tetrahydrofuran (5 ml) and methanol (5 ml) was stirred at 50° C. for 2 hr. The reaction mixture was concentrated, and acidified with 10% aqueous citric acid solution, and the resulting crystals were collected by filtration, washed with water, and dried to give the title compound (0.88 g, yield 95%) as colorless crystals. melting point >290° C. (decomposition).

Reference Example 86

6-chloro-7-[(2-thienylsulfonyl)amino]-1H-indole-2-carboxamide

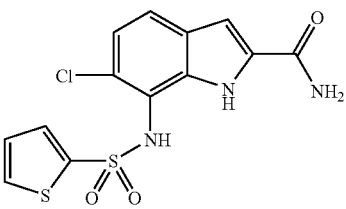

To a mixture of 6-chloro-7-[(2-thienylsulfonyl)amino]-1H-indole-2-carboxylic acid (0.83 g), 1H-1,2,3-benzotriazol-1-ol (0.38 g) and N,N-dimethylformamide (10 ml) was added N-[3-(dimethylamino)propyl]-N'-ethylcarbodiimide hydrochloride (0.54 g) at room temperature, and the mixture was stirred at 50° C. for 20 min, and allowed to cool to room temperature. 28% Aqueous ammonia (0.30 ml) was added, and the reaction mixture was stirred at room temperature for 1 hr, and acidified with 10% aqueous citric acid solution. The resulting crystals were filtrated, washed with water, and dried to give the title compound (0.80 g, yield 96%) as colorless crystals. melting point >300° C. (decomposition).

Reference Example 87

6-chloro-7-[(2-thienylsulfonyl)amino]-1H-indole-2-carbothioamide

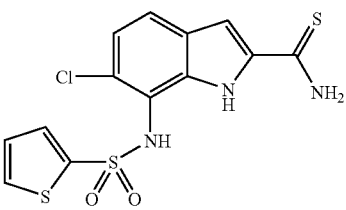

A mixture of 6-chloro-7-[(2-thienylsulfonyl)amino]-1H-indole-2-carboxamide (0.80 g), Lawesson's reagent (0.90 g) and tetrahydrofuran (15 ml) was stirred at 60° C. for 3 hr. The reaction mixture was concentrated, toluene was added, and the resulting crystals were filtrated, washed with toluene, and dried to give the title compound (0.75 g, yield 91%) as yellow crystals. melting point 228-230° C. (decomposition).

Reference Example 88 ethyl 6-chloro-7-[methyl(2-thienylsulfonyl)amino]-1H-indole-2-carboxylate

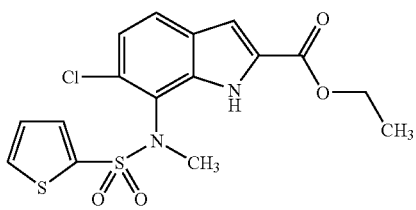

A mixture of ethyl 6-chloro-7-[(2-thienylsulfonyl)amino]-1H-indole-2-carboxylate (1.00 g), methyl iodide (0.17 ml), potassium carbonate (0.36 g) and N,N-dimethylformamide (10 ml) was stirred overnight at room temperature. Water was added to the reaction mixture, and the resulting crystals were collected by filtration, washed with water, and dried. The obtained crystals were subjected to basic silica gel column chromatography to give the title compound (0.80 g, yield 77%) as colorless crystals from a fraction eluted with ethyl acetate-hexane (1:2, volume ratio). melting point 156-157° C.

Reference Example 89

6-chloro-7-[methyl(2-thienylsulfonyl)amino]-1H-indole-2-carboxylic acid

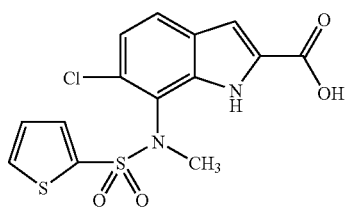

A mixture of ethyl 6-chloro-7-[methyl(2-thienylsulfonyl)amino]-1H-indole-2-carboxylate (0.74 g), 4N aqueous sodium hydroxide solution (1.2 ml), tetrahydrofuran (6 ml) and methanol (4 ml) was stirred at 60° C. for 2 hr. The reaction mixture was concentrated, and acidified with 10% aqueous citric acid solution, and the resulting crystals were collected by filtration, washed with water, and dried to give the title compound (0.69 g, quantitative) as colorless crystals. melting point 286-288° C.

Reference Example 90

6-chloro-7-[methyl(2-thienylsulfonyl)amino]-1H-indole-2-carboxamide

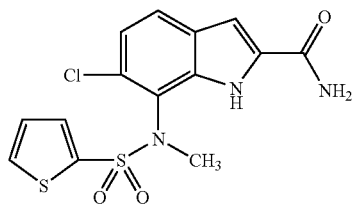

To a mixture of 6-chloro-7-[methyl(2-thienylsulfonyl)amino]-1H-indole-2-carboxylic acid (0.69 g), 1H-1,2,3-benzotriazol-1-ol (0.31 g) and N,N-dimethylformamide (10 ml) was added N-[3-(dimethylamino)propyl]-N'-ethylcarbodiimide hydrochloride (0.44 g) at room temperature, and the mixture was stirred at 50° C. for 20 min, and allowed to cool to room temperature. 28% Aqueous ammonia (0.30 ml) was added, and the reaction mixture was stirred at room temperature for 2 hr, and acidified with 10% aqueous citric acid solution. The resulting crystals were filtrated, washed with water, and dried to give the title compound (0.70 g, quantitative) as colorless crystals. melting point 225-226° C. (decomposition).

Reference Example 91

6-chloro-7-[methyl(2-thienylsulfonyl)amino]-1H-indole-2-carbothioamide

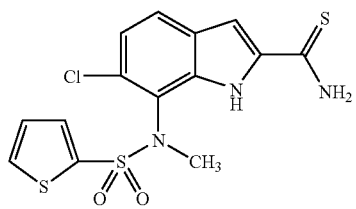

A mixture of 6-chloro-7-[methyl(2-thienylsulfonyl)amino]-1H-indole-2-carboxamide (0.70 g), Lawesson's reagent (0.77 g) and tetrahydrofuran (20 ml) was stirred at 60° C. for 2 hr. The reaction mixture was concentrated, toluene was added, and the resulting crystals were filtrated, washed with toluene, and dried to give the title compound (0.60 g, yield 84%) as yellow crystals. melting point 200-201° C.

Reference Example 92

N-{6-chloro-2-[5-(hydroxymethyl)-1,3-thiazol-2-yl]-1H-indol-7-yl}-N-methylthiophene-2-sulfonamide

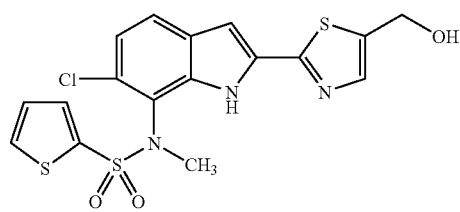

A mixture of 6-chloro-7-[methyl(2-thienylsulfonyl)amino]-1H-indole-2-carbothioamide (0.60 g), bromomalonaldehyde (0.38 g) and N,N-dimethylacetamide (10 ml) was stirred at 90° C. for 3 hr. Water was added to the reaction mixture, and the resulting crystals were collected by filtration, washed with water, and dried. To a mixture of the obtained crystals, tetrahydrofuran (10 ml) and methanol (5 ml) was added sodium borohydride (70 mg) at 0° C., and the mixture was stirred at the same temperature for 30 min. 10% Aqueous citric acid solution was added to the reaction mixture, and the mixture was extracted with ethyl acetate. The ethyl acetate layer was washed with saturated brine, dried (MgSO$_4$), and concentrated. The residue was subjected to silica gel column chromatography to give the title compound (0.38 g, yield 54%) as pale-yellow crystals from a fraction eluted with tetrahydrofuran-hexane (2:1, volume ratio). melting point 214-215° C.

Reference Example 93

N-(2-{[(2-{7-[methyl(2-thienylsulfonyl)amino]-1H-indol-2-yl}-1,3-thiazol-5-yl)methyl]amino}ethyl) acetamide

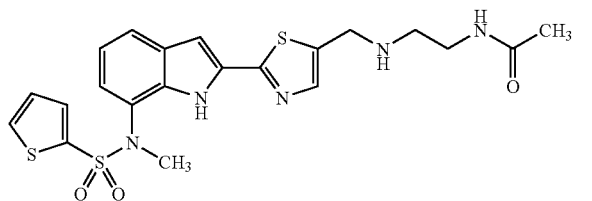

In the same manner as in Example 186 to be mentioned later, the title compound (0.41 g, yield 49%) was obtained as colorless crystals from N-{2-[5-(chloromethyl)-1,3-thiazol-2-yl]-1H-indol-7-yl}-N-methylthiophene-2-sulfonamide (0.70 g) and N-(2-aminoethyl)acetamide (0.41 g). melting point 154-155° C.

Example 1 N-methyl-N-[2-(5-{[methyl(pyridin-2-ylmethyl)amino]methyl}-1,3-thiazol-2-yl)-1H-indol-7-yl]thiophene-2-sulfonamide ditrifluoroacetate

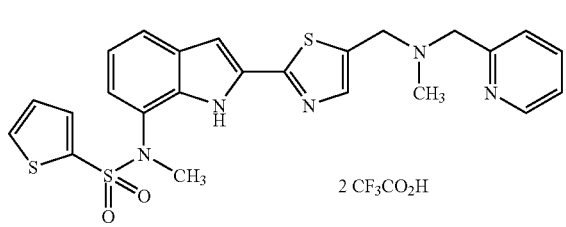

A solution (1 ml) of N-{2-[5-(chloromethyl)-1,3-thiazol-2-yl]-1H-indol-7-yl}-N-methylthiophene-2-sulfonamide (23 mg), triethylamine (28 mg) and N-methyl-1-pyridin-2-ylmethanamine hydrochloride (19 mg) in N,N-dimethylformamide was stirred at room temperature for 18 hr. The reaction mixture was diluted with water, and extracted with ethyl acetate. The extract was concentrated, and the residue was purified by preparative HPLC to give the title compound (14.6 mg, yield 37%).
HPLC purity 100%.
MS m/z 510 (M+H$^+$).
$^1$H-NMR (400 MHz, CDCl$_3$) δ: 2.78 (3H, s), 3.34 (3H, s), 4.32 (2H, s), 4.63 (2H, s), 6.55 (1H, d, J=7.7 Hz), 6.98 (1H, t, J=7.7 Hz), 7.06 (1H, d, J=2.1 Hz), 7.12 (1H, dd, J=4.9, 3.8 Hz), 7.39 (1H, dd, J=3.8, 1.3 Hz), 7.45 (1H, dd, J=7.0, 5.1 Hz), 7.56-7.66 (3H, m), 7.77-7.97 (2H, m), 8.74 (1H, dd, J=5.0, 0.8 Hz), 9.65 (1H, s).

Example 2

N-methyl-N-[2-(5-{[methyl(2-pyridin-2-ylethyl)amino]methyl}-1,3-thiazol-2-yl)-1H-indol-7-yl]thiophene-2-sulfonamide ditrifluoroacetate

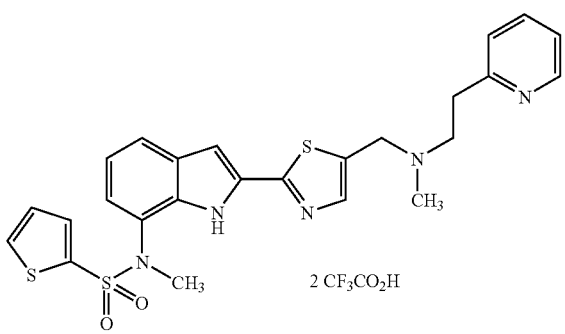

In the same manner as in Example 1, the title compound (12.6 mg, yield 31%) was obtained from N-{2-[5-(chloromethyl)-1,3-thiazol-2-yl]-1H-indol-7-yl}-N-methylthiophene-2-sulfonamide (23 mg) and N-methyl-2-(pyridin-2-yl)ethanamine (16 mg).
HPLC purity 100%.
MS m/z 524 (M+H$^+$).

Example 3

N-methyl-N-(2-{5-[(2-(pyridin-2-yl)pyrrolidin-1-yl)methyl]-1,3-thiazol-2-yl}-1H-indol-7-yl)thiophene-2-sulfonamide ditrifluoroacetate

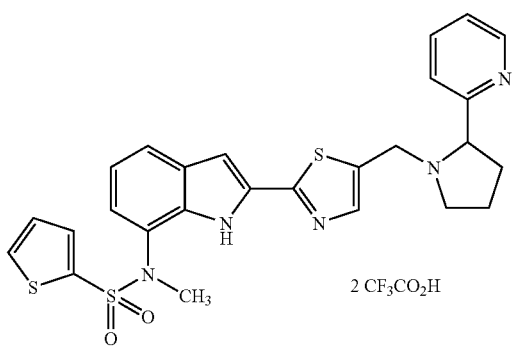

In the same manner as in Example 1, the title compound (15.6 mg, yield 38%) was obtained from N-{2-[5-(chloromethyl)-1,3-thiazol-2-yl]-1H-indol-7-yl}-N-methylthiophene-2-sulfonamide (23 mg) and 2-(pyrrolidin-2-yl)pyridine (18 mg).
HPLC purity 100%.
MS m/z 536 (M+H$^+$).

Example 4

N-methyl-N-[2-(5-{[methyl(pyridin-3-ylmethyl)amino]methyl}-1,3-thiazol-2-yl)-1H-indol-7-yl]thiophene-2-sulfonamide ditrifluoroacetate

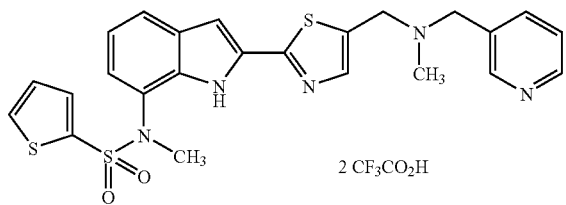

In the same manner as in Example 1, the title compound (11.0 mg, yield 28%) was obtained from N-{2-[5-(chloromethyl)-1,3-thiazol-2-yl]-1H-indol-7-yl}-N-methylthiophene-2-sulfonamide (23 mg) and N-methyl-1-(pyridin-3-yl)methanamine hydrochloride (19 mg).
HPLC purity 100%.
MS m/z 510 (M+H$^+$).

Example 5

N-methyl-N-[2-(5-{[3-(methylsulfonyl)pyrrolidin-1-yl]methyl}-1,3-thiazol-2-yl)-1H-indol-7-yl]thiophene-2-sulfonamide trifluoroacetate

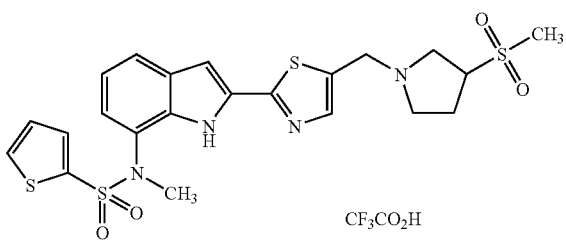

In the same manner as in Example 1, the title compound (9.5 mg, yield 27%) was obtained from N-{2-[5-(chloromethyl)-1,3-thiazol-2-yl]-1H-indol-7-yl}-N-methylthiophene-2-sulfonamide (23 mg) and 3-(methylsulfonyl)pyrrolidine (18 mg).
HPLC purity 96%.
MS m/z 537 (M+H$^+$).

Example 6

N-methyl-N-{2-[5-({methyl[2-(methylsulfonyl)ethyl]amino}methyl)-1,3-thiazol-2-yl]-1H-indol-7-yl}thiophene-2-sulfonamide trifluoroacetate

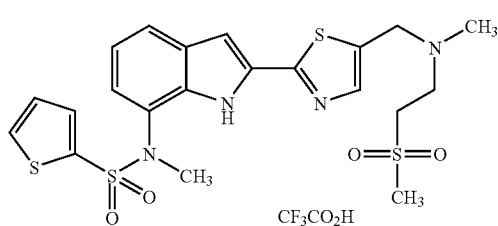

In the same manner as in Example 1, the title compound (6.0 mg, yield 17%) was obtained from N-{2-[5-(chloromethyl)-1,3-thiazol-2-yl]-1H-indol-7-yl}-N-methylthiophene-2-sulfonamide (23 mg) and N-methyl-2-(methylsulfonyl)ethanamine (16 mg).
HPLC purity 100%.
MS m/z 525 (M+H$^+$).
$^1$H-NMR (400 MHz, CDCl$_3$) δ: 2.68 (3H, s), 3.05 (3H, s), 3.34 (3H, s), 3.43 (2H, t), 3.54 (2H, t, J=7.1 Hz), 4.31 (2H, s), 6.56 (1H, d, J=7.5 Hz), 6.99 (1H, t, J=7.8 Hz), 7.05 (1H, d, J=2.1 Hz), 7.13 (1H, dd, J=4.9, 3.8 Hz), 7.41 (1H, dd, J=3.7, 1.2 Hz), 7.59 (1H, d, J=7.9 Hz), 7.65 (1H, dd, J=5.0, 1.2 Hz), 7.78 (1H, s), 9.76 (1H, brs).

Example 7

N-methyl-N-[2-(5-{[4-(pyrimidin-2-yloxy)piperidino]methyl}-1,3-thiazol-2-yl)-1H-indol-7-yl]thiophene-2-sulfonamide trifluoroacetate

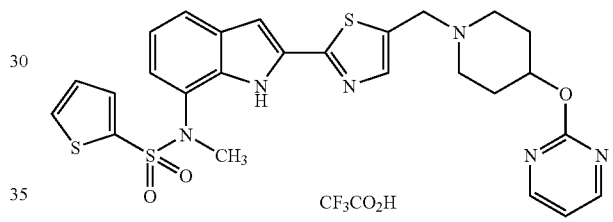

In the same manner as in Example 1, the title compound (20.2 mg, yield 55%) was obtained from N-{2-[5-(chloromethyl)-1,3-thiazol-2-yl]-1H-indol-7-yl}-N-methylthiophene-2-sulfonamide (23 mg) and 2-(piperidin-4-yloxy)pyrimidine dihydrochloride (30 mg).
HPLC purity 94%.
MS m/z 567 (M+H$^+$).

Example 8

N-methyl-N-[2-(5-{[4-(pyrazin-2-yloxy)piperidino]methyl}-1,3-thiazol-2-yl)-1H-indol-7-yl]thiophene-2-sulfonamide trifluoroacetate

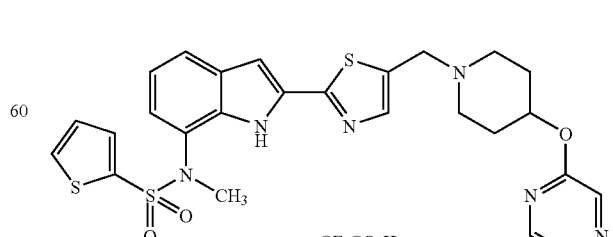

In the same manner as in Example 1, the title compound (20.1 mg, yield 55%) was obtained from N-{2-[5-(chloromethyl)-1,3-thiazol-2-yl]-1H-indol-7-yl}-N-methylthiophene-2-sulfonamide (23 mg) and 2-(piperidin-4-yloxy)pyrazine dihydrochloride (30 mg).

HPLC purity 100%.

MS m/z 567 (M+H⁺).

Example 9

N-methyl-N-[2-(5-{[4-(tetrahydrofuran-2-ylmethyl)piperazin-1-yl]methyl}-1,3-thiazol-2-yl)-1H-indol-7-yl]thiophene-2-sulfonamide ditrifluoroacetate

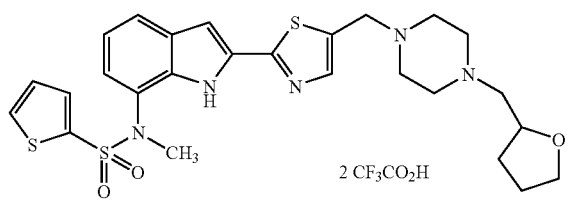

In the same manner as in Example 1, the title compound (18.5 mg, yield 43%) was obtained from N-{2-[5-(chloromethyl)-1,3-thiazol-2-yl]-1H-indol-7-yl}-N-methylthiophene-2-sulfonamide (23 mg) and 1-(tetrahydrofuran-2-ylmethyl)piperazine (20 mg).

HPLC purity 92%.

MS m/z 558 (M+H⁺).

Example 10

N,N-dimethyl-2-{4-[(2-{7-[methyl(2-thienylsulfonyl)amino]-1H-indol-2-yl}-1,3-thiazol-5-yl)methyl]piperazin-1-yl}acetamide ditrifluoroacetate

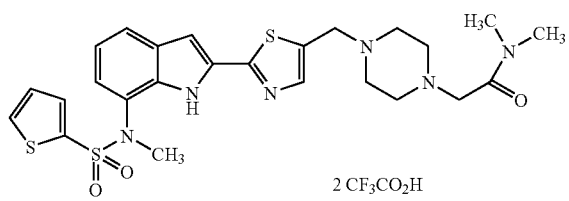

In the same manner as in Example 1, the title compound (10.7 mg, yield 25%) was obtained from N-{2-[5-(chloromethyl)-1,3-thiazol-2-yl]-1H-indol-7-yl}-N-methylthiophene-2-sulfonamide (23 mg) and N,N-dimethyl-2-(piperazin-1-yl)acetamide (21 mg).

HPLC purity 92%.

MS m/z 559 (M+H⁺).

Example 11

N-methyl-N-[2-(5-{[4-(6-methylpyridin-2-yl)piperazin-1-yl]methyl}-1,3-thiazol-2-yl)-1H-indol-7-yl]thiophene-2-sulfonamide trifluoroacetate

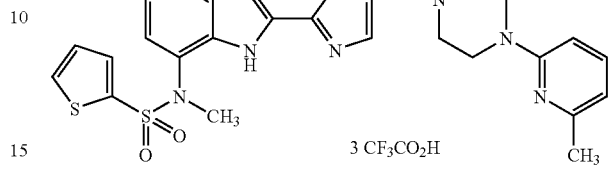

In the same manner as in Example 1, the title compound (11.4 mg, yield 23%) was obtained from N-{2-[5-(chloromethyl)-1,3-thiazol-2-yl]-1H-indol-7-yl}-N-methylthiophene-2-sulfonamide (23 mg) and 1-(6-methylpyridin-2-yl)piperazine (21 mg).

HPLC purity 100%.

MS m/z 565 (M+H⁺).

Example 12

N-methyl-N-(2-{5-[(3-(pyrimidin-2-yl)pyrrolidin-1-yl)methyl]-1,3-thiazol-2-yl}-1H-indol-7-yl)thiophene-2-sulfonamide trifluoroacetate

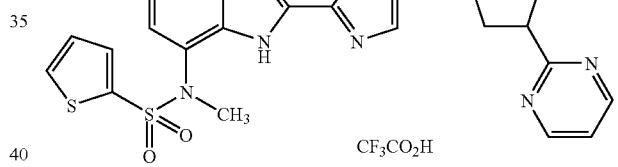

In the same manner as in Example 1, the title compound (11.5 mg, yield 33%) was obtained from N-{2-[5-(chloromethyl)-1,3-thiazol-2-yl]-1H-indol-7-yl}-N-methylthiophene-2-sulfonamide (23 mg) and 2-(pyrrolidin-3-yl)pyrimidine trihydrochloride (31 mg).

HPLC purity 94%.

MS m/z 537 (M+H⁺).

Example 13

N-methyl-N-(2-{5-[(3-(pyridin-2-yl)piperidino)methyl]-1,3-thiazol-2-yl}-1H-indol-7-yl)thiophene-2-sulfonamide-sulfonamide ditrifluoroacetate

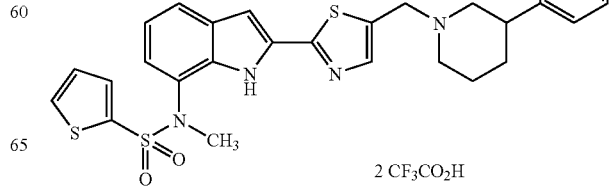

In the same manner as in Example 1, the title compound (21.3 mg, yield 51%) was obtained from N-{2-[5-(chloromethyl)-1,3-thiazol-2-yl]-1H-indol-7-yl}-N-methylthiophene-2-sulfonamide (23 mg) and 2-(piperidin-3-yl)pyridine (19 mg).

HPLC purity 97%.
MS m/z 550 (M+H$^+$).

Example 14

N-methyl-N-(2-{5-[(4-(pyridin-2-yl)piperidino)methyl]-1,3-thiazol-2-yl}-1H-indol-7-yl)thiophene-2-sulfonamide ditrifluoroacetate

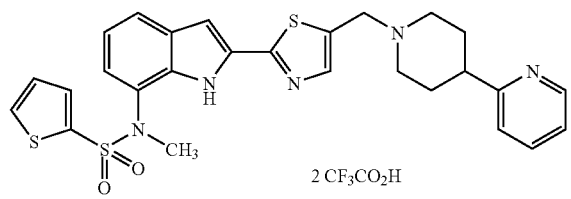

2 CF$_3$CO$_2$H

In the same manner as in Example 1, the title compound (17.8 mg, yield 42%) was obtained from N-{2-[5-(chloromethyl)-1,3-thiazol-2-yl]-1H-indol-7-yl}-N-methylthiophene-2-sulfonamide (23 mg) and 2-(piperidin-4-yl)pyridine (19 mg).

HPLC purity 100%.
MS m/z 550 (M+H$^+$).

Example 15

N-methyl-N-(2-{5-[(5-methyl-4,6-dioxohexahydropyrrolo[3,4-c]pyrrol-2(1H)-yl)methyl]-1,3-thiazol-2-yl}-1H-indol-7-yl)thiophene-2-sulfonamide trifluoroacetate

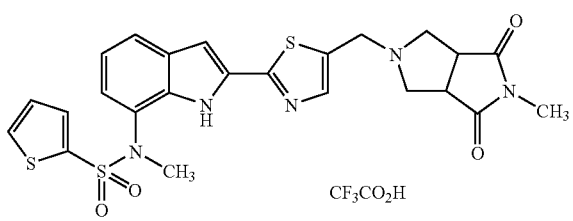

CF$_3$CO$_2$H

In the same manner as in Example 1, the title compound (7.8 mg, yield 22%) was obtained from N-{2-[5-(chloromethyl)-1,3-thiazol-2-yl]-1H-indol-7-yl}-N-methylthiophene-2-sulfonamide (23 mg) and 2-methyltetrahydropyrrolo[3,4-c]pyrrole-1,3(2H,3aH)-dione hydrochloride (23 mg).

HPLC purity 100%.
MS m/z 542 (M+H$^+$).

Example 16

N-(2-{5-[(4-hydroxy-4-methylpiperidino)methyl]-1,3-thiazol-2-yl}-1H-indol-7-yl)-N-methylthiophene-2-sulfonamide trifluoroacetate

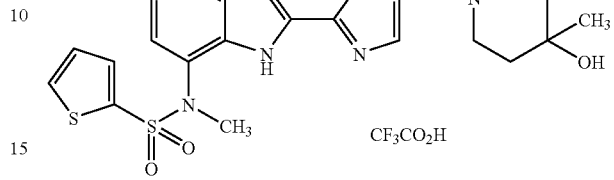

CF$_3$CO$_2$H

In the same manner as in Example 1, the title compound (9.9 mg, yield 30%) was obtained from N-{2-[5-(chloromethyl)-1,3-thiazol-2-yl]-1H-indol-7-yl}-N-methylthiophene-2-sulfonamide (23 mg) and 4-methylpiperidin-4-ol hydrochloride (18 mg).

HPLC purity 96%.
MS m/z 503 (M+H$^+$).

Example 17

N-[2-(5-{[cyclopropyl(isobutyl)amino]methyl}-1,3-thiazol-2-yl)-1H-indol-7-yl]-N-methylthiophene-2-sulfonamide trifluoroacetate

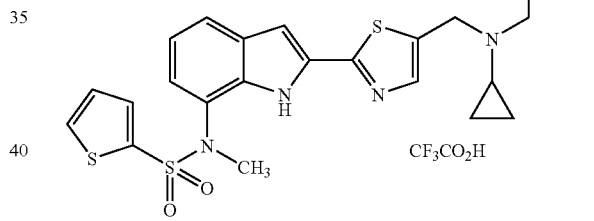

CF$_3$CO$_2$H

In the same manner as in Example 1, the title compound (4.0 mg, yield 12%) was obtained from N-{2-[5-(chloromethyl)-1,3-thiazol-2-yl]-1H-indol-7-yl}-N-methylthiophene-2-sulfonamide (23 mg) and N-isobutyl-cyclopropanamine hydrochloride (18 mg).

HPLC purity 98%.
MS m/z 501 (M+H$^+$).

Example 18

N-(2-{5-[(4-tert-butylpiperidino)methyl]-1,3-thiazol-2-yl}-1H-indol-7-yl)-N-methylthiophene-2-sulfonamide trifluoroacetate

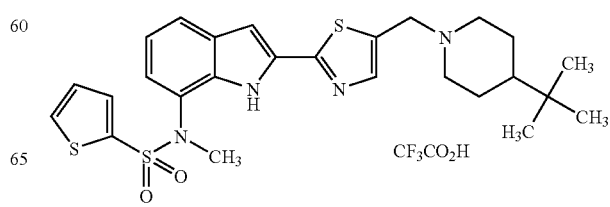

CF$_3$CO$_2$H

In the same manner as in Example 1, the title compound (12.6 mg, yield 36%) was obtained from N-{2-[5-(chloromethyl)-1,3-thiazol-2-yl]-1H-indol-7-yl}-N-methylthiophene-2-sulfonamide (23 mg) and 4-tert-butylpiperidine hydrochloride (21 mg).

HPLC purity 95%.

MS m/z 529 (M+H⁺).

Example 19

N-methyl-N-[2-(5-{[3-(pyrrolidin-1-ylcarbonyl)piperidino]methyl}-1,3-thiazol-2-yl)-1H-indol-7-yl]thiophene-2-sulfonamide trifluoroacetate

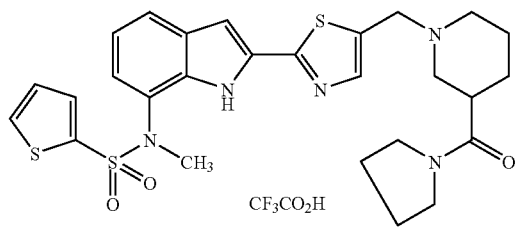

In the same manner as in Example 1, the title compound (13.4 mg, yield 36%) was obtained from N-{2-[5-(chloromethyl)-1,3-thiazol-2-yl]-1H-indol-7-yl}-N-methylthiophene-2-sulfonamide (23 mg) and 3-(pyrrolidin-1-ylcarbonyl)piperidine (22 mg).

HPLC purity 100%.

MS m/z 570 (M+H⁺).

Example 20

N-methyl-N-{2-[5-(pyrrolidin-1-ylmethyl)-1,3-thiazol-2-yl]-1H-indol-7-yl}thiophene-2-sulfonamide trifluoroacetate

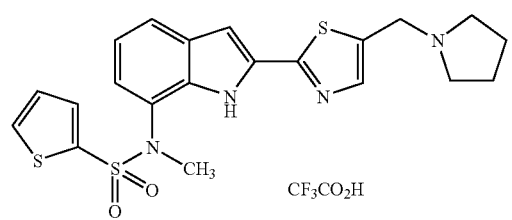

In the same manner as in Example 1, the title compound (3.8 mg, yield 12%) was obtained from N-{2-[5-(chloromethyl)-1,3-thiazol-2-yl]-1H-indol-7-yl}-N-methylthiophene-2-sulfonamide (23 mg) and pyrrolidine (9 mg).

HPLC purity 100%.

MS m/z 459 (M+H⁺).

Example 21

N-(2-{5-[(diethylamino)methyl]-1,3-thiazol-2-yl}-1H-indol-7-yl)-N-methylthiophene-2-sulfonamide trifluoroacetate

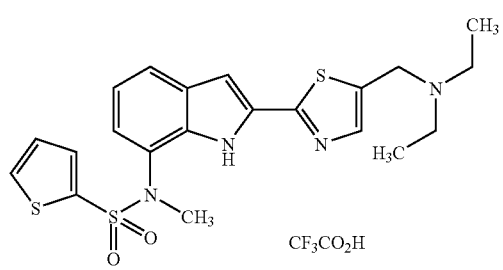

In the same manner as in Example 1, the title compound (3.7 mg, yield 12%) was obtained from N-{2-[5-(chloromethyl)-1,3-thiazol-2-yl]-1H-indol-7-yl}-N-methylthiophene-2-sulfonamide (23 mg) and diethylamine (8 mg).

HPLC purity 95%.

MS m/z 461 (M+H⁺).

Example 22

N-methyl-N-{2-[5-(piperidinomethyl)-1,3-thiazol-2-yl]-1H-indol-7-yl}thiophene-2-sulfonamide trifluoroacetate

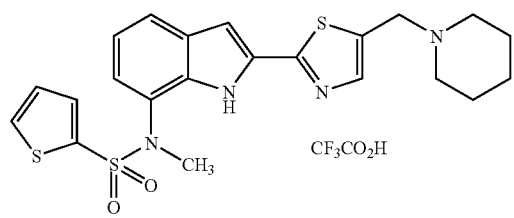

In the same manner as in Example 1, the title compound (11.1 mg, yield 35%) was obtained from N-{2-[5-(chloromethyl)-1,3-thiazol-2-yl]-1H-indol-7-yl}-N-methylthiophene-2-sulfonamide (23 mg) and piperidine (10 mg).

HPLC purity 95%.

MS m/z 473 (M+H⁺).

Example 23

N-(2-{5-[(4-hydroxypiperidino)methyl]-1,3-thiazol-2-yl}-1H-indol-7-yl)-N-methylthiophene-2-sulfonamide trifluoroacetate

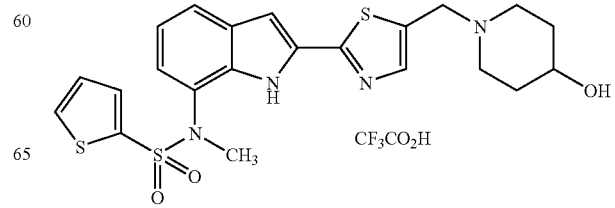

In the same manner as in Example 1, the title compound (8.7 mg, yield 27%) was obtained from N-{2-[5-(chloromethyl)-1,3-thiazol-2-yl]-1H-indol-7-yl}-N-methylthiophene-2-sulfonamide (23 mg) and 4-hydroxypiperidine (12 mg).
HPLC purity 100%.
MS m/z 489 (M+H$^+$).
$^1$H-NMR (400 MHz, CDCl$_3$) δ: 1.94 (2H, brs), 2.20 (2H, brs), 3.19 (2H, brs), 3.35 (3H, s), 3.41 (2H, brs), 4.24 (1H, brs), 4.47 (2H, s), 6.56 (1H, d, J=7.5 Hz), 6.99 (1H, t, J=7.8 Hz), 7.05 (1H, d, J=2.1 Hz), 7.12 (1H, dd, J=5.0, 3.9 Hz), 7.40 (1H, dd, J=3.8, 1.3 Hz), 7.59 (1H, d, J=8.1 Hz), 7.64 (1H, dd, J=4.9, 1.3 Hz), 7.80 (1H, s), 9.69 (1H, brs).

Example 24

N-(2-{5-[(3-hydroxypiperidino)methyl]-1,3-thiazol-2-yl}-1H-indol-7-yl)-N-methylthiophene-2-sulfonamide trifluoroacetate

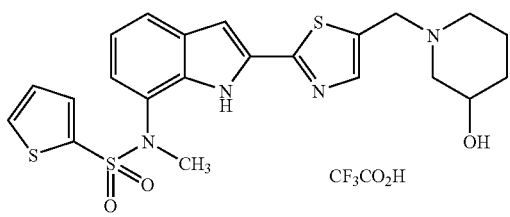

In the same manner as in Example 1, the title compound (14.3 mg, yield 44%) was obtained from N-{2-[5-(chloromethyl)-1,3-thiazol-2-yl]-1H-indol-7-yl}-N-methylthiophene-2-sulfonamide (23 mg) and 3-hydroxypiperidine (12 mg).
HPLC purity 97%.
MS m/z 489 (M+H$^+$).

Example 25

N-[2-(5-{[(2-methoxyethyl)(methyl)amino]methyl}-1,3-thiazol-2-yl)-1H-indol-7-yl]-N-methylthiophene-2-sulfonamide trifluoroacetate

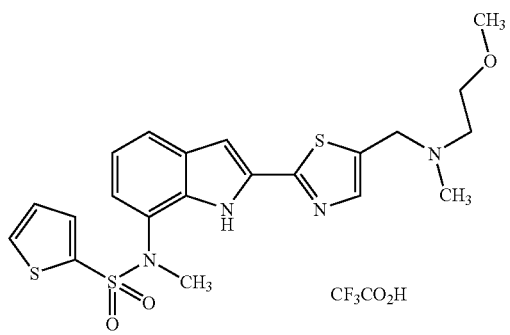

In the same manner as in Example 1, the title compound (10.3 mg, yield 32%) was obtained from N-{2-[5-(chloromethyl)-1,3-thiazol-2-yl]-1H-indol-7-yl}-N-methylthiophene-2-sulfonamide (23 mg) and N-(2-methoxyethyl)methylamine (11 mg).
HPLC purity 100%.
MS m/z 477 (M+H$^+$).

Example 26

N-[2-(5-{[(2S)-2-(methoxymethyl)pyrrolidin-1-yl]methyl}-1,3-thiazol-2-yl)-1H-indol-7-yl]-N-methylthiophene-2-sulfonamide trifluoroacetate

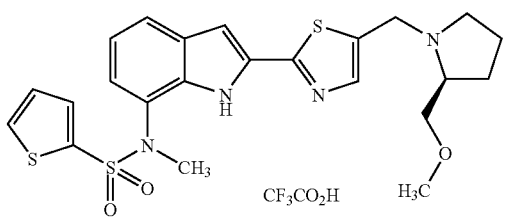

In the same manner as in Example 1, the title compound (11.7 mg, yield 35%) was obtained from N-{2-[5-(chloromethyl)-1,3-thiazol-2-yl]-1H-indol-7-yl}-N-methylthiophene-2-sulfonamide (23 mg) and (S)-2-(methoxymethyl)pyrrolidine (14 mg).
HPLC purity 100%.
MS m/z 503 (M+H$^+$).

Example 27

N-{1-[(2-{7-[methyl(2-thienylsulfonyl)amino]-1H-indol-2-yl}-1,3-thiazol-5-yl)methyl]pyrrolidin-3-yl}acetamide trifluoroacetate

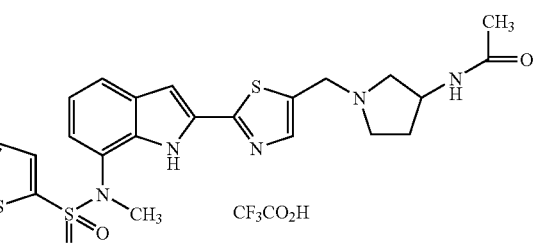

In the same manner as in Example 1, the title compound (11.0 mg, yield 32%) was obtained from N-{2-[5-(chloromethyl)-1,3-thiazol-2-yl]-1H-indol-7-yl}-N-methylthiophene-2-sulfonamide (23 mg) and 3-acetamidopyrrolidine (15 mg).
HPLC purity 100%.
MS m/z 516 (M+H$^+$).

Example 28

1-[(2-{7-[methyl(2-thienylsulfonyl)amino]-1H-indol-2-yl}-1,3-thiazol-5-yl)methyl]piperidine-4-carboxamide trifluoroacetate

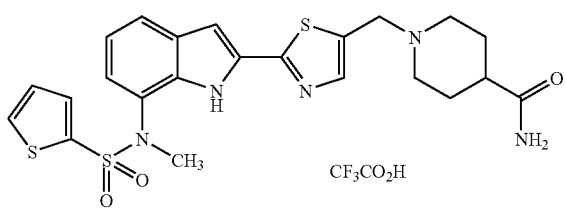

In the same manner as in Example 1, the title compound (7.0 mg, yield 21%) was obtained from N-{2-[5-(chloromethyl)-1,3-thiazol-2-yl]-1H-indol-7-yl}-N-methylthiophene-2-sulfonamide (23 mg) and isonipecotamide (15 mg).
HPLC purity 94%.
MS m/z 516 (M+H$^+$).

Example 29

N-[2-(5-{[4-(2-hydroxyethyl)piperidino]methyl}-1,3-thiazol-2-yl)-1H-indol-7-yl]-N-methylthiophene-2-sulfonamide trifluoroacetate

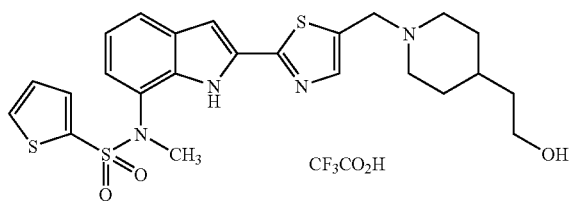

In the same manner as in Example 1, the title compound (13.2 mg, yield 39%) was obtained from N-{2-[5-(chloromethyl)-1,3-thiazol-2-yl]-1H-indol-7-yl}-N-methylthiophene-2-sulfonamide (23 mg) and 2-(piperidin-4-yl)ethanol (16 mg).
HPLC purity 95%.
MS m/z 517 (M+H$^+$)

Example 30

N-[2-(5-{[bis(2-methoxyethyl)amino]methyl}-1,3-thiazol-2-yl)-1H-indol-7-yl]-N-methylthiophene-2-sulfonamide trifluoroacetate

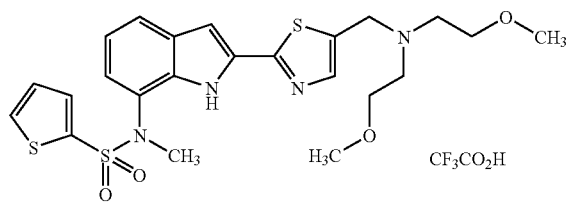

In the same manner as in Example 1, the title compound (8.4 mg, yield 24%) was obtained from N-{2-[5-(chloromethyl)-1,3-thiazol-2-yl]-1H-indol-7-yl}-N-methylthiophene-2-sulfonamide (23 mg) and bis(2-methoxyethyl)amine (16 mg).
HPLC purity 100%.
MS m/z 521 (M+H$^+$).
$^1$H-NMR (400 MHz, CDCl$_3$) δ: 3.32-3.39 (7H, m), 3.42 (6H, s), 3.84-3.89 (4H, m), 4.83 (2H, s), 6.56 (1H, d, J=7.7 Hz), 6.99 (1H, t, J=7.7 Hz), 7.07 (1H, d, J=1.7 Hz), 7.10-7.14 (1H, m), 7.39 (1H, dd, J=3.8, 1.3 Hz), 7.58 (1H, d, J=8.1 Hz), 7.64 (1H, dd, J=5.0, 1.2 Hz), 7.93 (1H, s), 9.66 (1H, brs).

Example 31 ethyl 1-[(2-{7-[methyl(2-thienylsulfonyl)amino]-1H-indol-2-yl}-1,3-thiazol-5-yl)methyl]piperidine-4-carboxylate trifluoroacetate

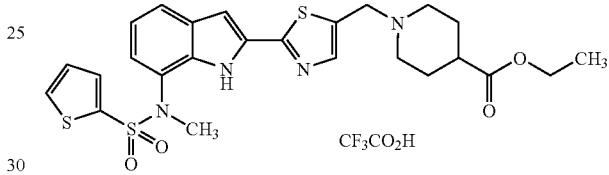

In the same manner as in Example 1, the title compound (13.9 mg, yield 39%) was obtained from N-{2-[5-(chloromethyl)-1,3-thiazol-2-yl]-1H-indol-7-yl}-N-methylthiophene-2-sulfonamide (23 mg) and ethyl isonipecotate (19 mg).
HPLC purity 100%.
MS m/z 545 (M+H$^+$).

Example 32 ethyl 1-[(2-{7-[methyl(2-thienylsulfonyl)amino]-1H-indol-2-yl}-1,3-thiazol-5-yl)methyl]piperidine-3-carboxylate trifluoroacetate

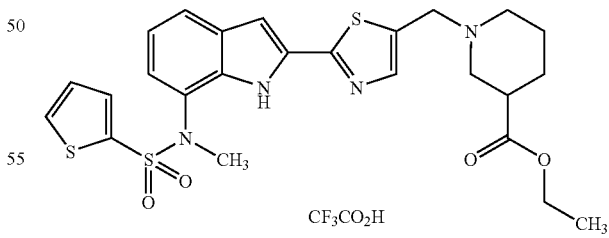

In the same manner as in Example 1, the title compound (13.0 mg, yield 36%) was obtained from N-{2-[5-(chloromethyl)-1,3-thiazol-2-yl]-1H-indol-7-yl}-N-methylthiophene-2-sulfonamide (23 mg) and ethyl nipecotate (19 mg).
HPLC purity 100%.
MS m/z 545 (M+H$^+$).

Example 33

N-(2-{5-[(3-hydroxypyrrolidin-1-yl)methyl]-1,3-thiazol-2-yl}-1H-indol-7-yl)-N-methylthiophene-2-sulfonamide trifluoroacetate

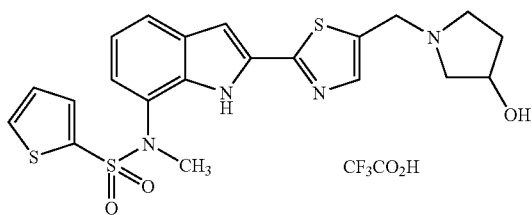

In the same manner as in Example 1, the title compound (10.7 mg, yield 34%) was obtained from N-{2-[5-(chloromethyl)-1,3-thiazol-2-yl]-1H-indol-7-yl}-N-methylthiophene-2-sulfonamide (23 mg) and DL-3-pyrrolidinol (10 mg).
HPLC purity 100%.
MS m/z 475 (M+H$^+$).

Example 34

N-[2-(5-{[2-(hydroxymethyl)piperidino]methyl}-1,3-thiazol-2-yl)-1H-indol-7-yl]-N-methylthiophene-2-sulfonamide trifluoroacetate

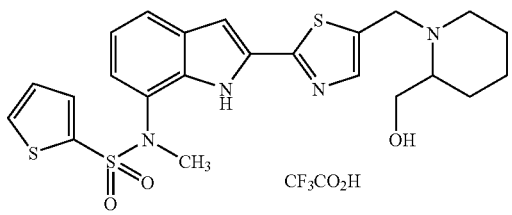

In the same manner as in Example 1, the title compound (7.8 mg, yield 23%) was obtained from N-{2-[5-(chloromethyl)-1,3-thiazol-2-yl]-1H-indol-7-yl}-N-methylthiophene-2-sulfonamide (23 mg) and piperidin-2-ylmethanol (14 mg).
HPLC purity 100%.
MS m/z 503 (M+H$^+$).

Example 35 ethyl N-methyl-N-[(2-{7-[methyl(2-thienylsulfonyl)amino]-1H-indol-2-yl}-1,3-thiazol-5-yl)methyl]glycinate trifluoroacetate

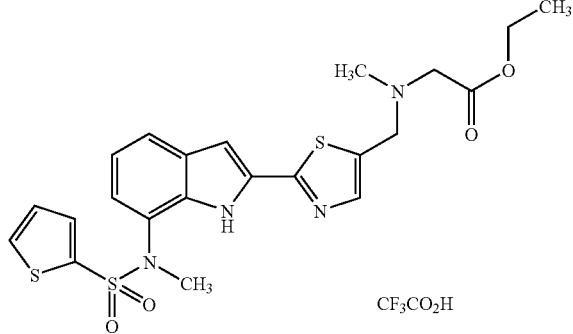

In the same manner as in Example 1, the title compound (14.5 mg, yield 43%) was obtained from N-{2-[5-(chloromethyl)-1,3-thiazol-2-yl]-1H-indol-7-yl}-N-methylthiophene-2-sulfonamide (23 mg) and sarcosine ethyl ester hydrochloride (18 mg).
HPLC purity 100%.
MS m/z 505 (M+H$^+$).

Example 36 ethyl 4-[(2-{7-[methyl(2-thienylsulfonyl)amino]-1H-indol-2-yl}-1,3-thiazol-5-yl)methyl]piperazine-1-carboxylate trifluoroacetate

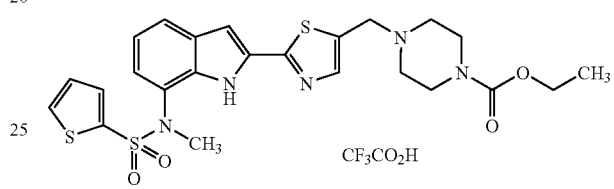

In the same manner as in Example 1, the title compound (12.4 mg, yield 35%) was obtained from N-{2-[5-(chloromethyl)-1,3-thiazol-2-yl]-1H-indol-7-yl}-N-methylthiophene-2-sulfonamide (23 mg) and 1-ethoxycarbonylpiperazine (19 mg).
HPLC purity 100%.
MS m/z 546 (M+H$^+$).

Example 37

N-[2-(5-{[4-(ethylsulfonyl)piperazin-1-yl]methyl}-1,3-thiazol-2-yl)-1H-indol-7-yl]-N-methylthiophene-2-sulfonamide trifluoroacetate

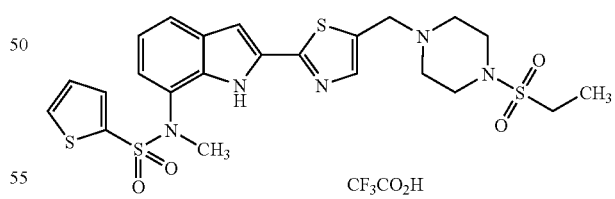

In the same manner as in Example 1, the title compound (10.0 mg, yield 27%) was obtained from N-{2-[5-(chloromethyl)-1,3-thiazol-2-yl]-1H-indol-7-yl}-N-methylthiophene-2-sulfonamide (23 mg) and 1-ethylsulfonylpiperazine (21 mg).
HPLC purity 100%.
MS m/z 566 (M+H$^+$).

Example 38

N-ethyl-N-[2-(5-{[methyl(pyridin-2-ylmethyl)amino]methyl}-1,3-thiazol-2-yl)-1H-indol-7-yl]thiophene-2-sulfonamide ditrifluoroacetate

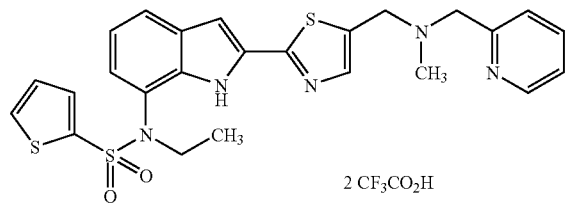

In the same manner as in Example 1, the title compound (14.4 mg, yield 40%) was obtained from N-{2-[5-(chloromethyl)-1,3-thiazol-2-yl]-1H-indol-7-yl}-N-ethylthiophene-2-sulfonamide (20 mg) and N-methyl-1-(pyridin-2-yl)methanamine hydrochloride (19 mg).

HPLC purity 100%.

MS m/z 524 (M+H$^+$).

Example 39

N-ethyl-N-[2-(5-{[methyl(2-(pyridin-2-yl)ethyl)amino]methyl}-1,3-thiazol-2-yl)-1H-indol-7-yl]thiophene-2-sulfonamide ditrifluoroacetate

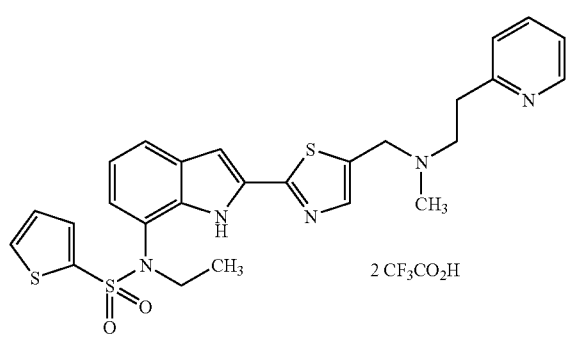

In the same manner as in Example 1, the title compound (11.0 mg, yield 30%) was obtained from N-{2-[5-(chloromethyl)-1,3-thiazol-2-yl]-1H-indol-7-yl}-N-ethylthiophene-2-sulfonamide (20 mg) and N-methyl-2-(pyridin-2-yl)ethanamine (16 mg).

HPLC purity 100%.

MS m/z 538 (M+H$^+$).

Example 40

N-ethyl-N-(2-{5-[(2-pyridin-2-ylpyrrolidin-1-yl)methyl]-1,3-thiazol-2-yl}-1H-indol-7-yl)thiophene-2-sulfonamide ditrifluoroacetate

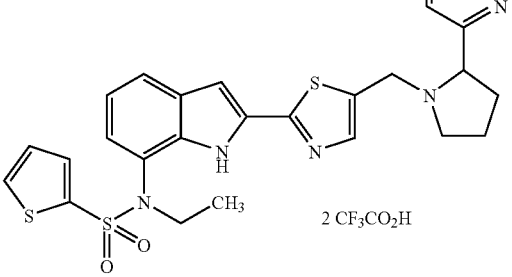

In the same manner as in Example 1, the title compound (10.7 mg, yield 29%) was obtained from N-{2-[5-(chloromethyl)-1,3-thiazol-2-yl]-1H-indol-7-yl}-N-ethylthiophene-2-sulfonamide (20 mg) and 2-(pyrrolidin-2-yl)pyridine (18 mg).

HPLC purity 100%.

MS m/z 550 (M+H$^+$).

Example 41

N-ethyl-N-[2-(5-{[methyl(pyridin-3-ylmethyl)amino]methyl}-1,3-thiazol-2-yl)-1H-indol-7-yl]thiophene-2-sulfonamide ditrifluoroacetate

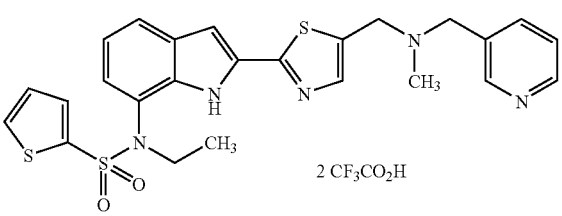

In the same manner as in Example 1, the title compound (7.9 mg, yield 22%) was obtained from N-{2-[5-(chloromethyl)-1,3-thiazol-2-yl]-1H-indol-7-yl}-N-ethylthiophene-2-sulfonamide (20 mg) and N-methyl-1-(pyridin-3-yl)methanamine hydrochloride (19 mg).

HPLC purity 100%.

MS m/z 524 (M+H$^+$).

Example 42

N-ethyl-N-[2-(5-{[3-(methylsulfonyl)pyrrolidin-1-yl]methyl}-1,3-thiazol-2-yl)-1H-indol-7-yl]thiophene-2-sulfonamide trifluoroacetate

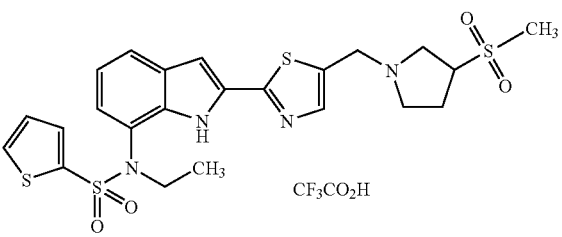

In the same manner as in Example 1, the title compound (6.2 mg, yield 20%) was obtained from N-{2-[5-(chloromethyl)-1,3-thiazol-2-yl]-1H-indol-7-yl}-N-ethylthiophene-2-sulfonamide (20 mg) and 3-(methylsulfonyl)pyrrolidine (18 mg).

HPLC purity 100%.

MS m/z 551 (M+H$^+$).

Example 43

N-ethyl-N-{2-[5-({methyl[2-(methylsulfonyl)ethyl]amino}methyl)-1,3-thiazol-2-yl]-1H-indol-7-yl}thiophene-2-sulfonamide trifluoroacetate

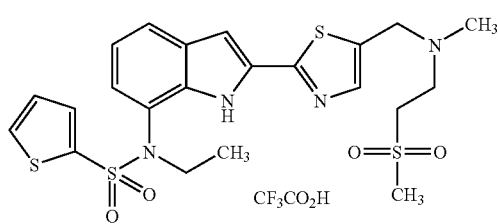

In the same manner as in Example 1, the title compound (5.4 mg, yield 18%) was obtained from N-{2-[5-(chloromethyl)-1,3-thiazol-2-yl]-1H-indol-7-yl}-N-ethylthiophene-2-sulfonamide (20 mg) and N-methyl-2-(methylsulfonyl)ethanamine (16 mg).

HPLC purity 100%.

MS m/z 539 (M+H$^+$).

Example 44

N-ethyl-N-[2-(5-{[4-(pyrimidin-2-yloxy)piperidino]methyl}-1,3-thiazol-2-yl)-1H-indol-7-yl]thiophene-2-sulfonamide trifluoroacetate

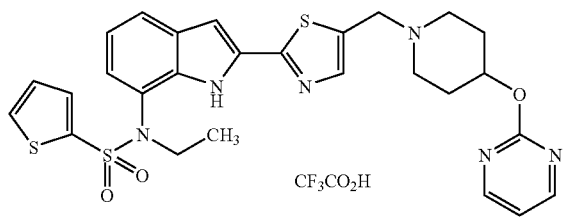

In the same manner as in Example 1, the title compound (12.8 mg, yield 39%) was obtained from N-{2-[5-(chloromethyl)-1,3-thiazol-2-yl]-1H-indol-7-yl}-N-ethylthiophene-2-sulfonamide (20 mg) and 2-(piperidin-4-yloxy)pyrimidine dihydrochloride (30 mg).

HPLC purity 100%.

MS m/z 581 (M+H$^+$).

$^1$H-NMR (400 MHz, CDCl$_3$) δ: 1.11 (3H, t, J=7.2 Hz), 2.32 (4H, brs), 3.27 (2H, brs), 3.54 (2H, brs), 3.77 (2H, d, J=7.3 Hz), 4.52 (2H, s), 5.47 (1H, brs), 6.58 (1H, d, J=7.3 Hz), 6.96-7.13 (4H, m), 7.39 (1H, dd, J=3.7, 1.2 Hz), 7.61 (2H, dd, J=4.7, 3.4 Hz), 7.80 (1H, s), 8.56 (2H, d, J=4.7 Hz), 9.56 (1H, brs).

Example 45

N-ethyl-N-[2-(5-{[4-(pyrazin-2-yloxy)piperidino]methyl}-1,3-thiazol-2-yl)-1H-indol-7-yl]thiophene-2-sulfonamide trifluoroacetate

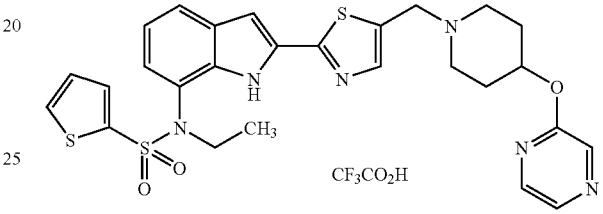

In the same manner as in Example 1, the title compound (10.3 mg, yield 31%) was obtained from N-{2-[5-(chloromethyl)-1,3-thiazol-2-yl]-1H-indol-7-yl}-N-ethylthiophene-2-sulfonamide (20 mg) and 2-(piperidin-4-yloxy)pyrazine dihydrochloride (30 mg).

HPLC purity 100%.

MS m/z 581 (M+H$^+$).

Example 46

N-ethyl-N-[2-(5-{[4-(tetrahydrofuran-2-ylmethyl)piperazin-1-yl]methyl}-1,3-thiazol-2-yl)-1H-indol-7-yl]thiophene-2-sulfonamide ditrifluoroacetate

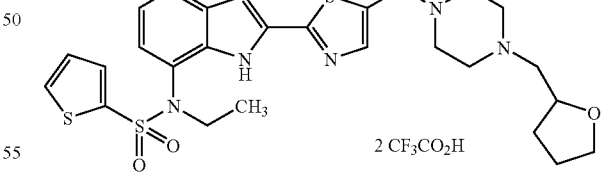

In the same manner as in Example 1, the title compound (12.9 mg, yield 34%) was obtained from N-{2-[5-(chloromethyl)-1,3-thiazol-2-yl]-1H-indol-7-yl}-N-ethylthiophene-2-sulfonamide (20 mg) and 1-(tetrahydrofuran-2-ylmethyl)piperazine (20 mg).

HPLC purity 95%.

MS m/z 572 (M+H$^+$).

Example 47

2-{4-[(2-{7-[ethyl(2-thienylsulfonyl)amino]-1H-indol-2-yl}-1,3-thiazol-5-yl)methyl]piperazin-1-yl}-N,N-dimethylacetamide ditrifluoroacetate

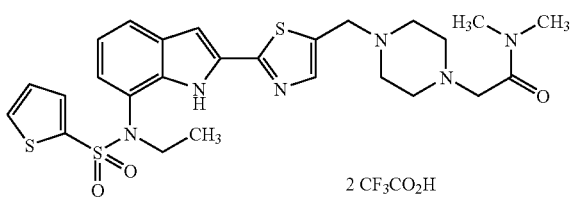

In the same manner as in Example 1, the title compound (16.7 mg, yield 44%) was obtained from N-{2-[5-(chloromethyl)-1,3-thiazol-2-yl]-1H-indol-7-yl}-N-ethylthiophene-2-sulfonamide (20 mg) and N,N-dimethyl-2-(piperazin-1-yl)acetamide (20 mg).
HPLC purity 100%.
MS m/z 573 (M+H$^+$).

Example 48

N-ethyl-N-[2-(5-{[4-(6-methylpyridin-2-yl)piperazin-1-yl]methyl}-1,3-thiazol-2-yl)-1H-indol-7-yl]thiophene-2-sulfonamide trifluoroacetate

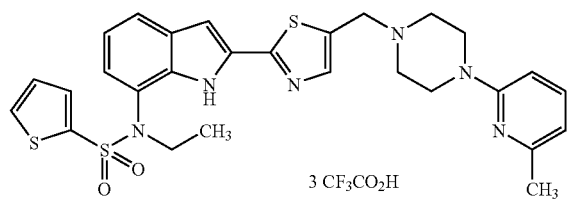

In the same manner as in Example 1, the title compound (16.3 mg, yield 37%) was obtained from N-{2-[5-(chloromethyl)-1,3-thiazol-2-yl]-1H-indol-7-yl}-N-ethylthiophene-2-sulfonamide (20 mg) and 1-(6-methylpyridin-2-yl)piperazine (21 mg).
HPLC purity 100%.
MS m/z 579 (M+H$^+$).

Example 49

N-ethyl-N-(2-{5-[(3-(pyrimidin-2-yl)pyrrolidin-1-yl)methyl]-1,3-thiazol-2-yl}-1H-indol-7-yl)thiophene-2-sulfonamide trifluoroacetate

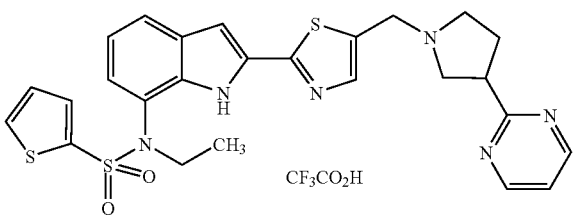

In the same manner as in Example 1, the title compound (11.0 mg, yield 35%) was obtained from N-{2-[5-(chloromethyl)-1,3-thiazol-2-yl]-1H-indol-7-yl}-N-ethylthiophene-2-sulfonamide (20 mg) and 2-(pyrrolidin-3-yl)pyrimidine trihydrochloride (31 mg).
HPLC purity 100%.
MS m/z 551 (M+H$^+$).

Example 50

N-ethyl-N-(2-{5-[(3-(pyridin-2-yl)piperidino)methyl]-1,3-thiazol-2-yl}-1H-indol-7-yl)thiophene-2-sulfonamide ditrifluoroacetate

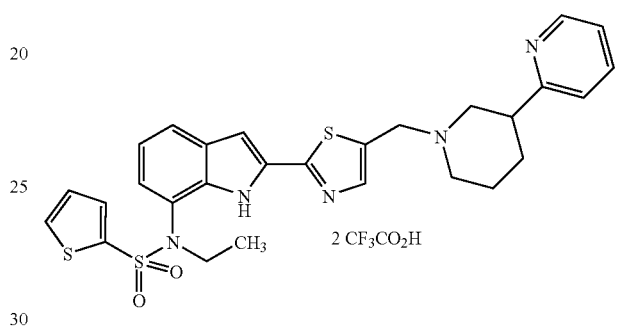

In the same manner as in Example 1, the title compound (16.6 mg, yield 44%) was obtained from N-{2-[5-(chloromethyl)-1,3-thiazol-2-yl]-1H-indol-7-yl}-N-ethylthiophene-2-sulfonamide (20 mg) and 2-(piperidin-3-yl)pyridine (19 mg).
HPLC purity 100%.
MS m/z 564 (M+H$^+$).

Example 51

N-ethyl-N-(2-{5-[(4-(pyridin-2-yl)piperidino)methyl]-1,3-thiazol-2-yl}-1H-indol-7-yl)thiophene-2-sulfonamide ditrifluoroacetate

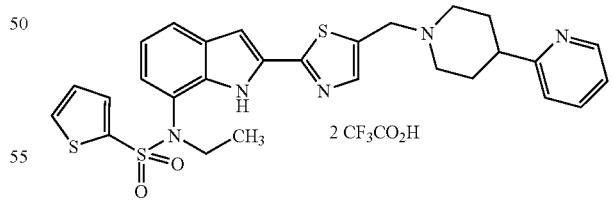

In the same manner as in Example 1, the title compound (13.1 mg, yield 35%) was obtained from N-{2-[5-(chloromethyl)-1,3-thiazol-2-yl]-1H-indol-7-yl}-N-ethylthiophene-2-sulfonamide (20 mg) and 2-(piperidin-4-yl)pyridine (19 mg).
HPLC purity 100%.
MS m/z 564 (M+H$^+$).

Example 52

N-ethyl-N-(2-{5-[(5-methyl-4,6-dioxohexahydropyr-rolo[3,4-c]pyrrol-2(1H)-yl)methyl]-1,3-thiazol-2-yl}-1H-indol-7-yl)thiophene-2-sulfonamide trifluoroacetate

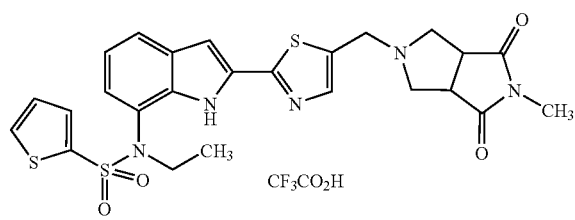

In the same manner as in Example 1, the title compound (7.4 mg, yield 23%) was obtained from N-{2-[5-(chloromethyl)-1,3-thiazol-2-yl]-1H-indol-7-yl}-N-ethylthiophene-2-sulfonamide (20 mg) and 2-methyltetrahydropyrrolo[3,4-c]pyrrole-1,3(2H,3aH)-dione hydrochloride (23 mg).

HPLC purity 100%.

MS m/z 556 (M+H$^+$). $^1$H-NMR (400 MHz, CDCl$_3$) δ: 1.09 (3H, t, J=7.1 Hz), 2.85 (2H, brs), 3.02 (3H, s), 3.37 (2H, d, J=7.2 Hz), 3.59 (2H, d, J=10.5 Hz), 3.76 (2H, d, J=7.2 Hz), 4.13 (2H, s), 6.58 (1H, d, J=7.5 Hz), 7.00 (1H, t, J=7.8 Hz), 7.03 (1H, d, J=2.3 Hz), 7.09 (1H, dd, J=4.9, 3.8 Hz), 7.39 (1H, dd, J=3.8, 1.3 Hz), 7.58-7.63 (2H, m), 7.69 (1H, s), 9.74 (1H, brs).

Example 53

N-ethyl-N-(2-{5-[(4-hydroxy-4-methylpiperidino)methyl]-1,3-thiazol-2-yl}-1H-indol-7-yl)thiophene-2-sulfonamide trifluoroacetate

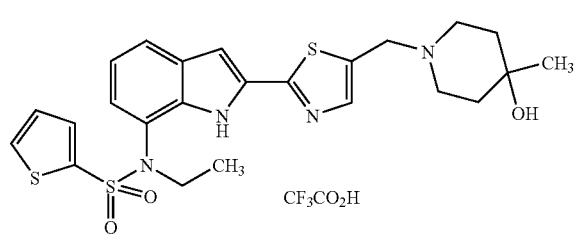

In the same manner as in Example 1, the title compound (9.6 mg, yield 32%) was obtained from N-{2-[5-(chloromethyl)-1,3-thiazol-2-yl]-1H-indol-7-yl}-N-ethylthiophene-2-sulfonamide (20 mg) and 4-methylpiperidin-4-ol hydrochloride (18 mg).

HPLC purity 100%.
MS m/z 517 (M+H$^+$).

Example 54

N-[2-(5-{[cyclopropyl(isobutyl)amino]methyl}-1,3-thiazol-2-yl)-1H-indol-7-yl]-N-ethylthiophene-2-sulfonamide trifluoroacetate

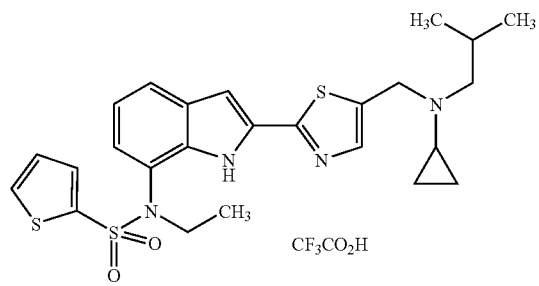

In the same manner as in Example 1, the title compound (3.9 mg, yield 13%) was obtained from N-{2-[5-(chloromethyl)-1,3-thiazol-2-yl]-1H-indol-7-yl}-N-ethylthiophene-2-sulfonamide (20 mg) and N-isobutyl-cyclopropanamine hydrochloride (18 mg).

HPLC purity 100%.
MS m/z 515 (M+H$^+$).

Example 55

N-(2-{5-[(4-tert-butylpiperidino)methyl]-1,3-thiazol-2-yl}-1H-indol-7-yl)-N-ethylthiophene-2-sulfonamide trifluoroacetate

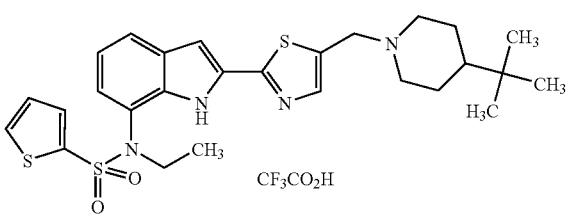

In the same manner as in Example 1, the title compound (9.8 mg, yield 32%) was obtained from N-{2-[5-(chloromethyl)-1,3-thiazol-2-yl]-1H-indol-7-yl}-N-ethylthiophene-2-sulfonamide (20 mg) and 4-tert-butylpiperidine hydrochloride (21 mg).

HPLC purity 98%.
MS m/z 543 (M+H$^+$).

Example 56

N-ethyl-N-[2-(5-{[3-(pyrrolidin-1-ylcarbonyl)piperidino]methyl}-1,3-thiazol-2-yl)-1H-indol-7-yl]thiophene-2-sulfonamide trifluoroacetate

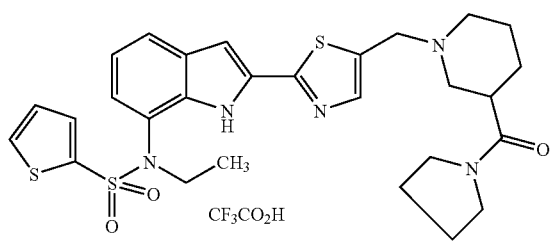

In the same manner as in Example 1, the title compound (14.0 mg, yield 43%) was obtained from N-{2-[5-(chloromethyl)-1,3-thiazol-2-yl]-1H-indol-7-yl}-N-ethylthiophene-2-sulfonamide (20 mg) and 3-(pyrrolidin-1-ylcarbonyl)piperidine (22 mg).
HPLC purity 100%.
MS m/z 584 (M+H$^+$).

Example 57

N-ethyl-N-{2-[5-(pyrrolidin-1-ylmethyl)-1,3-thiazol-2-yl]-1H-indol-7-yl}thiophene-2-sulfonamide trifluoroacetate

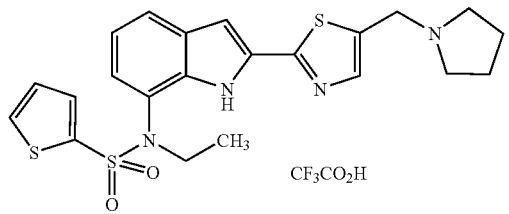

In the same manner as in Example 1, the title compound (7.1 mg, yield 26%) was obtained from N-{2-[5-(chloromethyl)-1,3-thiazol-2-yl]-1H-indol-7-yl}-N-ethylthiophene-2-sulfonamide (20 mg) and pyrrolidine (9 mg).
HPLC purity 100%.
MS m/z 473 (M+H$^+$).

Example 58

N-(2-{5-[(diethylamino)methyl]-1,3-thiazol-2-yl}-1H-indol-7-yl)-N-ethylthiophene-2-sulfonamide trifluoroacetate

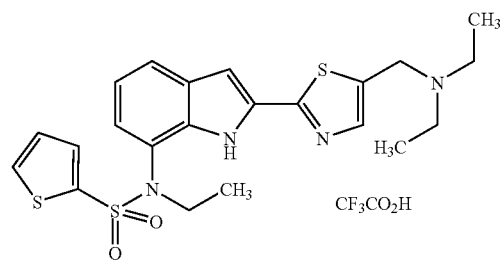

In the same manner as in Example 1, the title compound (2.5 mg, yield 9%) was obtained from N-{2-[5-(chloromethyl)-1,3-thiazol-2-yl]-1H-indol-7-yl}-N-ethylthiophene-2-sulfonamide (20 mg) and diethylamine (8 mg).
HPLC purity 94%.
MS m/z 475 (M+H$^+$).

Example 59

N-ethyl-N-{2-[5-(piperidinomethyl)-1,3-thiazol-2-yl]-1H-indol-7-yl}thiophene-2-sulfonamide trifluoroacetate

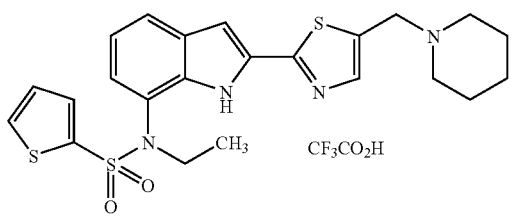

In the same manner as in Example 1, the title compound (8.6 mg, yield 30%) was obtained from N-{2-[5-(chloromethyl)-1,3-thiazol-2-yl]-1H-indol-7-yl}-N-ethylthiophene-2-sulfonamide (20 mg) and piperidine (10 mg).
HPLC purity 100%.
MS m/z 487 (M+H$^+$).

Example 60

N-ethyl-N-(2-{5-[(4-hydroxypiperidino)methyl]-1,3-thiazol-2-yl}-1H-indol-7-yl)thiophene-2-sulfonamide trifluoroacetate

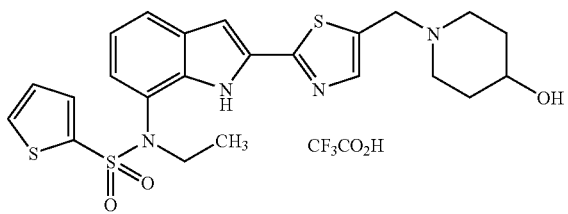

In the same manner as in Example 1, the title compound (10.4 mg, yield 36%) was obtained from N-{2-[5-(chloromethyl)-1,3-thiazol-2-yl]-1H-indol-7-yl}-N-ethylthiophene-2-sulfonamide (20 mg) and 4-hydroxypiperidine (12 mg).
HPLC purity 100%.
MS m/z 503 (M+H$^+$).

Example 61

N-ethyl-N-(2-{5-[(3-hydroxypiperidino)methyl]-1,3-thiazol-2-yl}-1H-indol-7-yl)thiophene-2-sulfonamide trifluoroacetate

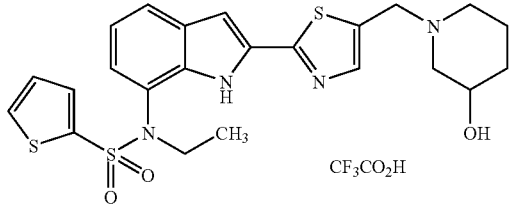

In the same manner as in Example 1, the title compound (12.4 mg, yield 43%) was obtained from N-{2-[5-(chloromethyl)-1,3-thiazol-2-yl]-1H-indol-7-yl}-N-ethylthiophene-2-sulfonamide (20 mg) and 3-hydroxypiperidine (12 mg).

HPLC purity 100%.

MS m/z 503 (M+H⁺).

Example 62

N-ethyl-N-[2-(5-{[(2-methoxyethyl)(methyl)amino]methyl}-1,3-thiazol-2-yl)-1H-indol-7-yl]thiophene-2-sulfonamide trifluoroacetate

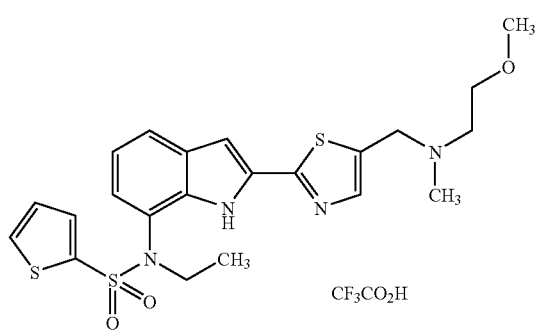

In the same manner as in Example 1, the title compound (7.1 mg, yield 25%) was obtained from N-{2-[5-(chloromethyl)-1,3-thiazol-2-yl]-1H-indol-7-yl}-N-ethylthiophene-2-sulfonamide (20 mg) and N-(2-methoxyethyl)methylamine (11 mg).

HPLC purity 100%.

MS m/z 491 (M+H⁺).

Example 63

N-ethyl-N-[2-(5-{[(2S)-2-(methoxymethyl)pyrrolidin-1-yl]methyl}-1,3-thiazol-2-yl)-1H-indol-7-yl]thiophene-2-sulfonamide trifluoroacetate

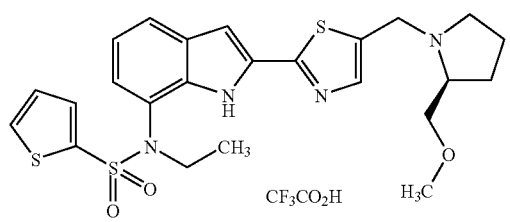

In the same manner as in Example 1, the title compound (10.1 mg, yield 34%) was obtained from N-{2-[5-(chloromethyl)-1,3-thiazol-2-yl]-1H-indol-7-yl}-N-ethylthiophene-2-sulfonamide (20 mg) and (S)-2-(methoxymethyl)pyrrolidine (14 mg).

HPLC purity 100%.

MS m/z 517 (M+H⁺).

Example 64

N-{1-[(2-{7-[ethyl(2-thienylsulfonyl)amino]-1H-indol-2-yl}-1,3-thiazol-5-yl)methyl]pyrrolidin-3-yl}acetamide trifluoroacetate

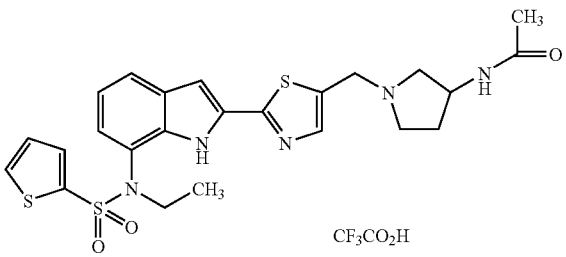

In the same manner as in Example 1, the title compound (9.6 mg, yield 32%) was obtained from N-{2-[5-(chloromethyl)-1,3-thiazol-2-yl]-1H-indol-7-yl}-N-ethylthiophene-2-sulfonamide (20 mg) and 3-acetamidopyrrolidine (15 mg).

HPLC purity 100%.

MS m/z 530 (M+H⁺).

Example 65

1-[(2-{7-[ethyl(2-thienylsulfonyl)amino]-1H-indol-2-yl}-1,3-thiazol-5-yl)methyl]piperidine-4-carboxamide trifluoroacetate

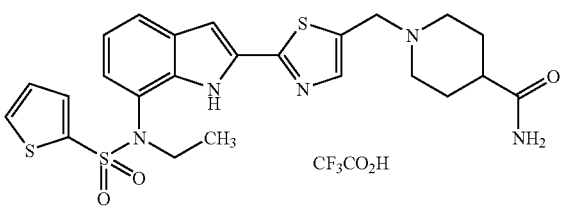

In the same manner as in Example 1, the title compound (8.0 mg, yield 26%) was obtained from N-{2-[5-(chloromethyl)-1,3-thiazol-2-yl]-1H-indol-7-yl}-N-ethylthiophene-2-sulfonamide (20 mg) and isonipecotamide (15 mg).

HPLC purity 100%.

MS m/z 530 (M+H⁺).

Example 66

N-ethyl-N-[2-(5-{[4-(2-hydroxyethyl)piperidino]methyl}-1,3-thiazol-2-yl)-1H-indol-7-yl]thiophene-2-sulfonamide trifluoroacetate

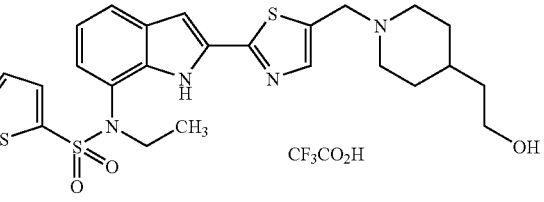

In the same manner as in Example 1, the title compound (11.7 mg, yield 38%) was obtained from N-{2-[5-(chloromethyl)-1,3-thiazol-2-yl]-1H-indol-7-yl}-N-ethylthiophene-2-sulfonamide (20 mg) and 2-(piperidin-4-yl)ethanol (15 mg).

HPLC purity 100%.
MS m/z 531 (M+H⁺).

Example 67

N-[2-(5-{[bis(2-methoxyethyl)amino]methyl}-1,3-thiazol-2-yl)-1H-indol-7-yl]-N-ethylthiophene-2-sulfonamide trifluoroacetate

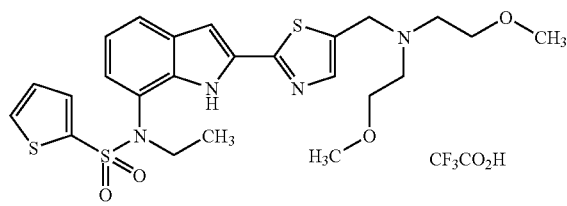

In the same manner as in Example 1, the title compound (6.6 mg, yield 22%) was obtained from N-{2-[5-(chloromethyl)-1,3-thiazol-2-yl]-1H-indol-7-yl}-N-ethylthiophene-2-sulfonamide (20 mg) and bis(2-methoxyethyl)amine (16 mg).

HPLC purity 100%.
MS m/z 535 (M+H⁺).

Example 68 ethyl 1-[(2-{7-[ethyl(2-thienylsulfonyl)amino]-1H-indol-2-yl}-1,3-thiazol-5-yl)methyl]piperidine-4-carboxylate trifluoroacetate

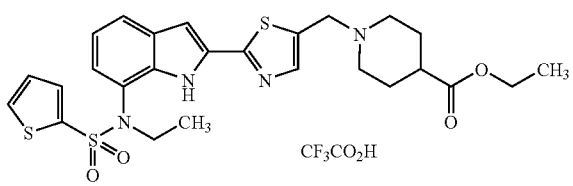

In the same manner as in Example 1, the title compound (12.3 mg, yield 39%) was obtained from N-{2-[5-(chloromethyl)-1,3-thiazol-2-yl]-1H-indol-7-yl}-N-ethylthiophene-2-sulfonamide (20 mg) and ethyl isonipecotate (19 mg).

HPLC purity 97%.
MS m/z 559 (M+H⁺).

Example 69 ethyl 1-[(2-{7-[ethyl(2-thienylsulfonyl)amino]-1H-indol-2-yl}-1,3-thiazol-5-yl)methyl]piperidine-3-carboxylate trifluoroacetate

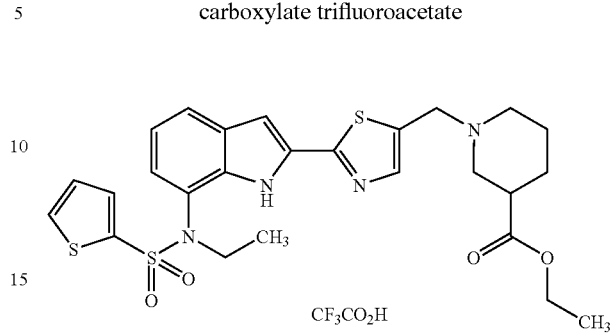

In the same manner as in Example 1, the title compound (12.8 mg, yield 40%) was obtained from N-{2-[5-(chloromethyl)-1,3-thiazol-2-yl]-1H-indol-7-yl}-N-ethylthiophene-2-sulfonamide (20 mg) and ethyl nipecotate (19 mg).

HPLC purity 97%.
MS m/z 559 (M+H⁺).

Example 70

N-ethyl-N-(2-{5-[(3-hydroxypyrrolidin-1-yl)methyl]-1,3-thiazol-2-yl}-1H-indol-7-yl)thiophene-2-sulfonamide trifluoroacetate

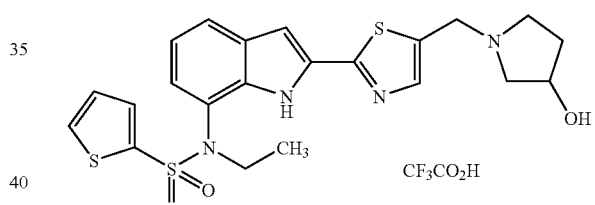

In the same manner as in Example 1, the title compound (10.0 mg, yield 35%) was obtained from N-{2-[5-(chloromethyl)-1,3-thiazol-2-yl]-1H-indol-7-yl}-N-ethylthiophene-2-sulfonamide (20 mg) and DL-3-pyrrolidinol (10 mg).

HPLC purity 95%.
MS m/z 489 (M+H⁺).

Example 71

N-ethyl-N-[2-(5-{[2-(hydroxymethyl)piperidino]methyl}-1,3-thiazol-2-yl)-1H-indol-7-yl]thiophene-2-sulfonamide trifluoroacetate

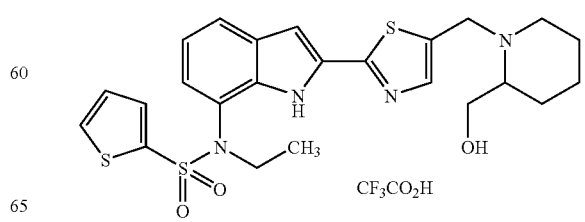

In the same manner as in Example 1, the title compound (6.9 mg, yield 23%) was obtained from N-{2-[5-(chloromethyl)-1,3-thiazol-2-yl]-1H-indol-7-yl}-N-ethylthiophene-2-sulfonamide (20 mg) and piperidin-2-ylmethanol (14 mg).
HPLC purity 100%.
MS m/z 517 (M+H⁺).

Example 72 ethyl N-[(2-{7-[ethyl(2-thienylsulfonyl)amino]-1H-indol-2-yl}-1,3-thiazol-5-yl)methyl]-N-methylglycinate trifluoroacetate

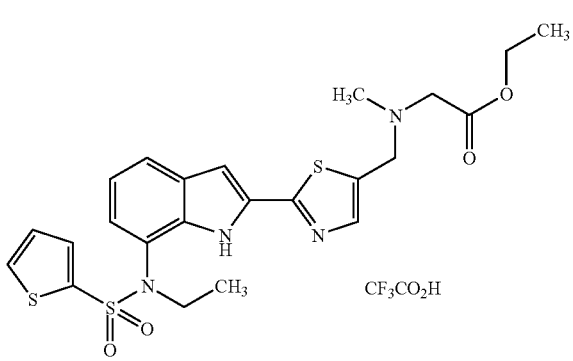

In the same manner as in Example 1, the title compound (12.7 mg, yield 43%) was obtained from N-{2-[5-(chloromethyl)-1,3-thiazol-2-yl]-1H-indol-7-yl}-N-ethylthiophene-2-sulfonamide (20 mg) and sarcosine ethyl ester hydrochloride (18 mg).
HPLC purity 97%.
MS m/z 519 (M+H⁺).

Example 73 ethyl 4-[(2-{7-[ethyl(2-thienylsulfonyl)amino]-1H-indol-2-yl}-1,3-thiazol-5-yl)methyl]piperazine-1-carboxylate trifluoroacetate

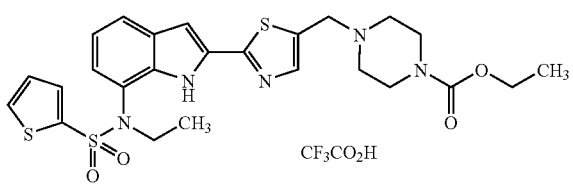

In the same manner as in Example 1, the title compound (10.4 mg, yield 33%) was obtained from N-{2-[5-(chloromethyl)-1,3-thiazol-2-yl]-1H-indol-7-yl}-N-ethylthiophene-2-sulfonamide (20 mg) and 1-ethoxycarbonylpiperazine (19 mg).
HPLC purity 100%.
MS m/z 560 (M+H⁺).

Example 74

N-ethyl-N-[2-(5-{[4-(ethylsulfonyl)piperazin-1-yl]methyl}-1,3-thiazol-2-yl)-1H-indol-7-yl]thiophene-2-sulfonamide trifluoroacetate

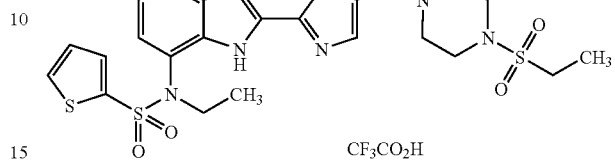

In the same manner as in Example 1, the title compound (10.6 mg, yield 32%) was obtained from N-{2-[5-(chloromethyl)-1,3-thiazol-2-yl]-1H-indol-7-yl}-N-ethylthiophene-2-sulfonamide (20 mg) and 1-ethylsulfonylpiperazine (21 mg).
HPLC purity 100%.
MS m/z 580 (M+H⁺).

Example 75

N-(cyclopropylmethyl)-N-[2-(5-{[methyl(pyridin-2-ylmethyl)amino]methyl}-1,3-thiazol-2-yl)-1H-indol-7-yl]thiophene-2-sulfonamide ditrifluoroacetate

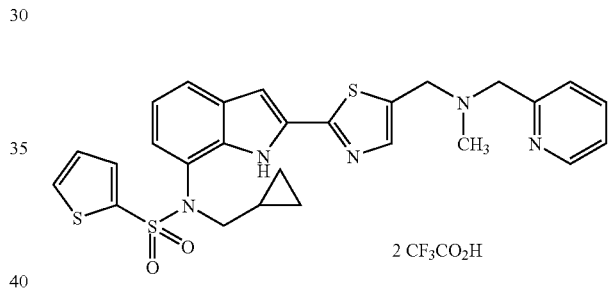

In the same manner as in Example 1, the title compound (17.1 mg, yield 50%) was obtained from N-{2-[5-(chloromethyl)-1,3-thiazol-2-yl]-1H-indol-7-yl}-N-(cyclopropylmethyl)thiophene-2-sulfonamide (20 mg) and N-methyl-1-(pyridin-2-yl)methanamine hydrochloride (19 mg).
HPLC purity 96%.
MS m/z 550 (M+H⁺).

Example 76

N-(cyclopropylmethyl)-N-[2-(5-{[methyl(2-(pyridin-2-yl)ethyl)amino]methyl}-1,3-thiazol-2-yl)-1H-indol-7-yl]thiophene-2-sulfonamide ditrifluoroacetate

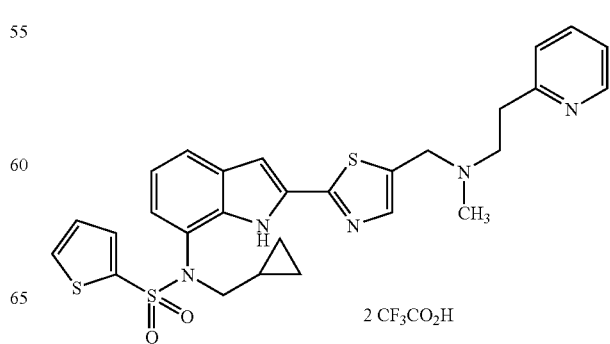

In the same manner as in Example 1, the title compound (11.4 mg, yield 33%) was obtained from N-{2-[5-(chloromethyl)-1,3-thiazol-2-yl]-1H-indol-7-yl}-N-(cyclopropylmethyl)thiophene-2-sulfonamide (20 mg) and N-methyl-2-(pyridin-2-yl)ethanamine (16 mg).

HPLC purity 100%.

MS m/z 564 (M+H$^+$).

Example 77

N-(cyclopropylmethyl)-N-(2-{5-[(2-(pyridin-2-yl)pyrrolidin-1-yl)methyl]-1,3-thiazol-2-yl}-1H-indol-7-yl)thiophene-2-sulfonamide ditrifluoroacetate

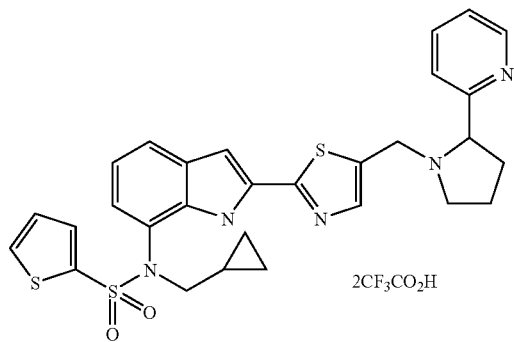

In the same manner as in Example 1, the title compound (13.3 mg, yield 38%) was obtained from N-{2-[5-(chloromethyl)-1,3-thiazol-2-yl]-1H-indol-7-yl}-N-(cyclopropylmethyl)thiophene-2-sulfonamide (20 mg) and 2-(pyrrolidin-2-yl)pyridine (18 mg).

HPLC purity 97%.

MS m/z 576 (M+H$^+$).

Example 78

1 N-(cyclopropylmethyl)-N-[2-(5-{[methyl(pyridin-3-ylmethyl)amino]methyl}-1,3-thiazol-2-yl)-1H-indol-7-yl]thiophene-2-sulfonamide ditrifluoroacetate

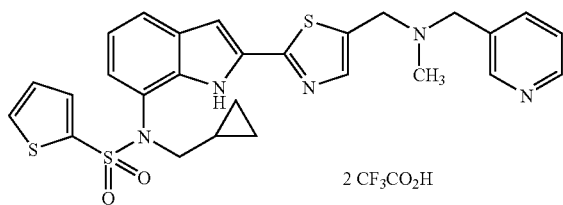

In the same manner as in Example 1, the title compound (14.0 mg, yield 41%) was obtained from N-{2-[5-(chloromethyl)-1,3-thiazol-2-yl]-1H-indol-7-yl}-N-(cyclopropylmethyl)thiophene-2-sulfonamide (20 mg) and N-methyl-1-(pyridin-3-yl)methanamine hydrochloride (19 mg).

HPLC purity 100%.

MS m/z 550 (M+H$^+$).

Example 79

N-(cyclopropylmethyl)-N-[2-(5-{[3-(methylsulfonyl)pyrrolidin-1-yl]methyl}-1,3-thiazol-2-yl)-1H-indol-7-yl]thiophene-2-sulfonamide trifluoroacetate

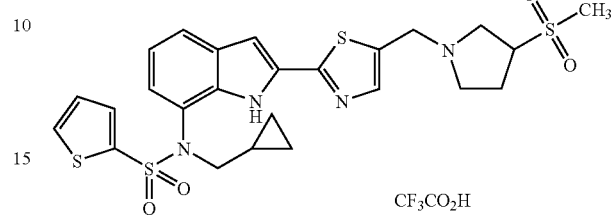

In the same manner as in Example 1, the title compound (10.5 mg, yield 34%) was obtained from N-{2-[5-(chloromethyl)-1,3-thiazol-2-yl]-1H-indol-7-yl}-N-(cyclopropylmethyl)thiophene-2-sulfonamide (20 mg) and 3-(methylsulfonyl)pyrrolidine (18 mg).

HPLC purity 100%.

MS m/z 577 (M+H$^+$).

Example 80

N-(cyclopropylmethyl)-N-{2-[5-({methyl[2-(methylsulfonyl)ethyl]amino}methyl)-1,3-thiazol-2-yl]-1H-indol-7-yl}thiophene-2-sulfonamide trifluoroacetate

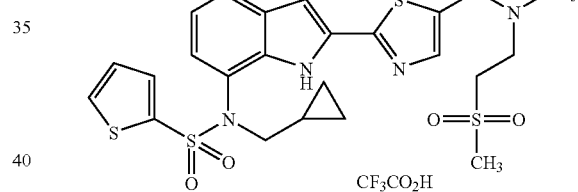

In the same manner as in Example 1, the title compound (8.0 mg, yield 26.8%) was obtained from N-{2-[5-(chloromethyl)-1,3-thiazol-2-yl]-1H-indol-7-yl}-N-(cyclopropylmethyl)thiophene-2-sulfonamide (20 mg) and N-methyl-2-(methylsulfonyl)ethanamine (16 mg).

HPLC purity 100%.

MS m/z 565 (M+H$^+$).

Example 81

N-(cyclopropylmethyl)-N-[2-(5-{[4-(pyrimidin-2-yloxy)piperidino]methyl}-1,3-thiazol-2-yl)-1H-indol-7-yl]thiophene-2-sulfonamide ditrifluoroacetate

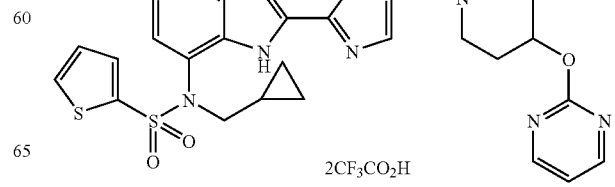

In the same manner as in Example 1, the title compound (13.9 mg, yield 44%) was obtained from N-{2-[5-(chloromethyl)-1,3-thiazol-2-yl]-1H-indol-7-yl}-N-(cyclopropylmethyl)thiophene-2-sulfonamide (20 mg) and 2-(piperidin-4-yloxy)pyrimidine dihydrochloride (30 mg).

HPLC purity 100%.

MS m/z 607 (M+H$^+$).

Example 82

N-(cyclopropylmethyl)-N-[2-(5-{[4-(pyrazin-2-yloxy)piperidino]methyl}-1,3-thiazol-2-yl)-1H-indol-7-yl]thiophene-2-sulfonamide ditrifluoroacetate

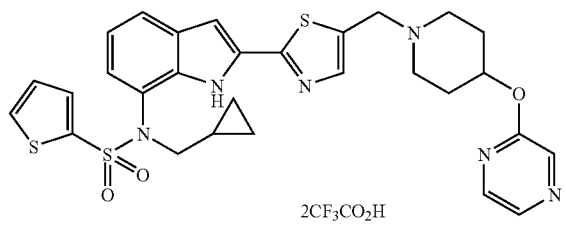

In the same manner as in Example 1, the title compound (13.0 mg, yield 41%) was obtained from N-{2-[5-(chloromethyl)-1,3-thiazol-2-yl]-1H-indol-7-yl}-N-(cyclopropylmethyl)thiophene-2-sulfonamide (20 mg) and 2-(piperidin-4-yloxy)pyrazine dihydrochloride (30 mg).

HPLC purity 95%.

MS m/z 607 (M+H$^+$).

Example 83

N-(cyclopropylmethyl)-N-[2-(5-{[4-(tetrahydrofuran-2-ylmethyl)piperazin-1-yl]methyl}-1,3-thiazol-2-yl)-1H-indol-7-yl]thiophene-2-sulfonamide ditrifluoroacetate

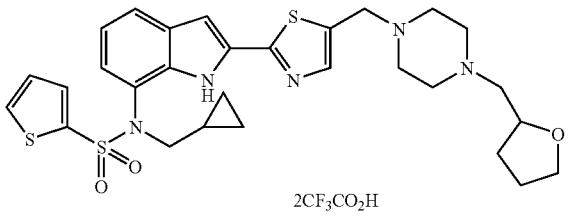

In the same manner as in Example 1, the title compound (18.6 mg, yield 51%) was obtained from N-{2-[5-(chloromethyl)-1,3-thiazol-2-yl]-1H-indol-7-yl}-N-(cyclopropylmethyl)thiophene-2-sulfonamide (20 mg) and 1-(tetrahydrofuran-2-ylmethyl)piperazine (20 mg).

HPLC purity 95%.

MS m/z 598 (M+H$^+$).

Example 84

2-{4-[(2-{7-[(cyclopropylmethyl)(2-thienylsulfonyl)amino]-1H-indol-2-yl}-1,3-thiazol-5-yl)methyl]piperazin-1-yl}-N,N-dimethylacetamide ditrifluoroacetate

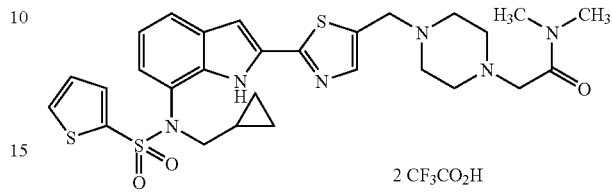

In the same manner as in Example 1, the title compound (24.6 mg, yield 68%) was obtained from N-{2-[5-(chloromethyl)-1,3-thiazol-2-yl]-1H-indol-7-yl}-N-(cyclopropylmethyl)thiophene-2-sulfonamide (20 mg) and N,N-dimethyl-2-(piperazin-1-yl)acetamide (21 mg).

HPLC purity 100%.

MS m/z 599 (M+H$^+$).

Example 85

N-(cyclopropylmethyl)-N-[2-(5-{[4-(6-methylpyridin-2-yl)piperazin-1-yl]methyl}-1,3-thiazol-2-yl)-1H-indol-7-yl]thiophene-2-sulfonamide trifluoroacetate

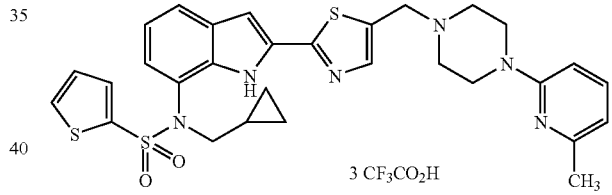

In the same manner as in Example 1, the title compound (22.6 mg, yield 54%) was obtained from N-{2-[5-(chloromethyl)-1,3-thiazol-2-yl]-1H-indol-7-yl}-N-(cyclopropylmethyl)thiophene-2-sulfonamide (20 mg) and 1-(6-methylpyridin-2-yl)piperazine (21 mg).

HPLC purity 97%.

MS m/z 605 (M+H$^+$).

Example 86

N-(cyclopropylmethyl)-N-(2-{5-[(3-(pyrimidin-2-yl)pyrrolidin-1-yl)methyl]-1,3-thiazol-2-yl}-1H-indol-7-yl)thiophene-2-sulfonamide trifluoroacetate

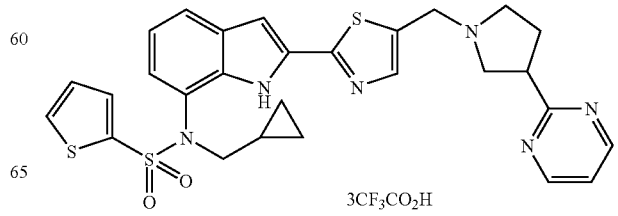

In the same manner as in Example 1, the title compound (12.3 mg, yield 40%) was obtained from N-{2-[5-(chloromethyl)-1,3-thiazol-2-yl]-1H-indol-7-yl}-N-(cyclopropylmethyl)thiophene-2-sulfonamide (20 mg) and 2-(pyrrolidin-3-yl)pyrimidine trihydrochloride (31 mg).

HPLC purity 100%.

MS m/z 577 (M+H⁺).

Example 87

N-(cyclopropylmethyl)-N-(2-{5-[(3-(pyridin-2-yl)piperidino)methyl]-1,3-thiazol-2-yl}-1H-indol-7-yl)thiophene-2-sulfonamide ditrifluoroacetate

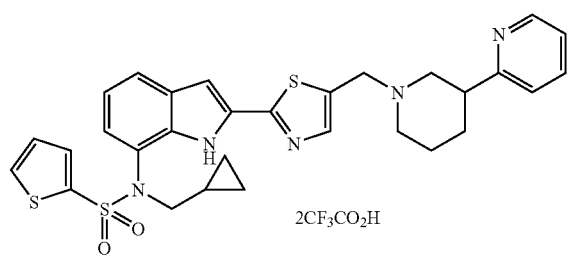

In the same manner as in Example 1, the title compound (12.2 mg, yield 34%) was obtained from N-{2-[5-(chloromethyl)-1,3-thiazol-2-yl]-1H-indol-7-yl}-N-(cyclopropylmethyl)thiophene-2-sulfonamide (20 mg) and 2-(piperidin-3-yl)pyridine (19 mg).

HPLC purity 100%.

MS m/z 590 (M+H⁺).

Example 88

N-(cyclopropylmethyl)-N-(2-{5-[(4-(pyridin-2-yl)piperidino)methyl]-1,3-thiazol-2-yl}-1H-indol-7-yl)thiophene-2-sulfonamide ditrifluoroacetate

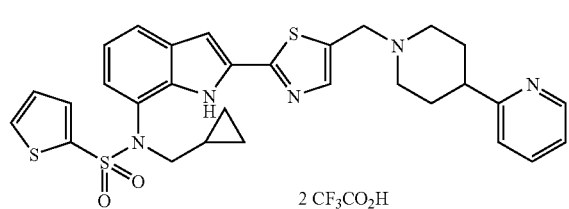

In the same manner as in Example 1, the title compound (18.0 mg, yield 50%) was obtained from N-{2-[5-(chloromethyl)-1,3-thiazol-2-yl]-1H-indol-7-yl}-N-(cyclopropylmethyl)thiophene-2-sulfonamide (20 mg) and 2-(piperidin-4-yl)pyridine (19 mg).

HPLC purity 100%.

MS m/z 590 (M+H⁺).

Example 89

N-(cyclopropylmethyl)-N-(2-{5-[(5-methyl-4,6-dioxohexahydropyrrolo[3,4-c]pyrrol-2(1H)-yl)methyl]-1,3-thiazol-2-yl}-1H-indol-7-yl)thiophene-2-sulfonamide trifluoroacetate

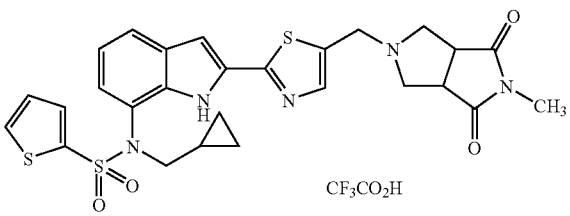

In the same manner as in Example 1, the title compound (9.9 mg, yield 32%) was obtained from N-{2-[5-(chloromethyl)-1,3-thiazol-2-yl]-1H-indol-7-yl}-N-(cyclopropylmethyl)thiophene-2-sulfonamide (20 mg) and 2-methyltetrahydropyrrolo[3,4-c]pyrrole-1,3(2H,3aH)-dione hydrochloride (23 mg).

HPLC purity 95%.

MS m/z 582 (M+H⁺).

Example 90

N-(cyclopropylmethyl)-N-(2-{5-[(4-hydroxy-4-methylpiperidino)methyl]-1,3-thiazol-2-yl}-1H-indol-7-yl)thiophene-2-sulfonamide trifluoroacetate

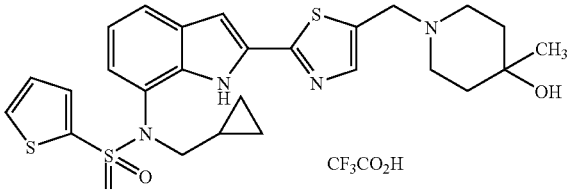

In the same manner as in Example 1, the title compound (11.3 mg, yield 39%) was obtained from N-{2-[5-(chloromethyl)-1,3-thiazol-2-yl]-1H-indol-7-yl}-N-(cyclopropylmethyl)thiophene-2-sulfonamide (20 mg) and 4-methylpiperidin-4-ol hydrochloride (18 mg).

HPLC purity 100%.

MS m/z 543 (M+H⁺).

Example 91

N-[2-(5-{[cyclopropyl(isobutyl)amino]methyl}-1,3-thiazol-2-yl)-1H-indol-7-yl]-N-(cyclopropylmethyl)thiophene-2-sulfonamide trifluoroacetate

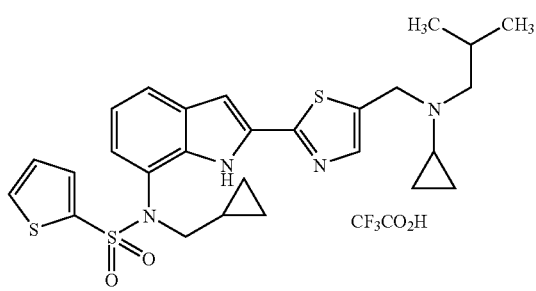

In the same manner as in Example 1, the title compound (3.1 mg, yield 11%) was obtained from N-{2-[5-(chloromethyl)-1,3-thiazol-2-yl]-1H-indol-7-yl}-N-(cyclopropylmethyl)thiophene-2-sulfonamide (20 mg) and N-isobutyl-cyclopropanamine hydrochloride (18 mg).

HPLC purity 100%.
MS m/z 541 (M+H$^+$).

Example 92

N-(2-{5-[(4-tert-butylpiperidino)methyl]-1,3-thiazol-2-yl}-1H-indol-7-yl)-N-(cyclopropylmethyl)thiophene-2-sulfonamide trifluoroacetate

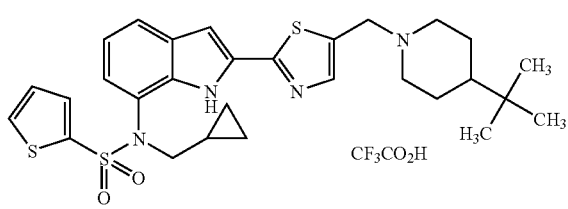

In the same manner as in Example 1, the title compound (10.6 mg, yield 35%) was obtained from N-{2-[5-(chloromethyl)-1,3-thiazol-2-yl]-1H-indol-7-yl}-N-(cyclopropylmethyl)thiophene-2-sulfonamide (20 mg) and 4-tert-butylpiperidine hydrochloride (21 mg).

HPLC purity 100%.
MS m/z 569 (M+H$^+$).

Example 93

N-(cyclopropylmethyl)-N-[2-(5-{[3-(pyrrolidin-1-ylcarbonyl)piperidino]methyl}-1,3-thiazol-2-yl)-1H-indol-7-yl]thiophene-2-sulfonamide trifluoroacetate

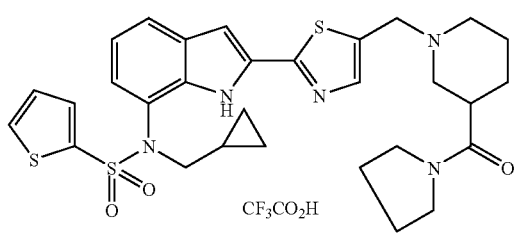

In the same manner as in Example 1, the title compound (18.5 mg, yield 58%) was obtained from N-{2-[5-(chloromethyl)-1,3-thiazol-2-yl]-1H-indol-7-yl}-N-(cyclopropylmethyl)thiophene-2-sulfonamide (20 mg) and 3-(pyrrolidin-1-ylcarbonyl)piperidine (22 mg).

HPLC purity 97%.
MS m/z 610 (M+H$^+$).

Example 94

N-(cyclopropylmethyl)-N-{2-[5-(pyrrolidin-1-ylmethyl)-1,3-thiazol-2-yl]-1H-indol-7-yl}thiophene-2-sulfonamide trifluoroacetate

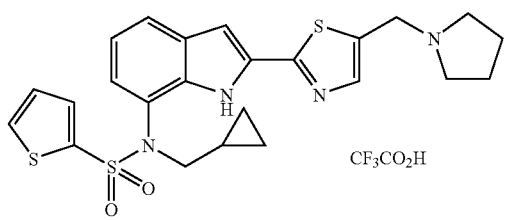

In the same manner as in Example 1, the title compound (7.9 mg, yield 29%) was obtained from N-{2-[5-(chloromethyl)-1,3-thiazol-2-yl]-1H-indol-7-yl}-N-(cyclopropylmethyl)thiophene-2-sulfonamide (20 mg) and pyrrolidine (8 mg).

HPLC purity 100%.
MS m/z 499 (M+H$^+$).

Example 95

N-(cyclopropylmethyl)-N-(2-{5-[(diethylamino)methyl]-1,3-thiazol-2-yl}-1H-indol-7-yl)thiophene-2-sulfonamide trifluoroacetate

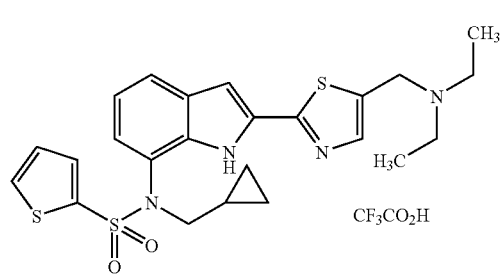

In the same manner as in Example 1, the title compound (3.5 mg, yield 13%) was obtained from N-{2-[5-(chloromethyl)-1,3-thiazol-2-yl]-1H-indol-7-yl}-N-(cyclopropylmethyl)thiophene-2-sulfonamide (20 mg) and diethylamine (8 mg).

HPLC purity 92%.
MS m/z 501 (M+H$^+$).

Example 96

N-(cyclopropylmethyl)-N-{2-[5-(piperidinomethyl)-1,3-thiazol-2-yl]-1H-indol-7-yl}thiophene-2-sulfonamide trifluoroacetate

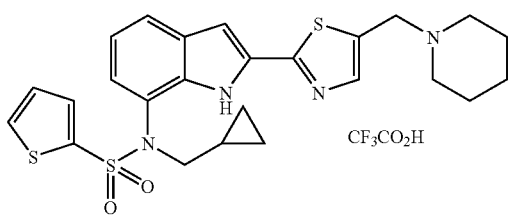

In the same manner as in Example 1, the title compound (11.2 mg, yield 41%) was obtained from N-{2-[5-(chloromethyl)-1,3-thiazol-2-yl]-1H-indol-7-yl}-N-(cyclopropylmethyl)thiophene-2-sulfonamide (20 mg) and piperidine (10 mg).
HPLC purity 100%.
MS m/z 513 (M+H$^+$).

Example 97

N-(cyclopropylmethyl)-N-(2-{5-[(4-hydroxypiperidino)methyl]-1,3-thiazol-2-yl}-1H-indol-7-yl)thiophene-2-sulfonamide trifluoroacetate

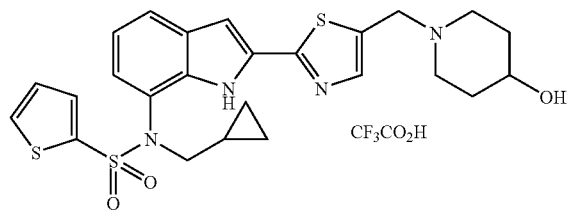

In the same manner as in Example 1, the title compound (13.5 mg, yield 48%) was obtained from N-{2-[5-(chloromethyl)-1,3-thiazol-2-yl]-1H-indol-7-yl}-N-(cyclopropylmethyl)thiophene-2-sulfonamide (20 mg) and 4-hydroxypiperidine (12 mg).
HPLC purity 100%.
MS m/z 529 (M+H$^+$).

Example 98

N-(cyclopropylmethyl)-N-(2-{5-[(3-hydroxypiperidino)methyl]-1,3-thiazol-2-yl}-1H-indol-7-yl)thiophene-2-sulfonamide trifluoroacetate

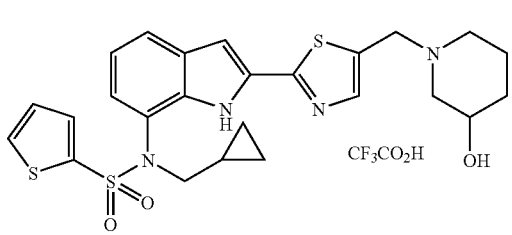

In the same manner as in Example 1, the title compound (14.9 mg, yield 53%) was obtained from N-{2-[5-(chloromethyl)-1,3-thiazol-2-yl]-1H-indol-7-yl}-N-(cyclopropylmethyl)thiophene-2-sulfonamide (20 mg) and 3-hydroxypiperidine (12 mg).
HPLC purity 100%.
MS m/z 529 (M+H$^+$).

Example 99

N-(cyclopropylmethyl)-N-[2-(5-{[(2-methoxyethyl)(methyl)amino]methyl}-1,3-thiazol-2-yl)-1H-indol-7-yl]thiophene-2-sulfonamide trifluoroacetate

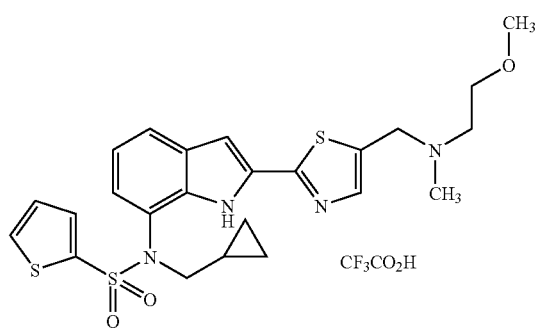

In the same manner as in Example 1, the title compound (9.5 mg, yield 34%) was obtained from N-{2-[5-(chloromethyl)-1,3-thiazol-2-yl]-1H-indol-7-yl}-N-(cyclopropylmethyl)thiophene-2-sulfonamide (20 mg) and N-(2-methoxyethyl)methylamine (11 mg).
HPLC purity 100%.
MS m/z 517 (M+H$^+$). $^1$H-NMR (400 MHz, CDCl$_3$) δ: 0.15 (2H, d, J=4.3 Hz), 0.37 (2H, d, J=7.7 Hz), 0.87-0.94 (1H, m), 2.86 (3H, s), 3.31 (2H, brs), 3.44 (3H, s), 3.57 (2H, brs), 3.83 (2H, t, J=4.2 Hz), 4.66 (2H, s), 6.62 (1H, d, J=7.7 Hz), 6.96-7.04 (1H, m), 7.06-7.11 (2H, m), 7.38-7.42 (1H, m), 7.58-7.64 (2H, m), 7.87 (1H, s), 9.61 (1H, brs).

Example 100

N-(cyclopropylmethyl)-N-[2-(5-{[(2S)-2-(methoxymethyl)pyrrolidin-1-yl]methyl}-1,3-thiazol-2-yl)-1H-indol-7-yl]thiophene-2-sulfonamide trifluoroacetate

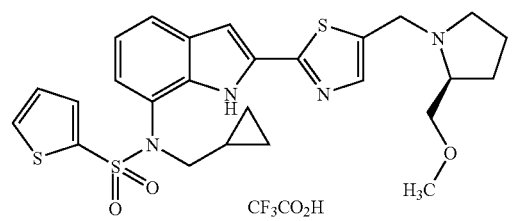

In the same manner as in Example 1, the title compound (14.6 mg, yield 50%) was obtained from N-{2-[5-(chloromethyl)-1,3-thiazol-2-yl]-1H-indol-7-yl}-N-(cyclopropylmethyl)thiophene-2-sulfonamide (20 mg) and (S)-2-(methoxymethyl)pyrrolidine (14 mg).

HPLC purity 100%.
MS m/z 543 (M+H$^+$).

Example 101

N-{1-[(2-{7-[(cyclopropylmethyl)(2-thienylsulfonyl)amino]-1H-indol-2-yl}-1,3-thiazol-5-yl)methyl]pyrrolidin-3-yl}acetamide trifluoroacetate

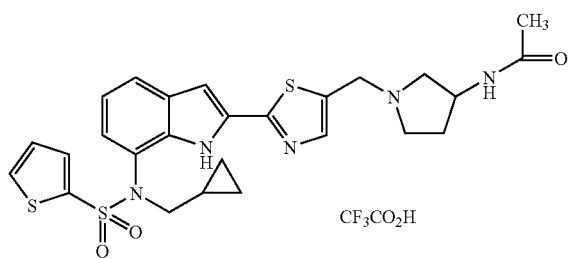

In the same manner as in Example 1, the title compound (13.8 mg, yield 47%) was obtained from N-{2-[5-(chloromethyl)-1,3-thiazol-2-yl]-1H-indol-7-yl}-N-(cyclopropylmethyl)thiophene-2-sulfonamide (20 mg) and 3-acetamidopyrrolidine (15 mg).

HPLC purity 100%.
MS m/z 556 (M+H$^+$).

Example 102

1-[(2-{7-[(cyclopropylmethyl)(2-thienylsulfonyl)amino]-1H-indol-2-yl}-1,3-thiazol-5-yl)methyl]piperidine-4-carboxamide trifluoroacetate

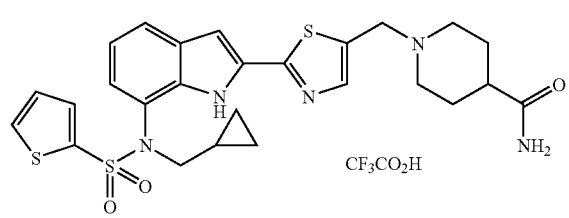

In the same manner as in Example 1, the title compound (13.2 mg, yield 45%) was obtained from N-{2-[5-(chloromethyl)-1,3-thiazol-2-yl]-1H-indol-7-yl}-N-(cyclopropylmethyl)thiophene-2-sulfonamide (20 mg) and isonipecotamide (15 mg).

HPLC purity 97%.
MS m/z 556 (M+H$^+$).

Example 103

N-(cyclopropylmethyl)-N-[2-(5-{[4-(2-hydroxyethyl)piperidino]methyl}-1,3-thiazol-2-yl)-1H-indol-7-yl]thiophene-2-sulfonamide trifluoroacetate

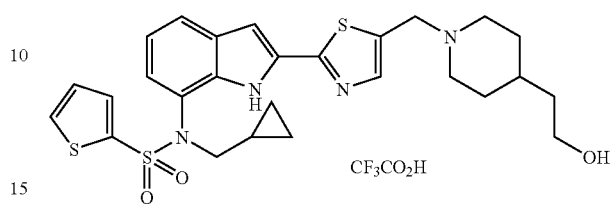

In the same manner as in Example 1, the title compound (14.2 mg, yield 48%) was obtained from N-{2-[5-(chloromethyl)-1,3-thiazol-2-yl]-1H-indol-7-yl}-N-(cyclopropylmethyl)thiophene-2-sulfonamide (20 mg) and 2-(piperidin-4-yl)ethanol (16 mg).

HPLC purity 100%.
MS m/z 557 (M+H$^+$).

Example 104

N-[2-(5-{[bis(2-methoxyethyl)amino]methyl}-1,3-thiazol-2-yl)-1H-indol-7-yl]-N-(cyclopropylmethyl)thiophene-2-sulfonamide trifluoroacetate

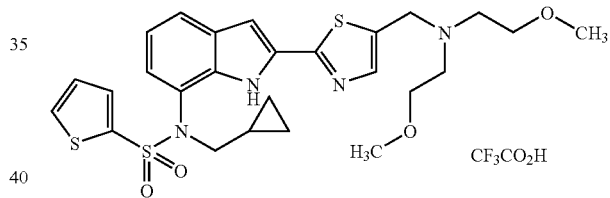

In the same manner as in Example 1, the title compound (7.9 mg, yield 27%) was obtained from N-{2-[5-(chloromethyl)-1,3-thiazol-2-yl]-1H-indol-7-yl}-N-(cyclopropylmethyl)thiophene-2-sulfonamide (20 mg) and bis(2-methoxyethyl)amine (16 mg).

HPLC purity 96%.
MS m/z 561 (M+H$^+$).

Example 105 ethyl 1-[(2-{7-[(cyclopropylmethyl)(2-thienylsulfonyl)amino]-1H-indol-2-yl}-1,3-thiazol-5-yl)methyl]piperidine-4-carboxylate trifluoroacetate

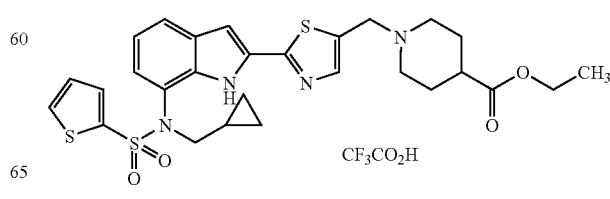

In the same manner as in Example 1, the title compound (13.6 mg, yield 44%) was obtained from N-{2-[5-(chloromethyl)-1,3-thiazol-2-yl]-1H-indol-7-yl}-N-(cyclopropylmethyl)thiophene-2-sulfonamide (20 mg) and ethyl isonipecotate (19 mg).

HPLC purity 97%.
MS m/z 585 (M+H$^+$).

Example 106 ethyl 1-[(2-{7-[(cyclopropylmethyl)(2-thienylsulfonyl)amino]-1H-indol-2-yl}-1,3-thiazol-5-yl)methyl]piperidine-3-carboxylate trifluoroacetate

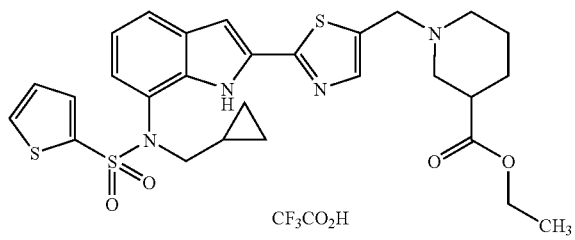

In the same manner as in Example 1, the title compound (13.4 mg, yield 44%) was obtained from N-{2-[5-(chloromethyl)-1,3-thiazol-2-yl]-1H-indol-7-yl}-N-(cyclopropylmethyl)thiophene-2-sulfonamide (20 mg) and ethyl nipecotate (19 mg).

HPLC purity 100%.
MS m/z 585 (M+H$^+$).

Example 107

N-(cyclopropylmethyl)-N-(2-{5-[(3-hydroxypyrrolidin-1-yl)methyl]-1,3-thiazol-2-yl}-1H-indol-7-yl)thiophene-2-sulfonamide trifluoroacetate

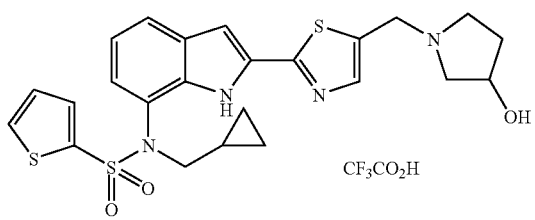

In the same manner as in Example 1, the title compound (13.0 mg, yield 47%) was obtained from N-{2-[5-(chloromethyl)-1,3-thiazol-2-yl]-1H-indol-7-yl}-N-(cyclopropylmethyl)thiophene-2-sulfonamide (20 mg) and DL-3-pyrrolidinol (10 mg).

HPLC purity 100%.
MS m/z 515 (M+H$^+$).

Example 108

N-(cyclopropylmethyl)-N-[2-(5-{[2-(hydroxymethyl)piperidino]methyl}-1,3-thiazol-2-yl)-1H-indol-7-yl]thiophene-2-sulfonamide trifluoroacetate

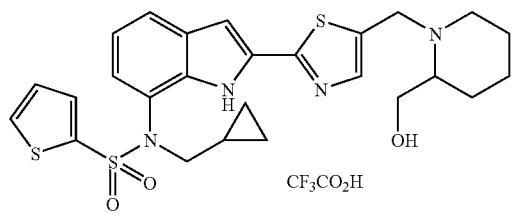

In the same manner as in Example 1, the title compound (10.2 mg, yield 35%) was obtained from N-{2-[5-(chloromethyl)-1,3-thiazol-2-yl]-1H-indol-7-yl}-N-(cyclopropylmethyl)thiophene-2-sulfonamide (20 mg) and piperidin-2-ylmethanol (14 mg).

HPLC purity 100%.
MS m/z 543 (M+H$^+$).

Example 109

N-[(2-{7-[(cyclopropylmethyl)(2-thienylsulfonyl)amino]-1H-indol-2-yl}-1,3-thiazol-5-yl)methyl]-N-methylglycine ethyl ester trifluoroacetate In the same manner as in Example 1, the title compound (14.9 mg, yield 51%) was obtained from N-{2-[5-(chloromethyl)-1,3-thiazol-2-yl]-1H-indol-7-yl}-N-(cyclopropylmethyl)thiophene-2-sulfonamide (20 mg) and sarcosine ethyl ester hydrochloride (18 mg)

HPLC purity 96%.
MS m/z 545 (M+H$^+$).

Example 110 ethyl 4-[(2-{7-[(cyclopropylmethyl)(2-thienylsulfonyl)amino]-1H-indol-2-yl}-1,3-thiazol-5-yl)methyl]piperazine-1-carboxylate trifluoroacetate In the same manner as in Example 1, the title compound (15.2 mg, yield 49%) was obtained from N-{2-[5-(chloromethyl)-1,3-thiazol-2-yl]-1H-indol-7-yl}-N-(cyclopropylmethyl)thiophene-2-sulfonamide (20 mg) and 1-ethoxycarbonylpiperazine (19 mg).

HPLC purity 97%.

MS m/z 586 (M+H$^+$).

Example 111

N-(cyclopropylmethyl)-N-[2-(5-{[4-(ethylsulfonyl)piperazin-1-yl]methyl}-1,3-thiazol-2-yl)-1H-indol-7-yl]thiophene-2-sulfonamide trifluoroacetate

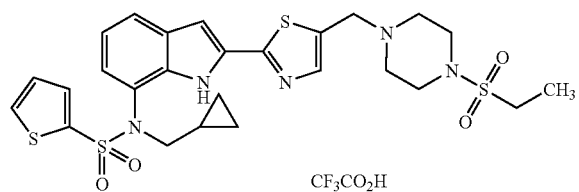

In the same manner as in Example 1, the title compound (12.0 mg, yield 38%) was obtained from N-{2-[5-(chloromethyl)-1,3-thiazol-2-yl]-1H-indol-7-yl}-N-(cyclopropylmethyl)thiophene-2-sulfonamide (20 mg) and 1-ethylsulfonylpiperazine (21 mg).

HPLC purity 96%.

MS m/z 606 (M+H$^+$).

Example 112

N-isopropyl-N-[2-(5-{[methyl(pyridin-2-ylmethyl)amino]methyl}-1,3-thiazol-2-yl)-1H-indol-7-yl]thiophene-2-sulfonamide ditrifluoroacetate

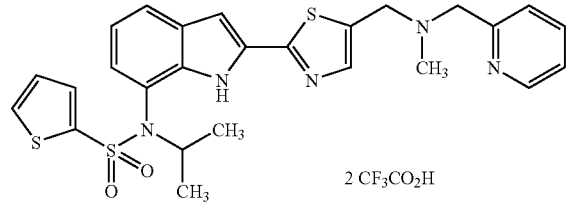

In the same manner as in Example 1, the title compound (18.1 mg, yield 49%) was obtained from N-{2-[5-(chloromethyl)-1,3-thiazol-2-yl]-1H-indol-7-yl}-N-isopropylthiophene-2-sulfonamide and (21 mg) and N-methyl-1-(pyridin-2-yl)methanamine hydrochloride (19 mg).

HPLC purity 100%.

MS m/z 538 (M+H$^+$).

Example 113

N-isopropyl-N-[2-(5-{[methyl(2-pyridin-2-ylethyl)amino]methyl}-1,3-thiazol-2-yl)-1H-indol-7-yl]thiophene-2-sulfonamide ditrifluoroacetate

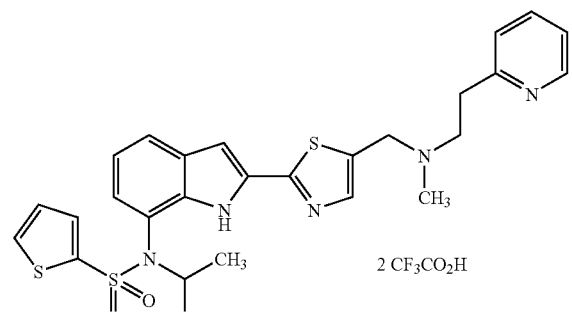

In the same manner as in Example 1, the title compound (14.2 mg, yield 38%) was obtained from N-{2-[5-(chloromethyl)-1,3-thiazol-2-yl]-1H-indol-7-yl}-N-isopropylthiophene-2-sulfonamide (21 mg) and N-methyl-2-(pyridin-2-yl)ethanamine (16 mg).

HPLC purity 100%.

MS m/z 552 (M+H$^+$).

Example 114

N-isopropyl-N-(2-{5-[(2-(pyridin-2-yl)pyrrolidin-1-yl)methyl]-1,3-thiazol-2-yl}-1H-indol-7-yl)thiophene-2-sulfonamide ditrifluoroacetate

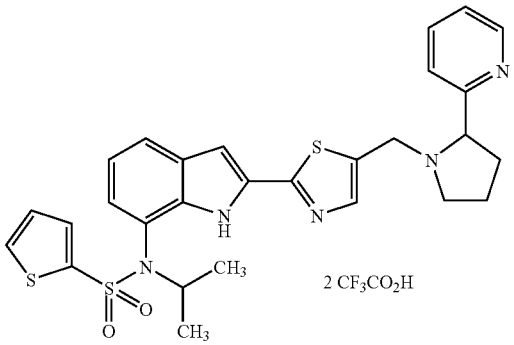

In the same manner as in Example 1, the title compound (18.6 mg, yield 49%) was obtained from N-{2-[5-(chloromethyl)-1,3-thiazol-2-yl]-1H-indol-7-yl}-N-isopropylthiophene-2-sulfonamide (21 mg) and 2-(pyrrolidin-2-yl)pyridine (18 mg).

HPLC purity 100%.

MS m/z 564 (M+H$^+$).

Example 115

N-isopropyl-N-[2-(5-{[methyl(pyridin-3-ylmethyl)amino]methyl}-1,3-thiazol-2-yl)-1H-indol-7-yl]thiophene-2-sulfonamide ditrifluoroacetate

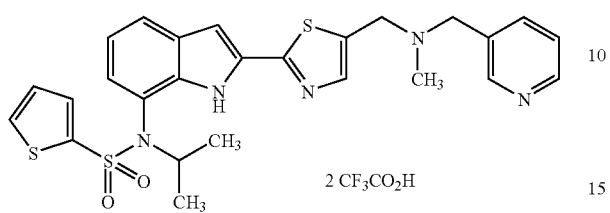

In the same manner as in Example 1, the title compound (13.0 mg, yield 35%) was obtained from N-{2-[5-(chloromethyl)-1,3-thiazol-2-yl]-1H-indol-7-yl}-N-isopropylthiophene-2-sulfonamide (21 mg) and N-methyl-1-(pyridin-3-yl)methanamine hydrochloride (19 mg).
HPLC purity 100%.
MS m/z 538 (M+H$^+$).

Example 116

N-isopropyl-N-[2-(5-{[3-(methylsulfonyl)pyrrolidin-1-yl]methyl}-1,3-thiazol-2-yl)-1H-indol-7-yl]thiophene-2-sulfonamide trifluoroacetate

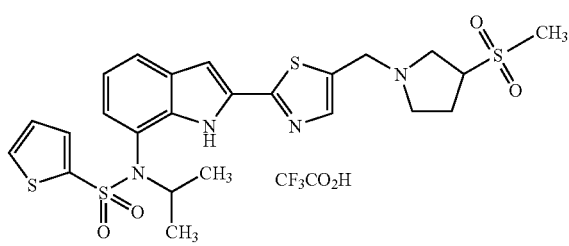

In the same manner as in Example 1, the title compound (12.3 mg, yield 38%) was obtained from N-{2-[5-(chloromethyl)-1,3-thiazol-2-yl]-1H-indol-7-yl}-N-isopropylthiophene-2-sulfonamide (21 mg) and 3-(methylsulfonyl)pyrrolidine (18 mg).
HPLC purity 100%.
MS m/z 565 (M+H$^+$).

Example 117

N-isopropyl-N-{2-[5-({methyl[2-(methylsulfonyl)ethyl]amino}methyl)-1,3-thiazol-2-yl]-1H-indol-7-yl}thiophene-2-sulfonamide trifluoroacetate

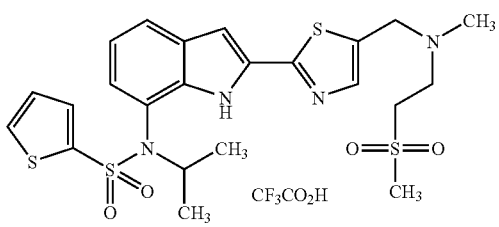

In the same manner as in Example 1, the title compound (8.4 mg, yield 26%) was obtained from N-{2-[5-(chloromethyl)-1,3-thiazol-2-yl]-1H-indol-7-yl}-N-isopropylthiophene-2-sulfonamide (21 mg) and N-methyl-2-(methylsulfonyl)ethanamine (16 mg).
HPLC purity 100%.
MS m/z 553 (M+H$^+$).

Example 118

N-isopropyl-N-[2-(5-{[4-(pyrimidin-2-yloxy)piperidino]methyl}-1,3-thiazol-2-yl)-1H-indol-7-yl]thiophene-2-sulfonamide ditrifluoroacetate

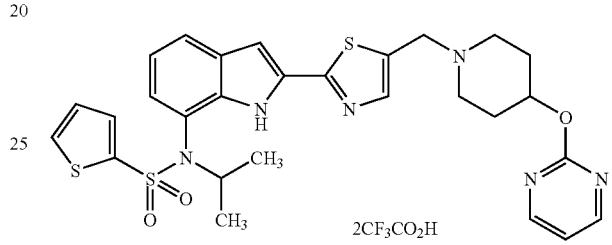

In the same manner as in Example 1, the title compound (14.1 mg, yield 41%) was obtained from N-{2-[5-(chloromethyl)-1,3-thiazol-2-yl]-1H-indol-7-yl}-N-isopropylthiophene-2-sulfonamide (21 mg) and 2-(piperidin-4-yloxy)pyrimidine dihydrochloride (30 mg).
HPLC purity 100%.
MS m/z 595 (M+H$^+$).

Example 119

N-isopropyl-N-[2-(5-{[4-(pyrazin-2-yloxy)piperidino]methyl}-1,3-thiazol-2-yl)-1H-indol-7-yl]thiophene-2-sulfonamide ditrifluoroacetate

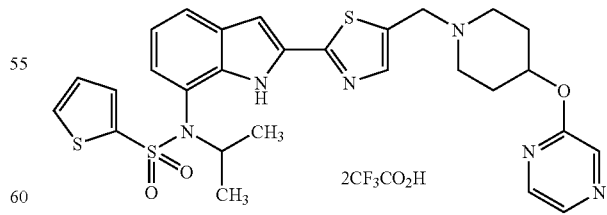

In the same manner as in Example 1, the title compound (16.1 mg, yield 47%) was obtained from N-{2-[5-(chloromethyl)-1,3-thiazol-2-yl]-1H-indol-7-yl}-N-isopropylthiophene-2-sulfonamide (21 mg) and 2-(piperidin-4-yloxy) pyrazine dihydrochloride (30 mg).

HPLC purity 100%.

MS m/z 595 (M+H⁺).

Example 120

N-isopropyl-N-[2-(5-{[4-(tetrahydrofuran-2-ylmethyl)piperazin-1-yl]methyl}-1,3-thiazol-2-yl)-1H-indol-7-yl]thiophene-2-sulfonamide ditrifluoroacetate

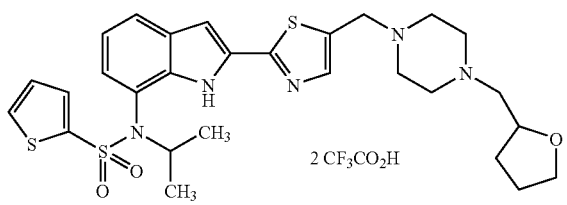

In the same manner as in Example 1, the title compound (22.7 mg, yield 58%) was obtained from N-{2-[5-(chloromethyl)-1,3-thiazol-2-yl]-1H-indol-7-yl}-N-isopropylthiophene-2-sulfonamide (21 mg) and 1-(tetrahydrofuran-2-ylmethyl)piperazine (20 mg).

HPLC purity 94%.

MS m/z 586 (M+H⁺).

Example 121

2-{4-[(2-{7-[isopropyl(2-thienylsulfonyl)amino]-1H-indol-2-yl}-1,3-thiazol-5-yl)methyl]piperazin-1-yl}-N,N-dimethylacetamide ditrifluoroacetate

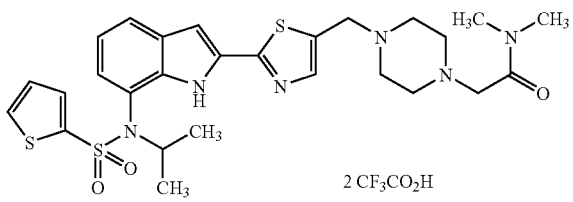

In the same manner as in Example 1, the title compound (26.2 mg, yield 67%) was obtained from N-{2-[5-(chloromethyl)-1,3-thiazol-2-yl]-1H-indol-7-yl}-N-isopropylthiophene-2-sulfonamide (21 mg) and N,N-dimethyl-2-piperazin-1-ylacetamide (20 mg).

HPLC purity 91%.

MS m/z 587 (M+H⁺).

Example 122

N-isopropyl-N-[2-(5-{[4-(6-methylpyridin-2-yl)piperazin-1-yl]methyl}-1,3-thiazol-2-yl)-1H-indol-7-yl]thiophene-2-sulfonamide trifluoroacetate

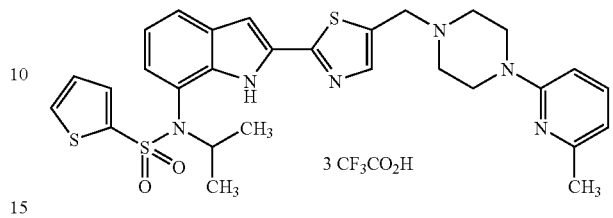

In the same manner as in Example 1, the title compound (23.4 mg, yield 52%) was obtained from N-{2-[5-(chloromethyl)-1,3-thiazol-2-yl]-1H-indol-7-yl}-N-isopropylthiophene-2-sulfonamide (21 mg) and 1-(6-methylpyridin-2-yl)piperazine (21 mg).

HPLC purity 98%.

MS m/z 593 (M+H⁺).

Example 123

N-isopropyl-N-(2-{5-[(3-(pyrimidin-2-yl)pyrrolidin-1-yl)methyl]-1,3-thiazol-2-yl}-1H-indol-7-yl)thiophene-2-sulfonamide trifluoroacetate

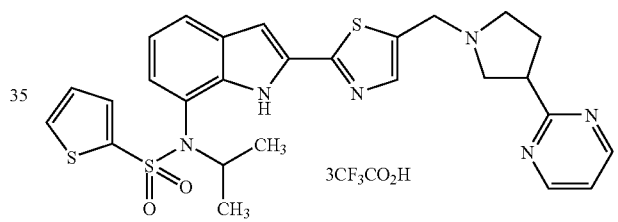

In the same manner as in Example 1, the title compound (15.1 mg, yield 46%) was obtained from N-{2-[5-(chloromethyl)-1,3-thiazol-2-yl]-1H-indol-7-yl}-N-isopropylthiophene-2-sulfonamide (21 mg) and 2-(pyrrolidin-3-yl)pyrimidine trihydrochloride (31 mg).

HPLC purity 100%.

MS m/z 565 (M+H⁺).

Example 124

N-isopropyl-N-(2-{5-[(3-(pyridin-2-yl)piperidino)methyl]-1,3-thiazol-2-yl}-1H-indol-7-yl)thiophene-2-sulfonamide ditrifluoroacetate

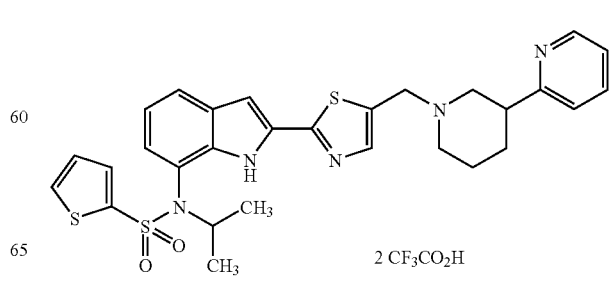

In the same manner as in Example 1, the title compound (7.5 mg, yield 19%) was obtained from N-{2-[5-(chloromethyl)-1,3-thiazol-2-yl]-1H-indol-7-yl}-N-isopropylthiophene-2-sulfonamide (21 mg) and 2-(piperidin-3-yl)pyridine (19 mg).

HPLC purity 100%.

MS m/z 578 (M+H$^+$).

Example 125

N-isopropyl-N-(2-{5-[(4-(pyridin-2-yl)piperidino)methyl]-1,3-thiazol-2-yl}-1H-indol-7-yl)thiophene-2-sulfonamide ditrifluoroacetate

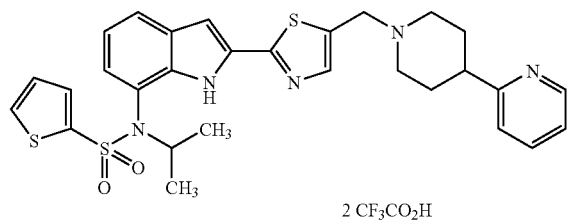

In the same manner as in Example 1, the title compound (21.8 mg, yield 56%) was obtained from N-{2-[5-(chloromethyl)-1,3-thiazol-2-yl]-1H-indol-7-yl}-N-isopropylthiophene-2-sulfonamide (21 mg) and 2-(piperidin-4-yl)pyridine (19 mg).

HPLC purity 100%.

MS m/z 578 (M+H$^+$).

Example 126

N-isopropyl-N-(2-{5-[(5-methyl-4,6-dioxohexahydropyrrolo[3,4-c]pyrrol-2(1H)-yl)methyl]-1,3-thiazol-2-yl}-1H-indol-7-yl)thiophene-2-sulfonamide trifluoroacetate

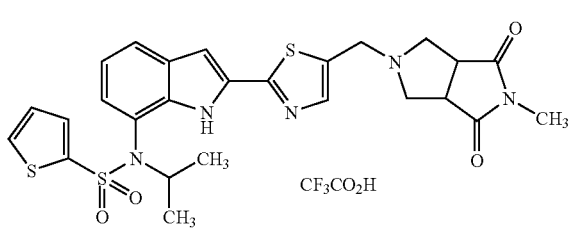

In the same manner as in Example 1, the title compound (9.9 mg, yield 30%) was obtained from N-{2-[5-(chloromethyl)-1,3-thiazol-2-yl]-1H-indol-7-yl}-N-isopropylthiophene-2-sulfonamide (21 mg) and 2-methyltetrahydropyrrolo[3,4-c]pyrrole-1,3(2H,3aH)-dione hydrochloride (23 mg).

HPLC purity 96%.

MS m/z 570 (M+H$^+$).

Example 127

N-(2-{5-[(4-hydroxy-4-methylpiperidino)methyl]-1,3-thiazol-2-yl}-1H-indol-7-yl)-N-isopropylthiophene-2-sulfonamide trifluoroacetate

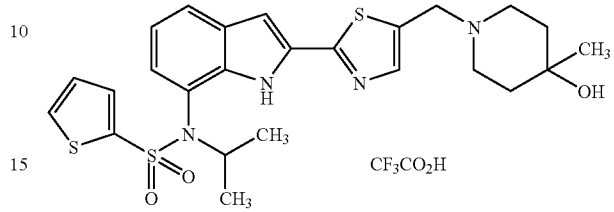

In the same manner as in Example 1, the title compound (15.6 mg, yield 50%) was obtained from N-{2-[5-(chloromethyl)-1,3-thiazol-2-yl]-1H-indol-7-yl}-N-isopropylthiophene-2-sulfonamide (21 mg) and 4-methylpiperidin-4-ol hydrochloride (18 mg).

HPLC purity 100%.

MS m/z 531 (M+H$^+$).

Example 128

N-[2-(5-{[cyclopropyl(isobutyl)amino]methyl}-1,3-thiazol-2-yl)-1H-indol-7-yl]-N-isopropylthiophene-2-sulfonamide trifluoroacetate

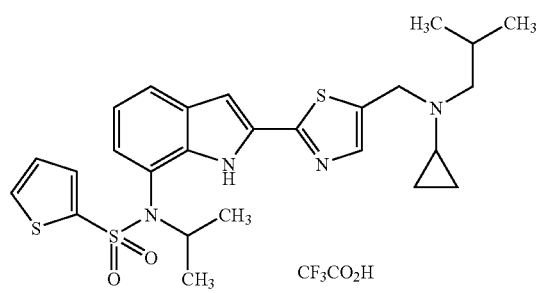

In the same manner as in Example 1, the title compound (5.3 mg, yield 17%) was obtained from N-{2-[5-(chloromethyl)-1,3-thiazol-2-yl]-1H-indol-7-yl}-N-isopropylthiophene-2-sulfonamide (21 mg) and N-isobutyl-cyclopropanamine hydrochloride (18 mg).

HPLC purity 100%.

MS m/z 529 (M+H$^+$).

Example 129

N-(2-{5-[(4-tert-butylpiperidino)methyl]-1,3-thiazol-2-yl}-1H-indol-7-yl)-N-isopropylthiophene-2-sulfonamide trifluoroacetate

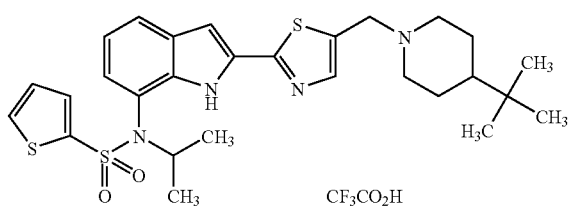

In the same manner as in Example 1, the title compound (13.1 mg, yield 41%) was obtained from N-{2-[5-(chloromethyl)-1,3-thiazol-2-yl]-1H-indol-7-yl}-N-isopropylthiophene-2-sulfonamide (21 mg) and 4-tert-butylpiperidine hydrochloride (21 mg).
HPLC purity 100%.
MS m/z 557 (M+H$^+$).

Example 130

N-isopropyl-N-[2-(5-{[3-(pyrrolidin-1-ylcarbonyl)piperidino]methyl}-1,3-thiazol-2-yl)-1H-indol-7-yl]thiophene-2-sulfonamide trifluoroacetate

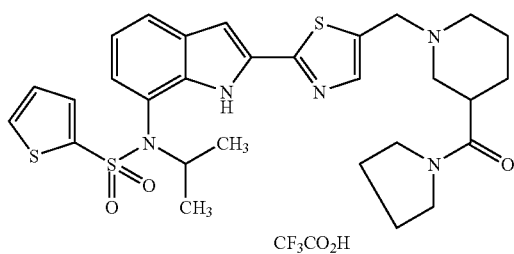

In the same manner as in Example 1, the title compound (22.0 mg, yield 64%) was obtained from N-{2-[5-(chloromethyl)-1,3-thiazol-2-yl]-1H-indol-7-yl}-N-isopropylthiophene-2-sulfonamide (21 mg) and 3-(pyrrolidin-1-ylcarbonyl)piperidine (22 mg).
HPLC purity 100%.
MS m/z 598 (M+H$^+$).

Example 131

N-isopropyl-N-{2-[5-(pyrrolidin-1-ylmethyl)-1,3-thiazol-2-yl]-1H-indol-7-yl}thiophene-2-sulfonamide trifluoroacetate

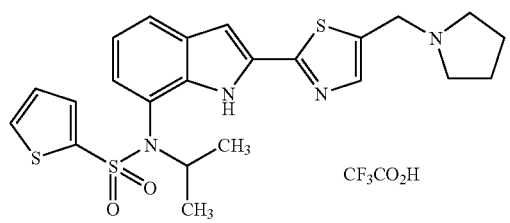

In the same manner as in Example 1, the title compound (10.9 mg, yield 38%) was obtained from N-{2-[5-(chloromethyl)-1,3-thiazol-2-yl]-1H-indol-7-yl}-N-isopropylthiophene-2-sulfonamide (21 mg) and pyrrolidine (8 mg).
HPLC purity 100%.
MS m/z 487 (M+H$^+$).
$^1$H-NMR (400 MHz, CDCl$_3$) δ: 1.14 (6H, d, J=12.1 Hz), 2.10 (4H, d, J=11.7 Hz), 2.79-3.06 (2H, m), 3.72 (2H, brs), 4.50 (2H, s), 4.69-4.95 (1H, m), 6.79 (1H, d, J=7.7 Hz), 7.02-7.09 (3H, m), 7.47 (1H, dd, J=3.7, 1.4 Hz), 7.60 (1H, dd, J=5.1, 1.3 Hz), 7.67 (1H, d, J=7.9 Hz), 7.81 (1H, s), 9.54 (1H, brs).

Example 132

N-(2-{5-[(diethylamino)methyl]-1,3-thiazol-2-yl}-1H-indol-7-yl)-N-isopropylthiophene-2-sulfonamide trifluoroacetate

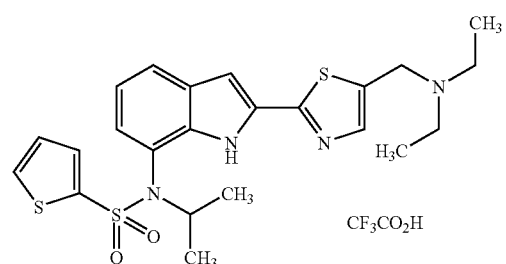

In the same manner as in Example 1, the title compound (3.0 mg, yield 10%) was obtained from N-{2-[5-(chloromethyl)-1,3-thiazol-2-yl]-1H-indol-7-yl}-N-isopropylthiophene-2-sulfonamide (21 mg) and diethylamine (9 mg).
HPLC purity 100%.
MS m/z 489 (M+H$^+$).

Example 133

N-isopropyl-N-{2-[5-(piperidinomethyl)-1,3-thiazol-2-yl]-1H-indol-7-yl}thiophene-2-sulfonamide trifluoroacetate

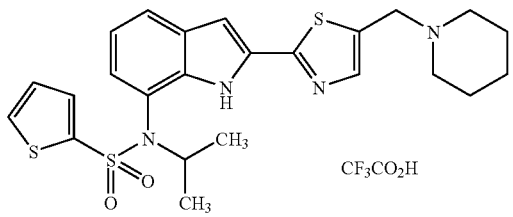

In the same manner as in Example 1, the title compound (11.7 mg, yield 40%) was obtained from N-{2-[5-(chloromethyl)-1,3-thiazol-2-yl]-1H-indol-7-yl}-N-isopropylthiophene-2-sulfonamide (21 mg) and piperidine (10 mg).

HPLC purity 100%.

MS m/z 501 (M+H⁺).

Example 134
N-(2-{5-[(4-hydroxypiperidino)methyl]-1,3-thiazol-2-yl}-1H-indol-7-yl)-N-isopropylthiophene-2-sulfonamide trifluoroacetate

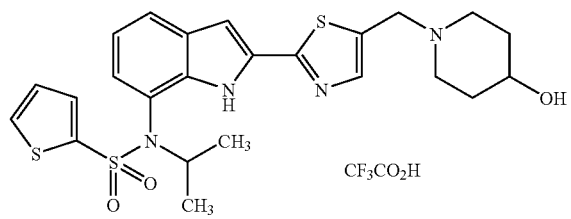

In the same manner as in Example 1, the title compound (15.2 mg, yield 50%) was obtained from N-{2-[5-(chloromethyl)-1,3-thiazol-2-yl]-1H-indol-7-yl}-N-isopropylthiophene-2-sulfonamide (21 mg) and 4-hydroxypiperidine (12 mg).

HPLC purity 100%.

MS m/z 517 (M+H⁺).

Example 135
N-(2-{5-[(3-hydroxypiperidino)methyl]-1,3-thiazol-2-yl}-1H-indol-7-yl)-N-isopropylthiophene-2-sulfonamide trifluoroacetate

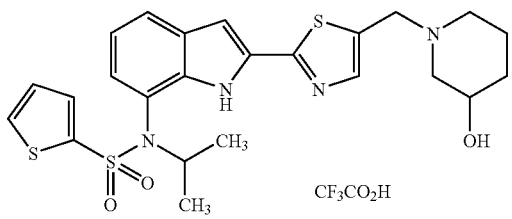

In the same manner as in Example 1, the title compound (8.0 mg, yield 26%) was obtained from N-{2-[5-(chloromethyl)-1,3-thiazol-2-yl]-1H-indol-7-yl}-N-isopropylthiophene-2-sulfonamide (21 mg) and 3-hydroxypiperidine (12 mg).

HPLC purity 100%.

MS m/z 517 (M+H⁺).

Example 136
N-isopropyl-N-[2-(5-{[(2-methoxyethyl)(methyl)amino]methyl}-1,3-thiazol-2-yl)-1H-indol-7-yl]thiophene-2-sulfonamide trifluoroacetate

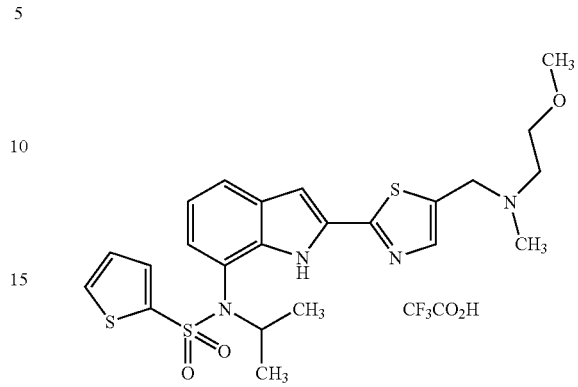

In the same manner as in Example 1, the title compound (12.0 mg, yield 40%) was obtained from N-{2-[5-(chloromethyl)-1,3-thiazol-2-yl]-1H-indol-7-yl}-N-isopropylthiophene-2-sulfonamide (21 mg) and N-(2-methoxyethyl)methylamine (11 mg).

HPLC purity 100%.

MS m/z 505 (M+H⁺).

Example 137
N-isopropyl-N-[2-(5-{[(2S)-2-(methoxymethyl)pyrrolidin-1-yl]methyl}-1,3-thiazol-2-yl)-1H-indol-7-yl]thiophene-2-sulfonamide trifluoroacetate

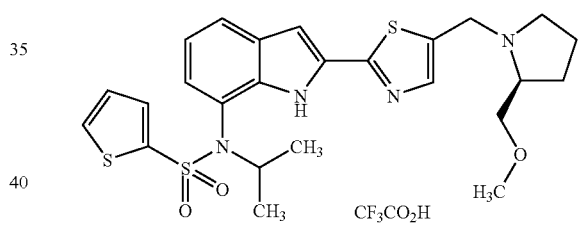

In the same manner as in Example 1, the title compound (14.1 mg, yield 46%) was obtained from N-{2-[5-(chloromethyl)-1,3-thiazol-2-yl]-1H-indol-7-yl}-N-isopropylthiophene-2-sulfonamide (21 mg) and (S)-2-(methoxymethyl)pyrrolidine (14 mg).

HPLC purity 100%.

MS m/z 531 (M+H⁺).

Example 138
N-{1-[(2-{7-[isopropyl(2-thienylsulfonyl)amino]-1H-indol-2-yl}-1,3-thiazol-5-yl)methyl]pyrrolidin-3-yl}acetamide trifluoroacetate

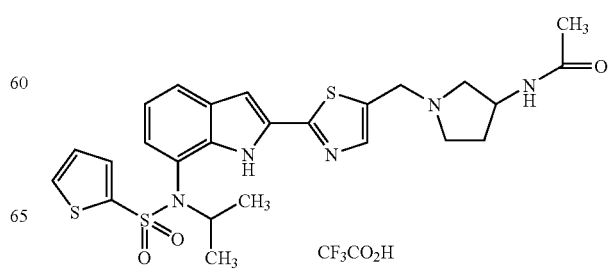

In the same manner as in Example 1, the title compound (15.3 mg, yield 48%) was obtained from N-{2-[5-(chloromethyl)-1,3-thiazol-2-yl]-1H-indol-7-yl}-N-isopropylthiophene-2-sulfonamide (21 mg) and 3-acetamidopyrrolidine (15 mg).

HPLC purity 100%.

MS m/z 544 (M+H$^+$).

Example 139

1-[(2-{7-[isopropyl(2-thienylsulfonyl)amino]-1H-indol-2-yl}-1,3-thiazol-5-yl)methyl]piperidine-4-carboxamide trifluoroacetate

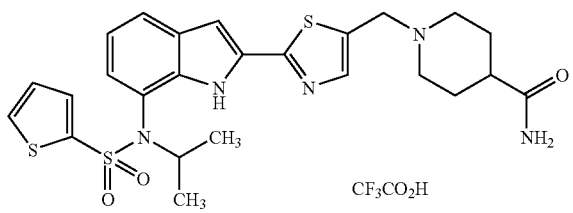

In the same manner as in Example 1, the title compound (15.0 mg, yield 47%) was obtained from N-{2-[5-(chloromethyl)-1,3-thiazol-2-yl]-1H-indol-7-yl}-N-isopropylthiophene-2-sulfonamide (21 mg) and isonipecotamide (15 mg).

HPLC purity 100%.

MS m/z 544 (M+H$^+$).

Example 140

N-[2-(5-{[4-(2-hydroxyethyl)piperidino]methyl}-1,3-thiazol-2-yl)-1H-indol-7-yl]-N-isopropylthiophene-2-sulfonamide trifluoroacetate

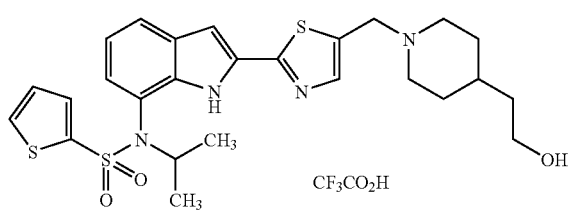

In the same manner as in Example 1, the title compound (15.0 mg, yield 47%) was obtained from N-{2-[5-(chloromethyl)-1,3-thiazol-2-yl]-1H-indol-7-yl}-N-isopropylthiophene-2-sulfonamide (21 mg) and 2-(piperidin-4-yl)ethanol (16 mg).

HPLC purity 100%.

MS m/z 545 (M+H$^+$).

Example 141

N-[2-(5-{[bis(2-methoxyethyl)amino]methyl}-1,3-thiazol-2-yl)-1H-indol-7-yl]-N-isopropylthiophene-2-sulfonamide trifluoroacetate

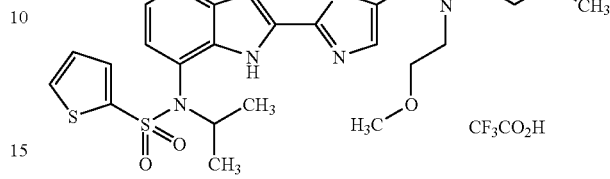

In the same manner as in Example 1, the title compound (8.7 mg, yield 28%) was obtained from N-{2-[5-(chloromethyl)-1,3-thiazol-2-yl]-1H-indol-7-yl}-N-isopropylthiophene-2-sulfonamide (21 mg) and bis(2-methoxyethyl)amine (16 mg).

HPLC purity 100%.

MS m/z 549 (M+H$^+$).

Example 142 ethyl 1-[(2-{7-[isopropyl(2-thienylsulfonyl)amino]-1H-indol-2-yl}-1,3-thiazol-5-yl)methyl]piperidine-4-carboxylate trifluoroacetate

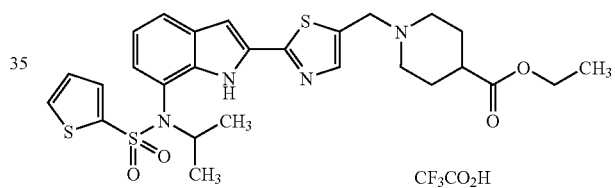

In the same manner as in Example 1, the title compound (17.9 mg, yield 54%) was obtained from N-{2-[5-(chloromethyl)-1,3-thiazol-2-yl]-1H-indol-7-yl}-N-isopropylthiophene-2-sulfonamide (21 mg) and ethyl isonipecotate (19 mg).

HPLC purity 100%.

MS m/z 573 (M+H$^+$).

Example 143 ethyl 1-[(2-{7-[isopropyl(2-thienylsulfonyl)amino]-1H-indol-2-yl}-1,3-thiazol-5-yl)methyl]piperidine-3-carboxylate trifluoroacetate

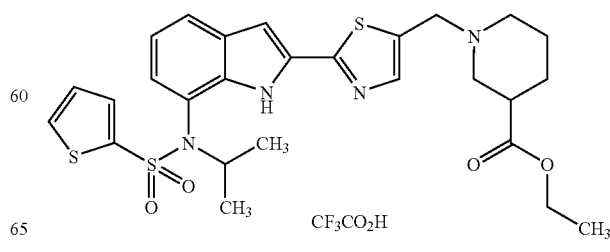

In the same manner as in Example 1, the title compound (16.6 mg, yield 50%) was obtained from N-{2-[5-(chloromethyl)-1,3-thiazol-2-yl]-1H-indol-7-yl}-N-isopropylthiophene-2-sulfonamide (21 mg) and ethyl nipecotate (19 mg).

HPLC purity 100%.

MS m/z 573 (M+H$^+$).

Example 144

N-(2-{5-[(3-hydroxypyrrolidin-1-yl)methyl]-1,3-thiazol-2-yl}-1H-indol-7-yl)-N-isopropylthiophene-2-sulfonamide trifluoroacetate

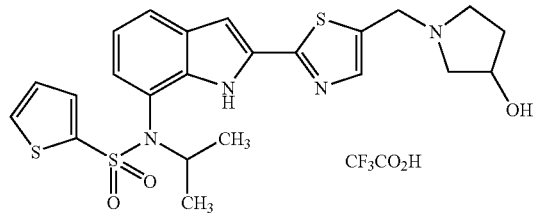

In the same manner as in Example 1, the title compound (13.7 mg, yield 46%) was obtained from N-{2-[5-(chloromethyl)-1,3-thiazol-2-yl]-1H-indol-7-yl}-N-isopropylthiophene-2-sulfonamide (21 mg) and DL-3-pyrrolidinol (10 mg).

HPLC purity 100%.

MS m/z 503 (M+H$^+$).

Example 145

N-[2-(5-{[2-(hydroxymethyl)piperidino]methyl}-1,3-thiazol-2-yl)-1H-indol-7-yl]-N-isopropylthiophene-2-sulfonamide trifluoroacetate

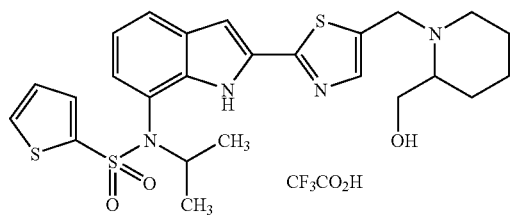

In the same manner as in Example 1, the title compound (11.1 mg, yield 36%) was obtained from N-{2-[5-(chloromethyl)-1,3-thiazol-2-yl]-1H-indol-7-yl}-N-isopropylthiophene-2-sulfonamide (21 mg) and piperidin-2-ylmethanol (14 mg).

HPLC purity 100%.

MS m/z 531 (M+H$^+$).

Example 146

N-[(2-{7-[isopropyl(2-thienylsulfonyl)amino]-1H-indol-2-yl}-1,3-thiazol-5-yl)methyl]-N-methylglycine ethyl ester trifluoroacetate

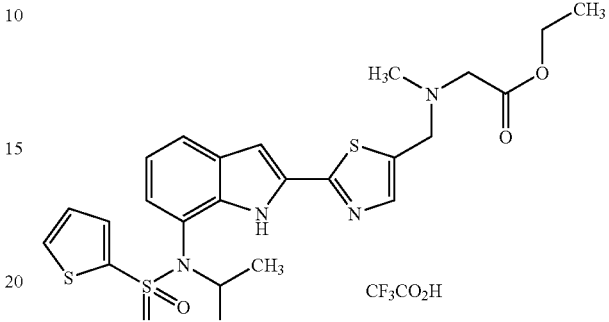

In the same manner as in Example 1, the title compound (16.2 mg, yield 52%) was obtained from N-{2-[5-(chloromethyl)-1,3-thiazol-2-yl]-1H-indol-7-yl}-N-isopropylthiophene-2-sulfonamide (21 mg) and sarcosine ethyl ester hydrochloride (18 mg).

HPLC purity 100%.

MS m/z 533 (M+H$^+$).

$^1$H-NMR (400 MHz, CDCl$_3$) δ: 1.09 (3H, d, J=5.6 Hz), 1.16 (3H, d, J=5.6 Hz), 1.32 (3H, t, J=7.2 Hz), 2.98 (3H, s), 3.82 (2H, s), 4.29 (2H, q, J=7.3 Hz), 4.72 (2H, s), 4.75-4.86 (1H, m), 6.77 (1H, d, J=7.0 Hz), 7.00-7.08 (3H, m), 7.45 (1H, dd, J=3.8, 1.3 Hz), 7.59 (1H, dd, J=5.1, 1.3 Hz), 7.66 (1H, d, J=7.9 Hz), 7.77 (1H, s), 9.62 (1H, brs).

Example 147 ethyl 4-[(2-{7-[isopropyl(2-thienylsulfonyl)amino]-1H-indol-2-yl}-1,3-thiazol-5-yl)methyl]piperazine-1-carboxylate trifluoroacetate

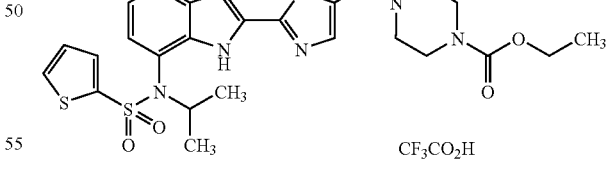

In the same manner as in Example 1, the title compound (14.1 mg, yield 43%) was obtained from N-{2-[5-(chloromethyl)-1,3-thiazol-2-yl]-1H-indol-7-yl}-N-isopropylthiophene-2-sulfonamide (21 mg) and 1-ethoxycarbonylpiperazine (19 mg).

HPLC purity 100%.

MS m/z 574 (M+H$^+$).

Example 148

N-[2-(5-{[4-(ethylsulfonyl)piperazin-1-yl]methyl}-1,3-thiazol-2-yl)-1H-indol-7-yl]-N-isopropylthiophene-2-sulfonamide trifluoroacetate

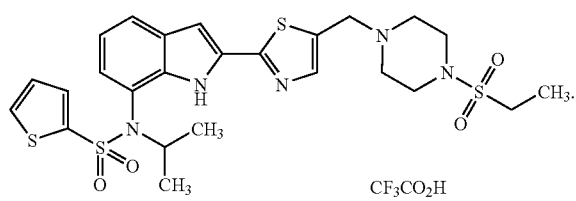

In the same manner as in Example 1, the title compound (10.6 mg, yield 31%) was obtained from N-{2-[5-(chloromethyl)-1,3-thiazol-2-yl]-1H-indol-7-yl}-N-isopropylthiophene-2-sulfonamide (21 mg) and 1-ethylsulfonylpiperazine (21 mg).
HPLC purity 100%.
MS m/z 594 (M+H$^+$).

Example 149

N-(2-ethoxyethyl)-N-[2-(5-{[methyl(pyridin-2-ylmethyl)amino]methyl}-1,3-thiazol-2-yl)-1H-indol-7-yl]thiophene-2-sulfonamide ditrifluoroacetate

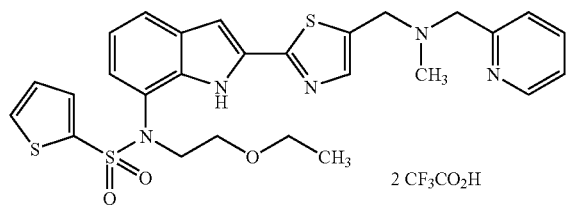

In the same manner as in Example 1, the title compound (15.5 mg, yield 51%) was obtained from N-{2-[5-(chloromethyl)-1,3-thiazol-2-yl]-1H-indol-7-yl}-N-(2-ethoxyethyl)thiophene-2-sulfonamide (18 mg) and N-methyl-1-(pyridin-2-yl)methanamine hydrochloride (19 mg).
HPLC purity 100%.
MS m/z 568 (M+H$^+$).

Example 150

N-(2-ethoxyethyl)-N-[2-(5-{[methyl(2-pyridin-2-ylethyl)amino]methyl}-1,3-thiazol-2-yl)-1H-indol-7-yl]thiophene-2-sulfonamide ditrifluoroacetate

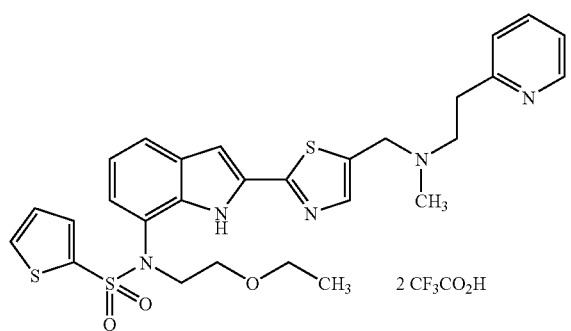

In the same manner as in Example 1, the title compound (9.8 mg, yield 32%) was obtained from N-{2-[5-(chloromethyl)-1,3-thiazol-2-yl]-1H-indol-7-yl}-N-(2-ethoxyethyl)thiophene-2-sulfonamide (18 mg) and N-methyl-2-(pyridin-2-yl)ethanamine (16 mg).
HPLC purity 100%.
MS m/z 582 (M+H$^+$).

Example 151

N-(2-ethoxyethyl)-N-(2-{5-[(2-(pyridin-2-yl)pyrrolidin-1-yl)methyl]-1,3-thiazol-2-yl}-1H-indol-7-yl)thiophene-2-sulfonamide ditrifluoroacetate

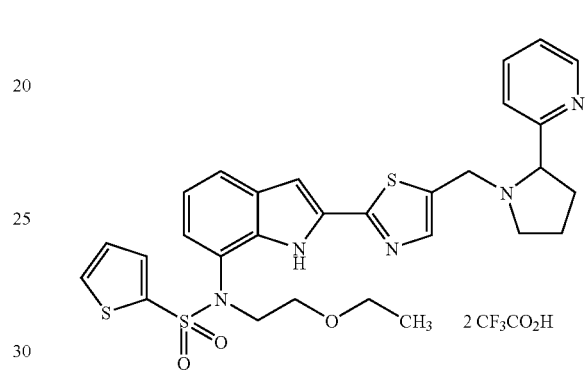

In the same manner as in Example 1, the title compound (10.5 mg, yield 34%) was obtained from N-{2-[5-(chloromethyl)-1,3-thiazol-2-yl]-1H-indol-7-yl}-N-(2-ethoxyethyl)thiophene-2-sulfonamide (18 mg) and 2-(pyrrolidin-2-yl)pyridine (18 mg).
HPLC purity 93%.
MS m/z 594 (M+H$^+$).

Example 152

N-(2-ethoxyethyl)-N-[2-(5-{[methyl(pyridin-3-ylmethyl)amino]methyl}-1,3-thiazol-2-yl)-1H-indol-7-yl]thiophene-2-sulfonamide ditrifluoroacetate

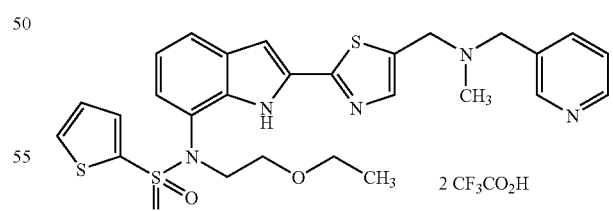

In the same manner as in Example 1, the title compound (10.6 mg, yield 35%) was obtained from N-{2-[5-(chloromethyl)-1,3-thiazol-2-yl]-1H-indol-7-yl}-N-(2-ethoxyethyl)thiophene-2-sulfonamide (18 mg) and N-methyl-1-(pyridin-3-yl)methanamine hydrochloride (19 mg).
HPLC purity 97%.
MS m/z 568 (M+H$^+$).

Example 153

N-(2-ethoxyethyl)-N-[2-(5-{[3-(methylsulfonyl)pyrrolidin-1-yl]methyl}-1,3-thiazol-2-yl)-1H-indol-7-yl]thiophene-2-sulfonamide trifluoroacetate

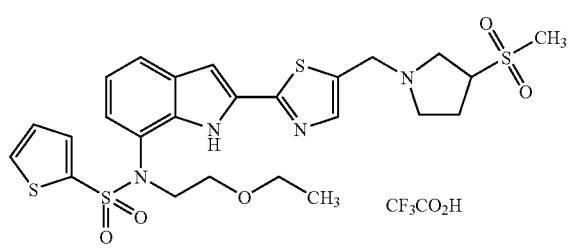

In the same manner as in Example 1, the title compound (8.2 mg, yield 30%) was obtained from N-{2-[5-(chloromethyl)-1,3-thiazol-2-yl]-1H-indol-7-yl}-N-(2-ethoxyethyl)thiophene-2-sulfonamide (18 mg) and 3-(methylsulfonyl)pyrrolidine (18 mg).

HPLC purity 100%.
MS m/z 595 (M+H$^+$).

Example 154

N-(2-ethoxyethyl)-N-{2-[5-({methyl[2-(methylsulfonyl)ethyl]amino}methyl)-1,3-thiazol-2-yl]-1H-indol-7-yl}thiophene-2-sulfonamide trifluoroacetate

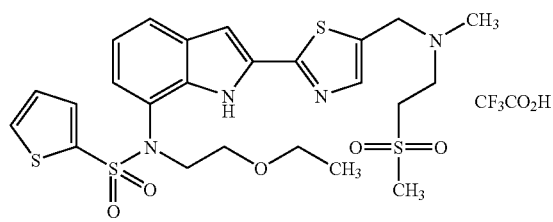

In the same manner as in Example 1, the title compound (6.6 mg, yield 25%) was obtained from N-{2-[5-(chloromethyl)-1,3-thiazol-2-yl]-1H-indol-7-yl}-N-(2-ethoxyethyl)thiophene-2-sulfonamide (18 mg) and N-methyl-2-(methylsulfonyl)ethanamine (16 mg).

HPLC purity 100%.
MS m/z 583 (M+H$^+$).

Example 155

N-(2-ethoxyethyl)-N-[2-(5-{[4-(pyrimidin-2-yloxy)piperidino]methyl}-1,3-thiazol-2-yl)-1H-indol-7-yl]thiophene-2-sulfonamide ditrifluoroacetate

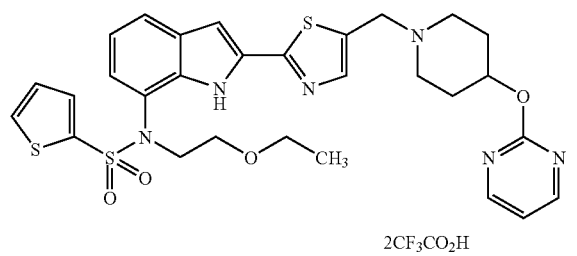

In the same manner as in Example 1, the title compound (10.3 mg, yield 37%) was obtained from N-{2-[5-(chloromethyl)-1,3-thiazol-2-yl]-1H-indol-7-yl}-N-(2-ethoxyethyl)thiophene-2-sulfonamide (18 mg) and 2-(piperidin-4-yloxy)pyrimidine dihydrochloride (30 mg).

HPLC purity 93%.
MS m/z 625 (M+H$^+$).

Example 156

N-(2-ethoxyethyl)-N-[2-(5-{[4-(pyrazin-2-yloxy)piperidino]methyl}-1,3-thiazol-2-yl)-1H-indol-7-yl]thiophene-2-sulfonamide ditrifluoroacetate

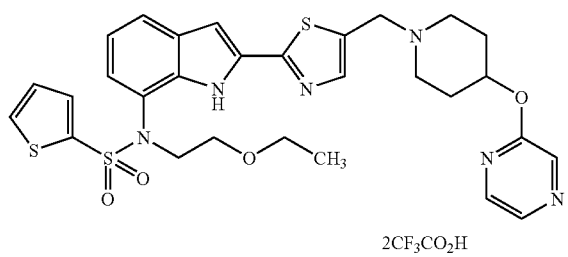

In the same manner as in Example 1, the title compound (11.1 mg, yield 39%) was obtained from N-{2-[5-(chloromethyl)-1,3-thiazol-2-yl]-1H-indol-7-yl}-N-(2-ethoxyethyl)thiophene-2-sulfonamide (18 mg) and 2-(piperidin-4-yloxy)pyrazine dihydrochloride (30 mg).

HPLC purity 100%.
MS m/z 625 (M+H$^+$).

Example 157

N-(2-ethoxyethyl)-N-[2-(5-{[4-(tetrahydrofuran-2-ylmethyl)piperazin-1-yl]methyl}-1,3-thiazol-2-yl)-1H-indol-7-yl]thiophene-2-sulfonamide ditrifluoroacetate

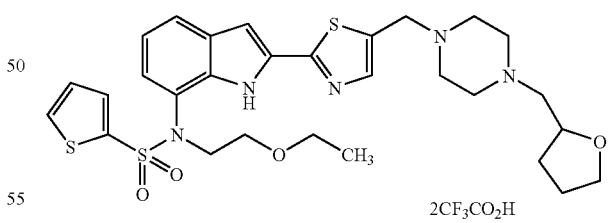

In the same manner as in Example 1, the title compound (12.9 mg, yield 40%) was obtained from N-{2-[5-(chloromethyl)-1,3-thiazol-2-yl]-1H-indol-7-yl}-N-(2-ethoxyethyl)thiophene-2-sulfonamide (18 mg) and 1-(tetrahydrofuran-2-ylmethyl)piperazine (20 mg).

HPLC purity 94%.
MS m/z 616 (M+H$^+$).

Example 158

2-{4-[(2-{7-[(2-ethoxyethyl)(2-thienylsulfonyl)amino]-1H-indol-2-yl}-1,3-thiazol-5-yl)methyl]piperazin-1-yl}-N,N-dimethylacetamide ditrifluoroacetate

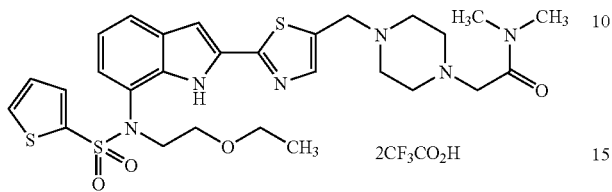

In the same manner as in Example 1, the title compound (10.1 mg, yield 31%) was obtained from N-{2-[5-(chloromethyl)-1,3-thiazol-2-yl]-1H-indol-7-yl}-N-(2-ethoxyethyl)thiophene-2-sulfonamide (18 mg) and N,N-dimethyl-2-piperazin-1-ylacetamide (20 mg).
HPLC purity 97%.
MS m/z 617 (M+H$^+$).

Example 159

N-(2-ethoxyethyl)-N-[2-(5-{[4-(6-methylpyridin-2-yl)piperazin-1-yl]methyl}-1,3-thiazol-2-yl)-1H-indol-7-yl]thiophene-2-sulfonamide trifluoroacetate


In the same manner as in Example 1, the title compound (17.3 mg, yield 47%) was obtained from N-{2-[5-(chloromethyl)-1,3-thiazol-2-yl]-1H-indol-7-yl}-N-(2-ethoxyethyl)thiophene-2-sulfonamide (18 mg) and 1-(6-methylpyridin-2-yl)piperazine (21 mg).
HPLC purity 100%.
MS m/z 623 (M+H$^+$).

Example 160

N-(2-ethoxyethyl)-N-(2-{5-[(3-(pyrimidin-2-yl)pyrrolidin-1-yl)methyl]-1,3-thiazol-2-yl}-1H-indol-7-yl)thiophene-2-sulfonamide trifluoroacetate

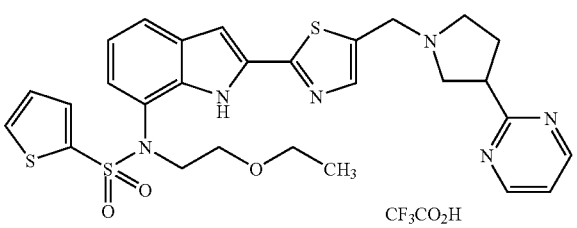

In the same manner as in Example 1, the title compound (10.8 mg, yield 40%) was obtained from N-{2-[5-(chloromethyl)-1,3-thiazol-2-yl]-1H-indol-7-yl}-N-(2-ethoxyethyl)thiophene-2-sulfonamide (18 mg) and 2-(pyrrolidin-3-yl)pyrimidine trihydrochloride (31 mg).
HPLC purity 100%.
MS m/z 595 (M+H$^+$).

Example 161

N-(2-ethoxyethyl)-N-(2-{5-[(3-(pyridin-2-yl)piperidino)methyl]-1,3-thiazol-2-yl}-1H-indol-7-yl)thiophene-2-sulfonamide ditrifluoroacetate

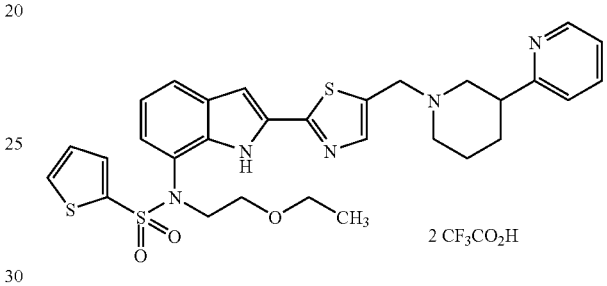

In the same manner as in Example 1, the title compound (14.2 mg, yield 45%) was obtained from N-{2-[5-(chloromethyl)-1,3-thiazol-2-yl]-1H-indol-7-yl}-N-(2-ethoxyethyl)thiophene-2-sulfonamide (18 mg) and 2-(piperidin-3-yl)pyridine (19 mg).
HPLC purity 100%.
MS m/z 608 (M+H$^+$).

Example 162

N-(2-ethoxyethyl)-N-(2-{5-[(4-(pyridin-2-yl)piperidino)methyl]-1,3-thiazol-2-yl}-1H-indol-7-yl)thiophene-2-sulfonamide ditrifluoroacetate

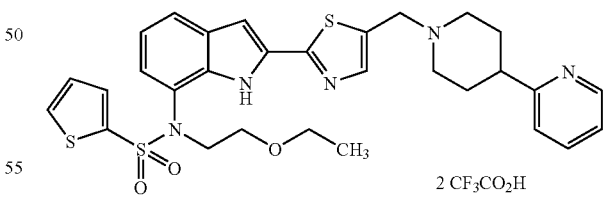

In the same manner as in Example 1, the title compound (14.5 mg, yield 45%) was obtained from N-{2-[5-(chloromethyl)-1,3-thiazol-2-yl]-1H-indol-7-yl}-N-(2-ethoxyethyl)thiophene-2-sulfonamide (18 mg) and 2-(piperidin-4-yl)pyridine (19 mg).
HPLC purity 97%.
MS m/z 608 (M+H$^+$).

Example 163

N-(2-ethoxyethyl)-N-(2-{5-[(5-methyl-4,6-dioxo-hexahydropyrrolo[3,4-c]pyrrol-2(1H)-yl)methyl]-1,3-thiazol-2-yl}-1H-indol-7-yl)thiophene-2-sulfonamide trifluoroacetate

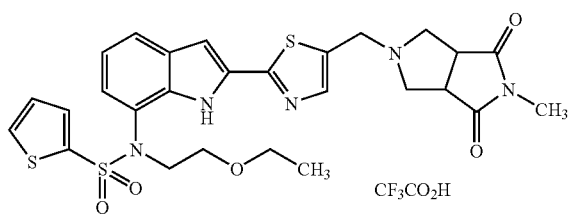

In the same manner as in Example 1, the title compound (5.9 mg, yield 22%) was obtained from N-{2-[5-(chloromethyl)-1,3-thiazol-2-yl]-1H-indol-7-yl}-N-(2-ethoxyethyl)thiophene-2-sulfonamide (18 mg) and 2-methyltetrahydropyrrolo[3,4-c]pyrrole-1,3(2H,3aH)-dione hydrochloride (23 mg).
HPLC purity 100%.
MS m/z 600 (M+H$^+$).

Example 164

N-(2-ethoxyethyl)-N-(2-{5-[(4-hydroxy-4-methylpiperidino)methyl]-1,3-thiazol-2-yl}-1H-indol-7-yl)thiophene-2-sulfonamide trifluoroacetate

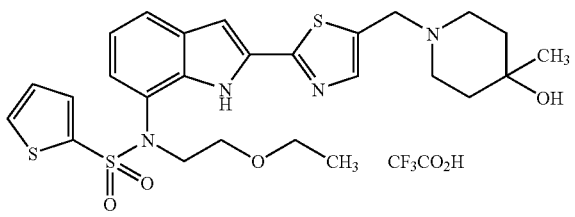

In the same manner as in Example 1, the title compound (11.7 mg, yield 46%) was obtained from N-{2-[5-(chloromethyl)-1,3-thiazol-2-yl]-1H-indol-7-yl}-N-(2-ethoxyethyl)thiophene-2-sulfonamide (18 mg) and 4-methylpiperidin-4-ol hydrochloride (18 mg).
HPLC purity 100%.
MS m/z 561 (M+H$^+$).

Example 165

N-[2-(5-{[cyclopropyl(isobutyl)amino]methyl}-1,3-thiazol-2-yl)-1H-indol-7-yl]-N-(2-ethoxyethyl)thiophene-2-sulfonamide trifluoroacetate

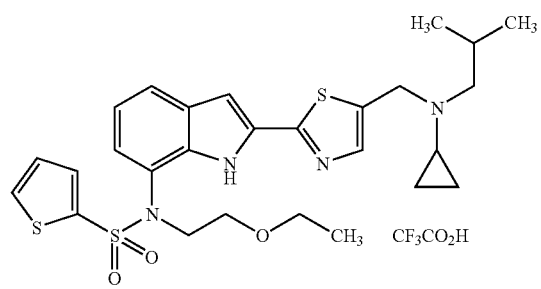

In the same manner as in Example 1, the title compound (3.9 mg, yield 15%) was obtained from N-{2-[5-(chloromethyl)-1,3-thiazol-2-yl]-1H-indol-7-yl}-N-(2-ethoxyethyl)thiophene-2-sulfonamide (18 mg) and N-isobutyl-cyclopropanamine hydrochloride (18 mg).
HPLC purity 97%.
MS m/z 559 (M+H$^+$).

Example 166

N-(2-{5-[(4-tert-butylpiperidino)methyl]-1,3-thiazol-2-yl}-1H-indol-7-yl)-N-(2-ethoxyethyl)thiophene-2-sulfonamide trifluoroacetate

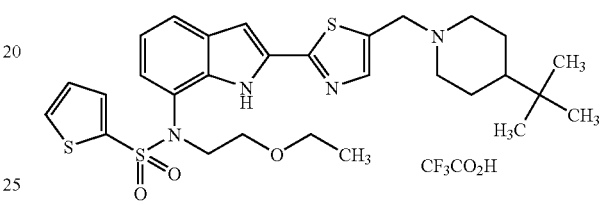

In the same manner as in Example 1, the title compound (10.6 mg, yield 40%) was obtained from N-{2-[5-(chloromethyl)-1,3-thiazol-2-yl]-1H-indol-7-yl}-N-(2-ethoxyethyl)thiophene-2-sulfonamide (18 mg) and 4-tert-butylpiperidine hydrochloride (21 mg).
HPLC purity 100%.
MS m/z 587 (M+H$^+$).

Example 167

N-(2-ethoxyethyl)-N-[2-(5-{[3-(pyrrolidin-1-ylcarbonyl)piperidino]methyl}-1,3-thiazol-2-yl)-1H-indol-7-yl]thiophene-2-sulfonamide trifluoroacetate

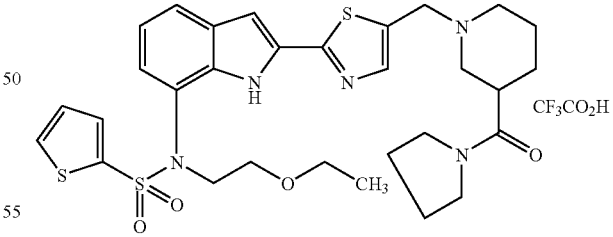

In the same manner as in Example 1, the title compound (17.1 mg, yield 61%) was obtained from N-{2-[5-(chloromethyl)-1,3-thiazol-2-yl]-1H-indol-7-yl}-N-(2-ethoxyethyl)thiophene-2-sulfonamide (18 mg) and 3-(pyrrolidin-1-ylcarbonyl)piperidine (22 mg).
HPLC purity 96%.
MS m/z 628 (M+H$^+$).

Example 168

N-(2-ethoxyethyl)-N-{2-[5-(pyrrolidin-1-ylmethyl)-1,3-thiazol-2-yl]-1H-indol-7-yl}thiophene-2-sulfonamide trifluoroacetate

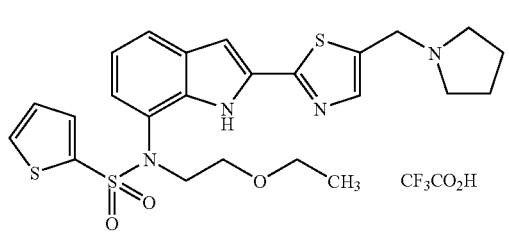

In the same manner as in Example 1, the title compound (8.9 mg, yield 37%) was obtained from N-{2-[5-(chloromethyl)-1,3-thiazol-2-yl]-1H-indol-7-yl}-N-(2-ethoxyethyl)thiophene-2-sulfonamide (18 mg) and pyrrolidine (9 mg).
HPLC purity 100%.

MS m/z 517 (M+H+).

Example 169

N-(2-{5-[(diethylamino)methyl]-1,3-thiazol-2-yl}-1H-indol-7-yl)-N-(2-ethoxyethyl)thiophene-2-sulfonamide trifluoroacetate

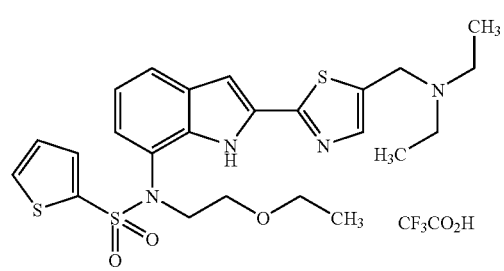

In the same manner as in Example 1, the title compound (6.4 mg, yield 27%) was obtained from N-{2-[5-(chloromethyl)-1,3-thiazol-2-yl]-1H-indol-7-yl}-N-(2-ethoxyethyl)thiophene-2-sulfonamide (18 mg) and diethylamine (9 mg).
HPLC purity 100%.
MS m/z 519 (M+H+).
$^1$H-NMR (400 MHz, CDCl$_3$) δ: 1.14 (3H, t, J=7.0 Hz), 1.42 (6H, t, J=7.3 Hz), 3.15 (4H, d, J=7.3 Hz), 3.32-3.57 (4H, m), 3.90 (2H, brs), 4.55 (2H, s), 6.68 (1H, d, J=8.0 Hz), 7.01 (1H, t, J=8.0 Hz), 7.04 (1H, d, J=2.1 Hz), 7.08 (1H, dd, J=5.1, 3.8 Hz), 7.44 (1H, dd, J=3.8, 1.3 Hz), 7.59-7.63 (2H, m), 7.81 (1H, s), 9.87 (1H, brs).

Example 170

N-(2-ethoxyethyl)-N-{2-[5-(piperidinomethyl)-1,3-thiazol-2-yl]-1H-indol-7-yl}thiophene-2-sulfonamide trifluoroacetate

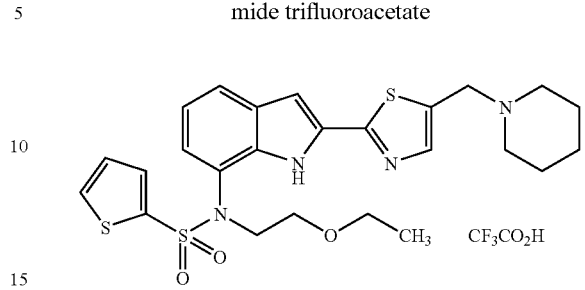

In the same manner as in Example 1, the title compound (9.5 mg, yield 39%) was obtained from N-{2-[5-(chloromethyl)-1,3-thiazol-2-yl]-1H-indol-7-yl}-N-(2-ethoxyethyl)thiophene-2-sulfonamide (18 mg) and piperidine (10 mg).
HPLC purity 100%.
MS m/z 531 (M+H+).

Example 171

N-(2-ethoxyethyl)-N-(2-{5-[(4-hydroxypiperidino)methyl]-1,3-thiazol-2-yl}-1H-indol-7-yl)thiophene-2-sulfonamide trifluoroacetate

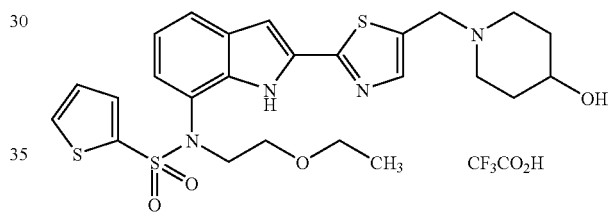

In the same manner as in Example 1, the title compound (11.3 mg, yield 45%) was obtained from N-{2-[5-(chloromethyl)-1,3-thiazol-2-yl]-1H-indol-7-yl}-N-(2-ethoxyethyl)thiophene-2-sulfonamide (18 mg) and 4-hydroxypiperidine (12 mg).
HPLC purity 100%.
MS m/z 547 (M+H+).

Example 172

N-(2-ethoxyethyl)-N-(2-{5-[(3-hydroxypiperidino)methyl]-1,3-thiazol-2-yl}-1H-indol-7-yl)thiophene-2-sulfonamide trifluoroacetate

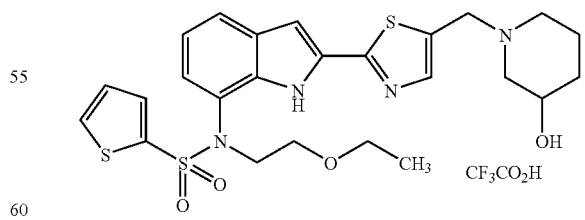

In the same manner as in Example 1, the title compound (13.5 mg, yield 54%) was obtained from N-{2-[5-(chloromethyl)-1,3-thiazol-2-yl]-1H-indol-7-yl}-N-(2-ethoxyethyl)thiophene-2-sulfonamide (18 mg) and 3-hydroxypiperidine (12 mg).
HPLC purity 100%.
MS m/z 547 (M+H+).

Example 173

N-(2-ethoxyethyl)-N-[2-(5-{[(2-methoxyethyl)(methyl)amino]methyl}-1,3-thiazol-2-yl)-1H-indol-7-yl]thiophene-2-sulfonamide trifluoroacetate

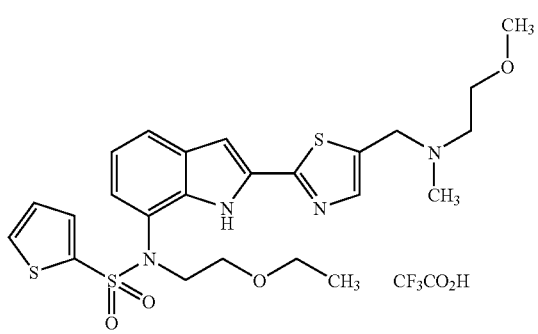

In the same manner as in Example 1, the title compound (7.4 mg, yield 30%) was obtained from N-{2-[5-(chloromethyl)-1,3-thiazol-2-yl]-1H-indol-7-yl}-N-(2-ethoxyethyl)thiophene-2-sulfonamide (18 mg) and N-(2-methoxyethyl)methylamine (11 mg).

HPLC purity 100%.
MS m/z 535 (M+H$^+$).

Example 174

N-(2-ethoxyethyl)-N-[2-(5-{[(2S)-2-(methoxymethyl)pyrrolidin-1-yl]methyl}-1,3-thiazol-2-yl)-1H-indol-7-yl]thiophene-2-sulfonamide trifluoroacetate

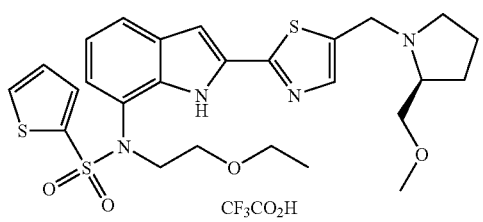

In the same manner as in Example 1, the title compound (9.2 mg, yield 36%) was obtained from N-{2-[5-(chloromethyl)-1,3-thiazol-2-yl]-1H-indol-7-yl}-N-(2-ethoxyethyl)thiophene-2-sulfonamide (18 mg) and (S)-2-(methoxymethyl)pyrrolidine (14 mg).

HPLC purity 100%.
MS m/z 561 (M+H$^+$).

Example 175

N-{1-[(2-{7-[(2-ethoxyethyl)(2-thienylsulfonyl)amino]-1H-indol-2-yl}-1,3-thiazol-5-yl)methyl]pyrrolidin-3-yl}acetamide trifluoroacetate

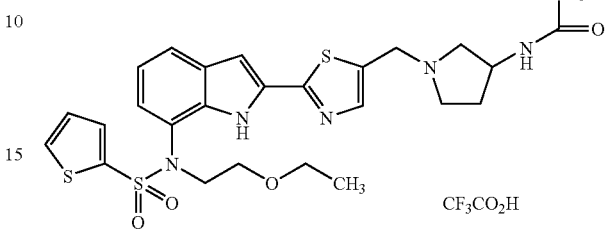

In the same manner as in Example 1, the title compound (9.6 mg, yield 37%) was obtained from N-{2-[5-(chloromethyl)-1,3-thiazol-2-yl]-1H-indol-7-yl}-N-(2-ethoxyethyl)thiophene-2-sulfonamide (18 mg) and 3-acetamidopyrrolidine (15 mg).

HPLC purity 100%.
MS m/z 574 (M+H$^+$).

Example 176

1-[(2-{7-[(2-ethoxyethyl)(2-thienylsulfonyl)amino]-1H-indol-2-yl}-1,3-thiazol-5-yl)methyl]piperidine-4-carboxamide trifluoroacetate

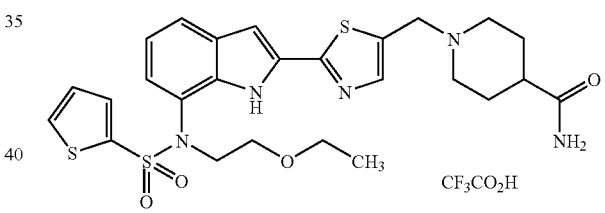

In the same manner as in Example 1, the title compound (9.1 mg, yield 35%) was obtained from N-{2-[5-(chloromethyl)-1,3-thiazol-2-yl]-1H-indol-7-yl}-N-(2-ethoxyethyl)thiophene-2-sulfonamide (18 mg) and isonipecotamide (15 mg).

HPLC purity 96%.
MS m/z 574 (M+H$^+$).

Example 177

N-(2-ethoxyethyl)-N-[2-(5-{[4-(2-hydroxyethyl)piperidino]methyl}-1,3-thiazol-2-yl)-1H-indol-7-yl]thiophene-2-sulfonamide trifluoroacetate

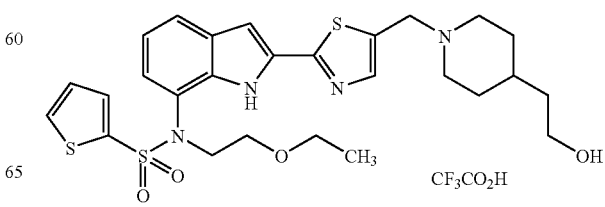

In the same manner as in Example 1, the title compound (10.7 mg, yield 41%) was obtained from N-{2-[5-(chloromethyl)-1,3-thiazol-2-yl]-1H-indol-7-yl}-N-(2-ethoxyethyl)thiophene-2-sulfonamide (18 mg) and 2-(piperidin-4-yl)ethanol (16 mg).

HPLC purity 100%.
MS m/z 575 (M+H⁺).

Example 178

N-[2-(5-{[bis(2-methoxyethyl)amino]methyl}-1,3-thiazol-2-yl)-1H-indol-7-yl]-N-(2-ethoxyethyl)thiophene-2-sulfonamide trifluoroacetate

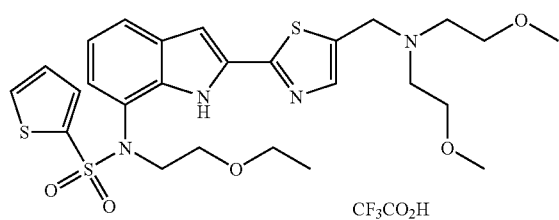

In the same manner as in Example 1, the title compound (5.8 mg, yield 22%) was obtained from N-{2-[5-(chloromethyl)-1,3-thiazol-2-yl]-1H-indol-7-yl}-N-(2-ethoxyethyl)thiophene-2-sulfonamide (18 mg) and bis(2-methoxyethyl)amine (16 mg).

HPLC purity 100%.
MS m/z 579 (M+H⁺).

Example 179 ethyl 1-[(2-{7-[(2-ethoxyethyl)(2-thienylsulfonyl)amino]-1H-indol-2-yl}-1,3-thiazol-5-yl)methyl]piperidine-4-carboxylate trifluoroacetate

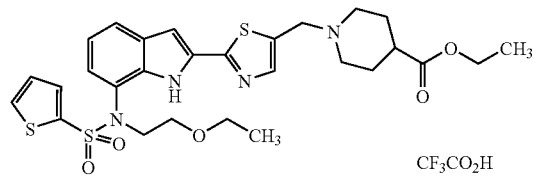

In the same manner as in Example 1, the title compound (10.9 mg, yield 40%) was obtained from N-{2-[5-(chloromethyl)-1,3-thiazol-2-yl]-1H-indol-7-yl}-N-(2-ethoxyethyl)thiophene-2-sulfonamide (18 mg) and ethyl isonipecotate (19 mg).

HPLC purity 100%.
MS m/z 603 (M+H⁺).

Example 180 ethyl 1-[(2-{7-[(2-ethoxyethyl)(2-thienylsulfonyl)amino]-1H-indol-2-yl}-1,3-thiazol-5-yl)methyl]piperidine-3-carboxylate trifluoroacetate

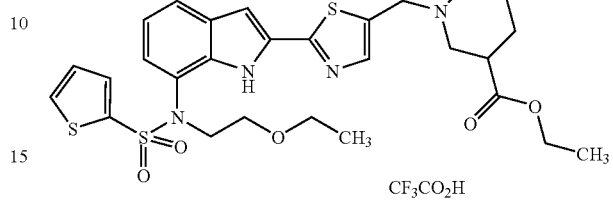

In the same manner as in Example 1, the title compound (13.3 mg, yield 49%) was obtained from N-{2-[5-(chloromethyl)-1,3-thiazol-2-yl]-1H-indol-7-yl}-N-(2-ethoxyethyl)thiophene-2-sulfonamide (18 mg) and ethyl nipecotate (19 mg).

HPLC purity 91%.
MS m/z 603 (M+H⁺).

Example 181

N-(2-ethoxyethyl)-N-(2-{5-[(3-hydroxypyrrolidin-1-yl)methyl]-1,3-thiazol-2-yl}-1H-indol-7-yl)thiophene-2-sulfonamide trifluoroacetate

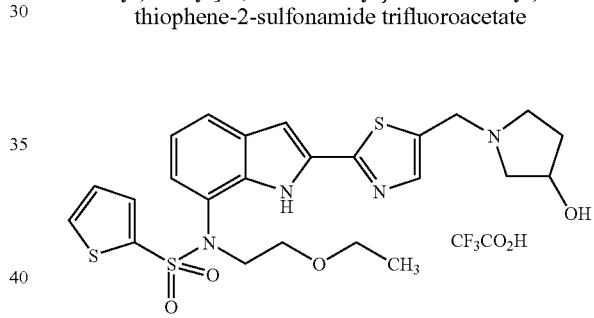

In the same manner as in Example 1, the title compound (10.4 mg, yield 42%) was obtained from N-{2-[5-(chloromethyl)-1,13-thiazol-2-yl]-1H-indol-7-yl}-N-(2-ethoxyethyl)thiophene-2-sulfonamide (18 mg) and DL-3-pyrrolidinol (10 mg).

HPLC purity 95%.
MS m/z 533 (M+H⁺).

Example 182

N-(2-ethoxyethyl)-N-[2-(5-{[2-(hydroxymethyl)piperidino]methyl}-1,3-thiazol-2-yl)-1H-indol-7-yl]thiophene-2-sulfonamide trifluoroacetate

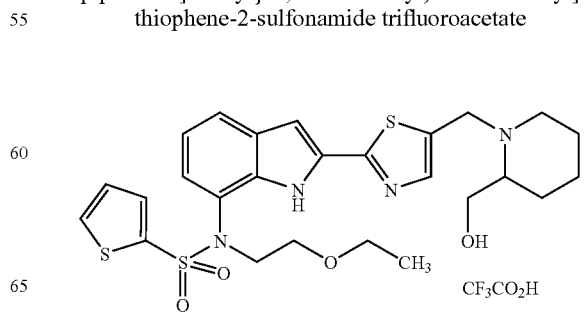

In the same manner as in Example 1, the title compound (7.3 mg, yield 28%) was obtained from N-{2-[5-(chloromethyl)-1,3-thiazol-2-yl]-1H-indol-7-yl}-N-(2-ethoxyethyl) thiophene-2-sulfonamide (18 mg) and piperidin-2-ylmethanol (14 mg).

HPLC purity 100%.

MS m/z 561 (M+H$^+$).

Example 183

N-[(2-{7-[(2-ethoxyethyl)(2-thienylsulfonyl)amino]-1H-indol-2-yl}-1,3-thiazol-5-yl)methyl]-N-methylglycine ethyl ester trifluoroacetate

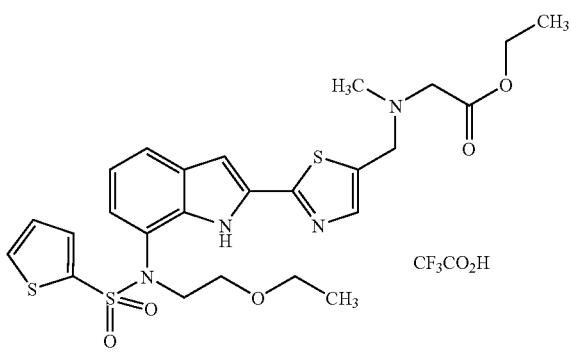

In the same manner as in Example 1, the title compound (14.0 mg, yield 54%) was obtained from N-{2-[5-(chloromethyl)-1,3-thiazol-2-yl]-1H-indol-7-yl}-N-(2-ethoxyethyl) thiophene-2-sulfonamide (18 mg) and sarcosine ethyl ester hydrochloride (18 g).

HPLC purity 100%.

m/z 563 (M+H$^+$).

Example 184 ethyl 4-[(2-{7-[(2-ethoxyethyl)(2-thienylsulfonyl) amino]-1H-indol-2-yl}-1,3-thiazol-5-yl)methyl]piperazine-1-carboxylate trifluoroacetate

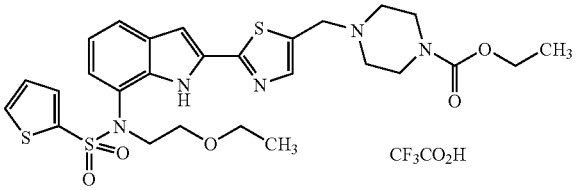

In the same manner as in Example 1, the title compound (9.0 mg, yield 33%) was obtained from N-{2-[5-(chloromethyl)-1,3-thiazol-2-yl]-1H-indol-7-yl}-N-(2-ethoxyethyl) thiophene-2-sulfonamide (18 mg) and 1-ethoxycarbonylpiperazine (19 mg).

HPLC purity 100%.

MS m/z 604 (M+H$^+$).

Example 185

N-(2-ethoxyethyl)-N-[2-(5-{[4-(ethylsulfonyl)piperazin-1-yl]methyl}-1,3-thiazol-2-yl)-1H-indol-7-yl] thiophene-2-sulfonamide trifluoroacetate

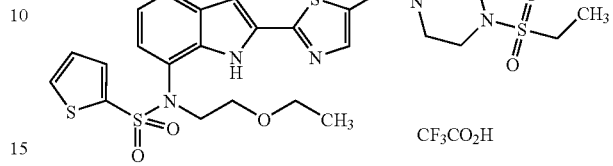

In the same manner as in Example 1, the title compound (8.0 mg, yield 28%) was obtained from N-{2-[5-(chloromethyl)-1,3-thiazol-2-yl]-1H-indol-7-yl}-N-(2-ethoxyethyl) thiophene-2-sulfonamide (18 mg) and 1-ethylsulfonylpiperazine (21 mg).

HPLC purity 100%.

MS m/z 624 (M+H$^+$).

Example 186

N-(2-{5-[(4-acetylpiperazin-1-yl)methyl]-1,3-thiazol-2-yl}-1H-indol-7-yl)-N-methylthiophene-2-sulfonamide

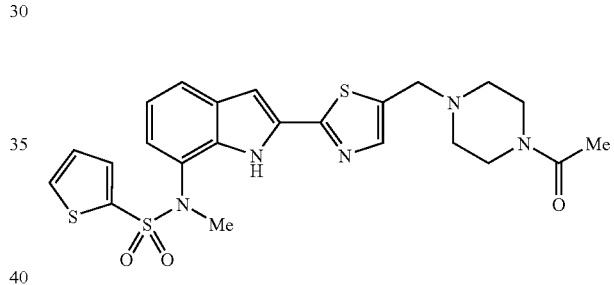

A mixture of N-{2-[5-(chloromethyl)-1,3-thiazol-2-yl]-1H-indol-7-yl}-N-methylthiophene-2-sulfonamide (0.40 g), 1-acetylpiperazine (0.24 g), triethylamine (0.26 ml) and N,N-dimethylformamide (15 ml) was stirred at room temperature for 2 hr. Water was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (0.33 g, yield 68%) as colorless crystals from a fraction eluted with ethyl acetate. melting point 177-178° C.

Example 187

N-methyl-N-{2-[5-(thiomorpholinomethyl)-1,3-thiazol-2-yl]-1H-indol-7-yl}thiophene-2-sulfonamide

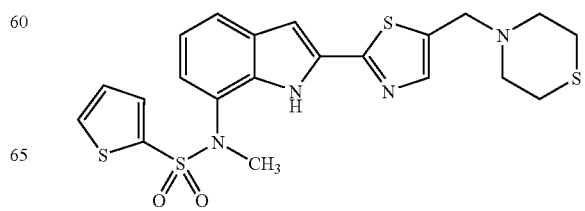

In the same manner as in Example 186, the title compound (0.51 g, yield 43%) was obtained as yellow crystals from N-{2-[5-(chloromethyl)-1,3-thiazol-2-yl]-1H-indol-7-yl}-N-methylthiophene-2-sulfonamide (0.96 g) and thiomorpholine (0.58 g). melting point 177-178° C.

Example 188

N-(2-{5-[(1,1-dioxidothiomorpholino)methyl]-1,3-thiazol-2-yl}-1H-indol-7-yl)-N-methylthiophene-2-sulfonamide

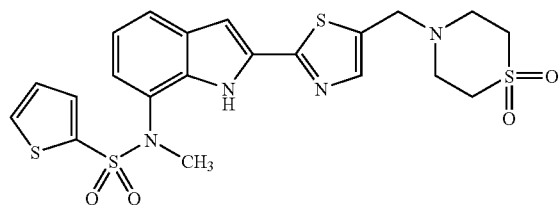

A mixture of N-methyl-N-{2-[5-(thiomorpholinomethyl)-1,3-thiazol-2-yl]-1H-indol-7-yl}thiophene-2-sulfonamide (0.35 g), sodium percarbonate (0.33 g), acetonitrile (6 ml) and water (2 ml) was stirred at 40° C. for 30 min. Sodium percarbonate (0.15 g) was added, and the mixture was further stirred at 40° C. for 1 hr. Water was added to the reaction mixture, and the resulting crystals were collected by filtration, washed with water, and dried. The obtained crystals were subjected to silica gel short column to give the title compound (0.28 g, yield 76%) as colorless crystals from a fraction eluted with tetrahydrofuran-hexane (3:1, volume ratio). melting point 225-226° C.

Example 189
methyl {4-[(2-{7-[methyl(2-thienylsulfonyl)amino]-1H-indol-2-yl}-1,3-thiazol-5-yl)methyl]-2-oxopiperazin-1-yl}acetate

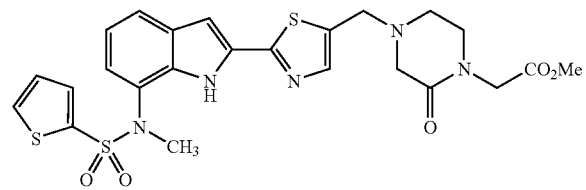

In the same manner as in Example 186, the title compound (0.32 g, yield 66%) was obtained as yellow crystals from N-{2-[5-(chloromethyl)-1,3-thiazol-2-yl]-1H-indol-7-yl}-N-methylthiophene-2-sulfonamide (0.37 g) and methyl (2-oxopiperazin-1-yl)acetate hydrochloride (0.27 g). melting point 182-183° C.

Example 190
N-(2-{5-[(4-acetylpiperazin-1-yl)methyl]-1,3-thiazol-2-yl}-1H-indol-7-yl)-N-isopropylthiophene-2-sulfonamide

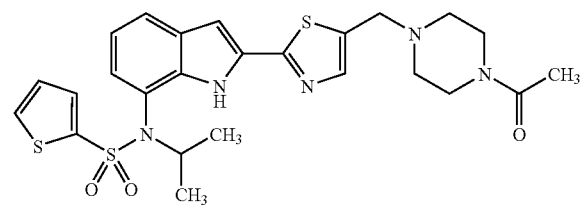

In the same manner as in Example 186, the title compound (0.15 g, yield 64%) was obtained as colorless crystals from N-{2-[5-(chloromethyl)-1,3-thiazol-2-yl]-1H-indol-7-yl}-N-isopropylthiophene-2-sulfonamide (0.20 g) and 1-acetylpiperazine (0.11 g). melting point 145-146° C.

Example 191

N-(2-{5-[(4-acetylpiperazin-1-yl)methyl]-1,3-thiazol-2-yl}-4-chloro-1H-indol-7-yl)-N-methylthiophene-2-sulfonamide

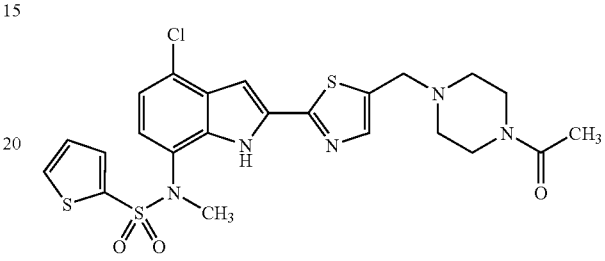

To a mixture of N-{4-chloro-2-[5-(hydroxymethyl)-1,3-thiazol-2-yl]-1H-indol-7-yl}-N-methylthiophene-2-sulfonamide (0.26 g) and tetrahydrofuran (10 ml) was added thionyl chloride (0.08 ml) at 0° C., and the mixture was stirred overnight at room temperature. Water was added to the reaction mixture, and the mixture was extracted with ethyl acetate. The ethyl acetate layer was washed with saturated brine, dried (MgSO$_4$), and concentrated. A mixture of the obtained residue, 1-acetylpiperazine (0.15 g), triethylamine (0.17 ml) and N,N-dimethylformamide (10 ml) was stirred at room temperature for 3 hr. Water was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (0.08 g, yield 25%) as colorless crystals from a fraction eluted with ethyl acetate. melting point 224-225° C.

Example 192

N-(2-{5-[(4-acetylpiperazin-1-yl)methyl]-1,3-thiazol-2-yl}-1H-indol-7-yl)thiophene-2-sulfonamide

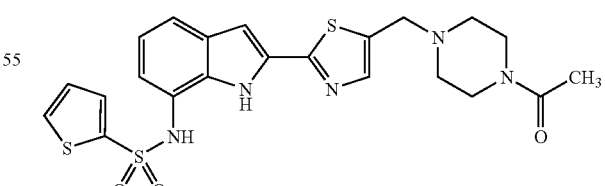

In the same manner as in Example 191, the title compound (0.37 g, yield 41%) was obtained as colorless crystals from N-{2-[5-(hydroxymethyl)-1,3-thiazol-2-yl]-1H-indol-7-yl}thiophene-2-sulfonamide (0.63 g). melting point 221-222° C.

Example 193

N-(2-{5-[(4-acetyl-2-oxopiperazin-1-yl)methyl]-1,3-thiazol-2-yl}-1H-indol-7-yl)-N-methylthiophene-2-sulfonamide

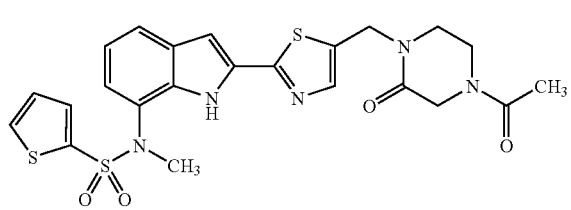

To a mixture of N-(2-{[(2-{7-[methyl(2-thienylsulfonyl)amino]-1H-indol-2-yl}-1,3-thiazol-5-yl)methyl]amino}ethyl)acetamide (0.33 g) and N,N-dimethylacetamide (6 ml) was added chloroacetyl chloride (0.06 ml) at 0° C., and the mixture was stirred at 0° C. for 30 min. Water was added to the reaction mixture, and the mixture was extracted with ethyl acetate. The ethyl acetate layer was washed with saturated brine, dried (MgSO$_4$), and concentrated.

To a mixture of the obtained residue and N,N-dimethylformamide (6 ml) was added sodium hydride (60%, in oil, 0.06 g) at 0° C., and the mixture was stirred overnight at room temperature. Water was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (0.07 g, yield 19%) as a colorless amorphous solid from a fraction eluted with ethyl acetate-methanol (3:2, volume ratio). MS: MH$^+$=530.

Example 194

N-(2-{5-[(4-acetylpiperazin-1-yl)methyl]-1,3-thiazol-2-yl}-6-chloro-1H-indol-7-yl)thiophene-2-sulfonamide

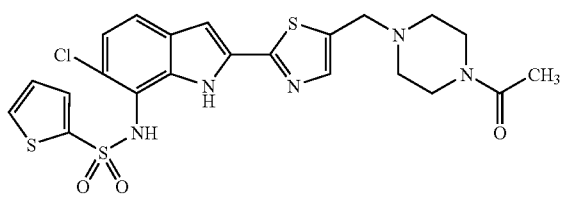

In the same manner as in Example 191, the title compound (0.18 g, yield 34%) was obtained as colorless crystals from N-{6-chloro-2-[5-(hydroxymethyl)-1,3-thiazol-2-yl]-1H-indol-7-yl}thiophene-2-sulfonamide (0.42 g). melting point 200-201° C.

Example 195

N-(2-{5-[(4-acetylpiperazin-1-yl)methyl]-1,3-thiazol-2-yl}-6-chloro-1H-indol-7-yl)-N-methylthiophene-2-sulfonamide

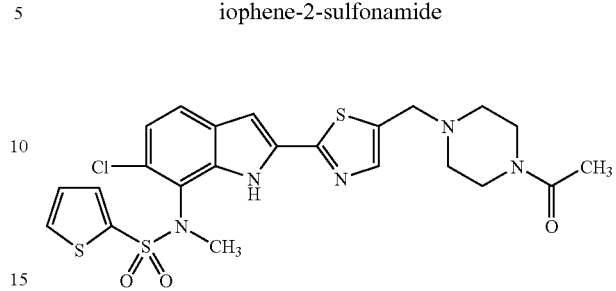

In the same manner as in Example 191, the title compound (0.14 g, yield 34%) was obtained as colorless crystals from N-{6-chloro-2-[5-(hydroxymethyl)-1,3-thiazol-2-yl]-1H-indol-7-yl}-N-methylthiophene-2-sulfonamide (0.32 g). melting point 193-194° C.

Example 196

N-{(3R)-1-[(2-{7-[methyl(2-thienylsulfonyl)amino]-1H-indol-2-yl}-1,3-thiazol-5-yl)methyl]pyrrolidin-3-yl}acetamide

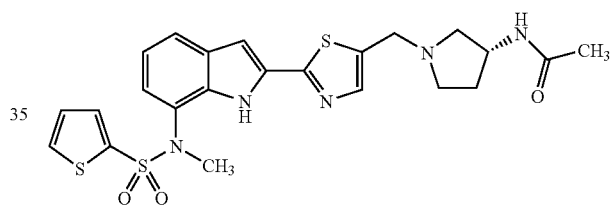

In the same manner as in Example 186, the title compound (0.10 g, yield 41%) was obtained as yellow crystals from N-{2-[5-(chloromethyl)-1,3-thiazol-2-yl]-1H-indol-7-yl}-N-methylthiophene-2-sulfonamide (0.20 g) and N-[(3R)-pyrrolidin-3-yl]acetamide (0.10 g). melting point 129-130° C.

Example 197

N-{(3S)-1-[(2-{7-[methyl(2-thienylsulfonyl)amino]-1H-indol-2-yl}-1,3-thiazol-5-yl)methyl]pyrrolidin-3-yl}acetamide

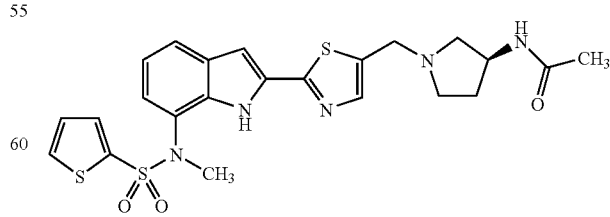

In the same manner as in Example 186, the title compound (0.12 g, yield 47%) was obtained as yellow crystals from N-{2-[5-(chloromethyl)-1,3-thiazol-2-yl]-1H-indol-7-yl}-

N-methylthiophene-2-sulfonamide (0.20 g) and N-[(3S)-pyrrolidin-3-yl]acetamide (0.10 g). melting point 130-131° C.

Example 198

N-(2-{5-[(4-acetylpiperazin-1-yl)methyl]-1,3,4-thiadiazol-2-yl}-1H-indol-7-yl)-N-methylthiophene-2-sulfonamide

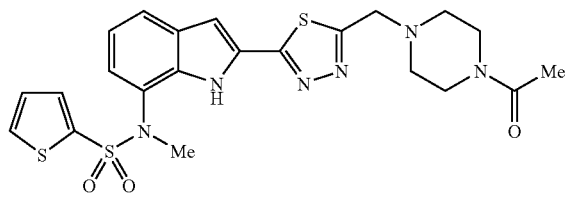

A mixture of N-{2-[5-(hydroxymethyl)-1,3,4-thiadiazol-2-yl]-1H-indol-7-yl}-N-methylthiophene-2-sulfonamide (0.50 g), thionyl chloride (0.13 ml) and tetrahydrofuran (25 ml) was stirred overnight at room temperature. The reaction mixture was diluted with ethyl acetate, washed twice with saturated brine, dried (MgSO$_4$), and concentrated to give a residue.

A mixture of the obtained residue, 1-acetylpiperazine (0.31 g), sodium hydrogencarbonate (0.21 g) and N,N-dimethylformamide (15 ml) was stirred overnight at room temperature. Water was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (0.32 g, yield 50%) as pale-yellow crystals from a fraction eluted with ethyl acetate. melting point 194-195° C.

Example 199

N-{2-[5-(2-hydroxyethyl)-5-methyl-4,5-dihydro-1,3-thiazol-2-yl]-1H-indol-7-yl}-N-methylthiophene-2-sulfonamide

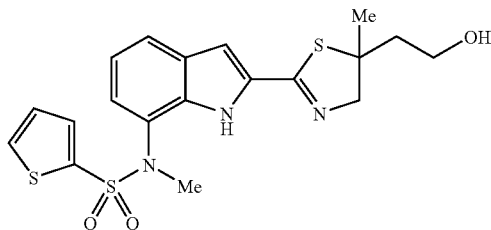

To a solution of triphenylphosphine oxide (1.28 g) in acetonitrile (25 ml) was slowly added trifluoromethanesulfonic anhydride (0.39 ml) at 0° C., and the mixture was stirred for 10 min. N-[2-(Benzylthio)-4-hydroxy-2-methylbutyl]-7-[methyl(2-thienylsulfonyl)amino]-1H-indole-2-carboxamide (0.50 g) was added, and the reaction mixture was stirred at 0° C. for 30 min. Saturated aqueous sodium hydrogencarbonate was added, and the mixture was extracted with ethyl acetate. The ethyl acetate layer was washed with saturated brine, dried (MgSO$_4$), and concentrated. The residue was subjected to silica gel column chromatography to give the title compound (0.17 g, yield 42%) as colorless crystals from a fraction eluted with ethyl acetate-hexane (2:1, volume ratio). melting point 149-150° C.

Example 200

N-methyl-N-{2-[5-methyl-5-(2-(morpholino)ethyl)-4,5-dihydro-1,3-thiazol-2-yl]-1H-indol-7-yl}thiophene-2-sulfonamide

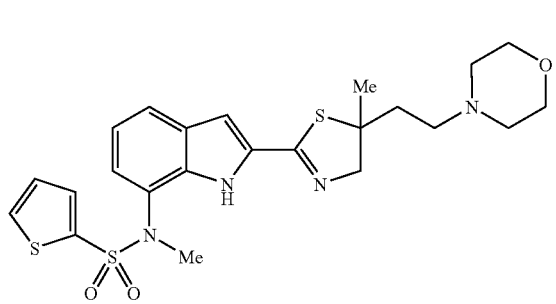

To a solution of triphenylphosphine oxide (1.90 g) in acetonitrile (25 ml) was slowly added trifluoromethanesulfonic anhydride (0.57 ml) at 0° C., and the mixture was stirred for 10 min. N-[2-(Benzylthio)-2-methyl-4-(morpholino)butyl]-7-[methyl(2-thienylsulfonyl)amino]-1H-indole-2-carboxamide (1.39 g) was added, and the reaction mixture was stirred at 0° C. for 30 min. Saturated aqueous sodium hydrogencarbonate was added, and the mixture was extracted with ethyl acetate. The ethyl acetate layer was washed with saturated brine, dried (MgSO$_4$), and concentrated. The residue was subjected to basic silica gel column chromatography to give the title compound (0.80 g, yield 70%) as colorless crystals from a fraction eluted with ethyl acetate-hexane (5:1, volume ratio). melting point 154-155° C.

Example 201

N-methyl-N-{2-[5-methyl-5-(morpholinomethyl)-4,5-dihydro-1,3-thiazol-2-yl]-1H-indol-7-yl}thiophene-2-sulfonamide

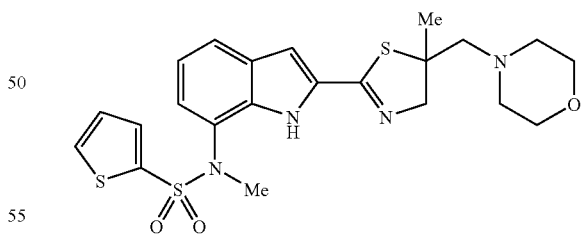

To a solution of triphenylphosphine oxide (1.00 g) in acetonitrile (20 ml) was slowly added trifluoromethanesulfonic anhydride (0.30 ml) at 0° C., and the mixture was stirred for 10 min. N-[2-(Benzylthio)-2-methyl-3-(morpholino)propyl]-7-[methyl(2-thienylsulfonyl)amino]-1H-indole-2-carboxamide (0.43 g) was added, and the reaction mixture was stirred at 0° C. for 30 min. Saturated aqueous sodium hydrogencarbonate was added, and the mixture was extracted with ethyl acetate. The ethyl acetate layer was washed with saturated brine, dried (MgSO$_4$), and concentrated. The residue was subjected to silica gel column chromatography to give the title compound (0.20 g, yield 57%) as colorless crystals from a fraction eluted with ethyl acetate-hexane (2:1, volume ratio). melting point 146-147° C.

Example 202

N-methyl-N-{2-[5-methyl-5-(piperazine-1-ylmethyl)-4,5-dihydro-1,3-thiazol-2-yl]-1H-indol-7-yl}thiophene-2-sulfonamide

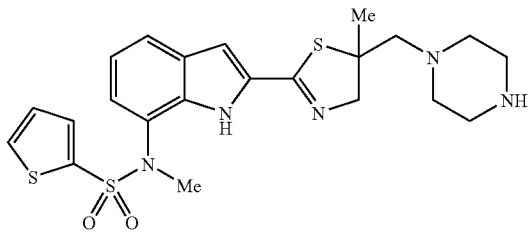

To a solution of triphenylphosphine oxide (3.09 g) in acetonitrile (20 ml) was slowly added trifluoromethanesulfonic anhydride (0.93 ml) at 0° C., and the mixture was stirred for 10 min. tert-Butyl 4-{2-(benzylthio)-2-methyl-3-[({7-[methyl(2-thienylsulfonyl)amino]-1H-indol-2-yl}carbonyl)amino]propyl}piperazine-1-carboxylate (1.55 g) was added, and the reaction mixture was stirred at 0° C. for 30 min. Saturated aqueous sodium hydrogencarbonate was added, and the mixture was extracted with ethyl acetate. The ethyl acetate layer was washed with saturated brine, and dried (MgSO₄). 4N Hydrogen chloride-ethyl acetate solution was added to the ethyl acetate layer, and the precipitated solid was collected by filtration, and washed with ethyl acetate. The obtained solid was suspended in saturated aqueous sodium hydrogencarbonate, and the mixture was stirred for 30 min. The solid was collected by filtration, washed with water and ethyl acetate, and dried to give the title compound (0.49 g, yield 45%) as colorless crystals. melting point 178-180° C.

Example 203

N-(2-{5-[(4-acetylpiperazin-1-yl)methyl]-5-methyl-4,5-dihydro-1,3-thiazol-2-yl}-1H-indol-7-yl)-N-methylthiophene-2-sulfonamide

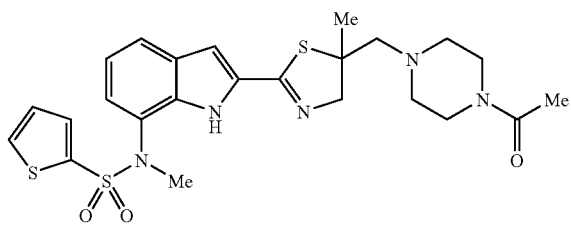

A mixture of N-methyl-N-{2-[5-methyl-5-(piperazine-1-ylmethyl)-4,5-dihydro-1,3-thiazol-2-yl]-1H-indol-7-yl}thiophene-2-sulfonamide (0.21 g), acetic anhydride (0.30 ml) and pyridine (6 ml) was stirred at 0° C. for 1 hr, and concentrated. Water was added to the residue, and the mixture was extracted with ethyl acetate. The ethyl acetate layer was washed with saturated brine, dried (MgSO₄), and concentrated. The residue was subjected to silica gel column chromatography to give the title compound (0.19 g, yield 84%) as a colorless amorphous solid from a fraction eluted with ethyl acetate-methanol (6:1, volume ratio).

MS: 532 (MH⁺).

Example 204

N-methyl-N-[2-(5-methyl-5-{[4-(methylsulfonyl)piperazin-1-yl]methyl}-4,5-dihydro-1,3-thiazol-2-yl)-1H-indol-7-yl]thiophene-2-sulfonamide

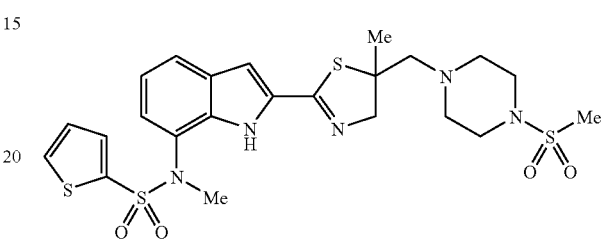

To a mixture of N-methyl-N-{2-[5-methyl-5-(piperazine-1-ylmethyl)-4,5-dihydro-1,3-thiazol-2-yl]-1H-indol-7-yl}thiophene-2-sulfonamide (0.28 g), triethylamine (0.17 ml) and tetrahydrofuran (6 ml) was added methanesulfonyl chloride (0.06 ml) at 0° C., and the reaction mixture was stirred overnight at room temperature, and concentrated. The residue was subjected to basic silica gel column chromatography to give the title compound (0.26 g, yield 81%) as colorless crystals from a fraction eluted with ethyl acetate-hexane (4:1, volume ratio).

melting point 209-210° C.

Example 205

N-{2-[5-(dimethoxymethyl)-5-methyl-4,5-dihydro-1,3-thiazol-2-yl]-1H-indol-7-yl}-N-methylthiophene-2-sulfonamide

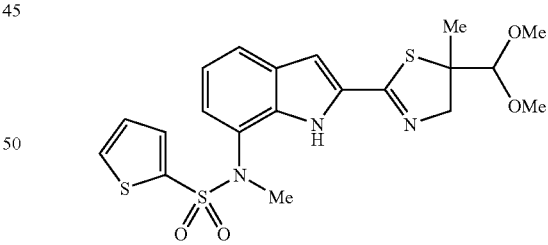

To a solution of triphenylphosphine oxide (1.02 g) in dichloromethane (10 ml) was slowly added trifluoromethanesulfonic anhydride (0.31 ml) at 0° C., and the mixture was stirred for 10 min. N-[2-(Benzylthio)-3,3-dimethoxy-2-methylpropyl]-7-[methyl(2-thienylsulfonyl)amino]-1H-indole-2-carboxamide (0.70 g) was added, and the reaction mixture was stirred at 0° C. for 30 min. Saturated aqueous sodium hydrogencarbonate was added, and the mixture was extracted with ethyl acetate. The ethyl acetate layer was washed with saturated brine, dried (MgSO₄), and concentrated. The residue was subjected to silica gel column chromatography to give the title compound (0.28 g, yield 50%) as colorless

Example 206

N-[2-(5-cyano-5-methyl-4,5-dihydro-1,3-thiazol-2-yl)-1H-indol-7-yl]-N-methylthiophene-2-sulfonamide

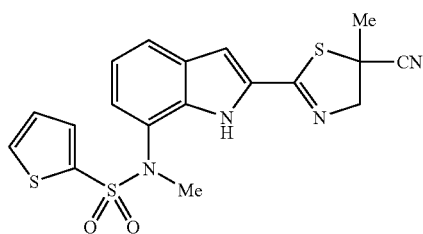

To a solution of triphenylphosphine oxide (0.68 g) in acetonitrile (10 ml) was slowly added trifluoromethanesulfonic anhydride (0.21 ml) at 0° C., and the mixture was stirred for 10 min. N-[2-(Benzylthio)-2-cyanopropyl]-7-[methyl(2-thienylsulfonyl)amino]-1H-indole-2-carboxamide (0.43 g) was added, and the reaction mixture was stirred at 0° C. for 30 min. Saturated aqueous sodium hydrogencarbonate was added, and the mixture was extracted with ethyl acetate. The ethyl acetate layer was washed with saturated brine, dried (MgSO$_4$), and concentrated. The residue was subjected to silica gel column chromatography to give the title compound (0.27 g, yield 79%) as colorless crystals from a fraction eluted with ethyl acetate-hexane (2:3, volume ratio). melting point 178-179° C.

Example 207

5-methyl-2-{7-[methyl(2-thienylsulfonyl)amino]-1H-indol-2-yl}-4,5-dihydro-1,3-thiazole-5-carboxylic acid

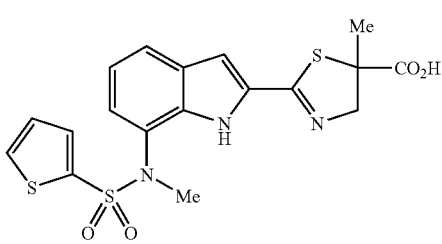

A mixture of N-[2-(5-cyano-5-methyl-4,5-dihydro-1,3-thiazol-2-yl)-1H-indol-7-yl]-N-methylthiophene-2-sulfonamide (0.15 g), 2N aqueous sodium hydroxide solution (0.36 ml), tetrahydrofuran (3 ml) and ethanol (3 ml) was heated under reflux for 4 hr. 10% Aqueous citric acid solution was added to the reaction mixture, and the mixture was extracted with ethyl acetate. The ethyl acetate layer was washed with saturated brine, dried (MgSO$_4$), and concentrated. The residue was subjected to silica gel column chromatography to give the title compound (0.11 g, yield 69%) as yellow crystals from a fraction eluted with tetrahydrofuran. melting point >232° C. (decomposition).

Example 208 ethyl {4-[(2-{7-[methyl(2-thienylsulfonyl)amino]-1H-indol-2-yl}-1,3-thiazol-5-yl)methyl]piperazin-1-yl}acetate

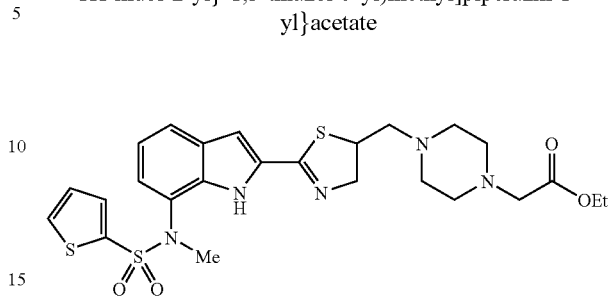

To a solution of N-{2-[5-(chloromethyl)-1,3-thiazol-2-yl]-1H-indol-7-yl}-N-methylthiophene-2-sulfonamide (0.700 g) in N,N-dimethylformamide (16 ml) were added ethyl piperazin-1-ylacetate (0.568 g) and triethylamine (0.46 ml), and the mixture was stirred at room temperature for 5 hr. Water was added to the reaction solution, and the mixture was extracted with ethyl acetate. The extract was washed successively with water and saturated brine, dried over anhydrous magnesium sulfate, and concentrated under reduced pressure. The residue was purified by basic silica gel column chromatography (ethyl acetate:hexane=50:50-100:0), and recrystallized from ethyl acetate-hexane to give the title compound (0.531 g, yield 57%) as colorless crystals.

melting point 167-169° C.

Example 209

{4-[(2-{7-[methyl(2-thienylsulfonyl)amino]-1H-indol-2-yl}-1,3-thiazol-5-yl)methyl]piperazin-1-yl}acetic acid

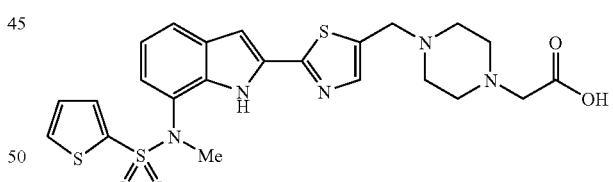

To a solution of ethyl {4-[(2-{7-[methyl(2-thienylsulfonyl)amino]-1H-indol-2-yl}-1,3-thiazol-5-yl)methyl]piperazin-1-yl}acetate (0.490 g) in a mixed solvent of tetrahydrofuran (10 ml) and methanol (5 ml) was added 8N aqueous sodium hydroxide solution (1.5 ml), and the mixture was stirred at room temperature for 16 hr. Saturated aqueous ammonium chloride solution was added to the reaction solution, and the precipitated crystals were collected by filtration, washed with ethyl acetate and water, and dried to give the title compound (0.360 g, yield 57%) as colorless crystals.

melting point 171-173° C.

Example 210

N-methyl-2-{4-[(2-{7-[methyl(2-thienylsulfonyl)amino]-1H-indol-2-yl}-1,3-thiazol-5-yl)methyl]piperazin-1-yl}acetamide

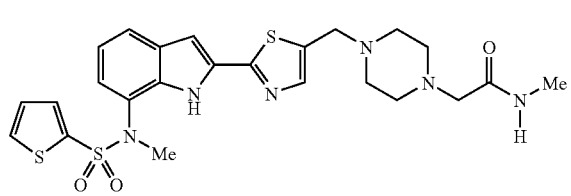

To a solution of {4-[(2-{7-[methyl(2-thienylsulfonyl)amino]-1H-indol-2-yl}-1,3-thiazol-5-yl)methyl]piperazin-1-yl}acetic acid (0.200 g) in N,N-dimethylformamide (10 ml) were added 1H-1,2,3-benzotriazol-1-ol (0.061 g), N-[3-(dimethylamino)propyl]-N'-ethylcarbodiimide hydrochloride (0.087 g) and 2.0 mol/L solution of N-methylamine in THF (0.25 ml), and the mixture was stirred at room temperature for 15 hr. Saturated aqueous sodium hydrogencarbonate solution was added to the reaction solution, and the mixture was extracted with ethyl acetate. The extract was washed with saturated brine, dried over anhydrous magnesium sulfate, and concentrated under reduced pressure. The residue was purified by silica gel column chromatography (methanol), and recrystallized from ethyl acetate-hexane to give the title compound (0.150 g, yield 67%) as colorless crystals.

melting point 190-192° C.

Example 211

N,N-dimethyl-2-{4-[(2-{7-[(2-thienylsulfonyl)amino]-1H-indol-2-yl}-1,3-thiazol-5-yl)methyl]piperazin-1-yl}acetamide

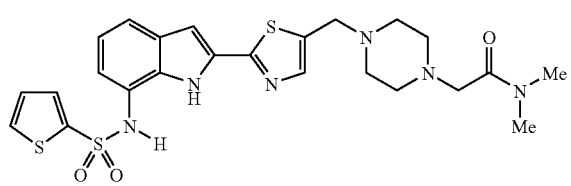

To a solution of N-{2-[5-(chloromethyl)-1,3-thiazol-2-yl]-1H-indol-7-yl}thiophene-2-sulfonamide (0.250 g) in N,N-dimethylformamide (6 ml) were added N,N-dimethyl-2-piperazin-1-ylacetamide (0.208 g) and triethylamine (0.17 ml), and the mixture was stirred at room temperature for 15 hr. Water was added to the reaction solution, and the mixture was extracted with ethyl acetate. The extract was washed with saturated brine, dried over anhydrous magnesium sulfate, and concentrated under reduced pressure. The residue was purified by silica gel column chromatography (methanol), and recrystallized from ethyl acetate-hexane to give the title compound (0.230 g, yield 69%) as colorless crystals.

MS m/z 545 (M+H$^+$).

Example 212 ethyl {4-[(2-{7-[(2-thienylsulfonyl)amino]-1H-indol-2-yl}-1,3-thiazol-5-yl)methyl]piperazin-1-yl}acetate

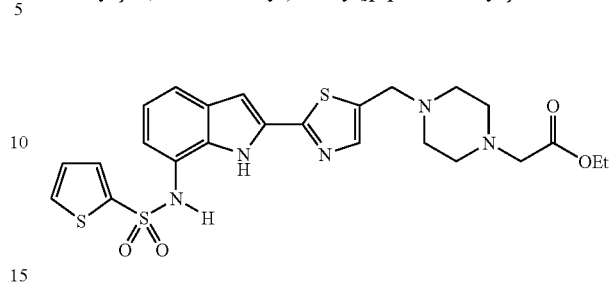

To a solution of N-{2-[5-(chloromethyl)-1,3-thiazol-2-yl]-1H-indol-7-yl}thiophene-2-sulfonamide (0.460 g) in N,N-dimethylformamide (12 ml) were added ethyl piperazin-1-ylacetate (0.385 g) and triethylamine (0.31 ml), and the mixture was stirred at room temperature for 15 hr. Saturated aqueous ammonium chloride solution was added to the reaction solution, and the mixture was extracted with ethyl acetate. The extract was washed successively with water and saturated brine, dried over anhydrous magnesium sulfate, and concentrated under reduced pressure. The residue was recrystallized from tetrahydrofuran-hexane to give the title compound (0.507 g, yield 83%) as colorless crystals.

MS m/z 546 (M+H$^+$).

Example 213

{4-[(2-{7-[(2-thienylsulfonyl)amino]-1H-indol-2-yl}-1,3-thiazol-5-yl)methyl]piperazin-1-yl}acetic acid

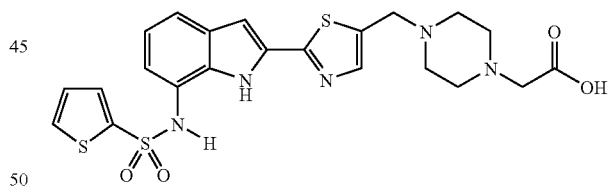

To a solution of ethyl {4-[(2-{7-[(2-thienylsulfonyl)amino]-1H-indol-2-yl}-1,3-thiazol-5-yl)methyl]piperazin-1-yl}acetate (0.500 g) in a mixed solvent of tetrahydrofuran (15 ml) and methanol (5 ml) was added 2N aqueous sodium hydroxide solution (1.5 ml), and the mixture was stirred at 50° C. for 2 hr. 10% Aqueous citric acid solution, ethyl acetate, sodium chloride and tetrahydrofuran were successively added to the reaction solution, and the precipitated crystals were collected by filtration, washed with ethyl acetate, and dried to give the title compound (0.360 g, yield 76%) as colorless crystals.

MS m/z 518 (M+H$^+$).

Example 214

N-methyl-2-{4-[(2-{7-[(2-thienylsulfonyl)amino]-1H-indol-2-yl}-1,3-thiazol-5-yl)methyl]piperazin-1-yl}acetamide

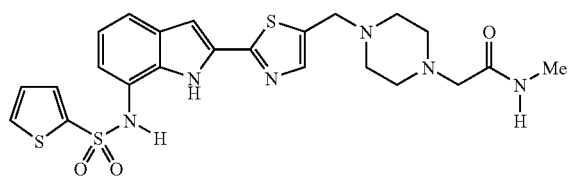

To a solution of {4-[(2-{7-[(2-thienylsulfonyl)amino]-1H-indol-2-yl}-1,3-thiazol-5-yl)methyl]piperazin-1-yl}acetic acid (0.230 g) in N,N-dimethylformamide (4 ml) were added 1H-1,2,3-benzotriazol-1-ol (0.066 g) and N-[3-(dimethylamino)propyl]-N'-ethylcarbodiimide hydrochloride (0.093 g), and the mixture was stirred at 50° C. for 1 hr. A 2.0 mol/L solution of N-methylamine in THF (0.60 ml) was added to the reaction solution, and the mixture was stirred at 50° C. for 1 hr. Water was added to the reaction solution, and the mixture was extracted with ethyl acetate. The extract was washed with saturated brine, dried over anhydrous magnesium sulfate, and concentrated under reduced pressure. The residue was purified by silica gel column chromatography (methanol), and recrystallized from tetrahydrofuran-hexane to give the title compound (0.100 g, yield 42%) as colorless crystals.

MS m/z 531 (M+H$^+$).

Example 215

N-[2-(8-benzyl-1-thia-3,8-diazaspiro[4.5]dec-2-en-2-yl)-1H-indol-7-yl]-N-methylthiophene-2-sulfonamide

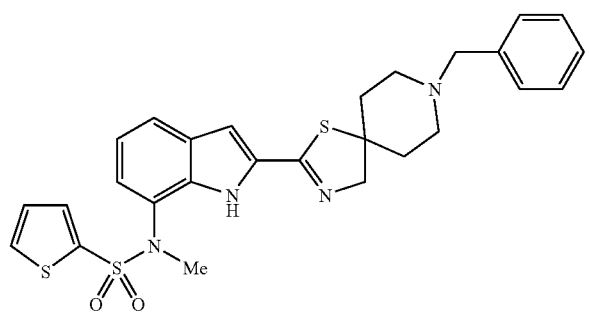

To a solution of N-[(1-benzyl-4-hydroxypiperidin-4-yl)methyl]-7-[methyl(2-thienylsulfonyl)amino]-1H-indole-2-carboxamide (1.30 g) in a mixed solvent of toluene (60 ml) and tetrahydrofuran (30 ml) was added Lawesson's reagent (1.94 g), and the mixture was heated under reflux for 3 hr. The reaction solution was concentrated under reduced pressure, and the residue was purified by basic silica gel column chromatography (ethyl acetate:hexane=5:95-40:60), and recrystallized from ethyl acetate-hexane to give the title compound (0.063 g, yield 5%) as colorless crystals.

melting point 197-199° C.

Example 216

N-{2-[5-(dimethoxymethyl)-4,5-dihydro-1,3-thiazol-2-yl]-1H-indol-7-yl}-N-methylthiophene-2-sulfonamide

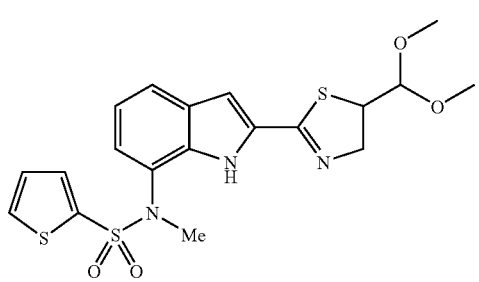

In the same manner as in Example 200, the title compound (0.240 g, 49%) was obtained as colorless crystals from N-[2-(benzylthio)-3,3-dimethoxypropyl]-7-[methyl(2-thienylsulfonyl)amino]-1H-indole-2-carboxamide (0.628 g).

melting point 138-140° C.

Example 217

N-methyl-N-{2-[5-(morpholinomethyl)-4,5-dihydro-1,3-thiazol-2-yl]-1H-indol-7-yl}thiophene-2-sulfonamide dihydrochloride

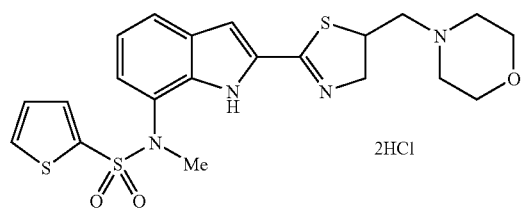

To a solution of triphenylphosphine oxide (0.409 g) in acetonitrile (3.6 ml) was added dropwise trifluoromethanesulfonic anhydride (0.124 ml) under ice-cooling, and the mixture was stirred at 0° C. for 10 min. A solution of N-[2-(benzylthio)-3-(morpholino)propyl]-7-[methyl(2-thienylsulfonyl)amino]-1H-indole-2-carboxamide (0.215 g) in acetonitrile (3.6 ml) was added to the reaction solution, and the mixture was stirred at 0° C. for 10 min. Saturated aqueous sodium hydrogencarbonate solution was added to the reaction solution, and the mixture was extracted with ethyl acetate. The extract was washed with saturated brine, dried over anhydrous magnesium sulfate, and concentrated under reduced pressure. The residue was purified by basic silica gel column chromatography (ethyl acetate:hexane=30:70-100:0). The obtained product was dissolved in ethyl acetate, 4N hydrogen chloride-ethyl acetate solution was added to give the title compound (0.092 g, yield 45%) as pale-yellow crystals.

melting point 218-221° C.

Example 218

N-(2-{5-[(4-acetylpiperazin-1-yl)methyl]-4,5-dihydro-1,3-thiazol-2-yl}-1H-indol-7-yl)-N-methylthiophene-2-sulfonamide

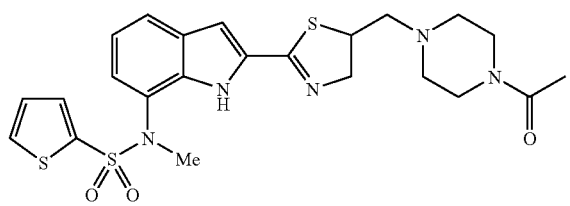

In the same manners as in Example 202 and Example 203, the title compound (0.026 g, yield 11% in two steps) was obtained as colorless crystals from tert-butyl 4-{2-(benzylthio)-3-[({7-[methyl(2-thienylsulfonyl)amino]-1H-indol-2-yl}carbonyl)amino]propyl}piperazine-1-carboxylate (0.330 g).

melting point 177-180° C.

Example 219

N-(2-{5-[(3,3-difluoropiperidino)methyl]-4,5-dihydro-1,3-thiazol-2-yl}-1H-indol-7-yl)-N-methylthiophene-2-sulfonamide

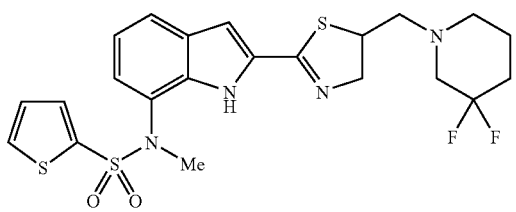

In the same manner as in Example 200, the title compound (0.013 g, yield 10%) was obtained as colorless crystals from N-[2-(benzylthio)-3-(2,2-difluoromorpholino)propyl]-7-[methyl(2-thienylsulfonyl)amino]-1H-indole-2-carboxamide (0.155 g).

melting point 205-208° C.

Example 220

N-[2-(5-cyano-4,5-dihydro-1,3-thiazol-2-yl)-1H-indol-7-yl]-N-methylthiophene-2-sulfonamide

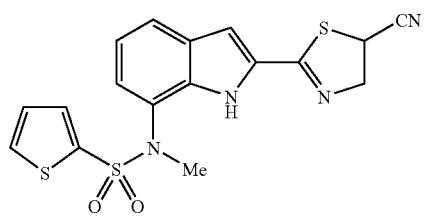

In the same manner as in Example 206, the title compound (2.32 g, 82%) was obtained as colorless crystals from N-[2-(benzylthio)-2-cyanoethyl]-7-[methyl(2-thienylsulfonyl)amino]-1H-indole-2-carboxamide (3.60 g).

melting point 188-189° C.

Example 221

2-{7-[methyl(2-thienylsulfonyl)amino]-1H-indol-2-yl}-4,5-dihydro-1,3-thiazole-5-carboxylic acid

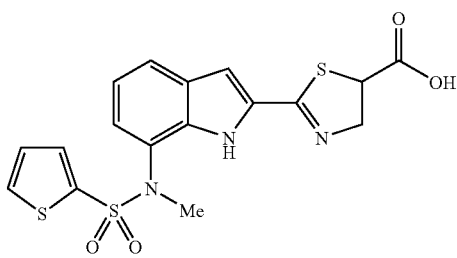

In the same manner as in Example 207, the title compound (0.259 g, 88%) was obtained as colorless crystals from N-[2-(5-cyano-4,5-dihydro-1,3-thiazol-2-yl)-1H-indol-7-yl]-N-methylthiophene-2-sulfonamide (0.280 g).

melting point 235-238° C.

Example 222

N-{2-[5-(aminomethyl)-4,5-dihydro-1,3-thiazol-2-yl]-1H-indol-7-yl}-N-methylthiophene-2-sulfonamide

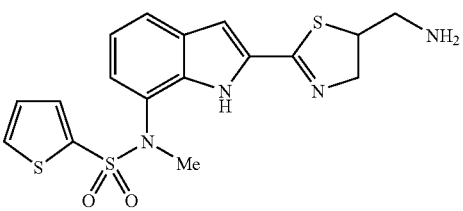

To a suspension of lithium aluminum hydride (0.015 g) in tetrahydrofuran (2 ml) was added dropwise a solution of N-[2-(5-cyano-4,5-dihydro-1,3-thiazol-2-yl)-1H-indol-7-yl]-N-methylthiophene-2-sulfonamide (0.080 g) in tetrahydrofuran (3 ml) under ice-cooling, and the reaction mixture was stirred at 0° C. for 2 hr. 1N Aqueous sodium hydroxide solution was added to the reaction mixture, and the mixture was extracted with ethyl acetate. The extract was washed with saturated brine, dried over anhydrous magnesium sulfate, and concentrated under reduced pressure. The residue was purified by basic silica gel column chromatography (ethyl acetate:hexane=80:20-100:0), and recrystallized from hexane-ethyl acetate to give the title compound (0.029 g, yield 36%) as colorless crystals.

melting point 185-187° C.

Example 223

2-{7-[methyl(2-thienylsulfonyl)amino]-1H-indol-2-yl}-4,5-dihydro-1,3-thiazole-5-carboxamide

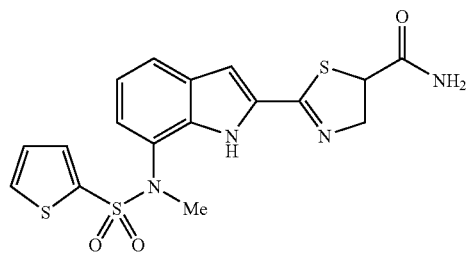

To a solution of 2-{7-[methyl(2-thienylsulfonyl)amino]-1H-indol-2-yl}-4,5-dihydro-1,3-thiazole-5-carboxylic acid (0.090 g) in N,N-dimethylformamide (6 ml) were added 1H-1,2,3-benzotriazol-1-ol (0.034 g) and N-[3-(dimethylamino)propyl]-N'-ethylcarbodiimide hydrochloride (0.049 g), and the mixture was stirred at 50° C. for 45 min. 28% Aqueous ammonia (2 ml) was added to the reaction, and the mixture was stirred at room temperature for 15 hr. Water was added to the reaction mixture, and the mixture was extracted with ethyl acetate. The extract was washed with water and saturated brine, dried over anhydrous magnesium sulfate, and concentrated under reduced pressure. The residue was purified by basic silica gel column chromatography (ethyl acetate:methanol=100:0-90:10), and recrystallized from hexane-ethyl acetate to give the title compound (0.010 g, yield 11%) as colorless crystals.

melting point 230-232° C.

Example 224

N-methyl-N-{2-[5-(pyrrolidin-1-ylcarbonyl)-4,5-dihydro-1,3-thiazol-2-yl]-1H-indol-7-yl}thiophene-2-sulfonamide

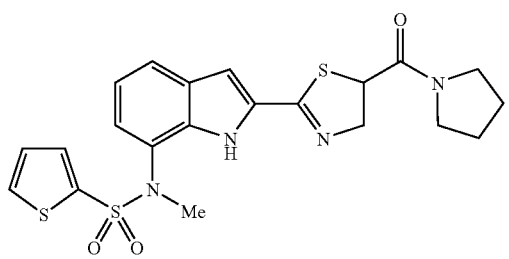

In the same manner as in Example 223, the title compound (0.034 g, yield 47%) was obtained as colorless crystals from 2-{7-[methyl(2-thienylsulfonyl)amino]-1H-indol-2-yl}-4,5-dihydro-1,3-thiazole-5-carboxylic acid (0.065 g) and pyrrolidine (0.025 ml).

melting point 202-204° C.

Example 225 methyl 2-{7-[methyl(2-thienylsulfonyl)amino]-1H-indol-2-yl}-4,5-dihydro-1,3-thiazole-5-carboxylate

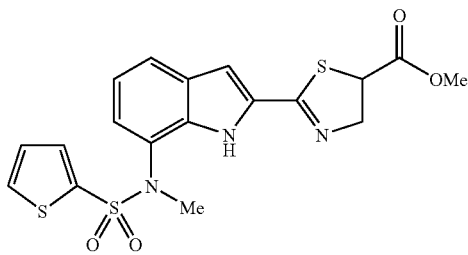

To a solution of 2-{7-[methyl(2-thienylsulfonyl)amino]-1H-indol-2-yl}-4,5-dihydro-1,3-thiazole-5-carboxylic acid (1.48 g) in N,N-dimethylformamide (30 ml) were added 1H-1,2,3-benzotriazol-1-ol (0.716 g), N-[3-(dimethylamino)propyl]-N'-ethylcarbodiimide hydrochloride (1.02 g), N,N-dimethyl-4-aminopyridine (0.043 g) and methanol (0.215 ml), and the mixture was stirred at room temperature for 3 days. 10% Aqueous citric acid solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=50:50-100:0), and recrystallized from hexane-ethyl acetate to give the title compound (1.00 g, yield 65%) as colorless crystals.

melting point 175-176° C.

Example 226

N-{2-[5-(1-hydroxy-1-methylethyl)-4,5-dihydro-1,3-thiazol-2-yl]-1H-indol-7-yl}-N-methylthiophene-2-sulfonamide

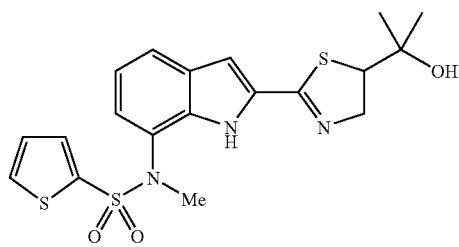

To a solution of methyl 2-{7-[methyl(2-thienylsulfonyl)amino]-1H-indol-2-yl}-4,5-dihydro-1,3-thiazole-5-carboxylate (0.181 g) in tetrahydrofuran (10 ml) was added 1.0 mol/L methylmagnesium bromide (1.04 ml), and the mixture was stirred at 50° C. for 5 hr. Saturated aqueous sodium chloride solution was added to the reaction solution, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=20:80-80:20), and recrystallized from hexane-ethyl acetate to give the title compound (0.054 g, yield 30%) as pale-yellow crystals.

melting point 174-175° C.

Example 227

N-{2-[5-(hydroxymethyl)-4,5-dihydro-1,3-thiazol-2-yl]-1H-indol-7-yl}-N-methylthiophene-2-sulfonamide

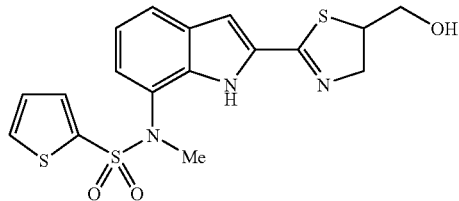

To a solution of methyl 2-{7-[methyl(2-thienylsulfonyl)amino]-1H-indol-2-yl}-4,5-dihydro-1,3-thiazole-5-carboxylate (0.126 g) in tetrahydrofuran (5 ml) were successively added lithium borohydride (0.035 g) and methanol (1 ml), and the mixture was stirred at room temperature for 2 hr. Saturated aqueous sodium chloride solution was added to the reaction solution, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=20:80-100:0), and recrystallized from hexane-ethyl acetate to give the title compound (0.105 g, yield 89%) as colorless crystals.

melting point 207-208° C.

Example 228

N-methyl-N-(2-{5-[(4-oxohexahydropyrazino[2,1-c][1,4]oxazin-8(1H)-yl)methyl]-1,3-thiazol-2-yl}-1H-indol-7-yl)thiophene-2-sulfonamide

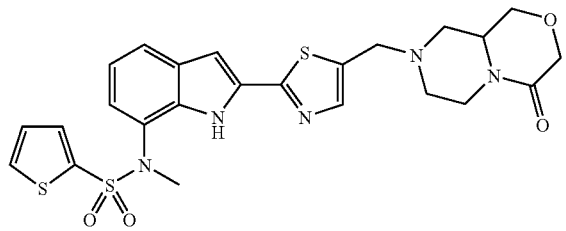

A mixture of N-{2-[5-(chloromethyl)-1,3-thiazol-2-yl]-1H-indol-7-yl}-N-methylthiophene-2-sulfonamide (150 mg), triethylamine (150 μL), hexahydropyrazino[2,1-c][1,4]oxazin-4(3H)-one hydrochloride (135 mg) and N,N-dimethylformamide (2 ml) was stirred at room temperature for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (85 mg, yield 45%) as a colorless amorphous form from a fraction eluted with ethyl acetate. MS 544 (M+1).

Example 229

N-methyl-N-(2-{5-[(3-oxotetrahydro[1,3]oxazolo[3,4-a]pyrazin-7(1H)-yl)methyl]-1,3-thiazol-2-yl}-1H-indol-7-yl)thiophene-2-sulfonamide

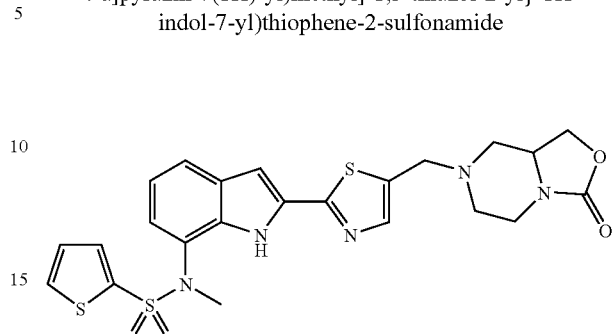

A mixture of N-{2-[5-(chloromethyl)-1,3-thiazol-2-yl]-1H-indol-7-yl}-N-methylthiophene-2-sulfonamide (150 mg), triethylamine (150 μL), hexahydro[1,3]oxazolo[3,4-a]pyrazin-3-one hydrochloride (125 mg) and N,N-dimethylformamide (2 ml) was stirred at room temperature for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (103 mg, yield 56%) as a colorless amorphous form from a fraction eluted with ethyl acetate. MS 530 (M+1).

Example 230

N-methyl-N-(2-{5-[(2-oxo-1-oxa-3,8-diazaspiro[4.5]dec-8-yl)methyl]-1,3-thiazol-2-yl}-1H-indol-7-yl)thiophene-2-sulfonamide

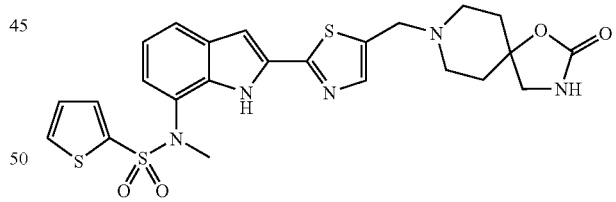

A mixture of N-{2-[5-(chloromethyl)-1,3-thiazol-2-yl]-1H-indol-7-yl}-N-methylthiophene-2-sulfonamide (150 mg), triethylamine (150 μL), 1-oxa-3,8-diazaspiro[4.5]decan-2-one (110 mg) and N,N-dimethylformamide (2 ml) was stirred at room temperature for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (82 mg, yield 43%) as colorless crystals from a fraction eluted with ethyl acetate. melting point 224° C.

Example 231

N-(2-{5-[(4-acetylpiperazin-1-yl)methyl]-1,3-thia-zol-2-yl}-1H-indol-7-yl)-N-(cyclopropylmethyl)thiophene-2-sulfonamide

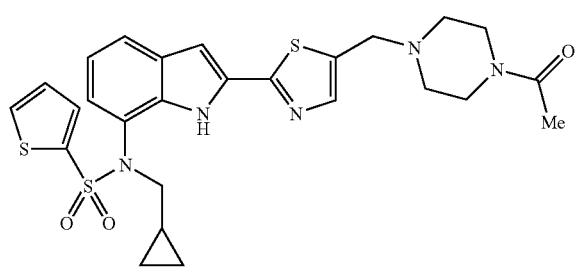

A mixture of N-{2-[5-(chloromethyl)-1,3-thiazol-2-yl]-1H-indol-7-yl}-N-(cyclopropylmethyl)thiophene-2-sulfonamide (100 mg), triethylamine (60 μL), 1-acetylpiperazine (55 mg) and N,N-dimethylformamide (3 ml) was stirred at room temperature for 16 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (91 mg, yield 76%) as colorless crystals from a fraction eluted with ethyl acetate. MS 556 (M+1).

Example 232

N-(2-{5-[(4-acetylpiperazin-1-yl)methyl]-1,3-thia-zol-2-yl}-1H-indol-7-yl)-N-ethylthiophene-2-sul-fonamide

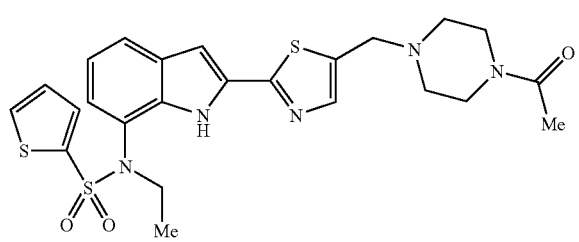

In the same manner as in Example 186, the title compound (180 mg, yield 50%) was obtained as colorless crystals from N-{2-[5-(chloromethyl)-1,3-thiazol-2-yl]-1H-indol-7-yl}-N-ethylthiophene-2-sulfonamide (300 mg) and 1-acetylpiperazine (176 mg). MS 530 (M+1).

Example 233

N-(2-{5-[(4-acetylpiperazin-1-yl)methyl]-1,3-thia-zol-2-yl}-1H-indol-7-yl)-N-(ethoxyethyl)thiophene-2-sulfonamide

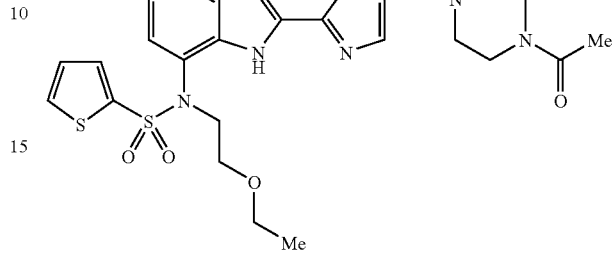

In the same manner as in Example 186, the title compound (48 mg, yield 50%) was obtained as colorless crystals from N-{2-[5-(chloromethyl)-1,3-thiazol-2-yl]-1H-indol-7-yl}-N-(ethoxyethyl)thiophene-2-sulfonamide (82 mg) and 1-acetylpiperazine (176 mg). MS 574 (M+1).

Example 234

N-methyl-N-(2-{5-[(2-oxopyrrolidin-1-yl)methyl]-1,3-thiazol-2-yl}-1H-indol-7-yl)thiophene-2-sulfona-mide

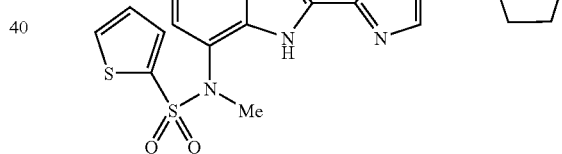

A mixture of N-{2-[5-(chloromethyl)-1,3-thiazol-2-yl]-1H-indol-7-yl}-N-methylthiophene-2-sulfonamide (424 mg), triethylamine (693 μL), ethyl 4-aminobutanoate dihydrochloride (335 mg) and N,N-dimethylformamide (5 ml) was stirred at room temperature for 16 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give ethyl 4-{[(2-{7-[methyl(2-thienylsulfonyl)amino]-1H-indol-2-yl}-1,3-thiazol-5-yl)methyl]amino}butanoate as a crude product from a fraction eluted with ethyl acetate. A mixture of this product, methanol (2 ml), 1N aqueous sodium hydroxide solution (4 ml) and tetrahydrofuran (4 ml) was stirred at 45° C. for 20 hr. The mixture was neutralized with 1N aqueous hydrochloric acid solution, water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (49 mg, yield 10%) as colorless crystals from a fraction eluted with ethyl acetate. MS 473 (M+1).

Example 235

N-ethyl-N-(2-{5-[(3-oxopiperazin-1-yl)methyl]-1,3-thiazol-2-yl}-1H-indol-7-yl)thiophene-2-sulfonamide

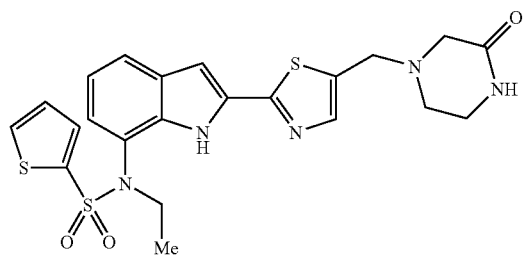

In the same manner as in Example 186, the title compound (176 mg, yield 52%) was obtained as colorless crystals from N-{2-[5-(chloromethyl)-1,3-thiazol-2-yl]-1H-indol-7-yl}-N-ethylthiophene-2-sulfonamide (300 mg) and piperazin-2-one (137 mg). MS 502 (M+1).

Example 236

N-{2-[5-(5,6-dihydro[1,2,4]triazolo[4,3-a]pyrazin-7(8H)-ylmethyl)-1,3-thiazol-2-yl]-1H-indol-7-yl}-N-ethylthiophene-2-sulfonamide

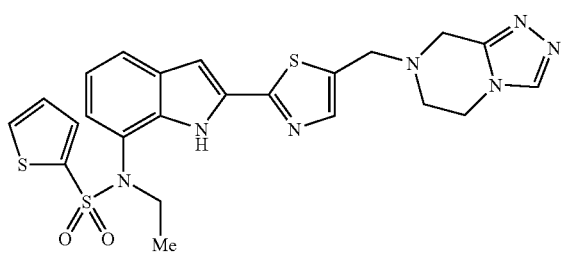

In the same manner as in Example 228, the title compound (280 mg, yield 53%) was obtained as colorless crystals from 5,6,7,8-tetrahydro[1,2,4]triazolo[4,3-a]pyrazine monohydrochloride (360 mg) prepared according to J. Med. Chem. 2005, 48, 141-151 and N-{2-[5-(chloromethyl)-1,3-thiazol-2-yl]-1H-indol-7-yl}-N-ethylthiophene-2-sulfonamide (438 mg). MS 526 (M+1).

Example 237

N-ethyl-N-(2-{5-[(4-methyl-3-oxopiperazin-1-yl)methyl]-1,3-thiazol-2-yl}-1H-indol-7-yl)thiophene-2-sulfonamide

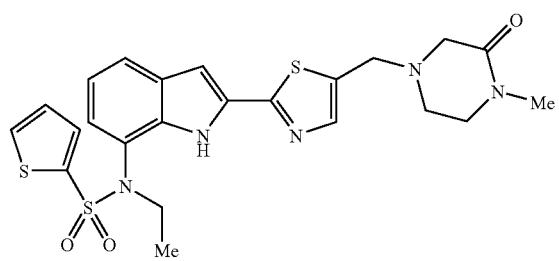

In the same manner as in Example 186, the title compound (280 mg, yield 80%) was obtained as colorless crystals from N-{2-[5-(chloromethyl)-1,3-thiazol-2-yl]-1H-indol-7-yl}-N-ethylthiophene-2-sulfonamide (300 mg) and 1-methylpiperazin-2-one (300 mg). MS 516 (M+1).

Example 238

N-ethyl-N-[2-(5-{[3-(trifluoromethyl)-5,6-dihydro[1,2,4]triazolo[4,3-a]pyrazin-7(8H)-yl]methyl}-1,3-thiazol-2-yl)-1H-indol-7-yl]thiophene-2-sulfonamide

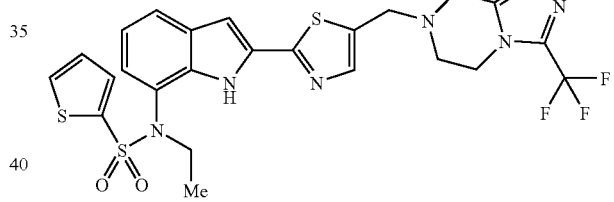

In the same manner as in Example 228, the title compound (220 mg, yield 54%) was obtained as colorless crystals from 3-(trifluoromethyl)-5,6,7,8-tetrahydro[1,2,4]triazolo[4,3-a]pyrazine monohydrochloride (300 mg) prepared according to J. Med. Chem. 2005, 48, 141-151 and N-{2-[5-(chloromethyl)-1,3-thiazol-2-yl]-1H-indol-7-yl}-N-ethylthiophene-2-sulfonamide (280 mg). MS 594 (M+1).

Example 239

N-ethyl-N-(2-{5-[(3-methyl-5,6-dihydro[1,2,4]triazolo[4,3-a]pyrazin-7(8H)-yl)methyl]-1,3-thiazol-2-yl}-1H-indol-7-yl)thiophene-2-sulfonamide

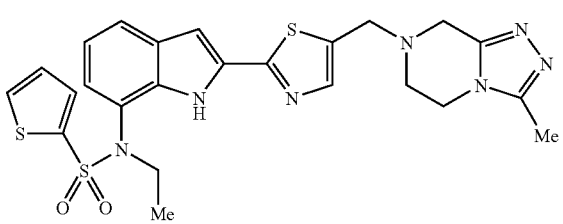

A mixture of 3-methyl[1,2,4]triazolo[4,3-a]pyrazine (81 mg) prepared according to Heterocycles, 1989, 28, 239-248, methanol (10 ml) and 10% palladium carbon (30 mg) was stirred for 3 days under hydrogen atmosphere. The mixture was filtrated through celite, and the filtrate was concentrated to give an oil. In the same manner as in Example 186, the title compound (31 mg, yield 7%) was obtained as colorless crystals from this oil and N-{2-[5-(chloromethyl)-1,3-thiazol-2-yl]-1H-indol-7-yl}-N-ethylthiophene-2-sulfonamide (300 mg). MS 540 (M+1).

Example 240

N-{2-[5-(5,6-dihydro[1,2,4]triazolo[4,3-a]pyrazin-7(8H)-ylmethyl)-1,3-thiazol-2-yl]-1H-indol-7-yl}-N-methylthiophene-2-sulfonamide

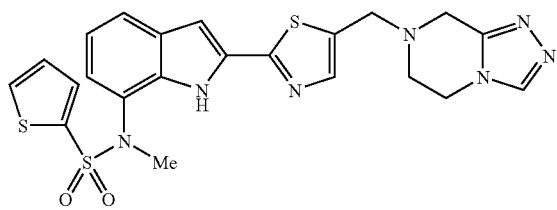

In the same manner as in Example 228, the title compound (49 mg, yield 21%) was obtained as colorless crystals from 5,6,7,8-tetrahydro[1,2,4]triazolo[4,3-a]pyrazine monohydrochloride (240 mg) prepared according to J. Med. Chem. 2005, 48, 141-151 and N-{2-[5-(chloromethyl)-1,3-thiazol-2-yl]-1H-indol-7-yl}-N-methylthiophene-2-sulfonamide (200 mg). MS 512 (M+1).

Example 241

N-methyl-N-(2-{5-[(4-methyl-3-oxopiperazin-1-yl)methyl]-1,3-thiazol-2-yl}-1H-indol-7-yl)thiophene-2-sulfonamide

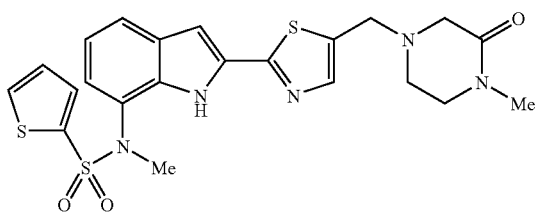

In the same manner as in Example 186, the title compound (50 mg, yield 21%) was obtained as colorless crystals from N-{2-[5-(chloromethyl)-1,3-thiazol-2-yl]-1H-indol-7-yl}-N-methylthiophene-2-sulfonamide (200 mg) and 1-methylpiperazin-2-one (200 mg). MS 502 (M+1).

Example 242

N-methyl-N-(2-{5-[(3-methyl-5,6-dihydro[1,2,4]triazolo[4,3-a]pyrazin-7(8H)-yl)methyl]-1,3-thiazol-2-yl}-1H-indol-7-yl)thiophene-2-sulfonamide

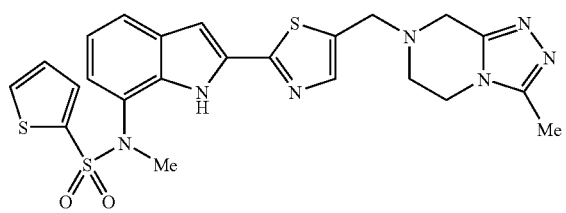

A mixture of 3-methyl[1,2,4]triazolo[4,3-a]pyrazine (81 mg) prepared according to Heterocycles, 1989, 28, 239-248, methanol (10 ml) and 10% palladium carbon (30 mg) was stirred for 3 days under hydrogen atmosphere. The mixture was filtrated through celite, and the filtrate was concentrated to give an oil. In the same manner as in Example 186, the title compound (50 mg, yield 19%) was obtained as colorless crystals from this oil and N-{2-[5-(chloromethyl)-1,3-thiazol-2-yl]-1H-indol-7-yl}-N-methylthiophene-2-sulfonamide (216 mg). MS 526 (M+1).

Example 243

N-methyl-N-[2-(8-oxa-1-thia-3-azaspiro[4.5]dec-2-en-2-yl)-1H-indol-7-yl]thiophene-2-sulfonamide

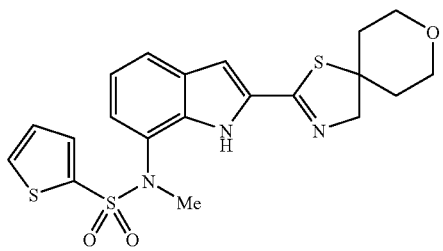

To a solution of triphenylphosphine oxide (1.15 g) in acetonitrile (20 ml) was slowly added trifluoromethanesulfonic anhydride (0.35 ml) at 0° C., and the mixture was stirred for 10 min. N-{[4-(Benzylthio)tetrahydro-2H-pyran-4-yl]methyl}-7-[methyl(2-thienylsulfonyl)amino]-1H-indole-2-carboxamide (0.76 g) was added, and the reaction mixture was stirred at 10° C. for 1 hr. Saturated aqueous sodium hydrogencarbonate was added, and the mixture was extracted with ethyl acetate. The ethyl acetate layer was washed with saturated brine, dried (MgSO$_4$), and concentrated. The residue was subjected to silica gel column chromatography to give the title compound (0.22 g, yield 36%) as colorless crystals from a fraction eluted with ethyl acetate-hexane (1:1, volume ratio). melting point 189-191° C.

Example 244

N-methyl-N-[2-(1-thia-3,8-diazaspiro[4.5]dec-2-en-2-yl)-1H-indol-7-yl]thiophene-2-sulfonamide hydrochloride

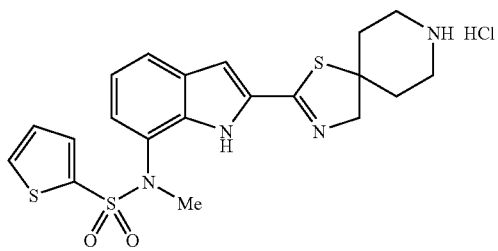

In the same manner as in Example 243, N-methyl-N-[2-(1-thia-3,8-diazaspiro[4.5]dec-2-en-2-yl)-1H-indol-7-yl]thiophene-2-sulfonamide (515 mg, 63%) was obtained as colorless crystals from tert-butyl 4-(benzylthio)-4-{[({7-[methyl(2-thienylsulfonyl)amino]-1H-indol-2-yl}carbonyl)amino]methyl}piperidine-1-carboxylate (1.20 g).

To a mixture of the obtained crystals (100 mg) and methanol (5 ml) was added 10% hydrogen chloride-methanol solution (0.5 ml) at 0° C. The reaction solution was concentrated, and the resulting crystals were washed with methanol, and dried to give the title compound (53 mg, yield 50%) as yellow crystals. melting point 248-250° C. (decomposition).

Example 245

N-[2-(8-acetyl-1-thia-3,8-diazaspiro[4.5]dec-2-en-2-yl)-1H-indol-7-yl]-N-methylthiophene-2-sulfonamide

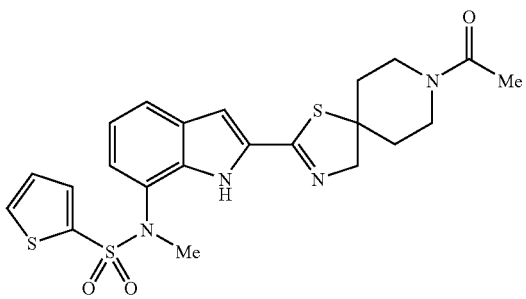

To a solution of N-methyl-N-[2-(1-thia-3,8-diazaspiro[4.5]dec-2-en-2-yl)-1H-indol-7-yl]thiophene-2-sulfonamide (100 mg), pyridine (0.022 ml), tetrahydrofuran (2 ml) and acetonitrile (1 ml) was slowly added acetic anhydride (0.022 ml) at 0° C., and the mixture was stirred for 1 hr. Water was added to the reaction mixture, and the mixture was extracted with ethyl acetate. The ethyl acetate layer was washed successively with 1N hydrochloric acid, saturated aqueous sodium hydrogencarbonate and saturated brine, dried ($Na_2SO_4$), and concentrated. The obtained crystals were recrystallized from tetrahydrofuran-heptane to give the title compound (88 mg, yield 82%) as colorless crystals. melting point 216-218° C.

Example 246

N,N-dimethyl-2-{7-[methyl(2-thienylsulfonyl)amino]-1H-indol-2-yl}-1-thia-3,8-diazaspiro[4.5]dec-2-ene-8-carboxamide

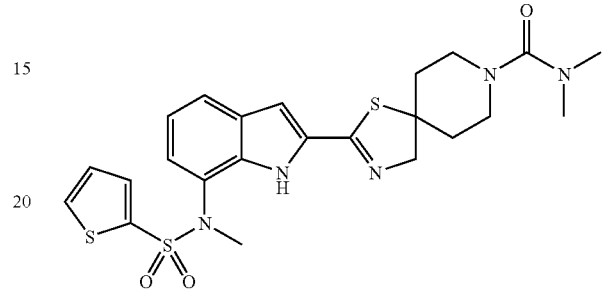

To a solution of N-methyl-N-[2-(1-thia-3,8-diazaspiro[4.5]dec-2-en-2-yl)-1H-indol-7-yl]thiophene-2-sulfonamide (82 mg) and dimethylcarbamoyl chloride (100 μL) in tetrahydrofuran (3 ml) was added triethylamine (100 μL), and the mixture was stirred at room temperature for 30 min. Water was added to the reaction mixture, and the mixture was extracted with ethyl acetate. The ethyl acetate layer was washed with saturated brine, dried ($MgSO_4$), and concentrated. The obtained residue was subjected to silica gel column chromatography to give the title compound (43 mg, yield 46%) as colorless crystals from a fraction eluted with ethyl acetate. melting point 245° C.

Example 247

N-methyl-N-(2-{8-[(1-methyl-1H-imidazol-2-yl)methyl]-1-thia-3,8-diazaspiro[4.5]dec-2-en-2-yl}-1H-indol-7-yl)thiophene-2-sulfonamide

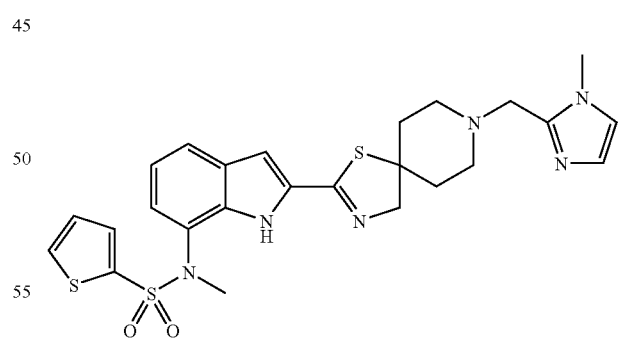

To a solution of N-methyl-N-[2-(1-thia-3,8-diazaspiro[4.5]dec-2-en-2-yl)-1H-indol-7-yl]thiophene-2-sulfonamide (100 mg) and 1-methyl-1H-imidazole-2-carbaldehyde (33 mg) in tetrahydrofuran (3 ml) was added sodium triacetoxyborohydride (125 mg), and the mixture was stirred at room temperature for 18 hr. Water was added to the reaction mixture, and the mixture was extracted with ethyl acetate. The ethyl acetate layer was washed with saturated brine, dried ($MgSO_4$), and concentrated. The obtained residue was subjected to silica gel column chromatography to give the title compound (14 mg, yield 12%) as colorless crystals from a fraction eluted with ethyl acetate. melting point 103° C.

Example 248

N-methyl-N-{2-[8-(methylsulfonyl)-1-thia-3,8-diazaspiro[4.5]dec-2-en-2-yl]-1H-indol-7-yl}thiophene-2-sulfonamide

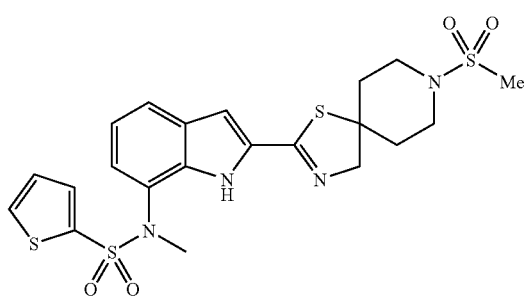

To a solution of N-methyl-N-[2-(1-thia-3,8-diazaspiro[4.5]dec-2-en-2-yl)-1H-indol-7-yl]thiophene-2-sulfonamide (82 mg) and methanesulfonyl chloride (100 μL) in tetrahydrofuran (3 ml) was added triethylamine (100 μL), and the mixture was stirred at room temperature for 30 min. The reaction mixture was concentrated, and water was added. The precipitated crystals were collected by filtration, and washed with water. The obtained crystals were recrystallized from tetrahydrofuran to give the title compound (42 mg, yield 36%) as colorless crystals. melting point 251° C.

Example 249

N-[2-(8-ethyl-1-thia-3,8-diazaspiro[4.5]dec-2-en-2-yl)-1H-indol-7-yl]-N-methylthiophene-2-sulfonamide

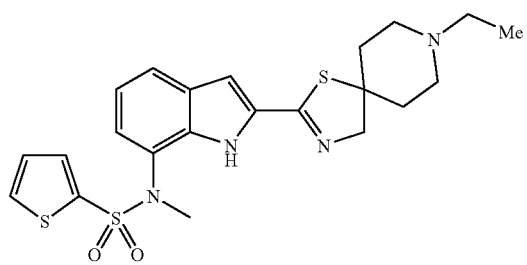

To a solution of N-methyl-N-[2-(1-thia-3,8-diazaspiro[4.5]dec-2-en-2-yl)-1H-indol-7-yl]thiophene-2-sulfonamide (100 mg) and acetaldehyde (90%) (100 μL) in tetrahydrofuran (3 ml) was added sodium triacetoxyborohydride (125 mg), and the mixture was stirred at room temperature for 30 min. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (83 mg, yield 80%) as colorless crystals from a fraction eluted with ethyl acetate. melting point 215° C.

Example 250

N-(2-{5-[(4-acetylpiperazin-1-yl)methyl]-1,3-thiazol-2-yl}-4-methyl-1H-indol-7-yl)-N-methylthiophene-2-sulfonamide

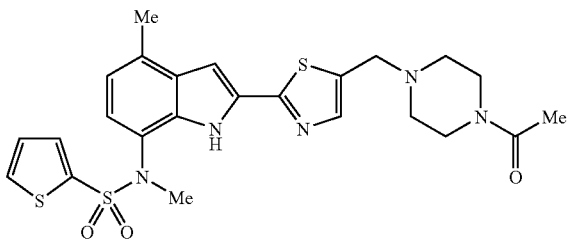

To a solution of N-{2-[5-(chloromethyl)-1,3-thiazol-2-yl]-4-methyl-1H-indol-7-yl}-N-methylthiophene-2-sulfonamide (0.15 g) and N-acetylpiperazine (90 mg) in N,N-dimethylformamide (10 ml) was added potassium carbonate (120 mg) under ice-cooling, and the mixture was stirred at room temperature for 18 hr. The reaction solution was poured into water, and the mixture was extracted with ethyl acetate. The extract was washed with water and brine, dried over anhydrous magnesium sulfate, and concentrated under reduced pressure. The obtained residue was subjected to silica gel column chromatography (ethyl acetate:hexane=1:1-7:3), and the obtained pale-yellow oil was crystallized from ethyl acetate-hexane to give the title compound (95 mg, yield 52%) as colorless crystals. melting point 171-172° C.

Example 251

N-(2-{5-[(3-hydroxypyrrolidin-1-yl)methyl]-1,3-thiazol-2-yl}-4-methyl-1H-indol-7-yl)-N-methylthiophene-2-sulfonamide

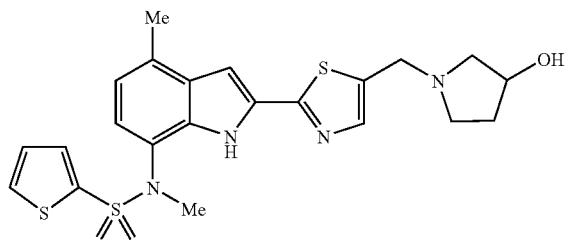

To a solution of N-{2-[5-(chloromethyl)-1,3-thiazol-2-yl]-4-methyl-1H-indol-7-yl}-N-methylthiophene-2-sulfonamide (0.13 g) and 3-pyrrolidinol (60 mg) in N,N-dimethylformamide (8 ml) was added potassium carbonate (110 mg) under ice-cooling, and the mixture was stirred at room temperature for 18 hr. The reaction solution was poured into water, and the mixture was extracted with ethyl acetate. The extract was washed with water and brine, dried over anhydrous magnesium sulfate, and concentrated under reduced pressure. The obtained residue was subjected to silica gel column chromatography (ethyl acetate:hexane=1:1-7:3), and

Example 252

N-(2-{5-[(4-acetylpiperazin-1-yl)methyl]-1,3-thiazol-2-yl}-4-methyl-1H-indol-7-yl)-N-ethylthiophene-2-sulfonamide

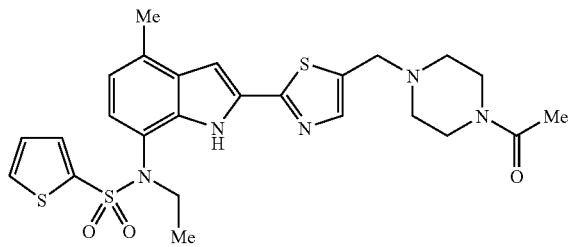

To a solution of N-methyl-N-{2-[5-(chloromethyl)-1,3-thiazol-2-yl]-4-methyl-1H-indol-7-yl}thiophene-2-sulfonamide (0.20 g) and N-acetylpiperazine (0.11 g) in N,N-dimethylformamide (10 ml) was added potassium carbonate (0.14 g) under ice-cooling, and the mixture was stirred at room temperature for 18 hr. The reaction solution was poured into water, and the mixture was extracted with ethyl acetate. The extract was washed with water and brine, dried over anhydrous magnesium sulfate, and concentrated under reduced pressure. The obtained residue was subjected to basic silica gel column chromatography (ethyl acetate:hexane=3:7-6:4), and the obtained colorless crystals was recrystallized from ethyl acetate-hexane to give the title compound (112 mg, yield 47%) as colorless crystals. melting point 157-158° C.

Reference Example 94 optically active form of N-[2-(benzylthio)-3-morpholinopropyl]-7-[methyl(2-thienylsulfonyl)amino]-1H-indole-2-carboxamide

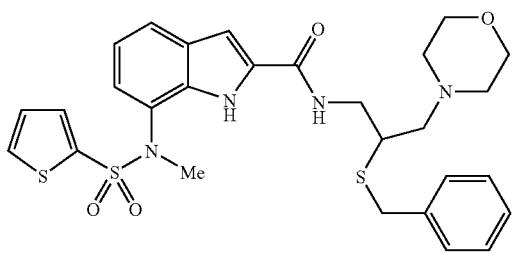

N-[2-(Benzylthio)-3-morpholinopropyl]-7-[methyl(2-thienylsulfonyl)amino]-1H-indole-2-carboxamide (2.0 g) was subjected to an optical resolution using chiral column [Column; CHIRALPAK AD 50 mmID×500 mL, Mobile phase; Hexane/EtOH=50/50, Flow rate; 60 mL/min, Temperature; 40° C., Detection; UV 220 nm, Injection; 120 mg in mobile phase (25 mL)/load] to give an optically active form (retention time: longer, 980 mg) and (retention time: shorter, 984 mg).

retention time: longer, MS m/z 585 (M+H$^+$).
retention time: shorter, MS m/z 585 (M+H$^+$).

Reference Example 95

N-[2-(benzylthio)-3-(1,4-dioxa-8-azaspiro[4.5]dec-8-yl)-2-methylpropyl]-7-[methyl(2-thienylsulfonyl)amino]-1H-indole-2-carboxamide

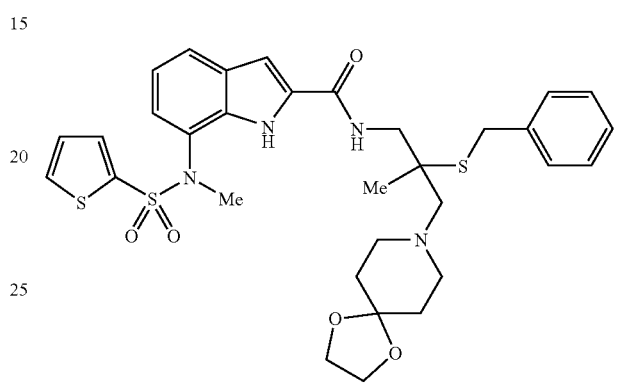

In the same manner as in Reference Example 41, the title compound (0.72 g, yield 53%) was obtained as a colorless amorphous solid from N-[2-(benzylthio)-2-methyl-3-oxopropyl]-7-[methyl(2-thienylsulfonyl)amino]-1H-indole-2-carboxamide (1.00 g) and 1,4-dioxa-8-azaspiro[4.5]decane (0.54 g).

MS: 655 (MH$^+$).

Reference Example 96

8-(benzylthio)-8-(nitromethyl)-1,4-dioxaspiro[4.5]decane

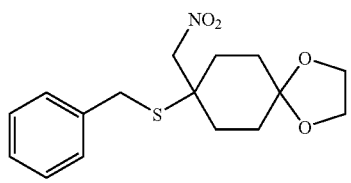

A mixture of 1,4-dioxaspiro[4.5]decan-8-one (6.00 g), benzylmercaptan (5.00 mL), nitromethane (20 mL), ethylenediamine (2.83 mL) and acetonitrile (25 mL) was heated under reflux for 3 hr. The reaction mixture was concentrated, and the obtained residue was subjected to silica gel column chromatography to give the title compound (8.96 g, yield 72%) as colorless crystals from a fraction eluted with ethyl acetate-hexane (2:3, volume ratio). melting point 121-122° C.

Reference Example 97

N-{[8-(benzylthio)-1,4-dioxaspiro[4.5]dec-8-yl]methyl}-7-[methyl(2-thienylsulfonyl)amino]-1H-indole-2-carboxamide

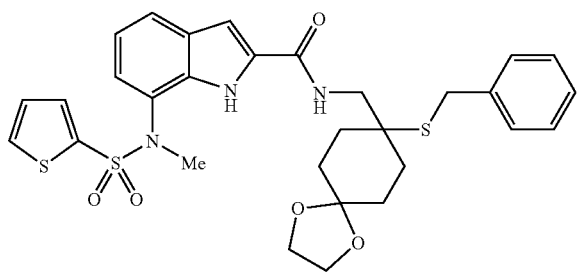

To a mixture of lithium aluminum hydride (2.63 g) and tetrahydrofuran (50 mL) was added a solution of 8-(benzylthio)-8-(nitromethyl)-1,4-dioxaspiro[4.5]decane (8.96 g) in tetrahydrofuran (80 mL) over 1 hr at room temperature, and the reaction mixture was stirred at room temperature for 30 min. Ethanol (15 mL) and water (10 mL) was successively added, and the resulting inorganic salt was removed by filtration. The filtrate was concentrated, and the residue was dissolved in ethyl acetate. The solution was dried (MgSO$_4$), and concentrated to give 1-[8-(benzylthio)-1,4-dioxaspiro[4.5]dec-8-yl]methanamine (10.02 g) as a crude oil.

To a mixture of the above-mentioned crude oil (1.30 g), 7-[methyl(2-thienylsulfonyl)amino]-1H-indole-2-carboxylic acid (1.00 g), 1H-1,2,3-benzotriazol-1-ol (0.48 g) and N,N-dimethylformamide (10 mL) was added N-[3-(dimethylamino)propyl]-N'-ethylcarbodiimide hydrochloride (0.68 g) at room temperature, and the mixture was stirred at 50° C. for 2 hr. Water was added to the reaction mixture, and the mixture was extracted with ethyl acetate. The ethyl acetate layer was washed with saturated brine, dried (MgSO$_4$), and concentrated. The residue was subjected to silica gel column chromatography to give the title compound (1.45 g, yield 80%) as colorless crystals from a fraction eluted with ethyl acetate. melting point 211-212° C.

Reference Example 98

N-{[1-(benzylthio)-4-oxocyclohexyl]methyl}-7-[methyl(2-thienylsulfonyl)amino]-1H-indole-2-carboxamide

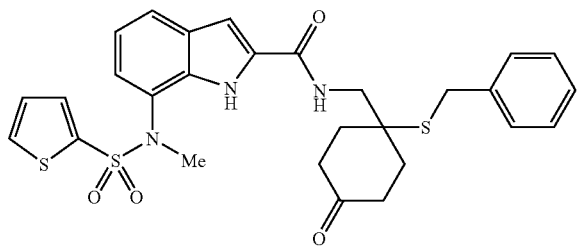

A mixture of N-{[8-(benzylthio)-1,4-dioxaspiro[4.5]dec-8-yl]methyl}-7-[methyl(2-thienylsulfonyl)amino]-1H-indole-2-carboxamide (1.21 g) and acetic acid (15 mL) was added at 80° C. for 24 hr, water was added, and the mixture was extracted with ethyl acetate. The ethyl acetate layer was washed successively with saturated aqueous sodium hydrogencarbonate and saturated brine, dried (MgSO$_4$), and concentrated. The residue was subjected to basic silica gel column chromatography to give the title compound (0.79 g, yield 71%) as a colorless amorphous solid from a fraction eluted with tetrahydrofuran-methanol (1:1, volume ratio). MS: 568 (MH$^+$).

Reference Example 99 ethyl 7-[[(2-chloropyridin-3-yl)sulfonyl](methyl)amino]-4-methyl-1H-indole-2-carboxylate

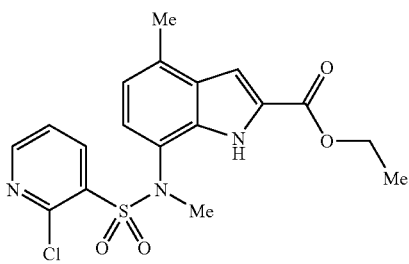

To a solution of ethyl 7-amino-4-methyl-1H-indole-2-carboxylate (1.00 g) in pyridine (10 mL) was added 2-chloropyridine-3-sulfonyl chloride (1.99 g) at 0° C., and the mixture was stirred overnight at room temperature. The reaction mixture was concentrated, 10% aqueous citric acid solution was added, and the mixture was extracted with ethyl acetate. The ethyl acetate layer was washed successively with 10% aqueous citric acid solution and saturated brine, dried (MgSO$_4$), and concentrated to give ethyl 7-{[(2-chloropyridin-3-yl)sulfonyl]amino}-4-methyl-1H-indole-2-carboxylate (1.32 g) as a crude oil.

A mixture of the above-mentioned crude oil (1.32 g), methyl iodide (0.20 mL), potassium carbonate (0.46 g) and N,N-dimethylformamide (8 mL) was stirred at room temperature for 4 hr. Water was added to the reaction mixture, and the mixture was extracted with ethyl acetate. The ethyl acetate layer was washed with saturated brine, dried (MgSO$_4$), and concentrated. The residue was subjected to basic silica gel column chromatography to give the title compound (0.86 g, yield 63%) as colorless crystals from a fraction eluted with ethyl acetate-hexane (1:2, volume ratio). melting point 158-159° C.

Reference Example 100

N-[2-(benzylthio)-3,3-dimethoxypropyl]-7-[[(2-chloropyridin-3-yl)sulfonyl](methyl)amino]-4-methyl-1H-indole-2-carboxamide

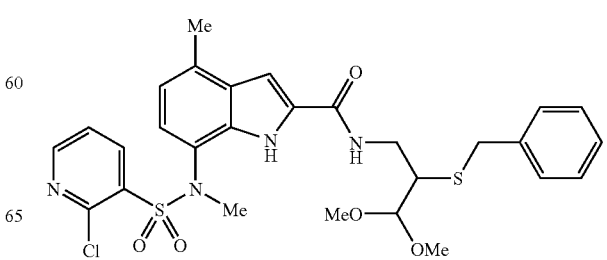

A mixture of ethyl 7-[[(2-chloropyridin-3-yl)sulfonyl](methyl)amino]-4-methyl-1H-indole-2-carboxylate (0.86 g), 1N aqueous sodium hydroxide solution (4.2 mL), methanol (6 mL) and tetrahydrofuran (6 mL) was stirred at 50° C. for 1 hr. 10% Aqueous citric acid solution was added to the reaction mixture, and the mixture was concentrated. The resulting crystals were collected by filtration, washed with water, dried, and concentrated to give 7-[[(2-chloropyridin-3-yl)sulfonyl](methyl)amino]-4-methyl-1H-indole-2-carboxylic acid as crude crystals.

To a mixture of the above-mentioned crude crystals, 2-(benzylthio)-3,3-dimethoxypropan-1-amine (0.82 g), 1H-1,2,3-benzotriazol-1-ol (0.85 g) and N,N-dimethylformamide (10 mL) was added N-[3-(dimethylamino)propyl]-N'-ethylcarbodiimide hydrochloride (1.21 g) at room temperature, and the mixture was stirred at room temperature for 2 hr. Water was added to the reaction mixture, and the mixture was extracted with ethyl acetate. The ethyl acetate layer was washed with saturated brine, dried (MgSO$_4$), and concentrated. The residue was subjected to silica gel column chromatography to give the title compound (1.07 g, yield 85%) as a pale-yellow oil from a fraction eluted with ethyl acetate-hexane (1:1, volume ratio).

$^1$H-NMR (CDCl$_3$) δ: 2.50 (3H, s), 2.94 (1H, q, J=5.6 Hz), 3.40 (3H, s), 3.47 (3H, s), 3.50-3.62 (4H, m), 3.80-3.92 (3H, m), 4.36 (1H, d, J=4.8 Hz), 6.66-6.78 (4H, m), 7.14-7.37 (6H, m), 8.04 (1H, dd, J=2.1, 8.1 Hz), 8.50 (1H, dd, J=2.1, 4.8 Hz), 9.54 (1H, brs).

Reference Example 101

N-[2-(benzylthio)-3-oxopropyl]-7-[[(2-chloropyridin-3-yl)sulfonyl](methyl)amino]-4-methyl-1H-indole-2-carboxamide

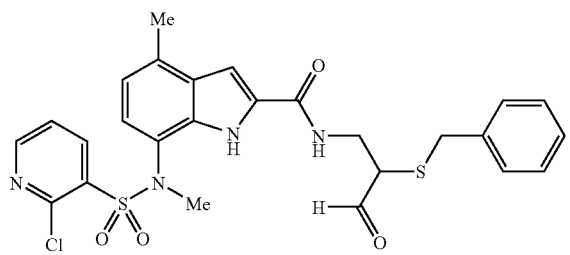

In the same manner as in Reference Example 40, the title compound (1.00 g, quantitative) was obtained as a yellow oil from N-[2-(benzylthio)-3,3-dimethoxypropyl]-7-[[(2-chloropyridin-3-yl)sulfonyl](methyl)amino]-4-methyl-1H-indole-2-carboxamide (1.07 g). MS: 557 (MH$^+$).

Reference Example 102

N-[2-(benzylthio)-3-morpholinopropyl]-7-[[(2-chloropyridin-3-yl)sulfonyl](methyl)amino]-4-methyl-1H-indole-2-carboxamide

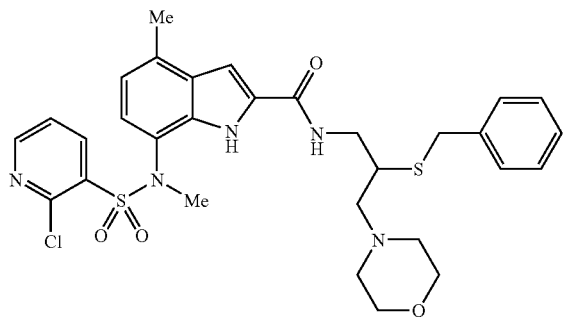

In the same manner as in Reference Example 41, the title compound (1.10 g, yield 98%) was obtained as a yellow amorphous solid from N-[2-(benzylthio)-3-oxopropyl]-7-[[(2-chloropyridin-3-yl)sulfonyl](methyl)amino]-4-methyl-1H-indole-2-carboxamide (1.00 g) and morpholine (0.31 g). MS: 628 (MH$^+$).

Reference Example 103

N-[2-(benzylthio)-3,3-dimethoxypropyl]-4-methyl-7-[methyl(2-thienylsulfonyl)amino]-1H-indole-2-carboxamide

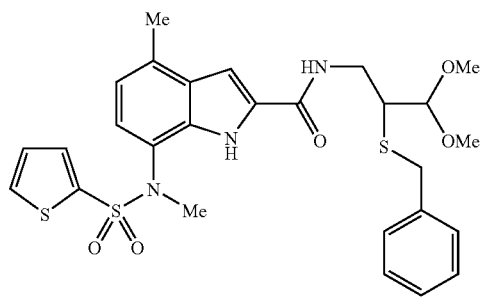

A solution of 4-methyl-7-[methyl(2-thienylsulfonyl)amino]-1H-indole-2-carboxylic acid (3.0 g), 2-(benzylthio)-3,3-dimethoxypropan-1-amine (2.4 g), N-ethyldiisopropylamine (3.7 mL) and O-(7-azabenzotriazol-1-yl)-N,N,N',N'-tetramethyluronium hexafluorophosphate (4.2 g) in N,N-dimethylformamide (40 mL) was stirred at room temperature for 8 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chroma-

Reference Example 104

N-[2-(benzylthio)-3-oxopropyl]-4-methyl-7-[methyl(2-thienylsulfonyl)amino]-1H-indole-2-carboxamide

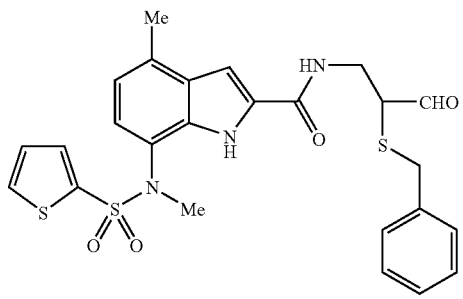

A mixture of N-[2-(benzylthio)-3,3-dimethoxypropyl]-4-methyl-7-[methyl(2-thienylsulfonyl)amino]-1H-indole-2-carboxamide (4.75 g), Amberlyst (registered trade mark) 15 ion exchange resin (1.0 g), acetone (100 mL) and water (0.4 mL) was stirred at room temperature for 20 hr. Amberlyst (registered trade mark) 15 ion exchange resin was filtered off, and washed with ethyl acetate. The filtrate was concentrated under reduced pressure, and the obtained residue was subjected to silica gel column chromatography (ethyl acetate:hexane=2:3-3:2) to give the title compound (4.4 g, yield: 100%) as a colorless amorphous solid. MS: 528 (MH⁺).

Reference Example 105

N-[2-(benzylthio)-3-morpholinopropyl]-4-methyl-7-[methyl(2-thienylsulfonyl)amino]-1H-indole-2-carboxamide

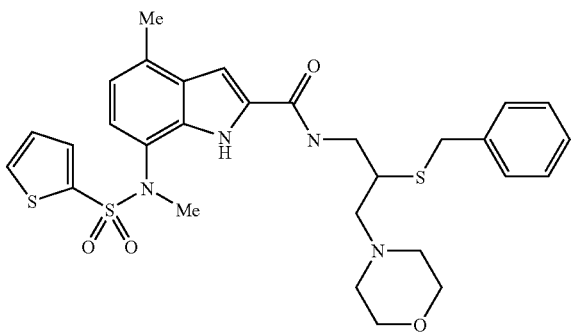

In the same manner as in Reference Example 41, the title compound (1.01 g, yield 85%) was obtained as a colorless amorphous solid from N-[2-(benzylthio)-3-oxopropyl]-4-methyl-7-[methyl(2-thienylsulfonyl)amino]-1H-indole-2-carboxamide (1.05 g) and morpholine (0.35 g). MS: 599 (MH⁺).

Reference Example 106

N-[2-(benzylthio)-2-cyanoethyl]-4-methyl-7-[methyl(2-thienylsulfonyl)amino]-1H-indole-2-carboxamide

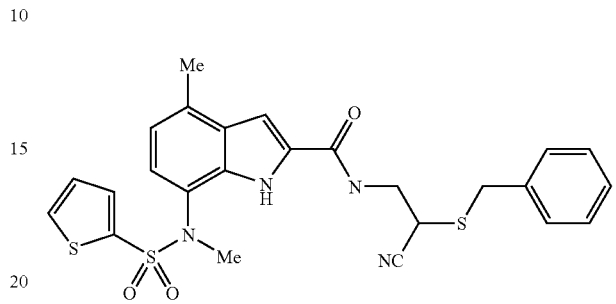

In the same manner as in Reference Example 43, N-[2-(Benzylthio)-3-(hydroxyimino)propyl]-4-methyl-7-[methyl(2-thienylsulfonyl)amino]-1H-indole-2-carboxamide (1.20 g) was obtained as a colorless amorphous solid from N-[2-(benzylthio)-3-oxopropyl]-4-methyl-7-[methyl(2-thienylsulfonyl)amino]-1H-indole-2-carboxamide (1.78 g). In the same manner as in Reference Example 44, the title compound (1.10 g, yield 95%) was obtained as a yellow amorphous solid from the amorphous solid (1.20 g). MS: 525 (MH⁺).

Reference Example 107

7-[methyl(pyridin-3-ylsulfonyl)amino]-1H-indole-2-carboxylic acid

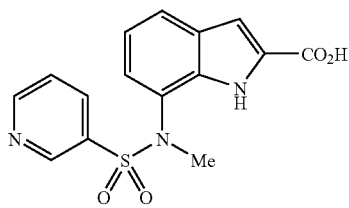

A mixture of pyridine-3-sulfonyl chloride (10.0 g), ethyl 7-amino-1-(methoxymethyl)-1H-indole-2-carboxylate (10.0 g) and pyridine (30 mL) was stirred at 50° C. for 2 hr. The reaction mixture was concentrated, and the residue was diluted with ethyl acetate (500 mL) and 1N hydrochloric acid (500 mL). The organic layer was washed with saturated aqueous sodium hydrogencarbonate solution and saturated brine, dried over sodium sulfate, and filtrated, and the filtrate was concentrated. The residue was purified by silica gel column chromatography (ethyl acetate-hexane=3:7, volume ratio) to give a pale-yellow solid. The obtained solid was dissolved in N,N-dimethylformamide (100 mL), and potassium carbonate (11.6 g) and methyl iodide (8.0 g) were added. The reaction mixture was stirred at room temperature for 1 hr, and diluted with ethyl acetate (500 mL) and saturated brine (500 mL). The organic layer was washed with saturated brine, dried over sodium sulfate, and filtrated, and the filtrate was concentrated. The obtained residue was dissolved in a mixture of 6N hydrochloric acid (80 mL), tetrahydrofuran (100 mL) and ethanol (100 mL), and the mixture was stirred at 100° C. for 3 hr, and diluted with ethyl acetate (500 mL) and saturated brine (500 mL). The organic layer was dried over sodium sulfate, and filtrated, and the filtrate was concentrated. The residue was dissolved in a mixture of 2N aqueous sodium hydroxide solution (100 mL), tetrahydrofuran (100 mL) and ethanol (100 mL), and the mixture was stirred at 80° C. for 1 hr, and diluted with ethyl acetate (500 mL) and 1N hydrochloric acid (500 mL). The organic layer was washed with saturated brine, dried over sodium sulfate, and filtrated, and the filtrate was concentrated. The obtained crude solid was washed with ethyl acetate and hexane to give the title compound (4.92 g, yield 37%) as a pale-yellow solid. LC-MS: 332 (MH+).

Reference Example 108

N-[2-(benzylthio)-3-morpholinopropyl]-7-[methyl(pyridin-3-ylsulfonyl)amino]-1H-indole-2-carboxamide

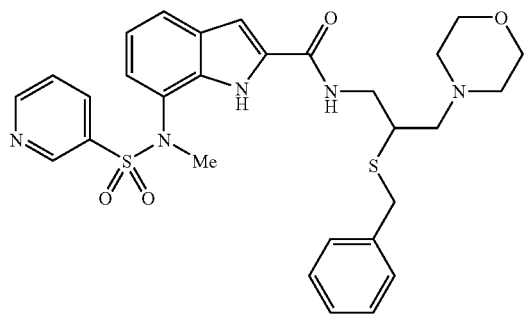

A mixture of 7-[methyl(pyridin-3-ylsulfonyl)amino]-1H-indole-2-carboxylic acid (658 mg), 2-(benzylthio)-3,3-dimethoxypropan-1-amine (576 mg), O-(7-azabenzotriazol-1-yl)-N,N,N',N'-tetramethyluronium hexafluorophosphate (1021 mg), N,N-diisopropylethylamine (0.86 mL) and N,N-dimethylformamide (10 mL) was stirred overnight at room temperature. The reaction mixture was diluted with ethyl acetate (100 mL) and 1N hydrochloric acid (100 mL). The organic layer was washed successively with saturated aqueous sodium hydrogencarbonate solution and saturated brine, dried over sodium sulfate, and filtrated, and the filtrate was concentrated. The obtained residue was purified by silica gel column chromatography (ethyl acetate:hexane=4:6, volume ratio) to give a pale-yellow solid. A mixture of this solid, Amberlyst (registered trade mark) 15 ion exchange resin (176 mg), water (88 µL) and acetone (20 mL) was stirred overnight at room temperature. The reaction mixture was filtrated, and the filtrate was concentrated. The obtained residue was purified by silica gel column chromatography (ethyl acetate:hexane=4:6, volume ratio) to give a pale-yellow oil (790 mg). A mixture of the obtained oil, morpholine (280 mg), sodium triacetoxyborohydride (1.02 g) and 1,2-dichloroethane (5 mL) was stirred at room temperature for 16 hr. The reaction mixture was diluted with ethyl acetate (100 mL) and saturated aqueous sodium hydrogencarbonate (100 mL). The organic layer was washed with saturated brine, dried over sodium sulfate, and filtrated, and the filtrate was concentrated. The obtained residue was purified by silica gel column chromatography (ethyl acetate:hexane=1:1, volume ratio) to give the title compound (410 mg, yield 39%) as a white solid. LC-MS: 580 (MH+).

Reference Example 109

7-[methyl(pyridin-3-ylsulfonyl)amino]-1H-indole-2-carbothioamide

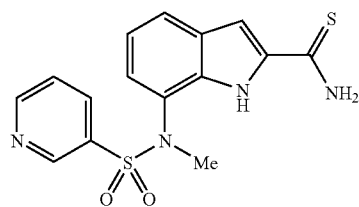

A mixture of 7-[methyl(pyridin-3-ylsulfonyl)amino]-1H-indole-2-carboxylic acid (1.99 g), 1H-1,2,3-benzotriazol-1-ol (1.22 g), N-[3-(dimethylamino)propyl]-N'-ethylcarbodiimide hydrochloride (1.73 g) and N,N-dimethylformamide (50 mL) was stirred at 60° C. for 30 min. The mixture was cooled to 0° C., 28% aqueous ammonia (912 µL) was added, and the mixture was stirred for 30 min. The reaction mixture was diluted with ethyl acetate (200 mL) and water (200 mL). The organic layer was washed with saturated brine (200 mL), dried over sodium sulfate, and filtrated, and the filtrate was concentrated. A mixture of the obtained residue (780 mg), Lawesson's reagent (573 mg) and tetrahydrofuran (10 mL) was stirred at 70° C. for 2 hr. Toluene was added to the reaction mixture, and the precipitated solid was collected by filtration to give the title compound (450 mg, yield 55%) as a pale-yellow solid.

$^1$H-NMR (DMSO-d$_6$) δ: 3.29 (3H, s), 6.59 (1H, d, J=7.2 Hz), 6.96 (1H, t, J=7.8 Hz), 7.36 (1H, d, J=2.3 Hz), 7.67 (2H, t, J=7.6 Hz), 8.01 (1H, dd, J=6.3, 2.1 Hz), 8.73 (1H, d, J=1.9 Hz), 8.91 (1H, d, J=3.0 Hz), 9.61 (1H, s), 9.80 (1H, s), 10.63 (1H, s).

Reference Example 110

1,3-thiazole-2-sulfonyl chloride

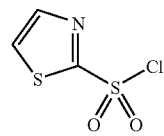

A mixture of 1,3-thiazole-2-thiol (5.0 g), acetic acid (150 mL) and water (50 mL) was cooled to 0° C., and chlorine gas was blown into the reaction mixture at less than 20° C. When the reaction temperature ceased to rise, blowing of the chlorine gas was stopped, and nitrogen gas was blown thereinto. The reaction mixture was diluted with diethyl ether (100 mL) and saturated brine (100 mL). The organic layer was washed successively with 10% aqueous sodium sulfite solution (100 mL), aqueous sodium hydrogencarbonate (300 mL) and saturated brine (300 mL), dried over sodium sulfate, and filtrated, the filtrate was concentrated to give the title compound (6.61 g, yield 84%) as a red oil.

$^1$H-NMR (CDCl$_3$) δ: 7.91 (1H, d, J=3.2 Hz), 8.14 (1H, d, J=3.2 Hz).

IR (KBr) cm$^{-1}$: 1391, 1196.

Reference Example 111

7-[methyl(1,3-thiazol-2-ylsulfonyl)amino]-1H-indole-2-carboxylic acid

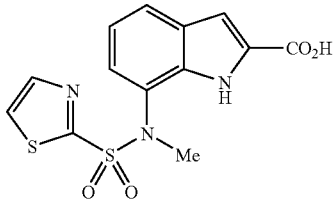

A mixture of 1,3-thiazole-2-sulfonyl chloride (2.5 g), ethyl 7-amino-1-(methoxymethyl)-1H-indole-2-carboxylate (2.47 g) and pyridine (5 mL) was stirred at room temperature for 16 hr. The reaction mixture was diluted with ethyl acetate (100 mL) and 1N hydrochloric acid (100 mL). The organic layer was washed with aqueous sodium hydrogencarbonate and saturated, dried over sodium sulfate, and filtrated, and the filtrate was concentrated. The residue was purified by silica gel column chromatography (ethyl acetate:hexane=3:7, volume ratio) to give a pale-yellow solid (2.50 g). This solid was dissolved in N,N-dimethylformamide (50 mL), potassium carbonate (2.61 g) and methyl iodide (1.79 g) were added, and the reaction mixture was stirred overnight, and diluted with ethyl acetate (200 mL) and saturated brine (200 mL). The organic layer was washed with saturated brine, dried over sodium sulfate, and filtrated, and the filtrate was concentrated to give a pale-yellow oil. The solid was dissolved in a mixture of 6N hydrochloric acid (30 mL), tetrahydrofuran (30 mL) and ethanol (30 mL), and the mixture was stirred at 100° C. for 3 hr, and diluted with ethyl acetate (100 mL) and saturated brine (100 mL). The organic layer was dried over sodium sulfate, and filtrated, and the filtrate was concentrated. The residue was dissolved in a mixture of 2N aqueous sodium hydroxide solution (36 mL), tetrahydrofuran (30 mL) and ethanol (30 mL), and the mixture was stirred at room temperature for 4 hr, and diluted with ethyl acetate (200 mL) and 1N hydrochloric acid (100 mL). The organic layer was washed with saturated brine, dried over sodium sulfate, and filtrated, and the filtrate was concentrated. The crude solid was washed with ethyl acetate and hexane to give the title compound (1.65 g, yield 80%) as a pale-yellow solid.

$^1$H-NMR (DMSO-$d_6$) δ: 3.40 (3H, s), 6.74 (1H, d, J=7.6 Hz), 6.98 (1H, t, J=7.4 Hz), 7.18 (1H, s), 8.24 (2H, s), 12.2 (1H, s), 13.1 (1H, brs).

Reference Example 112

7-[methyl(1,3-thiazol-2-ylsulfonyl)amino]-1H-indole-2-carboxamide

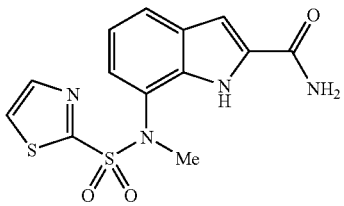

A mixture of 7-[methyl(1,3-thiazol-2-ylsulfonyl)amino]-1H-indole-2-carboxylic acid (1.65 g), 1H-1,2,3-benzotriazol-1-ol (991 mg), N-[3-(dimethylamino)propyl]-N'-ethylcarbodiimide hydrochloride (1.41 g) and N,N-dimethylformamide (10 mL) was stirred at 60° C. for 30 min. The mixture was cooled to 0° C., 28% aqueous ammonia (600 μL) was added, and the mixture was stirred overnight at room temperature. The reaction mixture was diluted with ethyl acetate (200 mL) and water (200 mL). The organic layer was washed with saturated brine (200 mL), dried over sodium sulfate, and filtrated, and the filtrate was concentrated. The obtained residue was purified by silica gel column chromatography with 50% ethyl acetate-hexane mixture as an eluate to give the title compound (1.30 g, yield 79%) as a white solid. melting point 220-221° C.

Reference Example 113 ethyl 1-(methoxymethyl)-7-[(pyridin-2-ylsulfonyl)amino]-1H-indole-2-carboxylate

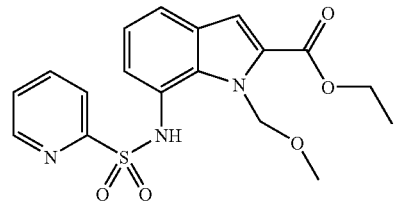

In the same manner as in Reference Example 3, the title compound (1.33 g, yield 73%) was obtained as a colorless amorphous solid from ethyl 7-amino-1-(methoxymethyl)-1H-indole-2-carboxylate (1.28 g) and pyridine-2-sulfonyl chloride monohydrochloride (1.00 g).

$^1$H-NMR (DMSO-$d_6$) δ: 1.35 (3H, t), 3.10 (3H, s), 4.34 (2H, q, J=7.1 Hz), 6.31 (2H, s), 6.58-6.67 (1H, m), 6.93 (1H, t, J=7.7 Hz), 7.37-7.42 (1H, m), 7.59 (1H, d, J=7.9 Hz), 7.67-7.74 (1H, m), 7.79 (1H, d, J=7.9 Hz), 7.99-8.07 (1H, m), 8.83 (1H, d, J=3.8 Hz), 10.26 (1H, s).

Reference Example 114 ethyl 1-(methoxymethyl)-7-[methyl(pyridin-2-ylsulfonyl)amino]-1H-indole-2-carboxylate

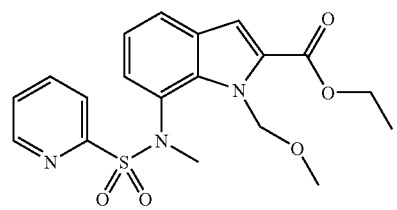

In the same manner as in Reference Example 4, the title compound (1.25 g, yield 91%) was obtained as a colorless amorphous solid from ethyl 1-(methoxymethyl)-7-[(pyridin-2-ylsulfonyl)amino]-1H-indole-2-carboxylate (1.33 g).

$^1$H-NMR (DMSO-$d_6$) δ: 1.35 (3H, t, J=7.1 Hz), 3.15 (3H, s), 3.47 (3H, s), 4.30-4.42 (2H, m), 6.26 (2H, d, J=1.1 Hz), 6.66 (1H, dd, J=7.6, 1.0 Hz), 7.01 (1H, t, J=7.7 Hz), 7.43-7.46 (1H, m), 7.68-7.83 (3H, m), 8.04-8.12 (1H, m), 8.89-8.93 (1H, m).

Reference Example 115 ethyl 7-[methyl(pyridin-2-ylsulfonyl)amino]-1H-indole-2-carboxylate

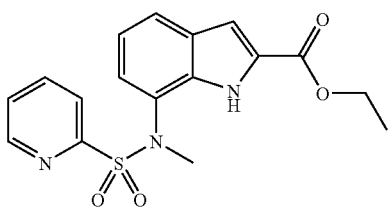

In the same manner as in Reference Example 5, the title compound (800 mg, yield 72%) was obtained as a colorless amorphous solid from ethyl 1-(methoxymethyl)-7-[methyl(pyridin-2-ylsulfonyl)amino]-1H-indole-2-carboxylate (1.25 g). MS: 360 (MH$^+$).

Reference Example 116

7-[methyl(pyridin-2-ylsulfonyl)amino]-1H-indole-2-carboxylic acid

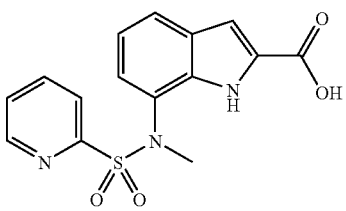

In the same manner as in Reference Example 6, the title compound (658 mg, yield 89%) was obtained as a white solid from ethyl 7-[methyl(pyridin-2-ylsulfonyl)amino]-1H-indole-2-carboxylate (800 mg). MS: 332 (MH$^+$).

Reference Example 117

N-[2-(benzylthio)-3,3-dimethoxypropyl]-7-[methyl(pyridin-2-ylsulfonyl)amino]-1H-indole-2-carboxamide

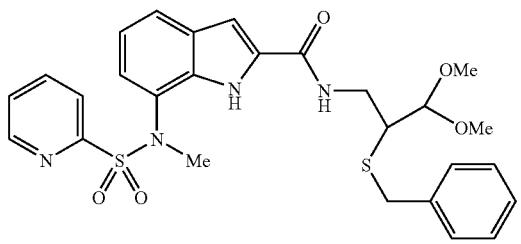

In the same manner as in Reference Example 48, the title compound (1050 mg, yield 95%) was obtained as a colorless amorphous solid from 7-[methyl(pyridin-2-ylsulfonyl)amino]-1H-indole-2-carboxylic acid (658 mg) and 2-(benzylthio)-3,3-dimethoxypropan-1-amine (576 mg).

$^1$H-NMR (CDCl$_3$) δ: 2.80-3.04 (1H, m), 3.32 (3H, s), 3.39 (3H, s), 3.48 (3H, s), 3.55-3.73 (1H, m), 3.78-3.92 (3H, m), 4.36 (1H, d, J=4.5 Hz), 6.73 (1H, d, J=2.1 Hz), 6.82 (1H, s), 7.11 (1H, t, J=7.7 Hz), 7.16-7.22 (1H, m), 7.23-7.30 (3H, m), 7.32-7.38 (2H, m), 7.57-7.69 (2H, m), 7.90-8.03 (1H, m), 8.07-8.15 (1H, m), 9.18-9.32 (1H, m), 12.33 (1H, brs).

Reference Example 118

N-[2-(benzylthio)-3-oxopropyl]-7-[methyl(pyridin-2-ylsulfonyl)amino]-1H-indole-2-carboxamide

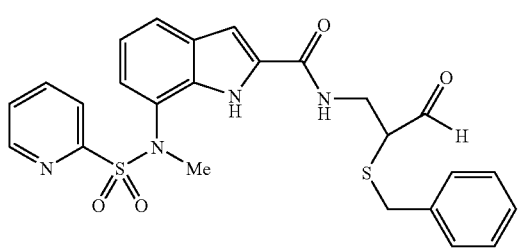

In the same manner as in Reference Example 40, the title compound (800 mg, yield 83%) was obtained as a colorless amorphous solid from N-[2-(benzylthio)-3,3-dimethoxypropyl]-7-[methyl(pyridin-2-ylsulfonyl)amino]-1H-indole-2-carboxamide (1050 mg).

$^1$H-NMR (CDCl$_3$) δ: 3.31 (3H, s), 3.55-3.62 (1H, m), 3.66-3.92 (4H, m), 6.43 (1H, t, J=6.1 Hz), 6.77 (1H, d, J=2.3 Hz), 7.11 (1H, t, J=7.7 Hz), 7.21-7.25 (1H, m), 7.26-7.39 (5H, m), 7.58-7.68 (2H, m), 7.93-8.05 (1H, m), 8.12 (1H, d, J=7.9 Hz), 9.19-9.25 (1H, m), 9.43 (1H, d, J=1.9 Hz), 12.42 (1H, brs).

Reference Example 119

N-[2-(benzylthio)-3-morpholinopropyl]-7-[methyl(pyridin-2-ylsulfonyl)amino]-1H-indole-2-carboxamide

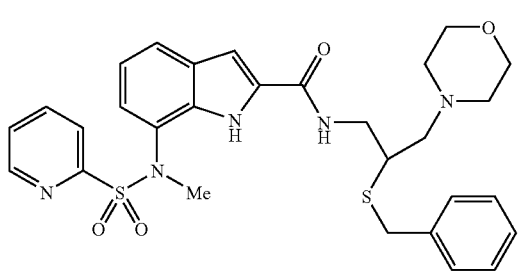

In the same manner as in Reference Example 41, the title compound (80 mg, yield 26%) was obtained as a colorless amorphous solid from N-[2-(benzylthio)-3-oxopropyl]-7-[methyl(pyridin-2-ylsulfonyl)amino]-1H-indole-2-carboxamide (275 mg) and morpholine (47.1 mg). MS: 580 (MH$^+$).

Reference Example 120

7-[methyl(pyridin-2-ylsulfonyl)amino]-1H-indole-2-carboxamide

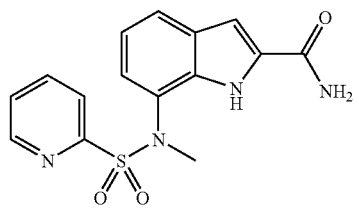

In the same manner as in Reference Example 7, the title compound (1.13 g, yield 100%) was obtained as a colorless amorphous solid from 7-[methyl(pyridin-2-ylsulfonyl)amino]-1H-indole-2-carboxylic acid (1.14 g). MS: 331 (MH$^+$).

Reference Example 121

7-[methyl(pyridin-2-ylsulfonyl)amino]-1H-indole-2-carbothioamide

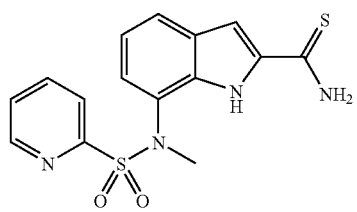

In the same manner as in Reference Example 14, the title compound (1.19 g, yield 100%) was obtained as a yellow amorphous solid from 7-[methyl(pyridin-2-ylsulfonyl)amino]-1H-indole-2-carboxamide (1.13 g). MS: 347 (MH$^+$).

Reference Example 122 ethyl 7-[(2-furylsulfonyl)amino]-1-(methoxymethyl)-1H-indole-2-carboxylate

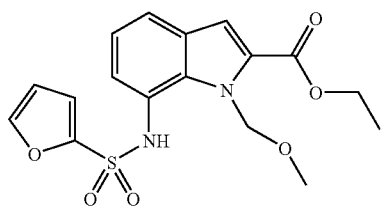

In the same manner as in Reference Example 3, the title compound (4.00 g, yield 70%) was obtained as a colorless amorphous solid from ethyl 7-amino-1-(methoxymethyl)-1H-indole-2-carboxylate (4.10 g) and furan-2-sulfonyl chloride (2.50 g).

$^1$H-NMR (DMSO-d$_6$) δ: 1.34 (3H, t), 3.08 (3H, s), 4.34 (2H, q, J=7.2 Hz), 6.24 (2H, s), 6.57 (1H, dd, J=7.5, 1.1 Hz), 6.68 (1H, dd, J=3.6, 1.7 Hz), 6.97 (1H, dd, J=3.5, 0.8 Hz), 7.04 (1H, t, J=7.7 Hz), 7.38-7.43 (1H, m), 7.67 (1H, d, J=7.3 Hz), 8.07 (1H, d, J=0.9 Hz), 10.32 (1H, s).

Reference Example 123 ethyl 7-[(2-furylsulfonyl)(methyl)amino]-1-(methoxymethyl)-1H-indole-2-carboxylate

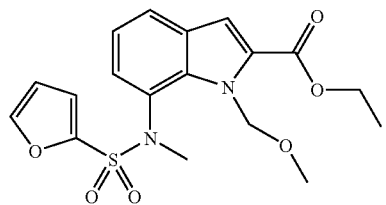

In the same manner as in Reference Example 4, the title compound (3.90 g, yield 94%) was obtained as a colorless amorphous solid from ethyl 7-[(2-furylsulfonyl)amino]-1-(methoxymethyl)-1H-indole-2-carboxylate (4.00 g).

$^1$H-NMR (CDCl$_3$) δ: 1.41 (3H, t, J=7.0 Hz), 3.31 (3H, s), 3.44 (3H, s), 4.32-4.45 (2H, m), 6.24-6.46 (2H, m), 6.57 (1H, dd, J=3.4, 1.9 Hz), 6.65 (1H, d, J=6.8 Hz), 6.94 (1H, d, J=3.0 Hz), 7.03 (1H, t, J=7.8 Hz), 7.38 (1H, s), 7.60-7.72 (2H, m).

Reference Example 124 ethyl 7-[(2-furylsulfonyl)(methyl)amino]-1H-indole-2-carboxylate

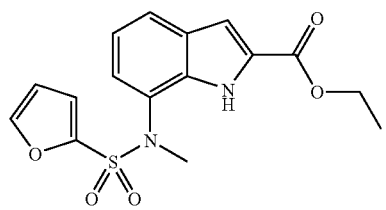

In the same manner as in Reference Example 5, the title compound (2.58 g, yield 100%) was obtained as a colorless amorphous solid from ethyl 7-[(2-furylsulfonyl)(methyl)amino]-1-(methoxymethyl)-1H-indole-2-carboxylate (2.90 g).

MS: 349 (MH$^+$).

Reference Example 125

7-[(2-furylsulfonyl)(methyl)amino]-1H-indole-2-carboxylic acid

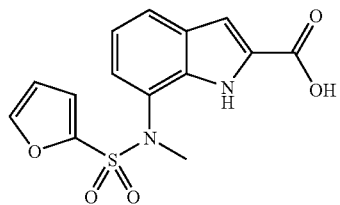

In the same manner as in Reference Example 6, the title compound (2.76 g, yield 100%) was obtained as a white solid from ethyl 7-[(2-furylsulfonyl)(methyl)amino]-1H-indole-2-carboxylate (3.00 g). MS: 321 (MH⁺).

Reference Example 126

N-[2-(benzylthio)-3,3-dimethoxypropyl]-7-[(2-furyl-sulfonyl)(methyl)amino]-1H-indole-2-carboxamide

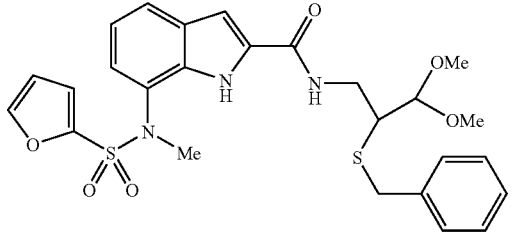

In the same manner as in Reference Example 48, the title compound (2.04 g, yield 100%) was obtained as a colorless amorphous solid from 7-[(2-furylsulfonyl)(methyl)amino]-1H-indole-2-carboxylic acid (1.20 g) and 2-(benzylthio)-3,3-dimethoxypropan-1-amine (1.09 g).

¹H-NMR (CDCl₃) δ: 2.87-2.99 (1H, m), 3.37-3.39 (3H, m), 3.47 (3H, s), 3.52-3.68 (1H, m), 3.77-3.90 (3H, m), 4.34 (1H, d, J=4.5 Hz), 6.51 (1H, dd, J=3.5, 1.8 Hz), 6.72 (1H, d, J=2.3 Hz), 6.81 (1H, dd, J=7.6, 0.8 Hz), 6.92 (1H, dd, J=3.5, 0.8 Hz), 7.04 (1H, t, J=7.7 Hz), 7.15-7.25 (2H, m), 7.27-7.40 (4H, m), 7.56-7.63 (1H, m), 7.67 (1H, dd, J=1.8, 0.8 Hz), 9.42 (1H, d, J=1.1 Hz).

Reference Example 127

N-[2-(benzylthio)-3-oxopropyl]-7-[(2-furylsulfonyl)(methyl)amino]-1H-indole-2-carboxamide

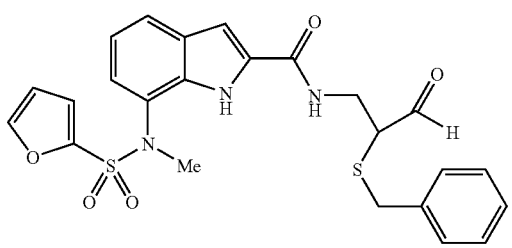

In the same manner as in Reference Example 40, the title compound (830 mg, yield 44%) was obtained as a colorless amorphous solid from N-[2-(benzylthio)-3,3-dimethoxypropyl]-7-[(2-furylsulfonyl)(methyl)amino]-1H-indole-2-carboxamide (2.04 g).

¹H-NMR (CDCl₃) δ: 3.40 (3H, s), 3.53-3.63 (1H, m), 3.67-3.85 (4H, m), 6.41 (1H, s), 6.51 (1H, dd, J=3.6, 1.9 Hz), 6.73-6.83 (2H, m), 6.91 (1H, dd, J=3.5, 0.8 Hz), 7.03 (1H, t, J=7.8 Hz), 7.28-7.32 (1H, m), 7.33-7.40 (4H, m), 7.58 (1H, d, J=8.1 Hz), 7.66 (1H, dd, J=1.8, 0.8 Hz), 9.35-9.53 (2H, m).

Reference Example 128

N-[2-(benzylthio)-3-morpholinopropyl]-7-[(2-furyl-sulfonyl)(methyl)amino]-1H-indole-2-carboxamide

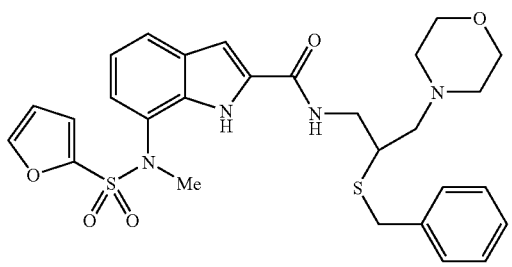

In the same manner as in Reference Example 41, the title compound (860 mg, yield 91%) was obtained as a colorless amorphous solid from N-[2-(benzylthio)-3-oxopropyl]-7-[(2-furylsulfonyl)(methyl)amino]-1H-indole-2-carboxamide (830 mg) and morpholine (292 mg). MS: 569 (MH⁺).

Reference Example 129

7-[(2-furylsulfonyl)(methyl)amino]-1H-indole-2-carboxamide

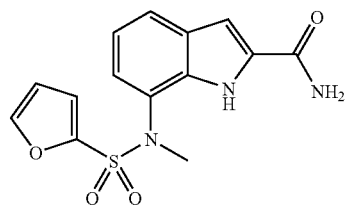

In the same manner as in Reference Example 7, the title compound (1495 mg, yield 100%) was obtained as a colorless amorphous solid from 7-[(2-furylsulfonyl)(methyl)amino]-1H-indole-2-carboxylic acid (1500 mg). MS: 320 (MH⁺).

Reference Example 130

7-[(2-furylsulfonyl)(methyl)amino]-1H-indole-2-carbothioamide

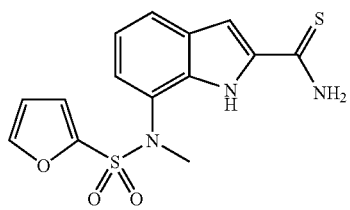

In the same manner as in Reference Example 14, the title compound (1280 mg, yield 80%) was obtained as a yellow amorphous solid from 7-[(2-furylsulfonyl)(methyl)amino]-1H-indole-2-carboxamide (1520 mg). MS: 336 (MH⁺).

Reference Example 131

N-[2-(benzylthio)-3,3-dimethoxypropyl]-7-[(2-thienylsulfonyl)amino]-1H-indole-2-carboxamide

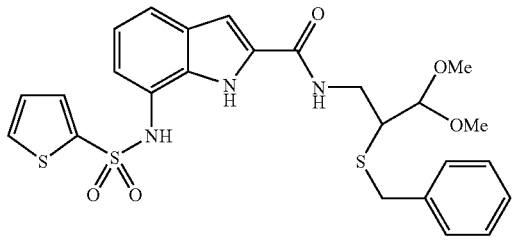

In the same manner as in Reference Example 48, the title compound (7.00 g, yield 83%) was obtained as a colorless amorphous solid from 7-[(2-thienylsulfonyl)amino]-1H-indole-2-carboxylic acid (5.00 g) and 2-(benzylthio)-3,3-dimethoxypropan-1-amine (4.5 g).

$^1$H-NMR (CDCl$_3$) δ: 3.00-3.09 (1H, m), 3.42 (3H, s), 3.48 (3H, s), 3.84 (2H, d, J=1.3 Hz), 4.02-4.17 (2H, m), 4.40 (1H, d, J=3.8 Hz), 6.62-6.67 (1H, m), 6.75 (1H, d, J=2.1 Hz), 7.10-7.24 (6H, m), 7.27-7.36 (3H, m), 7.46-7.54 (2H, m), 9.40 (1H, s), 11.15 (1H, s).

Reference Example 132

N-[2-(benzylthio)-3-oxopropyl]-7-[(2-thienylsulfonyl)amino]-1H-indole-2-carboxamide

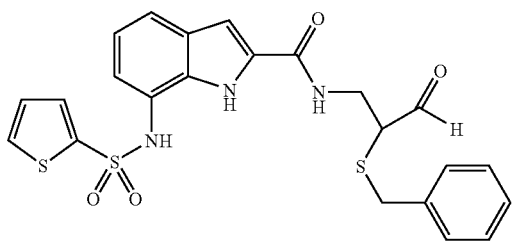

In the same manner as in Reference Example 40, the title compound (3.00 g, yield 47%) was obtained as a colorless amorphous solid from N-[2-(benzylthio)-3,3-dimethoxypropyl]-7-[(2-thienylsulfonyl)amino]-1H-indole-2-carboxamide (7.00 g).

MS: 500 (MH⁺).

Reference Example 133

N-[2-(benzylthio)-3-morpholinopropyl]-7-[(2-thienylsulfonyl)amino]-1H-indole-2-carboxamide

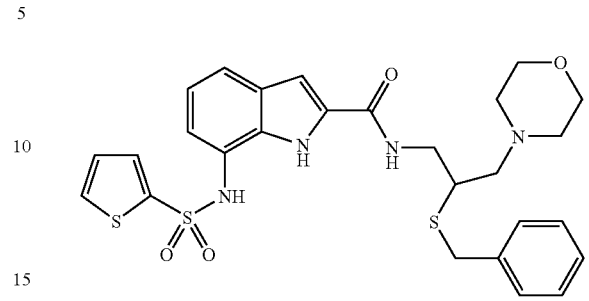

In the same manner as in Reference Example 41, the title compound (2.74 g, yield 80%) was obtained as a colorless amorphous solid from N-[2-(benzylthio)-3-oxopropyl]-7-[(2-thienylsulfonyl)amino]-1H-indole-2-carboxamide (3.00 g) and morpholine (1.06 g). MS: 571 (MH⁺).

Reference Example 134

1-(methoxymethyl)-7-[(pyridin-2-ylsulfonyl)amino]-1H-indole-2-carboxylic acid

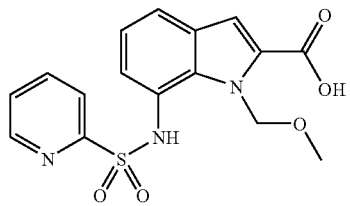

Ethyl 1-(methoxymethyl)-7-[(pyridin-2-ylsulfonyl)amino]-1H-indole-2-carboxylate (7.0 g) was dissolved in a mixed solvent of tetrahydrofuran (30 mL)-methanol (20 mL). Aqueous potassium hydroxide solution (prepared by dissolving potassium hydroxide (3.0 g) in water (10 mL)) was added to this solution, and the mixture was stirred at room temperature for 15 hr. The reaction solution was acidified with aqueous citric acid solution, and extracted with ethyl acetate. The organic layer was washed with saturated brine, dried over anhydrous magnesium sulfate, and concentrated under reduced pressure. The obtained pale-pink crystals were washed with ethyl acetate-hexane to give the title compound (5.94 g, yield: 91%) as colorless crystals.

MS: 332 (MH⁺). melting point: 199-200° C.

Reference Example 135

7-[(pyridin-2-ylsulfonyl)amino]-1H-indole-2-carboxamide

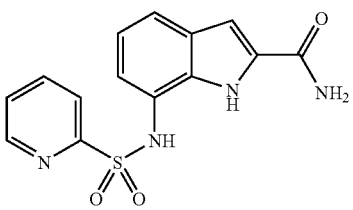

In the same manner as in Reference Example 7, 1-(methoxymethyl)-7-[(pyridin-2-ylsulfonyl)amino]-1H-indole-2-carboxamide (4.99 g) was obtained as a colorless amorphous solid from 1-(methoxymethyl)-7-[(pyridin-2-ylsulfonyl)amino]-1H-indole-2-carboxylic acid (5.00 g). In the same manner as in Reference Example 5, the title compound (3.10 g, yield 71%) was obtained as a colorless amorphous solid from 1-(methoxymethyl)-7-[(pyridin-2-ylsulfonyl)amino]-1H-indole-2-carboxamide. MS: 317 (MH$^+$).

Reference Example 136

7-[(pyridin-2-ylsulfonyl)amino]-1H-indole-2-carbothioamide

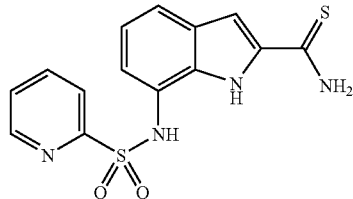

In the same manner as in Reference Example 14, the title compound (3.20 g, yield 98%) was obtained as a yellow amorphous solid from 7-[(pyridin-2-ylsulfonyl)amino]-1H-indole-2-carboxamide (3.10 g). MS: 333 (MH$^+$).

Reference Example 137

N-[2-(benzylthio)-3,3-dimethoxypropyl]-1-(methoxymethyl)-7-[(pyridin-2-ylsulfonyl)amino]-1H-indole-2-carboxamide

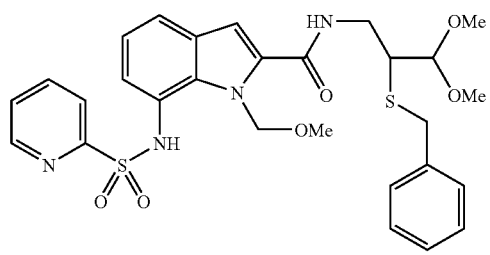

A solution of 1-(methoxymethyl)-7-[(pyridin-2-ylsulfonyl)amino]-1H-indole-2-carboxylic acid (0.94 g), 2-(benzylthio)-3,3-dimethoxypropan-1-amine (0.70 g), N-ethyldiisopropylamine (1.0 mL) and O-(7-azabenzotriazol-1-yl)-N,N,N',N'-tetramethyluronium hexafluorophosphate (1.2 g) in N,N-dimethylformamide (20 mL) was stirred at room temperature for 20 hr. The reaction solution was diluted with ethyl acetate, washed with water, aqueous citric acid solution and saturated brine, dried over anhydrous magnesium sulfate, and concentrated under reduced pressure. The obtained residue was subjected to silica gel column chromatography (ethyl acetate:hexane=4:6-6:4) to give the title compound (1.6 g, yield: 100%) as a pale-yellow oil. MS: 553 (MH$^+$).

Reference Example 138

N-[2-(benzylthio)-3,3-dimethoxypropyl]-1-(methoxymethyl)-7-[methyl(pyridin-2-ylsulfonyl)amino]-1H-indole-2-carboxamide

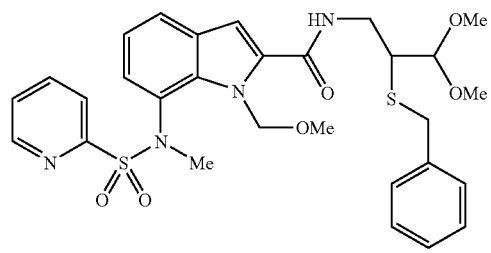

To a solution of N-[2-(benzylthio)-3,3-dimethoxypropyl]-1-(methoxymethyl)-7-[(pyridin-2-ylsulfonyl)amino]-1H-indole-2-carboxamide (1.52 g) and potassium carbonate (0.54 g) in N,N-dimethylformamide (14 mL) was added methyl iodide (0.16 mL) under ice-cooling, and the mixture was stirred from under ice-cooling to room temperature for 18 hr. The reaction solution was ice-cooled, potassium carbonate (0.30 g) and methyl iodide (0.16 mL) were added again, and the mixture was further stirred from under ice-cooling to room temperature for 15 hr. The reaction solution was diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=4:6-6:4) to give the title compound (1.6 g, yield: 100%) as a colorless oil.

MS: 599 (MH$^+$).

Reference Example 139

N-[2-(benzylthio)-3-thiomorpholinopropyl]-7-[methyl(pyridin-2-ylsulfonyl)amino]-1H-indole-2-carboxamide

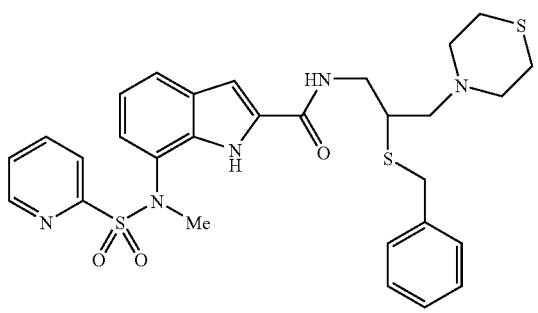

To a mixture of N-[2-(benzylthio)-3-oxopropyl]-7-[methyl(pyridin-2-ylsulfonyl)amino]-1H-indole-2-carboxamide (0.60 g), thiomorpholine (0.21 mL) and 1,2-dichloroethane (25 mL) was added sodium triacetoxyborohydride (0.65 g), and the mixture was stirred at room temperature for 15 hr. The reaction solution was acidified with diluted hydrochloric acid, and extracted with ethyl acetate. The organic layer was washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=35:65-55:45) to give the title compound (0.67 g, yield: 95%) as a colorless oil. MS: 596 (MH$^+$).

Reference Example 140 ethyl 1-(methoxymethyl)-7-{[(2-methoxyphenyl)sulfonyl]amino}-1H-indole-2-carboxylate

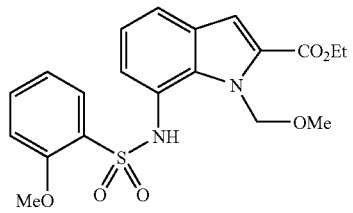

To a mixture of ethyl 7-amino-1-(methoxymethyl)-1H-indole-2-carboxylate (12.0 g) and pyridine (100 mL) was added 2-methoxybenzenesulfonyl chloride (10.0 g) under ice-cooling, and the mixture was stirred from under ice-cooling to room temperature for 20 hr. The reaction mixture was concentrated, and the residue was diluted with ethyl acetate. The solution was washed with aqueous citric acid solution and saturated brine, dried over anhydrous magnesium sulfate, and concentrated under reduced pressure. The obtained crystals were washed with ethyl acetate-hexane to give the title compound (16.58 g, yield 89%) as pale-gray crystals. melting point: 106-107° C.

Reference Example 141 ethyl 1-(methoxymethyl)-7-[[(2-methoxyphenyl)sulfonyl](methyl)amino]-1H-indole-2-carboxylate

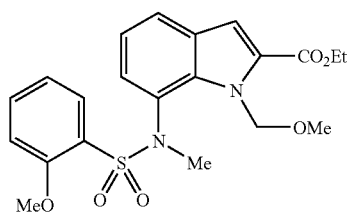

To a solution of ethyl 1-(methoxymethyl)-7-{[(2-methoxyphenyl)sulfonyl]amino}-1H-indole-2-carboxylate (11.0 g) and potassium carbonate (5.9 g) in N,N-dimethylformamide (80 mL) was added methyl iodide (2.7 mL) under ice-cooling, and the mixture was stirred from under ice-cooling to room temperature for 18 hr. The reaction solution was diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=3:2-4:1), and the obtained crystals were washed with ethyl acetate-hexane to give the title compound (10.9 g, yield: 89%) as colorless needle crystals. melting point: 124-125° C.

Reference Example 142

7-[[(2-methoxyphenyl)sulfonyl](methyl)amino]-1H-indole-2-carboxylic acid

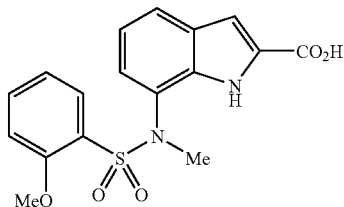

A mixture of ethyl 1-(methoxymethyl)-7-[[(2-methoxyphenyl)sulfonyl](methyl)amino]-1H-indole-2-carboxylate (10.9 g), 6N-hydrochloric acid (50 mL), tetrahydrofuran (50 mL) and methanol (50 mL) was stirred at 90° C. for 24 hr. The organic solvent of the reaction solution was evaporated under reduced pressure, and the residue was diluted with ethyl acetate. The solution was washed with water and saturated brine, dried over anhydrous magnesium sulfate, and concentrated under reduced pressure. The obtained residue was dissolved in a mixed solvent of tetrahydrofuran (50 mL)-methanol (50 mL), aqueous potassium hydroxide solution (prepared by dissolving potassium hydroxide (4.2 g) in water (30 mL)) was added to this solution, and the mixture was stirred at room temperature for 15 hr. The reaction solution was acidified with aqueous citric acid solution, and extracted with ethyl acetate. The organic layer was washed with saturated brine, dried over anhydrous magnesium sulfate, and concentrated under reduced pressure. The obtained pale-brown crystals were filtered off, and washed with ethyl acetate-hexane. The filtrate was concentrated under reduced pressure, and the obtained crystals were washed with ethyl acetate-hexane to give the title compound (6.47 g, crude yield: 71%) as pale-yellow crystals. MS: 361 (MH$^+$).

Reference Example 143

7-[[(2-methoxyphenyl)sulfonyl](methyl)amino]-1H-indole-2-carboxamide

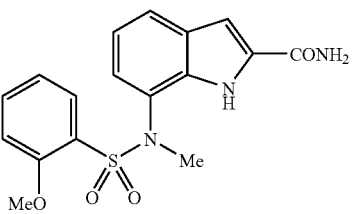

To a mixture of 7-[[(2-methoxyphenyl)sulfonyl](methyl)amino]-1H-indole-2-carboxylic acid (3.0 g), 1H-1,2,3-benzotriazol-1-ol-ammonia complex (1.65 g) and N,N-dimethylformamide (30 mL) was added N-[3-(dimethylamino)propyl]-N'-ethylcarbodiimide hydrochloride (2.1 g) under ice-cooling, and the mixture was stirred from under ice-cool-

Reference Example 144

7-[[(2-methoxyphenyl)sulfonyl](methyl)amino]-1H-indole-2-carbothioamide

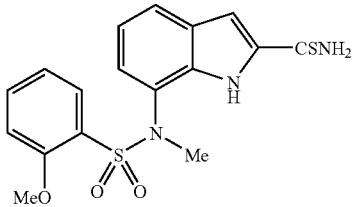

A mixture of 7-[[(2-methoxyphenyl)sulfonyl](methyl) amino]-1H-indole-2-carboxamide (2.82 g), Lawesson's reagent (1.6 g) and tetrahydrofuran (250 mL) was stirred at 70° C. for 3 hr. The reaction solution was concentrated under reduced pressure, and the obtained oil was crystallized from ethyl acetate-hexane to give the title compound (2.3 g, yield: 78%) as pale-yellow crystals.

MS: 376 (MH$^+$).

Reference Example 145 ethyl 7-({[2-(trifluoromethyl)phenyl] sulfonyl}amino)-1H-indole-2-carboxylate

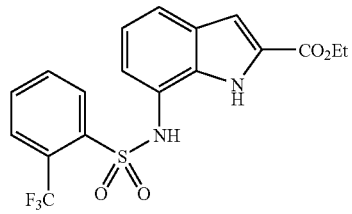

To a mixture of ethyl 7-amino-1H-indole-2-carboxylate (4.1 g) and pyridine (60 mL) was added 2-trifluoromethyl-benzenesulfonyl chloride (5.0 g) under ice-cooling, and the mixture was stirred from under ice-cooling to room temperature for 18 hr. The reaction mixture was concentrated, and the residue was diluted with ethyl acetate. The solution was washed with aqueous citric acid solution and saturated brine, and filtrated through silica gel. The eluate was concentrated under reduced pressure, and the obtained pale-brown oil was crystallized from ethyl acetate-hexane to give the title compound (7.3 g, yield 88%) as pale-brown crystals. MS: 413 (MH$^+$). melting point: 138-139° C.

Reference Example 146 ethyl 7-(methyl{[2-(trifluoromethyl)phenyl] sulfonyl}amino)-1H-indole-2-carboxylate

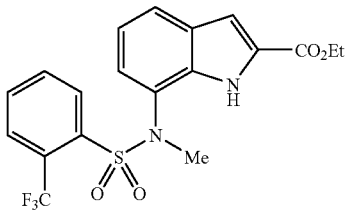

To a solution of ethyl 7-({[2-(trifluoromethyl)phenyl] sulfonyl}amino)-1H-indole-2-carboxylate (5.0 g) and potassium carbonate (2.0 g) in N,N-dimethylformamide (50 mL) was added methyl iodide (0.75 mL) under ice-cooling, and the mixture was stirred from under ice-cooling to room temperature for 18 hr. The reaction solution was ice-cooled, methyl iodide (0.75 mL) was added again, and the mixture was stirred from under ice-cooling to room temperature for 18 hr. The reaction solution was diluted with ethyl acetate, washed with water, aqueous citric acid solution and saturated brine, dried over anhydrous magnesium sulfate, and concentrated under reduced pressure. The obtained residue was subjected to basic silica gel column chromatography (ethyl acetate:hexane=20:80-35:65), and the obtained crude product was subjected three times to silica gel column chromatography (ethyl acetate:hexane=5:95-10:90) to give the title compound (3.7 g, yield: 72%) as a pale-yellow oil. MS: 427 (MH$^+$).

Reference Example 147

7-(methyl{[2-(trifluoromethyl)phenyl] sulfonyl}amino)-1H-indole-2-carboxylic acid

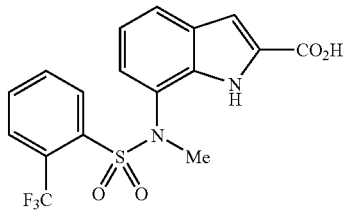

Ethyl 7-(methyl{[2-(trifluoromethyl)phenyl] sulfonyl}amino)-1H-indole-2-carboxylate (3.7 g) was dissolved in a mixed solvent of tetrahydrofuran (25 ml)-methanol (25 mL). Aqueous potassium hydroxide solution (prepared by dissolving potassium hydroxide (1.5 g) in water (20 mL)) was added to this solution, and the mixture was stirred at room temperature for 2 days. The reaction solution was acidified with aqueous citric acid solution, and extracted with ethyl acetate. The organic layer was washed with saturated brine, dried over anhydrous magnesium sulfate, and concentrated under reduced pressure. The obtained colorless crystals were washed with ethyl acetate-hexane to give the title compound (2.7 g, yield: 63%) as colorless crystals. MS: 399 (MH⁺). melting point: 211-212° C.

Reference Example 148

7-(methyl{[2-(trifluoromethyl)phenyl]sulfonyl}amino)-1H-indole-2-carboxamide

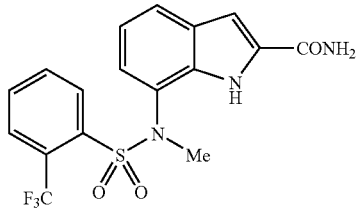

To a mixture of 7-(methyl{[2-(trifluoromethyl)phenyl]sulfonyl}amino)-1H-indole-2-carboxylic acid (2.65 g), 1H-1,2,3-benzotriazol-1-ol-ammonia complex (1.3 g) and N,N-dimethylformamide (30 mL) was added N-[3-(dimethylamino)propyl]-N'-ethylcarbodiimide hydrochloride (1.7 g) under ice-cooling, and the mixture was stirred from under ice-cooling to room temperature for 18 hr. The reaction solution was diluted with ethyl acetate, washed with water, aqueous sodium hydrogencarbonate solution and saturated brine, dried over anhydrous magnesium sulfate, and concentrated under reduced pressure. The obtained colorless crystals were washed with ethyl acetate-hexane to give the title compound (2.6 g, yield 98%) as colorless crystals. MS: 398 (MH⁺). melting point 223-224° C.

Reference Example 149

7-(methyl{[2-(trifluoromethyl)phenyl]sulfonyl}amino)-1H-indole-2-carbothioamide

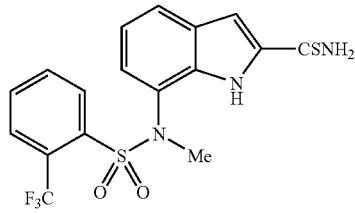

A mixture of 7-(methyl{[2-(trifluoromethyl)phenyl]sulfonyl}amino)-1H-indole-2-carboxamide (2.6 g), Lawesson's reagent (1.3 g) and tetrahydrofuran (50 mL) was stirred at 60° C. for 3 hr. The reaction solution was concentrated under reduced pressure, and the obtained oil was crystallized from toluene to give the title compound (2.65 g, yield: 100%) as pale-yellow crystals.

MS: 414 (MH⁺).

Reference Example 150

N-[2-(benzylthio)-3-(1,1-dioxidothiomorpholino)propyl]-7-[methyl(pyridin-2-ylsulfonyl)amino]-1H-indole-2-carboxamide

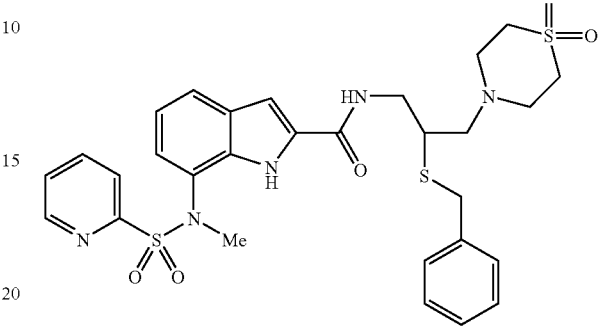

To a mixture of N-[2-(benzylthio)-3-oxopropyl]-7-[methyl(pyridin-2-ylsulfonyl)amino]-1H-indole-2-carboxamide (0.30 g), thiomorpholine 1,1-dioxide (0.15 g) and 1,2-dichloroethane (12 mL) was added sodium triacetoxyborohydride (0.25 g), and the mixture was stirred at room temperature for 2 days. The reaction solution was acidified with aqueous citric acid solution, and extracted with ethyl acetate. The organic layer was washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=25:75-40:60) to give the title compound (0.37 g, yield: 100%) as a colorless oil. MS: 628 (MH⁺).

Reference Example 151 ethyl 7-{methyl[(1-methyl-1H-imidazol-2-yl)sulfonyl]amino}-1H-indole-2-carboxylate

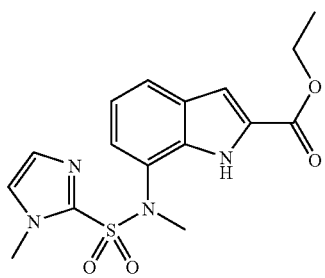

To a solution of ethyl 7-amino-1H-indole-2-carboxylate (3 g) in pyridine (30 mL) was added 1-methyl-1H-imidazole-2-sulfonyl chloride (3.6 g) under ice-cooling, and the mixture was stirred for 1 hr. The reaction mixture was concentrated, and the residue was dissolved in ethyl acetate. The solution was washed with water. The ethyl acetate layer was washed with 1N hydrochloric acid, saturated brine and saturated aqueous sodium hydrogencarbonate solution, dried (MgSO₄), and concentrated. The obtained residue was dissolved in DMF (30 mL), potassium carbonate (2.1 g) and methyl iodide (2.1 g) were added at room temperature, and the mixture was stirred for 3 hr at room temperature. Water was added to the reaction mixture, and the mixture was extracted with ethyl acetate. The ethyl acetate layer was washed with 1N hydrochloric acid, saturated brine and saturated aqueous sodium hydrogencarbonate solution, dried (MgSO$_4$), and concentrated. The obtained residue was subjected to silica gel column chromatography to give the title compound (3.0 g, yield 59%) as white crystals from a fraction eluted with ethyl acetate:hexane=50:50. melting point 120° C.

Reference Example 152

7-{methyl[(1-methyl-1H-imidazol-2-yl)sulfonyl]amino}-1H-indole-2-carboxylic acid

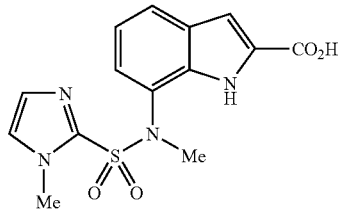

Ethyl 7-{methyl[(1-methyl-1H-imidazol-2-yl)sulfonyl]amino}-1H-indole-2-carboxylate (2.87 g) was dissolved in a mixed solvent of tetrahydrofuran (30 mL)-methanol (20 mL). Aqueous potassium hydroxide solution (prepared by dissolving potassium hydroxide (2.0 g) in water (20 mL)) was added to this solution, and the mixture was stirred at room temperature for 16 hr, and concentrated under reduced pressure to evaporate methanol. The obtained residue was acidified with aqueous citric acid solution, and the mixture was extracted with ethyl acetate. The organic layer was washed with saturated brine, dried over anhydrous magnesium sulfate, and concentrated under reduced pressure to give the title compound (2.65 g, yield: 100%) as colorless crystals. MS: 335 (MH$^+$). melting point: 241-242° C.

Reference Example 153

N-[2-(benzylthio)-3,3-dimethoxypropyl]-7-{methyl[(1-methyl-1H-imidazol-2-yl)sulfonyl]amino}-1H-indole-2-carboxamide

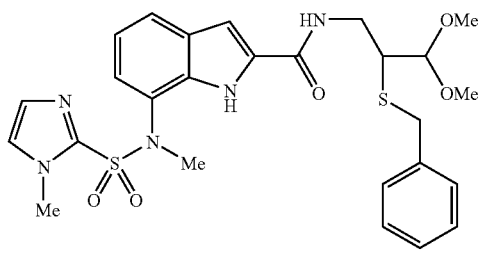

A solution of 7-{methyl[(1-methyl-1H-imidazol-2-yl)sulfonyl]amino}-1H-indole-2-carboxylic acid (2.64 g), 2-(benzylthio)-3,3-dimethoxypropan-1-amine (2.10 g), N-ethyldiisopropylamine (3.2 mL) and O-(7-azabenzotriazol-1-yl)-N,N,N',N'-tetramethyluronium hexafluorophosphate (3.6 g) in N,N-dimethylformamide (40 mL) was stirred at room temperature for 16 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=35:65-50:50) to give the title compound (4.5 g, yield: 100%) as a pale-yellow oil.

$^1$H-NMR (CDCl$_3$) δ: 2.92 (1H, td, J=10.5, 6.3 Hz), 3.38 (3H, s), 3.46 (3H, s), 3.53 (3H, s), 3.54-3.68 (1H, m), 3.80-3.90 (1H, m), 3.83 (3H, s), 4.34 (1H, d, J=4.5 Hz), 6.72 (1H, d, J=2.1 Hz), 6.78 (1H, brt, J=5.4 Hz), 6.97 (1H, d, J=0.9 Hz), 7.08-7.40 (8H, m), 7.65 (1H, d, J=8.1 Hz), 12.46 (1H, brs).

Reference Example 154 ethyl 2-{[2-nitro-4-(trifluoromethoxy)phenyl]hydrazono}propanoate

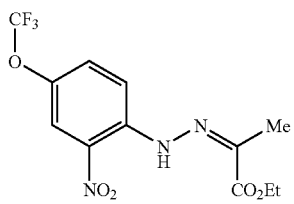

To a mixture of 2-nitro-4-(trifluoromethoxy)aniline (56.0 g) and 6N hydrochloric acid (210 mL) was added dropwise an aqueous solution (100 mL) of sodium nitrite (18.6 g) at 4 to 10° C. After the completion of the dropwise addition, the mixture was stirred at 5° C. for 1 hr. The insoluble substance was removed by filtration, and the filtrate was added dropwise to a mixture of ethyl 2-methylacetoacetate (40.4 g), potassium hydroxide (85%, 99.0 g), ethanol (200 mL) and water (500 mL) at 0° C. After the completion of the dropwise addition, the mixture was stirred for 30 min. Water was added to the reaction mixture, the mixture was stirred at room temperature, and the precipitated crystals were collected by filtration. The obtained crystals were dissolved in ethyl acetate, and the ethyl acetate layer was washed with saturated brine, dried (MgSO$_4$), and concentrated. The residue was subjected to silica gel column chromatography to give the title compound (7.41 g, yield 8.8%) as yellow crystals from a fraction eluted with hexane-ethyl acetate (4:1, volume ratio).

$^1$H-NMR (CDCl$_3$) δ: 1.40 (3H, t, J=7.06 Hz), 2.25 (3H, s), 4.36 (2H, q, J=7.16 Hz), 7.50 (1H, dd, J=9.42, 2.64 Hz), 8.02-8.15 (2H, m), 10.90 (1H, s).

Reference Example 155 ethyl 7-nitro-5-(trifluoromethoxy)-1H-indole-2-carboxylate

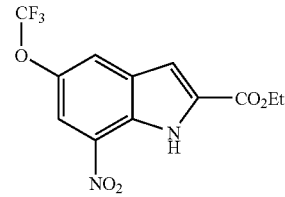

A mixture of ethyl 2-{[2-nitro-4-(trifluoromethoxy)phenyl]hydrazono}propanoate (6.30 g) and polyphosphoric acid (60 g) was stirred at 95° C. for 1 hr. The reaction mixture was added to ice water, and the obtained mixture was extracted with ethyl acetate. The ethyl acetate layer was washed successively with saturated aqueous sodium hydrogencarbonate and saturated brine, dried (MgSO$_4$), and concentrated. The residue was subjected to basic silica gel column chromatography, and eluted with hexane-ethyl acetate (98:2 to 4:1, volume ratio), and the obtained crystals were washed with hexane to give the title compound (3.06 g, yield 51%) as yellow crystals.

$^1$H-NMR (CDCl$_3$) δ: 1.45 (3H, t, J=7.19 Hz), 4.48 (2H, q, J=7.19 Hz), 7.38 (1H, d, J=2.27 Hz), 7.93 (1H, s), 8.19 (1H, s), 10.36 (1H, brs).

Reference Example 156 ethyl 7-amino-5-(trifluoromethoxy)-1H-indole-2-carboxylate

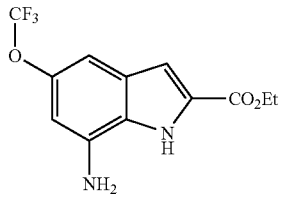

A mixture of ethyl 7-nitro-5-(trifluoromethoxy)-1H-indole-2-carboxylate (3.06 g), 10% palladium-carbon (50% containing water, 600 mg) and tetrahydrofuran (150 mL) was subjected to catalytic reduction under hydrogen atmosphere at normal pressure. The palladium-carbon was removed by filtration, and the filtrate was concentrated. The obtained crystals were washed with hexane to give the title compound (2.63 g, yield 95%) as colorless crystals. The crystals were recrystallized from ethyl acetate-hexane to give colorless prism crystals. melting point 190-191° C.

Reference Example 157 ethyl 7-[(2-thienylsulfonyl)amino]-5-(trifluoromethoxy)-1H-indole-2-carboxylate

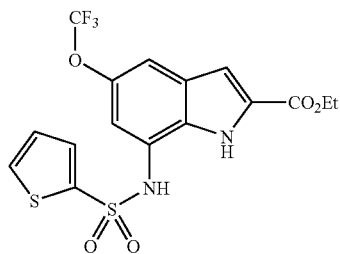

To a mixture of ethyl 7-amino-5-(trifluoromethoxy)-1H-indole-2-carboxylate (2.53 g) and pyridine (50 mL) was added thiophene-2-sulfonyl chloride (1.94 g) at 0° C., and the mixture was stirred at room temperature for 4 hr, and concentrated. 1N Hydrochloric acid was added, and the mixture was extracted with ethyl acetate. The ethyl acetate layer was washed with saturated brine, dried (MgSO$_4$), and concentrated. The obtained crystals were washed with diisopropyl ether to give the title compound (3.40 g, yield 89%) as colorless crystals. The crystals were recrystallized from ethyl acetate-hexane to give colorless prism crystals. melting point 196-197° C.

Reference Example 158 ethyl 7-[methyl(2-thienylsulfonyl)amino]-5-(trifluoromethoxy)-1H-indole-2-carboxylate

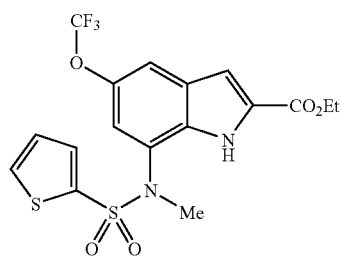

A mixture of ethyl 7-[(2-thienylsulfonyl)amino]-5-(trifluoromethoxy)-1H-indole-2-carboxylate (3.30 g), potassium carbonate (1.05 g) and N,N-dimethylformamide (50 mL) was stirred at 0° C. for 30 min. Methyl iodide (1.08 g) was added to the reaction mixture at 0° C., and the mixture was stirred at room temperature for 15 hr. Aqueous citric acid solution was added to the reaction mixture, and the mixture was extracted with ethyl acetate. The ethyl acetate layer was washed with saturated brine, dried over magnesium sulfate, and concentrated. The obtained residue was subjected to silica gel column chromatography, and eluted with ethyl acetate-hexane (9:1-3:1, volume ratio) to give the title compound (2.26 g, yield 66%) as colorless crystals. The crystals were recrystallized from ethyl acetate-hexane to give colorless prism crystals. melting point 149-150° C.

Reference Example 159

7-[methyl(2-thienylsulfonyl)amino]-5-(trifluoromethoxy)-1H-indole-2-carboxylic acid

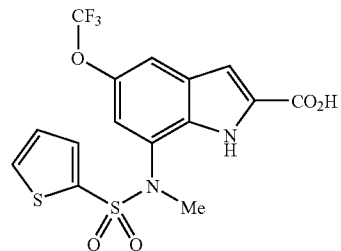

A mixture of ethyl 7-[methyl(2-thienylsulfonyl)amino]-5-(trifluoromethoxy)-1H-indole-2-carboxylate (2.19 g), 1N aqueous sodium hydroxide solution (10 mL), tetrahydrofuran (10 mL) and ethanol (10 mL) was stirred at room temperature for 15 hr. The reaction mixture was acidified with aqueous citric acid solution, and extracted with ethyl acetate. The ethyl acetate layer was washed with saturated brine, dried (MgSO$_4$), and concentrated. The residue was washed with hexane to give the title compound (2.05 g, yield 100%) as colorless crystals.

$^1$H-NMR (DMSO-d$_6$) δ: 3.27 (3H, s), 6.50 (1H, d, J=1.51 Hz), 7.23 (1H, d, J=2.07 Hz), 7.28 (1H, dd, J=5.09, 3.77 Hz), 7.56 (1H, dd, J=3.77, 1.32 Hz), 7.71 (1H, s), 8.08 (1H, dd, J=5.09, 1.32 Hz), 12.29 (1H, d, J=1.13 Hz), 13.23 (1H, brs).

Reference Example 160

7-[methyl(2-thienylsulfonyl)amino]-5-(trifluoromethoxy)-1H-indole-2-carboxamide

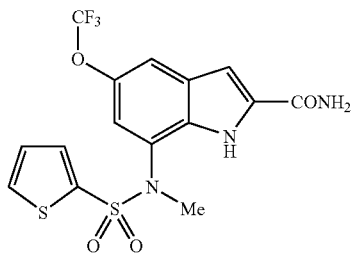

A mixture of 7-[methyl(2-thienylsulfonyl)amino]-5-(trifluoromethoxy)-1H-indole-2-carboxylic acid (1.60 g), 1H-1,2,3-benzotriazol-1-ol (0.77 g), N-[3-(dimethylamino)propyl]-N'-ethylcarbodiimide hydrochloride (1.09 g) and N,N-dimethylformamide (50 mL) was stirred at room temperature for 15 hr. 28% Aqueous ammonia (320 mg) was added to the reaction mixture, and the mixture was further stirred at room temperature for 2 hr. Water was added to the reaction mixture, and the mixture was extracted with ethyl acetate. The ethyl acetate layer was washed successively with aqueous citric acid solution, saturated aqueous sodium hydrogencarbonate and saturated brine, dried (MgSO$_4$), and concentrated. The residue was washed with hexane to give the title compound (1.25 g, yield 79%) as pale-brown crystals. The crystals were recrystallized from ethyl acetate-hexane to give pale-yellow prism crystals. melting point 228-229° C.

Reference Example 161

N-[2-(benzylthio)-3,3-dimethoxypropyl]-7-[methyl(2-thienylsulfonyl)amino]-5-(trifluoromethoxy)-1H-indole-2-carboxamide

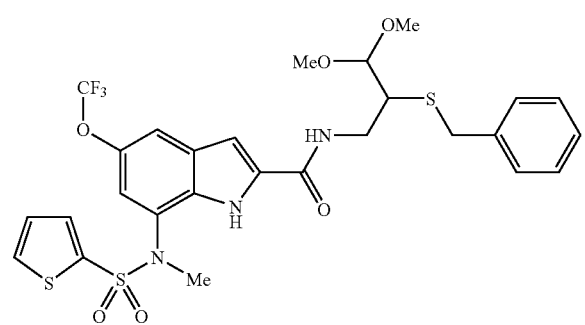

To a mixture of 7-[methyl(2-thienylsulfonyl)amino]-5-(trifluoromethoxy)-1H-indole-2-carboxylic acid (600 mg), 2-(benzylthio)-3,3-dimethoxypropan-1-amine (410 mg), diisopropylethylamine (450 mg) and N,N-dimethylformamide (10 mL) was added O-(7-azabenzotriazol-1-yl)-N,N,N',N'-tetramethyluronium hexafluorophosphate (HATU, 720 mg) at room temperature, and the mixture was stirred for 2.5 days. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (4:1-2:1, volume ratio) to give the title compound (600 mg, yield 67%) as a colorless amorphous solid.

$^1$H-NMR (CDCl$_3$) δ: 2.89-2.94 (1H, m), 3.32 (3H, s), 3.38 (3H, s), 3.48 (3H, s), 3.56-3.65 (1H, m), 3.79-3.88 (3H, m), 4.34 (1H, d, J=4.5 Hz), 6.44 (1H, d, J=1.2 Hz), 6.72 (1H, d, J=2.4 Hz), 6.80-6.84 (1H, m), 7.11-7.36 (6H, m), 7.41-7.47 (2H, m), 7.64-7.67 (1H, m), 9.89 (1H, brs).

Reference Example 162

N-[2-(benzylthio)-3-oxopropyl]-7-[methyl(2-thienylsulfonyl)amino]-5-(trifluoromethoxy)-1H-indole-2-carboxamide

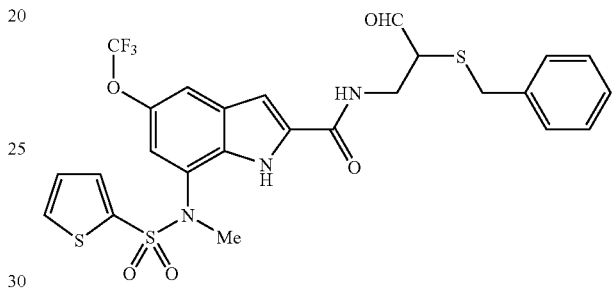

A mixture of N-[2-(benzylthio)-3,3-dimethoxypropyl]-7-[methyl(2-thienylsulfonyl)amino]-5-(trifluoromethoxy)-1H-indole-2-carboxamide (600 mg), Amberlyst (registered trade ark) 15 ion exchange resin (120 mg), water (0.05 mL) and acetone (15 mL) was stirred at room temperature for 15 hr. The insoluble substance was removed by filtration, and the filtrate was concentrated. The residue was subjected to silica gel column chromatography, and eluted with hexane-ethyl acetate (4:1-3:1, volume ratio) to give the title compound (560 mg, yield 100%) as a colorless amorphous solid.

$^1$H-NMR (CDCl$_3$) δ: 3.30 (3H, s), 3.55-3.68 (1H, m), 3.73-3.85 (4H, m), 6.38-6.56 (2H, m), 6.75 (1H, d, J=2.27 Hz), 7.05-7.19 (1H, m), 7.23-7.48 (7H, m), 7.64-7.71 (1H, m), 9.43 (1H, d, J=1.51 Hz), 9.67 (1H, brs).

Reference Example 163

N-[2-(benzylthio)-3-morpholinopropyl]-7-[methyl(2-thienylsulfonyl)amino]-5-(trifluoromethoxy)-1H-indole-2-carboxamide

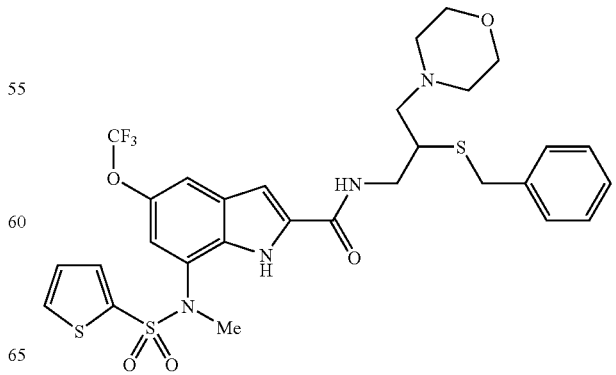

To a mixture of N-[2-(benzylthio)-3-oxopropyl]-7-[methyl (2-thienylsulfonyl)amino]-5-(trifluoromethoxy)-1H-indole-2-carboxamide (560 mg) and 1,2-dichloroethane (15 mL) was added morpholine (170 mg) at room temperature, and the reaction mixture was stirred at room temperature for 30 min. Sodium triacetoxyborohydride (590 mg) was added at room temperature, and the mixture was further stirred at room temperature for 15 hr. Morpholine (170 mg) was added to the reaction mixture at room temperature, and the mixture was stirred at room temperature for 30 min. Sodium triacetoxyborohydride (590 mg) was added at room temperature, and the mixture was further stirred at room temperature for 3 hr. Water was added to the reaction mixture, and the mixture was extracted with ethyl acetate. The ethyl acetate layer was washed with saturated brine, dried (MgSO$_4$), and concentrated. The obtained residue was subjected to basic silica gel column chromatography, and eluted with hexane-ethyl acetate (4:1-2:1, volume ratio) to give the title compound (400 mg, yield 63%) as colorless crystals.

$^1$H-NMR (CDCl$_3$) δ: 2.28-2.63 (6H, m), 2.80-3.00 (1H, m), 3.31 (3H, s), 3.50-3.94 (8H, m), 6.44 (1H, d, J=1.13 Hz), 6.80 (1H, d, J=2.26 Hz), 7.14 (1H, dd, J=4.99, 3.86 Hz), 7.19-7.43 (5H, m), 7.48 (1H, d, J=0.94 Hz), 7.61 (1H, brs), 7.67 (1H, dd, J=5.09, 1.32 Hz), 9.62 (1H, brs).

Reference Example 164

7-[(2-thienylsulfonyl)amino]-5-(trifluoromethoxy)-1H-indole-2-carboxylic acid

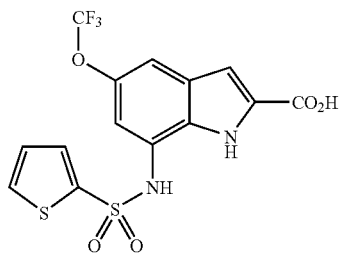

A mixture of ethyl 7-[(2-thienylsulfonyl)amino]-5-(trifluoromethoxy)-1H-indole-2-carboxylate (3.0 g), 1N aqueous sodium hydroxide solution (20 mL), tetrahydrofuran (10 mL) and ethanol (10 mL) was stirred at 60° C. for 1 hr. The reaction mixture was acidified with 1N hydrochloric acid, and extracted with ethyl acetate. The ethyl acetate layer was washed with saturated brine, dried (MgSO$_4$), and concentrated. The residue was washed with hexane to give the title compound (2.60 g, yield 93%) as pale-yellow crystals. The crystals were recrystallized from ethyl acetate-hexane to give pale-yellow prism crystals. melting point 288-290° C. (decomposition).

Reference Example 165

7-[(2-thienylsulfonyl)amino]-5-(trifluoromethoxy)-1H-indole-2-carboxamide

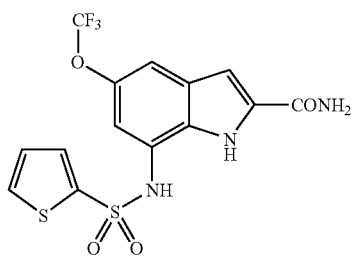

A mixture of 7-[(2-thienylsulfonyl)amino]-5-(trifluoromethoxy)-1H-indole-2-carboxylic acid (2.50 g), 1H-1,2,3-benzotriazol-1-ol-ammonia complex (1.89 g), N-[3-(dimethylamino)propyl]-N'-ethylcarbodiimide hydrochloride (2.38 g) and N,N-dimethylformamide (20 mL) was stirred at room temperature for 15 hr. Water was added to the reaction mixture, and the mixture was extracted with ethyl acetate. The ethyl acetate layer was washed successively with saturated aqueous sodium hydrogencarbonate and saturated brine, dried (MgSO$_4$), and concentrated. The residue was washed with hexane to give the title compound (2.23 g, yield 89%) as pale-yellow crystals. The crystals were recrystallized from ethyl acetate-hexane to give colorless prism crystals. melting point >300° C.

Reference Example 166

4-(2-methoxyethoxy)-2-nitroaniline

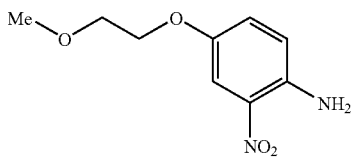

To a mixture of 4-hydroxy-2-nitroaniline (25.0 g), 2-methoxyethanol (21.0 g), tributylphosphine (49.2 g) and tetrahydrofuran (700 mL) was added 1,1'-(azodicarbonyl)dipiperidine (61.3 g) at room temperature, and the mixture was stirred at room temperature for 2.5 days. The precipitate was filtered off, and the filtrate was concentrated. Diisopropyl ether was added to the residue, and the insoluble substance was filtered off. The filtrate was concentrated, and the residue was subjected to basic silica gel column chromatography, and eluted with hexane-ethyl acetate (2:1, volume ratio). The obtained crude product was further subjected to silica gel column chromatography, and eluted with hexane-ethyl acetate (4:1-2:1, volume ratio) to give the title compound (30.9 g, yield 90%) as orange crystals. The crystals were recrystallized from hexane-ethyl acetate to give orange prism crystals. melting point 89-90° C.

Reference Example 167 ethyl 2-{[4-(2-methoxyethoxy)-2-nitrophenyl]hydrazono}propanoate

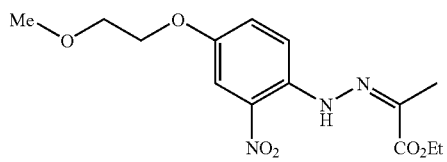

To a mixture of 4-(2-methoxyethoxy)-2-nitroaniline (15.0 g), 6N hydrochloric acid (59 mL) and acetonitrile (50 mL) was added dropwise an aqueous solution (50 mL) of sodium nitrite (4.88 g) at 5-10° C. The reaction mixture was stirred at 5-10° C. for 1.5 hr. This mixture was added to a mixture of ethyl 2-methylacetoacetate (11.2 g), 85% potassium hydroxide (23.8 g), ethanol (50 mL) and water (50 mL) at 10-20° C. The reaction mixture was stirred at 10° C. for 10 min, water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (4:1-2:1, volume ratio) to give the title compound (1.39 g, yield 6%) as orange crystals.

$^1$H-NMR (CDCl$_3$) δ: 1.40 (3H, t, J=7.19 Hz), 2.22 (3H, s), 3.47 (3H, s), 3.74-3.82 (2H, m), 4.12-4.20 (2H, m), 4.35 (2H, q, J=6.94 Hz), 7.33 (1H, dd, J=9.47, 3.03 Hz), 7.65 (1H, d, J=3.03 Hz), 7.99 (1H, d, J=9.47 Hz), 10.84 (1H, brs).

Reference Example 168 ethyl 5-(2-methoxyethoxy)-7-nitro-1H-indole-2-carboxylate

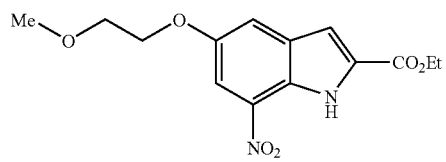

A mixture of ethyl 2-{[4-(2-methoxyethoxy)-2-nitrophenyl]hydrazono}propanoate (250 mg) and polyphosphoric acid (2.0 g) was stirred at 110° C. for 1 hr. After cooling, water and ethyl acetate were added to the reaction mixture, and the mixture was extracted with ethyl acetate. The ethyl acetate layer was washed with saturated brine, dried (MgSO$_4$), and concentrated. The obtained residue was subjected to basic silica gel column chromatography, and eluted with hexane-ethyl acetate (4:1-2:1, volume ratio) to give the title compound (40 mg, yield 17%) as yellow crystals. The crystals were recrystallized from ethyl acetate-hexane to give yellow prism crystals. melting point 90-91° C.

Reference Example 169 ethyl 7-amino-5-(2-methoxyethoxy)-1H-indole-2-carboxylate

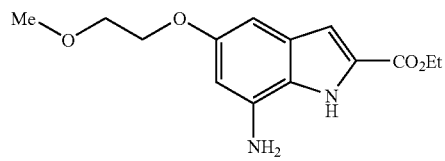

A mixture of ethyl 5-(2-methoxyethoxy)-7-nitro-1H-indole-2-carboxylate (2.30 g), 10% palladium carbon (50% containing water, 500 mg) and tetrahydrofuran (100 mL) was subjected to catalytic reduction at room temperature under hydrogen atmosphere at normal pressure. The catalyst was removed by filtration, and the filtrate was concentrated. The residue was washed with hexane to give the title compound (2.07 g, yield 99%) as pale-brown crystals. The crystals were recrystallized from ethyl acetate-hexane to give pale-brown prism crystals. melting point 162-163° C.

Reference Example 170 ethyl 5-(2-methoxyethoxy)-7-[(2-thienylsulfonyl)amino]-1H-indole-2-carboxylate

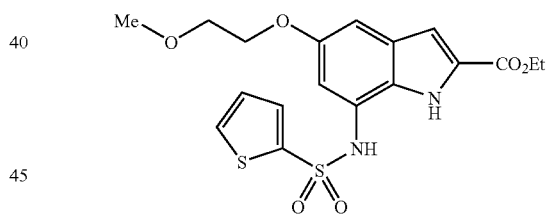

To a mixture of ethyl 7-amino-5-(2-methoxyethoxy)-1H-indole-2-carboxylate (2.00 g) and pyridine (30 mL) was added thiophene-2-sulfonyl chloride (1.57 g) at 0° C., and the mixture was stirred at room temperature for 15 hr. The reaction mixture was concentrated, aqueous citric acid solution was added to the residue, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (4:1-1:1, volume ratio) to give the title compound (1.62 g, yield 53%) as colorless crystals. The crystals were recrystallized from ethyl acetate-hexane to give colorless prism crystals. melting point 106-107° C.

Reference Example 171 ethyl 5-(2-methoxyethoxy)-7-[methyl(2-thienylsulfonyl)amino]-1H-indole-2-carboxylate

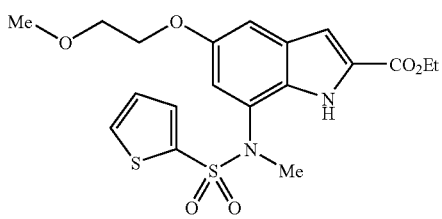

A mixture of ethyl 5-(2-methoxyethoxy)-7-[(2-thienylsulfonyl)amino]-1H-indole-2-carboxylate (1.50 g), potassium carbonate (480 mg) and N,N-dimethylformamide (20 mL) was stirred at 0° C. for 30 min. Methyl iodide (550 mg) was added at 0° C. to the reaction mixture, and the mixture was stirred at room temperature for 15 hr. Water was added to the reaction mixture, and the mixture was extracted with ethyl acetate. The ethyl acetate layer was washed with saturated brine, dried over magnesium sulfate, and concentrated. The obtained residue was subjected to basic silica gel column chromatography, and eluted with ethyl acetate-hexane (4:1-2:1) to give the title compound (1.30 g, yield 85%) as a colorless oil.

$^1$H-NMR (CDCl$_3$) δ: 1.42 (3H, t, J=7.00 Hz), 3.29 (3H, s), 3.43 (3H, s), 3.64-3.79 (2H, m), 3.96-4.10 (2H, m), 4.42 (2H, q, J=7.19 Hz), 6.41 (1H, d, J=1.89 Hz), 7.05 (1H, d, J=1.89 Hz), 7.09-7.20 (2H, m), 7.35-7.45 (1H, m), 7.55-7.69 (1H, m), 9.22 (1H, brs).

Reference Example 172

5-(2-methoxyethoxy)-7-[methyl(2-thienylsulfonyl)amino]-1H-indole-2-carboxylic acid

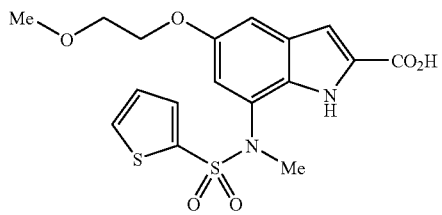

A mixture of ethyl 5-(2-methoxyethoxy)-7-[methyl(2-thienylsulfonyl)amino]-1H-indole-2-carboxylate (1.30 g), 1N aqueous sodium hydroxide solution (10 mL), tetrahydrofuran (10 mL) and ethanol (10 mL) was stirred at room temperature for 15 hr. The reaction mixture was acidified with aqueous citric acid solution, and extracted with ethyl acetate. The ethyl acetate layer was washed successively with water and saturated brine, dried (MgSO$_4$), and concentrated to give the title compound (1.15 g, yield 93%) as colorless crystals. The crystals were recrystallized from ethyl acetate-hexane to give colorless prism crystals. melting point 198-199° C.

Reference Example 173

5-(2-methoxyethoxy)-7-[methyl(2-thienylsulfonyl)amino]-1H-indole-2-carboxamide

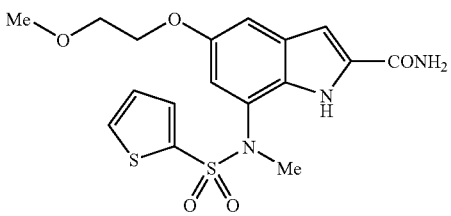

A mixture of 5-(2-methoxyethoxy)-7-[methyl(2-thienylsulfonyl)amino]-1H-indole-2-carboxylic acid (1.05 g), 1H-1,2,3-benzotriazol-1-ol-ammonia complex (590 mg), N-[3-(dimethylamino)propyl]-N'-ethylcarbodiimide hydrochloride (750 mg) and N,N-dimethylformamide (5 mL) was stirred at room temperature for 15 hr. Water was added to the reaction mixture, and the mixture was extracted with ethyl acetate. The ethyl acetate layer was washed successively with aqueous citric acid solution, saturated aqueous sodium hydrogencarbonate and saturated brine, dried (MgSO$_4$), and concentrated to give the title compound (1.00 g, yield 94%) as colorless crystals. The crystals were recrystallized from acetone-hexane to give colorless prism crystals. melting point 214-215° C.

Reference Example 174 ethyl 2-[(4-hydroxy-2-nitrophenyl)hydrazono]propanoate

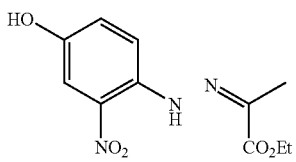

To a mixture of 4-hydroxy-2-nitroaniline (5.0 g), 1N hydrochloric acid (65 mL) and acetonitrile (20 mL) was added dropwise an aqueous solution (10 mL) of sodium nitrite (2.44 g) at 0-5° C., and the reaction mixture was stirred at 0° C. for 10 min. This mixture was added dropwise to a mixture of ethyl 2-methylacetoacetate (5.61 g), 85% potassium hydroxide (4.37 g), ethanol (50 mL) and water (50 mL) at 0-5° C. After the completion of the dropwise addition, 1N hydrochloric acid (13 mL) and water were added, and the mixture was extracted with ethyl acetate. The organic layer was washed with saturated brine, dried (MgSO$_4$), and concentrated. The obtained residue was washed with hexane to give the title compound (4.94 g, yield 57%) as brown crystals.

$^1$H-NMR (DMSO-d$_6$) δ: 1.29 (3H, t, J=7.06 Hz), 2.13 (3H, s), 4.24 (2H, q, J=7.03 Hz), 7.30 (1H, dd, J=9.14, 2.73 Hz), 7.46-7.52 (1H, m), 7.74 (1H, d, J=9.23 Hz), 9.95 (1H, s), 10.44 (1H, s).

Reference Example 175 ethyl 5-hydroxy-7-nitro-1H-indole-2-carboxylate

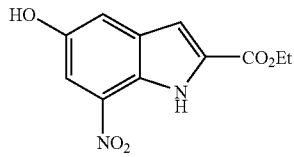

A mixture of Eaton's reagent (1.0 g) and methanesulfonic acid (1.0 g) was stirred at 100° C. for 10 min.

A mixture of ethyl 2-[(4-hydroxy-2-nitrophenyl)hydrazono]propanoate (1.0 g) and toluene (10 mL) was added to the mixture, and the mixture was further stirred at 100° C. for 1 hr. Water was added to the reaction mixture, and the mixture was extracted with ethyl acetate. The ethyl acetate layer was washed with saturated brine, dried (MgSO$_4$), and concentrated. The residue was subjected to basic silica gel column chromatography, and eluted with ethyl acetate-methanol (98: 2-95:5, volume ratio) to give the title compound (250 mg, yield 27%) as orange crystals.

$^1$H-NMR (DMSO-d$_6$) δ: 1.35 (3H, t, J=7.00 Hz), 4.37 (2H, q, J=7.07 Hz), 7.30 (1H, s), 7.56 (1H, d, J=2.27 Hz), 7.74 (1H, d, J=2.27 Hz), 9.93 (1H, brs), 11.05 (1H, brs).

Reference Example 176 ethyl 5-[3-(methylsulfonyl)propoxy]-7-nitro-1H-indole-2-carboxylate

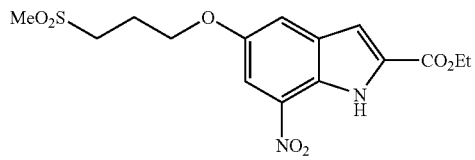

A mixture of ethyl 5-hydroxy-7-nitro-1H-indole-2-carboxylate (300 mg), 3-(methylsulfonyl)propyl 4-methylbenzenesulfonate (410 mg), potassium carbonate (170 mg) and N,N-dimethylformamide (10 mL) was stirred at room temperature for 15 hr. Ethyl 5-hydroxy-7-nitro-1H-indole-2-carboxylate (100 mg) was added to the reaction mixture, and the mixture was further stirred at 50° C. for 3 hr. Water was added to the reaction mixture, and the mixture was extracted with ethyl acetate. The ethyl acetate layer was washed with saturated brine, dried (MgSO$_4$), and concentrated. The obtained residue was washed with diisopropyl ether to give the title compound (400 mg, yield 77%) as yellow crystals. The crystals were recrystallized from acetone-hexane to give yellow prism crystals. melting point 162-163° C.

Reference Example 177 ethyl 7-amino-5-[3-(methylsulfonyl)propoxy]-1H-indole-2-carboxylate

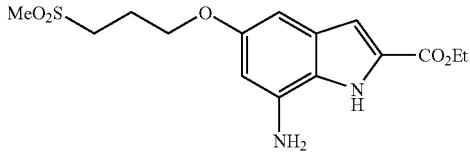

A mixture of ethyl 5-[3-(methylsulfonyl)propoxy]-7-nitro-1H-indole-2-carboxylate (200 mg), 10% palladium-carbon (50% containing water, 100 mg) and tetrahydrofuran (20 mL) was subjected to catalytic reduction at room temperature under hydrogen atmosphere at normal pressure. The catalyst was filtered off, and the filtrate was concentrated. The obtained crystals were washed with hexane to give the title compound (140 mg, yield 78%) as pale-yellow crystals. The crystals were recrystallized from ethyl acetate-hexane to give pale-yellow prism crystals. melting point 187-188° C.

Reference Example 178 ethyl 5-[3-(methylsulfonyl)propoxy]-7-[(pyridin-2-ylsulfonyl)amino]-1H-indole-2-carboxylate

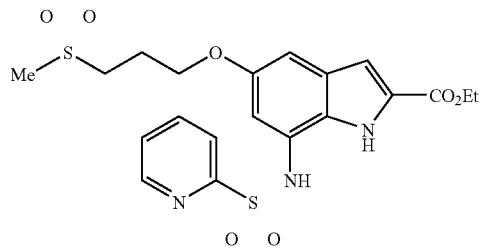

To a mixture of ethyl 7-amino-5-[3-(methylsulfonyl)propoxy]-1H-indole-2-carboxylate (4.8 g) and pyridine (50 mL) was added pyridine-2-sulfonyl chloride (3.0 g) at 0° C., and the mixture was stirred at 0° C. for 1 hr. The reaction mixture was concentrated, aqueous citric acid solution was added to the residue, and the mixture was extracted with ethyl acetate. The ethyl acetate layer was washed successively with water and saturated brine, dried (MgSO$_4$), and concentrated. The obtained crystals were washed with diisopropyl ether, and recrystallized from acetone-hexane to give the title compound (4.68 g, yield 69%) as pale-brown prism crystals. melting point 194-195° C.

Reference Example 179 ethyl 7-[methyl(pyridin-2-ylsulfonyl)amino]-5-[3-(methylsulfonyl)propoxy]-1H-indole-2-carboxylate

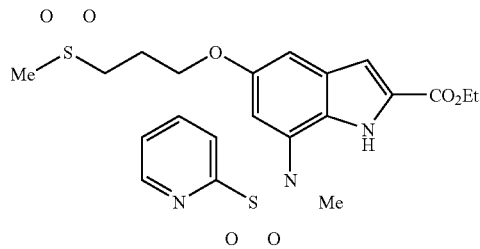

To a mixture of ethyl 5-[3-(methylsulfonyl)propoxy]-7-[(pyridin-2-ylsulfonyl)amino]-1H-indole-2-carboxylate (3.50 g), potassium carbonate (1.01 g) and N,N-dimethylformamide (50 mL) was added methyl iodide (1.14 g) at 0° C., and the reaction mixture was stirred at room temperature for 15 hr. Water was added to the reaction mixture, and the mixture was extracted with a mixed solvent of ethyl acetate-tetrahydrofuran. The organic layer was washed with saturated brine, dried (MgSO$_4$), and concentrated. The obtained residue was subjected to basic silica gel column chromatography, and eluted with hexane-ethyl acetate (1:1-1:4, volume ratio) to give the title compound (2.70 g, yield 75%) as colorless crystals. The crystals were recrystallized from ethyl acetate-hexane to give colorless prism crystals. melting point 176-177° C.

Reference Example 180

7-[methyl(pyridin-2-ylsulfonyl)amino]-5-[3-(methylsulfonyl)propoxy]-1H-indole-2-carboxylic acid

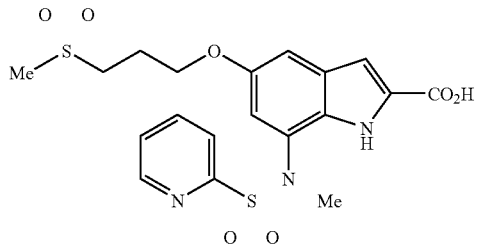

A mixture of ethyl 7-[methyl(pyridin-2-ylsulfonyl)amino]-5-[3-(methylsulfonyl)propoxy]-1H-indole-2-carboxylate (2.50 g), 1N aqueous sodium hydroxide solution (10 mL), ethanol (10 mL) and tetrahydrofuran (10 mL) was stirred at 60° C. for 1.5 hr. 1N Hydrochloric acid (10 mL) and water were added to the reaction mixture, and the mixture was extracted with ethyl acetate. The ethyl acetate layer was washed with saturated brine, dried (MgSO$_4$), and concentrated to give the title compound (2.30 g, yield 98%) as colorless crystals. The crystals were recrystallized from acetone-hexane to give colorless prism crystals. melting point 207-208° C.

Reference Example 181

N-[2-(benzylthio)-3,3-dimethoxypropyl]-7-[methyl(pyridin-2-ylsulfonyl)amino]-5-[3-(methylsulfonyl)propoxy]-1H-indole-2-carboxamide

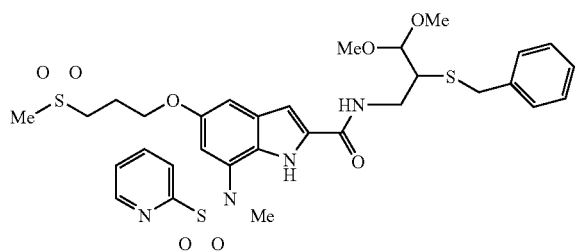

A mixture of 7-[methyl(pyridin-2-ylsulfonyl)amino]-5-[3-(methylsulfonyl)propoxy]-1H-indole-2-carboxylic acid (2.10 g), 2-(benzylthio)-3,3-dimethoxypropan-1-amine (1.30 g), 1H-1,2,3-benzotriazol-1-ol (730 mg), N-[3-(dimethylamino)propyl]-N'-ethylcarbodiimide hydrochloride (1.04 g) and N,N-dimethylformamide (50 mL) was stirred at room temperature for 15 hr. Water was added to the reaction mixture, and the mixture was extracted with ethyl acetate. The ethyl acetate layer was washed successively with saturated aqueous sodium hydrogencarbonate and saturated brine, dried (MgSO$_4$), and concentrated. The obtained residue was subjected to silica gel column chromatography, and eluted with hexane-ethyl acetate (1:4-1:9, volume ratio) to give the title compound (2.70 g, yield 87%) as a colorless amorphous solid.

$^1$H-NMR (CDCl$_3$) δ: 2.29-2.43 (2H, m), 2.86-3.01 (1H, m), 2.96 (3H, s), 3.22-3.33 (5H, m), 3.39 (3H, s), 3.48 (3H, s), 3.56-3.71 (1H, m), 3.76-3.93 (3H, m), 4.04-4.19 (2H, m), 4.31-4.40 (1H, m), 6.62-6.68 (1H, m), 6.80 (1H, t, J=5.68 Hz), 6.93-7.01 (1H, m), 7.07 (1H, d, J=1.89 Hz), 7.14-7.31 (3H, m), 7.31-7.40 (2H, m), 7.63 (1H, dd, J=7.57, 4.92 Hz), 7.99 (1H, t, J=7.00 Hz), 8.13 (1H, d, J=7.95 Hz), 9.24 (1H, d, J=4.54 Hz), 12.31 (1H, brs).

Reference Example 182

N-[2-(benzylthio)-3-oxopropyl]-7-[methyl(pyridin-2-ylsulfonyl)amino]-5-[3-(methylsulfonyl)propoxy]-1H-indole-2-carboxamide

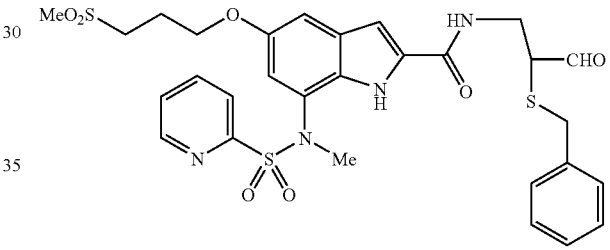

A mixture of N-[2-(benzylthio)-3,3-dimethoxypropyl]-7-[methyl(pyridin-2-ylsulfonyl)amino]-5-[3-(methylsulfonyl)propoxy]-1H-indole-2-carboxamide (1.5 g), Amberlyst (registered trade mark) 15 ion exchange resin (0.35 g), acetone (30 mL) and water (0.15 mL) was stirred at room temperature for 18 hr. Amberlyst (registered trade mark) 15 ion exchange resin was filtered off, and washed with ethyl acetate. The filtrate was concentrated under reduced pressure to give the title compound (1.4 g, yield: 100%) as a pale-yellow amorphous solid. MS: 645 (MH$^+$).

Reference Example 183

N-[2-(benzylthio)-3-morpholinopropyl]-7-[methyl(pyridin-2-ylsulfonyl)amino]-5-[3-(methylsulfonyl)propoxy]-1H-indole-2-carboxamide

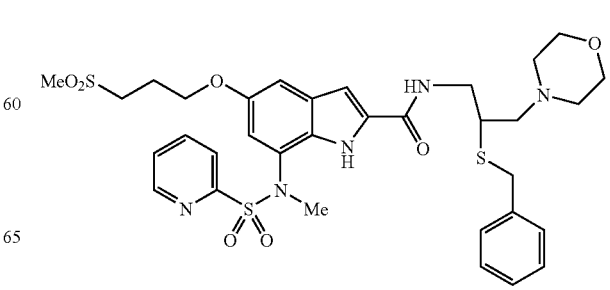

A solution of N-[2-(benzylthio)-3-oxopropyl]-7-[methyl(pyridin-2-ylsulfonyl)amino]-5-[3-(methylsulfonyl)propoxy]-1H-indole-2-carboxamide (0.90 g) and morpholine (0.15 mL) in tetrahydrofuran (20 mL) was stirred at room temperature for 30 min, and ice-cooled. Sodium triacetoxyborohydride (0.39 g) was added to this solution, and the mixture was stirred from under ice-cooling to room temperature for 16 hr. The reaction solution was acidified with aqueous citric acid solution, basified with aqueous sodium hydrogencarbonate solution, and extracted with ethyl acetate. The organic layer was washed with saturated brine, dried over anhydrous magnesium sulfate, and concentrated under reduced pressure. The obtained residue was subjected to silica gel column chromatography (ethyl acetate:hexane=6:4-10:0) to give the title compound (0.89 g, yield: 89%) as a colorless amorphous solid. MS: 716 (MH$^+$).

Reference Example 184

N-[2-(benzylthio)-3-thiomorpholinopropyl]-7-[methyl(pyridin-2-ylsulfonyl)amino]-5-[3-(methylsulfonyl)propoxy]-1H-indole-2-carboxamide

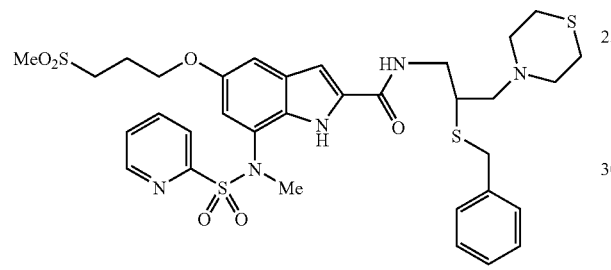

A mixture of N-[2-(benzylthio)-3-oxopropyl]-7-[methyl(pyridin-2-ylsulfonyl)amino]-5-[3-(methylsulfonyl)propoxy]-1H-indole-2-carboxamide (0.75 g), thiomorpholine (0.24 mL) and 1,2-dichloroethane (20 mL) was stirred at room temperature for 15 min. Sodium triacetoxyborohydride (0.74 g) was added to the reaction solution, and the mixture was stirred at room temperature for 5 hr. The reaction solution was acidified with aqueous citric acid solution, basified with aqueous sodium hydrogencarbonate solution, and extracted with ethyl acetate. The organic layer was washed with saturated brine, dried over anhydrous magnesium sulfate, and concentrated under reduced pressure. The obtained residue was subjected to silica gel column chromatography (ethyl acetate:hexane=5:5-10:0) to give the title compound (0.76 g, yield: 89%) as a colorless amorphous solid. MS: 733 (MH$^+$).

Reference Example 185

N-[3-(4-acetylpiperazin-1-yl)-2-(benzylthio)propyl]-7-[methyl(pyridin-2-ylsulfonyl)amino]-5-[3-(methylsulfonyl)propoxy]-1H-indole-2-carboxamide

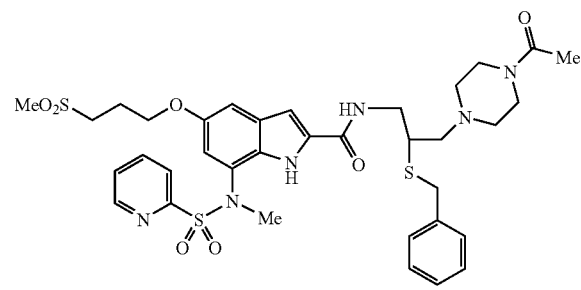

A mixture of N-[2-(benzylthio)-3-oxopropyl]-7-[methyl(pyridin-2-ylsulfonyl)amino]-5-[3-(methylsulfonyl)propoxy]-1H-indole-2-carboxamide (0.35 g), N-acetylpiperazine (0.14 g) and 1,2-dichloroethane (8 mL) was stirred at room temperature for 10 min. Sodium triacetoxyborohydride (345 mg) was added to the reaction solution, and the mixture was stirred at room temperature for 16 hr. The reaction solution was acidified with aqueous citric acid solution, basified with aqueous sodium hydrogencarbonate solution, and extracted with ethyl acetate. The organic layer was washed with saturated brine, dried over anhydrous magnesium sulfate, and concentrated under reduced pressure. The obtained residue was subjected to silica gel column chromatography (ethyl acetate:methanol=10:0-9:1) to give the title compound (0.35 g, yield: 85%) as a colorless amorphous solid. MS: 756 (MH$^+$).

Reference Example 186

N-{2-(benzylthio)-3-[4-(methylsulfonyl)piperazin-1-yl]propyl}-7-[methyl(pyridin-2-ylsulfonyl)amino]-5-[3-(methylsulfonyl)propoxy]-1H-indole-2-carboxamide

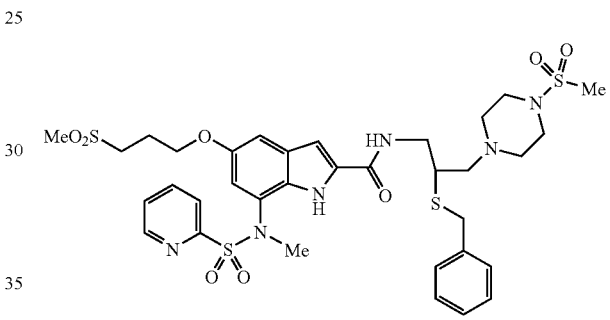

A mixture of N-[2-(benzylthio)-3-oxopropyl]-7-[methyl(pyridin-2-ylsulfonyl)amino]-5-[3-(methylsulfonyl)propoxy]-1H-indole-2-carboxamide (0.35 g), N-methylsulfonylpiperazine (0.18 g) and 1,2-dichloroethane (8 mL) was stirred at room temperature for 20 min. Sodium triacetoxyborohydride (345 mg) was added to the reaction solution, and the mixture was stirred at room temperature for 16 hr. The reaction solution was acidified with aqueous citric acid solution, and basified with aqueous sodium hydrogencarbonate solution. The precipitated crystals were collected by filtration, washed with water and ethyl acetate, and dried to give the title compound (341 mg, yield: 43%) as colorless crystals. MS: 794 (MH$^+$). melting point: 195-196° C.

Reference Example 187

N-[2-(benzylthio)-3,3-dimethoxypropyl]-5-(2-methoxyethoxy)-7-[methyl(pyridin-2-ylsulfonyl)amino]-1H-indole-2-carboxamide

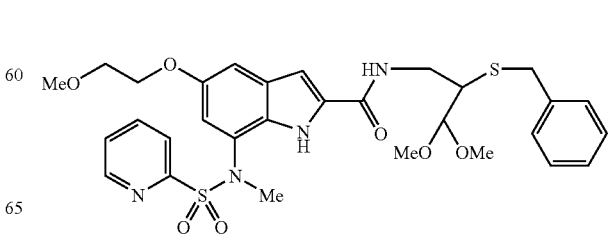

5-(2-methoxyethoxy)-7-[methyl(pyridin-2-ylsulfonyl) amino]-1H-indole-2-carboxylic acid (2.50 g), 2-(benzylthio)-3,3-dimethoxypropan-1-amine (1.79 g), diisopropylethylamine (2.00 g) and N,N-dimethylformamide (30 mL) was added O-(7-azabenzotriazol-1-yl)-N,N,N',N'-tetramethyluronium hexafluorophosphate (HATU, 3.19 g) at room temperature, and the mixture was stirred at room temperature for 2.5 days. Water was added to the reaction mixture, and the mixture was extracted with ethyl acetate. The ethyl acetate layer was washed successively with aqueous citric acid solution, saturated aqueous sodium hydrogencarbonate and saturated brine, dried (MgSO$_4$), and concentrated. The obtained residue was subjected to silica gel column chromatography, and eluted with hexane-ethyl acetate (1:1-1:4, volume ratio) to give the title compound (3.11 g, yield 80%) as a colorless amorphous solid.

$^1$H-NMR (CDCl$_3$) δ: 2.85-2.99 (1H, m), 3.29 (3H, s), 3.39 (3H, s), 3.47 (6H, s), 3.55-3.69 (1H, m), 3.72-3.93 (5H, m), 4.10-4.21 (2H, m), 4.35 (1H, d, J=4.54 Hz), 6.64 (1H, d, J=2.27 Hz), 6.78 (1H, t, J=5.49 Hz), 7.00 (1H, d, J=2.27 Hz), 7.09 (1H, d, J=1.89 Hz), 7.14-7.22 (1H, m), 7.22-7.38 (4H, m), 7.61 (1H, dd, J=7.00, 3.98 Hz), 7.92-8.03 (1H, m), 8.10 (1H, d, J=7.95 Hz), 9.21 (1H, d, J=4.17 Hz), 12.15 (1H, brs).

Reference Example 188

5-(2-methoxyethoxy)-7-[(pyridin-2-ylsulfonyl) amino]-1H-indole-2-carboxylic acid

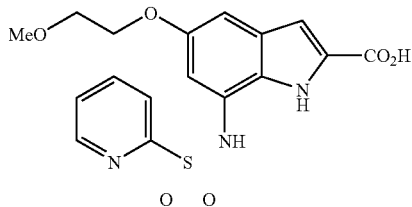

To a mixture of ethyl 5-(2-methoxyethoxy)-7-[(pyridin-2-ylsulfonyl)amino]-1H-indole-2-carboxylate (5.40 g), tetrahydrofuran (50 mL) and methanol (50 mL) was added a 85% aqueous solution (30 mL) of potassium hydroxide (3.0 g), and the mixture was stirred at room temperature for 15 hr. The reaction mixture was concentrated, aqueous citric acid solution was added to the residue, and the mixture was extracted with ethyl acetate. The ethyl acetate layer was washed with water, and concentrated to give a white solid. The obtained solid was washed with a mixed solvent of ethyl acetate-hexane to give the title compound (4.24 g, yield 84%) as colorless crystals. melting point 230-232° C.

Reference Example 189

N-[2-(benzylthio)-3,3-dimethoxypropyl]-5-(2-methoxyethoxy)-7-[(pyridin-2-ylsulfonyl)amino]-1H-indole-2-carboxamide

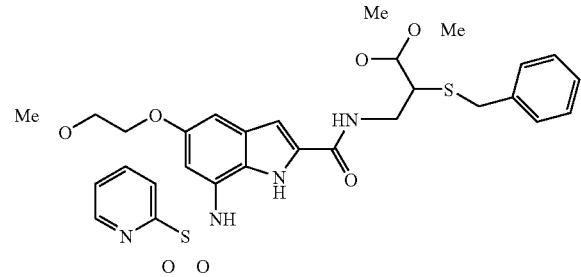

A mixture of 5-(2-methoxyethoxy)-7-[(pyridin-2-ylsulfonyl)amino]-1H-indole-2-carboxylic acid (4.24 g), 2-(benzylthio)-3,3-dimethoxypropan-1-amine (2.88 g), 1H-1,2,3-benzotriazol-1-ol (1.80 g), N-[3-(dimethylamino)propyl]-N'-ethylcarbodiimide hydrochloride (2.70 g) and N,N-dimethylformamide (40 mL) was stirred at room temperature for 3 days. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (2:3-1:4, volume ratio) to give the title compound (6.03 g, yield 91%) as a colorless amorphous solid.

$^1$H-NMR (CDCl$_3$) δ: 2.95-3.06 (1H, m), 3.12-3.36 (1H, m), 3.38 (3H, s), 3.45 (3H, s), 3.46 (3H, s), 3.72-3.80 (3H, m), 3.83 (2H, s), 4.06-4.16 (2H, m), 4.37 (1H, d, J=4.16 Hz), 6.59 (1H, d, J=1.89 Hz), 6.87 (1H, d, J=1.89 Hz), 7.07-7.23 (5H, m), 7.28-7.34 (2H, m), 7.37-7.45 (1H, m), 7.56-7.67 (1H, m), 7.83 (1H, d, J=7.57 Hz), 8.27 (1H, d, J=4.17 Hz), 9.18 (1H, brs), 11.30 (1H, brs).

Reference Example 190

N-[2-(benzylthio)-3-oxopropyl]-5-(2-methoxyethoxy)-7-[(pyridin-2-ylsulfonyl)amino]-1H-indole-2-carboxamide

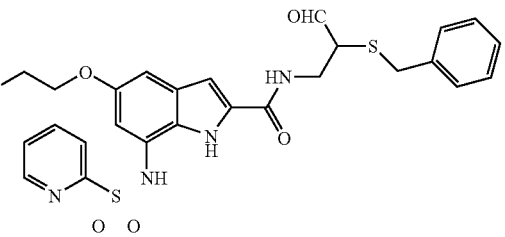

A mixture of N-[2-(benzylthio)-3,3-dimethoxypropyl]-5-(2-methoxyethoxy)-7-[(pyridin-2-ylsulfonyl)amino]-1H-indole-2-carboxamide (3.0 g), Amberlyst (registered trademark) 15 ion exchange resin (600 mg), acetone (80 mL) and water (260 mg) was stirred at room temperature for 15 hr. The insoluble substance was removed by filtration, and the filtrate was concentrated. The residue was subjected to silica gel column chromatography, and eluted with hexane-ethyl acetate (2:3-1:9, volume ratio) to give the title compound (2.09 g, yield 75%) as colorless crystals.

$^1$H-NMR (CDCl$_3$) δ: 3.46 (3H, s), 3.70-3.79 (5H, m), 3.86-4.01 (2H, m), 4.05-4.13 (2H, m), 6.67 (1H, d, J=2.07 Hz), 6.71-6.80 (1H, m), 6.84 (1H, d, J=1.88 Hz), 7.10 (1H, d, J=1.88 Hz), 7.16-7.37 (5H, m), 7.57-7.69 (1H, m), 7.83 (1H, d, J=7.72 Hz), 8.25 (1H, d, J=3.01 Hz), 8.86 (1H, brs), 9.39 (1H, d, J=1.32 Hz), 11.21 (1H, brs).

Reference Example 191

N-[2-(benzylthio)-3-(1,1-dioxidothiomorpholino)propyl]-5-(2-methoxyethoxy)-7-[(pyridin-2-ylsulfonyl)amino]-1H-indole-2-carboxamide

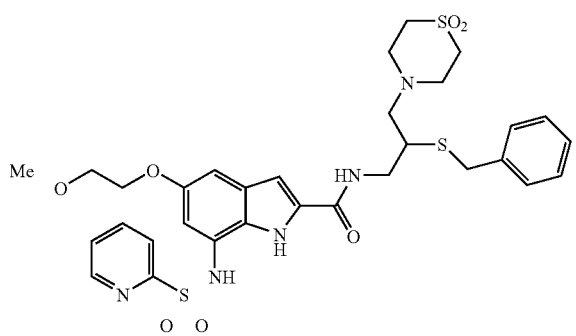

A mixture of N-[2-(benzylthio)-3-oxopropyl]-5-(2-methoxyethoxy)-7-[(pyridin-2-ylsulfonyl)amino]-1H-indole-2-carboxamide (500 mg), thiomorpholine 1,1-dioxide (240 mg) and tetrahydrofuran (10 mL) was stirred at room temperature for 30 min. Sodium triacetoxyborohydride (280 mg) was added at room temperature, and the mixture was stirred at room temperature for 2 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (3:7-1:9, volume ratio) to give the title compound (210 mg, yield 35%) as a colorless amorphous solid.

$^1$H-NMR (CDCl$_3$) δ: 2.65 (2H, d, J=7.19 Hz), 2.79-3.14 (8H, m), 3.47 (3H, s), 3.49-3.63 (1H, m), 3.68-3.85 (4H, m), 4.03-4.20 (3H, m), 6.64 (1H, d, J=1.51 Hz), 6.88 (1H, d, J=1.51 Hz), 6.95-7.08 (1H, m), 7.08-7.36 (8H, m), 7.53-7.70 (1H, m), 7.84 (1H, d, J=7.95 Hz), 8.05 (1H, d, J=4.17 Hz), 9.10 (1H, brs), 11.44 (1H, brs).

Reference Example 192

N-[2-(benzylthio)-3-thiomorpholinopropyl]-5-(2-methoxyethoxy)-7-[(pyridin-2-ylsulfonyl)amino]-1H-indole-2-carboxamide

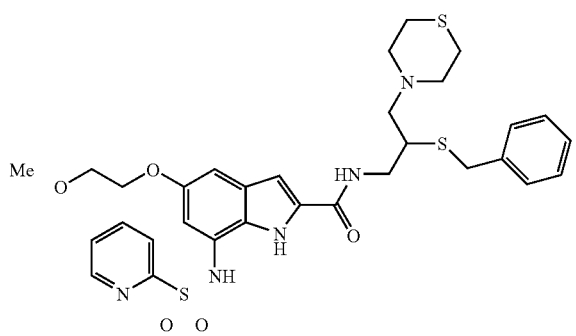

A mixture of N-[2-(benzylthio)-3-oxopropyl]-5-(2-methoxyethoxy)-7-[(pyridin-2-ylsulfonyl)amino]-1H-indole-2-carboxamide (800 mg), thiomorpholine (290 mg) and tetrahydrofuran (30 mL) was stirred at room temperature for 30 min. Sodium triacetoxyborohydride (450 mg) was added at room temperature, and the mixture was stirred at room temperature for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (3:2-1:4, volume ratio) to give the title compound (590 mg, yield 64%) as colorless crystals. The crystals were recrystallized from acetone-hexane to give colorless prism crystals. melting point 160-161° C.

Reference Example 193 ethyl 2-{[4-(3-methoxypropoxy)-2-nitrophenyl]hydrazono}propanoate

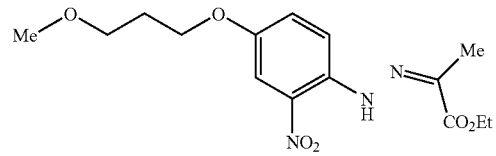

To a mixture of ethyl 2-[(4-hydroxy-2-nitrophenyl)hydrazono]propanoate (6.81 g), potassium carbonate (3.52 g) and N,N-dimethylformamide (100 mL) was added 1-bromo-3-methoxypropane (3.90 g) at 60° C., and the mixture was stirred at 60° C. for 15 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (4:1-1:1, volume ratio) to give the title compound (3.67 g, yield 42%) as orange crystals.

$^1$H-NMR (CDCl$_3$) δ: 1.39 (3H, t, J=7.19 Hz), 2.01-2.14 (2H, m), 2.22 (3H, s), 3.37 (3H, s), 3.56 (2H, t, J=6.06 Hz), 4.09 (2H, t, J=6.25 Hz), 4.35 (2H, q, J=7.07 Hz), 7.23-7.31 (1H, m), 7.64 (1H, d, J=2.65 Hz), 7.98 (1H, d, J=9.09 Hz), 10.82 (1H, s).

Reference Example 194 ethyl 5-(3-methoxypropoxy)-7-nitro-1H-indole-2-carboxylate

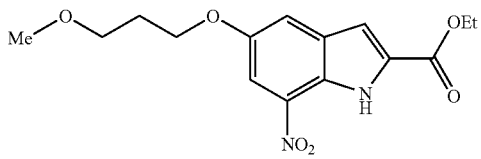

Methanesulfonic acid (15 g) was added to Eaton's reagent (15 g) at 90° C., and the mixture was stirred at 90° C. for 30 min. A toluene solution (150 mL) of ethyl 2-{[4-(3-methoxypropoxy)-2-nitrophenyl]hydrazono}propanoate (16.17 g) was added dropwise to the mixture, and the reaction mixture was stirred at 90° C. for 30 min. Ice water was added to the reaction mixture, and the mixture was extracted with ethyl acetate. The ethyl acetate layer was washed successively with water, saturated aqueous sodium hydrogencarbonate and saturated brine, dried (MgSO$_4$), and concentrated. The obtained residue was subjected to silica gel column chromatography, and eluted with hexane-ethyl acetate (4:1-2:1, volume ratio) to give the title compound (6.51 g, yield 42%) as orange crystals. The crystals were recrystallized from ethyl acetate-hexane to give orange prism crystals. melting point 94-95° C.

Reference Example 195 ethyl 7-amino-5-(3-methoxypropoxy)-1H-indole-2-carboxylate

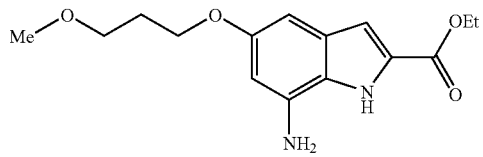

A mixture of ethyl 5-(3-methoxypropoxy)-7-nitro-1H-indole-2-carboxylate (6.15 g), 10% palladium-carbon (50% containing water, 1.0 g) and tetrahydrofuran (150 mL) was subjected to catalytic reduction at room temperature under hydrogen atmosphere at normal pressure. The catalyst was filtered off, and the filtrate was concentrated. The obtained crystals were washed with diisopropyl ether to give the title compound (5.41 g, yield 97%) as yellow crystals. The crystals were recrystallized from ethyl acetate-diisopropyl ether to give pale-yellow prism crystals. melting point 139-140° C.

Reference Example 196 ethyl 5-(3-methoxypropoxy)-7-[(pyridin-2-ylsulfonyl)amino]-1H-indole-2-carboxylate

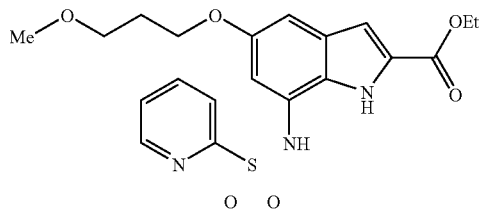

To a mixture of ethyl 7-amino-5-(3-methoxypropoxy)-1H-indole-2-carboxylate (3.00 g) and pyridine (50 mL) was added pyridine-2-sulfonyl chloride (2.0 g) at 0° C., and the mixture was stirred at room temperature for 15 hr. The reaction mixture was concentrated, 1N hydrochloric acid and ethyl acetate were added to the residue, and the mixture was extracted with ethyl acetate. The ethyl acetate layer was washed successively with water and saturated brine, dried (MgSO$_4$), and concentrated. The obtained residue was subjected to silica gel column chromatography, and eluted with hexane-ethyl acetate (2:1-1:1, volume ratio) to give the title compound (4.02 g, yield 90%) as colorless crystals. The crystals were recrystallized from ethyl acetate-hexane to give colorless prism crystals. melting point 126-127° C.

Reference Example 197 ethyl 5-(3-methoxypropoxy)-7-[methyl(pyridin-2-ylsulfonyl)amino]-1H-indole-2-carboxylate

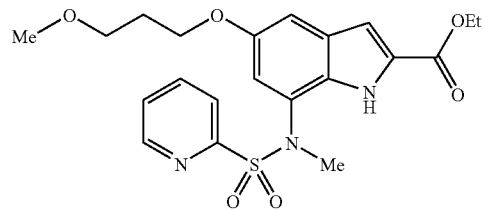

To a mixture of ethyl 5-(3-methoxypropoxy)-7-[(pyridin-2-ylsulfonyl)amino]-1H-indole-2-carboxylate (3.97 g), potassium carbonate (1.27 g) and N,N-dimethylformamide (30 mL) was added methyl iodide (1.56 g) at room temperature, and the reaction mixture was stirred at room temperature for 2 hr. Water was added to the reaction mixture, and the mixture was extracted with ethyl acetate. The ethyl acetate layer was washed with saturated brine, dried (MgSO$_4$), and concentrated. The obtained residue was crystallized from ethyl acetate-hexane, and the crystals were washed with hexane to give the title compound (3.63 g, yield 88%) as colorless crystals. The crystals were recrystallized from ethyl acetate-hexane to give colorless prism crystals. melting point 98-99° C.

Reference Example 198

5-(3-methoxypropoxy)-7-[methyl(pyridin-2-ylsulfonyl)amino]-1H-indole-2-carboxylic acid

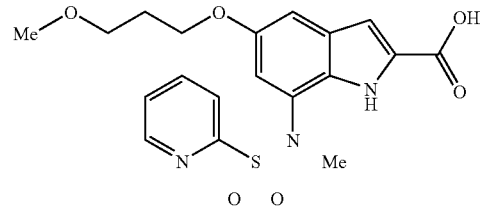

A mixture of ethyl 5-(3-methoxypropoxy)-7-[methyl(pyridin-2-ylsulfonyl)amino]-1H-indole-2-carboxylate (3.50 g), 1N aqueous sodium hydroxide solution (10 mL), ethanol (10 mL) and tetrahydrofuran (10 mL) was stirred at 50° C. for 1 hr. 1N Hydrochloric acid (10 mL) and water were added to the reaction mixture, and the mixture was extracted with a mixed solvent of tetrahydrofuran-ethyl acetate. The organic layer was washed with saturated brine, dried (MgSO$_4$), and concentrated. The obtained crystals were washed with hexane to give the title compound (3.26 g, 100%) as colorless crystals.

MS: 420 (MH$^+$).

Reference Example 199

N-[2-(benzylthio)-3-thiomorpholinopropyl]-5-(3-methoxypropoxy)-7-[methyl(pyridin-2-ylsulfonyl)amino]-1H-indole-2-carboxamide

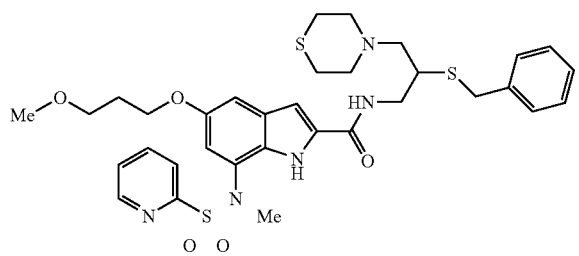

A mixture of 5-(3-methoxypropoxy)-7-[methyl(pyridin-2-ylsulfonyl)amino]-1H-indole-2-carboxylic acid (330 mg), 2-(benzylthio)-3-thiomorpholinopropan-1-amine (200 mg), 1H-1,2,3-benzotriazol-1-ol (120 mg), N-[3-(dimethylamino)propyl]-N'-ethylcarbodiimide hydrochloride (180 mg) and N,N-dimethylformamide (5 mL) was stirred at room temperature for 3 hr. Water was added to the reaction mixture, and the mixture was extracted with ethyl acetate. The ethyl acetate layer was washed successively with saturated aqueous sodium hydrogencarbonate and saturated brine, dried ($MgSO_4$), and concentrated. The obtained residue was subjected to silica gel column chromatography, and eluted with hexane-ethyl acetate (1:1-1:2, volume ratio) to give the title compound (380 mg, yield 78%) as a pale-yellow amorphous solid.

$^1$H-NMR (CDCl$_3$) δ: 2.00-2.12 (2H, m), 2.43-2.82 (10H, m), 2.91 (1H, dd, J=11.55, 4.73 Hz), 3.29 (3H, s), 3.38 (3H, s), 3.50-3.63 (3H, m), 3.76-3.91 (3H, m), 4.08 (2H, t, J=6.25 Hz), 6.69 (1H, d, J=1.89 Hz), 6.96 (1H, d, J=1.89 Hz), 7.09 (1H, d, J=1.89 Hz), 7.16-7.41 (5H, m), 7.51 (1H, t, J=5.11 Hz), 7.62 (1H, dd, J=7.76, 4.73 Hz), 7.98 (1H, t, J=7.76 Hz), 8.11 (1H, d, J=7.95 Hz), 9.22 (1H, d, J=4.54 Hz), 12.23 (1H, brs).

Reference Example 200

3-fluoro-7-[methyl(2-thienylsulfonyl)amino]-1H-indole-2-carbothioamide

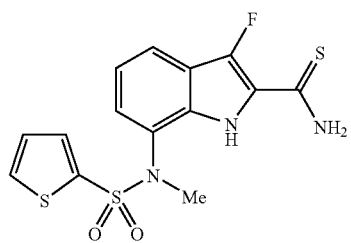

To a solution of 7-[methyl(2-thienylsulfonyl)amino]-1H-indole-2-carboxamide (5.60 g) in 1,2-dichloroethane (170 mL) was added N-fluoropyridinium triflate (8.23 g), and the mixture was heated under reflux for 4 hr. Saturated aqueous sodium hydrogen solution and 1N aqueous sodium thiosulfate solution were added to the reaction solution, and the mixture was extracted with ethyl acetate. The organic layer was washed with saturated brine, dried over anhydrous magnesium sulfate, and concentrated under reduced pressure. The residue was purified by silica gel column chromatography (ethyl acetate:hexane=50:50-100:0) to give the title compound (1.43 g, crude product) as a pale-yellow solid. To a solution of this solid in tetrahydrofuran (40 mL) was added Lawesson's reagent (1.56 g), and the mixture was stirred at 60° C. for 5 hr, and concentrated under reduced pressure. The precipitated solid was washed with toluene to give the title compound (494 mg, yield 8%) as pale-yellow crystals. MS: 370 (MH$^+$).

Reference Example 201

N-[2-(benzylthio)-3,3-dimethoxypropyl]-5-hydroxy-7-nitro-1H-indole-2-carboxamide

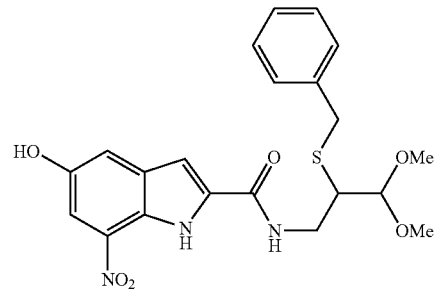

To a solution of ethyl 5-hydroxy-7-nitro-1H-indole-2-carboxylate (5.11 g) in tetrahydrofuran (80 mL) and ethanol (80 mL) was added 1N aqueous sodium hydroxide solution (45 mL), and the mixture was stirred at room temperature for 3 hr. The organic solvent was evaporated under reduced pressure, ethyl acetate was added, and the mixture was acidified with 6N hydrochloric acid. The organic layer was dried (MgSO$_4$), and concentrated to give a pale-yellow solid (5.2 g). To a solution of this solid and 2-(benzylthio)-3,3-dimethoxypropan-1-amine (5.2 g) in tetrahydrofuran (100 mL) and acetonitrile (100 mL) were added 1-ethyl-3-(3-dimethylaminopropyl)carbodiimide hydrochloride (4.95 g) and 1-hydroxybenzotriazole monohydrate (3.96 g), and the mixture was stirred overnight at room temperature. The mixture was diluted with ethyl acetate, washed with saturated aqueous sodium hydrogencarbonate, water and saturated brine, dried over anhydrous magnesium sulfate, and filtrated, and the filtrate was concentrated under reduced pressure. The residue was subjected to silica gel column chromatography (hexane:ethyl acetate=10:1-0:1), and the obtained solid was recrystallized (ethyl acetate-diisopropyl ether) to give the title compound (4.77 g, yield 50%) as a colorless solid. melting point 134-135° C.

Reference Example 202

2-({[2-(benzylthio)-3,3-dimethoxypropyl]amino}carbonyl)-7-nitro-1H-indol-5-yl pivalate

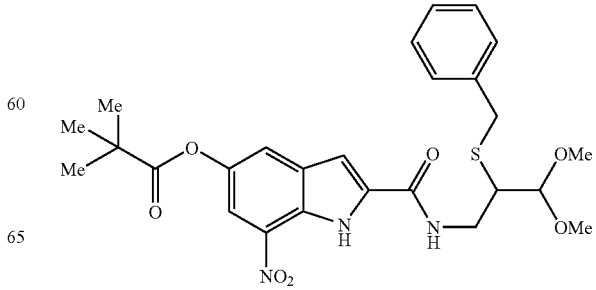

To a solution of N-[2-(benzylthio)-3,3-dimethoxypropyl]-5-hydroxy-7-nitro-1H-indole-2-carboxamide (1.0 g) in tetrahydrofuran (10 mL) were added dropwise triethylamine (0.38 mL) and pivaloyl chloride (0.30 mL) under ice-cooling. The mixture was stirred overnight at room temperature, diluted with ethyl acetate, washed with water, 1N hydrochloric acid and saturated brine, dried (MgSO$_4$), and concentrated. The residue was purified by basic silica gel column chromatography (hexane:ethyl acetate=1:1) to give the title compound (1.18 g, yield 99%) as a pale-yellow amorphous powder.

$^1$H-NMR (DMSO-d$_6$) δ: 1.36 (9H, s), 3.02-3.12 (1H, m), 3.31 (3H, s), 3.32-3.35 (3H, m), 3.36-3.46 (1H, m), 3.61-3.76 (1H, m), 3.83 (2H, s), 4.38 (1H, d, J=4.3 Hz), 7.08-7.17 (1H, m), 7.17-7.25 (2H, m), 7.26-7.33 (2H, m), 7.39 (1H, s), 7.87-8.21 (2H, m), 9.14 (1H, t, J=5.7 Hz), 11.44 (1H, brs).

Reference Example 203

2-[5-(dimethoxymethyl)-4,5-dihydro-1,3-thiazol-2-yl]-7-nitro-1H-indol-5-yl pivalate

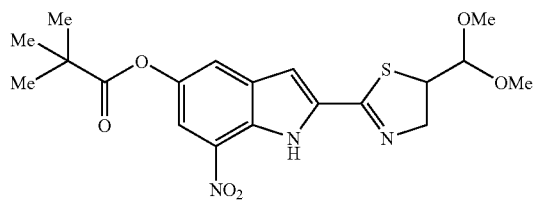

To a solution of triphenylphosphine oxide (14.8 g) in dichloromethane (50 mL) was added dropwise trifluoromethanesulfonic anhydride (3.0 mL) under ice-cooling, and the mixture was stirred for 30 min. A solution of 2-({[2-(benzylthio)-3,3-dimethoxypropyl]amino}carbonyl)-7-nitro-1H-indol-5-yl pivalate (9.38 g) and thioanisole (10.4 mL) in dichloromethane (100 mL) was added dropwise to this solution at −78° C., and the reaction mixture was stirred at −78° C. for 1 hr, and then at 0° C. for 1 hr. Saturated aqueous sodium hydrogencarbonate was added, and the mixture was extracted with ethyl acetate. The combined organic layer was washed with water and saturated brine, dried (MgSO$_4$), and concentrated. The residue was purified by basic silica gel column chromatography (hexane:ethyl acetate=1:0-4:6) to give the title compound (4.32 g, yield 58%) as a pale-yellow amorphous powder. MS: 422 (MH$^+$).

Reference Example 204

7-amino-2-[5-(dimethoxymethyl)-4,5-dihydro-1,3-thiazol-2-yl]-1H-indol-5-yl pivalate

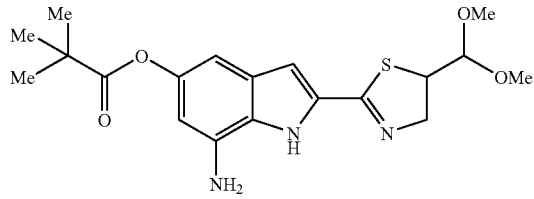

To a solution of 2-[5-(dimethoxymethyl)-4,5-dihydro-1,3-thiazol-2-yl]-7-nitro-1H-indol-5-yl pivalate (4.32 g) in ethanol (100 mL) were added water (10 mL), calcium chloride (1.13 g) and iron (3.42 g), and the mixture was stirred at 90° C. for 2 hr. The mixture was allowed to cool, and basified with saturated aqueous sodium hydrogencarbonate, and the insoluble substance was filtered off. The filtrate was extracted with ethyl acetate, and the combined organic layers were washed with water and saturated brine, dried (MgSO$_4$), and concentrated. The residue was purified by basic silica gel column chromatography (hexane:ethyl acetate=4:1-1:3) to give the title compound (2.55 g, yield 64%) as a pale-yellow amorphous powder. MS: 392 (MH$^+$).

Reference Example 205

2-[5-(dimethoxymethyl)-4,5-dihydro-1,3-thiazol-2-yl]-7-[methyl(pyridin-2-ylsulfonyl)amino]-1H-indol-5-yl pivalate

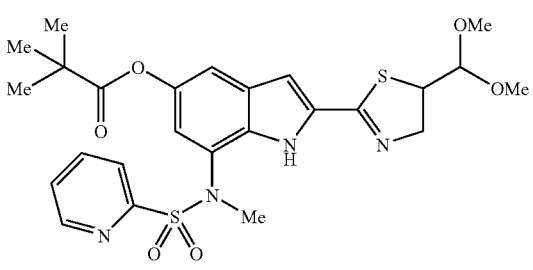

To a solution of 7-amino-2-[5-(dimethoxymethyl)-4,5-dihydro-1,3-thiazol-2-yl]-1H-indol-5-yl pivalate (2.55 g) in pyridine (50 mL) was added dropwise a pyridine solution (10 mL) of pyridine-2-sulfonyl chloride (1.27 g) under ice-cooling, and the mixture was stirred at room temperature for 30 min. The reaction solution was diluted with ethyl acetate and diethyl ether, washed with water and saturated brine, dried (MgSO$_4$), and concentrated. The residue was dissolved in N,N-dimethylformamide (50 mL), and potassium carbonate (1.1 g) and methyl iodide (0.45 mL) were added under ice-cooling. The mixture was stirred at room temperature for 30 min, diluted with ethyl acetate, washed with water and saturated brine, dried (MgSO$_4$), and concentrated under reduced pressure. The residue was purified by basic silica gel column chromatography (hexane:ethyl acetate=95:5-4:6) to give the title compound (3.1 g, yield 87%) as a pale-yellow amorphous powder.

MS: 547 (MH$^+$).

Reference Example 206

N-{5-hydroxy-2-[5-(thiomorpholinomethyl)-4,5-dihydro-1,3-thiazol-2-yl]-1H-indol-7-yl}-N-methylpyridine-2-sulfonamide

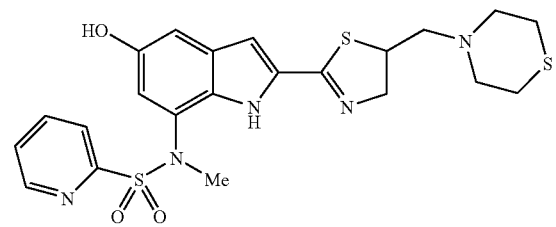

To a solution of 2-[5-(dimethoxymethyl)-4,5-dihydro-1,3-thiazol-2-yl]-7-[methyl(pyridin-2-ylsulfonyl)amino]-1H-indol-5-yl pivalate (273 mg) in trifluoroacetic acid (2 mL) were added water (4 mL) and concentrated sulfuric acid (2 mL), and the mixture was stirred at 80° C. for 5 hr, basified with saturated aqueous sodium hydrogencarbonate, and extracted with ethyl acetate. The organic layer was diluted with ethyl acetate, washed with water and saturated brine, dried (MgSO$_4$), and concentrated under reduced pressure. To a tetrahydrofuran solution (5 mL) of the residue were added thiomorpholine (0.041 mL) and sodium triacetoxyborohydride (215 mg), and the mixture was stirred overnight at room temperature. Saturated aqueous sodium hydrogencarbonate and ethyl acetate were added to the reaction solution, and the organic layer was washed with water and saturated brine, dried (MgSO$_4$), and concentrated under reduced pressure. The residue was purified by silica gel column chromatography (hexane:ethyl acetate=5:1-1:2) to give the title compound (145 mg, yield 85%) as a colorless amorphous powder. MS: 504 (MH$^+$).

Reference Example 207

5-(2-methoxyethoxy)-7-nitro-1H-indole-2-carboxylic acid

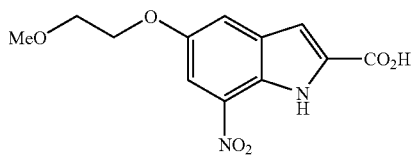

Ethyl 5-(2-methoxyethoxy)-7-nitro-1H-indole-2-carboxylate (7.7 g) was dissolved in a mixed solvent of ethanol (75 mL) and tetrahydrofuran (75 mL), 1N aqueous sodium hydroxide solution (75 mL) was added to this solution, and the mixture was stirred at 50° C. for 1.5 hr. Aqueous citric acid solution was added to the reaction solution, and the mixture was extracted with ethyl acetate. The organic layer was washed successively with water and saturated brine, dried over magnesium sulfate, and filtrated, and the filtrate was concentrated under reduced pressure. The obtained crude product was crystallized from ethyl acetate-hexane to give the title compound (6.8 g, yield 97%) as yellow crystals. melting point 192-193° C.

Reference Example 208

N-[2-(benzylthio)-3,3-dimethoxypropyl]-5-(2-methoxyethoxy)-7-nitro-1H-indole-2-carboxamide

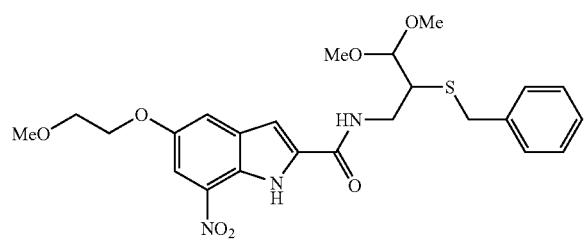

A mixture of 5-(2-methoxyethoxy)-7-nitro-1H-indole-2-carboxylic acid (4.7 g), 2-(benzylthio)-3,3-dimethoxypropan-1-amine (4.9 g), 1H-1,2,3-benzotriazol-1-ol (3.4 g), N-[3-(dimethylamino)propyl]-N'-ethylcarbodiimide hydrochloride (4.9 g) and N,N-dimethylformamide (150 mL) was stirred at room temperature for 15 hr. The reaction solution was concentrated under reduced pressure, ethyl acetate and water were added, and the mixture was extracted with ethyl acetate. The obtained organic layer was washed successively with aqueous citric acid solution, saturated aqueous sodium hydrogencarbonate solution and saturated brine, dried over magnesium sulfate, and filtrated, and the filtrate was concentrated under reduced pressure. The obtained crude product was subjected to silica gel column chromatography (ethyl acetate:hexane=20:80-80:20) to give the title compound (6.8 g, yield 97%) as a orange oil.

$^1$H-NMR (CDCl$_3$) δ: 2.85-2.99 (1H, m), 3.39 (3H, s), 3.48 (6H, s), 3.52-3.65 (1H, m), 3.76-3.94 (5H, m), 4.18-4.29 (2H, m), 4.35 (1H, d, J=4.2 Hz), 6.73 (1H, d, J=2.3 Hz), 6.80 (1H, brs), 7.09-7.45 (5H, m), 7.55 (1H, d, J=2.3 Hz), 7.94 (1H, d, J=2.3 Hz), 10.27 (1H, s).

Reference Example 209

2-[5-(dimethoxymethyl)-4,5-dihydro-1,3-thiazol-2-yl]-5-(2-methoxyethoxy)-7-nitro-1H-indole

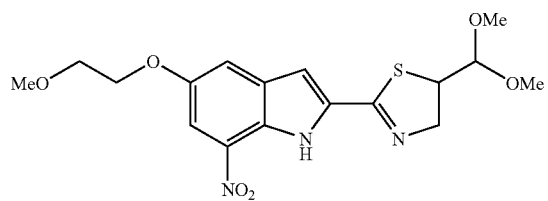

Triphenylphosphine oxide (3 g) was dissolved in dichloromethane (30 mL), trifluoroacetic anhydride (3.1 g) was added under ice-cooling, and the mixture was stirred for 10 min. A solution of N-[2-(benzylthio)-3,3-dimethoxypropyl]-5-(2-methoxyethoxy)-7-nitro-1H-indole-2-carboxamide (5.0 g) and thioanisole (2.5 g) in dichloromethane (20 mL) was added dropwise to this suspension under ice-cooling. The reaction solution was allowed to warm to room temperature, and stirred for 10 min. Water was added, and the mixture was extracted with ethyl acetate. The organic layer was washed with saturated brine, dried over magnesium sulfate, and filtrated, and the filtrate was concentrated under reduced pressure. The obtained crude product was subjected to silica gel column chromatography (ethyl acetate:hexane=10:90-40:60), and the obtained solid was washed with ethyl acetate-hexane to give the title compound (6.8 g, yield 97%) as yellow crystals. melting point 100-101° C.

Reference Example 210

2-[5-(dimethoxymethyl)-4,5-dihydro-1,3-thiazol-2-yl]-5-(2-methoxyethoxy)-1H-indol-7-amine

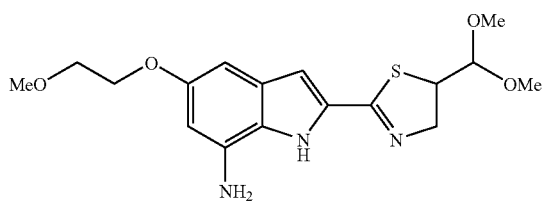

2-[5-(Dimethoxymethyl)-4,5-dihydro-1,3-thiazol-2-yl]-5-(2-methoxyethoxy)-7-nitro-1H-indole (100 mg) was suspended in ethanol, and 10% palladium-carbon (50% containing water, 50 mg) was added under nitrogen atmosphere. Hydrazine monohydrate (0.07 mL) was added to the mixture, and the mixture was stirred at 90° C. for 2 hr. Hydrazine monohydrate (0.07 mL) was added again, and the mixture was further stirred at 90° C. for 1 hr. The reaction solution was allowed to cool to room temperature, the catalyst was filtered off, and the filtrate was concentrated under reduced pressure. The obtained crude product was subjected to silica gel column chromatography (ethyl acetate:hexane=30:70-80:20) to give the title compound (27 mg, yield 29%) as a orange oil.

$^1$H-NMR (CDCl$_3$) δ: 3.38 (3H, s), 3.41 (3H, s), 3.43 (3H, s), 4.07-4.16 (3H, m), 4.30-4.48 (3H, m), 6.29 (1H, brs), 6.52 (1H, brs), 6.77 (1H, s), 10.28 (1H, s).

Reference Example 211 ethyl 5-(2-methoxyethoxy)-7-{[(1-methyl-1H-imidazol-2-yl)sulfonyl]amino}-1H-indole-2-carboxylate

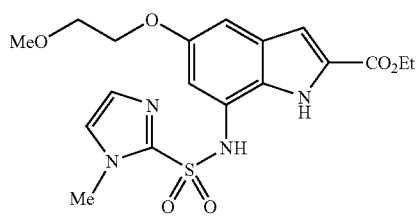

Ethyl 7-amino-5-(2-methoxyethoxy)-1H-indole-2-carboxylate (1 g) was dissolved in tetrahydrofuran (10 mL), then 2,6-lutidine (2.5 mL) and 1-methyl-1H-imidazole-2-sulfonyl chloride (0.98 g) were added under ice-cooling, and the mixture was stirred at room temperature for 2 hr. 1N Hydrochloric acid was added to the reaction solution under ice-cooling, and the mixture was extracted with ethyl acetate. The organic layer was washed successively with saturated aqueous sodium hydrogencarbonate solution and saturated brine, dried over magnesium sulfate, and filtrated, and the filtrate was concentrated under reduced pressure. The obtained crude product was subjected to silica gel column chromatography (ethyl acetate:hexane=10:90-100:0) to give the title compound (780 mg, yield 51%) as a white solid. MS: 566 (MH$^+$).

Reference Example 212 ethyl 5-(2-methoxyethoxy)-7-{methyl[(1-15' methyl-1H-imidazol-2-yl)sulfonyl]amino}-1H-indole-2-carboxylate

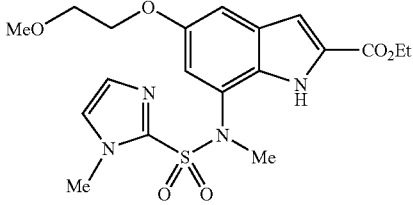

Ethyl 5-(2-methoxyethoxy)-7-{[(1-methyl-1H-imidazol-2-yl)sulfonyl]amino}-1H-indole-2-carboxylate (780 mg) was 20, dissolved in N,N-dimethylformamide (10 mL), potassium carbonate (256 mg) and methyl iodide (0.15 mL) were added, and the mixture was stirred at room temperature for 15.5 hr. Water was added to the reaction solution, and the mixture was extracted with ethyl acetate. The organic layer was washed successively with aqueous sodium thiosulfate solution and saturated brine, dried over magnesium sulfate, and filtrated, and the filtrate was concentrated under reduced pressure. The obtained crude product was subjected to basic silica gel column chromatography (ethyl acetate:hexane=10:90-40:60) to give the title compound (740 mg, yield 92%) as a colorless oil.

MS: 437 (MH$^+$).

Reference Example 213

5-(2-methoxyethoxy)-7-{methyl[(1-methyl-1H-imidazol-2-yl)sulfonyl]amino}-1H-indole-2-carboxylic acid

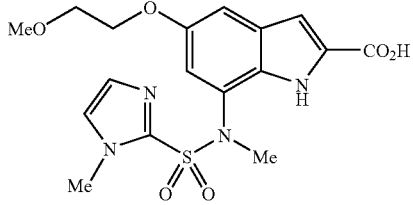

Ethyl 5-(2-methoxyethoxy)-7-{methyl[(1-methyl-1H-imidazol-2-yl)sulfonyl]amino}-1H-indole-2-carboxylate (2.8 g) was dissolved in a mixed solvent of tetrahydrofuran (12 mL) and ethanol (12 mL), 1N aqueous sodium hydroxide solution (12 mL) was added, and the mixture was stirred at 60° C. for 1.5 hr. The reaction solution was acidified with 1N hydrochloric acid, and extracted with ethyl acetate. The organic layer was washed successively with water and saturated brine, dried over magnesium sulfate, and filtrated, and the filtrate was concentrated under reduced pressure. The obtained crude product was recrystallized from ethyl acetate-

Reference Example 214

N-[2-(benzylthio)-3,3-dimethoxypropyl]-5-(2-methoxyethoxy)-7-{methyl[(1-methyl-1H-imidazol-2-yl)sulfonyl]amino}-1H-indole-2-carboxamide

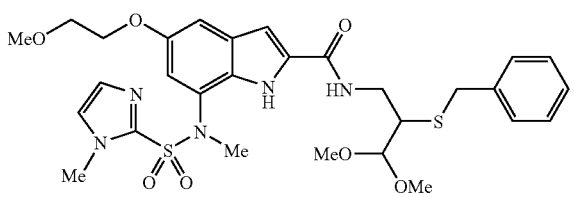

A mixture of 5-(2-methoxyethoxy)-7-{methyl[(1-methyl-1H-imidazol-2-yl)sulfonyl]amino}-1H-indole-2-carboxylic acid (2.3 g), 2-(benzylthio)-3,3-dimethoxypropan-1-amine (1.7 g), 1H-1,2,3-benzotriazol-1-ol (1.2 g), N-[3-(dimethylamino)propyl]-N'-ethylcarbodiimide hydrochloride (1.6 g) and N,N-dimethylformamide (70 mL) was stirred at room temperature for 14 hr. The reaction solution was concentrated under reduced pressure, ethyl acetate and water were added, and the mixture was extracted with ethyl acetate. The organic layer was washed successively with water, aqueous citric acid solution, saturated aqueous sodium hydrogencarbonate solution and saturated brine, dried over magnesium sulfate, and filtrated, and the filtrate was concentrated under reduced pressure. The obtained crude product was subjected to silica gel column chromatography (ethyl acetate:hexane=20:80-80:20) to give the title compound (3.2 g, yield 89%) as a colorless oil.

$^1$H-NMR (CDCl$_3$) δ: 2.87-2.96 (1H, m), 3.37 (3H, s), 3.46 (3H, s), 3.47 (3H, s), 3.50 (3H, s), 3.54-3.66 (1H, m), 3.74-3.80 (2H, m), 3.80-3.89 (6H, m), 4.12-4.19 (2H, m), 4.34 (1H, d, J=4.5 Hz), 6.63 (1H, d, J=2.3 Hz), 6.74 (1H, t, J=5.5 Hz), 6.97 (1H, s), 7.05 (1H, d, J=2.3 Hz), 7.13 (1H, d, J=2.3 Hz), 7.14-7.21 (1H, m), 7.22-7.29 (1H, m), 7.30-7.38 (3H, m), 12.24 (1H, s).

Reference Example 215

N-{[4-(benzylthio)tetrahydro-2H-pyran-4-yl]methyl}-5-(2-methoxyethoxy)-7-[methyl(pyridin-2-ylsulfonyl)amino]-1H-indole-2-carboxamide

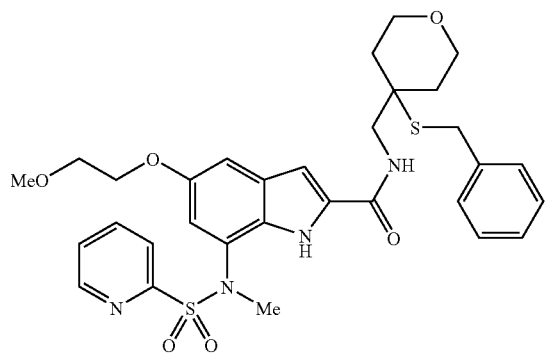

A mixture of 5-(2-methoxyethoxy)-7-[methyl(pyridin-2-ylsulfonyl)amino]-1H-indole-2-carboxylic acid (1.0 g), 1-[4-(benzylthio)tetrahydro-2H-pyran-4-yl]methanamine (0.65 g), 1H-1,2,3-benzotriazol-1-ol (0.44 g), N-[3-(dimethylamino)propyl]-N'-ethylcarbodiimide hydrochloride (0.62 g) and N,N-dimethylformamide (15 mL) was stirred at room temperature for 18 hr. The reaction solution was concentrated under reduced pressure, ethyl acetate and water were added, and the mixture was extracted with ethyl acetate. The organic layer was washed successively with water, aqueous citric acid solution, saturated aqueous sodium hydrogencarbonate solution and saturated brine, dried over magnesium sulfate, and filtrated, and the filtrate was concentrated under reduced pressure. The obtained crude product was subjected to silica gel column chromatography (ethyl acetate:hexane=20:80-80:20) to give the title compound (1.4 g, yield 90%) as a white solid.

MS: 625 (MH$^+$).

Reference Example 216

N-[2-(benzylthio)-3,3-dimethoxy-2-methylpropyl]-5-(2-methoxyethoxy)-7-[methyl(pyridin-2-ylsulfonyl)amino]-1H-indole-2-carboxamide

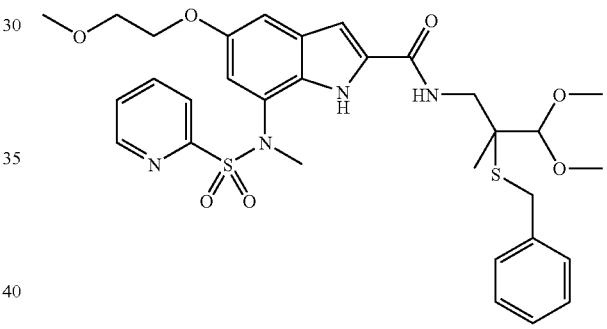

To a mixture of 5-(2-methoxyethoxy)-7-[methyl(pyridin-2-ylsulfonyl)amino]-1H-indole-2-carboxylic acid (1.62 g), 1H-1,2,3-benzotriazol-1-ol (919 mg), 2-(benzylthio)-3,3-dimethoxy-2-methylpropan-1-amine (1.02 g) and N,N-dimethylformamide (30 mL) was added N-[3-(dimethylamino)propyl]-N'-ethylcarbodiimide hydrochloride (1.53 g) at room temperature, and the mixture was added overnight at room temperature, and concentrated under reduced pressure. The residue was diluted with ethyl acetate and water. The organic layer was washed with saturated brine, dried over sodium sulfate, and filtrated, and the filtrate was concentrated under reduced pressure. The obtained residue was subjected to silica gel column chromatography to give the title compound (1.96 g, yield 76%) as a colorless amorphous solid from a fraction eluted with ethyl acetate-hexane (4:1).

$^1$H-NMR (CDCl$_3$) δ: 1.36 (3H, s), 3.29 (3H, s), 3.47 (3H, s), 3.60 (6H, s), 3.66-3.83 (4H, m), 3.89 (2H, s), 4.04-4.17 (2H, m), 4.25 (1H, s), 6.66 (1H, d, J=2.3 Hz), 6.91 (1H, t, J=5.3 Hz), 7.01 (1H, d, J=2.3 Hz), 7.09 (1H, d, J=2.3 Hz), 7.20-7.37 (4H, m), 7.60 (1H, dd, J=6.6, 4.7 Hz), 7.96 (1H, td, J=7.8, 1.9 Hz), 8.03-8.17 (1H, m), 9.22 (1H, d, J=4.9 Hz), 12.21 (1H, brs).

Reference Example 217

N-[2-(benzylthio)-2-methyl-3-oxopropyl]-5-(2-methoxyethoxy)-7-[methyl(pyridin-2-ylsulfonyl)amino]-1H-indole-2-carboxamide

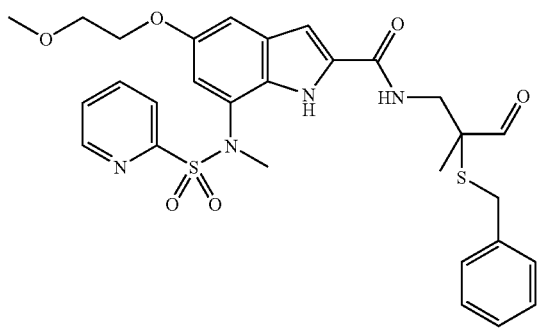

To a mixture of N-[2-(benzylthio)-3,3-dimethoxy-2-methylpropyl]-5-(2-methoxyethoxy)-7-[methyl(pyridin-2-ylsulfonyl)amino]-1H-indole-2-carboxamide (1.95 g), water (0.16 mL) and acetone (30 mL) was added Amberlyst (registered trade mark) 15 ion exchange resin (500 mg) at room temperature, and the mixture was added overnight at room temperature. The insoluble substance was filtered off. The filtrate was concentrated under reduced pressure, and the residue was subjected to silica gel column chromatography to give the title compound (1.56 g, yield 87%) as a colorless amorphous solid from a fraction eluted with ethyl acetate-hexane (9:1).

$^1$H-NMR (CDCl$_3$) δ: 1.41 (3H, s), 3.26 (3H, s), 3.47 (3H, s), 3.62 (2H, s), 3.74-3.84 (4H, m), 4.09-4.19 (2H, m), 6.28 (1H, t, J=6.3 Hz), 6.66 (1H, d, J=2.1 Hz), 7.01 (1H, d, J=2.3 Hz), 7.06 (1H, d, J=2.1 Hz), 7.22-7.38 (3H, m), 7.61 (1H, ddd, J=7.7, 4.7, 1.1 Hz), 7.97 (1H, td, J=7.7, 1.8 Hz), 8.10 (1H, d, J=7.9 Hz), 9.12-9.22 (1H, m), 9.24 (1H, s), 12.27 (1H, brs).

Reference Example 218

N-[2-(benzylthio)-2-methyl-3-thiomorpholinopropyl]-5-(2-methoxyethoxy)-7-[methyl(pyridin-2-ylsulfonyl)amino]-1H-indole-2-carboxamide

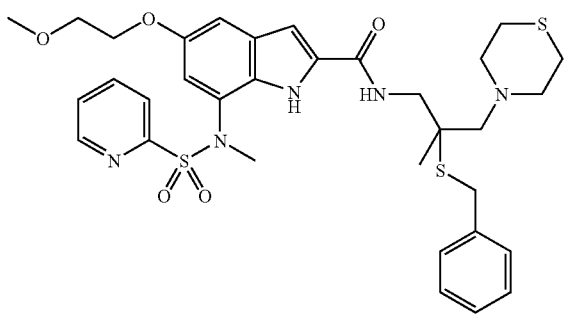

To a mixture of N-[2-(benzylthio)-2-methyl-3-oxopropyl]-5-(2-methoxyethoxy)-7-[methyl(pyridin-2-ylsulfonyl)amino]-1H-indole-2-carboxamide (1.56 g) and 1,2-dichloroethane (50 mL) was added thiomorpholine (1.31 mL) at room temperature, and the mixture was stirred at room temperature for 30 min. Sodium triacetoxyborohydride (1.66 g) was added, and the reaction mixture was stirred overnight at room temperature. Aqueous sodium bicarbonate was added, and the mixture was extracted with 1,2-dichloroethane. The extract was washed with saturated brine, dried over sodium sulfate, and filtrated, and the filtrate was concentrated under reduced pressure. The obtained residue was subjected to silica gel column chromatography to give the title compound (998 mg, yield 56%) as a colorless amorphous solid from a fraction eluted with ethyl acetate-hexane (9:1).

$^1$H-NMR (CDCl$_3$) δ: 1.35 (3H, s), 2.49-2.78 (6H, m), 2.80-3.01 (4H, m), 3.29 (3H, s), 3.47 (3H, s), 3.58-3.71 (1H, m), 3.72-3.87 (4H, m), 4.08-4.24 (2H, m), 6.75 (1H, s), 7.02 (1H, d, J=2.3 Hz), 7.11 (1H, d, J=1.9 Hz), 7.19-7.36 (4H, m), 7.45-7.56 (1H, m), 7.54-7.71 (1H, m), 7.94-8.04 (1H, m), 8.11 (1H, d, J=7.9 Hz), 9.22 (1H, d, J=0.8 Hz), 12.28 (1H, brs).

Reference Example 219 tert-butyl [2-(benzylthio)-3,3-dimethoxypropyl]carbamate

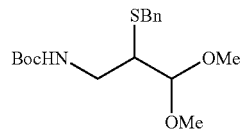

2-(Benzylthio)-3,3-dimethoxypropan-1-amine (1 g) was dissolved in tetrahydrofuran (7 mL), and 1N aqueous sodium hydroxide solution (10 mL) was added. A solution of t-butyl bicarbonate (993 mg) in tetrahydrofuran (3 mL) was added dropwise to the reaction solution under ice-cooling, and the mixture was stirred overnight at room temperature. The reaction mixture was extracted with ethyl acetate, and the organic layer was washed with saturated brine, and dried over sodium sulfate. The obtained solution was filtered through basic silica gel, and concentrated to give the title compound (1.39 g, yield 99%) as a pale-yellow oil.

$^1$H-NMR (CDCl$_3$) δ: 1.44 (9H, s), 2.80 (1H, q, J=5.8 Hz), 3.15-3.30 (1H, m), 3.32 (3H, s), 3.37 (3H, s), 3.40-3.55 (1H, m), 3.81 (2H, d, J=1.5 Hz), 4.25 (1H, d, J=4.9 Hz), 5.00 (1H, brs), 7.20-7.37 (5H, m).

Reference Example 220 tert-butyl [2-(benzylthio)-3-oxopropyl]carbamate

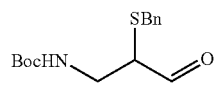

tert-Butyl [2-(benzylthio)-3,3-dimethoxypropyl]carbamate (9.4 g) was dissolved in tetrahydrofuran (50 mL) and water (50 mL), and acetic acid (100 mL) was added. The reaction mixture was stirred overnight at 50° C., and concentrated, and the residue was partitioned between ethyl acetate and saturated aqueous sodium hydrogencarbonate solution. The organic layer was washed with saturated brine, dried over sodium sulfate, and filtrated, and the filtrate was concentrated under reduced pressure. The residue was subjected to silica gel chromatography to give the title compound (5.35 g, yield 66%) as a pale-yellow oil from a fraction eluted with ethyl acetate-hexane (1:19).

¹H-NMR (CDCl₃) δ: 1.42 (9H, s), 3.31-3.44 (3H, m), 3.59-3.75 (2H, m), 4.83 (1H, brs), 7.20-7.37 (5H, m), 9.35 (1H, d, J=2.3 Hz).

Reference Example 221 tert-butyl [2-(benzylthio)-3-thiomorpholinopropyl]carbamate

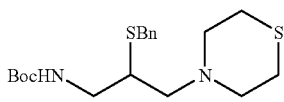

To a solution of tert-butyl [2-(benzylthio)-3-oxopropyl]carbamate (820 mg) in tetrahydrofuran (30 mL) was added thiomorpholine (0.42 mL), and the mixture was stirred at room temperature for 1 hr. Sodium triacetoxyborohydride (1.76 g) was added to the reaction mixture under ice-cooling, and the mixture was stirred overnight at room temperature. Saturated aqueous sodium hydrogencarbonate solution was added to the reaction mixture under ice-cooling, and the mixture was extracted with ethyl acetate. The organic layer was washed with saturated brine, dried over sodium sulfate, and concentrated under reduced pressure. The residue was subjected to silica gel chromatography to give the title compound (936 mg, yield 91%) as a colorless oil from a fraction eluted with ethyl acetate-hexane (3:7).

¹H-NMR (CDCl₃) δ: 1.45 (9H, s), 2.29-2.85 (11H, m), 3.09-3.56 (2H, m), 3.78 (2H, s), 7.20-7.37 (5H, m).

Reference Example 222

2-(benzylthio)-3-thiomorpholinopropan-1-amine

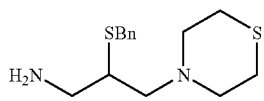

To a solution of tert-butyl [2-(benzylthio)-3-thiomorpholinopropyl]carbamate (21.46 g) in a mixed solvent of ethyl acetate (60 mL) and methanol (60 mL) was added hydrogen chloride-ethyl acetate solution (120 mL) at 0° C., and the mixture was stirred at room temperature for 4 hr. The reaction solution was concentrated, and the residue was partitioned between ethyl acetate and saturated aqueous potassium carbonate solution. The organic layer was washed with saturated brine, and dried over sodium sulfate, and the solvent was evaporated to give the title compound (14.41 g, yield 91%) as a yellow oil.

¹H-NMR (CDCl₃) δ: 1.41 (2H, brs), 2.21-2.80 (12H, m), 2.91 (1H, d, J=8.7 Hz), 3.76 (2H, s), 7.19-7.36 (5H, m).

Reference Example 223

4-(benzylthio)-4-(nitromethyl)tetrahydro-2H-thiopyran

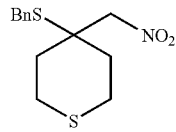

In the same manner as in Reference Example 58, the title compound (10.4 g, yield 74%) was obtained as colorless crystals from 4-oxothiane (5.81 g).

¹H-NMR (CDCl₃) δ: 2.03-2.18 (4H, m), 2.42 (2H, d, J=13.9 Hz), 3.13-3.30 (2H, m), 3.68 (2H, s), 4.49 (2H, s), 7.22-7.39 (5H, m).

Reference Example 224

1-[4-(benzylthio)tetrahydro-2H-thiopyran-4-yl]methanamine

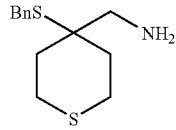

In the same manner as in Reference Example 60, the title compound (2.57 g, yield >99%) was obtained as a yellow oil from 4-(benzylthio)-4-(nitromethyl)tetrahydro-2H-thiopyran (2.83 g).

¹H-NMR (CDCl₃) δ: 1.56 (2H, brs), 1.62-1.76 (2H, m), 1.97-2.11 (2H, m), 2.33-2.48 (2H, m), 2.66 (2H, s), 3.02-3.18 (2H, m), 3.57 (2H, s), 7.21-7.38 (5H, m).

Reference Example 225

N-{[4-(benzylthio)tetrahydro-2H-thiopyran-4-yl]methyl}-5-(2-methoxyethoxy)-7-[methyl(pyridin-2-ylsulfonyl)amino]-1H-indole-2-carboxamide

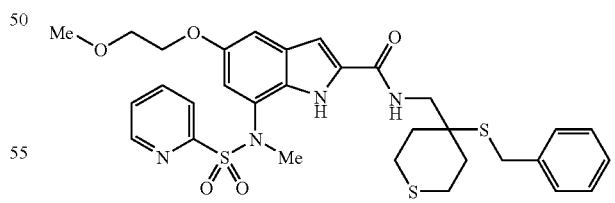

A mixture of 5-(2-methoxyethoxy)-7-[methyl(pyridin-2-ylsulfonyl)amino]-1H-indole-2-carboxylic acid (1.60 g), 1-[4-(benzylthio)tetrahydro-2H-thiopyran-4-yl]methanamine (1.00 g), 1H-1,2,3-benzotriazol-1-ol (0.90 g), N-[3-(dimethylamino)propyl]-N'-ethylcarbodiimide hydrochloride (1.12 g) and N,N-dimethylformamide (20 mL) was stirred at room temperature for 15 hr. The reaction mixture was concentrated, water was added, and the mixture was extracted with ethyl acetate. The organic layer was washed with 1N hydrochloric acid, saturated aqueous sodium hydrogencarbonate solution and saturated brine, dried (MgSO₄), and concentrated. The obtained residue was subjected to silica gel column chromatography, and eluted with hexane-ethyl acetate (4:1-1:1, volume ratio) to give the title compound (1.92 g, yield 77%) as a colorless amorphous solid.

¹H-NMR (CDCl₃) δ: 1.85-1.97 (2H, m), 2.05-2.16 (2H, m), 2.44-2.55 (2H, m), 3.00-3.14 (2H, m), 3.27 (3H, s), 3.43-3.57 (2H, m), 3.47 (3H, s), 3.70 (2H, s), 3.73-3.82 (2H, m), 4.07-4.22 (2H, m), 6.52-6.62 (1H, m), 6.71 (1H, d, J=2.3 Hz), 7.02 (1H, d, J=2.3 Hz), 7.09 (1H, d, J=2.1 Hz), 7.20-7.29 (1H, m), 7.29-7.42 (4H, m), 7.60-7.68 (1H, m), 7.98 (1H, td, J=7.7, 1.7 Hz), 8.11 (1H, d, J=7.7 Hz), 9.17-9.30 (1H, m), 12.31 (1H, brs).

Reference Example 226

S-benzyl-N-({5-(2-methoxyethoxy)-7-[methyl(pyridin-2-ylsulfonyl)amino]-1H-indol-2-yl}carbonyl)-L-cysteine methyl ester

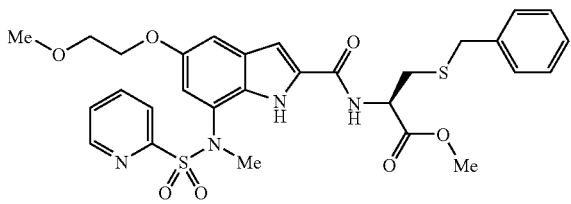

A mixture of 5-(2-methoxyethoxy)-7-[methyl(pyridin-2-ylsulfonyl)amino]-1H-indole-2-carboxylic acid (3.00 g), S-benzyl-L-cysteine methyl ester hydrochloride (1.90 g), 1H-1,2,3-benzotriazol-1-ol (1.70 g), N-[3-(dimethylamino)propyl]-N'-ethylcarbodiimide hydrochloride (2.10 g), triethylamine (1.50 mL) and N,N-dimethylformamide (40 mL) was stirred at room temperature for 18 hr. The reaction mixture was concentrated, water was added, and the mixture was extracted with ethyl acetate. The organic layer was washed with 1N hydrochloric acid, saturated aqueous sodium hydrogencarbonate solution and saturated brine, dried (MgSO₄), and concentrated. The obtained residue was subjected to silica gel column chromatography, and eluted with hexane-ethyl acetate (1:1-1:2, volume ratio) to give the title compound (4.30 g, yield 94%) as a colorless amorphous solid.

¹H-NMR (CDCl₃) δ: 3.04 (2H, t, J=5.2 Hz), 3.29 (3H, s), 3.47 (3H, s), 3.75 (2H, s), 3.76-3.79 (2H, m), 3.80 (3H, s), 4.07-4.22 (2H, m), 4.95-5.12 (1H, m), 6.87 (1H, d, J=2.3 Hz), 6.87-6.96 (1H, m), 7.02 (1H, d, J=2.3 Hz), 7.09 (1H, d, J=2.1 Hz), 7.16-7.33 (5H, m), 7.52-7.68 (1H, m), 7.97 (1H, td, J=7.8, 1.6 Hz), 8.10 (1H, d, J=7.7 Hz), 9.17 (1H, d, J=4.7 Hz), 12.23 (1H, brs).

Reference Example 227

S-trityl-D-cysteine methyl ester hydrochloride

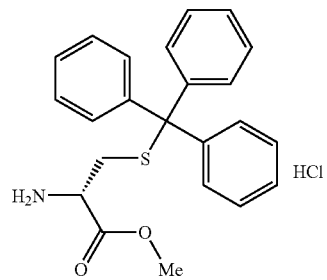

D-Cysteine methyl ester hydrochloride (2.0 g) was suspended in N,N-dimethylformamide (12 mL), 4N hydrochloric acid/ethyl acetate solution (0.5 mL) was added, and the mixture was stirred at room temperature for 20 min. Trityl chloride (3.2 g) was added, and the mixture was stirred at 50° C. for 18 hr, diluted with diethyl ether, and poured into ice water. The mixture was neutralized with saturated aqueous sodium hydrogencarbonate solution, and extracted with ethyl acetate. The ethyl acetate layer was washed with water and saturated brine, dried (MgSO₄), and concentrated. The obtained residue was diluted with ethyl acetate, and 4N hydrochloric acid/ethyl acetate solution (5 mL) was added. The precipitated solid was collected by filtration to give the title compound (3.0 g, yield 64%) as a colorless amorphous solid.

¹H-NMR (DMSO-d₆) δ: 2.52-2.68 (2H, m), 3.71 (3H, s), 3.85 (1H, t, J=5.5 Hz), 7.25-7.41 (15H, m), 8.47 (3H, brs).

Reference Example 228

N-({5-(2-methoxyethoxy)-7-[methyl(pyridin-2-ylsulfonyl)amino]-1H-indol-2-yl}carbonyl)-S-trityl-D-cysteine methyl ester

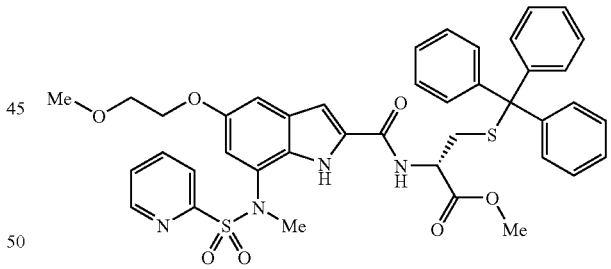

A mixture of 5-(2-methoxyethoxy)-7-[methyl(pyridin-2-ylsulfonyl)amino]-1H-indole-2-carboxylic acid (0.45 g), S-trityl-D-cysteine methyl ester hydrochloride (0.46 g), 1H-1,2,3-benzotriazol-1-ol (0.26 g), N-[3-(dimethylamino)propyl]-N'-ethylcarbodiimide hydrochloride (0.32 g), triethylamine (0.19 mL) and N,N-dimethylformamide (5 mL) was stirred at room temperature for 64 hr. The reaction mixture was concentrated, water was added, and the mixture was extracted with ethyl acetate. The organic layer was washed with 1N hydrochloric acid, saturated aqueous sodium hydrogencarbonate solution and saturated brine, dried (MgSO₄), and concentrated. The obtained residue was subjected to silica gel column chromatography, and eluted with hexane-ethyl acetate (4:1-1:4, volume ratio) to give the title compound (0.60 g, yield 72%) as a colorless amorphous solid.

$^1$H-NMR (CDCl$_3$) δ: 2.67-2.90 (2H, m), 3.29 (3H, s), 3.47 (3H, s), 3.72-3.84 (2H, m), 3.77 (3H, s), 4.12-4.25 (2H, m), 4.80-4.94 (1H, m), 6.71 (1H, d, J=7.9 Hz), 6.84 (1H, d, J=2.1 Hz), 7.02 (1H, d, J=2.1 Hz), 7.10 (1H, d, J=2.1 Hz), 7.13-7.29 (10H, m), 7.37 (5H, d, J=7.9 Hz), 7.53-7.67 (1H, m), 7.91-8.01 (1H, m), 8.09 (1H, d, J=0.9 Hz), 9.13 (1H, dd, J=3.9, 0.8 Hz), 12.18 (1H, brs).

Reference Example 229 ethyl 2-[(4-methyl-2-nitrophenyl)hydrazono]propanoate

In the same manner as in Reference Example 154, the title compound (42 g, yield 32%) was obtained as brown crystals from 4-methyl-2-nitroaniline (75 g). MS: 266 (MH$^+$).

Reference Example 230 ethyl 5-methyl-7-nitro-1H-indole-2-carboxylate

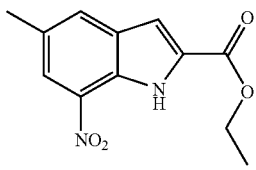

In the same manner as in Reference Example 155, the title compound (23 g, yield 58%) was obtained as brown crystals from ethyl 2-[(4-methyl-2-nitrophenyl)hydrazono]propanoate (42 g). MS: 249 (MH$^+$).

Reference Example 231 ethyl 7-amino-5-methyl-1H-indole-2-carboxylate

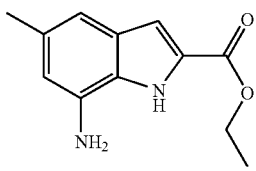

In the same manner as in Reference Example 156, the title compound (11.4 g, yield 56%) was obtained as yellow crystals from ethyl 5-methyl-7-nitro-1H-indole-2-carboxylate (23 g). MS: 219 (MH$^+$).

Reference Example 232 ethyl 5-methyl-7-[(2-thienylsulfonyl)amino]-1H-indole-2-carboxylate

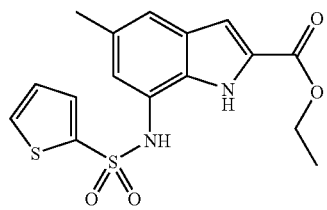

In the same manner as in Reference Example 157, the title compound (14.4 g, yield 93%) was obtained as pale-yellow crystals from ethyl 7-amino-5-methyl-1H-indole-2-carboxylate (9.6 g) and thiophene-2-sulfonyl chloride (9.1 g). MS: 351 (MH$^+$).

Reference Example 233 ethyl 5-methyl-7-[methyl(2-thienylsulfonyl)amino]-1H-indole-2-carboxylate

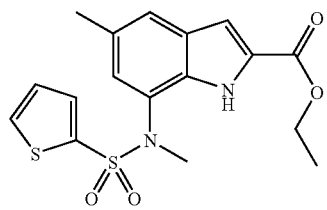

In the same manner as in Reference Example 158, the title compound (10.7 g, yield 95%) was obtained as pale-yellow crystals from ethyl 5-methyl-7-[(2-thienylsulfonyl)amino]-1H-indole-2-carboxylate (11.4 g). MS: 379 (MH$^+$).

Reference Example 234

5-methyl-7-[methyl(2-thienylsulfonyl)amino]-1H-indole-2-carboxylic acid

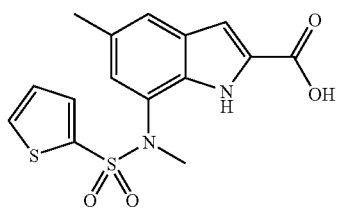

In the same manner as in Reference Example 159, the title compound (9.0 g, yield 83%) was obtained as pale-yellow crystals from ethyl 5-methyl-7-[methyl(2-thienylsulfonyl)amino]-1H-indole-2-carboxylate (10.7 g).
MS: 351 (MH$^+$).

Reference Example 235

5-methyl-7-[methyl(2-thienylsulfonyl)amino]-1H-indole-2-carboxamide

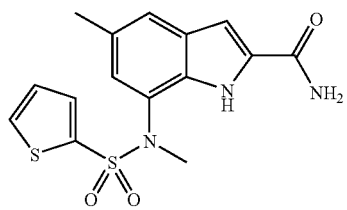

In the same manner as in Reference Example 160, the title compound (2.25 g, yield 56%) was obtained as pale-yellow crystals from 5-methyl-7-[methyl(2-thienylsulfonyl)amino]-1H-indole-2-carboxylic acid (4 g). MS: 350 (MH$^+$).

Reference Example 236

5-methyl-7-[methyl(2-thienylsulfonyl)amino]-1H-indole-2-carbothioamide

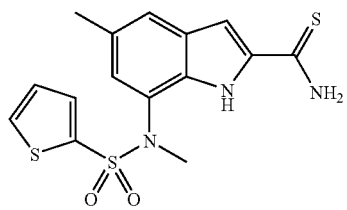

In the same manner as in Reference Example 13, the title compound (2.15 g, yield 92%) was obtained as yellow crystals from 5-methyl-7-[methyl(2-thienylsulfonyl)amino]-1H-indole-2-carboxamide (2.25 g). MS: 366 (MH$^+$).

Reference Example 237

N-[2-(benzylthio)-3,3-dimethoxypropyl]-5-methyl-7-[methyl(2-thienylsulfonyl)amino]-1H-indole-2-carboxamide

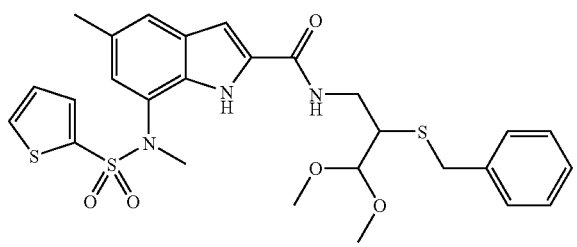

In the same manner as in Reference Example 48, the title compound (8.2 g, yield 99%) was obtained as a pale-yellow oil from 5-methyl-7-[methyl(2-thienylsulfonyl)amino]-1H-indole-2-carboxylic acid (5 g) and 2-(benzylthio)-3,3-dimethoxypropan-1-amine (4.1 g). MS: 574 (MH$^+$).

Reference Example 238

N-[2-(benzylthio)-3-oxopropyl]-5-methyl-7-[methyl(2-thienylsulfonyl)amino]-1H-indole-2-carboxamide

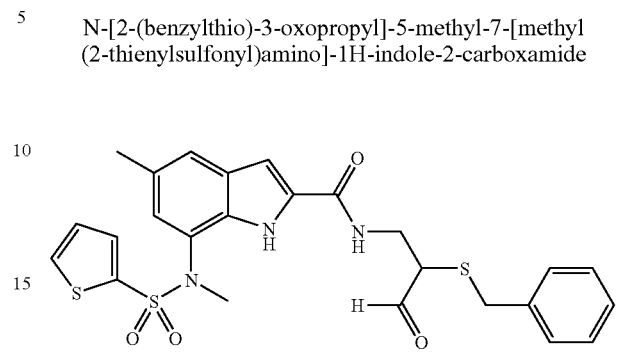

In the same manner as in Reference Example 40, the title compound (7.5 g, yield 99%) was obtained as a pale-yellow amorphous solid from N-[2-(benzylthio)-3,3-dimethoxypropyl]-5-methyl-7-[methyl(2-thienylsulfonyl)amino]-1H-indole-2-carboxamide (8.2 g). MS: 528 (MH$^+$).

Reference Example 239

N-[2-(benzylthio)-3-morpholinopropyl]-5-methyl-7-[methyl(2-thienylsulfonyl)amino]-1H-indole-2-carboxamide

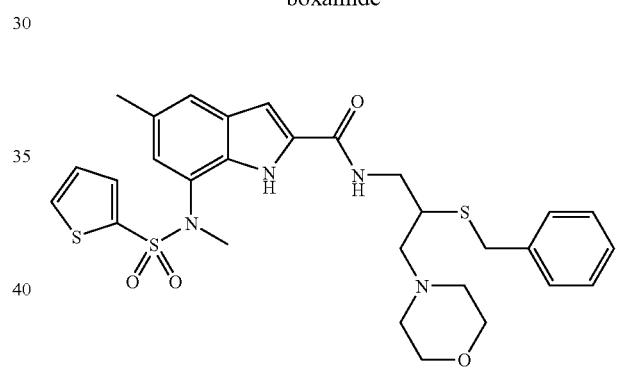

In the same manner as in Reference Example 41, the title compound (926 mg, yield 82%) was obtained as white crystals from N-[2-(benzylthio)-3-oxopropyl]-5-methyl-7-[methyl(2-thienylsulfonyl)amino]-1H-indole-2-carboxamide (1 g) and morpholine (175 mg). melting point 163° C.

Reference Example 240

N-[(3E)-2-(benzylthio)-3-(hydroxyimino)propyl]-5-methyl-7-[methyl(2-thienylsulfonyl)amino]-1H-indole-2-carboxamide

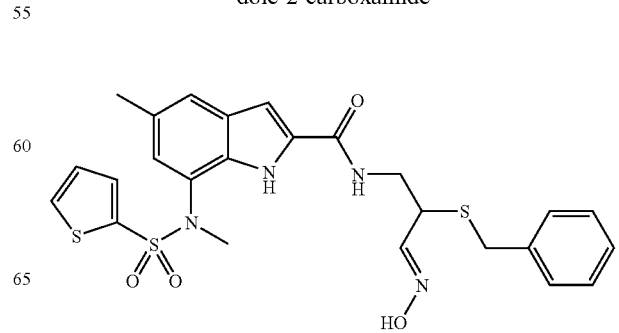

In the same manner as in Reference Example 43, the title compound (2.03 g, yield 66%) was obtained as a white amorphous solid from N-[2-(benzylthio)-3-oxopropyl]-5-methyl-7-[methyl(2-thienylsulfonyl)amino]-1H-indole-2-carboxamide (3 g). MS: 543 (MH⁺).

Reference Example 241

N-[2-(benzylthio)-2-cyanoethyl]-5-methyl-7-[methyl(2-thienylsulfonyl)amino]-1H-indole-2-carboxamide

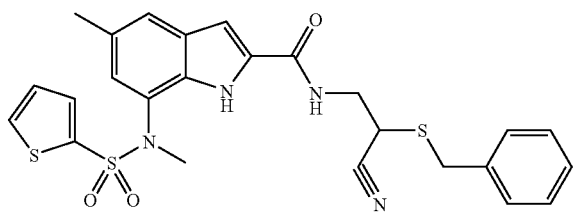

To a solution of N-[(3E)-2-(benzylthio)-3-(hydroxyimino)propyl]-5-methyl-7-[methyl(2-thienylsulfonyl)amino]-1H-indole-2-carboxamide (2.03 g) in N,N-dimethylformamide (10 mL) was added cyanuric chloride (700 mg) under ice-cooling, and the mixture was stirred for 1 hr. 1N Hydrochloric acid was added to the reaction mixture, and the mixture was extracted with ethyl acetate. The organic layer was washed with saturated brine, dried (MgSO₄), and concentrated under reduced pressure. The obtained residue was subjected to silica gel column chromatography to give the title compound (1.7 g, yield 88%) as a white amorphous solid from a fraction eluted with ethyl acetate. MS: 525 (MH⁺).

Reference Example 242

N-[2-(benzylthio)-3,3-dimethoxypropyl]-7-nitro-1H-indole-2-carboxamide

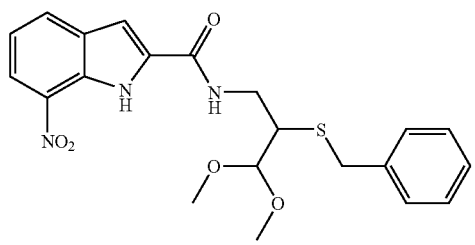

In the same manner as in Reference Example 48, the title compound (53.6 g, yield 87%) was obtained as yellow crystals from 7-nitro-1H-indole-2-carboxylic acid (30 g) and 2-(benzylthio)-3,3-dimethoxypropan-1-amine (36 g). melting point 78° C.

Reference Example 243

2-[5-(dimethoxymethyl)-4,5-dihydro-1,3-thiazol-2-yl]-7-nitro-1H-indole

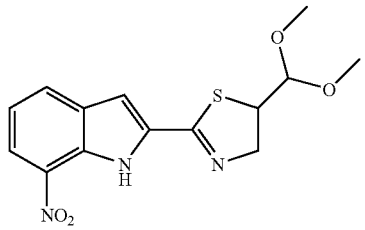

In the same manner as in Example 205, the title compound (16.5 g, yield 48%) was obtained as yellow crystals from N-[2-(benzylthio)-3,3-dimethoxypropyl]-7-nitro-1H-indole-2-carboxamide (46 g). melting point 90° C.

Reference Example 244

2-[5-(dimethoxymethyl)-4,5-dihydro-1,3-thiazol-2-yl]-1H-indol-7-amine

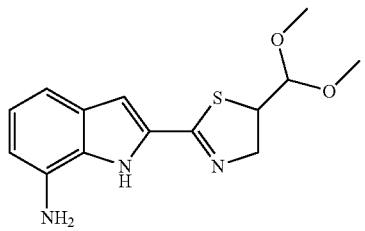

To a solution of 2-[5-(dimethoxymethyl)-4,5-dihydro-1,3-thiazol-2-yl]-7-nitro-1H-indole (16.25 g) in ethanol (200 mL) and tetrahydrofuran (100 mL) was added 10% palladium carbon (50% containing water, 2 g) under nitrogen atmosphere, and hydrazine monohydrate (14.5 mL) was added dropwise at room temperature. The reaction mixture was stirred at 80° C. for 20 min, and allowed to cool to room temperature. The palladium carbon was removed by the filtration, and the filtrate was concentrated. The obtained residue was subjected to silica gel column chromatography to give the title compound (11.2 g, yield 76%) as yellow crystals from a fraction eluted with ethyl acetate-hexane (50:50, volume ratio). MS: 292 (MH⁺).

Reference Example 245 ethyl 2-[(4-methoxy-2-nitrophenyl)hydrazono]propanoate

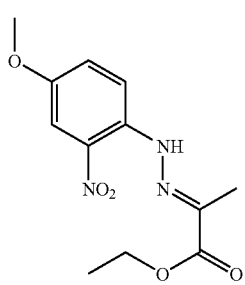

A mixture of ethyl 2-[(4-hydroxy-2-nitrophenyl)hydrazono]propanoate (30 g), methyl iodide (21.3 g), potassium carbonate (21 g) and N,N-dimethylformamide (300 mL) was stirred at room temperature for 2 hr. Water was added to the reaction mixture, and the mixture was extracted with ethyl acetate. The ethyl acetate layer was washed with 1N hydrochloric acid and saturated brine, dried (MgSO$_4$), and concentrated. The obtained residue was crystallized from diethyl ether to give the title compound (28 g, yield 89%) as orange crystals. MS: 282 (MH$^+$).

Reference Example 246 ethyl 5-methoxy-7-nitro-1H-indole-2-carboxylate

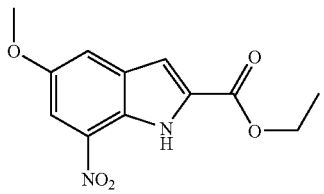

In the same manner as in Reference Example 155, the title compound (8.7 g, yield 38%) was obtained as orange crystals from ethyl 2-[(4-methoxy-2-nitrophenyl)hydrazono]propanoate (24.5 g). MS: 265 (MH$^+$).

Reference Example 247 ethyl 7-amino-5-methoxy-1H-indole-2-carboxylate

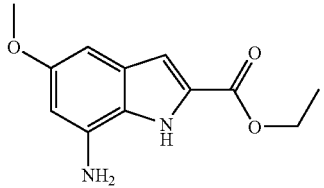

In the same manner as in Reference Example 156, the title compound (2.5 g, yield 96%) was obtained as pale-yellow crystals from ethyl 5-methoxy-7-nitro-1H-indole-2-carboxylate (3 g). MS: 235 (MH$^+$).

Reference Example 248 ethyl 5-methoxy-7-[methyl(pyridin-2-ylsulfonyl)amino]-1H-indole-2-carboxylate

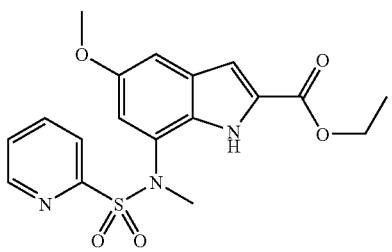

To a solution of ethyl 7-amino-5-methoxy-1H-indole-2-carboxylate (2.5 g) in pyridine (20 mL) was added 2-pyridinesulfonyl chloride (2.1 g) under ice-cooling, and the mixture was stirred for 2 hr. The reaction mixture was concentrated, water was added, and the mixture was extracted with ethyl acetate. The ethyl acetate layer was washed with saturated brine, dried (MgSO$_4$), and concentrated. The obtained residue was dissolved in N,N-dimethylformamide (20 mL), methyl iodide (1.5 g) and potassium carbonate (2 g) were added, and the mixture was stirred at room temperature for 3 hr. Water was added to the reaction mixture, and the mixture was extracted with ethyl acetate. The organic layer was washed with 1N hydrochloric acid and saturated brine, dried (MgSO$_4$), and concentrated under reduced pressure. The obtained residue was subjected to silica gel column chromatography to give the title compound (2.7 g, yield 68%) as pale-yellow crystals from a fraction eluted with ethyl acetate-hexane (50:50, volume ratio). MS: 390 (MH$^+$).

Reference Example 249

5-methoxy-7-[methyl(pyridin-2-ylsulfonyl)amino]-1H-indole-2-carboxylic acid

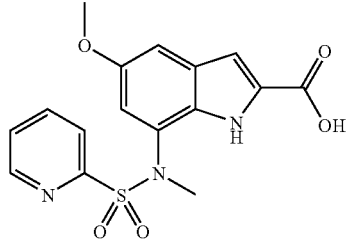

In the same manner as in Reference Example 159, the title compound (2.4 g, yield 99%) was obtained as pale-yellow crystals from ethyl 5-methoxy-7-[methyl(pyridin-2-ylsulfonyl)amino]-1H-indole-2-carboxylate (2.6 g). MS: 362 (MH$^+$).

Reference Example 250

N-[2-(benzylthio)-3,3-dimethoxypropyl]-5-methoxy-7-[methyl(pyridin-2-ylsulfonyl)amino]-1H-indole-2-carboxamide

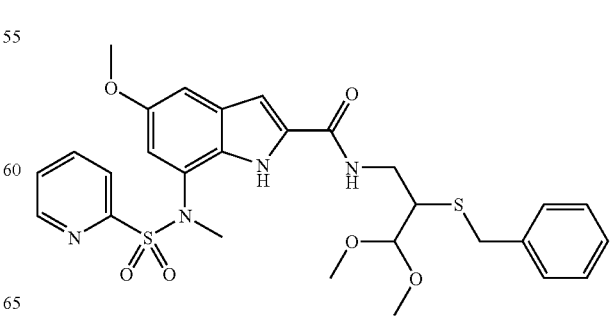

In the same manner as in Reference Example 48, the title compound (3.9 g, yield 99%) was obtained as a yellow oil from 5-methoxy-7-[methyl(pyridin-2-ylsulfonyl)amino]-1H-indole-2-carboxylic acid (2.4 g) and 2-(benzylthio)-3,3-dimethoxypropan-1-amine (1.7 g). MS: 585 (MH⁺).

Reference Example 251 ethyl 2-[(4-bromo-2-nitrophenyl)hydrazono]propanoate

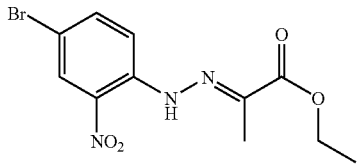

In the same manner as in Reference Example 154, the title compound (74 g, yield 49%) was obtained as brown crystals from 4-bromo-2-nitroaniline (100 g). MS: 331 (MH⁺).

Reference Example 252 ethyl 5-bromo-7-nitro-1H-indole-2-carboxylate

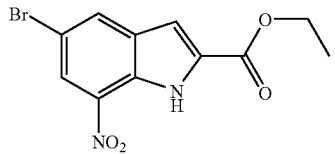

In the same manner as in Reference Example 155, the title compound (14 g, yield 20%) was obtained as brown crystals from ethyl 2-[(4-bromo-2-nitrophenyl)hydrazono]propanoate (74 g). MS: 331 (MH⁺).

Reference Example 253

5-bromo-7-nitro-1H-indole-2-carboxylic acid

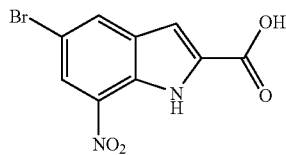

In the same manner as in Reference Example 159, the title compound (12.8 g, yield 95%) was obtained as pale-yellow crystals from ethyl 5-bromo-7-nitro-1H-indole-2-carboxylate (14 g). MS: 286 (MH⁺).

Reference Example 254

N-[2-(benzylthio)-3,3-dimethoxypropyl]-5-bromo-7-nitro-1H-indole-2-carboxamide

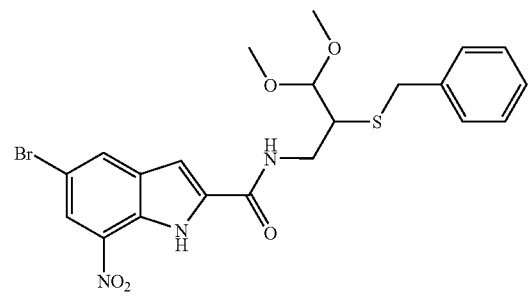

In the same manner as in Reference Example 48, the title compound (10.1 g, yield 46%) was obtained as a yellow oil from 5-bromo-7-nitro-1H-indole-2-carboxylic acid (12.2 g) and 2-(benzylthio)-3,3-dimethoxypropan-1-amine (12 g). MS: 509 (MH⁺)

Reference Example 255

N-[2-(benzylthio)-3-morpholinopropyl]-5-bromo-7-nitro-1H-indole-2-carboxamide

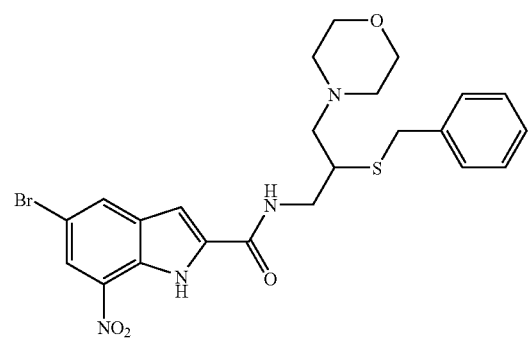

In the same manners as in Reference Example 40 and Reference Example 41, the title compound (8.86 g, yield 83%) was obtained as yellow crystals from N-[2-(benzylthio)-3,3-dimethoxypropyl]-5-bromo-7-nitro-1H-indole-2-carboxamide (10.1 g) and morpholine (3.5 g). MS: 534 (MH⁺).

Reference Example 256

5-bromo-2-[5-(morpholinomethyl)-4,5-dihydro-1,3-thiazol-2-yl]-7-nitro-1H-indole

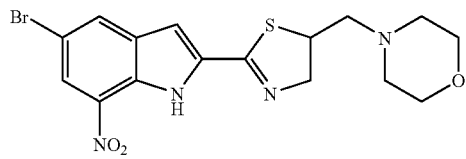

305

In the same manner as in Example 205, the title compound (2.4 g, yield 34%) was obtained as yellow crystals from N-[2-(benzylthio)-3-morpholinopropyl]-5-bromo-7-nitro-1H-indole-2-carboxamide (8.86 g). MS: 426 (MH+).

Reference Example 257

5-bromo-2-[5-(morpholinomethyl)-4,5-dihydro-1,3-thiazol-2-yl]-1H-indol-7-amine

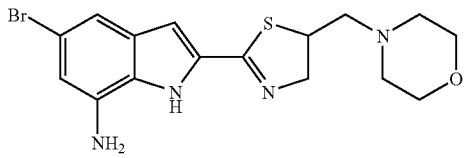

A mixture of 5-bromo-2-[5-(morpholinomethyl)-4,5-dihydro-1,3-thiazol-2-yl]-7-nitro-1H-indole (2.4 g), iron (1.7 g), calcium chloride (310 mg), ethanol (50 mL), tetrahydrofuran (25 mL) and water (5 mL) was stirred under heating at 80° C. for 18 hr. Water was added to the reaction mixture, and the mixture was extracted with ethyl acetate. The organic layer was washed with saturated brine, dried (MgSO4), and concentrated under reduced pressure. The obtained residue was subjected to silica gel column chromatography to give the title compound (500 mg, yield 22%) as yellow crystals from a fraction eluted with ethyl acetate:hexane=50:50. MS: 396 (MH+).

Reference Example 258 ethyl 5-(2-methoxyethoxy)-7-[(pyridin-2-ylsulfonyl)amino]-1H-indole-2-carboxylate

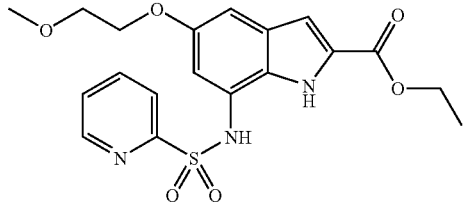

To a solution of ethyl 7-amino-5-(2-methoxyethoxy)-1H-indole-2-carboxylate (5.80 g) in pyridine (100 mL) was added pyridine-2-sulfonyl chloride monohydrochloride (14.0 g), and the mixture was stirred overnight at room temperature. The solvent was evaporated under reduced pressure, and the residue was dissolved in ethyl acetate. The ethyl acetate layer was washed with 1M hydrochloric acid, saturated aqueous sodium hydrogencarbonate and saturated brine, dried (MgSO4), and concentrated. The residue was subjected to silica gel column chromatography to give the title compound (5.70 g, yield 65%) as a colorless amorphous solid from a fraction eluted with ethyl acetate-hexane (1:1, volume ratio). MS: 420 (MH+).

306

Reference Example 259 ethyl 5-(2-methoxyethoxy)-7-[methyl(pyridin-2-ylsulfonyl)amino]-1H-indole-2-carboxylate

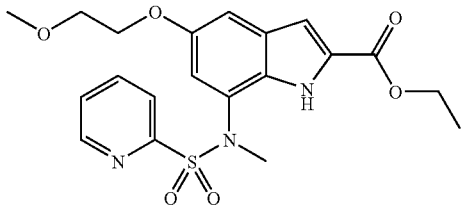

To a solution of ethyl 5-(2-methoxyethoxy)-7-[(pyridin-2-ylsulfonyl)amino]-1H-indole-2-carboxylate (5.70 g) in N,N-dimethylformamide (50 mL) were added potassium carbonate (2.85 g) and methyl iodide (930 µL), and the mixture was stirred overnight at room temperature. The reaction mixture was diluted with ethyl acetate, and washed with water and saturated brine, dried (MgSO4), and concentrated. The residue was subjected to basic silica gel column chromatography to give the title compound (5.67 g, yield 96%) as a colorless amorphous solid from a fraction eluted with ethyl acetate-hexane (1:1, volume ratio). MS: 434 (MH+).

Reference Example 260

5-(2-methoxyethoxy)-7-[methyl(pyridin-2-ylsulfonyl)amino]-1H-indole-2-carboxylic acid

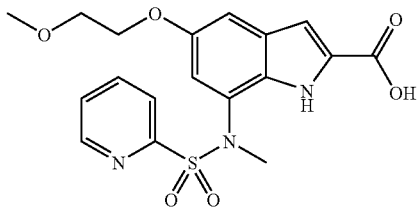

To a solution of ethyl 5-(2-methoxyethoxy)-7-[methyl(pyridin-2-ylsulfonyl)amino]-1H-indole-2-carboxylate (5.67 g) in tetrahydrofuran (50 mL) and methanol (25 mL) was added 2M aqueous sodium hydroxide solution, and the mixture was stirred at 50° C. for 4 hr. The reaction mixture was allowed to cool to room temperature, diluted with ethyl acetate, and neutralized with 1M hydrochloric acid. The ethyl acetate layer was washed with saturated brine, dried (MgSO4), and concentrated. The residue was recrystallized from a mixed solvent of ethyl acetate-hexane to give the title compound (5.30 g, yield 100%) as a white solid. MS: 406 (MH+).

Reference Example 261 ethyl 7-[(cyclopropylmethyl)(pyridin-2-ylsulfonyl)amino]-5-(2-methoxyethoxy)-1H-indole-2-carboxylate

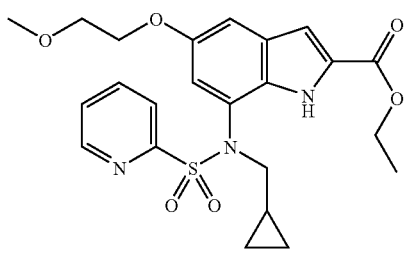

A mixture of ethyl 5-(2-methoxyethoxy)-7-[(pyridin-2-yl-sulfonyl)amino]-1H-indole-2-carboxylate (937 mg), (bromomethyl)cyclopropane (0.22 mL), potassium carbonate (401 mg) and N,N-dimethylformamide (20 mL) was stirred at 50° C. for 15 hr. The reaction mixture was diluted with ethyl acetate and saturated brine. The organic layer was washed with aqueous sodium bicarbonate solution and saturated brine, dried over anhydrous sodium sulfate, and filtered, and the filtrate was concentrated under reduced pressure. The residue was subjected to basic silica gel column chromatography to give the title compound (673 mg, yield 64%) as a pale-yellow amorphous solid from a fraction eluted with ethyl acetate.

1H-NMR (CDCl$_3$) δ: −0.16-−0.04 (2H, m), 0.19-0.34 (2H, m), 0.73-0.89 (1H, m), 1.43 (3H, t, J=7.2 Hz), 3.47 (3H, s), 3.54 (2H, d, J=7.0 Hz), 3.77 (2H, dd, J=5.6, 3.9 Hz), 4.14 (2H, dd, J=5.5, 4.0 Hz), 4.43 (2H, q, J=7.2 Hz), 7.05 (1H, d, J=2.3 Hz), 7.13 (2H, d, J=2.3 Hz), 7.61 (1H, ddd, J=7.5, 4.7, 1.1 Hz), 7.97 (1H, td, J=7.7, 1.7 Hz), 8.10 (1H, d, J=7.9 Hz), 9.10 (1H, dd, J=4.8, 0.8 Hz).

Reference Example 262

7-[(cyclopropylmethyl)(pyridin-2-ylsulfonyl)amino]-5-(2-methoxyethoxy)-1H-indole-2-carboxylic acid

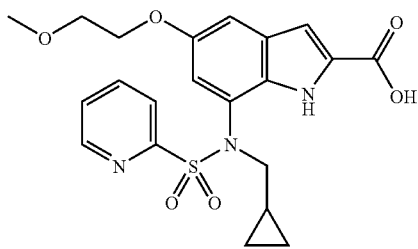

To a mixture of ethyl 7-[(cyclopropylmethyl)(pyridin-2-ylsulfonyl)amino]-5-(2-methoxyethoxy)-1H-indole-2-carboxylate (650 mg), ethanol (10 mL) and tetrahydrofuran (10 mL) was added 2N aqueous sodium hydroxide solution (3.43 mL) at room temperature, and the mixture was stirred at 50° C. for 5 hr. The reaction mixture was concentrated under reduced pressure, and the residue was diluted with ethyl acetate and 1N aqueous hydrochloric acid. The organic layer was washed with saturated brine, dried over anhydrous sodium sulfate, and filtered, and the filtrate was concentrated under reduced pressure to give the title compound (630 mg, yield 99%) as a colorless amorphous solid.

1H-NMR (DMSO-d$_6$) δ: −0.28-−0.14 (2H, m), 0.04-0.21 (2H, m), 0.67-0.87 (1H, m), 3.30 (3H, s), 3.57 (2H, d, J=7.2 Hz), 3.63 (2H, dd, J=5.4, 3.7 Hz), 4.04 (2H, dd, J=5.3, 3.8 Hz), 6.75 (1H, d, J=2.1 Hz), 7.06 (1H, d, J=1.9 Hz), 7.18 (1H, d, J=2.3 Hz), 7.85 (1H, dd, J=6.8, 4.7 Hz), 8.04 (1H, d, J=7.9 Hz), 8.12-8.25 (1H, m), 8.96 (1H, d, J=4.5 Hz), 12.39 (1H, s), 13.08 (1H, brs).

Reference Example 263

N-[2-(benzylthio)-3-thiomorpholinopropyl]-7-[(cyclopropylmethyl)(pyridin-2-ylsulfonyl)amino]-5-(2-methoxyethoxy)-1H-indole-2-carboxamide

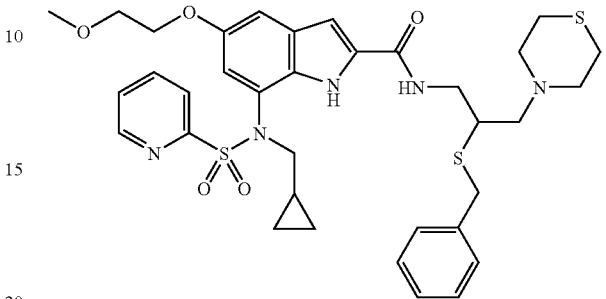

In the same manner as in Reference Example 216, the title compound (537 mg, yield 76%) was obtained as a colorless amorphous solid from 7-[(cyclopropylmethyl)(pyridin-2-ylsulfonyl)amino]-5-(2-methoxyethoxy)-1H-indole-2-carboxylic acid (445 mg) and 2-(benzylthio)-3-thiomorpholinopropan-1-amine (339 mg).

1H-NMR (CDCl$_3$) δ: −0.19-−0.07 (2H, m), 0.25-0.32 (1H, m), 0.76-0.91 (1H, m), 2.59-2.75 (9H, m), 2.84-2.97 (1H, m), 3.47 (3H, s), 3.51 (2H, d, J=7.2 Hz), 3.73-3.88 (5H, m), 4.08-4.24 (2H, m), 6.69 (1H, s), 7.06 (1H, d, J=2.1 Hz), 7.14 (1H, d, J=2.3 Hz), 7.22-7.38 (6H, m), 7.41-7.54 (1H, m), 7.61 (1H, ddd, J=7.6, 4.8, 1.1 Hz), 7.96 (1H, td, J=7.7, 1.7 Hz), 8.11 (1H, d, J=7.9 Hz), 9.22 (1H, d, J=0.9 Hz), 12.24 (1H, brs).

Reference Example 264 ethyl 7-[(2,2-difluoroethyl)(pyridin-2-ylsulfonyl)amino]-5-(2-methoxyethoxy)-1H-indole-2-carboxylate

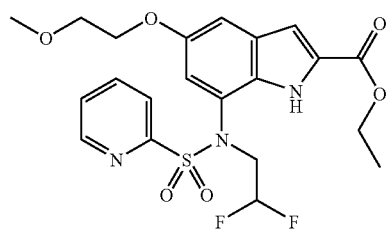

To a mixture of ethyl 5-(2-methoxyethoxy)-7-[(pyridin-2-ylsulfonyl)amino]-1H-indole-2-carboxylate (500 mg), 2,2-difluoroethanol (0.09 mL), tributylphosphine (0.59 mL) and toluene (30 mL) was added 1,1'-(azodicarbonyl)dipiperidine (600 mg), and the mixture was stirred at room temperature overnight. The insoluble substance was filtered off, and the filtrate was diluted with ethyl acetate and 1N aqueous hydrochloric acid solution. The organic layer was washed with aqueous sodium bicarbonate solution and saturated brine, dried over anhydrous magnesium sulfate, and filtered, and the filtrate was concentrated under reduced pressure. The residue was subjected to basic silica gel column chromatography to give the title compound (211 mg, yield 37%) as a colorless amorphous solid from a fraction eluted with ethyl acetate-hexane (1:4, volume ratio).

1H-NMR (CDCl$_3$) δ: 1.43 (3H, t, J=7.2 Hz), 3.45 (3H, s), 3.70-3.83 (2H, m), 4.06-4.20 (4H, m), 4.43 (2H, q, J=7.2 Hz), 5.85 (1H, tt, J=55.6, 4.3 Hz), 6.95 (1H, d, J=2.3 Hz), 7.12 (2H, d, J=2.1 Hz), 7.62 (1H, ddd, J=7.3, 4.7, 1.5 Hz), 7.97 (2H, dddd, J=14.9, 7.9, 7.6, 1.5 Hz), 9.06 (1H, dd, J=4.1, 0.8 Hz).

Reference Example 265

7-[(2,2-difluoroethyl)(pyridin-2-ylsulfonyl)amino]-5-(2-methoxyethoxy)-1H-indole-2-carboxylic acid

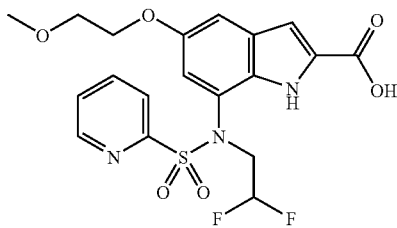

In the same manner as in Reference Example 262, the title compound (277 mg, yield 92%) was obtained as a colorless amorphous solid from ethyl 7-[(2,2-difluoroethyl)(pyridin-2-ylsulfonyl)amino]-5-(2-methoxyethoxy)-1H-indole-2-carboxylate (320 mg).

1H-NMR (DMSO-d$_6$) δ: 3.27 (3H, s), 3.50-3.64 (2H, m), 3.89-4.02 (2H, m), 4.19-4.35 (2H, m), 6.11-6.68 (1H, m), 6.45 (1H, d, J=2.1 Hz), 7.05 (1H, d, J=2.1 Hz), 7.15 (1H, d, J=2.1 Hz), 7.70-7.95 (2H, m), 7.99-8.28 (1H, m), 8.93 (1H, d, J=4.0 Hz), 12.10 (1H, s), 13.00 (1H, brs).

Reference Example 266

N-[2-(benzylthio)-3-thiomorpholinopropyl]-7-[(2,2-difluoroethyl)(pyridin-2-ylsulfonyl)amino]-5-(2-methoxyethoxy)-1H-indole-2-carboxamide

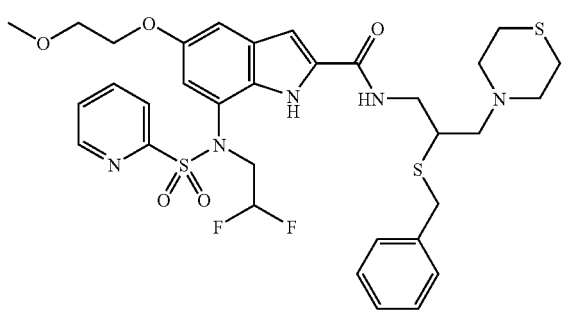

In the same manner as in Reference Example 216, the title compound (294 mg, yield 69%) was obtained as a colorless amorphous solid from 7-[(2,2-difluoroethyl)(pyridin-2-ylsulfonyl)amino]-5-(2-methoxyethoxy)-1H-indole-2-carboxylic acid (270 mg) and 2-(benzylthio)-3-thiomorpholinopropan-1-amine (201 mg).

1H-NMR (CDCl$_3$) δ: 2.62-2.98 (10H, m), 3.00-3.15 (1H, m), 3.45 (3H, s), 3.49-3.62 (1H, m), 3.69-3.87 (5H, m), 4.01-4.20 (3H, m), 5.63-6.19 (2H, m), 6.89 (2H, dd, J=8.8, 2.2 Hz), 7.07 (1H, d, J=2.1 Hz), 7.19-7.35 (6H, m), 7.55-7.70 (2H, m), 7.72-7.82 (1H, m), 7.89-8.06 (2H, m).

Reference Example 267

1-tert-butyl 2-ethyl 5-(2-methoxyethoxy)-7-nitro-1H-indole-1,2-dicarboxylate

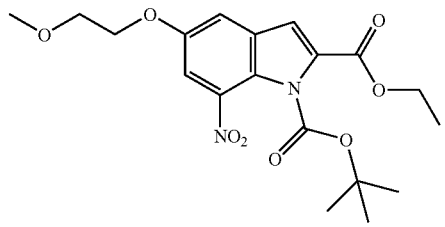

To a mixture of ethyl 5-(2-methoxyethoxy)-7-nitro-1H-indole-2-carboxylate (3.08 g), t-butyl bicarbonate (4.37 g) and tetrahydrofuran (100 mL) was added N,N-dimethyl-4-aminopyridine (122 mg), and the mixture was stirred at 50° C. for 4 hr. The reaction mixture was diluted with ethyl acetate and water, and the organic layer was washed successively with 10% aqueous citric acid solution, aqueous sodium bicarbonate solution and saturated brine, dried over anhydrous sodium sulfate, and filtered, and the filtrate was concentrated under reduced pressure. The residue was subjected to basic silica gel column chromatography to give the title compound (3.93 g, yield 96%) as a yellow oil from a fraction eluted with ethyl acetate-hexane (2:3, volume ratio).

1H-NMR (CDCl$_3$) δ: 1.40 (3H, t, J=7.2 Hz), 1.62 (9H, s), 3.72-3.86 (2H, m), 4.11-4.26 (2H, m), 4.40 (2H, q, J=7.2 Hz), 7.11 (1H, s), 7.37 (1H, d, J=2.4 Hz), 7.64 (1H, d, J=2.4 Hz).

Reference Example 268

1-tert-butyl 2-ethyl 7-amino-5-(2-methoxyethoxy) indoline-1,2-dicarboxylate

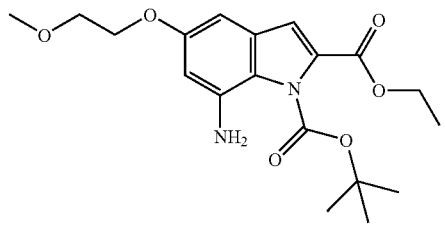

A mixture of 1-tert-butyl 2-ethyl 5-(2-methoxyethoxy)-7-nitro-1H-indole-1,2-dicarboxylate (3.9 g), 10% palladium-carbon (50% containing water, 400 mg) and tetrahydrofuran (80 mL) was stirred at room temperature under hydrogen atmosphere at normal pressure for 6 hr. The catalyst was filtered off, and the filtrate was concentrated. The residue was subjected to silica gel column chromatography to give the title compound (3.22 g, yield 89%) as a colorless solid from a fraction eluted with ethyl acetate-hexane (9:1, volume ratio).

1H-NMR (CDCl$_3$) δ: 1.25 (3H, t, J=7.2 Hz), 1.50 (9H, s), 2.99 (1H, dd, J=16.4, 2.8 Hz), 3.35-3.51 (1H, m), 3.42 (3H, s), 3.69 (2 H, dd, J=5.6, 4.1 Hz), 4.02 (2H, dd, J=5.2, 4.1 Hz), 4.08-4.25 (2H, m), 4.87-5.04 (3H, m), 6.12 (1H, d, J=2.4 Hz), 6.16 (1H, d, J=2.4 Hz).

Reference Example 269

1-tert-butyl 2-ethyl 7-(cyclopropylamino)-5-(2-methoxyethoxy)indoline-1,2-dicarboxylate

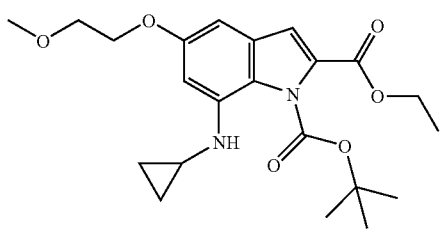

To a mixture of 1-tert-butyl 2-ethyl 7-amino-5-(2-methoxyethoxy)indoline-1,2-dicarboxylate (2.76 g), [(1-ethoxycyclopropyl)oxy](trimethyl)silane (7.29 mL), acetic acid (4.19 mL) and ethanol (70 mL) was added sodium cyanoborohydride (122 mg), and the mixture was refluxed for 3 hr. The reaction mixture was concentrated under reduced pressure, and the residue was diluted with ethyl acetate and water. The organic layer was washed with saturated brine, dried over anhydrous sodium sulfate, and filtered, and the filtrate was concentrated under reduced pressure. The residue was subjected to silica gel column chromatography to give the title compound (2.30 g, yield 75%) as a pale-yellow oil from a fraction eluted with ethyl acetate-hexane (4:1, volume ratio).

1H-NMR (CDCl$_3$) δ: 0.44-0.60 (2H, m), 0.62-0.76 (2H, m), 1.24 (3H, t, J=7.0 Hz), 1.49 (9H, s), 2.35-2.46 (1H, m), 2.97 (1H, dd, J=16.3, 2.7 Hz), 3.44 (3H, s), 3.37-3.54 (1H, m), 3.64-3.78 (2H, m), 4.01-4.25 (4H, m, J=10.6, 7.1, 7.1, 3.6 Hz), 4.93 (1H, dd, J=10.6, 3.0 Hz), 6.10 (1H, d, J=2.3 Hz), 6.58 (1H, d, J=2.3 Hz), 6.80 (1H, brs).

Reference Example 270

1-tert-butyl 2-ethyl 7-[cyclopropyl(pyridin-2-ylsulfonyl)amino]-5-(2-methoxyethoxy)indoline-1,2-dicarboxylate

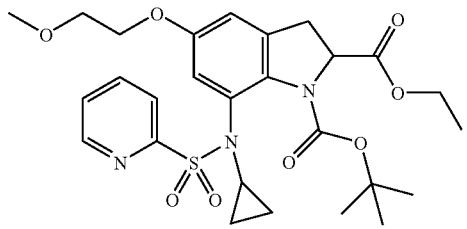

To a mixture of 1-tert-butyl 2-ethyl 7-(cyclopropylamino)-5-(2-methoxyethoxy)indoline-1,2-dicarboxylate (1.9 g) and pyridine (3 mL) was added a mixture of 2-pyridylsulfonyl chloride (1.2 g) and pyridine (2 mL) at 0° C., and the mixture was stirred at room temperature overnight. The reaction mixture was concentrated under reduced pressure, and the residue was diluted with ethyl acetate and water. The organic layer was washed with aqueous 10% aqueous citric acid solution, aqueous sodium bicarbonate solution and saturated brine, dried over anhydrous sodium sulfate, and filtered, and the filtrate was subjected to silica gel column chromatography to give the title compound (1.70 g, yield 67%) as a pale-yellow oil from a fraction eluted with ethyl acetate-hexane (9:1, volume ratio). MS: 562 (MH$^+$).

Reference Example 271 ethyl 7-[cyclopropyl(pyridin-2-ylsulfonyl)amino]-5-(2-methoxyethoxy)indoline-2-carboxylate

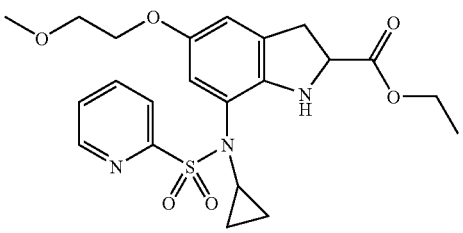

1-tert-Butyl 2-ethyl 7-[cyclopropyl(pyridin-2-ylsulfonyl)amino]-5-(2-methoxyethoxy)indoline-1,2-dicarboxylate (1.70 g) was added to 4N hydrogen chloride-ethyl acetate solution (50 mL), and the mixture was stirred at room temperature for 2 hr. The reaction mixture was concentrated under reduced pressure, and the residue was diluted with ethyl acetate and aqueous sodium bicarbonate solution. The organic layer was washed with saturated brine, dried over anhydrous sodium sulfate, and filtered, and the filtrate was concentrated under reduced pressure to give the title compound (1.34 g, yield 96%) as a pale-yellow amorphous solid.

1H-NMR (CDCl$_3$) δ: 0.49-0.97 (4H, m), 1.19-1.36 (4H, m), 3.08-3.23 (1H, m), 3.23-3.37 (2H, m), 3.40 (3H, s), 3.63 (2H, t, J=4.8 Hz), 3.77-3.93 (2H, m), 4.20 (2H, q, J=7.2 Hz), 4.30-4.46 (1H, m), 6.27 (1H, d, J=1.7 Hz), 6.67 (1H, d, J=2.4 Hz), 7.52 (1H, ddd, J=7.3, 4.8, 1.3 Hz), 7.81-7.97 (2H, m), 8.80 (1H, d, J=4.3 Hz).

Reference Example 272 ethyl 7-[cyclopropyl(pyridin-2-ylsulfonyl)amino]-5-(2-methoxyethoxy)-1H-indole-2-carboxylate

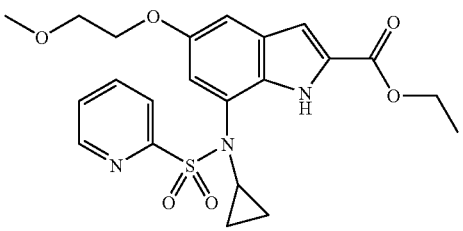

To a mixture of ethyl 7-[cyclopropyl(pyridin-2-ylsulfonyl)amino]-5-(2-methoxyethoxy)indoline-2-carboxylate (1.31 g) and toluene (30 mL) was added manganese (IV) oxide (0.99 g) at room temperature, and the mixture was refluxed for 3 hr. The catalyst was filtered off, and the filtrate was concentrated. The residue was subjected to silica gel column chromatography to give the title compound (1.23 g, yield 94%) as a colorless solid from a fraction eluted with ethyl acetate-hexane (4:1, volume ratio).

1H-NMR (CDCl$_3$) δ: 0.33 (2H, brs), 0.52-0.68 (2H, m), 1.43 (3H, t, J=7.1 Hz), 3.19-3.30 (1H, m), 3.47 (3H, s), 3.73-3.82 (2H, m), 4.12-4.21 (2H, m), 4.42 (2H, q, J=7.1 Hz), 7.08 (2H, s), 7.12 (1H, d, J=2.1 Hz), 7.64 (1H, ddd, J=7.7, 4.7, 0.9 Hz), 8.01 (1H, td, J=7.8, 1.7 Hz), 8.20 (1H, d, J=7.9 Hz), 9.13 (1H, d, J=4.0 Hz), 12.38 (1H, brs).

Reference Example 273

7-[cyclopropyl(pyridin-2-ylsulfonyl)amino]-5-(2-methoxyethoxy)-1H-indole-2-carboxylic acid

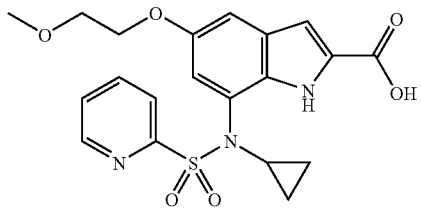

In the same manner as in Reference Example 262, the title compound (1.08 g, yield 95%) was obtained as a colorless amorphous solid from ethyl 7-[cyclopropyl(pyridin-2-ylsulfonyl)amino]-5-(2-methoxyethoxy)-1H-indole-2-carboxylate (1.21 g).

1H-NMR (DMSO-$d_6$) δ: 0.40 (2H, brs), 0.61 (2H, brs), 3.31 (3H, s), 3.32-3.42 (1H, m), 3.61-3.68 (2H, m), 4.00-4.10 (2H, m), 6.79 (1H, d, J=2.3 Hz), 7.06 (1H, d, J=2.1 Hz), 7.14 (1H, d, J=2.1 Hz), 7.82-7.93 (1H, m), 8.09 (1H, d, J=7.9 Hz), 8.18-8.26 (1H, m), 8.97 (1H, d, J=4.1 Hz), 12.48 (1H, s).

Reference Example 274

N-[2-(benzylthio)-3-thiomorpholinopropyl]-7-[cyclopropyl(pyridin-2-ylsulfonyl)amino]-5-(2-methoxyethoxy)-1H-indole-2-carboxamide

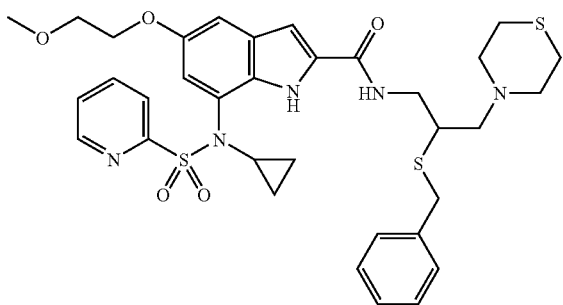

In the same manner as in Reference Example 216, the title compound (451 mg, yield 65%) was obtained as a colorless amorphous solid from 7-[cyclopropyl(pyridin-2-ylsulfonyl)amino]-5-(2-methoxyethoxy)-1H-indole-2-carboxylic acid (231 mg) and 2-(benzylthio)-3-thiomorpholinopropan-1-amine (339 mg).

1H-NMR (CDCl$_3$) δ: 0.34 (2H, brs), 0.5-0.64 (2H, m), 2.59-2.75 (10H, m), 2.84-3.00 (1H, m), 3.19-3.30 (1H, m), 3.48 (3H, s), 3.50-3.63 (1H, m), 3.73-3.88 (5H, m), 4.18 (2H, t, J=4.6 Hz), 6.69 (1H, d, J=1.7 Hz), 7.03-7.11 (2H, m), 7.22-7.37 (5H, m), 7.43-7.56 (1H, m), 7.64 (1H, ddd, J=7.6, 4.7, 1.0 Hz), 8.01 (1H, td, J=7.7, 1.7 Hz), 8.20 (1H, d, J=7.9 Hz), 9.26 (1H, dd, J=4.6, 0.8 Hz), 12.60 (1H, brs).

Example 253

N-[2-[(4R)-4-(hydroxymethyl)-4,5-dihydro-1,3-thiazol-2-yl]-5-(2-methoxyethoxy)-1H-indol-7-yl]-N-methylpyridine-2-sulfonamide

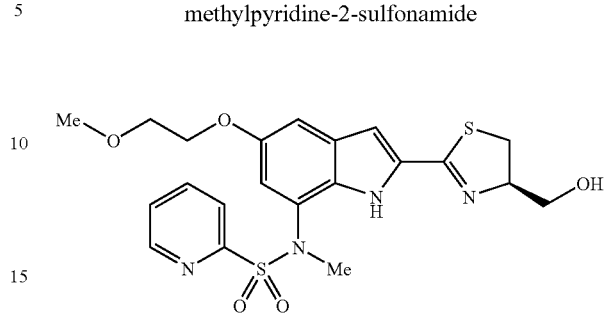

To a solution of triphenylphosphine oxide (2.7 g) in dichloromethane (6 mL) was added dropwise trifluoromethanesulfonic anhydride (1.2 mL) at 0° C., and the mixture was stirred at 0° C. for 15 min. The obtained suspension was diluted with dichloromethane (19 mL), and a solution of S-benzyl-N-({5-(2-methoxyethoxy)-7-[methyl(pyridin-2-ylsulfonyl)amino]-1H-indol-2-yl}carbonyl)-L-cysteine methyl ester (1.0 g) and thioanisole (1.5 mL) in dichloromethane (25 mL) was added. The reaction mixture was stirred at 0° C. for 1 hr, saturated aqueous sodium hydrogencarbonate solution was added, and the mixture was concentrated. The residue was extracted with ethyl acetate. The ethyl acetate layer was washed with water and saturated brine, dried (MgSO$_4$), and concentrated. The obtained residue was subjected to basic silica gel column chromatography, and eluted with hexane-ethyl acetate (1:1, volume ratio) to give a mixture of methyl (4R)-2-{5-(2-methoxyethoxy)-7-[methyl(pyridin-2-ylsulfonyl)amino]-1H-indol-2-yl}-4,5-dihydro-1,3-thiazole-4-carboxylate and triphenylphosphine oxide. The obtained mixture of the ester and triphenylphosphine oxide was dissolved in tetrahydrofuran (5 mL), sodium borohydride (0.053 mg) was added at 0° C., and methanol (2.5 mL) was added dropwise at 0° C. The reaction mixture was stirred at 0° C. for 1 hr, and then at room temperature for 3 hr. Water was added, the mixture was concentrated, and the residue was extracted with ethyl acetate. The ethyl acetate layer was washed with water and saturated brine, dried (MgSO$_4$), and concentrated. The obtained residue was subjected to silica gel column chromatography, and eluted with hexane-ethyl acetate (4:1-0:1, volume ratio) to give the title compound (0.27 g, yield 36%) as a colorless amorphous solid. MS: 477 (MH$^+$).

$^1$H-NMR (CDCl$_3$) δ: 1.97-2.03 (1H, m), 3.30-3.39 (1H, m), 3.33 (3H, s), 3.46 (3H, s), 3.47-3.58 (1H, m), 3.68-3.79 (2H, m), 3.79-3.95 (1H, m), 3.98-4.09 (1H, m), 4.08-4.14 (2H, m), 4.77-4.96 (1H, m), 6.86 (1H, d, J=2.1 Hz), 6.88 (1H, d, J=2.1 Hz), 7.06 (1H, d, J=2.1 Hz), 7.57-7.68 (1H, m), 7.90-7.99 (1H, m), 8.00-8.06 (1H, m), 9.04 (1H, d, J=4.0 Hz), 11.53 (1H, d, J=2.6 Hz).

Example 254

N-[2-[(4S)-4-(hydroxymethyl)-4,5-dihydro-1,3-thiazol-2-yl]-5-(2-methoxyethoxy)-1H-indol-7-yl]-N-methylpyridine-2-sulfonamide

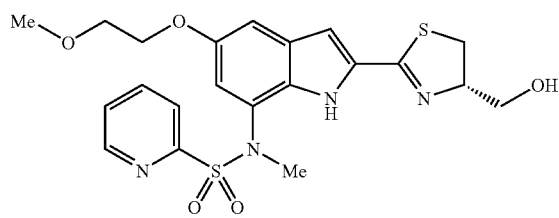

To a solution of triphenylphosphine oxide (1.3 g) in dichloromethane (3 mL) was added dropwise trifluoromethanesulfonic anhydride (0.59 mL) at 0° C., and the mixture was stirred at 0° C. for 15 min. The obtained suspension was diluted with dichloromethane (5 mL), and a solution of N-({5-(2-methoxyethoxy)-7-[methyl(pyridin-2-ylsulfonyl)amino]-1H-indol-2-yl}carbonyl)-S-trityl-D-cysteine methyl ester (0.60 g) and thioanisole (0.74 mL) in dichloromethane (8 mL) was added. The reaction mixture was stirred at 0° C. for 2 hr, and saturated aqueous sodium hydrogencarbonate solution was added. The mixture was concentrated, and the residue was extracted with ethyl acetate. The ethyl acetate layer was washed with water and saturated brine, dried (MgSO$_4$), and concentrated. The obtained residue was subjected to silica gel column chromatography, and eluted with hexane-ethyl acetate (4:1-1:1, volume ratio) to give a mixture (0.39 g) of methyl (4S)-2-{5-(2-methoxyethoxy)-7-[methyl(pyridin-2-ylsulfonyl)amino]-1H-indol-2-yl}-4,5-dihydro-1,3-thiazole-4-carboxylate and triphenylphosphine oxide. The obtained mixture of the ester and triphenylphosphine oxide was dissolved in tetrahydrofuran (3 mL), sodium borohydride (0.010 mg) was added at 0° C., and methanol (1.5 mL) was added dropwise at 0° C. The reaction mixture was stirred at 0° C. for 30 min, and then at room temperature for 2 hr. Water was added, the mixture was concentrated, and the residue was extracted with ethyl acetate. The ethyl acetate layer was washed with water and saturated brine, dried (MgSO$_4$), and concentrated. The obtained residue was subjected to basic silica gel column chromatography, and eluted with hexane-ethyl acetate-methanol (4:1:0-0:10:1, volume ratio) to give the title compound (0.076 g, yield 20%) as colorless crystals. melting point 146.6-146.7° C.

$^1$H-NMR (CDCl$_3$) δ: 2.22 (1H, brs), 3.27-3.39 (1H, m), 3.34 (3H, s), 3.45 (3H, s), 3.46-3.56 (1H, m), 3.70-3.77 (2H, m), 3.78-3.93 (1H, m), 4.01-4.07 (1H, m), 4.07-4.15 (2H, m), 4.79-4.91 (1H, m), 6.81-6.93 (2H, m), 7.05 (1H, d, J=2.3 Hz), 7.53-7.63 (1H, m), 7.89-7.98 (1H, m), 7.98-8.07 (1H, m), 9.03 (1H, d, J=4.5 Hz), 11.54 (1H, brs).

Example 255

((4R)-2-{5-(2-methoxyethoxy)-7-[methyl(pyridin-2-ylsulfonyl)amino]-1H-indol-2-yl}-4,5-dihydro-1,3-thiazol-4-yl)methyl methanesulfonate

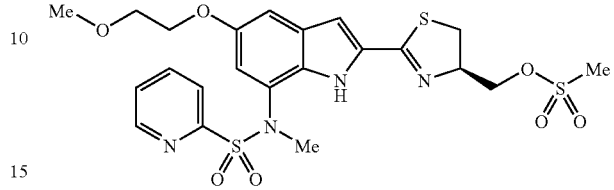

A solution of N-[2-[(4R)-4-(hydroxymethyl)-4,5-dihydro-1,3-thiazol-2-yl]-5-(2-methoxyethoxy)-1H-indol-7-yl]-N-methylpyridine-2-sulfonamide (0.28 g), methanesulfonyl chloride (0.10 g) and triethylamine (0.16 mL) in tetrahydrofuran (5.0 mL) was stirred at room temperature for 2 hr, and extracted with ethyl acetate. The organic layer was washed with water and saturated brine, dried (MgSO$_4$), and concentrated. The obtained residue was subjected to silica gel column chromatography, and eluted with hexane-ethyl acetate (4:1-1:4, volume ratio) to give the title compound (0.25 g, yield 77%) as a colorless oil.

$^1$H-NMR (CDCl$_3$) δ: 3.05 (3H, s), 3.28 (3H, s), 3.31-3.41 (1H, m), 3.46 (3H, s), 3.52-3.64 (1H, m), 3.69-3.81 (2H, m), 4.06-4.18 (2H, m), 4.49-4.59 (2H, m), 4.97-5.08 (1H, m), 6.88 (1H, d, J=1.9 Hz), 6.96 (1H, d, J=1.9 Hz), 7.07 (1H, s), 7.64-7.74 (1H, m), 7.98 (1H, t, J=7.8 Hz), 8.04-8.11 (1H, m), 9.13 (1H, d, J=4.0 Hz), 12.04 (1H, brs).

Example 256

N-[2-(1,8-dithia-3-azaspiro[4.5]dec-2-en-2-yl)-5-(2-methoxyethoxy)-1H-indol-7-yl]-N-methylpyridine-2-sulfonamide

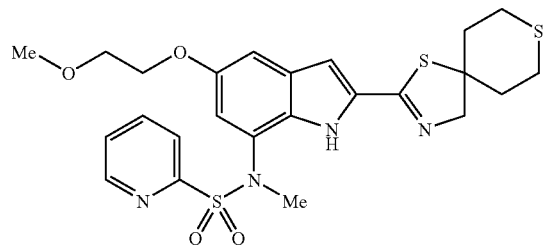

To a solution of triphenylphosphine oxide (2.0 g) in acetonitrile (14 mL) was added dropwise trifluoromethanesulfonic anhydride (1.0 mL) at 0° C., and the mixture was stirred at 0° C. for 30 min. The obtained suspension was diluted with acetonitrile (36 mL), and a solution of N-{[4-(benzylthio)tetrahydro-2H-thiopyran-4-yl]methyl}-5-(2-methoxyethoxy)-7-[methyl(pyridin-2-ylsulfonyl)amino]-1H-indole-2-carboxamide (1.9 g) and thioanisole (0.70 mL) in acetonitrile (50 mL) was added. The reaction mixture was stirred at 0° C. for 2 hr, saturated aqueous sodium hydrogencarbonate solution was added, and the mixture was extracted with ethyl acetate. The ethyl acetate layer was washed with water and saturated brine, dried (MgSO$_4$), and concentrated.

The obtained residue was subjected to silica gel column chromatography, and eluted with hexane-ethyl acetate (9:1-3:7, volume ratio) to give the title compound (0.26 g, yield 17%) as colorless crystals.

$^1$H-NMR (CDCl$_3$) δ: 1.90-2.20 (2H, m), 2.35 (2H, d, J=13.9 Hz), 2.61-2.76 (2H, m), 2.78-2.94 (2H, m), 3.30 (3H, s), 3.46 (3H, s), 3.64-3.80 (2H, m), 4.05-4.15 (2H, m), 4.18 (2H, s), 6.81 (1H, d, J=2.1 Hz), 6.90 (1H, d, J=2.3 Hz), 7.06 (1H, d, J=2.1 Hz), 7.56-7.64 (1H, m), 7.88-7.99 (1H, m), 8.01-8.10 (1H, m), 9.00-9.07 (1H, m), 11.71 (1H, brs).

Example 257

N-methyl-N-{2-[5-(morpholinomethyl)-4,5-dihydro-1,3-thiazol-2-yl]-1H-indol-7-yl}thiophene-2-sulfonamide

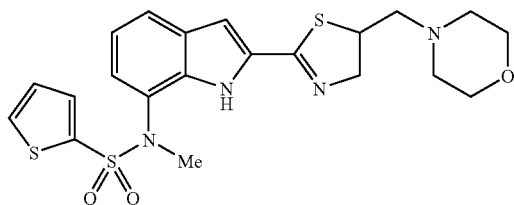

In the same manner as in Example 201, the title compound (0.125 g, yield 60%) was obtained as colorless crystals from N-[2-(benzylthio)-3-morpholinopropyl]-7-[methyl(2-thienylsulfonyl)amino]-1H-indole-2-carboxamide (an optically active form: retention time: longer) (0.255 g) obtained in Reference Example 94. melting point 137-138° C.

Example 258

N-methyl-N-{2-[5-(morpholinomethyl)-4,5-dihydro-1,3-thiazol-2-yl]-1H-indol-7-yl}thiophene-2-sulfonamide

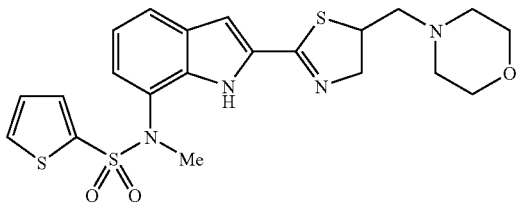

To a suspension of N-methyl-N-{2-[5-(morpholinomethyl)-4,5-dihydro-1,3-thiazol-2-yl]-1H-indol-7-yl}thiophene-2-sulfonamide dihydrochloride (0.010 g) in ethyl acetate (50 mL) was added 2N aqueous sodium hydroxide solution (20 mL), and the mixture was stirred at room temperature for 15 min. The organic layer was separated, and washed with saturated brine, dried over anhydrous magnesium sulfate, and concentrated under reduced pressure. The residue was recrystallized from hexane-ethyl acetate to give the title compound (0.004 g, yield 46%) as colorless crystals. melting point 199-201° C.

Example 259

N-{2-[5-(2-hydroxy-2-methylpropyl)-4,5-dihydro-1,3-thiazol-2-yl]-1H-indol-7-yl}-N-methylthiophene-2-sulfonamide

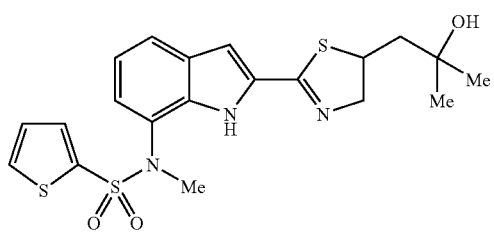

To a solution of ethyl (2-{7-[methyl(2-thienylsulfonyl)amino]-1H-indol-2-yl}-4,5-dihydro-1,3-thiazol-5-yl)acetate (0.204 g) in absolute tetrahydrofuran (10 mL) was added a 1.0M tetrahydrofuran solution (4.4 mL) of methylmagnesium bromide, and the mixture was stirred at room temperature for 2 hr. Saturated aqueous ammonium chloride solution was added to the reaction solution, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=30:70-80:20), and recrystallized from hexane-ethyl acetate to give the title compound (0.142 g, yield 72%) as colorless crystals. melting point 156-158° C.

Example 260

N-methyl-N-{2-[5-(2-morpholino-2-oxoethyl)-4,5-dihydro-1,3-thiazol-2-yl]-1H-indol-7-yl}thiophene-2-sulfonamide

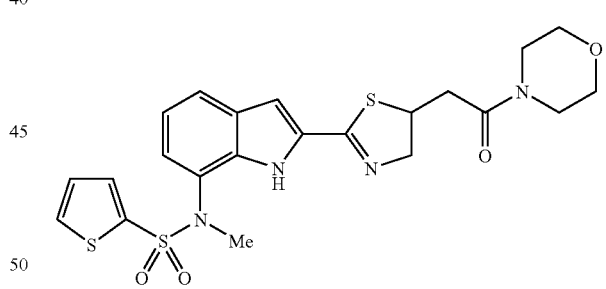

To a solution of (2-{7-[methyl(2-thienylsulfonyl)amino]-1H-indol-2-yl}-4,5-dihydro-1,3-thiazol-5-yl)acetic acid (0.150 g) in N,N-dimethylformamide (6 mL) were added 1H-1,2,3-benzotriazol-1-ol (0.063 g), N-[3-(dimethylamino)propyl]-N'-ethylcarbodiimide hydrochloride (0.079 g), N-ethyldiisopropylamine (0.12 mL) and morpholine (0.06 mL), and the mixture was stirred at room temperature for 20 hr. Water was added to the reaction mixture, and the mixture was extracted with ethyl acetate. The extract was washed with water and saturated brine, dried over anhydrous magnesium sulfate, and concentrated under reduced pressure. The residue was purified by basic silica gel column chromatography (ethyl acetate:methanol=50:50-0:100), and recrystallized from hexane-ethyl acetate to give the title compound (0.099 g, yield 57%) as colorless crystals. melting point 173-174° C.

Example 261

N-(2-{5-[2-(3,3-difluoropyrrolidin-1-yl)-2-oxoethyl]-4,5-dihydro-1,3-thiazol-2-yl}-1H-indol-7-yl)-N-methylthiophene-2-sulfonamide

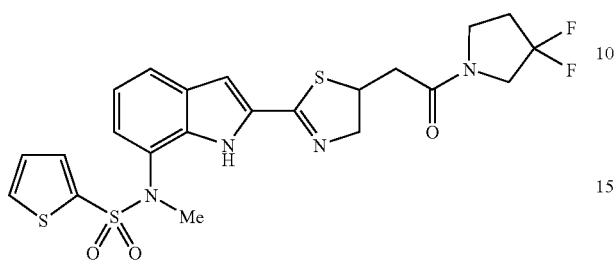

In the same manner as in Example 260, the title compound (0.030 g, yield 16%) was obtained as colorless crystals from (2-{7-[methyl(2-thienylsulfonyl)amino]-1H-indol-2-yl}-4,5-dihydro-1,3-thiazol-5-yl)acetic acid (0.150 g) and 3,3-difluoropyrrolidine (0.099 mg). melting point 172-173° C.

Example 262

N-cyclopropyl-2-(2-{7-[methyl(2-thienylsulfonyl)amino]-1H-indol-2-yl}-4,5-dihydro-1,3-thiazol-5-yl)acetamide

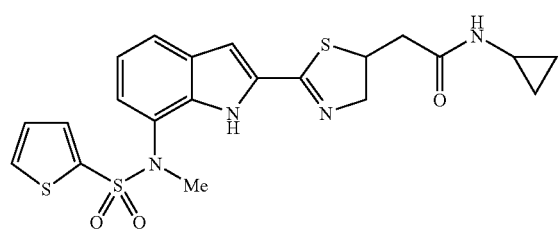

In the same manner as in Example 260, the title compound (0.085 g, yield 52%) was obtained as colorless crystals from (2-{7-[methyl(2-thienylsulfonyl)amino]-1H-indol-2-yl}-4,5-dihydro-1,3-thiazol-5-yl)acetic acid (0.150 g) and cyclopropylamine (0.099 mg). melting point 179-181° C.

Example 263

2-(2-{7-[methyl(2-thienylsulfonyl)amino]-1H-indol-2-yl}-4,5-dihydro-1,3-thiazol-5-yl)-N-(tetrahydro-2H-pyran-4-yl)acetamide

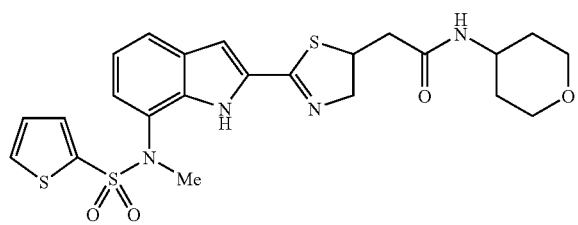

In the same manner as in Example 260, the title compound (0.155 g, yield 87%) was obtained as colorless crystals from (2-{7-[methyl(2-thienylsulfonyl)amino]-1H-indol-2-yl}-4,5-dihydro-1,3-thiazol-5-yl)acetic acid (0.150 g) and tetrahydro-2H-pyran-4-amine (0.069 mg). melting point 190-192° C.

Example 264

N-methyl-N-{2-[5-(2-oxo-2-(pyrrolidin-1-yl)ethyl)-4,5-dihydro-1,3-thiazol-2-yl]-1H-indol-7-yl}thiophene-2-sulfonamide

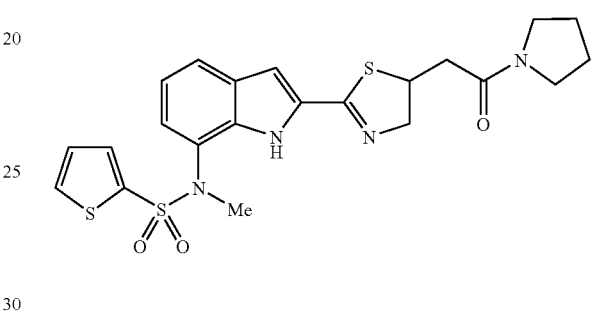

In the same manner as in Example 260, the title compound (0.131 g, yield 78%) was obtained as colorless crystals from (2-{7-[methyl(2-thienylsulfonyl)amino]-1H-indol-2-yl}-4,5-dihydro-1,3-thiazol-5-yl)acetic acid (0.150 g) and pyrrolidine (0.057 mL). melting point 175-176° C.

Example 265

N,N-diethyl-2-(2-{7-[methyl(2-thienylsulfonyl)amino]-1H-indol-2-yl}-4,5-dihydro-1,3-thiazol-5-yl)acetamide

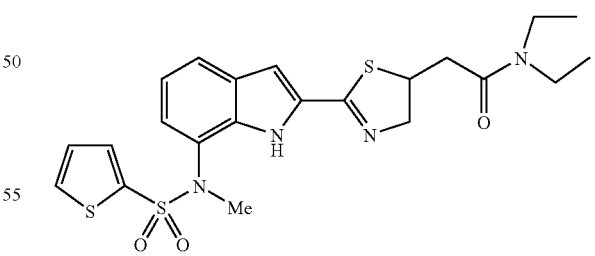

In the same manner as in Example 260, the title compound (0.108 g, yield 64%) was obtained as colorless crystals from (2-{7-[methyl(2-thienylsulfonyl)amino]-1H-indol-2-yl}-4,5-dihydro-1,3-thiazol-5-yl)acetic acid (0.150 g) and diethylamine (0.071 mL). melting point 144-148° C.

Example 266

N-{2-[5-(2-aminoethyl)-4,5-dihydro-1,3-thiazol-2-yl]-1H-indol-7-yl}-N-methylthiophene-2-sulfonamide

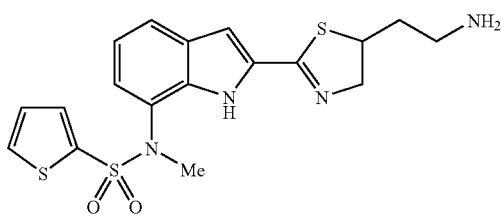

To a solution of N-{2-[5-(2-hydroxyethyl)-4,5-dihydro-1,3-thiazol-2-yl]-1H-indol-7-yl}-N-methylthiophene-2-sulfonamide (0.242 g) in tetrahydrofuran (5 mL) were added triphenylphosphine (0.301 g), a 40% toluene solution (0.500 g) of diethyl azodicarboxylate and diphenylphosphorylazide (0.247 mL), and the mixture was stirred at room temperature for 2 hr. The reaction solution was concentrated under reduced pressure, and the residue was purified by silica gel column chromatography (ethyl acetate:hexane=5:95-60:40) to give a yellow oil. To a solution of the obtained oil in tetrahydrofuran (5 mL) were added water (0.1 mL) and triphenylphosphine (0.226 g), and the mixture was stirred at room temperature for 24 hr. Saturated aqueous sodium hydrogencarbonate solution was added to the reaction solution, and the mixture was extracted with ethyl acetate. The extract was washed with saturated brine, dried over anhydrous sodium sulfate, and concentrated under reduced pressure. The residue was purified by basic silica gel column chromatography (ethyl acetate:methanol=100:0-80:20), and recrystallized from hexane-ethyl acetate to give the title compound (0.100 g, yield in two steps 41%) as pale-yellow crystals. melting point 172-174° C.

Example 267

N-{2-[5-(1,4-dioxa-8-azaspiro[4.5]dec-8-ylmethyl)-5-methyl-4,5-dihydro-1,3-thiazol-2-yl]-1H-indol-7-yl}-N-methylthiophene-2-sulfonamide

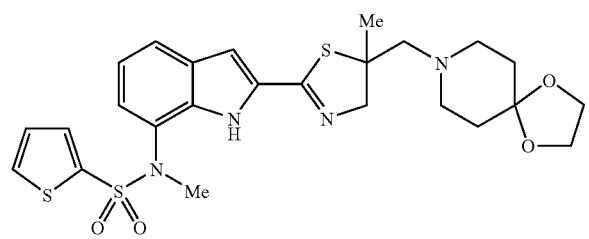

To a solution of triphenylphosphine oxide (0.83 g) in dichloromethane (6 mL) was slowly added trifluoromethanesulfonic anhydride (0.25 mL) at 0° C., and the mixture was added for 10 min. N-[2-(benzylthio)-3-(1,4-dioxa-8-azaspiro[4.5]dec-8-yl)-2-methylpropyl]-7-[methyl(2-thienylsulfonyl)amino]-1H-indole-2-carboxamide (0.72 g) and dimethylsulfide (0.22 mL) were added, and the reaction mixture was stirred at 0° C. for 20 min. Saturated aqueous sodium hydrogencarbonate was added, and the mixture was extracted with ethyl acetate. The ethyl acetate layer was washed with saturated brine, dried (MgSO$_4$), and concentrated. The residue was subjected to silica gel column chromatography from a fraction eluted with ethyl acetate-hexane (2:3, volume ratio) to give the title compound (0.28 g, yield 50%) as colorless crystals. melting point 172-173° C.

Example 268

N-[2-(9,12-dioxa-1-thia-3-azadispiro[4.2.4.2]tetradec-2-en-2-yl)-1H-indol-7-yl]-N-methylthiophene-2-sulfonamide

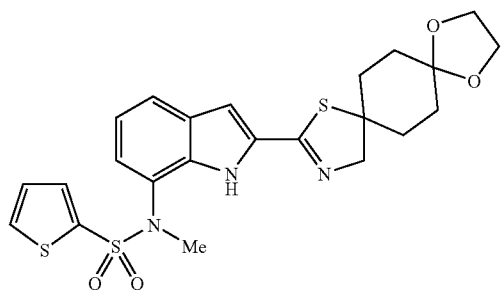

To a solution of triphenylphosphine oxide (1.98 g) in acetonitrile (30 mL) was slowly added trifluoromethanesulfonic anhydride (0.60 mL) at 0° C., and the mixture was stirred for 10 min. N-{[8-(Benzylthio)-1,4-dioxaspiro[4.5]dec-8-yl]methyl}-7-[methyl(2-thienylsulfonyl)amino]-1H-indole-2-carboxamide (1.45 g) and dimethylsulfide (0.52 mL) were added, and the reaction mixture was stirred at 0° C. for 30 min. Saturated aqueous sodium hydrogencarbonate was added, and the precipitated solid was collected by filtration, and washed with water. The obtained solid was washed with ethyl acetate, and dried to give the title compound (0.75 g, yield 63%) as colorless crystals. melting point 224-225° C.

Example 269

2-(5-methyl-2-{7-[methyl(2-thienylsulfonyl)amino]-1H-indol-2-yl}-4,5-dihydro-1,3-thiazol-5-yl)ethyl methanesulfonate

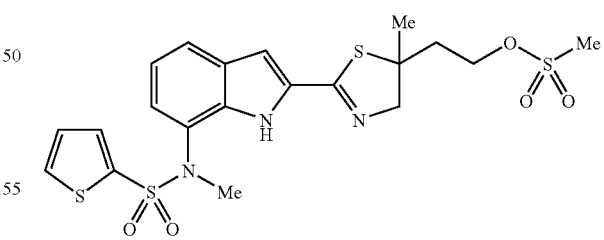

To a solution of N-{2-[5-(2-hydroxyethyl)-5-methyl-4,5-dihydro-1,3-thiazol-2-yl]-1H-indol-7-yl}-N-methylthiophene-2-sulfonamide (0.75 g) and triethylamine (0.50 mL) in tetrahydrofuran (10 mL) was slowly added methanesulfonyl chloride (0.20 mL) at 0° C., and the mixture was stirred at room temperature for 1 hr. Water was added to the reaction mixture, and the mixture was extracted with ethyl acetate. The ethyl acetate layer was washed with saturated brine, dried (MgSO$_4$), and concentrated. The residue was subjected to silica gel column chromatography to give the title compound (0.56 g, yield 65%) as colorless crystals from a fraction eluted with ethyl acetate-hexane (3:1, volume ratio). melting point 149-150° C.

Example 270

N-methyl-N-{2-[5-methyl-5-(piperazine-1-ylmethyl)-4,5-dihydro-1,3-thiazol-2-yl]-1H-indol-7-yl}thiophene-2-sulfonamide

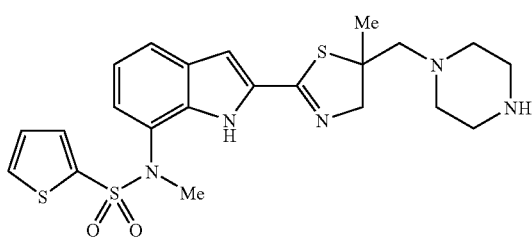

To a mixture of triphenylphosphine oxide (3.09 g) and acetonitrile (20 mL) was slowly added trifluoromethanesulfonic anhydride (0.93 mL) at 0° C., and the mixture was stirred for 10 min. tert-Butyl 4-{2-(benzylthio)-2-methyl-3-[({7-[methyl(2-thienylsulfonyl)amino]-1H-indol-2-yl}carbonyl)amino]propyl}piperazine-1-carboxylate (1.55 g) and dimethylsulfide (0.24 mL) were added, and the reaction mixture was stirred at 0° C. for 30 min. Saturated aqueous sodium hydrogencarbonate was added, and the mixture was extracted with ethyl acetate. The ethyl acetate layer was washed with saturated brine, dried (MgSO$_4$), and concentrated. The residue was added to 4N hydrogen chloride-ethyl acetate solution, and the resulting crystals were collected by filtration, and washed with ethyl acetate. The obtained crystals were added to saturated aqueous sodium hydrogencarbonate, and the mixture was stirred for 30 min. The crystals were collected by filtration, washed with water and ethyl acetate, and dried to give the title compound (0.49 g, yield 45%) as colorless crystals. melting point 178-180° C.

Example 271

N-methyl-N-[2-(8-oxo-1-thia-3-azaspiro[4.5]dec-2-en-2-yl)-1H-indol-7-yl]thiophene-2-sulfonamide

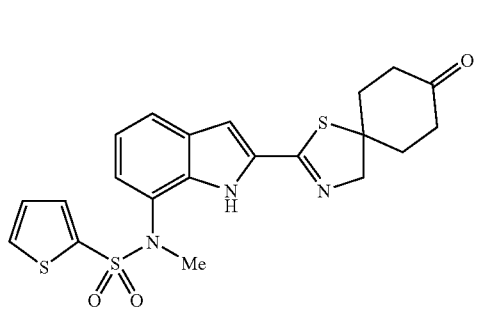

In the same manner as in Example 267, the title compound (0.34 g, yield 53%) was obtained as colorless crystals from N-{[1-(benzylthio)-4-oxocyclohexyl]methyl}-7-[methyl(2-thienylsulfonyl)amino]-1H-indole-2-carboxamide (0.79 g). melting point 207-208° C.

Example 272

N-methyl-N-{2-[5-(morpholinocarbonyl)-4,5-dihydro-1,3-thiazol-2-yl]-1H-indol-7-yl}thiophene-2-sulfonamide

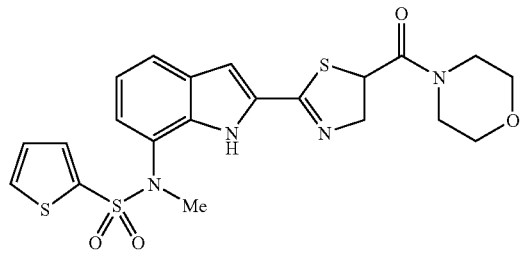

To a mixture of 2-{7-[methyl(2-thienylsulfonyl)amino]-1H-indol-2-yl}-4,5-dihydro-1,3-thiazole-5-carboxylic acid (0.25 g), morpholine (0.10 g), 1H-1,2,3-benzotriazol-1-ol (0.10 g) and N,N-dimethylformamide (4 mL) was added N-[3-(dimethylamino)propyl]-N'-ethylcarbodiimide hydrochloride (0.14 g) at room temperature, and the mixture was stirred overnight at room temperature. Water was added to the reaction mixture, and the precipitated solid was collected by filtration, washed with water, and dried. The obtained solid was subjected to basic silica gel column chromatography to give the title compound (0.25 g, yield 86%) as pale-yellow crystals from a fraction eluted with tetrahydrofuran. melting point 238-239° C.

Example 273

N-methyl-N-(2-{5-[(4-methylpiperazin-1-yl)carbonyl]-4,5-dihydro-1,3-thiazol-2-yl}-1H-indol-7-yl)thiophene-2-sulfonamide

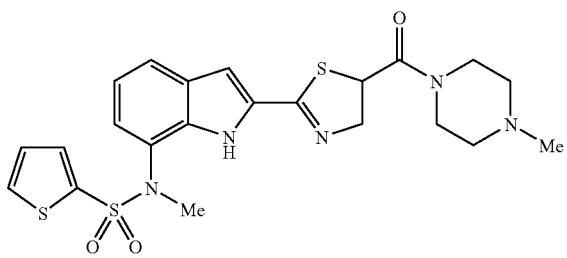

In the same manner as in Example 272, the title compound (0.21 g, yield 71%) was obtained as pale-yellow crystals from 2-{7-[methyl(2-thienylsulfonyl)amino]-1H-indol-2-yl}-4,5-dihydro-1,3-thiazole-5-carboxylic acid (0.25 g) and N-methylpiperazine (0.12 g). melting point 198-199° C.

Example 274

N-methyl-N-{2-[5-(morpholinomethyl)-4,5-dihydro-1,3-thiazol-2-yl]-1H-indol-7-yl}thiophene-2-sulfonamide

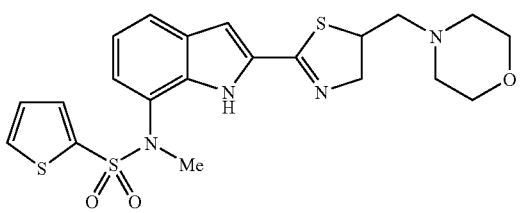

To a mixture of triphenylphosphine oxide (1.72 g) and acetonitrile (15 mL) was slowly added trifluoromethanesulfonic anhydride (0.52 mL) at 0° C., and the mixture was stirred for 10 min. N-[2-(benzylthio)-3-morpholinopropyl]-7-[methyl(2-thienylsulfonyl)amino]-1H-indole-2-carboxamide (an optically active form: retention time: shorter) (0.91 g) obtained in Reference Example 94 and dimethylsulfide (0.33 mL) were added. The reaction mixture was stirred at 0° C. for 15 min, saturated aqueous sodium hydrogencarbonate was added, and the mixture was extracted with ethyl acetate. The ethyl acetate layer was washed with saturated brine, dried (MgSO₄), and concentrated. The residue was subjected to basic silica gel column chromatography to give an oil containing the title compound and triphenylphosphine oxide from a fraction eluted with ethyl acetate-hexane (4:1, volume ratio). The obtained oil was added to 4N hydrogen chloride-ethyl acetate solution, and the resulting crystals were collected by filtration, and washed with ethyl acetate. The obtained crystals were added to saturated aqueous sodium hydrogencarbonate, and the mixture was extracted with ethyl acetate. The ethyl acetate layer was washed with saturated brine, dried (MgSO₄), and concentrated. The residue was subjected to basic silica gel column chromatography to give the title compound (0.62 g, yield 81%) as colorless crystals from a fraction eluted with ethyl acetate-hexane (4:1, volume ratio). melting point 139-140° C.

Example 275

N,N-diethyl-2-{7-[methyl(2-thienylsulfonyl)amino]-1H-indol-2-yl}-4,5-dihydro-1,3-thiazole-5-carboxamide

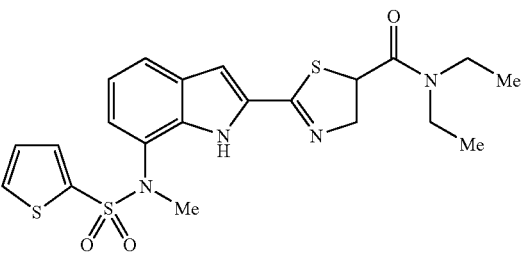

In the same manner as in Example 272, the title compound (0.24 g, yield 85%) was obtained as pale-yellow crystals from 2-{7-[methyl(2-thienylsulfonyl)amino]-1H-indol-2-yl}-4,5-dihydro-1,3-thiazole-5-carboxylic acid (0.25 g) and diethylamine (0.12 mL). melting point 218-219° C.

Example 276

N-[(2-{7-[methyl(2-thienylsulfonyl)amino]-1H-indol-2-yl}-4,5-dihydro-1,3-thiazol-5-yl)methyl]acetamide

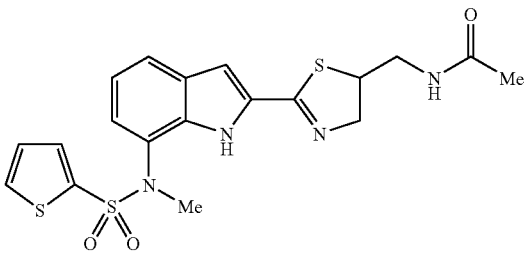

To a solution of N-{2-[5-(aminomethyl)-4,5-dihydro-1,3-thiazol-2-yl]-1H-indol-7-yl}-N-methylthiophene-2-sulfonamide (0.27 g) in N,N-dimethylacetamide (6 mL) was added acetic anhydride (0.10 mL) at 0° C., and the mixture was stirred for 30 min. Water was added to the reaction mixture, and the precipitated solid was collected by filtration, washed with water, and dried. The obtained solid was subjected to silica gel column chromatography to give the title compound (0.20 g, yield 68%) as pale-yellow crystals from a fraction eluted with ethyl acetate-hexane (95:5, volume ratio). melting point 212-213° C.

Example 277

N-{2-[5-(aminomethyl)-5-methyl-4,5-dihydro-1,3-thiazol-2-yl]-1H-indol-7-yl}-N-methylthiophene-2-sulfonamide

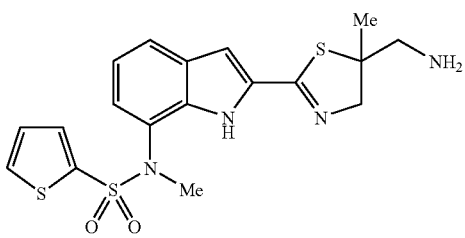

To a mixture of lithium aluminum hydride (0.05 g) and tetrahydrofuran (6 mL) was added N-[2-(5-cyano-5-methyl-4,5-dihydro-1,3-thiazol-2-yl)-1H-indol-7-yl]-N-methylthiophene-2-sulfonamide (0.40 g) at 0° C., and the mixture was stirred for 15 min. Ethanol (2 mL) and 1N aqueous sodium hydroxide solution (0.2 mL) were successively added, and the resulting inorganic salt was removed by filtration. The filtrate was concentrated, and the residue was subjected to basic silica gel column chromatography to give the title compound (0.23 g, yield 57%) as colorless crystals from a fraction eluted with ethyl acetate. melting point 164-165° C.

Example 278

5-methyl-2-{7-[methyl(2-thienylsulfonyl)amino]-1H-indol-2-yl}-4,5-dihydro-1,3-thiazole-5-carboxamide

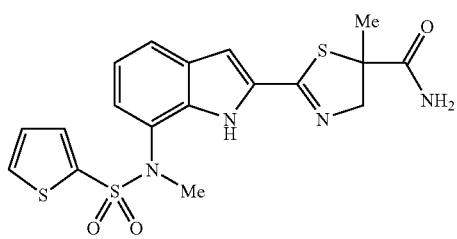

A mixture of N-[2-(5-cyano-5-methyl-4,5-dihydro-1,3-thiazol-2-yl)-1H-indol-7-yl]-N-methylthiophene-2-sulfonamide (0.38 g), 2N aqueous sodium hydroxide solution (0.90 mL), tetrahydrofuran (4 mL) and ethanol (4 mL) was heated under reflux for 4 hr. 10% Aqueous citric acid solution was added to the reaction mixture, and the mixture was extracted with ethyl acetate. The ethyl acetate layer was washed with saturated brine, dried (MgSO₄), and concentrated. A mixture of the obtained residue, 1H-1,2,3-benzotriazol-1-ol (0.15 g), N-[3-(dimethylamino)propyl]-N'-ethylcarbodiimide hydrochloride (0.21 g) and N,N-dimethylformamide (6 mL) was added at room temperature for 1 hr, and 28% aqueous ammonia (0.22 mL) was added. The mixture was stirred overnight at room temperature, water was added to the reaction mixture, and the precipitated solid was collected by filtration, washed with water, and dried. The obtained solid was suspended in ethanol, and the mixture was stirred for 15 min. The crystals were collected by filtration, washed with ethanol and ethyl acetate, and dried to give the title compound (0.29 g, yield 74%) as colorless crystals. melting point 248-249° C.

Example 279

2-chloro-N-methyl-N-{4-methyl-2-[5-(morpholinomethyl)-4,5-dihydro-1,3-thiazol-2-yl]-1H-indol-7-yl}pyridine-3-sulfonamide

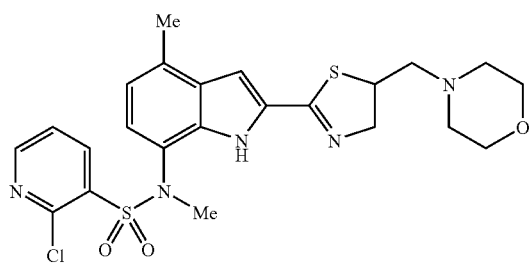

To a mixture of triphenylphosphine oxide (1.95 g) and acetonitrile (20 mL) was slowly added trifluoromethanesulfonic anhydride (0.59 mL) at 0° C., and the mixture was stirred for 10 min. N-[2-(Benzylthio)-3-morpholinopropyl]-7-[[(2-chloropyridin-3-yl)sulfonyl](methyl)amino]-4-methyl-1H-indole-2-carboxamide (1.10 g) and dimethylsulfide (0.20 mL) were added. The reaction mixture was stirred at 0° C. for 15 min. Saturated aqueous sodium hydrogencarbonate was added, and the mixture was extracted with ethyl acetate. The ethyl acetate layer was washed with saturated brine, dried (MgSO₄), and concentrated. The residue was subjected to basic silica gel column chromatography to give the title compound (0.69 g, yield 76%) as colorless crystals from a fraction eluted with ethyl acetate-hexane (3:1, volume ratio). melting point 151-153° C.

Example 280

N-methyl-N-{4-methyl-2-[5-(morpholinomethyl)-4,5-dihydro-1,3-thiazol-2-yl]-1H-indol-7-yl}thiophene-2-sulfonamide

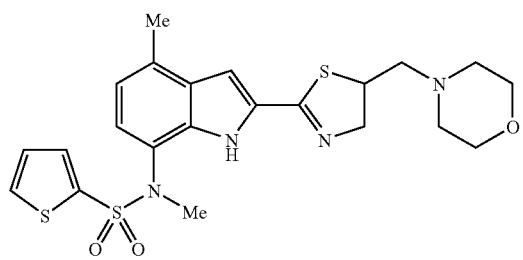

In the same manner as in Example 274, the title compound (0.45 g, yield 54%) was obtained as colorless crystals from N-[2-(benzylthio)-3-morpholinopropyl]-4-methyl-7-[methyl(2-thienylsulfonyl)amino]-1H-indole-2-carboxamide (1.01 g). melting point 192-193° C.

Example 281

N-[2-(5-cyano-4,5-dihydro-1,3-thiazol-2-yl)-4-methyl-1H-indol-7-yl]-N-methylthiophene-2-sulfonamide

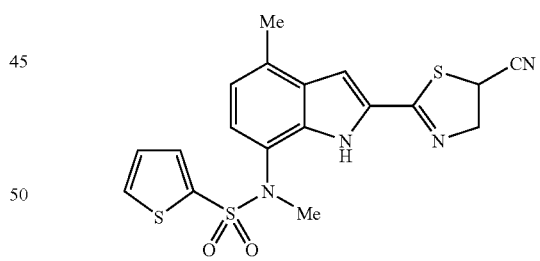

To a mixture of triphenylphosphine oxide (2.35 g) and acetonitrile (20 mL) was slowly added trifluoromethanesulfonic anhydride (0.71 mL) at 0° C., and the mixture was stirred for 10 min. N-[2-(Benzylthio)-2-cyanoethyl]-4-methyl-7-[methyl(2-thienylsulfonyl)amino]-1H-indole-2-carboxamide (1.10 g) and dimethylsulfide (0.46 mL) were added. The reaction mixture was stirred at 0° C. for 30 min, saturated aqueous sodium hydrogencarbonate was added, and the mixture was extracted with ethyl acetate. The ethyl acetate layer was washed with saturated brine, dried (MgSO₄), and concentrated. The residue was subjected to silica gel column chromatography to give the title compound (0.58 g, yield 67%) as colorless crystals from a fraction eluted with ethyl acetate-hexane (3:2, volume ratio). melting point 173-174° C.

Example 282

N-{2-[5-(aminomethyl)-4,5-dihydro-1,3-thiazol-2-yl]-4-methyl-1H-indol-7-yl}-N-methylthiophene-2-sulfonamide

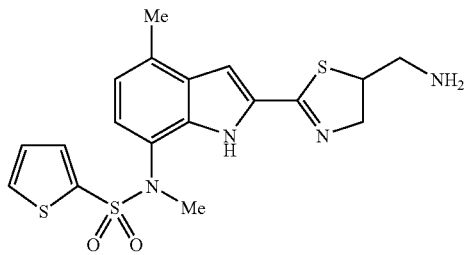

In the same manner as in Example 277, the title compound (0.58 g, yield 67%) was obtained as colorless crystals from N-[2-(5-cyano-4,5-dihydro-1,3-thiazol-2-yl)-4-methyl-1H-indol-7-yl]-N-methylthiophene-2-sulfonamide (1.10 g). melting point 146-147° C.

Example 283 ethyl (2-{7-[methyl(2-thienylsulfonyl)amino]-1H-indol-2-yl}-4,5-dihydro-1,3-thiazol-5-yl)acetate

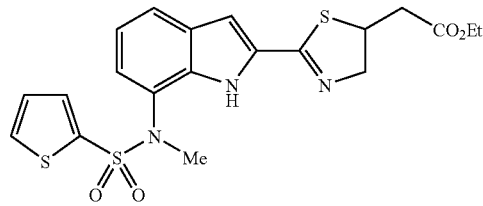

A solution of 7-[methyl(2-thienylsulfonyl)amino]-1H-indole-2-carbothioamide (0.50 g), ethyl but-2-ynoate (0.40 mL) and tributylphosphine (0.40 mL) in a mixed solvent of tetrahydrofuran (16 mL)-toluene (8 mL) was stirred at 50° C. for 3 hr. The reaction solution was concentrated under reduced pressure, and the obtained residue was subjected to silica gel column chromatography (ethyl acetate:hexane=1:4-1:1) to give the title compound (0.33 g, yield: 50%) as a pale-yellow oil. A part of the oil was crystallized from ethyl acetate-hexane to give pale-yellow crystals. MS: 464 (MH$^+$). melting point 101-102° C.

Example 284

(2-{7-[methyl(2-thienylsulfonyl)amino]-1H-indol-2-yl}-4,5-dihydro-1,3-thiazol-5-yl)acetic acid

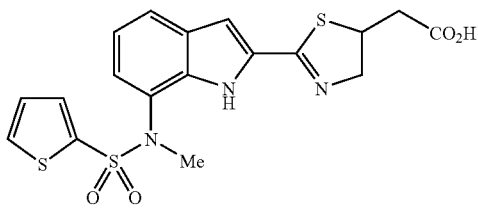

Ethyl (2-{7-[methyl(2-thienylsulfonyl)amino]-1H-indol-2-yl}-4,5-dihydro-1,3-thiazol-5-yl)acetate (0.52 g) was dissolved in a mixed solvent of tetrahydrofuran (6 mL)-methanol (6 mL), and the mixture was ice-cooled. Aqueous potassium hydroxide solution (prepared by dissolving potassium hydroxide (0.25 g) in water (5 mL))) was added to this solution, and the mixture was stirred from under ice-cooling to room temperature for 7 hr. The reaction solution was acidified with aqueous citric acid solution, and extracted with ethyl acetate. The organic layer was washed with saturated brine, dried over anhydrous magnesium sulfate, and concentrated under reduced pressure. The obtained amorphous solid was crystallized from ethyl acetate-hexane to give the title compound (407 mg, yield: 83%) as pale-yellow prism crystals. MS: 436 (MH$^+$). melting point 232-234° C.

Example 285

N-{2-[5-(2-hydroxyethyl)-4,5-dihydro-1,3-thiazol-2-yl]-1H-indol-7-yl}-N-methylthiophene-2-sulfonamide

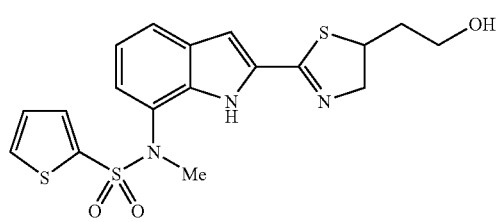

To a mixture of ethyl (2-{7-[methyl(2-thienylsulfonyl)amino]-1H-indol-2-yl}-4,5-dihydro-1,3-thiazol-5-yl)acetate (0.21 g), lithium borohydride (20 mg) and tetrahydrofuran (10 mL) was added methanol (2 mL), and the mixture was stirred at room temperature for 3 hr. Aqueous citric acid solution was added to the reaction solution, and the mixture was extracted with ethyl acetate. The organic layer was washed with saturated brine, dried over anhydrous magnesium sulfate, and concentrated under reduced pressure to give the title compound (182 mg, yield: 96%) as pale-yellow crystals. A part of the crystals was recrystallized from ethyl acetate-hexane to give pale-yellow crystals. MS: 422 (MH$^+$). melting point 174-175° C.

Example 286

N-methyl-N-(2-{5-[2-(4-methylpiperazin-1-yl)-2-oxoethyl]-4,5-dihydro-1,3-thiazol-2-yl}-1H-indol-7-yl)thiophene-2-sulfonamide

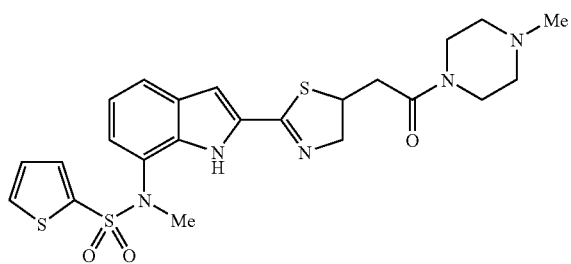

To a mixture of (2-{7-[methyl(2-thienylsulfonyl)amino]-1H-indol-2-yl}-4,5-dihydro-1,3-thiazol-5-yl)acetic acid (80 mg), N-methylpiperazine (25 μL), 1H-1,2,3-benzotriazol-1-ol (35 mg) and N,N-dimethylformamide (8 mL) was added N-[3-(dimethylamino)propyl]-N'-ethylcarbodiimide hydrochloride (50 mg) under ice-cooling, and the mixture was stirred from under ice-cooling to room temperature for 18 hr. The reaction solution was diluted with ethyl acetate, washed with water, aqueous sodium hydrogencarbonate solution and saturated brine, dried over anhydrous magnesium sulfate, and concentrated under reduced pressure. The obtained pale-yellow crystals were recrystallized from ethyl acetate-hexane to give the title compound (59 mg, yield: 62%) as colorless crystals.

MS: 518 (MH$^+$). melting point 151-153° C.

Example 287

2-(2-{7-[methyl(2-thienylsulfonyl)amino]-1H-indol-2-yl}-4,5-dihydro-1,3-thiazol-5-yl)acetamide

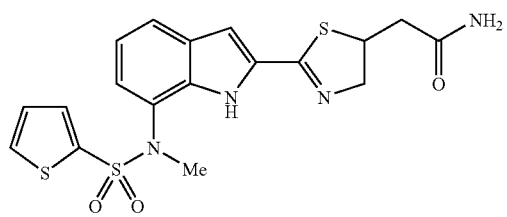

To a mixture of (2-{7-[methyl(2-thienylsulfonyl)amino]-1H-indol-2-yl}-4,5-dihydro-1,3-thiazol-5-yl)acetic acid (100 mg), 1H-1,2,3-benzotriazol-1-ol-ammonia complex (42 mg) and N,N-dimethylformamide (6 mL) was added N-[3-(dimethylamino)propyl]-N'-ethylcarbodiimide hydrochloride (53 mg) under ice-cooling, and the mixture was stirred from under ice-cooling to room temperature for 18 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=9:1-ethyl acetate), and the obtained pale-yellow oil was crystallized from ethyl acetate-hexane to give the title compound (82 mg, yield: 82%) as pale-yellow prism crystals. MS: 435 (MH$^+$). melting point 193-194° C.

Example 288

N-(2-{5-[2-(2,5-dioxopyrrolidin-1-yl)ethyl]-4,5-dihydro-1,3-thiazol-2-yl}-1H-indol-7-yl)-N-methylthiophene-2-sulfonamide

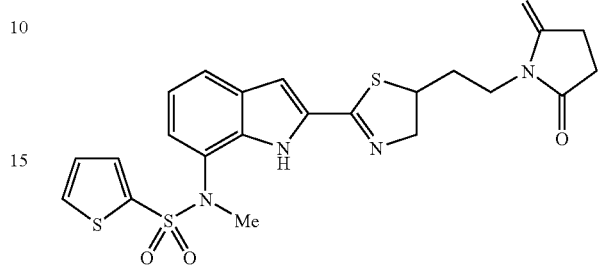

A solution (10 mL) of N-{2-[5-(2-hydroxyethyl)-4,5-dihydro-1,3-thiazol-2-yl]-1H-indol-7-yl}-N-methylthiophene-2-sulfonamide (100 mg), succinimide (29 mg) and triphenylphosphine (93 mg) in tetrahydrofuran was added a 40% toluene solution (0.155 mL) of diethyl azodicarboxylate, and the mixture was stirred at room temperature for 18 hr. A 40% toluene solution (0.155 mL) of diethyl azodicarboxylate was added again to the reaction solution, and the mixture was further stirred at room temperature for 5 days. The reaction solution was concentrated under reduced pressure, and the obtained residue was subjected to silica gel column chromatography (ethyl acetate:hexane=2:8-10:0), and the obtained colorless oil was crystallized from ethyl acetate-hexane to give the title compound (36 mg, yield: 30%) as colorless prism crystals. MS: 503 (MH$^+$). melting point 189-191° C.

Example 289 methyl [2-(2-{7-[methyl(2-thienylsulfonyl)amino]-1H-indol-2-yl}-4,5-dihydro-1,3-thiazol-5-yl)ethyl] carbamate

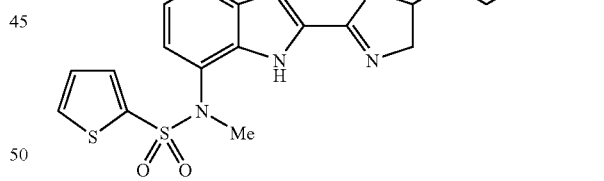

A mixture of (2-{7-[methyl(2-thienylsulfonyl)amino]-1H-indol-2-yl}-4,5-dihydro-1,3-thiazol-5-yl)acetic acid (40 mg), triethylamine (0.038 mL), diphenylphosphorylazide (0.024 mL) and N,N-dimethylformamide (3 mL) was stirred at room temperature for 1 hr. Methanol (3 mL) was added to the reaction solution, and the mixture was heated at 50° C. for 3 hr. The reaction solution was diluted with ethyl acetate, washed with water and saturated brine, dried over anhydrous magnesium sulfate, and concentrated under reduced pressure. The obtained residue was subjected to silica gel column chromatography (ethyl acetate:hexane=1:3-7:3), and the obtained pale-yellow oil was crystallized from ethyl acetate-hexane to give the title compound (11.7 mg, yield: 28%) as pale-yellow crystals.

MS: 465 (MH$^+$). melting point 201-203° C.

Example 290 ethyl (2-{4-methyl-7-[methyl(2-thienylsulfonyl)amino]-1H-indol-2-yl}-4,5-dihydro-1,3-thiazol-5-yl)acetate

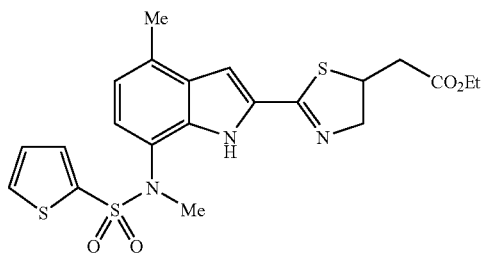

A solution of 4-methyl-7-[methyl(2-thienylsulfonyl)amino]-1H-indole-2-carbothioamide (1.62 g), ethyl but-2-ynoate (1.2 mL) and tributylphosphine (1.1 mL) in a mixed solvent of tetrahydrofuran (30 mL)-toluene (20 mL) was stirred at room temperature for 4 hr. The reaction solution was concentrated under reduced pressure, and the obtained residue was subjected to silica gel column chromatography (ethyl acetate:hexane=10:90-35:65). The obtained crystals were crystallized from ethyl acetate-hexane to give the title compound (1.35 g, yield: 64%) as pale-yellow crystals.

MS: 478 (MH$^+$). melting point 109-110° C.

Example 291

N-{2-[5-(2-hydroxyethyl)-4,5-dihydro-1,3-thiazol-2-yl]-4-methyl-1H-indol-7-yl}-N-methylthiophene-2-sulfonamide

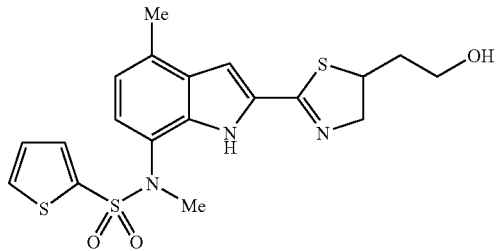

To a mixture of ethyl (2-{4-methyl-7-[methyl(2-thienylsulfonyl)amino]-1H-indol-2-yl}-4,5-dihydro-1,3-thiazol-5-yl)acetate (0.12 g), lithium borohydride (20 mg) and tetrahydrofuran (10 mL) was added methanol (2 mL), and the mixture was stirred at room temperature for 3 hr. Aqueous citric acid solution was added to the reaction solution, and the mixture was extracted with ethyl acetate. The organic layer was washed with water and saturated brine, dried over anhydrous magnesium sulfate, and concentrated under reduced pressure. The obtained crystals were washed with ethyl acetate-hexane to give the title compound (103 mg, yield: 94%) as pale-yellow crystals. MS: 436 (MH$^+$). melting point 168-169° C.

Example 292

(2-{4-methyl-7-[methyl(2-thienylsulfonyl)amino]-1H-indol-2-yl}-4,5-dihydro-1,3-thiazol-5-yl)acetic acid

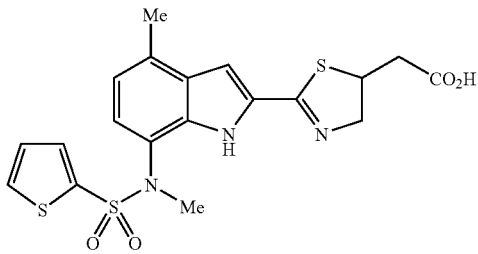

Ethyl (2-{4-methyl-7-[methyl(2-thienylsulfonyl)amino]-1H-indol-2-yl}-4,5-dihydro-1,3-thiazol-5-yl)acetate (0.99 g) was dissolved in a mixed solvent of tetrahydrofuran (12 mL)-methanol (12 mL), and the mixture was ice-cooled. Aqueous potassium hydroxide solution (prepared by dissolving potassium hydroxide (0.35 g) in water (5 mL)) was added to this solution, and the mixture was stirred from under ice-cooling to room temperature for 15 hr. The reaction solution was acidified with aqueous citric acid solution, and extracted with ethyl acetate. The organic layer was washed with saturated brine, dried over anhydrous magnesium sulfate, and concentrated under reduced pressure. The obtained pale-yellow crystals were washed with ethyl acetate-hexane to give the title compound (1.00 g, yield: 95%) as pale-yellow crystals. MS: 450 (MH$^+$). melting point 269-270° C.

Example 293

2-(2-{4-methyl-7-[methyl(2-thienylsulfonyl)amino]-1H-indol-2-yl}-4,5-dihydro-1,3-thiazol-5-yl)acetamide

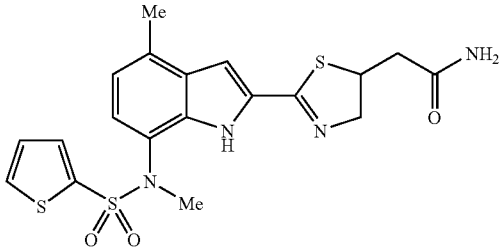

To a mixture of (2-{4-methyl-7-[methyl(2-thienylsulfonyl)amino]-1H-indol-2-yl}-4,5-dihydro-1,3-thiazol-5-yl)acetic acid (0.25 g), 1H-1,2,3-benzotriazol-1-ol-ammonia complex (0.11 g) and N,N-dimethylformamide (15 mL) was added N-[3-(dimethylamino)propyl]-N'-ethylcarbodiimide hydrochloride (0.14 g) under ice-cooling, and the mixture was stirred from under ice-cooling to room temperature for 2 days. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=9:1-10:0), and the obtained colorless oil was crystallized from ethyl acetate-hexane to give the title compound (228 mg, yield: 92%) as colorless crystals. MS: 449 (MH+). melting point 120-121° C.

Example 294

N,N-dimethyl-2-(2-{7-[methyl(2-thienylsulfonyl)amino]-1H-indol-2-yl}-4,5-dihydro-1,3-thiazol-5-yl)acetamide

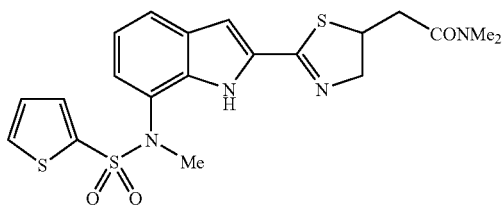

A mixture of (2-{7-[methyl(2-thienylsulfonyl)amino]-1H-indol-2-yl}-4,5-dihydro-1,3-thiazol-5-yl)acetic acid (70 mg), 1H-1,2,3-benzotriazol-1-ol (33 mg), N-[3-(dimethylamino)propyl]-N'-ethylcarbodiimide hydrochloride (46 mg) and N,N-dimethylformamide (4 mL) was stirred at room temperature for 2 hr. 2M tetrahydrofuran solution (0.25 mL) of dimethylamine was added to this solution, and the mixture was stirred at room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate), and the obtained colorless crystals were washed with ethyl acetate-hexane to give the title compound (53 mg, yield: 30%) as colorless crystals. MS: 463 (MH+). melting point 153-154° C.

Example 295

N-{2-[5-(2-hydroxyethyl)-4,5-dihydro-1,3-thiazol-2-yl]-1H-indol-7-yl}thiophene-2-sulfonamide

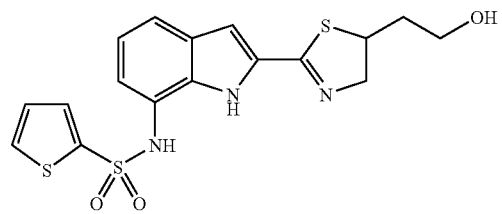

To a mixture of ethyl (2-{7-[(2-thienylsulfonyl)amino]-1H-indol-2-yl}-4,5-dihydro-1,3-thiazol-5-yl)acetate (0.27 g), lithium borohydride (70 mg) and tetrahydrofuran (10 mL) was added methanol (2 mL), and the mixture was stirred at room temperature for 5 hr. Diluted hydrochloric acid was added to the reaction solution, and the mixture was extracted with ethyl acetate. The organic layer was washed with water and saturated brine, dried over anhydrous magnesium sulfate, and concentrated under reduced pressure. The obtained residue was subjected to silica gel column chromatography (ethyl acetate:hexane=1:1-7:3), and the obtained colorless oil was crystallized from ethyl acetate-hexane to give the title compound (46 mg, yield: 19%) as colorless plate crystals.
MS: 408 (MH+). melting point 156-158° C.

Example 296

(2-{7-[(2-thienylsulfonyl)amino]-1H-indol-2-yl}-4,5-dihydro-1,3-thiazol-5-yl)acetic acid

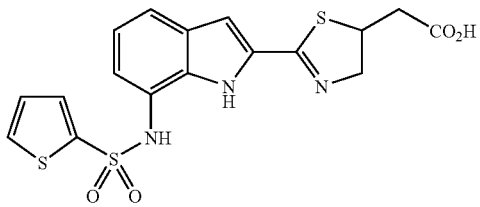

Ethyl (2-{7-[(2-thienylsulfonyl)amino]-1H-indol-2-yl}-4,5-dihydro-1,3-thiazol-5-yl)acetate (0.49 g) was dissolved in a mixed solvent of tetrahydrofuran (8 mL)-methanol (8 mL). Aqueous potassium hydroxide solution (prepared by dissolving potassium hydroxide (0.25 g) in water (4 mL)) was added to this solution, and the mixture was stirred at room temperature for 15 hr. The reaction solution was acidified with diluted hydrochloric acid, and extracted with ethyl acetate. The organic layer was washed with saturated brine, dried over anhydrous magnesium sulfate, and concentrated under reduced pressure. The obtained amorphous solid was crystallized from ethyl acetate-hexane to give the title compound (256 mg, yield: 56%) as pale-yellow crystals. MS: 422 (MH+). melting point >240° C. (decomposition).

Example 297

2-(2-{7-[(2-thienylsulfonyl)amino]-1H-indol-2-yl}-4,5-dihydro-1,3-thiazol-5-yl)acetamide

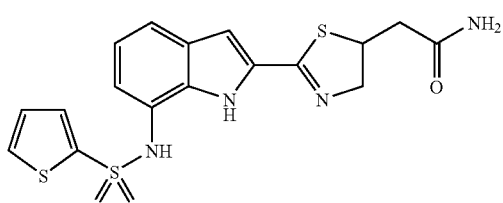

To a mixture of (2-{7-[(2-thienylsulfonyl)amino]-1H-indol-2-yl}-4,5-dihydro-1,3-thiazol-5-yl)acetic acid (153 mg), 1H-1,2,3-benzotriazol-1-ol-ammonia complex (72 mg) and N,N-dimethylformamide (8 mL) was added N-[3-(dimethylamino)propyl]-N'-ethylcarbodiimide hydrochloride (91 mg) under ice-cooling, and the mixture was stirred from under ice-cooling to room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate-ethyl acetate:methanol=95:5), and the obtained pale-yellow oil was crystallized from ethyl acetate-hexane to give the title compound (118 mg, yield: 77%) as pale-yellow crystals.
MS: 421 (MH+). melting point 130-131° C.

Example 298-A

N-{2-[5-(2-hydroxyethyl)-4,5-dihydro-1,3-thiazol-2-yl]-1H-indol-7-yl}-N-methylthiophene-2-sulfonamide

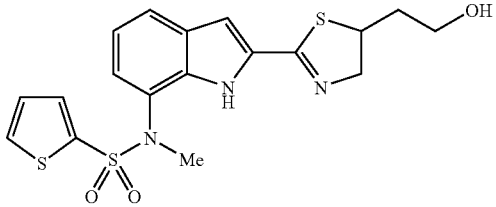

N-{2-[5-(2-Hydroxyethyl)-4,5-dihydro-1,3-thiazol-2-yl]-1H-indol-7-yl}-N-methylthiophene-2-sulfonamide (510 mg) was dissolved in hexane-ethanol (50:50, volume ratio) to prepare a 0.5 mg/mL solution. This solution was subjected to HPLC using CHIRALCEL OD (50 mmID×500 mL, manufactured by DAICEL CHEMICAL INDUSTRIES, LTD.), and eluted with hexane-ethanol (50:50, volume ratio) as a mobile phase at 30° C. at flow rate of 60 mL/min. A fraction with the retention time of 22 min was separated, and concentrated. The obtained solid was dissolved in ethyl acetate, the insoluble substance was removed by filtration, and the filtrate was concentrated. The obtained oil was crystallized from ethyl acetate-hexane to give the title compound (217 mg) as pale-yellow crystals. melting point 173-174° C.

Example 298-B

N-{2-[5-(2-hydroxyethyl)-4,5-dihydro-1,3-thiazol-2-yl]-1H-indol-7-yl}-N-methylthiophene-2-sulfonamide

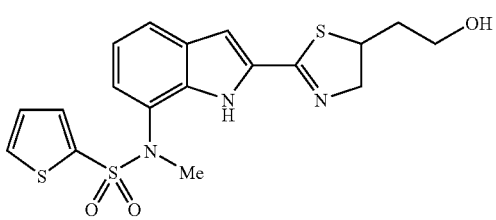

N-{2-[5-(2-Hydroxyethyl)-4,5-dihydro-1,3-thiazol-2-yl]-1H-indol-7-yl}-N-methylthiophene-2-sulfonamide (510 mg) was dissolved in hexane-ethanol (50:50, volume ratio) to prepare a 0.5 mg/mL solution. This solution was subjected to HPLC using CHIRALCEL OD (50 mmID×500 mL, manufactured by DAICEL CHEMICAL INDUSTRIES, LTD.), and eluted with hexane-ethanol (50:50, volume ratio) as a mobile phase at 30° C. at flow rate of 60 mL/min. A fraction with the retention time of 36 min was separated, and concentrated. The obtained solid was dissolved in ethyl acetate, the insoluble substance was removed by filtration, and the filtrate was concentrated. The obtained oil was crystallized from ethyl acetate-hexane to give the title compound (229 mg) as pale-yellow crystals. melting point 168-169° C.

Example 299

N-methoxy-N-methyl-2-(2-{7-[methyl(2-thienylsulfonyl)amino]-1H-indol-2-yl}-4,5-dihydro-1,3-thiazol-5-yl)acetamide

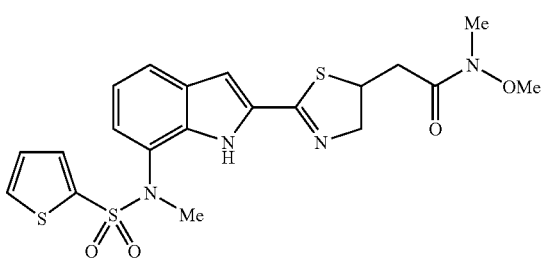

To a solution of N,O-dimethylhydroxylamine hydrochloride (0.28 g) in N,N-dimethylformamide (20 mL) was added triethylamine (0.43 mL) under ice-cooling, and the mixture was stirred for 10 min under ice-cooling. (2-{7-[Methyl(2-thienylsulfonyl)amino]-1H-indol-2-yl}-4,5-dihydro-1,3-thiazol-5-yl)acetic acid (1.03 g), 1H-1,2,3-benzotriazol-1-ol (0.42 g) and N-[3-(dimethylamino)propyl]-N'-ethylcarbodiimide hydrochloride (0.59 g) were added to the mixture, and the mixture was stirred from under ice-cooling to room temperature for 24 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=7:3-10:0), and the obtained pale-yellow crystals were washed with ethyl acetate-hexane to give the title compound (911 mg, yield: 81%) as pale-yellow crystals. MS: 479 (MH$^+$). melting point 153-154° C.

Example 300

N-methyl-N-{2-[5-(2-oxopropyl)-4,5-dihydro-1,3-thiazol-2-yl]-1H-indol-7-yl}thiophene-2-sulfonamide

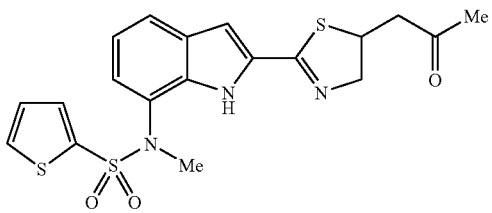

N-Methoxy-N-methyl-2-(2-{7-[methyl(2-thienylsulfonyl)amino]-1H-indol-2-yl}-4,5-dihydro-1,3-thiazol-5-yl)acetamide (0.20 g) was dissolved in absolute tetrahydrofuran (20 mL), and a 12% methylmagnesium bromide tetrahydrofuran solution (1.4 mL) was added under ice-cooling. The mixture was stirred at 10° C. for 5 hr under ice-cooling, acidified with aqueous citric acid solution, and extracted with ethyl acetate. The organic layer was washed with water and saturated brine, dried over anhydrous magnesium sulfate, and concentrated under reduced pressure. The obtained residue was subjected to silica gel column chromatography (ethyl acetate:hexane=35:65-50:50), and the obtained colorless oil was crystallized from ethyl acetate-hexane to give the title compound (121 mg, yield: 67%) as colorless crystals.

MS: 434 (MH$^+$). melting point 123-124° C.

Example 301

N-methyl-N-{2-[5-(2-oxobut-3-en-1-yl)-4,5-dihydro-1,3-thiazol-2-yl]-1H-indol-7-yl}thiophene-2-sulfonamide

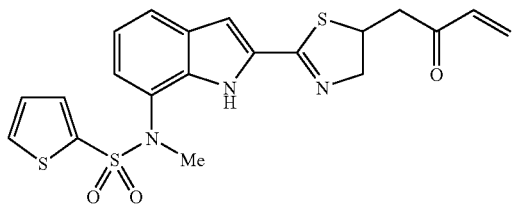

N-Methoxy-N-methyl-2-(2-{7-[methyl(2-thienylsulfonyl)amino]-1H-indol-2-yl}-4,5-dihydro-1,3-thiazol-5-yl)acetamide (589 mg) was dissolved in absolute tetrahydrofuran (20 mL), and 1M vinylmagnesium bromide tetrahydrofuran solution (3.7 mL) was added under ice-cooling. The mixture was stirred for 5 hr under ice-cooling, 1M vinylmagnesium bromide tetrahydrofuran solution (2.0 mL) was added again, and the mixture was further stirred under ice-cooling for 2 hr. The reaction solution was acidified with aqueous citric acid solution, and extracted with ethyl acetate. The organic layer was washed with water and saturated brine, dried over anhydrous magnesium sulfate, and concentrated under reduced pressure. The obtained residue was subjected to silica gel column chromatography (ethyl acetate), and the obtained pale-yellow crystals were washed with ethyl acetate-hexane to give the title compound (210 mg, yield: 38%) as pale-yellow crystals. MS: 446 (MH$^+$). melting point 157-158° C.

Example 302

N-methyl-N-(2-{5-[(1-methyl-4,5-dihydro-1H-pyrazol-3-yl)methyl]-4,5-dihydro-1,3-thiazol-2-yl}-1H-indol-7-yl)thiophene-2-sulfonamide

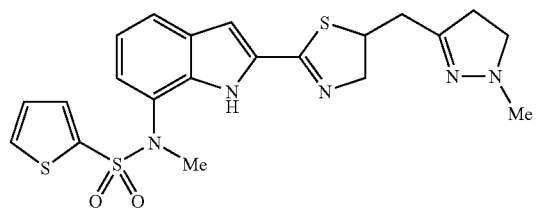

A mixture of N-methyl-N-{2-[5-(2-oxobut-3-en-1-yl)-4,5-dihydro-1,3-thiazol-2-yl]-1H-indol-7-yl}thiophene-2-sulfonamide (250 mg), methylhydrazine (0.050 mL) and tetrahydrofuran (20 mL) was stirred at room temperature for 3 hr. The reaction solution was diluted with ethyl acetate, washed with water and saturated brine, dried over anhydrous magnesium sulfate, and concentrated under reduced pressure.

Ethyl acetate was added to the obtained residue, the insoluble substance was filtered off, and the filtrate was concentrated. The obtained residue was subjected to basic silica gel column chromatography (ethyl acetate:hexane=3:7-5:5), and the obtained colorless oil was crystallized from ethyl acetate-hexane to give the title compound (156 mg, yield: 59%) as colorless needle crystals. MS: 474 (MH$^+$). melting point 149-150° C.

Example 303

N-methyl-N-{2-[5-(thiomorpholinomethyl)-4,5-dihydro-1,3-thiazol-2-yl]-1H-indol-7-yl}pyridine-2-sulfonamide

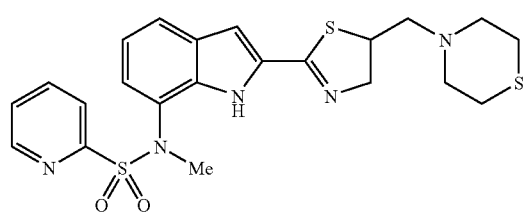

To a solution of triphenylphosphine oxide (0.79 g) in dichloromethane (5 mL) was slowly added trifluoromethanesulfonic anhydride (0.38 mL) under ice-cooling, and the mixture was stirred for 20 min. A solution of N-[2-(benzylthio)-3-thiomorpholinopropyl]-7-[methyl(pyridin-2-ylsulfonyl)amino]-1H-indole-2-carboxamide (0.67 g) in dichloromethane (5 mL) was added dropwise, and the mixture was stirred for 1 hr under ice-cooling. The reaction solution was diluted with ethyl acetate, washed with aqueous citric acid solution, water and saturated brine, dried over anhydrous magnesium sulfate, and concentrated under reduced pressure. The obtained solid was filtered off, and washed with ethyl acetate. The filtrate was concentrated under reduced pressure, and the obtained residue was subjected to silica gel column chromatography (ethyl acetate: hexane=4:6-6:4). The obtained colorless oil was crystallized from ethyl acetate-hexane to give the title compound (29 mg, yield: 5%) as colorless crystals. MS: 488 (MH$^+$). melting point 142-144° C.

Example 304

N-methyl-N-(2-{5-[(1-oxidothiomorpholino)methyl]-4,5-dihydro-1,3-thiazol-2-yl}-1H-indol-7-yl)pyridine-2-sulfonamide

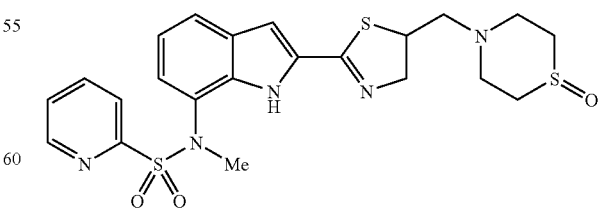

To a solution of N-methyl-N-{2-[5-(thiomorpholinomethyl)-4,5-dihydro-1,3-thiazol-2-yl]-1H-indol-7-yl}pyridine-2-sulfonamide (180 mg) in dichloromethane (8 mL) was added m-chloroperbenzoic acid (75 mL) under ice-cooling, and the mixture was stirred for 3 hr under ice-cooling. The reaction solution was diluted with ethyl acetate, washed with aqueous sodium hydrogencarbonate solution and saturated brine, dried over anhydrous magnesium sulfate, and concentrated under reduced pressure. The obtained residue was subjected to basic silica gel column chromatography (ethyl acetate:hexane=6:4-9:1), and the obtained colorless oil was crystallized from ethyl acetate-hexane to give the title compound (39 mg, yield: 21%) as colorless needle crystals. MS: 504 (MH$^+$). melting point 193-194° C.

Example 305 ethyl (2-{7-[[(2-methoxyphenyl)sulfonyl](methyl)amino]-1H-indol-2-yl}-4,5-dihydro-1,3-thiazol-5-yl)acetate

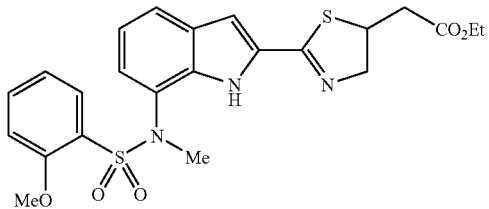

A mixture of 7-[[(2-methoxyphenyl)sulfonyl](methyl)amino]-1H-indole-2-carbothioamide (2.3 g), ethyl but-2-ynoate (1.5 mL), tributylphosphine (1.5 mL), toluene (25 mL) and tetrahydrofuran (25 mL) was stirred for 3 hr at room temperature. The reaction solution was concentrated, and the obtained residue was subjected to silica gel column chromatography (ethyl acetate:hexane=3:7-5:5) to give the title compound (1.23 g, yield: 41%) as a pale-brown amorphous solid.

$^1$H-NMR (CDCl$_3$) δ: 1.29 (3H, t, J=7.2 Hz), 2.72 (2H, d, J=7.5 Hz), 3.40 (3H, s), 3.95 (3H, s), 4.19 (2H, q, J=7.2 Hz), 4.22-4.48 (3H, m), 6.86-6.98 (4H, m), 7.03 (1H, d, J=8.7 Hz), 7.48-7.56 (2H, m), 7.72 (1H, dd, J=7.8, 1.8 Hz), 9.61 (1H, brs).

Example 306

N-{2-[5-(2-hydroxyethyl)-4,5-dihydro-1,3-thiazol-2-yl]-1H-indol-7-yl}-2-methoxy-N-methylbenzenesulfonamide

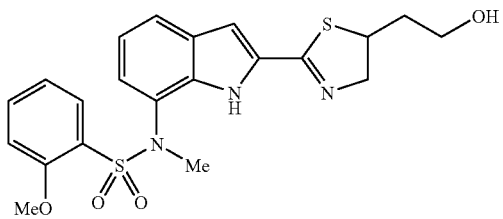

To a mixture of ethyl (2-{7-[[(2-methoxyphenyl)sulfonyl](methyl)amino]-1H-indol-2-yl}-4,5-dihydro-1,3-thiazol-5-yl)acetate (140 mg), lithium borohydride (40 mg) and tetrahydrofuran (5 mL) was added methanol (1 mL), and the mixture was stirred at room temperature for 2 hr. Aqueous citric acid solution was added to the reaction solution, and the mixture was extracted with ethyl acetate. The organic layer was washed with saturated brine, dried over anhydrous magnesium sulfate, and concentrated under reduced pressure. The obtained residue was subjected to silica gel column chromatography (ethyl acetate:hexane=6:4-10:0), and the obtained pale-yellow oil was crystallized from ethyl acetate-hexane to give the title compound (87 mg, yield: 69%) as colorless needle crystals. MS: 446 (MH$^+$). melting point 154-155° C.

Example 307

(2-{7-[[(2-methoxyphenyl)sulfonyl](methyl)amino]-1H-indol-2-yl}-4,5-dihydro-1,3-thiazol-5-yl)acetic acid

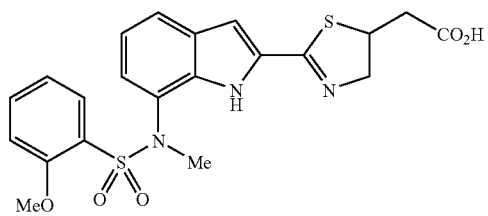

Ethyl (2-{7-[[(2-methoxyphenyl)sulfonyl](methyl)amino]-1H-indol-2-yl}-4,5-dihydro-1,3-thiazol-5-yl)acetate (1.0 g) was dissolved in a mixed solvent of tetrahydrofuran (10 mL)-methanol (10 mL). Aqueous potassium hydroxide solution (prepared by dissolving potassium hydroxide (0.50 g) in water (5 mL)) was added to this solution, and the mixture was stirred at room temperature for 7 hr. The reaction solution was acidified with aqueous citric acid solution, and extracted with ethyl acetate. The organic layer was washed with saturated brine, dried over anhydrous magnesium sulfate, and concentrated under reduced pressure. The obtained pale-brown oil was crystallized from ethyl acetate-hexane to give the title compound (730 mg, yield: 78%) as pale-yellow crystals.

MS: 460 (MH$^+$). melting point 197-198° C.

Example 308

2-(2-{7-[[(2-methoxyphenyl)sulfonyl](methyl)amino]-1H-indol-2-yl}-4,5-dihydro-1,3-thiazol-5-yl)acetamide

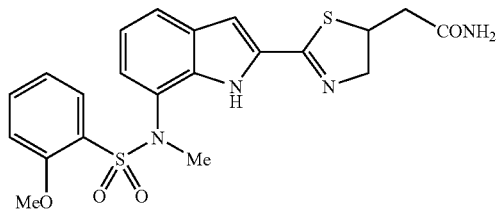

To a mixture of (2-{7-[[(2-methoxyphenyl)sulfonyl](methyl)amino]-1H-indol-2-yl}-4,5-dihydro-1,3-thiazol-5-yl)acetic acid (0.25 g), 1H-1,2,3-benzotriazol-1-ol-ammonia complex (0.13 g) and N,N-dimethylformamide (10 mL) was added N-[3-(dimethylamino)propyl]-N'-ethylcarbodiimide hydrochloride (0.16 g) under ice-cooling, and the mixture was stirred from under ice-cooling to room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:methanol=10:0-8:2), and the obtained pale-brown solid was washed with ethyl acetate-hexane to give the title compound (143 mg, yield 57%) as pale-brown crystals. MS: 459 (MH$^+$). melting point 227-228° C.

Example 309

N-methoxy-2-(2-{7-[[(2-methoxyphenyl)sulfonyl](methyl)amino]-1H-indol-2-yl}-4,5-dihydro-1,3-thiazol-5-yl)-N-methylacetamide

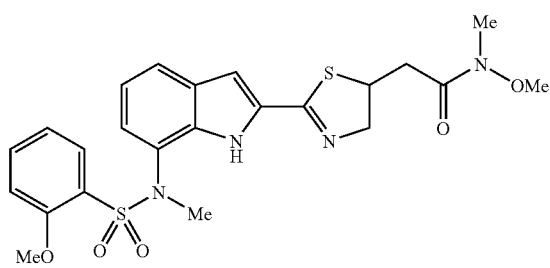

To a solution of N,O-dimethylhydroxylamine hydrochloride (48 mg) in N,N-dimethylformamide (10 mL) was added triethylamine (85 uL) under ice-cooling, and the mixture was stirred for 10 min under ice-cooling. (2-{7-[[(2-Methoxyphenyl)sulfonyl](methyl)amino]-1H-indol-2-yl}-4,5-dihydro-1,3-thiazol-5-yl)acetic acid (200 mg), 1H-1,2,3-benzotriazol-1-ol (90 mg) and N-[3-(dimethylamino)propyl]-N'-ethylcarbodiimide hydrochloride (130 mg) were added to the mixture, and the mixture was stirred from under ice-cooling to room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:methanol=100:0-95:5) to give the title compound (180 mg, yield: 85%) as a pale-yellow amorphous solid. MS: 489 (MH$^+$).

Example 310

2-(2-{7-[[(2-methoxyphenyl)sulfonyl](methyl)amino]-1H-indol-2-yl}-4,5-dihydro-1,3-thiazol-5-yl)-N-4H-1,2,4-triazol-3-ylacetamide

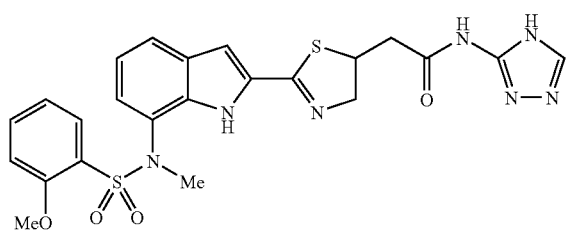

To a mixture of (2-{7-[[(2-methoxyphenyl)sulfonyl](methyl)amino]-1H-indol-2-yl}-4,5-dihydro-1,3-thiazol-5-yl) acetic acid (150 mg), 2-amino-1,2,4-triazole (36 mg), 1H-1,2,3-benzotriazol-1-ol (67 mg) and N,N-dimethylformamide (8 mL) was added N-[3-(dimethylamino)propyl]-N'-ethylcarbodiimide hydrochloride (94 mg) under ice-cooling, and the mixture was stirred from under ice-cooling to room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:methanol=100:0-95:5), and the obtained colorless oil was crystallized from ethyl acetate-hexane to give the title compound (118 mg, yield 69%) as colorless prism crystals. MS: 526 (MH$^+$). melting point 208-209° C.

Example 311

N-(2-{5-[2-(4-hydroxypiperidino)-2-oxoethyl]-4,5-dihydro-1,3-thiazol-2-yl}-1H-indol-7-yl)-2-methoxy-N-methylbenzenesulfonamide

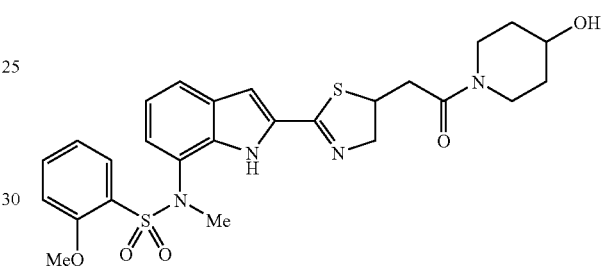

To a mixture of (2-{7-[[(2-methoxyphenyl)sulfonyl](methyl)amino]-1H-indol-2-yl}-4,5-dihydro-1,3-thiazol-5-yl) acetic acid (150 mg), 4-hydroxypiperidine (43 mg), 1H-1,2,3-benzotriazol-1-ol (67 mg) and N,N-dimethylformamide (8 mL) was added N-[3-(dimethylamino)propyl]-N'-ethylcarbodiimide hydrochloride (94 mg) under ice-cooling, and the mixture was stirred from under ice-cooling to room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:methanol=100:0-90:10), and the obtained colorless oil was crystallized from ethyl acetate-hexane to give the title compound (131 mg, yield 74%) as colorless prism crystals. MS: 543 (MH$^+$). melting point 166-167° C.

Example 312

2-(2-{7-[[(2-methoxyphenyl)sulfonyl](methyl)amino]-1H-indol-2-yl}-4,5-dihydro-1,3-thiazol-5-yl)-N-1H-tetrazol-5-ylacetamide

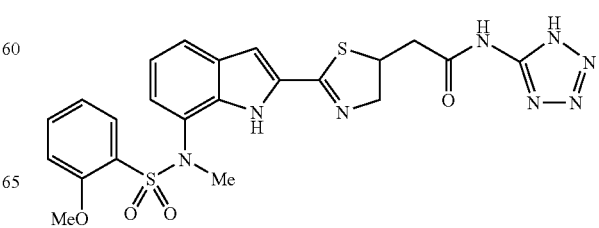

To a mixture of (2-{7-[[(2-methoxyphenyl)sulfonyl](methyl)amino]-1H-indol-2-yl}-4,5-dihydro-1,3-thiazol-5-yl)acetic acid (165 mg), 5-amino-tetrazole (37 mg), 1H-1,2,3-benzotriazol-1-ol (68 mg) and N,N-dimethylformamide (8 mL) was added N-[3-(dimethylamino)propyl]-N'-ethylcarbodiimide hydrochloride (96 mg) under ice-cooling, and the mixture was stirred from under ice-cooling to room temperature for 2 days. The reaction solution was diluted with ethyl acetate, washed with water, aqueous citric acid solution and saturated brine, dried over anhydrous magnesium sulfate, and concentrated under reduced pressure. The obtained residue was purified by preparative HPLC to give the title compound (107 mg, yield 56%) as a pale-yellow amorphous solid. MS: 527 (MH$^+$).

Example 313 ethyl {2-[7-(methyl{[2-(trifluoromethyl)phenyl]sulfonyl}amino)-1H-indol-2-yl]-4,5-dihydro-1,3-thiazol-5-yl}acetate

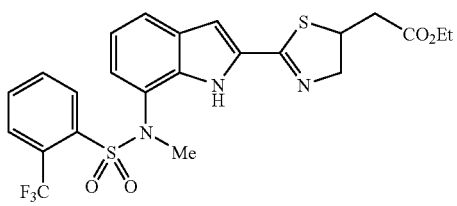

A mixture of 7-(methyl{[2-(trifluoromethyl)phenyl]sulfonyl}amino)-1H-indole-2-carbothioamide (2.65 g), ethyl but-2-ynoate (1.5 mL), tributylphosphine (1.6 mL), toluene (30 mL) and tetrahydrofuran (20 mL) was stirred for 2.5 hr at room temperature. The reaction solution was concentrated, and the obtained residue was subjected to silica gel column chromatography (ethyl acetate:hexane=2:8-4:6) to give the title compound (1.92 g, yield: 57%) as a pale-yellow oil.

MS: 526 (MH$^+$).

Example 314

{2-[7-(methyl{[2-(trifluoromethyl)phenyl]sulfonyl}amino)-1H-indol-2-yl]-4,5-dihydro-1,3-thiazol-5-yl}acetic acid

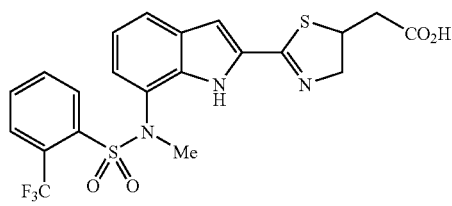

Ethyl {2-[7-(methyl{[2-(trifluoromethyl)phenyl]sulfonyl}amino)-1H-indol-2-yl]-4,5-dihydro-1,3-thiazol-5-yl}acetate (0.55 g) was dissolved in a mixed solvent of tetrahydrofuran (6 mL)-methanol (6 mL). Aqueous potassium hydroxide solution (prepared by dissolving potassium hydroxide (0.30 g) in water (5 mL)) was added to this solution, and the mixture was stirred at room temperature for 6 hr.

The reaction solution was acidified with aqueous citric acid solution, and extracted with ethyl acetate. The organic layer was washed with saturated brine, dried over anhydrous magnesium sulfate, and concentrated under reduced pressure. The obtained pale-yellow oil was crystallized from ethyl acetate-hexane to give the title compound (372 mg, yield: 72%) as pale-yellow crystals. MS: 498 (MH$^+$). melting point 170-172° C.

Example 315

N-{2-[5-(2-hydroxyethyl)-4,5-dihydro-1,3-thiazol-2-yl]-1H-indol-7-yl}-N-methyl-2-(trifluoromethyl)benzenesulfonamide

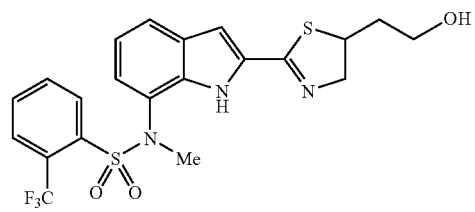

To a mixture of ethyl {2-[7-(methyl{[2-(trifluoromethyl)phenyl]sulfonyl}amino)-1H-indol-2-yl]-4,5-dihydro-1,3-thiazol-5-yl}acetate (1.4 g), lithium borohydride (0.30 g) and tetrahydrofuran (20 mL) was added methanol (3 mL), and the mixture was stirred at room temperature for 3 hr. Aqueous citric acid solution was added to the reaction solution, and the mixture was extracted with ethyl acetate. The organic layer was washed with saturated brine, dried over anhydrous magnesium sulfate, and concentrated under reduced pressure. The obtained residue was subjected to silica gel column chromatography (ethyl acetate:hexane=5:5-7:3), and the obtained pale-yellow oil was crystallized from ethyl acetate-hexane to give the title compound (0.79 g, yield: 61%) as colorless needle crystals. MS: 484 (MH$^+$). melting point 153-154° C.

Example 316

1-({2-[7-(methyl{[2-(trifluoromethyl)phenyl]sulfonyl}amino)-1H-indol-2-yl]-4,5-dihydro-1,3-thiazol-5-yl}acetyl)-L-proline

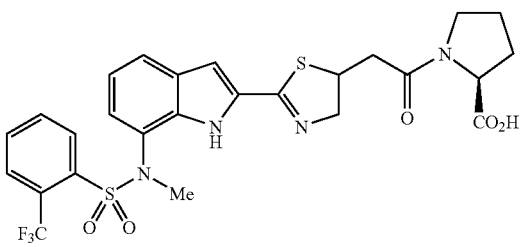

To a mixture of {2-[7-(methyl{[2-(trifluoromethyl)phenyl]sulfonyl}amino)-1H-indol-2-yl]-4,5-dihydro-1,3-thiazol-5-yl}acetic acid (150 mg), L-proline methyl ester hydrochloride (60 mg), triethylamine (50 μL), 1H-1,2,3-benzotriazol-1-ol (53 mg) and N,N-dimethylformamide (8 mL) was added N-[3-(dimethylamino)propyl]-N'-ethylcarbodiimide hydrochloride (75 mg) under ice-cooling, and the mixture was stirred from under ice-cooling to room temperature for 15 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate) to give pale-yellow crystals (180 mg). The obtained crystals were dissolved in a mixed solvent of tetrahydrofuran (5 mL)-methanol (5 mL). Aqueous potassium hydroxide solution (prepared by dissolving potassium hydroxide (0.10 g) in water (3 mL)) was added to this solution, and the mixture was stirred at room temperature for 15 hr. The reaction solution was acidified with aqueous citric acid solution, and extracted with ethyl acetate. The organic layer was washed with saturated brine, dried over anhydrous magnesium sulfate, and concentrated under reduced pressure. The obtained pale-yellow crystals were washed with ethyl acetate-hexane to give the title compound (139 mg, yield: 77%) as pale-yellow crystals.

MS: 595 (MH$^+$). melting point 132-135° C.

Example 317

[(2-{(2-[7-(methyl{[2-(trifluoromethyl)phenyl]sulfonyl}amino)-1H-indol-2-yl]-4,5-dihydro-1,3-thiazol-5-yl}ethyl)thio]acetic acid

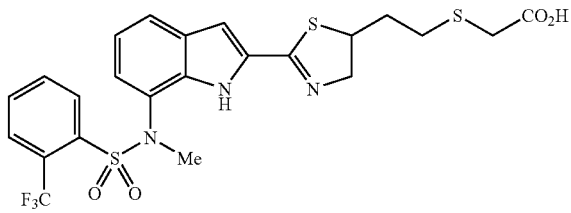

A solution (15 mL) of N-{2-[5-(2-hydroxyethyl)-4,5-dihydro-1,3-thiazol-2-yl]-1H-indol-7-yl}-N-methyl-2-(trifluoromethyl)benzenesulfonamide (710 mg) and thionyl chloride (0.32 mL) in tetrahydrofuran was stirred at 60° C. for 2 hr. The reaction solution was diluted with ethyl acetate, washed with water, dried over anhydrous magnesium sulfate, and concentrated under reduced pressure. The obtained pale-yellow oil was crystallized from diethyl ether to give pale-yellow crystals (667 mg). To a mixture of the obtained pale-yellow crystals, methyl mercaptoacetate (0.18 mL), tetrabutylammonium iodide (147 mg) and N,N-dimethylformamide (8 mL) was added potassium carbonate (140 mg), and the mixture was stirred 70° C. for 3 hr. The reaction solution was acidified with aqueous citric acid solution, and extracted with ethyl acetate. The organic layer was washed with saturated brine, dried over anhydrous magnesium sulfate, and concentrated under reduced pressure. The obtained residue was subjected to silica gel column chromatography (ethyl acetate:hexane=2:8-4:6) to give a pale-yellow oil (165 mg). The obtained oil was dissolved in a mixed solvent of tetrahydrofuran (5 mL)-methanol (5 mL). Aqueous potassium hydroxide solution (prepared by dissolving potassium hydroxide (90 mg) in water (3 mL)) was added to this solution, and the mixture was stirred at room temperature for 15 hr. The reaction solution was acidified with aqueous citric acid solution, and extracted with ethyl acetate. The organic layer was washed with saturated brine, dried over anhydrous magnesium sulfate, and concentrated under reduced pressure. The obtained residue was subjected to silica gel column chromatography (ethyl acetate-ethyl acetate:methanol=9:1) to give the title compound (80 mg, yield: 50%) as a pale-yellow amorphous solid. MS: 558 (MH$^+$).

Example 318

N-(2-{5-[(1,1-dioxidothiomorpholino)methyl]-4,5-dihydro-1,3-thiazol-2-yl}-1H-indol-7-yl)-N-methylpyridine-2-sulfonamide

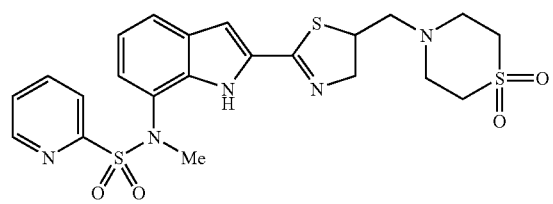

To a solution of triphenylphosphine oxide (0.50 g) in dichloromethane (5 mL) was slowly added trifluoromethanesulfonic anhydride (0.25 mL) under ice-cooling, and the mixture was stirred for 20 min. A solution of N-[2-(benzylthio)-3-(1,1-dioxidothiomorpholino)propyl]-7-[methyl(pyridin-2-ylsulfonyl)amino]-1H-indole-2-carboxamide (0.37 g) in dichloromethane (5 mL) was added dropwise, and the mixture was stirred for 30 min under ice-cooling. The reaction solution was diluted with ethyl acetate, washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=3:7-10:0). The obtained colorless oil was crystallized from ethyl acetate-hexane to give the title compound (87 mg, yield: 28%) as colorless prism crystals. MS: 520 (MH$^+$). melting point 188-189° C.

Example 319

N-{2-[5-(dimethoxymethyl)-4,5-dihydro-1,3-thiazol-2-yl]-1H-indol-7-yl}-N,1-dimethyl-1H-imidazole-2-sulfonamide

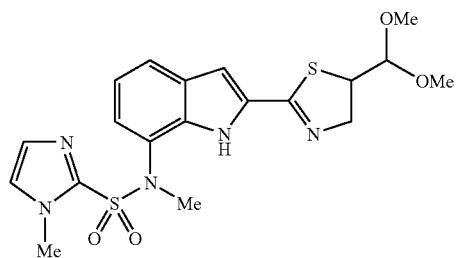

To a solution of triphenylphosphine oxide (2.41 g) in dichloromethane (15 mL) was slowly added trifluoromethanesulfonic anhydride (1.46 mL) under ice-cooling, and the mixture was stirred for 20 min. A solution of N-[2-(benzylthio)-3,3-dimethoxypropyl]-7-{methyl[(1-methyl- 1H-imidazol-2-yl)sulfonyl]amino}-1H-indole-2-carboxamide (4.4 g) and thioanisole (1.4 mL) in dichloromethane (20 mL) was added dropwise, and the mixture was stirred under ice-cooling for 1 hr. The reaction solution was diluted with ethyl acetate, washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=3:7-4:6) to give the title compound (1.7 g, yield: 48%) as a pale-yellow oil. MS: 450 (MH$^+$).

Example 320

N,1-dimethyl-N-(2-{5-[(1-oxidothiomorpholino)methyl]-4,5-dihydro-1,3-thiazol-2-yl}-1H-indol-7-yl)-1H-imidazole-2-sulfonamide

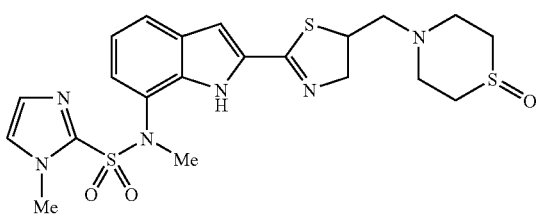

A mixture of N-{2-[5-(dimethoxymethyl)-4,5-dihydro-1,3-thiazol-2-yl]-1H-indol-7-yl}-N,1-dimethyl-1H-imidazole-2-sulfonamide (0.32 g), trifluoroacetic acid (2 mL), concentrated sulfuric acid (2 mL) and water (5 mL) was stirred at 65° C. for 3 hr. The reaction solution was neutralized with aqueous sodium hydrogencarbonate solution, and extracted with ethyl acetate. The organic layer was washed with saturated brine, dried over anhydrous magnesium sulfate, and concentrated under reduced pressure. The obtained pale-pink crystals and thiomorpholine 1-oxide hydrochloride (222 mg) were dissolved in tetrahydrofuran (25 mL), triethylamine (0.30 mL) was added to this solution, and the mixture was stirred at room temperature for 30 min. Sodium triacetoxyborohydride (0.46 g) was added, and the mixture was stirred at room temperature for 1 hr. The reaction solution was acidified with diluted hydrochloric acid, basified with aqueous sodium hydrogencarbonate solution, and extracted with ethyl acetate. The organic layer was washed with saturated brine, dried over anhydrous magnesium sulfate, and concentrated under reduced pressure. The obtained residue was subjected to basic silica gel column chromatography (ethyl acetate:hexane=50:50-90:10), and the obtained pale-yellow oil was crystallized from ethyl acetate-hexane to give the title compound (137 mg, yield: 38%) as pale-yellow crystals. MS: 507 (MH$^+$). melting point 161-162° C.

Example 321

N-methyl-N-{5-[3-(methylsulfonyl)propoxy]-2-[5-(morpholinomethyl)-4,5-dihydro-1,3-thiazol-2-yl]-1H-indol-7-yl}pyridine-2-sulfonamide

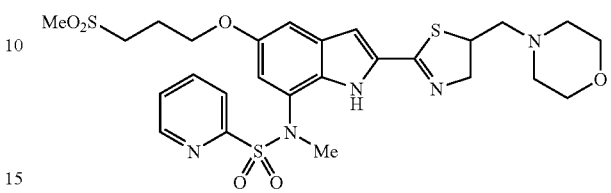

To a solution of triphenylphosphine oxide (1.0 g) in dichloromethane (4 mL) was slowly added trifluoromethanesulfonic anhydride (0.46 mL) under ice-cooling, and the mixture was stirred for 30 min. A solution of N-[2-(benzylthio)-3-morpholinopropyl]-7-[methyl(pyridin-2-ylsulfonyl)amino]-5-[3-(methylsulfonyl)propoxy]-1H-indole-2-carboxamide (0.88 g) and thioanisole (0.61 mL) in dichloromethane (25 mL) was added dropwise, and the mixture was stirred for 90 min under ice-cooling. The reaction solution was diluted with ethyl acetate, washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=50:50-85:15), and the obtained colorless oil was crystallized from ethyl acetate-hexane to give the title compound (174 mg, yield: 23%) as colorless prism crystals. MS: 608 (MH$^+$). melting point 168-169° C.

Example 322

N-methyl-N-{5-[3-(methylsulfonyl)propoxy]-2-[5-(thiomorpholinomethyl)-4,5-dihydro-1,3-thiazol-2-yl]-1H-indol-7-yl}pyridine-2-sulfonamide

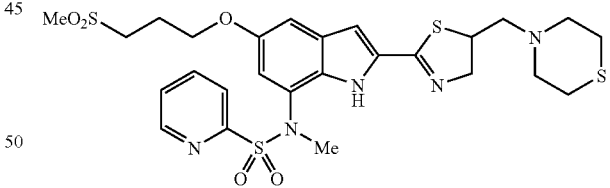

To a solution of triphenylphosphine oxide (0.70 g) in dichloromethane (3 mL) was slowly added trifluoromethanesulfonic anhydride (0.41 mL) under ice-cooling, and the mixture was stirred for 30 min. A solution of N-[2-(benzylthio)-3-thiomorpholinopropyl]-7-[methyl(pyridin-2-ylsulfonyl)amino]-5-[3-(methylsulfonyl)propoxy]-1H-indole-2-carboxamide (0.75 g) and thioanisole (0.30 mL) in dichloromethane (10 mL) was added dropwise, and the mixture was stirred for 30 min under ice-cooling. The reaction solution was diluted with ethyl acetate, washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=50:50-90:10) to give the title compound (350 mg, yield: 54%) as a colorless amorphous solid. MS: 625 (MH⁺).

Example 323

N-methyl-N-(5-[3-(methylsulfonyl)propoxy]-2-{5-[(1-oxidothiomorpholino)methyl]-4,5-dihydro-1,3-thiazol-2-yl}-1H-indol-7-yl)pyridine-2-sulfonamide

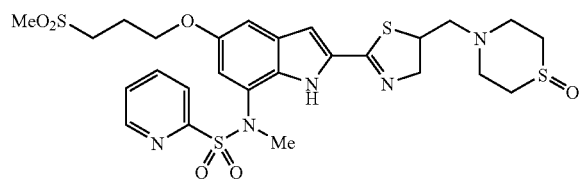

To a mixture of N-methyl-N-{5-[3-(methylsulfonyl)propoxy]-2-[5-(thiomorpholinomethyl)-4,5-dihydro-1,3-thiazol-2-yl]-1H-indol-7-yl}pyridine-2-sulfonamide (0.35 g), ethanol (60 mL), water (30 mL) and tetrahydrofuran (30 mL) was added OXONE (registered trade mark, 0.19 g), and the mixture was stirred at room temperature for 3 hr. Aqueous sodium sulfite solution was added to the reaction mixture, the mixture was stirred for 30 min, and the organic solvent was evaporated under reduced pressure. The residue was diluted with water, and the mixture was extracted with ethyl acetate. The organic layer was washed with saturated brine, dried over anhydrous magnesium sulfate, and concentrated under reduced pressure. The obtained colorless crystals were recrystallized from ethyl acetate-hexane to give the title compound (193 mg, yield: 54%) as colorless crystals. MS: 641 (MH⁺). melting point 107-110° C.

Example 324

N-{2-{5-[(4-acetylpiperazin-1-yl)methyl]-4,5-dihydro-1,3-thiazol-2-yl}-5-[3-(methylsulfonyl)propoxy]-1H-indol-7-yl}-N-methylpyridine-2-sulfonamide

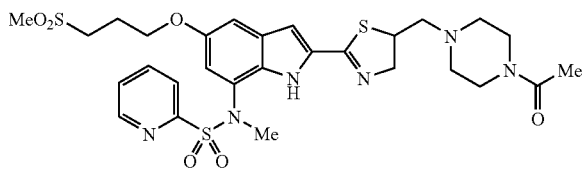

To a solution of triphenylphosphine oxide (0.38 g) in dichloromethane (3 mL) was slowly added trifluoromethanesulfonic anhydride (0.23 mL) under ice-cooling, and the mixture was stirred for 30 min. A solution of N-[3-(4-acetylpiperazin-1-yl)-2-(benzylthio)propyl]-7-[methyl(pyridin-2-ylsulfonyl)amino]-5-[3-(methylsulfonyl)propoxy]-1H-indole-2-carboxamide (0.34 g) and thioanisole (0.17 mL) in dichloromethane (5 mL) was added dropwise, and the mixture was stirred for 1 hr under ice-cooling. The reaction solution was diluted with ethyl acetate, washed with aqueous sodium hydrogencarbonate solution and saturated brine, dried over anhydrous magnesium sulfate, and concentrated under reduced pressure. The obtained residue was subjected to basic silica gel column chromatography (ethyl acetate), and the obtained colorless oil was crystallized from ethyl acetate-hexane to give the title compound (109 mg, yield: 37%) as colorless crystals. MS: 650 (MH⁺). melting point 165-167° C.

Example 325

N-methyl-N-{2-(5-{[4-(methylsulfonyl)piperazin-1-yl]methyl}-4,5-dihydro-1,3-thiazol-2-yl)-5-[3-(methylsulfonyl)propoxy]-1H-indol-7-yl}pyridine-2-sulfonamide

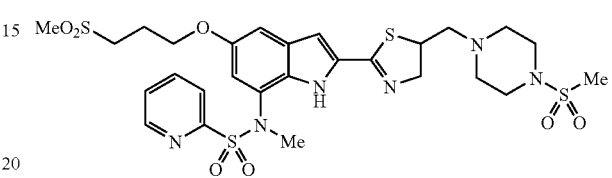

To a solution of triphenylphosphine oxide (0.48 g) in dichloromethane (3 mL) was slowly added trifluoromethanesulfonic anhydride (0.29 mL) under ice-cooling, and the mixture was stirred for 20 min. A solution of N-{2-(benzylthio)-3-[4-(methylsulfonyl)piperazin-1-yl]propyl}-7-[methyl(pyridin-2-ylsulfonyl)amino]-5-[3-(methylsulfonyl)propoxy]-1H-indole-2-carboxamide (0.34 g) in dichloromethane (15 mL) was added dropwise, and the mixture was stirred for 1 hr under ice-cooling. The reaction solution was diluted with ethyl acetate, washed with aqueous sodium hydrogencarbonate solution and saturated brine, dried over anhydrous magnesium sulfate, and concentrated under reduced pressure. The obtained residue was subjected to silica gel column chromatography (ethyl acetate:hexane=7:3-10:0-ethyl acetate:methanol=9:1), and the obtained colorless oil was crystallized from ethyl acetate-diethyl ether to give the title compound (142 mg, yield: 48%) as colorless crystals.

MS: 686 (MH⁺). melting point 151-153° C.

Example 326

N-methyl-N-{2-[5-(morpholinomethyl)-4,5-dihydro-1,3-thiazol-2-yl]-1H-indol-7-yl}pyridine-3-sulfonamide

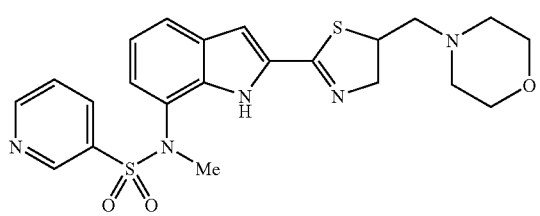

To a mixture of triphenylphosphine oxide (790 mg) and acetonitrile (15 mL) was added trifluoromethanesulfonic anhydride (238 μL), and the mixture was stirred at 0° C. for 10 min. A solution of N-[2-(benzylthio)-3-morpholinopropyl]-7-[methyl(pyridin-3-ylsulfonyl)amino]-1H-indole-2-carboxamide (410 mg) and dimethylsulfide (52 μL) in acetonitrile (15 mL) and dichloromethane (15 mL) was added to the mixture, and the mixture was stirred at 0° C. for 2 hr. The reaction mixture was diluted with ethyl acetate (100 mL) and saturated brine (100 mL). The organic layer was dried over sodium sulfate, and filtrated, and the filtrate was concentrated. The obtained residue was purified by preparative HPLC to give the title compound (38.3 mg, yield 11%) as a white solid. melting point 234-236° C.

Example 327 ethyl (2-{7-[methyl(1,3-thiazol-2-ylsulfonyl)amino]-1H-indol-2-yl}-4,5-dihydro-1,3-thiazol-5-yl)acetate

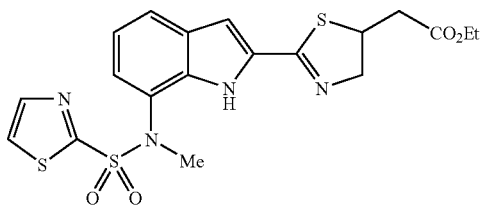

A mixture of 7-[methyl(1,3-thiazol-2-ylsulfonyl)amino]-1H-indole-2-carboxamide (1.30 g), Lawesson's reagent (937 mg) and tetrahydrofuran (10 mL) was stirred 80° C. for 30 min. The reaction mixture was concentrated, toluene was added, and the precipitated solid was collected by filtration. A mixture of the obtained solid, ethyl but-2-ynoate (388 mg), tributylphosphine (63 µL), tetrahydrofuran (10 mL) and toluene (5 mL) was stirred at 50° C. for 2 hr. The reaction mixture was diluted with ethyl acetate (200 mL) and saturated brine (100 mL). The organic layer was dried over sodium sulfate, and filtrated, and the filtrate was concentrated. The obtained residue was purified by silica gel column chromatography (ethyl acetate:hexane=1:1, volume ratio) to give the title compound (780 mg, yield 44%) as a pale-yellow solid.

MS: 465 (MH$^+$)

Example 328

(2-{7-[methyl(1,3-thiazol-2-ylsulfonyl)amino]-1H-indol-2-yl}-4,5-dihydro-1,3-thiazol-5-yl)acetic acid

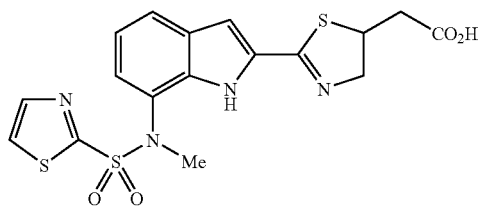

A mixture of ethyl (2-{7-[methyl(1,3-thiazol-2-ylsulfonyl)amino]-1H-indol-2-yl}-4,5-dihydro-1,3-thiazol-5-yl)acetate (300 mg), tetrahydrofuran (5 mL), ethanol (5 mL) and 2N aqueous sodium hydroxide solution (4 mL) was stirred at room temperature for 1 hr. The reaction mixture was diluted with ethyl acetate (100 mL) and 1N hydrochloric acid (50 mL). The organic layer was dried over sodium sulfate, and filtrated, and the filtrate was concentrated. The obtained solid was washed with ethyl acetate to give the title compound (278 mg, yield 98%) as a white solid. melting point 121-123° C.

Example 329

N-{2-[5-(2-hydroxyethyl)-4,5-dihydro-1,3-thiazol-2-yl]-1H-indol-7-yl}-N-methyl-1,3-thiazole-2-sulfonamide

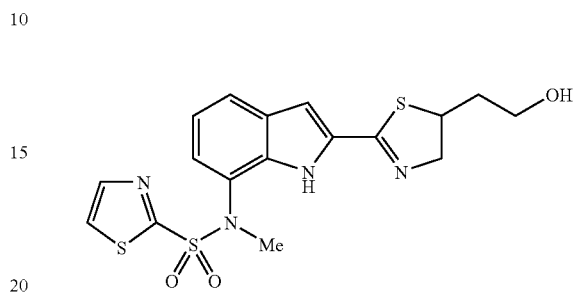

Ethyl (2-{7-[methyl(1,3-thiazol-2-ylsulfonyl)amino]-1H-indol-2-yl}-4,5-dihydro-1,3-thiazol-5-yl)acetate (200 mg) was dissolved in a mixed solvent of tetrahydrofuran (5 mL) and methanol (5 mL), and the mixture was cooled to 0° C. Lithium borohydride (20 mg) was added, and the mixture was stirred at room temperature for 2 hr. The reaction mixture was diluted with ethyl acetate (100 mL) and 1N hydrochloric acid (50 mL). The organic layer was dried over sodium sulfate, and filtrated, and the filtrate was concentrated. The obtained residue was purified by silica gel column chromatography (ethyl acetate) to give the title compound (25 mg, yield 14%) as a pale-yellow solid. MS: 423 (MH$^+$).

Example 330

2-(2-{7-[methyl(1,3-thiazol-2-ylsulfonyl)amino]-1H-indol-2-yl}-4,5-dihydro-1,3-thiazol-5-yl)acetamide

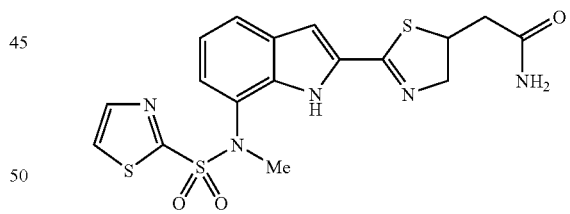

A mixture of (2-{7-[methyl(1,3-thiazol-2-ylsulfonyl)amino]-1H-indol-2-yl}-4,5-dihydro-1,3-thiazol-5-yl)acetic acid (250 mg), 1H-1,2,3-benzotriazol-1-ol-ammonia complex (114 mg), N-[3-(dimethylamino)propyl]-N'-ethylcarbodiimide hydrochloride (144 mg) and N,N-dimethylformamide (10 mL) was stirred overnight at room temperature. The reaction mixture was diluted with ethyl acetate (100 mL) and water (100 mL), and the organic layer was washed successively with saturated aqueous sodium hydrogencarbonate and saturated brine, dried over anhydrous magnesium sulfate, and concentrated under reduced pressure. The obtained solid was washed with ethyl acetate to give the title compound (166 mg, yield 67%) as a white solid. melting point 216-218° C.

Example 331

N-methyl-N-{2-[5-(morpholinomethyl)-4,5-dihydro-1,3-thiazol-2-yl]-1H-indol-7-yl}pyridine-2-sulfonamide

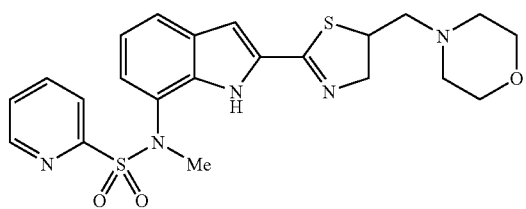

In the same manner as in Example 201, the title compound (63 mg, yield 47%) was obtained as a colorless amorphous solid from N-[2-(benzylthio)-3-morpholinopropyl]-7-[methyl(pyridin-2-ylsulfonyl)amino]-1H-indole-2-carboxamide (165 mg). MS: 472 (MH$^+$).

Example 332 ethyl (2-{7-[methyl(pyridin-2-ylsulfonyl)amino]-1H-indol-2-yl}-4,5-dihydro-1,3-thiazol-5-yl)acetate

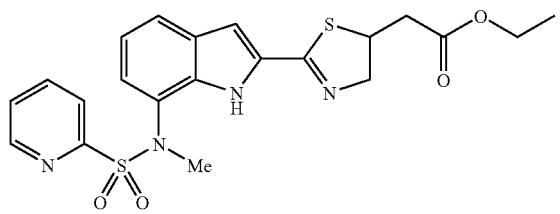

In the same manner as in Example 283, the title compound (670 mg, yield 42%) was obtained as a pale-yellow amorphous solid from 7-[methyl(pyridin-2-ylsulfonyl)amino]-1H-indole-2-carbothioamide (1190 mg) and ethyl but-2-ynoate (0.922 mL). MS: 459 (MH$^+$).

Example 333

(2-{7-[methyl(pyridin-2-ylsulfonyl)amino]-1H-indol-2-yl}-4,5-dihydro-1,3-thiazol-5-yl)acetic acid

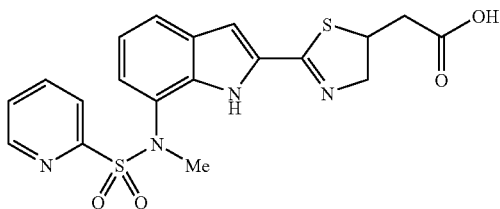

To a solution of ethyl (2-{7-[methyl(pyridin-2-ylsulfonyl)amino]-1H-indol-2-yl}-4,5-dihydro-1,3-thiazol-5-yl)acetate (470 mg) in tetrahydrofuran (6 mL) and methanol (6 mL) was added a solution of potassium hydroxide (85% purity, 170 mg) in water (2.5 mL), and the mixture was stirred at 0° C. for 1 hr, and then at room temperature for 3 hr. The reaction mixture was diluted with ethyl acetate, and neutralized with 1M hydrochloric acid. The ethyl acetate layer was washed with saturated brine, dried (MgSO$_4$), and concentrated. The residue was recrystallized from a mixed solvent of ethyl acetate-hexane to give the title compound (400 mg, yield 91%) as white crystals. MS: 431 (MH$^+$). melting point 231-233° C.

Example 334

2-(2-{7-[methyl(pyridin-2-ylsulfonyl)amino]-1H-indol-2-yl}-4,5-dihydro-1,3-thiazol-5-yl)acetamide

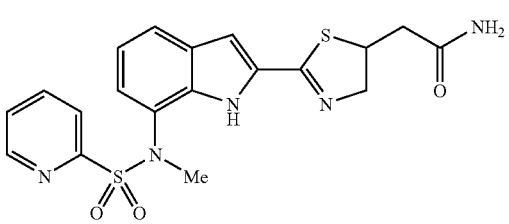

To a mixture of (2-{7-[methyl(pyridin-2-ylsulfonyl)amino]-1H-indol-2-yl}-4,5-dihydro-1,3-thiazol-5-yl)acetic acid (200 mg), 1H-1,2,3-benzotriazol-1-ol-ammonia complex (92 mg) and N,N-dimethylformamide (10 mL) was added N-[3-(dimethylamino)propyl]-N'-ethylcarbodiimide hydrochloride (120 mg) under ice-cooling, and the mixture was stirred from under ice-cooling to room temperature for 4 days. The reaction solution was diluted with ethyl acetate, washed with water, aqueous sodium hydrogencarbonate solution and saturated brine, dried over anhydrous magnesium sulfate, and concentrated under reduced pressure. The obtained residue was crystallized from ethyl acetate-hexane to give the title compound (166 mg, yield: 83%) as pale-yellow prism crystals. MS: 430 (MH$^+$). melting point 206-207° C.

Example 335

(2-{7-[methyl(pyridin-2-ylsulfonyl)amino]-1H-indol-2-yl}-4,5-dihydro-1,3-thiazol-5-yl)acetic acid

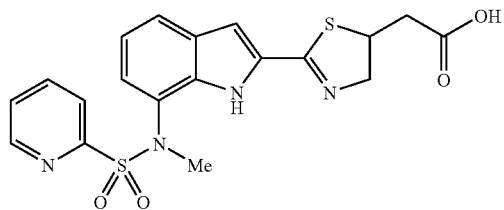

(2-{7-[Methyl(pyridin-2-ylsulfonyl)amino]-1H-indol-2-yl}-4,5-dihydro-1,3-thiazol-5-yl)acetic acid (180 mg) was dissolved in ethanol-acetic acid (1000:1, volume ratio, 360 mL). This solution was subjected to HPLC using CHIRALCEL OJ (50 mmID×500 mL, manufactured by DAICEL CHEMICAL INDUSTRIES, LTD.), and eluted with ethanol-acetic acid (1000:1, volume ratio) as a mobile phase at 30° C. at flow rate of 40 mL/min. A fraction with the retention time of 39.9 min was separated, and concentrated. The obtained solid was dissolved in ethyl acetate, the insoluble substance was removed by filtration, and the filtrate was concentrated to give the title compound (64.2 mg) as a colorless solid. MS: 431 (MH+).

Example 336

(2-{7-[methyl(pyridin-2-ylsulfonyl)amino]-1H-indol-2-yl}-4,5-dihydro-1,3-thiazol-5-yl)acetic acid

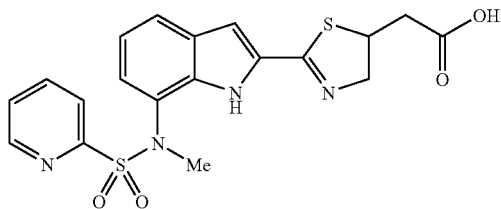

(2-{7-[Methyl(pyridin-2-ylsulfonyl)amino]-1H-indol-2-yl}-4,5-dihydro-1,3-thiazol-5-yl)acetic acid (180 mg) was dissolved in ethanol-acetic acid (1000:1, volume ratio, 360 mL). This solution was subjected to HPLC using CHIRALCEL OJ (50 mmID×500 mL, manufactured by DAICEL CHEMICAL INDUSTRIES, LTD.), and eluted with ethanol-acetic acid (1000:1, volume ratio) as a mobile phase at 30° C. at flow rate of 40 mL/min. A fraction with the retention time of 53.1 min was separated, and concentrated. The obtained solid was dissolved in ethyl acetate, the insoluble substance was removed by filtration, and the filtrate was concentrated to give the title compound (71.8 mg) as a white solid. MS: 431 (MH+).

Example 337

2-(2-{7-[methyl(pyridin-2-ylsulfonyl)amino]-1H-indol-2-yl}-4,5-dihydro-1,3-thiazol-5-yl)acetamide

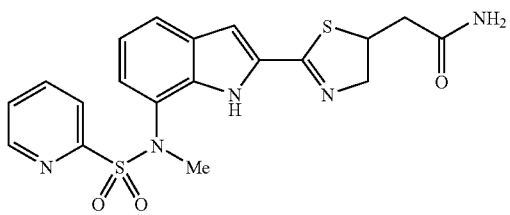

To a mixture of 2-{7-[methyl(pyridin-2-ylsulfonyl)amino]-1H-indol-2-yl}-4,5-dihydro-1,3-thiazol-5-yl)acetic acid (64 mg) obtained in Example 335, 1H-1,2,3-benzotriazol-1-ol-ammonia complex (35 mg) and N,N-dimethylformamide (3 mL) was added N-[3-(dimethylamino)propyl]-N'-ethylcarbodiimide hydrochloride (45 mg) under ice-cooling, and the mixture was stirred from under ice-cooling to room temperature for 18 hours. The reaction solution was diluted with ethyl acetate, washed with water, aqueous sodium hydrogencarbonate solution and saturated brine, dried over anhydrous magnesium sulfate, and concentrated under reduced pressure. The obtained residue was crystallized from ethyl acetate-hexane to give the title compound (54 mg, yield: 85%) as pale-yellow prism crystals. MS: 430 (MH+). melting point 149-150° C.

Example 338

2-(2-{7-[methyl(pyridin-2-ylsulfonyl)amino]-1H-indol-2-yl}-4,5-dihydro-1,3-thiazol-5-yl)acetamide

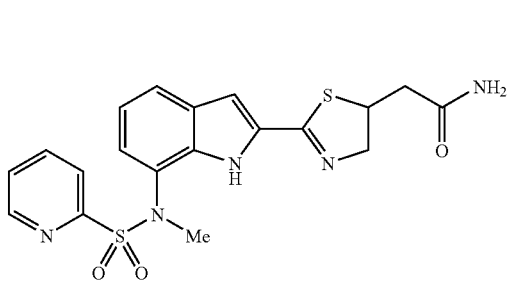

To a mixture of 2-{7-[methyl(pyridin-2-ylsulfonyl)amino]-1H-indol-2-yl}-4,5-dihydro-1,3-thiazol-5-yl)acetic acid (72 mg) obtained in Example 336, 1H-1,2,3-benzotriazol-1-ol-ammonia complex (40 mg) and N,N-dimethylformamide (3 mL) was added N-[3-(dimethylamino)propyl]-N'-ethylcarbodiimide hydrochloride (50 mg) under ice-cooling, and the mixture was stirred from under ice-cooling to room temperature for 18 hours. The reaction solution was diluted with ethyl acetate, washed with water, aqueous sodium hydrogencarbonate solution and saturated brine, dried over anhydrous magnesium sulfate, and concentrated under reduced pressure. The obtained residue was crystallized from ethyl acetate-hexane to give the title compound (57 mg, yield: 79%) as pale-yellow prism crystals. MS: 430 (MH+). melting point 148-149° C.

Example 339

N-{2-[5-(2-hydroxyethyl)-4,5-dihydro-1,3-thiazol-2-yl]-1H-indol-7-yl}-N-methylpyridine-2-sulfonamide

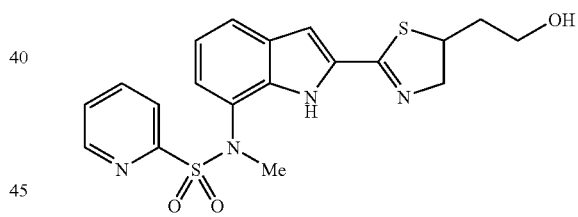

In the same manner as in Example 285, the title compound (141 mg, yield 78%) was obtained as a colorless amorphous solid from ethyl (2-{7-[methyl(pyridin-2-ylsulfonyl)amino]-1H-indol-2-yl}-4,5-dihydro-1,3-thiazol-5-yl)acetate (200 mg). MS: 417 (MH+).

Example 340

N-methyl-N-{2-[5-(morpholinomethyl)-4,5-dihydro-1,3-thiazol-2-yl]-1H-indol-7-yl}furan-2-sulfonamide

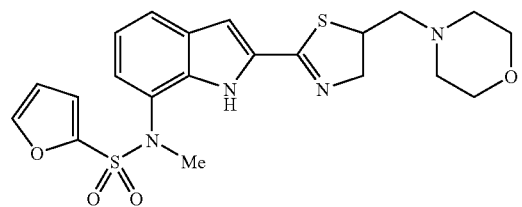

In the same manner as in Example 201, the title compound (200 mg, yield 29%) was obtained as white crystals from N-[2-(benzylthio)-3-morpholinopropyl]-7-[(2-furylsulfonyl)(methyl)amino]-1H-indole-2-carboxamide (840 mg). MS: 46.1 (MH+).

Example 341 ethyl (2-{7-[(2-furylsulfonyl)(methyl)amino]-1H-indol-2-yl}-4,5-dihydro-1,3-thiazol-5-yl)acetate

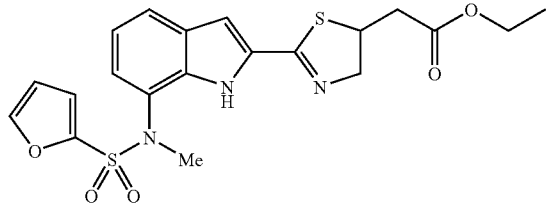

In the same manner as in Example 283, the title compound (605 mg, yield 35%) was obtained as a pale-yellow amorphous solid from 7-[(2-furylsulfonyl)(methyl)amino]-1H-indole-2-carbothioamide (1280 mg) and ethyl but-2-ynoate (1.025 mL). MS: 448 (MH+).

Example 342

(2-{7-[(2-furylsulfonyl)(methyl)amino]-1H-indol-2-yl}-4,5-dihydro-1,3-thiazol-5-yl)acetic acid

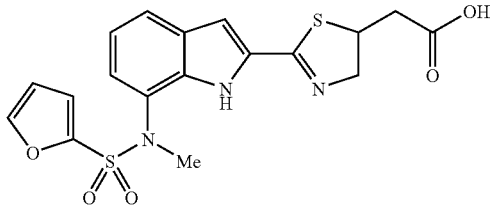

In the same manner as in Example 284, the title compound (250 mg, yield 67%) was obtained as white crystals from ethyl (2-{7-[(2-furylsulfonyl)(methyl)amino]-1H-indol-2-yl}-4,5-dihydro-1,3-thiazol-5-yl)acetate (400 mg). MS: 420 (MH+).

Example 343

2-(2-{7-[(2-furylsulfonyl)(methyl)amino]-1H-indol-2-yl}-4,5-dihydro-1,3-thiazol-5-yl)acetamide

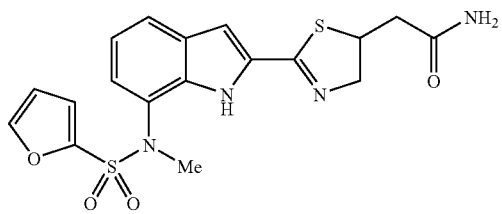

In the same manner as in Example 287, the title compound (120 mg, yield 60%) was obtained as white crystals from (2-{7-[(2-furylsulfonyl)(methyl)amino]-1H-indol-2-yl}-4,5-dihydro-1,3-thiazol-5-yl)acetic acid (150 mg). MS: 419 (MH+).

Example 344

N-{2-[5-(2-hydroxyethyl)-4,5-dihydro-1,3-thiazol-2-yl]-1H-indol-7-yl}-N-methylfuran-2-sulfonamide

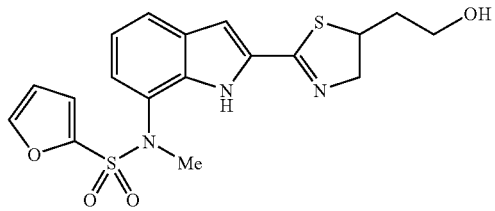

In the same manner as in Example 285, the title compound (150 mg, yield 83%) was obtained as white crystals from ethyl (2-{7-[(2-furylsulfonyl)(methyl)amino]-1H-indol-2-yl}-4,5-dihydro-1,3-thiazol-5-yl)acetate (200 mg)
MS: 406 (MH+).

Example 345

N-{2-[5-(morpholinomethyl)-4,5-dihydro-1,3-thiazol-2-yl]-1H-indol-7-yl}thiophene-2-sulfonamide

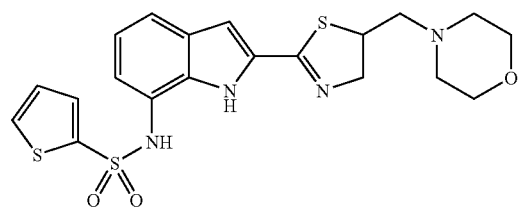

In the same manner as in Example 201, the title compound (330 mg, yield 41%) was obtained as white crystals from N-[2-(benzylthio)-3-morpholinopropyl]-7-[(2-thienylsulfonyl)amino]-1H-indole-2-carboxamide (1000 mg).
MS: 463 (MH+).

Example 346

N-(difluoromethyl)-N-{2-[5-(morpholinomethyl)-4,5-dihydro-1,3-thiazol-2-yl]-1H-indol-7-yl}thiophene-2-sulfonamide

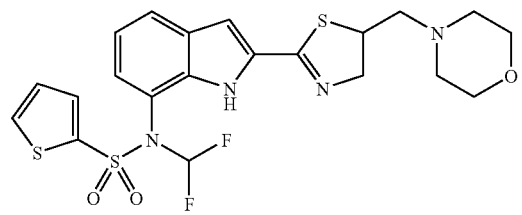

To a solution of N-{2-[5-(morpholinomethyl)-4,5-dihydro-1,3-thiazol-2-yl]-1H-indol-7-yl}thiophene-2-sulfonamide (200 mg) in N,N-dimethylformamide (3 mL) were added potassium carbonate (90.0 mg) and difluoroiodomethane (77.0 mg), and the mixture was stirred overnight at room temperature. The reaction mixture was diluted with ethyl acetate, washed with water and saturated brine, dried (MgSO$_4$), and concentrated. The residue was subjected to basic silica gel column chromatography to give the title compound (60 mg, yield 27%) as white crystals from a fraction eluted with ethyl acetate-hexane (1:1, volume ratio). MS: 513 (MH$^+$). melting point 185-186° C.

Example 347

N-(difluoromethyl)-N-{2-[5-(morpholinomethyl)-4,5-dihydro-1,3-thiazol-2-yl]-1H-indol-7-yl}thiophene-2-sulfonamide

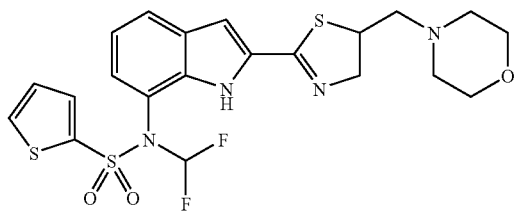

(N-(Difluoromethyl)-N-{2-[5-(morpholinomethyl)-4,5-dihydro-1,3-thiazol-2-yl]-1H-indol-7-yl}thiophene-2-sulfonamide (93 mg) obtained in Example 346 was dissolved in hexane-ethanol (700:300, volume ratio, 190 mL). This solution was subjected to HPLC using CHIRALCEL OD (50 mmIDx500 mL, manufactured by DAICEL CHEMICAL INDUSTRIES, LTD.), and eluted with hexane-ethanol (700:300, volume ratio) as a mobile phase at 30° C. at flow rate of 60 mL/min. A fraction with the retention time of 18.2 min was separated, and concentrated. The obtained solid was dissolved in ethyl acetate, the insoluble substance was removed by filtration, and the filtrate was concentrated to give the title compound (43.0 mg) as a colorless solid. MS: 513 (MH$^+$).

Example 348

N-(difluoromethyl)-N-{2-[5-(morpholinomethyl)-4,5-dihydro-1,3-thiazol-2-yl]-1H-indol-7-yl}thiophene-2-sulfonamide

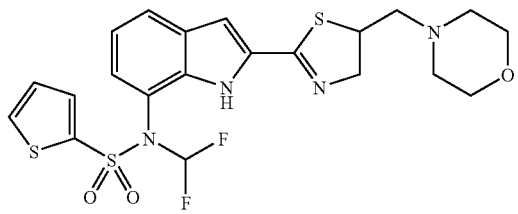

(N-(Difluoromethyl)-N-{2-[5-(morpholinomethyl)-4,5-dihydro-1,3-thiazol-2-yl]-1H-indol-7-yl}thiophene-2-sulfonamide (93 mg) obtained in Example 346 was dissolved in hexane-ethanol (700:300, volume ratio, 190 mL). This solution was subjected to HPLC using CHIRALCEL OD (50 mmIDx500 mL, manufactured by DAICEL CHEMICAL INDUSTRIES, LTD.), and eluted with hexane-ethanol (700:300, volume ratio) as a mobile phase at 30° C. at flow rate of 60 mL/min. A fraction with the retention time of 26.2 min was separated, and concentrated. The obtained solid was dissolved in ethyl acetate, the insoluble substance was removed by filtration, and the filtrate was concentrated to give the title compound (45.0 mg) as a colorless solid. MS: 513 (MH$^+$).

Example 349

N-(2,2-difluoroethyl)-N-{2-[5-(morpholinomethyl)-4,5-dihydro-1,3-thiazol-2-yl]-1H-indol-7-yl}thiophene-2-sulfonamide

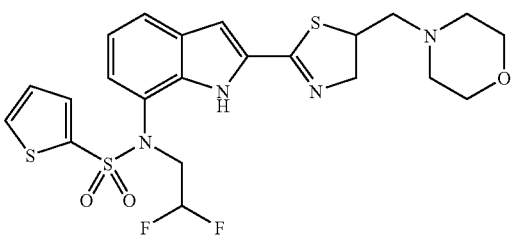

In the same manner as in Example 346, the title compound (80.0 mg, yield 35%) was obtained as white crystals from N-{2-[5-(morpholinomethyl)-4,5-dihydro-1,3-thiazol-2-yl]-1H-indol-7-yl}thiophene-2-sulfonamide (200 mg) and 1,1-difluoro-2-iodoethane (91.0 mg). MS: 527 (MH$^+$).

Example 350

N-(2-fluoroethyl)-N-{2-[5-(morpholinomethyl)-4,5-dihydro-1,3-thiazol-2-yl]-1H-indol-7-yl}thiophene-2-sulfonamide

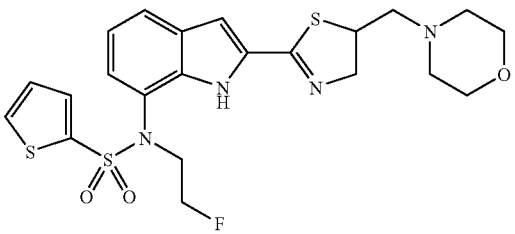

In the same manner as in Example 346, the title compound (200 mg, yield 91%) was obtained as white crystals from N-{2-[5-(morpholinomethyl)-4,5-dihydro-1,3-thiazol-2-yl]-1H-indol-7-yl}thiophene-2-sulfonamide (200 mg) and 1-fluoro-2-iodoethane (90.0 mg). MS: 509 (MH$^+$).

Example 351

N-(cyanomethyl)-N-{2-[5-(morpholinomethyl)-4,5-dihydro-1,3-thiazol-2-yl]-1H-indol-7-yl}thiophene-2-sulfonamide

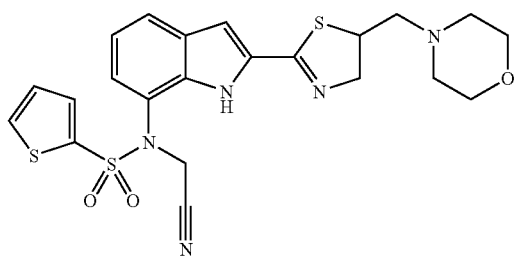

In the same manner as in Example 346, the title compound (85.0 mg, yield 26%) was obtained as white crystals from N-{2-[5-(morpholinomethyl)-4,5-dihydro-1,3-thiazol-2-yl]-1H-indol-7-yl}thiophene-2-sulfonamide (300 mg) and iodoacetonitrile (120 mg). MS: 502 (MH$^+$).

Example 352

N-ethyl-N-{2-[5-(morpholinomethyl)-4,5-dihydro-1,3-thiazol-2-yl]-1H-indol-7-yl}thiophene-2-sulfonamide

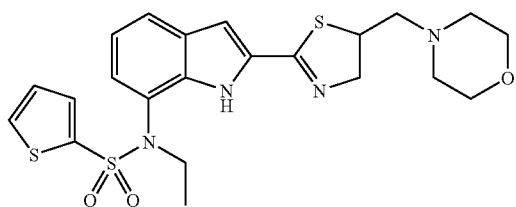

In the same manner as in Example 346, the title compound (63.4 mg, yield 60%) was obtained as white crystals from N-{2-[5-(morpholinomethyl)-4,5-dihydro-1,3-thiazol-2-yl]-1H-indol-7-yl}thiophene-2-sulfonamide (100 mg) and iodoethane (34.0 mg). MS: 491 (MH$^+$).

Example 353

N-{2-[5-(morpholinomethyl)-4,5-dihydro-1,3-thiazol-2-yl]-1H-indol-7-yl}-N-(2-thienylsulfonyl)glycine ethyl ester

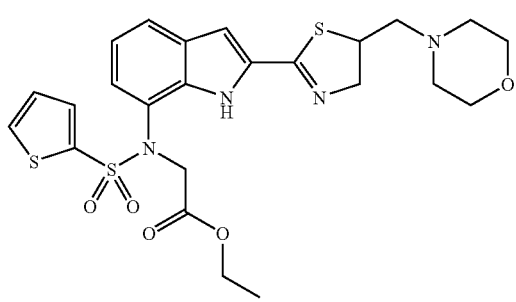

In the same manner as in Example 346, the title compound (400 mg, yield 67%) was obtained as white crystals from N-{2-[5-(morpholinomethyl)-4,5-dihydro-1,3-thiazol-2-yl]-1H-indol-7-yl}thiophene-2-sulfonamide (500 mg) and ethyl iodoacetate (255 mg). MS: 549 (MH$^+$).

Example 354

N-(2-hydroxyethyl)-N-{2-[5-(morpholinomethyl)-4,5-dihydro-1,3-thiazol-2-yl]-1H-indol-7-yl}thiophene-2-sulfonamide

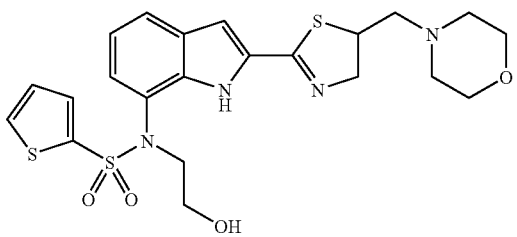

To a solution of N-{2-[5-(morpholinomethyl)-4,5-dihydro-1,3-thiazol-2-yl]-1H-indol-7-yl}-N-(2-thienylsulfonyl)glycine ethyl ester (100 mg) in tetrahydrofuran (10 mL) and methanol (2 mL) was added lithium borohydride (18.0 mg), and the mixture was stirred at room temperature for 4 hr. 1M Hydrochloric acid was added to the reaction mixture, and the mixture was extracted with ethyl acetate. The ethyl acetate layer was washed with saturated brine, dried (MgSO$_4$), and concentrated. The residue was recrystallized from a mixed solvent of ethyl acetate-hexane to give the title compound (70 mg, yield 76%) as white crystals.

MS: 507 (MH$^+$).

Example 355

N-{2-[5-(morpholinomethyl)-4,5-dihydro-1,3-thiazol-2-yl]-1H-indol-7-yl}-N-(2-thienylsulfonyl)glycine

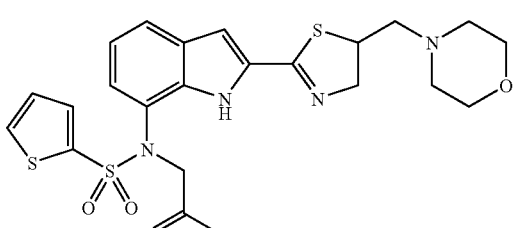

To a solution of N-{2-[5-(morpholinomethyl)-4,5-dihydro-1,3-thiazol-2-yl]-1H-indol-7-yl}-N-(2-thienylsulfonyl)glycine ethyl ester (120 mg) in tetrahydrofuran (3 mL) and methanol (3 mL) was added, under ice-cooling, a solution prepared by dissolving potassium hydroxide (purity 85%, 30 mg) in water (1 mL), and the mixture was stirred for 30 min, and then at room temperature for 1 hr. 1M Hydrochloric acid was added to the reaction mixture, and the mixture was extracted with ethyl acetate. The ethyl acetate layer was washed with saturated brine, dried (MgSO$_4$), and concentrated. The residue was recrystallized from a mixed solvent of ethyl acetate-hexane to give the title compound (106 mg, yield 93%) as white crystals. MS: 521 (MH$^+$).

Example 356

N-{2-[5-(morpholinomethyl)-4,5-dihydro-1,3-thiazol-2-yl]-1H-indol-7-yl}-N-(2-thienylsulfonyl)glycinamide

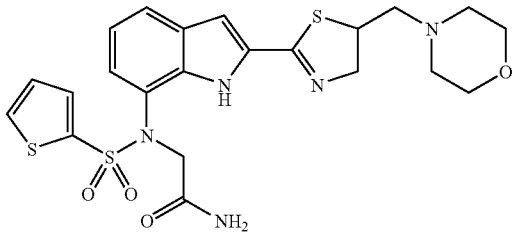

To a solution of N-{2-[5-(morpholinomethyl)-4,5-dihydro-1,3-thiazol-2-yl]-1H-indol-7-yl}-N-(2-thienylsulfonyl)glycine (60 mg) in N,N-dimethylformamide (5 mL) were added 1H-1,2,3-benzotriazol-1-ol-ammonia complex (30 mg) and N-[3-(dimethylamino)propyl]-N'-ethylcarbodiimide hydrochloride (35 mg) under ice-cooling, and the mixture was stirred overnight at room temperature. Saturated aqueous sodium hydrogencarbonate was added to the reaction mixture, and the mixture was extracted with ethyl acetate. The ethyl acetate layer was washed with water and saturated brine, dried (MgSO$_4$), and concentrated. The residue was recrystallized from a mixed solvent of ethyl acetate-hexane to give the title compound (43 mg, yield 71%) as white crystals. MS: 520 (MH$^+$).

Example 357

N-(2-hydroxy-2-methylpropyl)-N-{2-[5-(morpholinomethyl)-4,5-dihydro-1,3-thiazol-2-yl]-1H-indol-7-yl}thiophene-2-sulfonamide

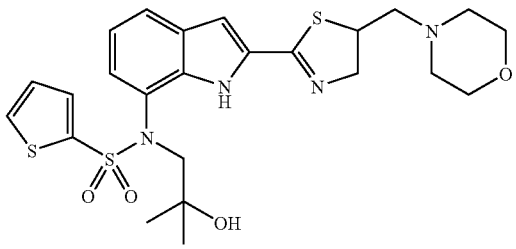

To a solution of N-{2-[5-(morpholinomethyl)-4,5-dihydro-1,3-thiazol-2-yl]-1H-indol-7-yl}-N-(2-thienylsulfonyl)glycine ethyl ester (110 mg) in tetrahydrofuran (5 mL) was added methylmagnesium bromide (1.0M tetrahydrofuran solution, 1 mL), and the mixture was stirred overnight at 50° C. 1M Hydrochloric acid was added to the reaction mixture, and the mixture was extracted with ethyl acetate. The ethyl acetate layer was washed with saturated aqueous sodium hydrogencarbonate and saturated brine, dried (MgSO$_4$), and concentrated. The residue was purified by preparative HPLC to give the title compound (30 mg, yield 28%) as white crystals. MS: 535 (MH$^+$).

Example 358

2-(2-{7-[methyl(2-thienylsulfonyl)amino]-1H-indol-2-yl}-4,5-dihydro-1,3-thiazol-5-yl)ethyl methanesulfonate and N-{2-[5-(2-chloroethyl)-4,5-dihydro-1,3-thiazol-2-yl]-1H-indol-7-yl}-N-methylthiophene-2-sulfonamide

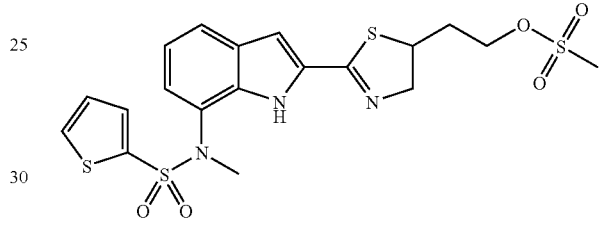

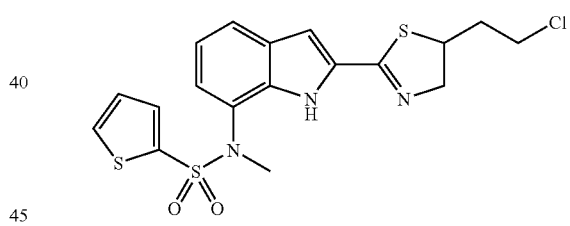

To a solution of N-{2-[5-(2-hydroxyethyl)-4,5-dihydro-1,3-thiazol-2-yl]-1H-indol-7-yl}-N-methylthiophene-2-sulfonamide (200 mg) and triethylamine (70 μL) in tetrahydrofuran (5 mL) was added methanesulfonyl chloride (60 mg) at room temperature, and the mixture was stirred for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give 2-(2-{7-[methyl(2-thienylsulfonyl)amino]-1H-indol-2-yl}-4,5-dihydro-1,3-thiazol-5-yl)ethyl methanesulfonate (126 mg, yield 54%, MS: 500 (MH$^+$)) and N-{2-[5-(2-chloroethyl)-4,5-dihydro-1,3-thiazol-2-yl]-1H-indol-7-yl}-N-methylthiophene-2-sulfonamide (16 mg, yield 8%, MS: 440 (MH$^+$)), as a white amorphous solid from a fraction eluted with ethyl acetate, respectively.

Example 359

2-(2-{7-[(difluoromethyl)(2-thienylsulfonyl)amino]-1H-indol-2-yl}-4,5-dihydro-1,3-thiazol-5-yl)acetamide

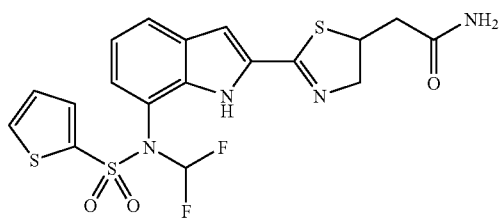

In the same manner as in Example 346, the title compound (50 mg, yield 22%) was obtained as a colorless solid from 2-(2-{7-[(2-thienylsulfonyl)amino]-1H-indol-2-yl}-4,5-dihydro-1,3-thiazol-5-yl)acetamide (200 mg) and difluoroiodomethane (102 mg). MS: 471 (MH$^+$).

Example 360 ethyl (2-{7-[(difluoromethyl)(2-thienylsulfonyl)amino]-1H-indol-2-yl}-4,5-dihydro-1,3-thiazol-5-yl)acetate

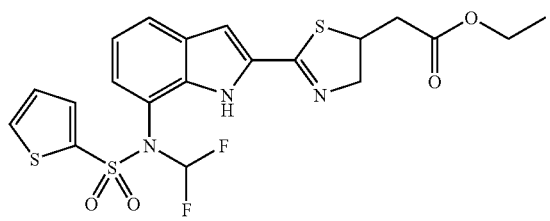

In the same manner as in Example 346, the title compound (150 mg, yield 27%) was obtained as a colorless amorphous solid from ethyl (2-{7-[(2-thienylsulfonyl)amino]-1H-indol-2-yl}-4,5-dihydro-1,3-thiazol-5-yl)acetate (500 mg) and difluoroiodomethane (238 mg). MS: 500 (MH$^+$).

Example 361

N-(difluoromethyl)-N-{2-[5-(2-hydroxyethyl)-4,5-dihydro-1,3-thiazol-2-yl]-1H-indol-7-yl}thiophene-2-sulfonamide

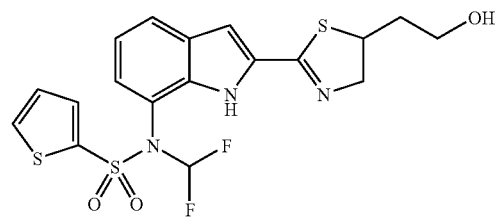

In the same manner as in Example 285, the title compound (120 mg, yield 88%) was obtained as a colorless solid from ethyl (2-{7-[(difluoromethyl)(2-thienylsulfonyl)amino]-1H-indol-2-yl}-4,5-dihydro-1,3-thiazol-5-yl)acetate (150 mg). MS: 458 (MH$^+$).

Example 362 ethyl (2-{7-[(2-fluoroethyl)(2-thienylsulfonyl)amino]-1H-indol-2-yl}-4,5-dihydro-1,3-thiazol-5-yl)acetate

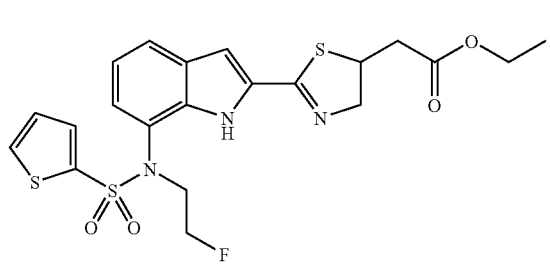

In the same manner as in Example 346, the title compound (400 mg, yield 61%) was obtained as a colorless amorphous solid from ethyl (2-{7-[(2-thienylsulfonyl)amino]-1H-indol-2-yl}-4,5-dihydro-1,3-thiazol-5-yl)acetate (600 mg) and 1-fluoro-2-iodoethane (280 mg). MS: 496 (MH$^+$).

Example 363

N-(2-fluoroethyl)-N-{2-[5-(2-hydroxyethyl)-4,5-dihydro-1,3-thiazol-2-yl]-1H-indol-7-yl}thiophene-2-sulfonamide

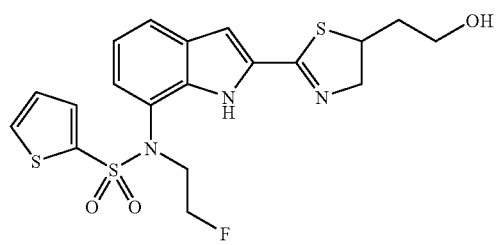

In the same manner as in Example 285, the title compound (90 mg, yield 66%) was obtained as a colorless solid from ethyl (2-{7-[(2-fluoroethyl)(2-thienylsulfonyl)amino]-1H-indol-2-yl}-4,5-dihydro-1,3-thiazol-5-yl)acetate (150 mg). MS: 454 (MH$^+$).

Example 364

(2-{7-[(2-fluoroethyl)(2-thienylsulfonyl)amino]-1H-indol-2-yl}-4,5-dihydro-1,3-thiazol-5-yl)acetic acid

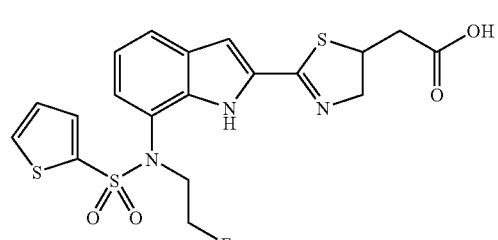

369

In the same manner as in Example 284, the title compound (140 mg, yield 98%) was obtained as a colorless solid from ethyl (2-{7-[(2-fluoroethyl)(2-thienylsulfonyl)amino]-1H-indol-2-yl}-4,5-dihydro-1,3-thiazol-5-yl)acetate (150 mg).
MS: 468 (MH$^+$).

Example 365

2-(2-{7-[(2-fluoroethyl)(2-thienylsulfonyl)amino]-1H-indol-2-yl}-4,5-dihydro-1,3-thiazol-5-yl)acetamide

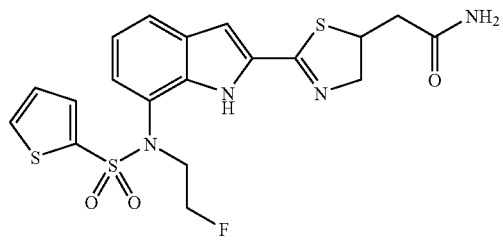

In the same manner as in Example 287, the title compound (100 mg, yield 72%) was obtained as a colorless solid from (2-{7-[(2-fluoroethyl)(2-thienylsulfonyl)amino]-1H-indol-2-yl}-4,5-dihydro-1,3-thiazol-5-yl)acetic acid (140 mg).

MS: 467 (MH$^+$).

Example 366 ethyl (2-{7-[ethyl(2-thienylsulfonyl)amino]-1H-indol-2-yl}-4,5-dihydro-1,3-thiazol-5-yl)acetate

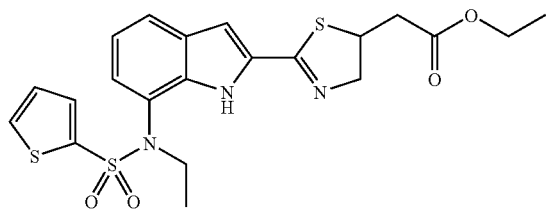

In the same manner as in Example 346, the title compound (300 mg, yield 69%) was obtained as a colorless amorphous solid from ethyl (2-{7-[(2-thienylsulfonyl)amino]-1H-indol-2-yl}-4,5-dihydro-1,3-thiazol-5-yl)acetate (410 mg) and iodoethane (75 μL). MS: 478 (MH$^+$).

370

Example 367

N-ethyl-N-{2-[5-(2-hydroxyethyl)-4,5-dihydro-1,3-thiazol-2-yl]-1H-indol-7-yl}thiophene-2-sulfonamide

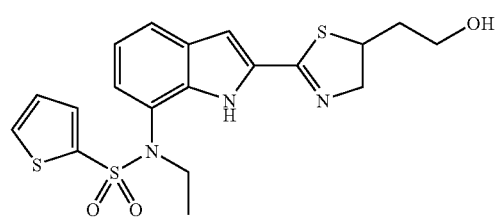

In the same manner as in Example 285, the title compound (70 mg, yield 77%) was obtained as a colorless amorphous solid from ethyl (2-{7-[ethyl(2-thienylsulfonyl)amino]-1H-indol-2-yl}-4,5-dihydro-1,3-thiazol-5-yl)acetate (100 mg). MS: 436 (MH$^+$).

Example 368

(2-{7-[ethyl(2-thienylsulfonyl)amino]-1H-indol-2-yl}-4,5-dihydro-1,3-thiazol-5-yl)acetic acid

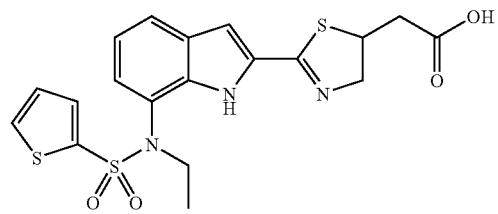

In the same manner as in Example 284, the title compound (140 mg, yield 89%) was obtained as a colorless solid from ethyl (2-{7-[ethyl(2-thienylsulfonyl)amino]-1H-indol-2-yl}-4,5-dihydro-1,3-thiazol-5-yl)acetate (167 mg). MS: 450 (MH$^+$).

Example 369

2-(2-{7-[ethyl(2-thienylsulfonyl)amino]-1H-indol-2-yl}-4,5-dihydro-1,3-thiazol-5-yl)acetamide

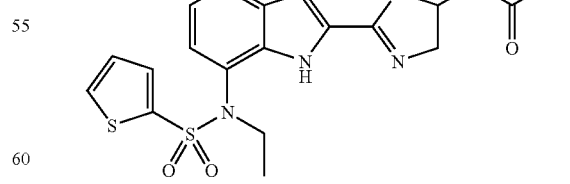

In the same manner as in Example 287, the title compound (70 mg, yield 58%) was obtained as a colorless solid from (2-{7-[ethyl(2-thienylsulfonyl)amino]-1H-indol-2-yl}-4,5-dihydro-1,3-thiazol-5-yl)acetic acid (120 mg). MS: 449 (MH$^+$).

Example 370 ethyl (2-{7-[(cyanomethyl)(2-thienylsulfonyl)amino]-1H-indol-2-yl}-4,5-dihydro-1,3-thiazol-5-yl)acetate

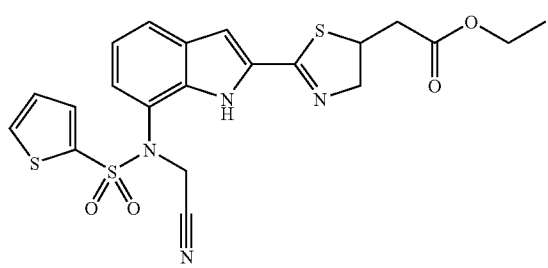

In the same manner as in Example 346, the title compound (400 mg, yield 62%) was obtained as a colorless solid from ethyl (2-{7-[(2-thienylsulfonyl)amino]-1H-indol-2-yl}-4,5-dihydro-1,3-thiazol-5-yl)acetate (600 mg) and iodoacetonitrile (245 mg). MS: 489 (MH$^+$).

Example 371 ethyl (2-{7-[(pyridin-2-ylsulfonyl)amino]-1H-indol-2-yl}-4,5-dihydro-1,3-thiazol-5-yl)acetate

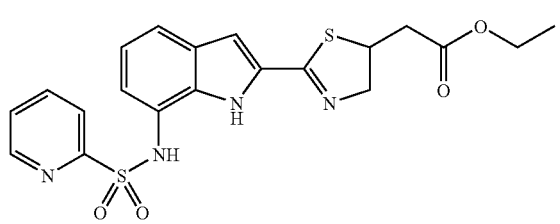

In the same manner as in Example 283, the title compound (920 mg, yield 21%) was obtained as a pale-yellow amorphous solid from 7-[(pyridin-2-ylsulfonyl)amino]-1H-indole-2-carbothioamide (3200 mg) and ethyl but-2-ynoate (2.6 mL). MS: 445 (MH$^+$).

Example 372

(2-{7-[(pyridin-2-ylsulfonyl)amino]-1H-indol-2-yl}-4,5-dihydro-1,3-thiazol-5-yl)acetic acid

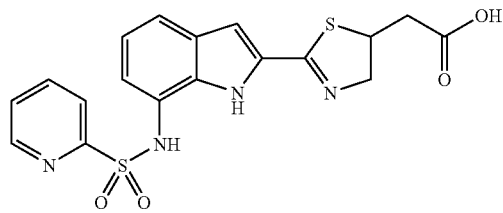

In the same manner as in Example 284, the title compound (650 mg, yield 76%) was obtained as a white solid from ethyl (2-{7-[(pyridin-2-ylsulfonyl)amino]-1H-indol-2-yl}-4,5-dihydro-1,3-thiazol-5-yl)acetate (920 mg). MS: 417 (MH$^+$).

Example 373

2-(2-{7-[(pyridin-2-ylsulfonyl)amino]-1H-indol-2-yl}-4,5-dihydro-1,3-thiazol-5-yl)acetamide

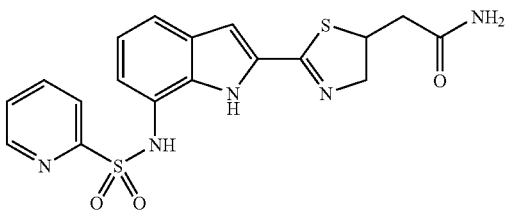

In the same manner as in Example 287, the title compound (310 mg, yield 50%) was obtained as a white solid from (2-{7-[(pyridin-2-ylsulfonyl)amino]-1H-indol-2-yl}-4,5-dihydro-1,3-thiazol-5-yl)acetic acid (620 mg). MS: 416 (MH$^+$).

Example 374

2-(2-{7-[(2-fluoroethyl)(pyridin-2-ylsulfonyl)amino]-1H-indol-2-yl}-4,5-dihydro-1,3-thiazol-5-yl)acetamide

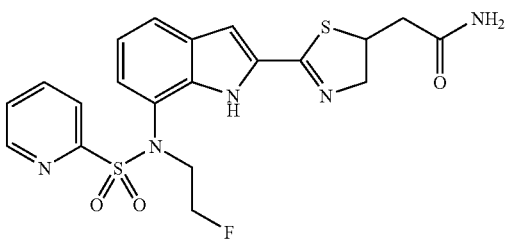

In the same manner as in Example 346, the title compound (100 mg, yield 90%) was obtained as a white solid from 2-(2-{7-[(pyridin-2-ylsulfonyl)amino]-1H-indol-2-yl}-4,5-dihydro-1,3-thiazol-5-yl)acetamide (100 mg) and 1-fluoro-2-iodoethane (55 mg). MS: 462 (MH$^+$).

Example 375 ethyl {[2-(2-{7-[methyl(2-thienylsulfonyl)amino]-1H-indol-2-yl}-4,5-dihydro-1,3-thiazol-5-yl)ethyl]thio}acetate

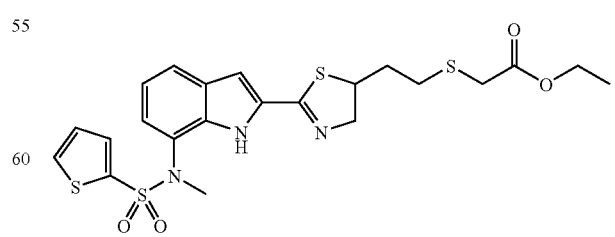

To a solution of N-{2-[5-(2-chloroethyl)-4,5-dihydro-1,3-thiazol-2-yl]-1H-indol-7-yl}-N-methylthiophene-2-sulfonamide (100 mg) in N,N-dimethylformamide (3 mL) were added potassium carbonate (65 mg) and ethyl mercaptoacetate (50 μL), and the mixture was stirred overnight at 50° C. Potassium carbonate (20 mg) was added to the reaction mixture, and the mixture was stirred at 50° C. for 3 hr, and cooled to room temperature. The reaction mixture was diluted with ethyl acetate, washed with water and saturated brine, dried (MgSO$_4$), and concentrated. The residue was subjected to silica gel column chromatography to give the title compound (60 mg, yield 50%) as a colorless amorphous solid from a fraction eluted with ethyl acetate-hexane (1:1, volume ratio). MS: 524 (MH$^+$).

Example 376

{[2-(2-{7-[methyl(2-thienylsulfonyl)amino]-1H-indol-2-yl}-4,5-dihydro-1,3-thiazol-5-yl)ethyl]thio}acetic acid

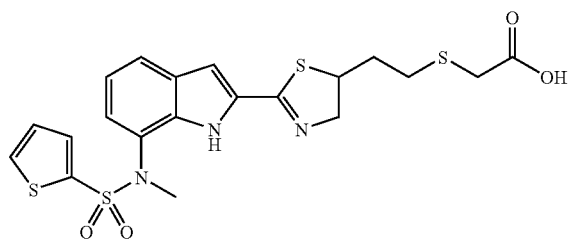

To a solution of ethyl {[2-(2-{7-[methyl(2-thienylsulfonyl)amino]-1H-indol-2-yl}-4,5-dihydro-1,3-thiazol-5-yl)ethyl]thio}acetate (60 mg) in tetrahydrofuran (2 mL) and methanol (2 mL) was added, under ice-cooling, a solution prepared by dissolving potassium hydroxide (purity 85%, 20 mg) in water (0.5 mL). The reaction mixture was allowed to warm to room temperature, and stirred for 1 hr. 1M Hydrochloric acid was added to the reaction mixture, and the mixture was extracted with ethyl acetate. The ethyl acetate layer was washed with water and saturated brine, dried (MgSO$_4$), and concentrated. The residue was recrystallized from a mixed solvent of ethyl acetate-hexane to give the title compound (35 mg, yield 61%) as white crystals. MS: 496 (MH$^+$).

Example 377

N-[2-(5-{2-[(2-hydroxyethyl)amino]ethyl}-4,5-dihydro-1,3-thiazol-2-yl)-1H-indol-7-yl]-N-methylthiophene-2-sulfonamide

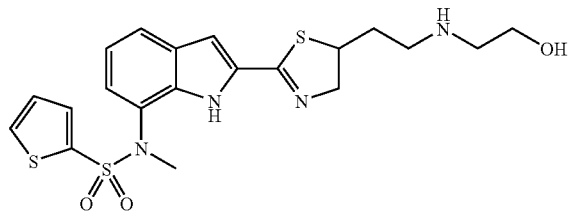

To a solution of N-methyl-N-{2-[5-(2-oxoethyl)-4,5-dihydro-1,3-thiazol-2-yl]-1H-indol-7-yl}thiophene-2-sulfonamide (300 mg) in methanol (5 mL) was added 2-aminoethanol (70 μL), and the mixture was stirred with heating under reflux for 4 hr. The reaction mixture was allowed to cool to room temperature, sodium borohydride (55 mg) was added, and the mixture was stirred for 30 min. The reaction mixture was diluted with ethyl acetate, washed with water and saturated brine, dried (MgSO$_4$), and concentrated. The residue was subjected to silica gel column chromatography to give the title compound (220 mg, yield 67%) as a colorless amorphous solid from a fraction eluted with ethyl acetate-methanol (10:1, volume ratio). MS: 465 (MH$^+$).

Example 378

N-methyl-N-(2-{5-[2-(3-oxomorpholino)ethyl]-4,5-dihydro-1,3-thiazol-2-yl}-1H-indol-7-yl)thiophene-2-sulfonamide

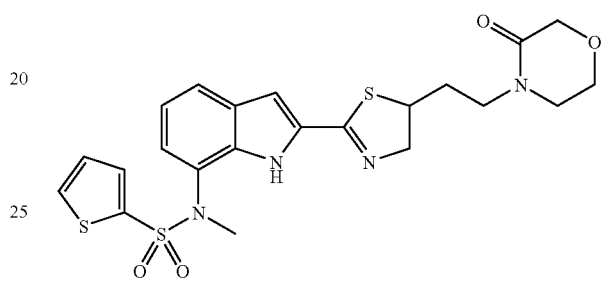

To a solution of N-[2-(5-{2-[(2-hydroxyethyl)amino]ethyl}-4,5-dihydro-1,3-thiazol-2-yl)-1H-indol-7-yl]-N-methylthiophene-2-sulfonamide (220 mg) in ethanol (2 mL) and water (1 mL) were added chloroacetyl chloride (95 μL) and 8M aqueous sodium hydroxide solution (310 μL), and the mixture was stirred at the inside temperature of 20° C. or less for 3 hr. 1M Hydrochloric acid was added to the reaction mixture, and the mixture was extracted with ethyl acetate. The ethyl acetate layer was washed with saturated aqueous sodium hydrogencarbonate and saturated brine, dried (MgSO$_4$), and concentrated. The residue was subjected to silica gel column chromatography to give the title compound (100 mg, yield 41%) as a colorless amorphous solid from a fraction eluted with ethyl acetate-methanol (10:1, volume ratio).

MS: 505 (MH$^+$).

Example 379

N-{5-(2-methoxyethoxy)-2-[(4R)-4-(morpholinomethyl)-4,5-dihydro-1,3-thiazol-2-yl]-1H-indol-7-yl}-N-methylpyridine-2-sulfonamide

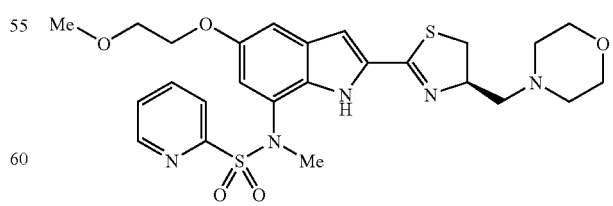

A solution of ((4R)-2-{5-(2-methoxyethoxy)-7-[methyl(pyridin-2-ylsulfonyl)amino]-1H-indol-2-yl}-4,5-dihydro-1,3-thiazol-4-yl)methyl methanesulfonate (0.1 g), morpholine (0.032 mL) and potassium carbonate (0.050 g) in N,N- dimethylformamide (5 mL) was stirred at room temperature for 18 hr, and the mixture was stirred at 50° C. for 6 hr. The same amount of morpholine (0.032 mL) and potassium carbonate (0.050 g) were added, and the mixture was stirred at 80° C. for 18 hr. The reaction mixture was concentrated, and the residue was extracted with ethyl acetate. The ethyl acetate layer was washed with 1N hydrochloric acid, saturated aqueous sodium hydrogencarbonate solution and saturated brine, dried (MgSO$_4$), and concentrated. The obtained residue was subjected to silica gel column chromatography, and eluted with hexane-ethyl acetate-methanol (4:1:0-0:10:1, volume ratio) to give the title compound (0.002 g, yield 2%) as a colorless amorphous solid.

$^1$H-NMR (CDCl$_3$) δ: 2.53-2.69 (4H, m), 2.75-2.89 (1H, m), 3.08-3.68 (4H, m), 3.27-3.37 (3H, m), 3.42-3.52 (3H, m), 3.72-3.84 (4H, m), 3.96-4.09 (1H, m), 4.06-4.21 (2H, m), 4.75-4.99 (1H, m), 6.84 (1H, d, J=2.1 Hz), 6.87 (1H, d, J=2.1 Hz), 7.06 (1H, d, J=2.3 Hz), 7.55-7.66 (1H, m), 7.95 (1H, td, J=7.6, 1.7 Hz), 7.98-8.06 (1H, m), 9.02-9.16 (1H, m), 11.57 (1H, brs)

Example 380

N-methyl-N-[2-[5-(morpholinomethyl)-4,5-dihydro-1,3-thiazol-2-yl]-5-(trifluoromethoxy)-1H-indol-7-yl]thiophene-2-sulfonamide

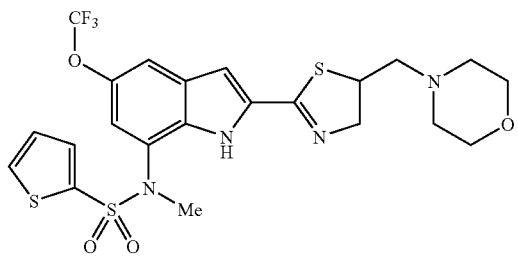

To a solution of triphenylphosphine oxide (670 mg) in dichloromethane (15 mL) was added trifluoromethanesulfonic anhydride (340 mg) under ice-cooling, and the mixture was stirred for 10 min. A solution of N-[2-(benzylthio)-3-morpholinopropyl]-7-[methyl(2-thienylsulfonyl)amino]-5-(trifluoromethoxy)-1H-indole-2-carboxamide (400 mg) and dimethylsulfide (40 mg) in dichloromethane (15 mL) was added dropwise to the reaction mixture under ice-cooling, and the mixture was stirred for 2 hr under ice-cooling. Water was added to the reaction mixture, and the mixture was extracted with ethyl acetate. The ethyl acetate layer was washed with saturated brine, dried (MgSO$_4$), and concentrated. The obtained residue was subjected to basic silica gel column chromatography, and eluted with hexane-ethyl acetate (4:1-2:1, volume ratio). The obtained compound was further purified by preparative HPLC to give the title compound (150 mg, yield 44%) as white crystals. The crystals were recrystallized from ethyl acetate-hexane to give colorless prism crystals. melting point 165-166° C.

Example 381 ethyl {2-[7-[methyl(2-thienylsulfonyl)amino]-5-(trifluoromethoxy)-1H-indol-2-yl]-4,5-dihydro-1,3-thiazol-5-yl}acetate

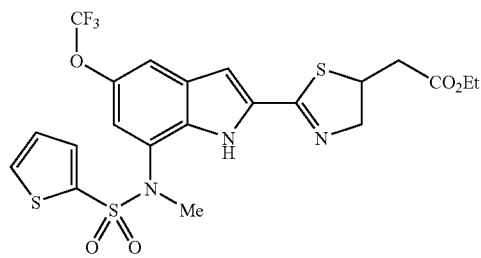

A mixture of 7-[methyl(2-thienylsulfonyl)amino]-5-(trifluoromethoxy)-1H-indole-2-carboxamide (1.15 g), Lawesson's reagent (1.09 g) and tetrahydrofuran (20 mL) was stirred at 50° C. for 30 min. The reaction mixture was concentrated, and the residue was washed with diisopropyl ether to give pale-yellow crystals. A mixture of the obtained crystals, ethyl but-2-ynoate (710 mg), tributylphosphine (510 mg), toluene (30 mL) and tetrahydrofuran (15 mL) was stirred at 50° C. for 2 hr. ethyl but-2-ynoate (710 mg) and tributylphosphine (510 mg) were added to the mixture, and the mixture was further stirred at room temperature for 2.5 days. The reaction mixture was concentrated, and the residue was subjected to silica gel column chromatography, and eluted with hexane-ethyl acetate (4:1-3:1, volume ratio). The obtained crystals were washed with hexane to give the title compound (600 mg, yield 41%) as pale-yellow crystals. melting point 93-94° C.

Example 382

{2-[7-[methyl(2-thienylsulfonyl)amino]-5-(trifluoromethoxy)-1H-indol-2-yl]-4,5-dihydro-1,3-thiazol-5-yl}acetic acid

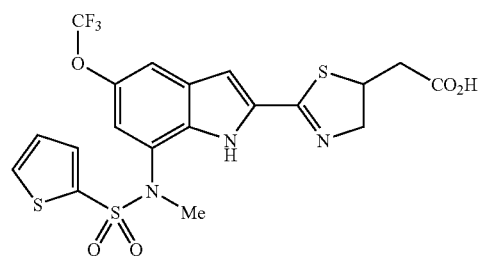

A mixture of ethyl {2-[7-[methyl(2-thienylsulfonyl)amino]-5-(trifluoromethoxy)-1H-indol-2-yl]-4,5-dihydro-1,3-thiazol-5-yl}acetate (300 mg), 1N aqueous sodium hydroxide solution (5 mL), tetrahydrofuran (5 mL) and ethanol (5 mL) was stirred at room temperature for 15 hr. The reaction mixture was acidified with aqueous citric acid solution, and extracted with ethyl acetate. The ethyl acetate layer was washed with saturated brine, dried (MgSO$_4$), and concentrated. The residue was crystallized from ethyl acetate-hexane to give the title compound (270 mg, yield 93%) as pale-yellow crystals. The crystals were purified by preparative HPLC, and recrystallized from ethyl acetate-hexane to give pale-yellow prism crystals. melting point 225-227° C.

Example 383

N-[2-[5-(2-hydroxyethyl)-4,5-dihydro-1,3-thiazol-2-yl]-5-(trifluoromethoxy)-1H-indol-7-yl]-N-methylthiophene-2-sulfonamide

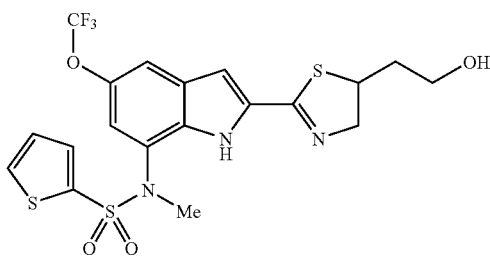

To a mixture of ethyl {2-[7-[methyl(2-thienylsulfonyl)amino]-5-(trifluoromethoxy)-1H-indol-2-yl]-4,5-dihydro-1,3-thiazol-5-yl}acetate (350 mg), tetrahydrofuran (15 mL) and methanol (3 mL) was added lithium borohydride (30 mg), and the mixture was stirred at room temperature for 2 hr. Lithium borohydride (15 mg) was added to the mixture, and the mixture was further stirred at room temperature for 2 hr. Water was added to the reaction mixture, and the mixture was extracted with ethyl acetate. The ethyl acetate layer was washed with saturated brine, dried (MgSO$_4$), and concentrated. The residue was subjected to silica gel column chromatography, and eluted with hexane-ethyl acetate (2:1-1:4, volume ratio) to give the title compound (110 mg, yield 34%) as colorless crystals. The crystals were recrystallized from ethyl acetate-hexane to give colorless prism crystals. melting point 152-153° C.

Example 384

2-{2-[7-[methyl(2-thienylsulfonyl)amino]-5-(trifluoromethoxy)-1H-indol-2-yl]-4,5-dihydro-1,3-thiazol-5-yl}acetamide

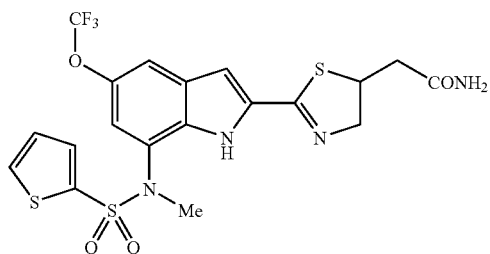

A mixture of {2-[7-[methyl(2-thienylsulfonyl)amino]-5-(trifluoromethoxy)-1H-indol-2-yl]-4,5-dihydro-1,3-thiazol-5-yl}acetic acid (210 mg), 1H-1,2,3-benzotriazol-1-ol-ammonia complex (90 mg), N-[3-(dimethylamino)propyl]-N'-ethylcarbodiimide hydrochloride (120 mg) and N,N-dimethylformamide (10 mL) was stirred at room temperature for 15 hr. 1H-1,2,3-Benzotriazol-1-ol-ammonia complex (150 mg) and N-[3-(dimethylamino)propyl]-N'-ethylcarbodiimide hydrochloride (190 mg) were added to the reaction mixture, and the mixture was further stirred at room temperature for 6 hr. Water was added to the reaction mixture, and the mixture was extracted with ethyl acetate. The ethyl acetate layer was washed successively with aqueous citric acid solution, saturated aqueous sodium hydrogencarbonate and saturated brine, dried (MgSO$_4$), and concentrated. The residue was purified by preparative HPLC to give the title compound (90 mg, yield 43%) as pale-yellow crystals. The crystals were recrystallized from ethyl acetate-hexane to give pale-yellow prism crystals. melting point 186-187° C. MS: 519 (MH$^+$).

Example 385 ethyl (2-{7-[methyl(pyridin-3-ylsulfonyl)amino]-1H-indol-2-yl}-4,5-dihydro-1,3-thiazol-5-yl)acetate

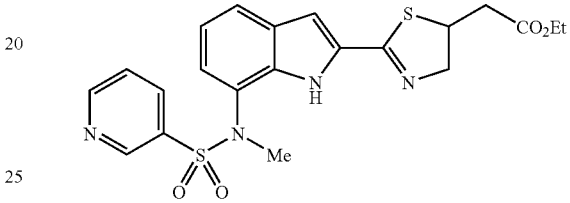

A mixture of 7-[methyl(pyridin-3-ylsulfonyl)amino]-1H-indole-2-carbothioamide (150 mg), ethyl but-2-ynoate (120 mg), tributylphosphine (90 mg), dichloromethane (20 mL) and tetrahydrofuran (40 mL) was stirred at room temperature for 15 hr, and the mixture was stirred at 50° C. for 3 hr. The reaction mixture was concentrated, and the residue was subjected to basic silica gel column chromatography, and eluted with hexane-ethyl acetate (4:1-1:4, volume ratio). The obtained crystals were further subjected to silica gel column chromatography, and eluted with hexane-ethyl acetate (4:1-1:4, volume ratio) to give pale-yellow crystals. The crystals were recrystallized from ethyl acetate-hexane to give the title compound (60 mg, yield 30%) as pale-yellow prism crystals. melting point 146-147° C.

Example 386

2-(2-{7-[methyl(pyridin-3-ylsulfonyl)amino]-1H-indol-2-yl}-4,5-dihydro-1,3-thiazol-5-yl)acetamide

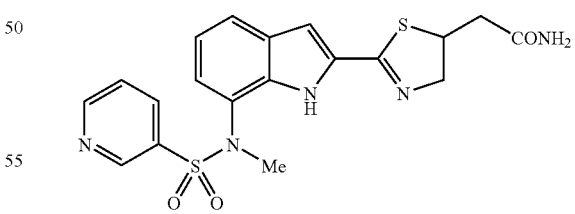

A mixture of ethyl (2-{7-[methyl(pyridin-3-ylsulfonyl)amino]-1H-indol-2-yl}-4,5-dihydro-1,3-thiazol-5-yl)acetate (330 mg), 1N aqueous sodium hydroxide solution (5 mL), tetrahydrofuran (5 mL) and ethanol (5 mL) was stirred at 50° C. for 30 min. The reaction mixture was acidified with aqueous citric acid solution, and extracted with ethyl acetate. The ethyl acetate layer was washed with saturated brine, dried (MgSO$_4$), and concentrated to give pale-yellow crystals. A mixture of the obtained crystals, 1H-1,2,3-benzotriazol-1-olammonia complex (1.10 g), N-[3-(dimethylamino)propyl]-N'-ethylcarbodiimide hydrochloride (1.38 g) and N,N-dimethylformamide (10 mL) was stirred at room temperature for 2.5 days. Water was added to the reaction mixture, and the mixture was extracted with ethyl acetate. The ethyl acetate layer was washed successively with saturated aqueous sodium hydrogencarbonate and saturated brine, dried (MgSO$_4$), and concentrated. The residue was subjected to silica gel column chromatography, and eluted with ethyl acetate-methanol (100:0-85:15, volume ratio) to give the title compound (130 mg, yield 42%) as colorless crystals. The crystals were recrystallized from ethyl acetate-hexane to give colorless prism crystals. melting point 185-186° C.

Example 387

2-{2-[7-[methyl(2-thienylsulfonyl)amino]-5-(trifluoromethoxy)-1H-indol-2-yl]-4,5-dihydro-1,3-thiazol-5-yl}acetamide

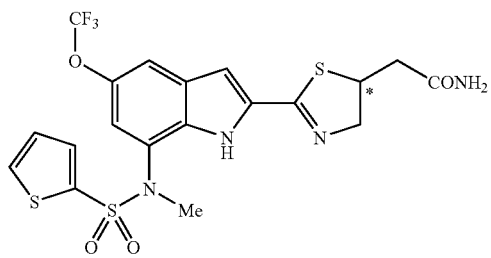

2-{2-[7-[Methyl(2-thienylsulfonyl)amino]-5-(trifluoromethoxy)-1H-indol-2-yl]-4,5-dihydro-1,3-thiazol-5-yl}acetamide (140 mg) was dissolved in hexane-ethanol (850:150, volume ratio, 700 mL). This solution was subjected to HPLC using CHIRALPAK AD (50 mmID×500 mL, manufactured by DAICEL CHEMICAL INDUSTRIES, LTD.), and eluted with hexane-ethanol (850:150, volume ratio) as a mobile phase at 35° C. at flow rate of 75 mL/min. A fraction with the retention time of 1 hr and 13 min was separated, and concentrated. The obtained solid was crystallized from ethyl acetate-hexane to give the title compound (62 mg) as colorless prism crystals. melting point 205-206° C.

Example 388

{2-[7-[(2-thienylsulfonyl)amino]-5-(trifluoromethoxy)-1H-indol-2-yl]-4,5-dihydro-1,3-thiazol-5-yl}acetic acid

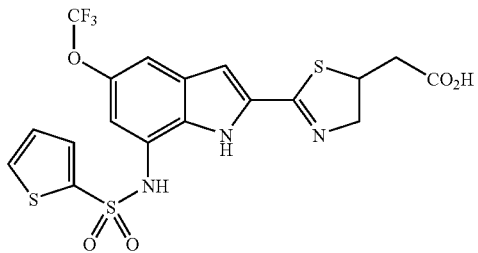

A mixture of ethyl {2-[7-[(2-thienylsulfonyl)amino]-5-(trifluoromethoxy)-1H-indol-2-yl]-4,5-dihydro-1,3-thiazol-5-yl}acetate (780 mg), 1N aqueous sodium hydroxide solution (5 mL), tetrahydrofuran (5 mL) and ethanol (5 mL) was stirred at 50° C. for 30 min. The reaction mixture was acidified with aqueous citric acid solution, and extracted with ethyl acetate. The ethyl acetate layer was washed with saturated brine, dried (MgSO$_4$), and concentrated. The residue was crystallized from ethyl acetate-diisopropyl ether to give the title compound (490 mg, yield 64%) as brown crystals. The crystals were recrystallized from ethyl acetate-hexane to give brown prism crystals. melting point 247-248° C. (decomposition).

Example 389

2-{2-[7-[(2-thienylsulfonyl)amino]-5-(trifluoromethoxy)-1H-indol-2-yl]-4,5-dihydro-1,3-thiazol-5-yl}acetamide

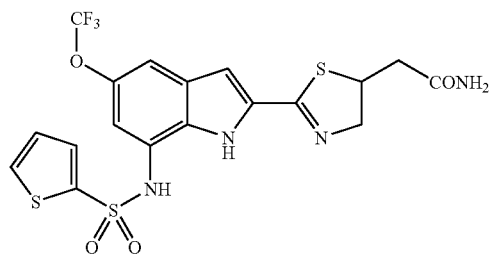

A mixture of {2-[7-[(2-thienylsulfonyl)amino]-5-(trifluoromethoxy)-1H-indol-2-yl]-4,5-dihydro-1,3-thiazol-5-yl}acetic acid (410 mg), 1H-1,2,3-benzotriazol-1-ol-ammonia complex (240 mg), N-[3-(dimethylamino)propyl]-N'-ethylcarbodiimide hydrochloride (310 mg) and N,N-dimethylformamide (5 mL) was stirred at room temperature for 15 hr. Water was added to the reaction mixture, and the mixture was extracted with ethyl acetate. The ethyl acetate layer was washed successively with 1N hydrochloric acid, saturated aqueous sodium hydrogencarbonate and saturated brine, dried (MgSO$_4$), and concentrated. The residue was subjected to silica gel column chromatography, and eluted with ethyl acetate-methanol (100:0-90:10, volume ratio), and the obtained solid was washed with hexane to give the title compound (260 mg, yield 63%) as brown crystals. The crystals were recrystallized from acetone-hexane to give pale-yellow prism crystals. melting point 239-240° C.

Example 390

(2-{5-(2-methoxyethoxy)-7-[methyl(2-thienylsulfonyl)amino]-1H-indol-2-yl}-4,5-dihydro-1,3-thiazol-5-yl)acetic acid

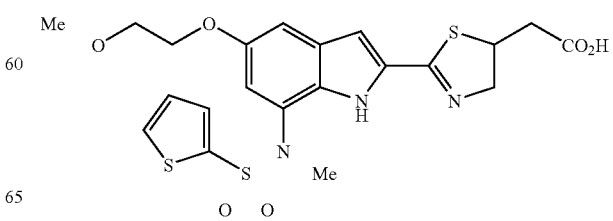

A mixture of ethyl (2-{5-(2-methoxyethoxy)-7-[methyl(2-thienylsulfonyl)amino]-1H-indol-2-yl}-4,5-dihydro-1,3-thiazol-5-yl)acetate (300 mg), 1N aqueous sodium hydroxide solution (2 mL), tetrahydrofuran (2 mL) and ethanol (2 mL) was stirred at room temperature for 15 hr. The reaction mixture was acidified with aqueous citric acid solution, and extracted with ethyl acetate. The ethyl acetate layer was washed with saturated brine, dried (MgSO$_4$), and concentrated to give the title compound (280 mg, yield 97%) as yellow crystals. The crystals were recrystallized from ethyl acetate-hexane to give yellow prism crystals. melting point 113-114° C.

Example 391

N-[2-[5-(2-hydroxyethyl)-4,5-dihydro-1,3-thiazol-2-yl]-5-(2-methoxyethoxy)-1H-indol-7-yl]-N-methylthiophene-2-sulfonamide

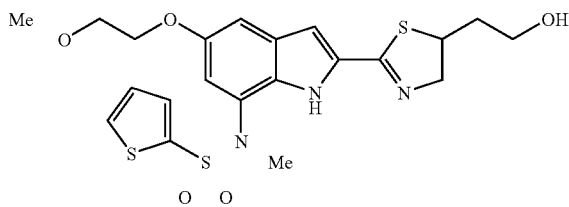

To a mixture of ethyl (2-{5-(2-methoxyethoxy)-7-[methyl(2-thienylsulfonyl)amino]-1H-indol-2-yl}-4,5-dihydro-1,3-thiazol-5-yl)acetate (200 mg), tetrahydrofuran (5 mL) and methanol (1 mL) was added lithium borohydride (16 mg), and the mixture was stirred at room temperature for 1 hr. Lithium borohydride (16 mg) was added to the mixture, and the mixture was further stirred at room temperature for 1 hr. Lithium borohydride (16 mg) was added to the mixture, and the mixture was further stirred at room temperature for 1 hr. Water was added to the reaction mixture, and the mixture was extracted with ethyl acetate. The ethyl acetate layer was washed with saturated brine, dried (MgSO$_4$), and concentrated. The residue was subjected to silica gel column chromatography, and eluted with hexane-ethyl acetate (1:1-1:9, volume ratio) to give yellow crystals. The crystals were recrystallized from ethyl acetate-hexane to give the title compound (100 mg, yield 56%) as a pale-yellow powder. melting point 122-123° C.

Example 392

2-(2-{5-(2-methoxyethoxy)-7-[methyl(2-thienylsulfonyl)amino]-1H-indol-2-yl}-4,5-dihydro-1,3-thiazol-5-yl)acetamide

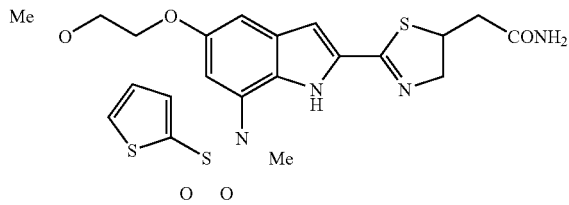

A mixture of (2-{5-(2-methoxyethoxy)-7-[methyl(2-thienylsulfonyl)amino]-1H-indol-2-yl}-4,5-dihydro-1,3-thiazol-5-yl)acetic acid (220 mg), 1H-1,2,3-benzotriazol-1-ol-ammonia complex (100 mg), N-[3-(dimethylamino)propyl]-N'-ethylcarbodiimide hydrochloride (120 mg) and N,N-dimethylformamide (3 mL) was stirred at room temperature for 15 hr. Water was added to the reaction mixture, and the mixture was extracted with ethyl acetate. The ethyl acetate layer was washed successively with aqueous citric acid solution, saturated aqueous sodium hydrogencarbonate and saturated brine, dried (MgSO$_4$), and concentrated. The residue was subjected to silica gel column chromatography, and eluted with ethyl acetate-methanol (97:3-90:10, volume ratio) to give pale-yellow crystals. The crystals were recrystallized from acetone-hexane to give the title compound (110 mg, yield 50%) as pale-yellow prism crystals. melting point 189-190° C.

Example 393

N-(5-(2-methoxyethoxy)-2-{5-[(1-oxidothiomorpholino)methyl]-4,5-dihydro-1,3-thiazol-2-yl}-1H-indol-7-yl)-N-methylpyridine-2-sulfonamide

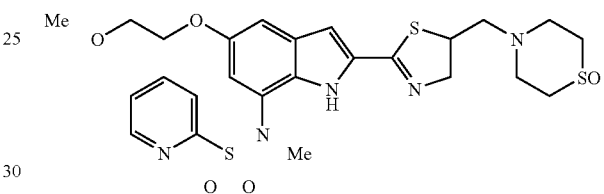

A mixture of trifluoromethanesulfonic anhydride (1.44 g), triphenylphosphine oxide (1.42 g) and dichloromethane (100 mL) was stirred at 0° C. for 10 min. A solution of N-[2-(benzylthio)-3,3-dimethoxypropyl]-5-(2-methoxyethoxy)-7-[methyl(pyridin-2-ylsulfonyl)amino]-1H-indole-2-carboxamide (2.92 g) and thioanisole (1.14 g) in dichloromethane (50 mL) was added dropwise to the reaction mixture under ice-cooling, and the mixture was stirred for 10 min under ice-cooling. Water was added to the reaction mixture, and the organic layer was separated. The aqueous layer was extracted with ethyl acetate, and the organic layers were combined, washed with saturated brine, dried (MgSO$_4$), and concentrated. The obtained residue was subjected to basic silica gel column chromatography, and eluted with hexane-ethyl acetate (2:1-1:4, volume ratio) to give a yellow oil. The obtained oil was crystallized from ethyl acetate-diisopropyl ether, and recrystallized from ethyl acetate-diisopropyl ether to give colorless crystals (1.03 g). To a mixture of the obtained crystals (400 mg), trifluoroacetic acid (5 mL) and water (15 mL) was added concentrated sulfuric acid (5 mL) at room temperature, and the mixture was stirred at 60° C. for 4 hr. Water was added to the reaction mixture, and trifluoroacetic acid was evaporated under reduced pressure. The residue was ice-cooled, and 8N aqueous sodium hydroxide solution (20 mL) was added. The mixture was basified with saturated aqueous sodium hydrogencarbonate, and extracted with ethyl acetate. The ethyl acetate layer was washed with saturated brine, dried (MgSO$_4$), and concentrated. The residue was dissolved in tetrahydrofuran (10 mL), and triethylamine (120 mg) and thiomorpholine 1-oxide hydrochloride (150 mg) were added to the obtained solution, and the mixture was stirred at room temperature for 15 min. Sodium triacetoxyborohydride (320 mg) was added to the reaction mixture at room temperature, and the mixture was stirred at room temperature for 2 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with ethyl acetate-methanol (100:0-70:30, volume ratio), and the obtained compound was further purified by preparative HPLC to give colorless crystals. The crystals were recrystallized from acetone-hexane to give the title compound (110 mg, yield 11%) as colorless prism crystals. melting point 182-183° C. MS: 578 (MH$^+$).

Example 394

(2-{5-(2-methoxyethoxy)-7-[methyl(pyridin-2-ylsulfonyl)amino]-1H-indol-2-yl}-4,5-dihydro-1,3-thiazol-5-yl)acetic acid

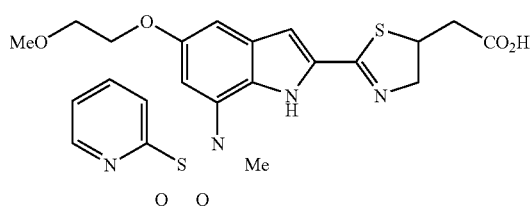

A mixture of ethyl (2-{5-(2-methoxyethoxy)-7-[methyl(pyridin-2-ylsulfonyl)amino]-1H-indol-2-yl}-4,5-dihydro-1,3-thiazol-5-yl)acetate (960 mg), 1N aqueous sodium hydroxide solution (5 mL), tetrahydrofuran (5 mL) and ethanol (5 mL) was stirred for 50° C. for 1 hr. 1N Hydrochloric acid (5 mL) was added to the reaction mixture, and the mixture was extracted with ethyl acetate. The ethyl acetate layer was washed with saturated brine, dried (MgSO$_4$), and concentrated to give the title compound (800 mg, yield 88%) as a yellow amorphous solid. The solid was crystallized from ethyl acetate-hexane, and recrystallized from ethyl acetate-hexane to give pale-yellow powder. melting point 107-109° C.

Example 395

2-(2-{5-(2-methoxyethoxy)-7-[methyl(pyridin-2-ylsulfonyl)amino]-1H-indol-2-yl}-4,5-dihydro-1,3-thiazol-5-yl)acetamide

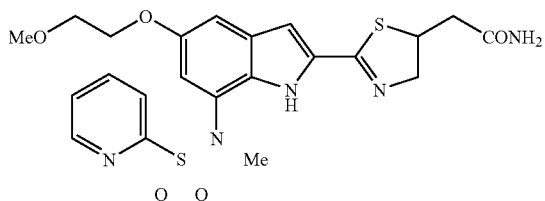

A mixture of (2-{5-(2-methoxyethoxy)-7-[methyl(pyridin-2-ylsulfonyl)amino]-1H-indol-2-yl}-4,5-dihydro-1,3-thiazol-5-yl)acetic acid (200 mg), 1H-1,2,3-benzotriazol-1-ol-ammonia complex (90 mg), N-[3-(dimethylamino)propyl]-N'-ethylcarbodiimide hydrochloride (120 mg) and N,N-dimethylformamide (5 mL) was stirred at room temperature for 15 hr. Water was added to the reaction mixture, and the mixture was extracted with ethyl acetate. The ethyl acetate layer was washed successively with saturated aqueous sodium hydrogencarbonate and saturated brine, dried (MgSO$_4$), and concentrated. The residue was subjected to silica gel column chromatography, and eluted with ethyl acetate-methanol (100:0-90:10, volume ratio) to give colorless crystals. The crystals were recrystallized from acetone-hexane to give the title compound (80 mg, yield 55%) as a colorless powder. melting point 100-102° C.

Example 396

N-(2-hydroxyethyl)-2-(2-{5-(2-methoxyethoxy)-7-[methyl(pyridin-2-ylsulfonyl)amino]-1H-indol-2-yl}-4,5-dihydro-1,3-thiazol-5-yl)-N-methylacetamide

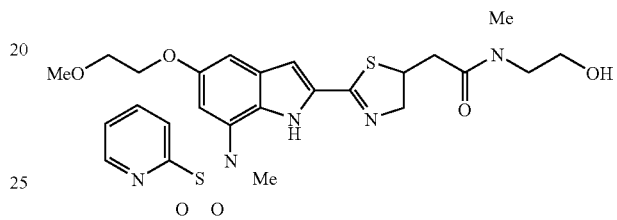

A mixture of (2-{5-(2-methoxyethoxy)-7-[methyl(pyridin-2-ylsulfonyl)amino]-1H-indol-2-yl}-4,5-dihydro-1,3-thiazol-5-yl)acetic acid (250 mg), 1H-1,2,3-benzotriazol-1-ol (100 mg), N-[3-(dimethylamino)propyl]-N'-ethylcarbodiimide hydrochloride (140 mg), 2-(methylamino)ethanol (60 mg) and N,N-dimethylformamide (5 mL) was stirred at room temperature for 15 hr. Water was added to the reaction mixture, and the mixture was extracted with ethyl acetate. The ethyl acetate layer was washed successively with saturated aqueous sodium hydrogencarbonate and saturated brine, dried (MgSO$_4$), and concentrated. The residue was subjected to silica gel column chromatography, and eluted with ethyl acetate-methanol (100:0-95:5, volume ratio) to give colorless crystals. The crystals were recrystallized from ethyl acetate-hexane to give the title compound (140 mg, yield 50%) as colorless crystals.

melting point 94-96° C.

Example 397

N-(5-(2-methoxyethoxy)-2-{5-[(1-oxidothiomorpholino)methyl]-4,5-dihydro-1,3-thiazol-2-yl}-1H-indol-7-yl)-N-methylpyridine-2-sulfonamide

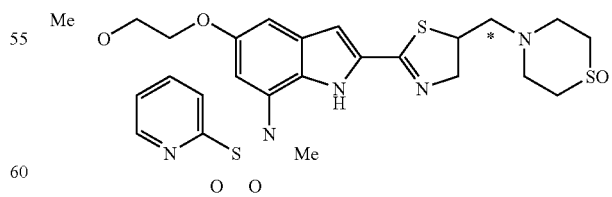

N-(5-(2-Methoxyethoxy)-2-{5-[(1-oxidothiomorpholino)methyl]-4,5-dihydro-1,3-thiazol-2-yl}-1H-indol-7-yl)-N-methylpyridine-2-sulfonamide (20 mg) was dissolved in hexane-ethanol (500:500, volume ratio, 200 mL). This solution was subjected to HPLC using CHIRALCEL OD (50 mmID×

Example 398

N-(5-(2-methoxyethoxy)-2-{5-[(1-oxidothiomorpholino)methyl]-4,5-dihydro-1,3-thiazol-2-yl}-1H-indol-7-yl)-N-methylpyridine-2-sulfonamide

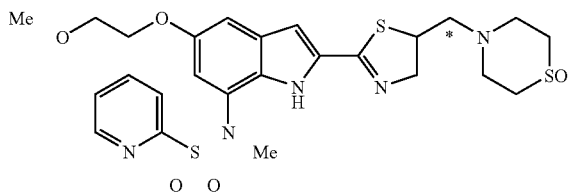

N-(5-(2-methoxyethoxy)-2-{5-[(1-oxidothiomorpholino)methyl]-4,5-dihydro-1,3-thiazol-2-yl}-1H-indol-7-yl)-N-methylpyridine-2-sulfonamide (20 mg) was dissolved in hexane-ethanol (500:500, volume ratio, 200 mL). This solution was subjected to HPLC using CHIRALCEL OD (50 mmID× 500 mL, manufactured by DAICEL CHEMICAL INDUSTRIES, LTD.), and eluted with hexane-ethanol (500:500, volume ratio) as a mobile phase at 30° C. at flow rate of 60 mL/min. A fraction with the retention time of 60.9 min was separated, and concentrated. The obtained crystals were dissolved in methanol, the insoluble substance was removed by filtration, and the filtrate was concentrated to give the title compound (11 mg) as colorless crystals. MS: 578 (MH$^+$).

Example 399

N-[2-{5-[2-(3-hydroxyazetidin-1-yl)-2-oxoethyl]-4,5-dihydro-1,3-thiazol-2-yl}-5-(2-methoxyethoxy)-1H-indol-7-yl]-N-methylpyridine-2-sulfonamide

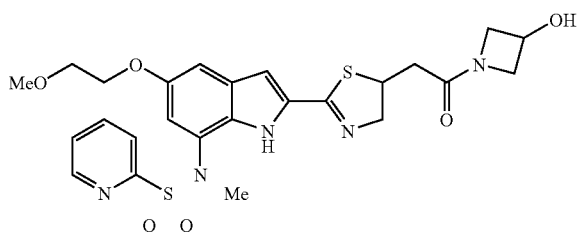

A mixture of azetidin-3-ol hydrochloride (80 mg), triethylamine (75 mg) and N,N-dimethylformamide (5 mL) was stirred at room temperature for 15 min. (2-{5-(2-Methoxyethoxy)-7-[methyl(pyridin-2-ylsulfonyl)amino]-1H-indol-2-yl}-4,5-dihydro-1,3-thiazol-5-yl)acetic acid (250 mg), 1H-1,2,3-benzotriazol-1-ol (100 mg) and N-[3-(dimethylamino)propyl]-N'-ethylcarbodiimide hydrochloride (140 mg) were added to the reaction mixture, and the mixture was stirred at room temperature for 15 hr. Water was added to the reaction mixture, and the mixture was extracted with ethyl acetate. The ethyl acetate layer was washed successively with saturated aqueous sodium hydrogencarbonate and saturated brine, dried (MgSO$_4$), and concentrated. The residue was subjected to silica gel column chromatography, and eluted with ethyl acetate-methanol (100:0-95:5, volume ratio) to give the title compound (80 mg, yield 29%) as a colorless amorphous solid.

$^1$H-NMR (CDCl$_3$) δ: 2.46 (3H, d, J=6.06 Hz), 3.29 (3H, s), 3.46 (3H, s), 3.75 (2H, t, J=4.16 Hz), 3.80-4.04 (2H, m), 4.06-4.16 (2H, m), 4.18-4.47 (5H, m), 4.54-4.74 (1H, m), 6.84 (1H, dd, J=5.49, 2.08 Hz), 6.91 (1H, dd, J=3.98, 2.08 Hz), 7.06 (1H, d, J=1.89 Hz), 7.61 (1H, t, J=6.06 Hz), 7.95 (1H, t, J=7.76 Hz), 8.01-8.14 (1H, m), 8.98-9.15 (1H, m), 11.71-11.97 (1H, m).

Example 400

N-methyl-N-{2-[5-(1H-1,2,4-triazol-1-ylmethyl)-4,5-dihydro-1,3-thiazol-2-yl]-1H-indol-7-yl}pyridine-2-sulfonamide and N-methyl-N-{2-[5-(4H-1,2,4-triazol-4-ylmethyl)-4,5-dihydro-1,3-thiazol-2-yl]-1H-indol-7-yl}pyridine-2-sulfonamide

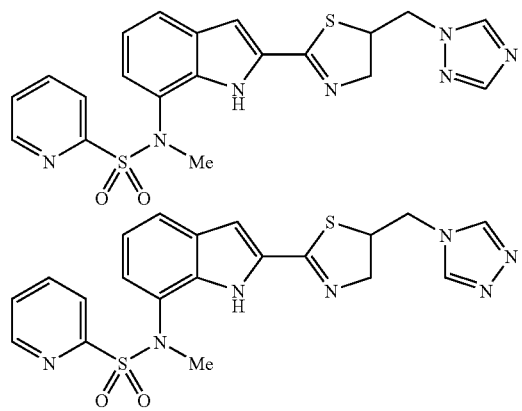

A mixture of (2-{7-[methyl(pyridin-2-ylsulfonyl)amino]-1H-indol-2-yl}-4,5-dihydro-1,3-thiazol-5-yl)methyl methanesulfonate (1.0 g), 1H-1,2,4-triazole (290 mg), potassium carbonate (580 mg) and N,N-dimethylformamide (10 mL) was stirred at 60° C. for 15 hr. Water was added to the reaction mixture, and the mixture was extracted with ethyl acetate. The ethyl acetate layer was washed with saturated brine, dried (MgSO$_4$), and concentrated. The residue was subjected to basic silica gel column chromatography, and eluted with hexane-ethyl acetate-methanol (50:50:0-0:100:0-0:95:5, volume ratio) to give N-methyl-N-{2-[5-(1H-1,2,4-triazol-1-ylmethyl)-4,5-dihydro-1,3-thiazol-2-yl]-1H-indol-7-yl}pyridine-2-sulfonamide (560 mg, yield 59%) as a pale-yellow amorphous solid.

$^1$H-NMR (CDCl$_3$) δ: 3.32 (3H, s), 4.20-4.62 (5H, m), 6.95 (1H, d, J=2.27 Hz), 7.09 (1H, t, J=7.76 Hz), 7.19 (1H, d, J=7.57 Hz), 7.54-7.68 (2H, m), 7.90-7.99 (1H, m), 8.01 (1H, s), 8.06-8.12 (1H, m), 8.13 (1H, s), 9.07 (1H, d, J=3.79 Hz), 12.13 (1H, brs).

N-Methyl-N-{2-[5-(4H-1,2,4-triazol-4-ylmethyl)-4,5-dihydro-1,3-thiazol-2-yl]-1H-indol-7-yl}pyridine-2-sulfonamide (10 mg, yield 1%) was obtained as brown crystals from the fraction eluted subsequently.

$^1$H-NMR (CDCl$_3$) δ: 3.32 (3H, s), 4.12-4.25 (3H, m), 4.30-4.53 (2H, m), 6.96 (1H, d, J=2.27 Hz), 7.09 (1H, t, J=7.57 Hz), 7.17-7.22 (1H, m), 7.59-7.68 (2H, m), 7.94-8.03 (1H, m), 8.06-8.13 (1H, m), 8.25 (2H, s), 9.04 (1H, d, J=3.79 Hz), 12.13 (1H, brs).

Example 401

N-[2-{5-[(1,1-dioxidothiomorpholino)methyl]-4,5-dihydro-1,3-thiazol-2-yl}-5-(2-methoxyethoxy)-1H-indol-7-yl]pyridine-2-sulfonamide

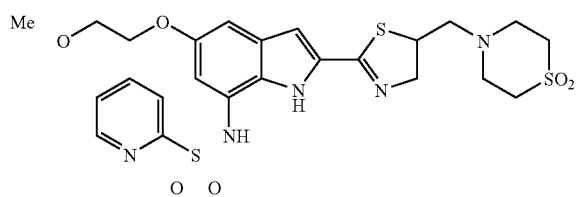

A mixture of trifluoromethanesulfonic anhydride (100 mg), triphenylphosphine oxide (95 mg) and dichloromethane (5 mL) was stirred at 0° C. for 10 min. A solution of N-[2-(benzylthio)-3-(1,1-dioxidothiomorpholino)propyl]-5-(2-methoxyethoxy)-7-[(pyridin-2-ylsulfonyl)amino]-1H-indole-2-carboxamide (210 mg) and thioanisole (80 mg) in dichloromethane (40 mL) was added dropwise to the reaction mixture under ice-cooling, and the mixture was stirred for 2 hr under ice-cooling. The reaction mixture was added dropwise to a mixture of trifluoromethanesulfonic anhydride (100 mg), triphenylphosphine oxide (95 mg) and dichloromethane (2 mL) under ice-cooling, and the mixture was stirred at room temperature for 15 hr. Water was added to the reaction mixture, and the mixture was extracted with ethyl acetate. The ethyl acetate layer was washed with saturated brine, dried (MgSO$_4$), and concentrated. The residue was subjected to silica gel column chromatography, and eluted with hexane-ethyl acetate (2:3-5:95, volume ratio) to give the title compound (80 mg, yield 44%) as colorless crystals. The crystals were recrystallized from acetone-hexane to give colorless prism crystals. melting point 218-219° C.

Example 402

N-(5-(2-methoxyethoxy)-2-{5-[(1-oxidothiomorpholino)methyl]-4,5-dihydro-1,3-thiazol-2-yl}-1H-indol-7-yl)pyridine-2-sulfonamide

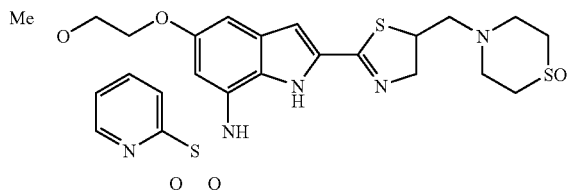

To a solution of triphenylphosphine oxide (470 mg) in dichloromethane (3 mL) was added trifluoromethanesulfonic anhydride (480 mg) under ice-cooling, and the mixture was stirred for 30 min. A solution of N-[2-(benzylthio)-3-thiomorpholinopropyl]-5-(2-methoxyethoxy)-7-[(pyridin-2-ylsulfonyl)amino]-1H-indole-2-carboxamide (570 mg) and thioanisole (210 mg) in dichloromethane (20 mL) was added dropwise to the reaction mixture under ice-cooling, and the mixture was stirred for 3 hr under ice-cooling. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with hexane-ethyl acetate (1:1-1:9, volume ratio) to give colorless crystals. To a mixture of the obtained crystals, ethanol (20 mL), water (10 mL) and tetrahydrofuran (10 mL) was added OXONE (registered trade mark, 43 mg) at room temperature, and the mixture was stirred at room temperature for 2 hr. Aqueous sodium sulfite solution was added to the reaction mixture, the mixture was stirred for 30 min, and the organic solvent was evaporated under reduced pressure. The residue was extracted with a mixed solvent of ethyl acetate-tetrahydrofuran. The organic layer was washed with saturated brine, dried (MgSO$_4$), and concentrated. The residue was subjected to silica gel column chromatography, and eluted with ethyl acetate-methanol (100:0-90:10, volume ratio) to give colorless crystals. The obtained crystals was further purified by preparative HPLC, and recrystallized from acetone-methanol to give the title compound (30 mg, yield 6.1%) as colorless prism crystals. melting point 235-236° C.

Example 403

N,N-dimethyl-2-{7-[methyl(2-thienylsulfonyl)amino]-1H-indol-2-yl}-1-thia-3,8-diazaspiro[4.5]dec-2-ene-8-carboxamide

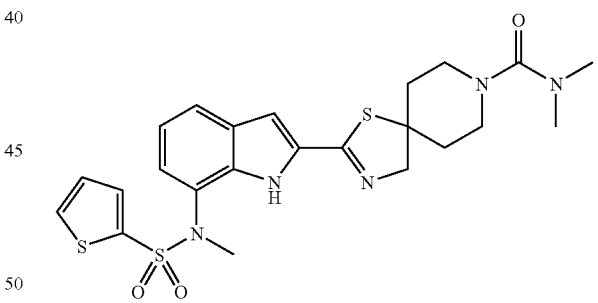

To a solution of N-methyl-N-[2-(1-thia-3,8-diazaspiro [4.5]dec-2-en-2-yl)-1H-indol-7-yl]thiophene-2-sulfonamide (82 mg) and dimethylcarbamoyl chloride (100 µL) in tetrahydrofuran (3 mL) was added triethylamine (100 µL), and the mixture was stirred at room temperature for 30 min. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (43 mg, yield 46%) as white crystals from a fraction eluted with ethyl acetate. melting point 245° C.

Example 404

N-methyl-N-(2-{8-[(1-methyl-1H-imidazol-2-yl)methyl]-1-thia-3,8-diazaspiro[4.5]dec-2-en-2-yl}-1H-indol-7-yl)thiophene-2-sulfonamide

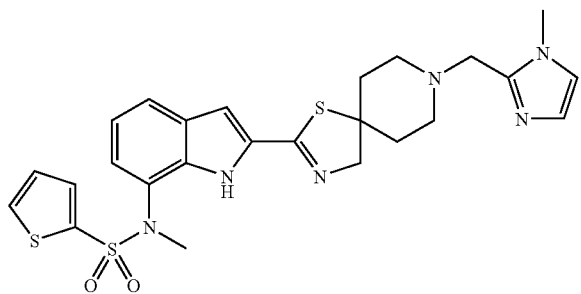

To a solution of N-methyl-N-[2-(1-thia-3,8-diazaspiro[4.5]dec-2-en-2-yl)-1H-indol-7-yl]thiophene-2-sulfonamide (100 mg) and 1-methyl-1H-imidazole-2-carbaldehyde (33 mg) in tetrahydrofuran (3 mL) was added sodium triacetoxyborohydride (125 mg), and the mixture was stirred at room temperature for 18 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (14 mg, yield 12%) as white crystals from a fraction eluted with ethyl acetate. melting point 103° C.

Example 405

N-methyl-N-{2-[8-(methylsulfonyl)-1-thia-3,8-diazaspiro[4.5]dec-2-en-2-yl]-1H-indol-7-yl}thiophene-2-sulfonamide

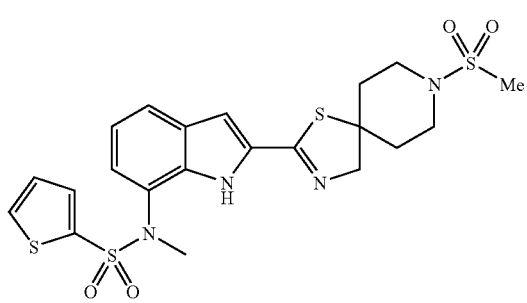

To a solution of N-methyl-N-[2-(1-thia-3,8-diazaspiro[4.5]dec-2-en-2-yl)-1H-indol-7-yl]thiophene-2-sulfonamide (82 mg) and methanesulfonyl chloride (100 µL) in tetrahydrofuran (3 mL) was added triethylamine (100 µL), and the mixture was stirred at room temperature for 30 min. The reaction mixture was concentrated, and water was added. The precipitated crystals were collected by filtration, and washed with water. The obtained crystals were recrystallized from tetrahydrofuran to give the title compound (42 mg, yield 36%) as white crystals. melting point 251° C.

Example 406

N-[2-(8-ethyl-1-thia-3,8-diazaspiro[4.5]dec-2-en-2-yl)-1H-indol-7-yl]-N-methylthiophene-2-sulfonamide

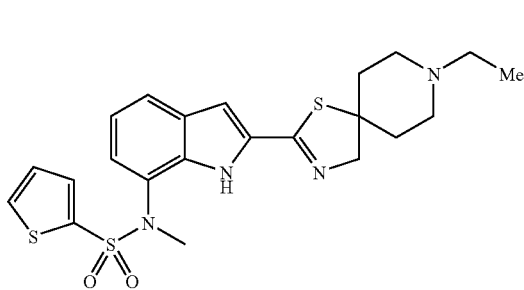

To a solution of N-methyl-N-[2-(1-thia-3,8-diazaspiro[4.5]dec-2-en-2-yl)-1H-indol-7-yl]thiophene-2-sulfonamide (100 mg) and acetaldehyde (90%, 100 µL) in tetrahydrofuran (3 mL) was added sodium triacetoxyborohydride (125 mg), and the mixture was stirred at room temperature for 30 min. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (83 mg, yield 80%) as white crystals from a fraction eluted with ethyl acetate. melting point 215° C.

Example 407

N-{2-[8-(cyanomethyl)-1-thia-3,8-diazaspiro[4.5]dec-2-en-2-yl]-1H-indol-7-yl}-N-methylthiophene-2-sulfonamide

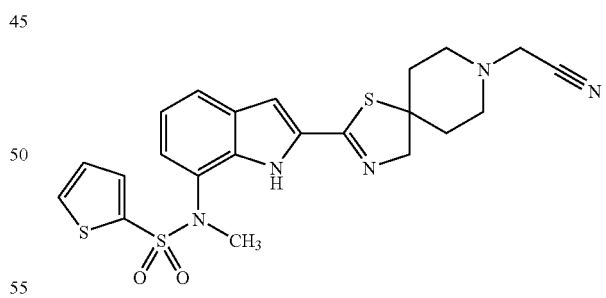

A mixture of N-Methyl-N-[2-(1-thia-3,8-diazaspiro[4.5]dec-2-en-2-yl)-1H-indol-7-yl]thiophene-2-sulfonamide (100 mg), 3-(chloromethyl)-1,2,4-oxadiazole (35 mg), potassium carbonate (44 mg) and N,N-dimethylformamide (5 mL) was stirred at 50° C. for 16 hr. Water was added to the reaction mixture, and the mixture was extracted with ethyl acetate. The ethyl acetate layer was washed with saturated brine, dried (MgSO$_4$), and concentrated. The obtained residue was purified by preparative HPLC to give the title compound (55 mg, yield 47%) as white crystals. melting point 211° C.

Example 408

N-{2-[8-(2-furylmethyl)-1-thia-3,8-diazaspiro[4.5]
dec-2-en-2-yl]-1H-indol-7-yl}-N-methylthiophene-
2-sulfonamide

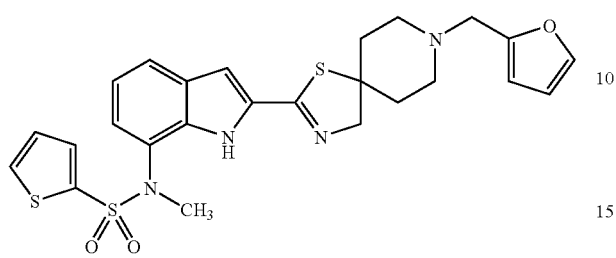

In the same manner as in Example 404, the title compound (92 mg, yield 79%) was obtained as white crystals from N-methyl-N-[2-(1-thia-3,8-diazaspiro[4.5]dec-2-en-2-yl)-1H-indol-7-yl]thiophene-2-sulfonamide (100 mg) and 2-furaldehyde (30 mg). melting point 196° C.

Example 409

N-methyl-N-{2-[8-(pyridin-2-ylmethyl)-1-thia-3,8-
diazaspiro[4.5]dec-2-en-2-yl]-1H-indol-7-
yl}thiophene-2-sulfonamide

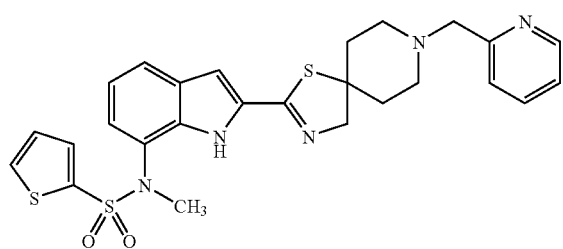

In the same manner as in Example 404, the title compound (88 mg, yield 74%) was obtained as white crystals from N-methyl-N-[2-(1-thia-3,8-diazaspiro[4.5]dec-2-en-2-yl)-1H-indol-7-yl]thiophene-2-sulfonamide (100 mg) and pyridine-2-carbaldehyde (33 mg). melting point 177° C.

Example 410

N,N-diethyl-2-(2-{7-[methyl(2-thienylsulfonyl)
amino]-1H-indol-2-yl}-1-thia-3,8-diazaspiro[4.5]
dec-2-en-8-yl)acetamide

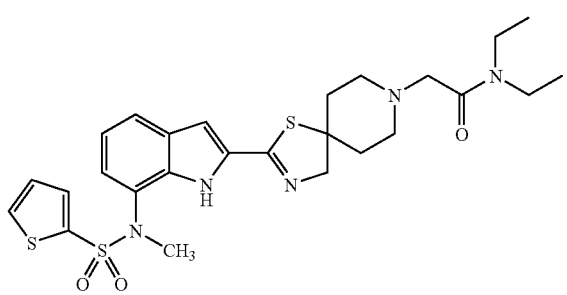

In the same manner as in Example 407, the title compound (74 mg, yield 60%) was obtained as white crystals from N-methyl-N-[2-(1-thia-3,8-diazaspiro[4.5]dec-2-en-2-yl)-1H-indol-7-yl]thiophene-2-sulfonamide (100 mg) and 2-chloro-N,N-diethylacetamide (45 mg). melting point 171° C.

Example 411

N-methyl-N-{2-[8-(2-oxopropyl)-1-thia-3,8-diaza-
spiro[4.5]dec-2-en-2-yl]-1H-indol-7-yl}thiophene-2-
sulfonamide

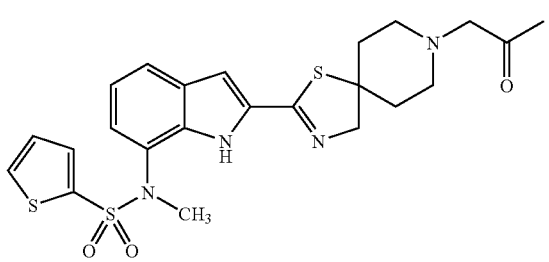

In the same manner as in Example 407, the title compound (58 mg, yield 53%) was obtained as white crystals from N-methyl-N-[2-(1-thia-3,8-diazaspiro[4.5]dec-2-en-2-yl)-1H-indol-7-yl]thiophene-2-sulfonamide (100 mg) and chloroacetone (30 mg). melting point 168° C.

Example 412 methyl (2-{7-[methyl(2-thienylsulfonyl)amino]-1H-
indol-2-yl}-1-thia-3,8-diazaspiro[4.5]dec-2-en-8-yl)
acetate

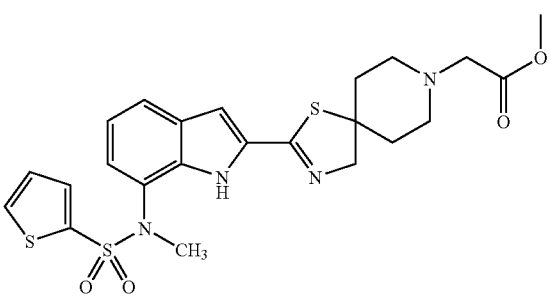

In the same manner as in Example 407, the title compound (165 mg, yield 72%) was obtained as white crystals from N-methyl-N-[2-(1-thia-3,8-diazaspiro[4.5]dec-2-en-2-yl)-1H-indol-7-yl]thiophene-2-sulfonamide (200 mg) and methyl bromoacetate (180 mg). melting point 156° C.

Example 413

(2-{7-[methyl(2-thienylsulfonyl)amino]-1H-indol-2-yl}-1-thia-3,8-diazaspiro[4.5]dec-2-en-8-yl)acetic acid

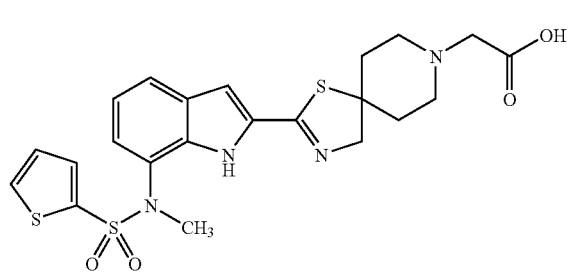

In the same manner as in Example 382, the title compound (98 mg, yield 99%) was obtained as white crystals from methyl (2-{7-[methyl(2-thienylsulfonyl)amino]-1H-indol-2-yl}-1-thia-3,8-diazaspiro[4.5]dec-2-en-8-yl)acetate (103 mg). melting point 236° C.

Example 414

2-(2-{7-[methyl(2-thienylsulfonyl)amino]-1H-indol-2-yl}-1-thia-3,8-diazaspiro[4.5]dec-2-en-8-yl)acetamide

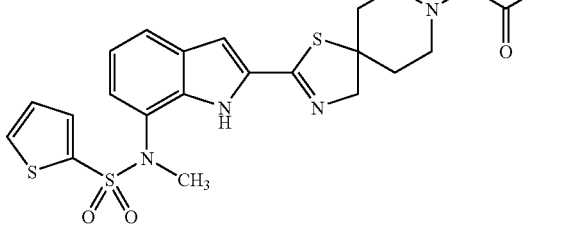

A mixture of N-methyl-N-[2-(1-thia-3,8-diazaspiro[4.5]dec-2-en-2-yl)-1H-indol-7-yl]thiophene-2-sulfonamide (100 mg), chloroacetamide (30 mg), potassium carbonate (40 mg) and N,N-dimethylformamide (3 mL) was stirred at room temperature for 1 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography, and eluted with ethyl acetate:hexane=1:1 from a fraction to give the title compound (62 mg, yield 56%) as white crystals. melting point 226° C.

MS: 504 (MH$^+$).

Example 415

N-{2-[8-(2-methoxyethyl)-1-thia-3,8-diazaspiro[4.5] dec-2-en-2-yl]-1H-indol-7-yl}-N-methylthiophene-2-sulfonamide

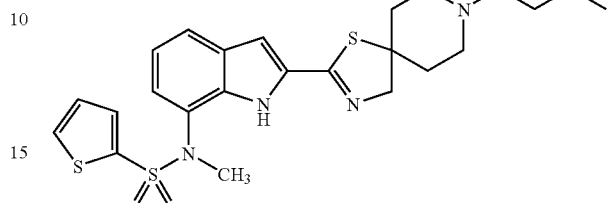

In the same manner as in Example 407, the title compound (84 mg, yield 76%) was obtained as white crystals from N-methyl-N-[2-(1-thia-3,8-diazaspiro[4.5]dec-2-en-2-yl)-1H-indol-7-yl]thiophene-2-sulfonamide (100 mg) and 2-bromoethyl methyl ether (35 mg). melting point 177° C.

Example 416

N-methyl-N-{2-[8-(tetrahydro-2H-pyran-4-yl)-1-thia-3,8-diazaspiro[4.5]dec-2-en-2-yl]-1H-indol-7-yl}thiophene-2-sulfonamide

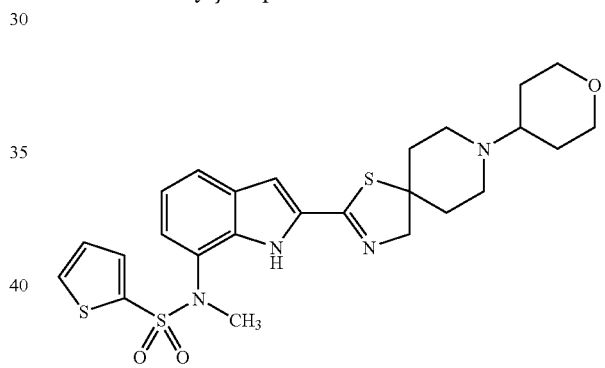

In the same manner as in Example 404, the title compound (92 mg, yield 79%) was obtained as white crystals from N-methyl-N-[2-(1-thia-3,8-diazaspiro[4.5]dec-2-en-2-yl)-1H-indol-7-yl]thiophene-2-sulfonamide (100 mg) and tetrahydro-4H-pyran-4-one (30 mg). melting point 225° C.

Example 417

N-methyl-N-{2-[8-(pyridin-3-ylmethyl)-1-thia-3,8-diazaspiro[4.5]dec-2-en-2-yl]-1H-indol-7-yl}thiophene-2-sulfonamide

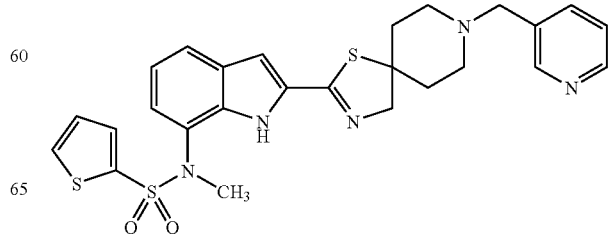

In the same manner as in Example 404, the title compound (91 mg, yield 77%) was obtained as white crystals from N-methyl-N-[2-(1-thia-3,8-diazaspiro[4.5]dec-2-en-2-yl)-1H-indol-7-yl]thiophene-2-sulfonamide (100 mg) and pyridine-3-carbaldehyde (33 mg). melting point 210° C.

Example 418

N-{2-[8-(2-hydroxyethyl)-1-thia-3,8-diazaspiro[4.5]dec-2-en-2-yl]-1H-indol-7-yl}-N-methylthiophene-2-sulfonamide

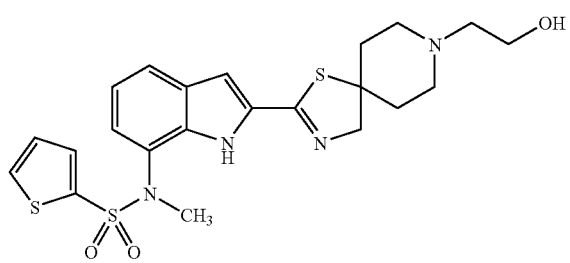

In the same manner as in Example 285, the title compound (62 mg, yield 31%) was obtained as white crystals from methyl (2-{7-[methyl(2-thienylsulfonyl)amino]-1H-indol-2-yl}-1-thia-3,8-diazaspiro[4.5]dec-2-en-8-yl)acetate. melting point 214° C.

Example 419

N-{2-[8-(2-hydroxy-2-methylpropyl)-1-thia-3,8-diazaspiro[4.5]dec-2-en-2-yl]-1H-indol-7-yl}-N-methylthiophene-2-sulfonamide

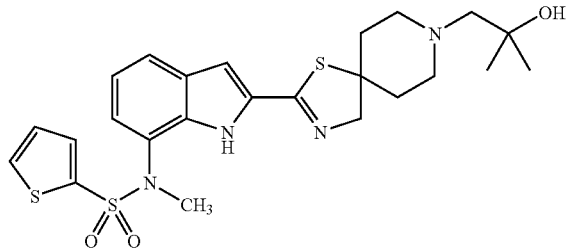

To a solution of methyl (2-{7-[methyl(2-thienylsulfonyl)amino]-1H-indol-2-yl}-1-thia-3,8-diazaspiro[4.5]dec-2-en-8-yl)acetate (211 mg) in tetrahydrofuran (3 mL) was added 1.5M methyllithium-diethyl ether solution (2 mL) at room temperature, and the mixture was stirred for 30 min. Saturated aqueous ammonium chloride solution was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (92 mg, yield 44%) as white crystals from a fraction eluted with ethyl acetate:hexane=1:3. melting point 191° C.

Example 420 ethyl (2-{5-methyl-7-[methyl(2-thienylsulfonyl)amino]-1H-indol-2-yl}-4,5-dihydro-1,3-thiazol-5-yl)acetate

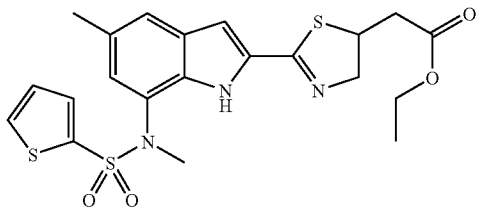

In the same manner as in Example 283, the title compound (1.59 g, yield 56%) was obtained as white crystals from 5-methyl-7-[methyl(2-thienylsulfonyl)amino]-1H-indole-2-carbothioamide (2.15 g) and ethyl but-2-ynoate (1.54 g). melting point 83° C.

Example 421

(2-{5-methyl-7-[methyl(2-thienylsulfonyl)amino]-1H-indol-2-yl}-4,5-dihydro-1,3-thiazol-5-yl)acetic acid

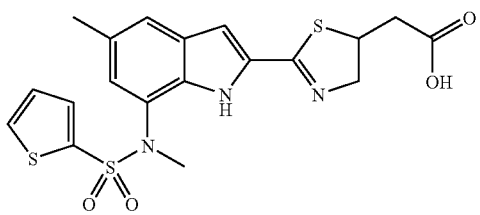

In the same manner as in Example 382, the title compound (0.49 g, yield 99%) was obtained as white crystals from ethyl (2-{5-methyl-7-[methyl(2-thienylsulfonyl)amino]-1H-indol-2-yl}-4,5-dihydro-1,3-thiazol-5-yl)acetate (0.5 g). melting point 209° C.

Example 422

2-(2-{5-methyl-7-[methyl(2-thienylsulfonyl)amino]-1H-indol-2-yl}-4,5-dihydro-1,3-thiazol-5-yl)acetamide

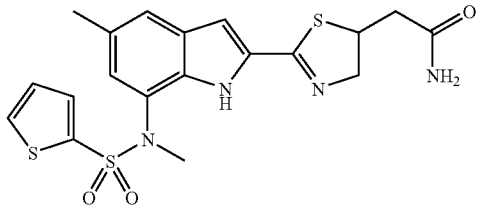

In the same manner as in Example 287, the title compound (104 mg, yield 56%) was obtained as white crystals from (2-{5-methyl-7-[methyl(2-thienylsulfonyl)amino]-1H-indol-2-yl}-4,5-dihydro-1,3-thiazol-5-yl)acetic acid (180 mg). melting point 179° C.

Example 423

N-{2-[5-(2-hydroxyethyl)-4,5-dihydro-1,3-thiazol-2-yl]-5-methyl-1H-indol-7-yl}-N-methylthiophene-2-sulfonamide

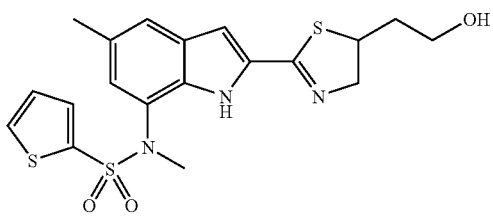

In the same manner as in Example 285, the title compound (180 mg, yield 66%) was obtained as white crystals from ethyl (2-{5-methyl-7-[methyl(2-thienylsulfonyl)amino]-1H-indol-2-yl}-4,5-dihydro-1,3-thiazol-5-yl)acetate (300 mg).
melting point 161° C.

Example 424

N-methyl-N-{5-methyl-2-[5-(morpholinomethyl)-4,5-dihydro-1,3-thiazol-2-yl]-1H-indol-7-yl}thiophene-2-sulfonamide

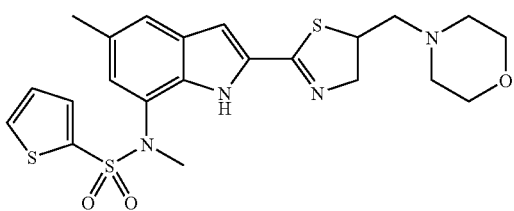

In the same manner as in Example 201, the title compound (544 mg, yield 72%) was obtained as white crystals from N-[2-(benzylthio)-3-morpholinopropyl]-5-methyl-7-[methyl(2-thienylsulfonyl)amino]-1H-indole-2-carboxamide (812 mg). melting point 189° C.

Example 425 benzyl [(2-{5-methyl-7-[methyl(2-thienylsulfonyl)amino]-1H-indol-2-yl}-4,5-dihydro-1,3-thiazol-5-yl)methyl]carbamate

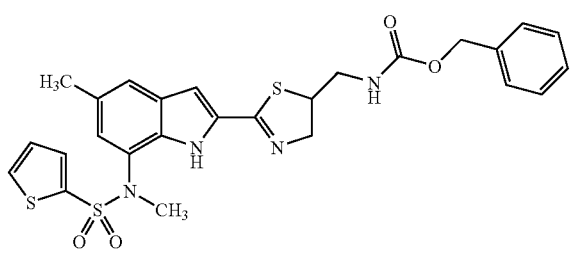

To a solution of (2-{5-methyl-7-[methyl(2-thienylsulfonyl)amino]-1H-indol-2-yl}-4,5-dihydro-1,3-thiazol-5-yl) acetic acid (500 mg), benzyl alcohol (570 μL) and triethylamine (185 μL) in N,N-dimethylformamide (10 mL) was added diphenylphosphorylazide (287 μL) at room temperature, and the mixture was stirred under heating at 100° C. for 30 min. The reaction mixture was allowed to cool to room temperature, water was added, and the mixture was extracted with ethyl acetate. The ethyl acetate layer was washed with saturated brine, dried (MgSO$_4$), and concentrated. The obtained residue was subjected to silica gel column chromatography to give the title compound (112 mg, yield 18%) as pale-yellow crystals from a fraction eluted with ethyl acetate: hexane=25:75.

melting point 160° C.

Example 426

N-[2-(5-cyano-4,5-dihydro-1,3-thiazol-2-yl)-5-methyl-1H-indol-7-yl]-N-methylthiophene-2-sulfonamide

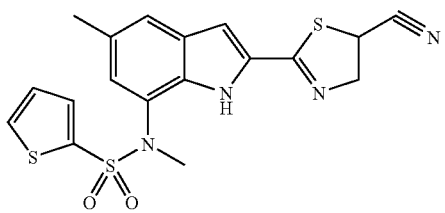

In the same manner as in Example 201, the title compound (406 mg, yield 30%) was obtained as white crystals from N-[2-(benzylthio)-2-cyanoethyl]-5-methyl-7-[methyl(2-thienylsulfonyl)amino]-1H-indole-2-carboxamide (1.7 g).
melting point 203° C.

Example 427

N-{2-[5-(aminomethyl)-4,5-dihydro-1,3-thiazol-2-yl]-5-methyl-1H-indol-7-yl}-N-methylthiophene-2-sulfonamide

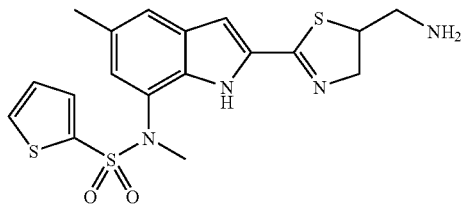

In the same manner as in Example 277, the title compound (140 mg, yield 44%) was obtained as white crystals from N-[2-(5-cyano-4,5-dihydro-1,3-thiazol-2-yl)-5-methyl-1H-indol-7-yl]-N-methylthiophene-2-sulfonamide (314 mg).
melting point 168° C.

Example 428

N-(2-hydroxyethyl)-2-(2-{7-[methyl(2-thienylsulfonyl)amino]-1H-indol-2-yl}-4,5-dihydro-1,3-thiazol-5-yl)acetamide

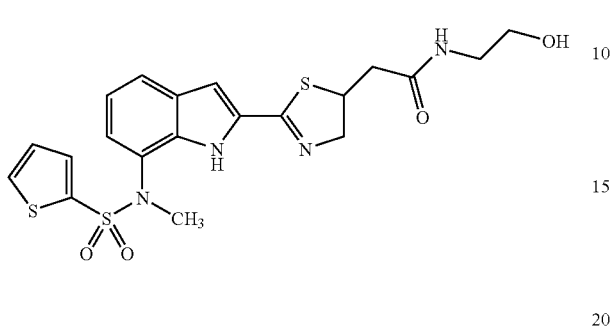

To a solution of (2-{7-[methyl(2-thienylsulfonyl)amino]-1H-indol-2-yl}-4,5-dihydro-1,3-thiazol-5-yl)acetic acid (200 mg), 1H-1,2,3-benzotriazol-1-ol (150 mg) and N-[3-(dimethylamino)propyl]-N'-ethylcarbodiimide hydrochloride (190 mg) in tetrahydrofuran (3 mL) and acetonitrile (3 mL) was added 2-aminoethanol (100 mg), and the mixture was stirred at room temperature for 3 hr. The reaction mixture was concentrated, water was added, and the mixture was extracted with ethyl acetate. The ethyl acetate layer was washed with saturated brine, dried (MgSO$_4$), and concentrated. The obtained residue was subjected to silica gel column chromatography to give the title compound (124 mg, yield 56%) as white crystals from a fraction eluted with ethyl acetate:hexane=50:50. melting point 214° C.

Example 429

N-(2-hydroxyethyl)-N-methyl-2-(2-{7-[methyl(2-thienylsulfonyl)amino]-1H-indol-2-yl}-4,5-dihydro-1,3-thiazol-5-yl)acetamide

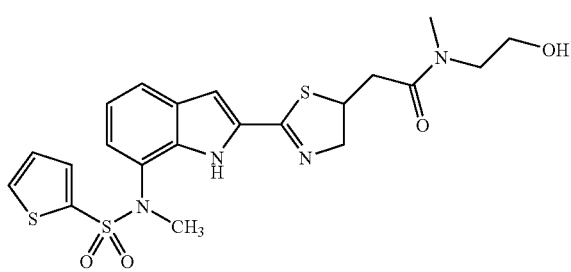

In the same manner as in Example 428, the title compound (49 mg, yield 22%) was obtained as white crystals from (2-{7-[methyl(2-thienylsulfonyl)amino]-1H-indol-2-yl}-4,5-dihydro-1,3-thiazol-5-yl)acetic acid (200 mg) and 2-(methylamino)ethanol (150 mg). melting point 112° C.

Example 430

N,N-bis(2-hydroxyethyl)-2-(2-{7-[methyl(2-thienylsulfonyl)amino]-1H-indol-2-yl}-4,5-dihydro-1,3-thiazol-5-yl)acetamide

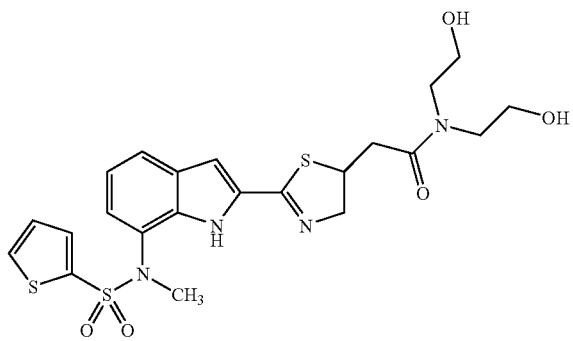

In the same manner as in Example 428, the title compound (14.5 mg, yield 6%) was obtained as white crystals from (2-{7-[methyl(2-thienylsulfonyl)amino]-1H-indol-2-yl}-4,5-dihydro-1,3-thiazol-5-yl)acetic acid (200 mg) and 2,2'-iminodiethanol (200 mg). melting point 104° C.

Example 431

N-(2-methoxyethyl)-2-(2-{7-[methyl(2-thienylsulfonyl)amino]-1H-indol-2-yl}-4,5-dihydro-1,3-thiazol-5-yl)acetamide

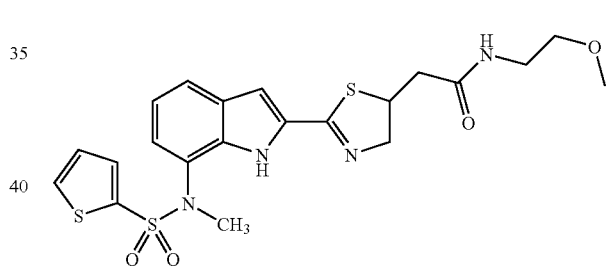

In the same manner as in Example 428, the title compound (134 mg, yield 59%) was obtained as white crystals from (2-{7-[methyl(2-thienylsulfonyl)amino]-1H-indol-2-yl}-4,5-dihydro-1,3-thiazol-5-yl)acetic acid (200 mg) and 2-methoxyethaneamine (150 mg). melting point 140° C.

Example 432

N-(2-methoxyethyl)-N-methyl-2-(2-{7-[methyl(2-thienylsulfonyl)amino]-1H-indol-2-yl}-4,5-dihydro-1,3-thiazol-5-yl)acetamide

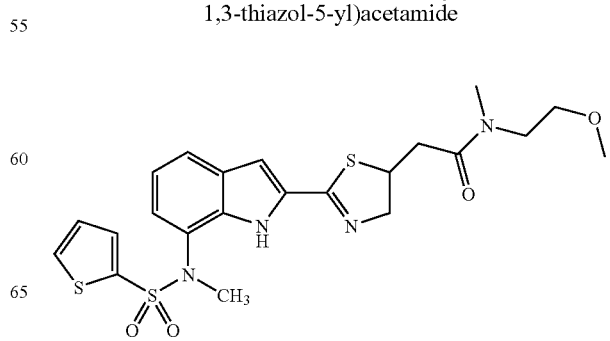

In the same manner as in Example 428, the title compound (167 mg, yield 72%) was obtained as white crystals from (2-{7-[methyl(2-thienylsulfonyl)amino]-1H-indol-2-yl}-4,5-dihydro-1,3-thiazol-5-yl)acetic acid (200 mg) and 2-methoxy-N-methylethaneamine (180 mg). melting point 103° C.

Example 433

N-[2-(methylsulfonyl)ethyl]-2-(2-{7-[methyl(2-thienylsulfonyl)amino]-1H-indol-2-yl}-4,5-dihydro-1,3-thiazol-5-yl)acetamide

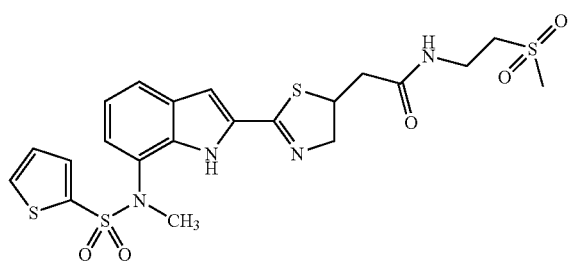

In the same manner as in Example 428, the title compound (109 mg, yield 44%) was obtained as white crystals from (2-{7-[methyl(2-thienylsulfonyl)amino]-1H-indol-2-yl}-4,5-dihydro-1,3-thiazol-5-yl)acetic acid (200 mg) and 2-(methylsulfonyl)ethaneamine (300 mg). melting point 146° C.

Example 434

N-methyl-N-[2-(methylsulfonyl)ethyl]-2-(2-{7-[methyl(2-thienylsulfonyl)amino]-1H-indol-2-yl}-4,5-dihydro-1,3-thiazol-5-yl)acetamide

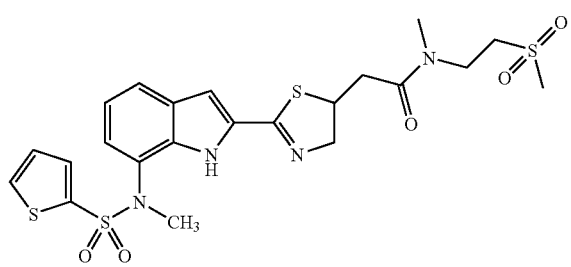

In the same manner as in Example 428, the title compound (95 mg, yield 37%) was obtained as white crystals from (2-{7-[methyl(2-thienylsulfonyl)amino]-1H-indol-2-yl}-4,5-dihydro-1,3-thiazol-5-yl)acetic acid (200 mg) and N-methyl-2-(methylsulfonyl)ethaneamine (350 mg). melting point 96° C.

Example 435

N-(2-{5-[2-(3-hydroxypyrrolidin-1-yl)-2-oxoethyl]-4,5-dihydro-1,3-thiazol-2-yl}-1H-indol-7-yl)-N-methylthiophene-2-sulfonamide

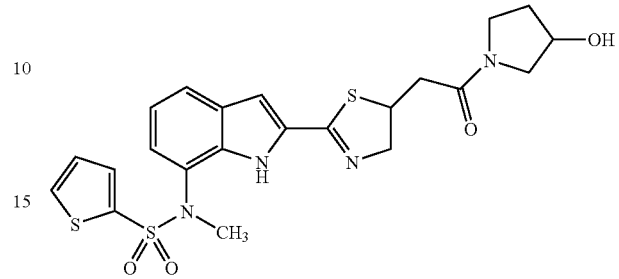

In the same manner as in Example 428, the title compound (206 mg, yield 89%) was obtained as white crystals from (2-{7-[methyl(2-thienylsulfonyl)amino]-1H-indol-2-yl}-4,5-dihydro-1,3-thiazol-5-yl)acetic acid (200 mg) and 3-hydroxypyrrolidine (60 mg). melting point 208° C.

Example 436

N-(2-{5-[2-(4-hydroxypiperidino)-2-oxoethyl]-4,5-dihydro-1,3-thiazol-2-yl}-1H-indol-7-yl)-N-methylthiophene-2-sulfonamide

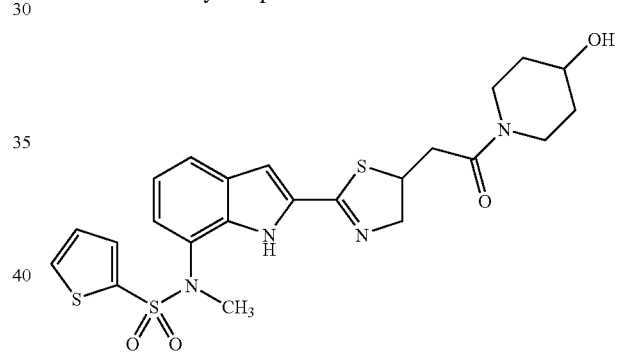

In the same manner as in Example 428, the title compound (210 mg, yield 88%) was obtained as white crystals from (2-{7-[methyl(2-thienylsulfonyl)amino]-1H-indol-2-yl}-4,5-dihydro-1,3-thiazol-5-yl)acetic acid (200 mg) and 4-hydroxypiperidine (60 mg). melting point 121° C.

Example 437

N-(methylsulfonyl)-2-(2-{7-[methyl(2-thienylsulfonyl)amino]-1H-indol-2-yl}-4,5-dihydro-1,3-thiazol-5-yl)acetamide

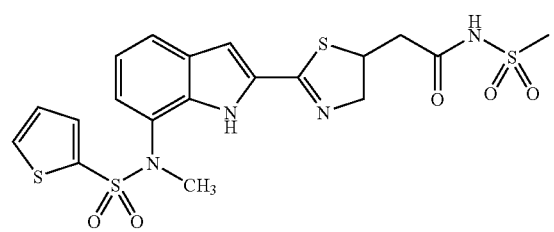

A solution of (2-{7-[methyl(2-thienylsulfonyl)amino]-1H-indol-2-yl}-4,5-dihydro-1,3-thiazol-5-yl)acetic acid (200 mg), 2-methyl-6-nitrobenzoic acid anhydride (190 mg), 4-dimethylaminopyridine (56 mg), triethylamine (200 μL) and methanesulfonamide (46 mg) in acetonitrile (5 mL) was stirred at room temperature for 18 hr. 1N Hydrochloric acid was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (76 mg, yield 33%) as white crystals from a fraction eluted with ethyl acetate. melting point 141° C.

Example 438

N-[2-(5-{2-[(2-hydroxyethyl)amino]ethyl}-4,5-dihydro-1,3-thiazol-2-yl)-1H-indol-7-yl]-N-methylthiophene-2-sulfonamide hydrochloride

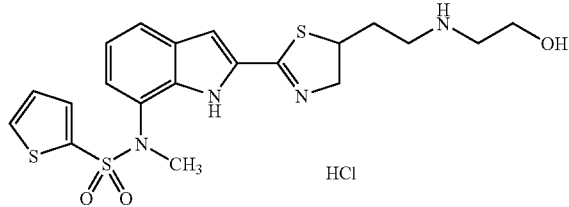

To a solution of 2-(2-{7-[methyl(2-thienylsulfonyl)amino]-1H-indol-2-yl}-4,5-dihydro-1,3-thiazol-5-yl)ethyl methanesulfonate (124 mg) in N,N-dimethylformamide (3 mL) was added 2-aminoethanol (60 mg), and the mixture was stirred under heating at 80° C. for 4 hr. The reaction mixture was allowed to cool to room temperature, saturated aqueous sodium hydrogencarbonate solution was added, and the mixture was extracted with ethyl acetate. The ethyl acetate layer was washed with saturated brine, dried (MgSO$_4$), and concentrated. The obtained residue was subjected to silica gel column chromatography to give colorless oil from a fraction eluted with ethyl acetate. To a solution of the obtained colorless oil in ethyl acetate (1 mL) was added 4N hydrogen chloride-ethyl acetate solution (1 mL). The precipitated crystals were collected by filtration, washed with diethyl ether, and dried to give the title compound (27 mg, yield 22%) as yellow crystals. melting point 196° C.

Example 439

N-[2-(5-{2-[4-(2-hydroxyethyl)piperidino]-2-oxoethyl}-4,5-dihydro-1,3-thiazol-2-yl)-1H-indol-7-yl]-N-methylthiophene-2-sulfonamide

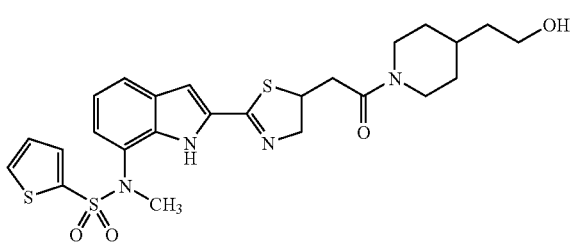

In the same manner as in Example 428, the title compound (102 mg, yield 41%) was obtained as white crystals from (2-{7-[methyl(2-thienylsulfonyl)amino]-1H-indol-2-yl}-4,5-dihydro-1,3-thiazol-5-yl)acetic acid (200 mg) and 2-(piperidin-4-yl)ethanol (100 mg). melting point 106° C.

Example 440

N-methyl-N-{2-[5-(2-oxo-2-thiomorpholinoethyl)-4,5-dihydro-1,3-thiazol-2-yl]-1H-indol-7-yl}thiophene-2-sulfonamide

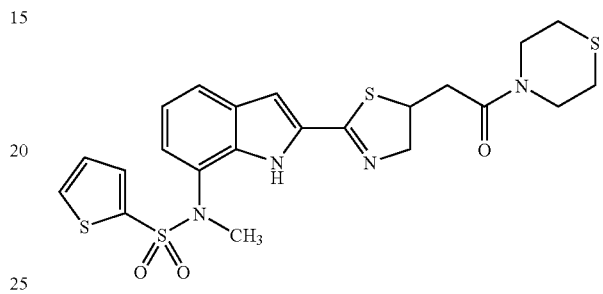

In the same manner as in Example 428, the title compound (624 mg, yield 52%) was obtained as white crystals from (2-{7-[methyl(2-thienylsulfonyl)amino]-1H-indol-2-yl}-4,5-dihydro-1,3-thiazol-5-yl)acetic acid (1.0 g) and thiomorpholine (300 mg). melting point 182° C.

Example 441

N-(2-{5-[2-(1,1-dioxidothiomorpholino)-2-oxoethyl]-4,5-dihydro-1,3-thiazol-2-yl}-1H-indol-7-yl)-N-methylthiophene-2-sulfonamide

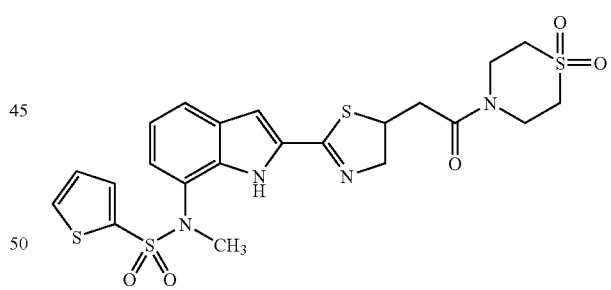

To a solution of N-methyl-N-{2-[5-(2-oxo-2-thiomorpholinoethyl)-4,5-dihydro-1,3-thiazol-2-yl]-1H-indol-7-yl}thiophene-2-sulfonamide (560 mg) in tetrahydrofuran (15 mL), ethanol (5 mL) and water (5 mL) was added OXONE (registered trade mark, 986 mg) at room temperature, and the mixture was stirred for 1 hr. Sodium sulfite (3 g) was added to the reaction mixture, and the mixture was stirred for 10 min. Water was added, and the mixture was extracted with ethyl acetate. The ethyl acetate layer was washed with saturated brine, dried (MgSO$_4$), and concentrated. The obtained residue was subjected to silica gel column chromatography to give the title compound (242 mg, yield 44%) as white crystals from a fraction eluted with ethyl acetate. melting point 158° C.

Example 442

N-methyl-N-(2-{5-[2-(1-oxidothiomorpholino)-2-oxoethyl]-4,5-dihydro-1,3-thiazol-2-yl}-1H-indol-7-yl)thiophene-2-sulfonamide

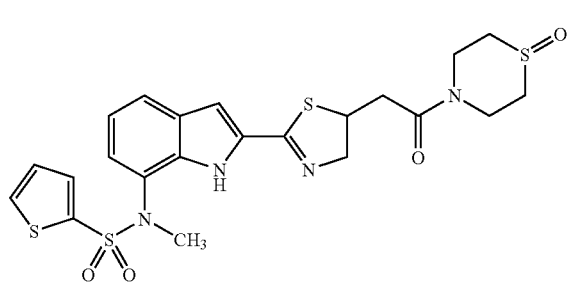

The title compound (92 mg, yield 17%) was obtained as white crystals from a fraction eluted after the elution of the compound of Example 441 with ethyl acetate in the silica gel column chromatography. melting point 149° C.

Example 443

2-(2-{7-[methyl(2-thienylsulfonyl)amino]-1H-indol-2-yl}-4,5-dihydro-1,3-thiazol-5-yl)ethyl (cis)-2,6-dimethylmorpholine-4-carboxylate hydrochloride

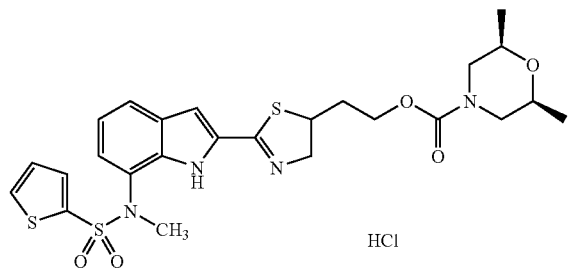

To a solution of 2-(2-{7-[methyl(2-thienylsulfonyl)amino]-1H-indol-2-yl}-4,5-dihydro-1,3-thiazol-5-yl)ethyl methanesulfonate (180 mg) in N,N-dimethylformamide (5 mL) were added potassium carbonate (60 mg) and cis-2,6-dimethylmorpholine (60 mg), and the mixture was stirred under heating at 50° C. for 3 days. The reaction mixture was allowed to cool to room temperature, water was added, and the mixture was extracted with ethyl acetate. The ethyl acetate layer was washed with saturated brine, dried ($MgSO_4$), and concentrated. The obtained residue was subjected to silica gel column chromatography to give colorless oil from a fraction eluted with ethyl acetate. The obtained colorless oil was dissolved in ethyl acetate (1 mL), and 4N hydrogen chloride-ethyl acetate solution (1 mL) was added. The precipitated crystals were collected by filtration, washed with diethyl ether, and dried to give the title compound (71 mg, yield 36%) as yellow crystals. melting point 154° C.

Example 444

N-[2-(5-{2-[(cis)-2,6-dimethylmorpholino]ethyl}-4,5-dihydro-1,3-thiazol-2-yl)-1H-indol-7-yl]-N-methylthiophene-2-sulfonamide hydrochloride

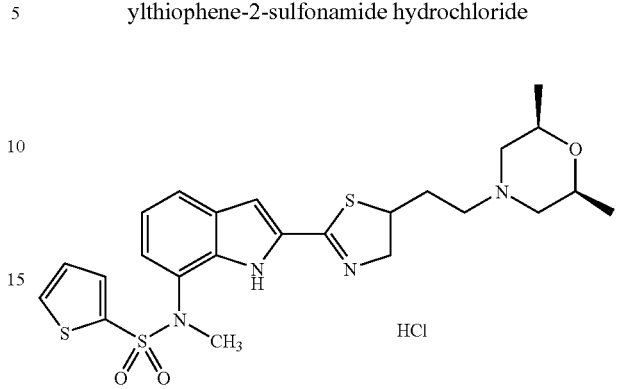

A colorless oil was obtained from a fraction eluted after the elution of the compound of Example 443 with ethyl acetate in the silica gel column chromatography. The obtained colorless oil was dissolved in ethyl acetate (1 mL), and 4N hydrogen chloride-ethyl acetate solution (1 mL) was added. The precipitated crystals were collected by filtration, washed with diethyl ether, and dried to give the title compound (37 mg, yield 21%) as yellow crystals. melting point 196° C.

Example 445

2-(2-{7-[methyl(2-thienylsulfonyl)amino]-1H-indol-2-yl}-4,5-dihydro-1,3-thiazol-5-yl)-N-4H-1,2,4-triazol-3-ylacetamide

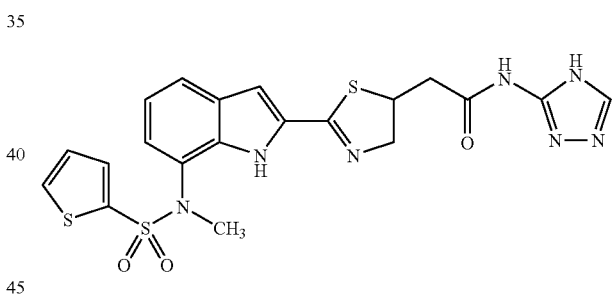

In the same manner as in Example 428, the title compound (164 mg, yield 71%) was obtained as white crystals from (2-{7-[methyl(2-thienylsulfonyl)amino]-1H-indol-2-yl}-4,5-dihydro-1,3-thiazol-5-yl)acetic acid (1.0 g) and 4H-1,2,4-triazol-3-amine (50 mg). melting point 194° C.

Example 446

2-(2-{7-[methyl(2-thienylsulfonyl)amino]-1H-indol-2-yl}-4,5-dihydro-1,3-thiazol-5-yl)-N-1H-tetrazol-5-ylacetamide

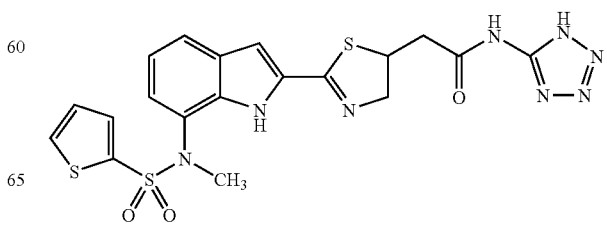

In the same manner as in Example 428, the title compound (69 mg, yield 30%) was obtained as white crystals from (2-{7-[methyl(2-thienylsulfonyl)amino]-1H-indol-2-yl}-4, 5-dihydro-1,3-thiazol-5-yl)acetic acid (1.0 g) and 1H-tetrazol-5-amine (50 mg). melting point 154° C.

Example 447

N-(2-{5-[2-(3-hydroxyazetidin-1-yl)-2-oxoethyl]-4, 5-dihydro-1,3-thiazol-2-yl}-1H-indol-7-yl)-N-methylthiophene-2-sulfonamide

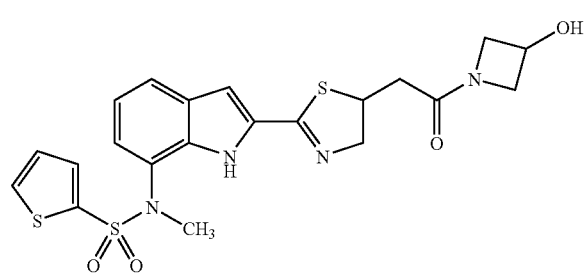

In the same manner as in Example 428, the title compound (190 mg, yield 84%) was obtained as white crystals from (2-{7-[methyl(2-thienylsulfonyl)amino]-1H-indol-2-yl}-4, 5-dihydro-1,3-thiazol-5-yl)acetic acid (1.0 g) and 3-hydroxyazetidine (60 mg). melting point 187° C.

Example 448

N-[2-(5-{2-[(cis)-2,6-dimethylmorpholino]-2-oxoethyl}-4,5-dihydro-1,3-thiazol-2-yl)-1H-indol-7-yl]-N-methylthiophene-2-sulfonamide

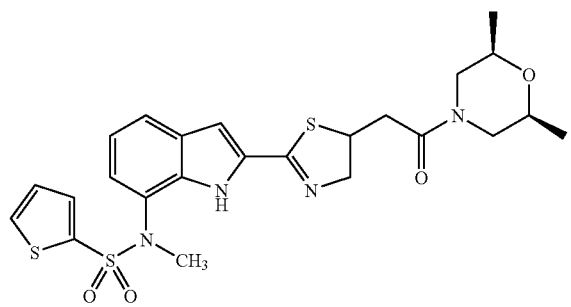

In the same manner as in Example 428, the title compound (206 mg, yield 84%) was obtained as white crystals from (2-{7-[methyl(2-thienylsulfonyl)amino]-1H-indol-2-yl}-4, 5-dihydro-1,3-thiazol-5-yl)acetic acid (1.0 g) and cis-2,6-dimethylmorpholine (60 mg). melting point 170° C.

Example 449
N-methyl-N-{2-[5-(2-oxoethyl)-4,5-dihydro-1,3-thiazol-2-yl]-1H-indol-7-yl}thiophene-2-sulfonamide

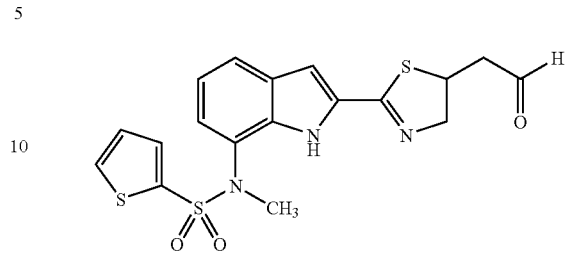

To a solution of N-{2-[5-(2-hydroxyethyl)-4,5-dihydro-1, 3-thiazol-2-yl]-1H-indol-7-yl}-N-methylthiophene-2-sulfonamide (2.78 g) in acetonitrile (150 mL) was added Dess-Martin reagent (3 g), and the mixture was stirred under heating at 70° C. for 30 min. The reaction mixture was allowed to cool to room temperature, water was added, and the mixture was extracted with ethyl acetate. The ethyl acetate layer was washed with saturated brine, dried (MgSO$_4$), and concentrated. The obtained residue was subjected to silica gel column chromatography to give the title compound (27 mg, yield 22%) as a brown amorphous solid from a fraction eluted with ethyl acetate:hexane=25:75. MS: 420 (MH$^+$).

Example 450
N-methyl-2-(2-{7-[methyl(2-thienylsulfonyl)amino]-1H-indol-2-yl}-4,5-dihydro-1,3-thiazol-5-yl)acetamide

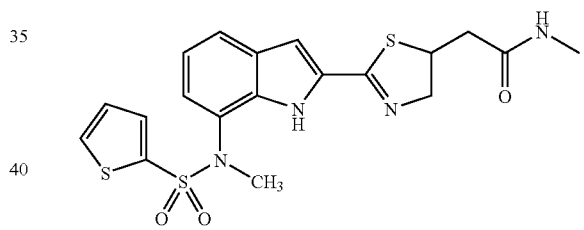

In the same manner as in Example 428, the title compound (56 mg, yield 27%) was obtained as white crystals from (2-{7-[methyl(2-thienylsulfonyl)amino]-1H-indol-2-yl}-4, 5-dihydro-1,3-thiazol-5-yl)acetic acid (1.0 g) and 2M methylamine tetrahydrofuran solution (2 mL). melting point 192° C.

Example 451

N-(2-{5-[2-(4-hydroxypiperidino)ethyl]-4,5-dihydro-1,3-thiazol-2-yl}-1H-indol-7-yl)-N-methylthiophene-2-sulfonamide

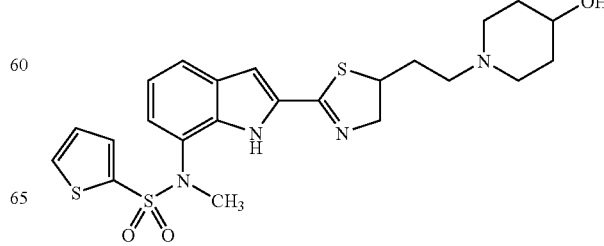

In the same manner as in Example 404, the title compound (248 mg, yield 77%) was obtained as white crystals from N-methyl-N-{2-[5-(2-oxoethyl)-4,5-dihydro-1,3-thiazol-2-yl]-1H-indol-7-yl}thiophene-2-sulfonamide (270 mg) and 4-hydroxypiperidine (100 mg). melting point 176° C.

Example 452

N-(2-{5-[2-(3-hydroxyazetidin-1-yl)ethyl]-4,5-dihydro-1,3-thiazol-2-yl}-1H-indol-7-yl)-N-methylthiophene-2-sulfonamide

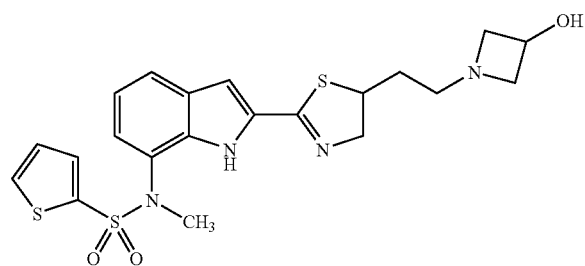

In the same manner as in Example 404, the title compound (195 mg, yield 64%) was obtained as white crystals from N-methyl-N-{2-[5-(2-oxoethyl)-4,5-dihydro-1,3-thiazol-2-yl]-1H-indol-7-yl}thiophene-2-sulfonamide (270 mg) and 3-hydroxyazetidine (110 mg). melting point 149° C.

Example 453

N-(2-{5-[2-(1,1-dioxidothiomorpholino)ethyl]-4,5-dihydro-1,3-thiazol-2-yl}-1H-indol-7-yl)-N-methylthiophene-2-sulfonamide

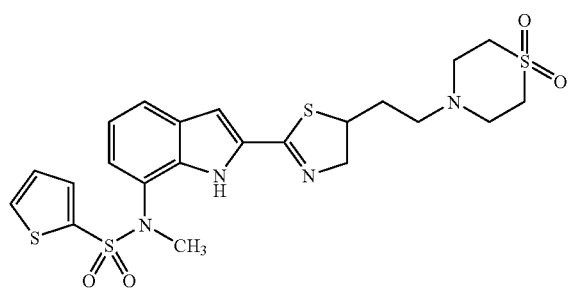

In the same manner as in Example 404, the title compound (145 mg, yield 56%) was obtained as white crystals from N-methyl-N-{2-[5-(2-oxoethyl)-4,5-dihydro-1,3-thiazol-2-yl]-1H-indol-7-yl}thiophene-2-sulfonamide (200 mg) and thiomorpholine 1,1-dioxide (95 mg). melting point 161° C.

Example 454

N-methyl-N-{2-[5-(2-thiomorpholinoethyl)-4,5-dihydro-1,3-thiazol-2-yl]-1H-indol-7-yl}thiophene-2-sulfonamide

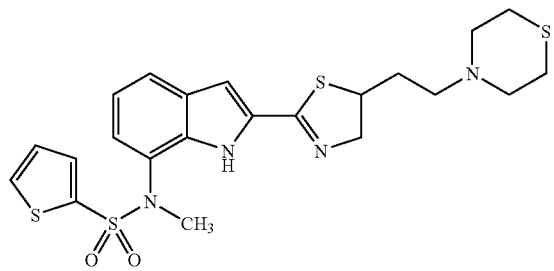

In the same manner as in Example 404, the title compound (606 mg, yield 84%) was obtained as white crystals from N-methyl-N-{2-[5-(2-oxoethyl)-4,5-dihydro-1,3-thiazol-2-yl]-1H-indol-7-yl}thiophene-2-sulfonamide (600 mg) and thiomorpholine (300 mg). melting point 164° C.

Example 455

N-methyl-N-(2-{5-[2-(1-oxidothiomorpholino)ethyl]-4,5-dihydro-1,3-thiazol-2-yl}-1H-indol-7-yl)thiophene-2-sulfonamide

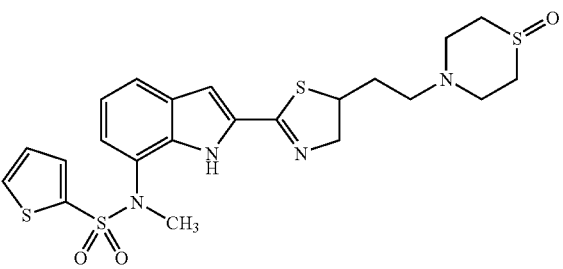

In the same manner as in Example 323, the title compound (87 mg, yield 15%) was obtained as white crystals from N-methyl-N-{2-[5-(2-thiomorpholinoethyl)-4,5-dihydro-1,3-thiazol-2-yl]-1H-indol-7-yl}thiophene-2-sulfonamide (559 mg). melting point 146° C.

Example 456

N-[2-(5-{2-[(cis)-3,5-dimethylpiperazin-1-yl]ethyl}-4,5-dihydro-1,3-thiazol-2-yl)-1H-indol-7-yl]-N-methylthiophene-2-sulfonamide dihydrochloride

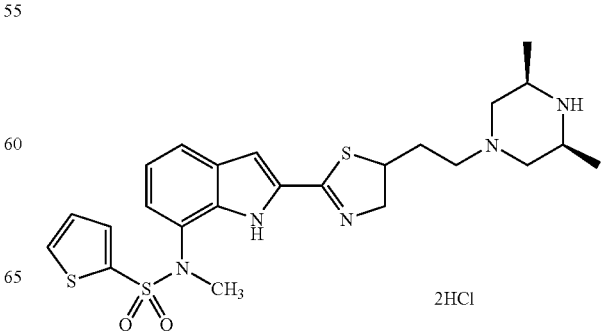

To a solution of N-methyl-N-{2-[5-(2-oxoethyl)-4,5-dihydro-1,3-thiazol-2-yl]-1H-indol-7-yl}thiophene-2-sulfonamide (200 mg) and 2,6-dimethylpiperazine (58 mg) in tetrahydrofuran (5 mL) was added sodium triacetoxyborohydride (200 mg) at room temperature, and the mixture was stirred for 10 min. Saturated aqueous sodium hydrogencarbonate solution was added to the reaction mixture, and the mixture was extracted with ethyl acetate. The ethyl acetate layer was washed with saturated brine, dried (MgSO$_4$), and concentrated. The obtained residue was subjected to basic silica gel column chromatography to give a colorless oil from a fraction eluted with ethyl acetate. The obtained colorless oil was dissolved in ethyl acetate (2 mL), and 4N hydrogen chloride-ethyl acetate solution (1 mL) was added. The precipitated crystals were collected by filtration, washed with diethyl ether, and dried to give the title compound (130 mg, yield 46%) as yellow crystals. melting point 217° C.

Example 457

N-methyl-N-[2-(5-{2-[(cis)-3,4,5-trimethylpiperazin-1-yl]ethyl}-4,5-dihydro-1,3-thiazol-2-yl)-1H-indol-7-yl]thiophene-2-sulfonamide

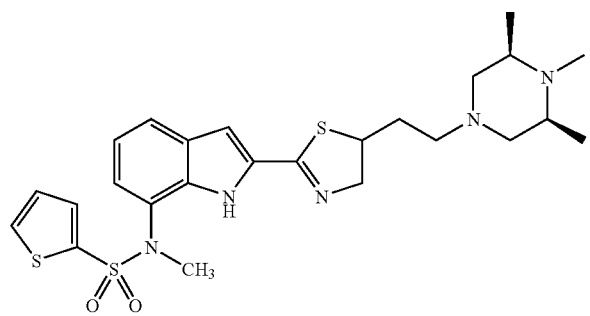

In the same manner as in Example 404, the title compound (138 mg, yield 99%) was obtained as white crystals from N-[2-(5-{2-[(cis)-3,5-dimethylpiperazin-1-yl]ethyl}-4,5-dihydro-1,3-thiazol-2-yl)-1H-indol-7-yl]-N-methylthiophene-2-sulfonamide dihydrochloride (135 mg) and 37% aqueous formaldehyde solution (1 mL). melting point 138° C.

Example 458

N-[2-(5-{2-[(cis)-3,5-dimethylpiperazin-1-yl]-2-oxoethyl}-4,5-dihydro-1,3-thiazol-2-yl)-1H-indol-7-yl]-N-methylthiophene-2-sulfonamide

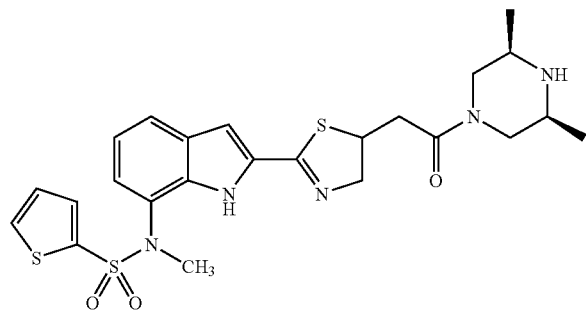

In the same manner as in Example 428, the title compound (421 mg, yield 86%) was obtained as white crystals from (2-{7-[methyl(2-thienylsulfonyl)amino]-1H-indol-2-yl}-4,5-dihydro-1,3-thiazol-5-yl)acetic acid (400 mg) and cis-2,6-dimethylpiperazine (114 mg). melting point 158° C.

Example 459

N-methyl-N-[2-(5-{2-oxo-2-[(cis)-3,4,5-trimethylpiperazin-1-yl]ethyl}-4,5-dihydro-1,3-thiazol-2-yl)-1H-indol-7-yl]thiophene-2-sulfonamide

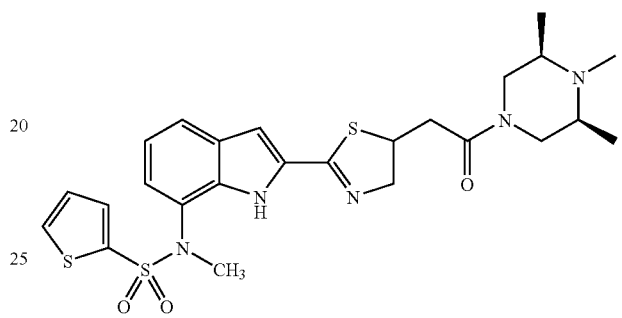

In the same manner as in Example 404, the title compound (286 mg, yield 99%) was obtained as white crystals from N-[2-(5-{2-[(cis)-3,5-dimethylpiperazin-1-yl]-2-oxoethyl}-4,5-dihydro-1,3-thiazol-2-yl)-1H-indol-7-yl]-N-methylthiophene-2-sulfonamide (277 mg) and 37% aqueous formaldehyde solution (0.5 mL). melting point 134° C.

Example 460

N-[2-(5-{[1-(2-hydroxyethyl)-4,5-dihydro-1H-pyrazol-3-yl]methyl}-4,5-dihydro-1,3-thiazol-2-yl)-1H-indol-7-yl]-N-methylthiophene-2-sulfonamide

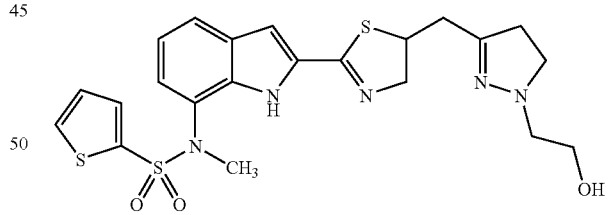

A solution of N-methyl-N-{2-[5-(2-oxobut-3-en-1-yl)-4,5-dihydro-1,3-thiazol-2-yl]-1H-indol-7-yl}thiophene-2-sulfonamide (223 mg) and 2-hydroxyethylhydrazine (60 mg) in tetrahydrofuran (5 mL) was stirred at room temperature for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (146 mg, yield 58%) as a white amorphous solid from a fraction eluted with ethyl acetate. MS: 504 (MH$^+$).

Example 461

N-[2-(5-{2-[(2-hydroxyethyl)(methyl)amino]ethyl}-4,5-dihydro-1,3-thiazol-2-yl)-1H-indol-7-yl]-N-methylthiophene-2-sulfonamide

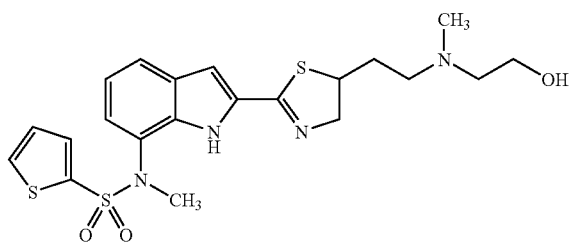

In the same manner as in Example 404, the title compound (110 mg, yield 48%) was obtained as white crystals from N-methyl-N-{2-[5-(2-oxoethyl)-4,5-dihydro-1,3-thiazol-2-yl]-1H-indol-7-yl}thiophene-2-sulfonamide (200 mg) and 2-(methylamino)ethanol (57 mg). melting point 116° C.

Example 462

N-methyl-N-{2-[5-(2-{methyl[2-(methylsulfonyl)ethyl]amino}ethyl)-4,5-dihydro-1,3-thiazol-2-yl]-1H-indol-7-yl}thiophene-2-sulfonamide hydrochloride

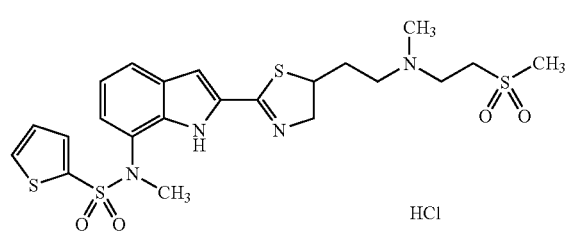

In the same manner as in Example 456, the title compound (190 mg, yield 68%) was obtained as yellow crystals from N-methyl-N-{2-[5-(2-oxoethyl)-4,5-dihydro-1,3-thiazol-2-yl]-1H-indol-7-yl}thiophene-2-sulfonamide (200 mg) and N-methyl-2-(methylsulfonyl)ethaneamine (100 mg). MS: 541 (MH+).

Example 463

N-methyl-N-(2-{5-[2-(4H-1,2,4-triazol-3-ylamino)ethyl]-4,5-dihydro-1,3-thiazol-2-yl}-1H-indol-7-yl)thiophene-2-sulfonamide

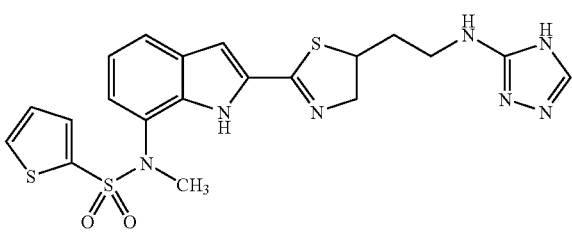

To a solution of N-methyl-N-{2-[5-(2-oxoethyl)-4,5-dihydro-1,3-thiazol-2-yl]-1H-indol-7-yl}thiophene-2-sulfonamide (200 mg) and 4H-1,2,4-triazol-3-amine (80 mg) in acetic acid (3 mL) was added sodium triacetoxyborohydride (200 mg) at room temperature, and the mixture was stirred for 10 min. The reaction mixture was neutralized with saturated aqueous sodium hydrogencarbonate solution, and extracted with ethyl acetate. The ethyl acetate layer was washed with saturated brine, dried (MgSO$_4$), and concentrated. The obtained residue was subjected to silica gel column chromatography to give the title compound (120 mg, yield 50%) as white crystals from a fraction eluted with ethyl acetate. melting point 195° C.

Example 464

N-[2-(5-{2-[(trans-4-hydroxy-4-methylcyclohexyl)amino]ethyl}-4,5-dihydro-1,3-thiazol-2-yl)-1H-indol-7-yl]-N-methylthiophene-2-sulfonamide hydrochloride

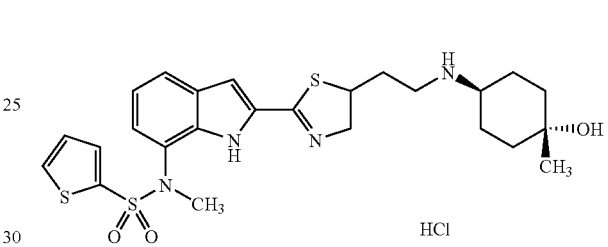

A mixture of N-methyl-N-{2-[5-(2-oxoethyl)-4,5-dihydro-1,3-thiazol-2-yl]-1H-indol-7-yl}thiophene-2-sulfonamide (200 mg) and trans-4-amino-1-methylcyclohexanol (80 mg) in methanol (5 mL) was stirred at 50° C. for 1 hr. The reaction mixture was allowed to cool to room temperature, sodium borohydride (38 mg) was added, and the mixture was stirred for 10 min. Saturated aqueous sodium hydrogencarbonate solution was added to the reaction mixture, and the mixture was extracted with ethyl acetate. The ethyl acetate layer was washed with saturated brine, dried (MgSO$_4$), and concentrated. The obtained residue was subjected to silica gel column chromatography to give a yellow oil from a fraction eluted with ethyl acetate. The obtained yellow oil was dissolved in ethyl acetate (3 mL), and 4N hydrogen chloride-ethyl acetate solution (2 mL) was added. The precipitated crystals were collected by filtration, washed with diethyl ether, and dried to give the title compound (148 mg, yield 54%) as yellow crystals. melting point 161° C.

Example 465

N-[2-(5-{2-[(2-hydroxy-2-methylpropyl)amino]ethyl}-4,5-dihydro-1,3-thiazol-2-yl)-1H-indol-7-yl]-N-methylthiophene-2-sulfonamide hydrochloride

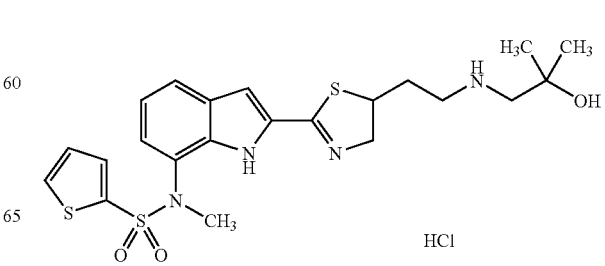

In the same manner as in Example 464, the title compound (116 mg, yield 46%) was obtained as yellow crystals from N-methyl-N-{2-[5-(2-oxoethyl)-4,5-dihydro-1,3-thiazol-2-yl]-1H-indol-7-yl}thiophene-2-sulfonamide (200 mg) and 1-amino-2-methylpropan-2-ol (50 mg). melting point 156° C.

Example 466

N-methyl-N-(2-{5-[2-(tetrahydro-2H-thiopyran-4-ylamino)ethyl]-4,5-dihydro-1,3-thiazol-2-yl}-1H-indol-7-yl)thiophene-2-sulfonamide

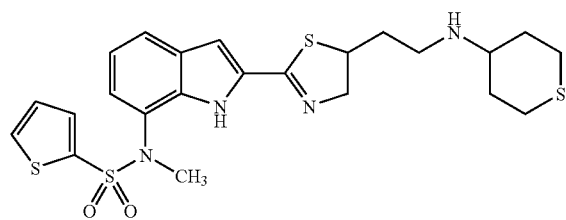

In the same manner as in Example 377, the title compound (403 mg, yield 55%) was obtained as white crystals from N-methyl-N-{2-[5-(2-oxoethyl)-4,5-dihydro-1,3-thiazol-2-yl]-1H-indol-7-yl}thiophene-2-sulfonamide (600 mg) and tetrahydro-2H-thiopyran-4-amine (300 mg). melting point 132° C.

Example 467

N-methyl-N-[2-(5-{2-[(1-oxidetetrahydro-2H-thiopyran-4-yl)amino]ethyl}-4,5-dihydro-1,3-thiazol-2-yl)-1H-indol-7-yl]thiophene-2-sulfonamide

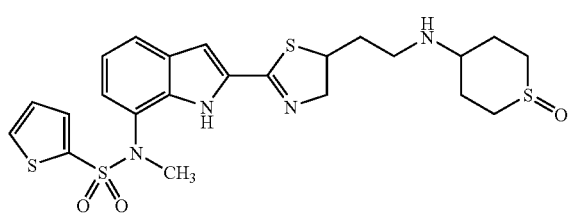

In the same manner as in Example 323, the title compound (55 mg, yield 16%) was obtained as yellow crystals from N-methyl-N-(2-{5-[2-(tetrahydro-2H-thiopyran-4-ylamino)ethyl]-4,5-dihydro-1,3-thiazol-2-yl}-1H-indol-7-yl)thiophene-2-sulfonamide (330 mg). melting point 172° C.

Example 468

N-[2-(5-{2-[(1,1-dioxidetetrahydro-2H-thiopyran-4-yl)amino]ethyl}-4,5-dihydro-1,3-thiazol-2-yl)-1H-indol-7-yl]-N-methylthiophene-2-sulfonamide hydrochloride

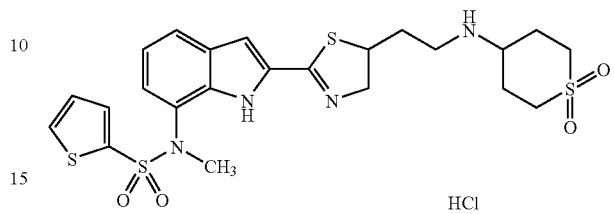

In the same manner as in Example 464, the title compound (108 mg, yield 38%) was obtained as yellow crystals from N-methyl-N-{2-[5-(2-oxoethyl)-4,5-dihydro-1,3-thiazol-2-yl]-1H-indol-7-yl}thiophene-2-sulfonamide (200 mg) and tetrahydro-2H-thiopyran-4-amine 1,1-dioxide (100 mg). melting point 195° C.

Example 469

N-[2-(5-formyl-4,5-dihydro-1,3-thiazol-2-yl)-1H-indol-7-yl]-N-methylthiophene-2-sulfonamide

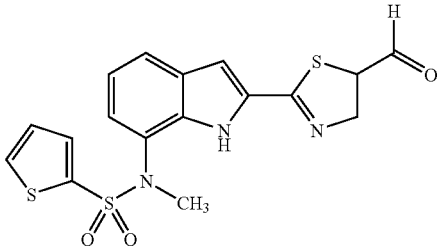

A mixture of N-{2-[5-(dimethoxymethyl)-4,5-dihydro-1,3-thiazol-2-yl]-1H-indol-7-yl}-N-methylthiophene-2-sulfonamide (1.18 g), trifluoroacetic acid (3 mL), concentrated sulfuric acid (3 mL) and water (10 mL) was stirred at 50° C. for 2 hr. The reaction mixture was allowed to cool to room temperature, neutralized with saturated aqueous sodium hydrogencarbonate solution, and extracted with ethyl acetate. The ethyl acetate layer was washed with saturated brine, dried (MgSO$_4$), and concentrated. The obtained residue was subjected to silica gel column chromatography to give the title compound (1.1 g, yield 99%) as a brown amorphous solid from a fraction eluted with ethyl acetate:hexane=50:50. MS: 406 (MH$^+$).

Example 470

N-methyl-N-{2-[5-(thiomorpholinomethyl)-4,5-dihydro-1,3-thiazol-2-yl]-1H-indol-7-yl}thiophene-2-sulfonamide

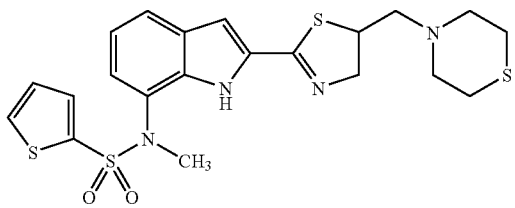

In the same manner as in Example 404, the title compound (18 mg, yield 17%) was obtained as white crystals from N-[2-(5-formyl-4,5-dihydro-1,3-thiazol-2-yl)-1H-indol-7-yl]-N-methylthiophene-2-sulfonamide (88 mg) and thiomorpholine (30 mg). melting point 178° C.

Example 471

N-methyl-N-(2-{5-[(1-oxidothiomorpholino)methyl]-4,5-dihydro-1,3-thiazol-2-yl}-1H-indol-7-yl)thiophene-2-sulfonamide

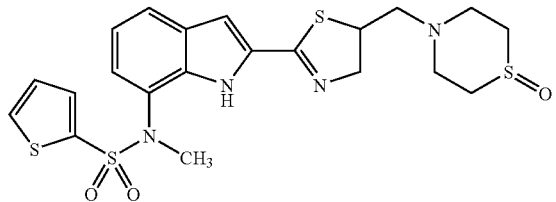

To a mixture of N-[2-(5-formyl-4,5-dihydro-1,3-thiazol-2-yl)-1H-indol-7-yl]-N-methylthiophene-2-sulfonamide (550 mg), thiomorpholine 1-oxide hydrochloride (310 mg), triethylamine (200 µL) and tetrahydrofuran (15 mL) was added sodium triacetoxyborohydride (420 mg) at room temperature, and the mixture was stirred for 10 min. Saturated aqueous sodium hydrogencarbonate solution was added to the reaction mixture, and the mixture was extracted with ethyl acetate. The ethyl acetate layer was washed with saturated brine, dried (MgSO₄), and concentrated. The obtained residue was subjected to silica gel column chromatography to give a colorless oil from a fraction eluted with ethyl acetate:methanol=90:10. The obtained colorless oil was purified by preparative HPLC to give the title compound (230 mg, yield 35%) as white crystals. melting point 204° C.

Example 472

N-(2-{5-[(1,1-dioxidothiomorpholino)methyl]-4,5-dihydro-1,3-thiazol-2-yl}-1H-indol-7-yl)-N-methylthiophene-2-sulfonamide

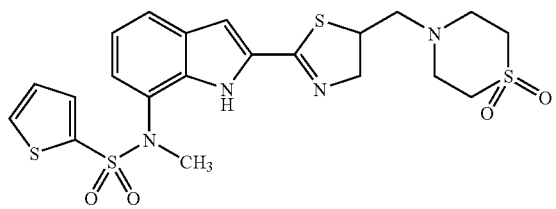

To a mixture of N-[2-(5-formyl-4,5-dihydro-1,3-thiazol-2-yl)-1H-indol-7-yl]-N-methylthiophene-2-sulfonamide (550 mg), thiomorpholine 1,1-dioxide (270 mg) and tetrahydrofuran (15 mL) was added sodium triacetoxyborohydride (420 mg) at room temperature, and the mixture was stirred for 10 min. Saturated aqueous sodium hydrogencarbonate solution was added to the reaction mixture, and the mixture was extracted with ethyl acetate. The ethyl acetate layer was washed with saturated brine, dried (MgSO₄), and concentrated. The obtained residue was subjected to silica gel column chromatography to give pale-pink crystals from a fraction eluted with ethyl acetate:hexane=50:50. The obtained pale-pink crystals were purified by preparative HPLC to give the title compound (140 mg, yield 20%) as white crystals. melting point 242° C.

Example 473

N-{2-[5-(dimethoxymethyl)-4,5-dihydro-1,3-thiazol-2-yl]-1H-indol-7-yl}pyridine-2-sulfonamide

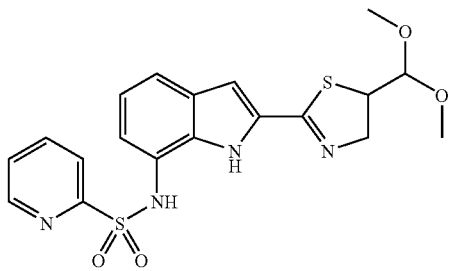

To a solution of triphenylphosphine oxide (849 mg) in dichloromethane (10 mL) was added trifluoromethanesulfonic anhydride (515 µL) under ice-cooling, and the mixture was stirred for 10 min. A solution of N-[2-(benzylthio)-3,3-dimethoxypropyl]-7-[(pyridin-2-ylsulfonyl)amino]-1H-indole-2-carboxamide (1.5 g) and thioanisole (690 mg) in dichloromethane (10 mL) was added dropwise to the reaction mixture under ice-cooling, and the mixture was stirred for 10 min. Saturated aqueous sodium hydrogencarbonate solution was added to the reaction mixture, and the mixture was extracted with ethyl acetate. The ethyl acetate layer was washed with saturated brine, dried (MgSO₄), and concentrated. The obtained residue was subjected to silica gel column chromatography to give white crystals from a fraction eluted with ethyl acetate:hexane=50:50. The white crystals were purified by preparative HPLC to give the title compound (487 mg, yield 40%) as white crystals. melting point 153° C.

Example 474

N-(2-{5-[(1-oxidothiomorpholino)methyl]-4,5-dihydro-1,3-thiazol-2-yl}-1H-indol-7-yl)pyridine-2-sulfonamide A mixture of N-{2-[5-(dimethoxymethyl)-4,5-dihydro-1,3-thiazol-2-yl]-1H-indol-7-yl}pyridine-2-sulfonamide (240 mg), trifluoroacetic acid (4 mL), concentrated sulfuric acid (4 mL) and water (10 mL) was stirred at 50° C. for 4 hr. The reaction mixture was allowed to cool to room temperature, neutralized with saturated aqueous sodium hydrogencarbonate solution, and extracted with ethyl acetate. The ethyl acetate layer was washed with saturated brine, dried (MgSO₄), and concentrated. The obtained residue was dissolved in tetrahydrofuran (5 mL), and then thiomorpholine 1-oxide (110 mg), triethylamine (140 μL) and sodium triacetoxyborohydride (235 mg) were added at room temperature. The mixture was stirred for 10 min. Saturated aqueous sodium hydrogencarbonate solution was added to the reaction mixture, and the mixture was extracted with ethyl acetate. The ethyl acetate layer was washed with saturated brine, dried (MgSO₄), and concentrated. The obtained residue was subjected to silica gel column chromatography to give the title compound (37.3 mg, yield 14%) as white crystals from a fraction eluted with ethyl acetate:methanol=90:10. melting point 270° C.

Example 475

N-(2-{5-[(1,1-dioxidothiomorpholino)methyl]-4,5-dihydro-1,3-thiazol-2-yl}-1H-indol-7-yl)pyridine-2-sulfonamide

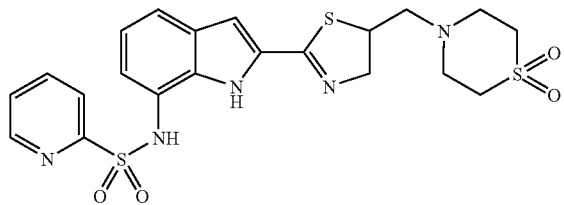

In the same manner as in Example 474, the title compound (10.1 mg, yield 1.8%) was obtained as white crystals from N-{2-[5-(dimethoxymethyl)-4,5-dihydro-1,3-thiazol-2-yl]-1H-indol-7-yl}pyridine-2-sulfonamide (500 mg) and thiomorpholine 1,1-dioxide (190 mg). melting point 252° C.

Example 476

N-{2-[5-(dimethoxymethyl)-4,5-dihydro-1,3-thiazol-2-yl]-1H-indol-7-yl}-N-methylpyridine-2-sulfonamide

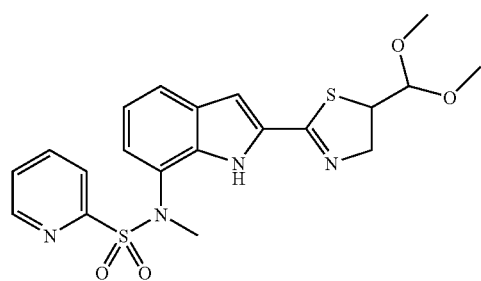

In the same manner as in Reference Example 197, the title compound (6.66 g, yield 92%) was obtained as white crystals from N-{2-[5-(dimethoxymethyl)-4,5-dihydro-1,3-thiazol-2-yl]-1H-indol-7-yl}pyridine-2-sulfonamide (7 g). melting point 131° C.

Example 477

N-[2-(5-formyl-4,5-dihydro-1,3-thiazol-2-yl)-1H-indol-7-yl]-N-methylpyridine-2-sulfonamide

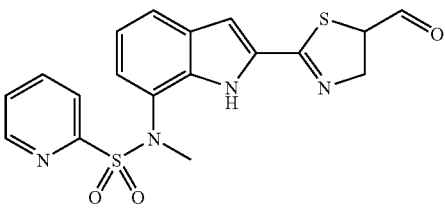

In the same manner as in Example 469, the title compound (4.3 g, yield 91%) was obtained as a pink amorphous solid from N-{2-[5-(dimethoxymethyl)-4,5-dihydro-1,3-thiazol-2-yl]-1H-indol-7-yl}-N-methylpyridine-2-sulfonamide (5.3 g).

MS: 401 (MH⁺).

Example 478

N-[2-(5-{[(2-hydroxyethyl)(methyl)amino]methyl}-4,5-dihydro-1,3-thiazol-2-yl)-1H-indol-7-yl]-N-methylpyridine-2-sulfonamide hydrochloride

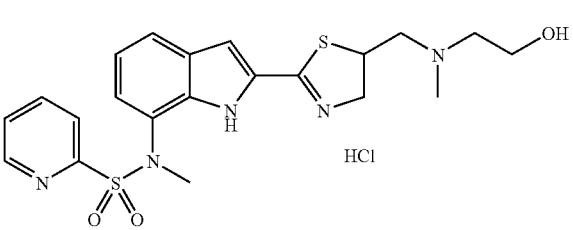

In the same manner as in Example 456, the title compound (40 mg, yield 16%) was obtained as white crystals from N-[2-(5-formyl-4,5-dihydro-1,3-thiazol-2-yl)-1H-indol-7-yl]-N-methylpyridine-2-sulfonamide (200 mg) and 2-(methylamino)ethanol (56 mg). melting point 185° C.

Example 479

N-(2-{5-[(3-hydroxyazetidin-1-yl)methyl]-4,5-dihydro-1,3-thiazol-2-yl}-1H-indol-7-yl)-N-methylpyridine-2-sulfonamide hydrochloride

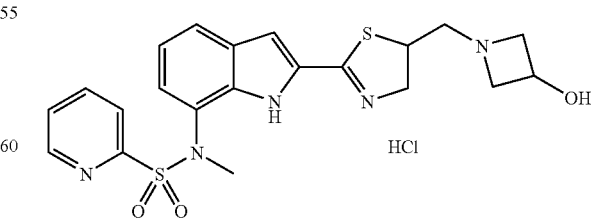

In the same manner as in Example 456, the title compound (166 mg, yield 67%) was obtained as white crystals from N-[2-(5-formyl-4,5-dihydro-1,3-thiazol-2-yl)-1H-indol-7- yl]-N-methylpyridine-2-sulfonamide (200 mg) and 3-hydroxyazetidine (82 mg). melting point 139° C.

Example 480

N-(2-{5-[(4-hydroxypiperidino)methyl]-4,5-dihydro-1,3-thiazol-2-yl}-1H-indol-7-yl)-N-methylpyridine-2-sulfonamide

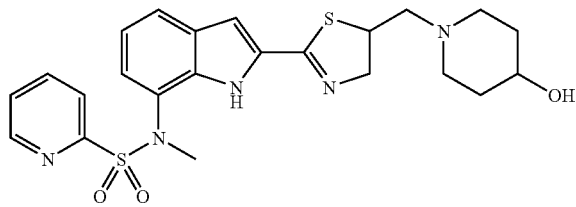

In the same manner as in Example 404, the title compound (184 mg, yield 74%) was obtained as white crystals from N-[2-(5-formyl-4,5-dihydro-1,3-thiazol-2-yl)-1H-indol-7-yl]-N-methylpyridine-2-sulfonamide (200 mg) and 4-hydroxypiperidine (75 mg). melting point 160° C.

Example 481

N-{2-[5-(hydroxymethyl)-4,5-dihydro-1,3-thiazol-2-yl]-1H-indol-7-yl}-N-methylpyridine-2-sulfonamide

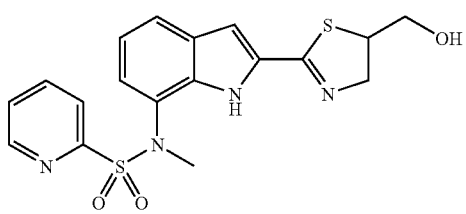

To a solution of N-[2-(5-formyl-4,5-dihydro-1,3-thiazol-2-yl)-1H-indol-7-yl]-N-methylpyridine-2-sulfonamide (200 mg) in tetrahydrofuran (2 mL) and ethanol (2 mL) was added sodium tetrahydroborate (38 mg), and the mixture was stirred at room temperature for 30 min. Saturated aqueous ammonium chloride solution was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (160 mg, yield 80%) as a white amorphous solid from a fraction eluted with ethyl acetate. MS: 403 (MH$^+$).

Example 482

(2-{7-[methyl(pyridin-2-ylsulfonyl)amino]-1H-indol-2-yl}-4,5-dihydro-1,3-thiazol-5-yl)methyl methanesulfonate

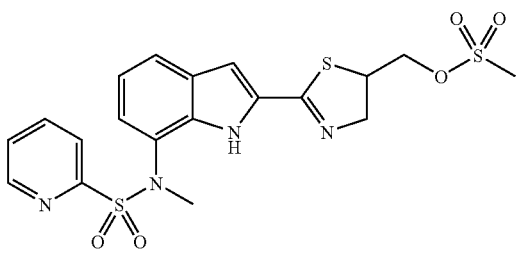

To a solution of N-{2-[5-(hydroxymethyl)-4,5-dihydro-1,3-thiazol-2-yl]-1H-indol-7-yl}-N-methylpyridine-2-sulfonamide (2.0 g) and triethylamine (1.4 mL) in tetrahydrofuran (50 mL) was added methanesulfonyl chloride (860 mg), and the mixture was stirred at room temperature for 1 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give the title compound (1.85 g, yield 77%) as a white amorphous solid from a fraction eluted with ethyl acetate. MS: 481 (MH$^+$).

Example 483

N-[2-(5-{[(2-hydroxyethyl)amino]methyl}-4,5-dihydro-1,3-thiazol-2-yl)-1H-indol-7-yl]-N-methylpyridine-2-sulfonamide dihydrochloride

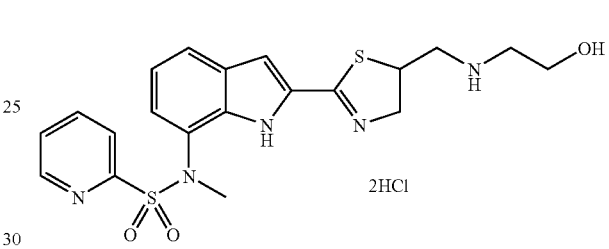

A mixture of (2-{7-[methyl(pyridin-2-ylsulfonyl)amino]-1H-indol-2-yl}-4,5-dihydro-1,3-thiazol-5-yl)methyl methanesulfonate (240 mg), 2-aminoethanol (61 mg), potassium carbonate (138 mg) and N,N-dimethylformamide (5 mL) was stirred at room temperature for 16 hr. Water was added to the reaction mixture, and the mixture was extracted with ethyl acetate. The ethyl acetate layer was washed with saturated brine, dried (MgSO$_4$), and concentrated. The obtained residue was purified by subjected to silica gel column chromatography to give a colorless oil from a fraction eluted with ethyl acetate:methanol=90:10. The colorless oil was dissolved in ethyl acetate (3 mL), and 4N hydrogen chloride-ethyl acetate solution (1 mL) was added. The precipitated crystals were collected by filtration, washed with diethyl ether, and dried to give the title compound (110 mg, yield 42%) as a white amorphous solid. MS: 446 (MH$^+$).

Example 484

N-[2-(5-{[(2-hydroxy-2-methylpropyl)amino]methyl}-4,5-dihydro-1,3-thiazol-2-yl)-1H-indol-7-yl]-N-methylpyridine-2-sulfonamide dihydrochloride

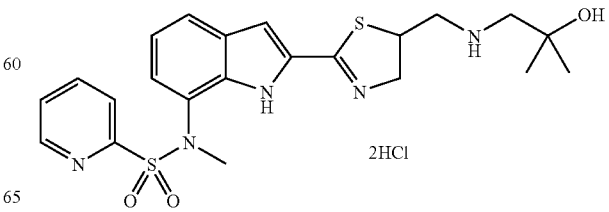

423

In the same manner as in Example 483, the title compound (75 mg, yield 27%) was obtained as a white amorphous solid from (2-{7-[methyl(pyridin-2-ylsulfonyl)amino]-1H-indol-2-yl}-4,5-dihydro-1,3-thiazol-5-yl)methyl methanesulfonate (240 mg) and 1-amino-2-methylpropan-2-ol (89 mg). MS: 474 (MH$^+$).

Example 485

N-(2-{5-[(2,5-dioxopyrrolidin-1-yl)methyl]-4,5-dihydro-1,3-thiazol-2-yl}-1H-indol-7-yl)-N-methylpyridine-2-sulfonamide hydrochloride

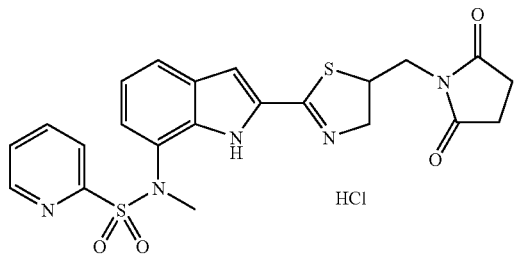

A mixture of (2-{7-[methyl(pyridin-2-ylsulfonyl)amino]-1H-indol-2-yl}-4,5-dihydro-1,3-thiazol-5-yl)methyl methanesulfonate (200 mg), succinimide (100 mg), potassium carbonate (200 mg) and N,N-dimethylformamide (5 mL) was stirred at 50° C. for 3 hr. Water was added to the reaction mixture, and the mixture was extracted with ethyl acetate. The ethyl acetate layer was washed with saturated brine, dried (MgSO$_4$), and concentrated. The obtained residue was subjected to silica gel column chromatography to give a colorless oil from a fraction eluted with ethyl acetate:methanol=90:10. The colorless oil was dissolved in ethyl acetate (3 mL), and 4N hydrogen chloride-ethyl acetate solution (1 mL) was added. The precipitated crystals were collected by filtration, washed with diethyl ether, and dried to give the title compound (192 mg, yield 89%) as white crystals. melting point 181° C.

Example 486

N-{2-[5-(1H-imidazol-1-ylmethyl)-4,5-dihydro-1,3-thiazol-2-yl]-1H-indol-7-yl}-N-methylpyridine-2-sulfonamide dihydrochloride

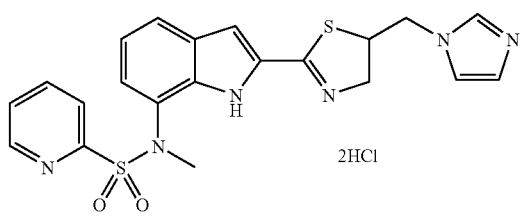

In the same manner as in Example 483, the title compound (138 mg, yield 66%) was obtained as yellow crystals from (2-{7-[methyl(pyridin-2-ylsulfonyl)amino]-1H-indol-2-yl}-4,5-dihydro-1,3-thiazol-5-yl)methyl methanesulfonate (195 mg) and imidazole (70 mg). melting point 142° C.

Example 487

N-methyl-N-(2-{5-[(3-oxopyrazolidin-1-yl)methyl]-4,5-dihydro-1,3-thiazol-2-yl}-1H-indol-7-yl)pyridine-2-sulfonamide

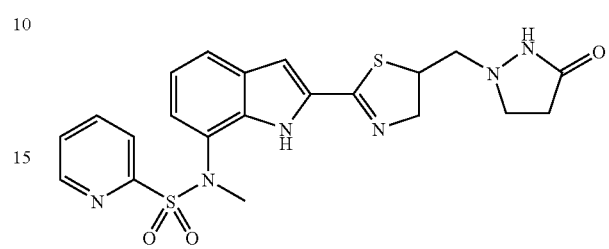

In the same manner as in Example 404, the title compound (86 mg, yield 36%) was obtained as a white amorphous solid from N-[2-(5-formyl-4,5-dihydro-1,3-thiazol-2-yl)-1H-indol-7-yl]-N-methylpyridine-2-sulfonamide (200 mg) and pyrazolidin-3-one (123 mg). MS: 471 (MH$^+$).

Example 488

N-{2-[5-(dimethoxymethyl)-4,5-dihydro-1,3-thiazol-2-yl]-5-methoxy-1H-indol-7-yl}-N-methylpyridine-2-sulfonamide

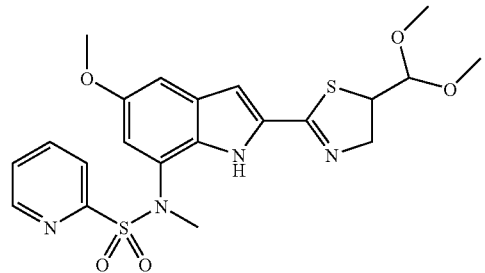

In the same manner as in Example 473, the title compound (910 mg, yield 28%) was obtained as a white amorphous solid from N-[2-(benzylthio)-3,3-dimethoxypropyl]-5-methoxy-7-[methyl(pyridin-2-ylsulfonyl)amino]-1H-indole-2-carboxamide (3.9 g). MS: 477 (MH$^+$).

Example 489

N-[2-(5-formyl-4,5-dihydro-1,3-thiazol-2-yl)-5-methoxy-1H-indol-7-yl]-N-methylpyridine-2-sulfonamide

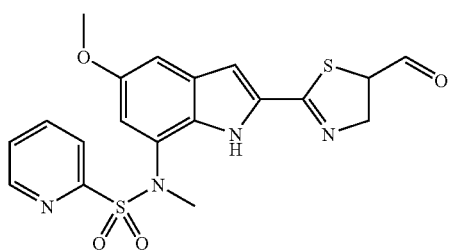

In the same manner as in Example 469, the title compound (495 mg, yield 61%) was obtained as a yellow amorphous solid from N-{2-[5-(dimethoxymethyl)-4,5-dihydro-1,3-thiazol-2-yl]-5-methoxy-1H-indol-7-yl}-N-methylpyridine-2-sulfonamide (910 mg). MS: 431 (MH$^+$).

Example 490

N-(5-methoxy-2-{5-[(1-oxidothiomorpholino)methyl]-4,5-dihydro-1,3-thiazol-2-yl}-1H-indol-7-yl)-N-methylpyridine-2-sulfonamide

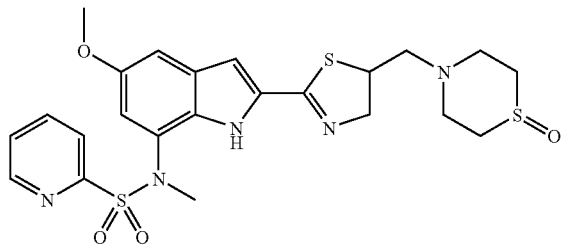

In the same manner as in Example 404, the title compound (101 mg, yield 50%) was obtained as white crystals from N-[2-(5-formyl-4,5-dihydro-1,3-thiazol-2-yl)-5-methoxy-1H-indol-7-yl]-N-methylpyridine-2-sulfonamide (165 mg) and thiomorpholine 1-oxide hydrochloride (156 mg). melting point 228° C.

Example 491

N-(2-{5-[(3-hydroxyazetidin-1-yl)methyl]-4,5-dihydro-1,3-thiazol-2-yl}-5-methoxy-1H-indol-7-yl)-N-methylpyridine-2-sulfonamide dihydrochloride

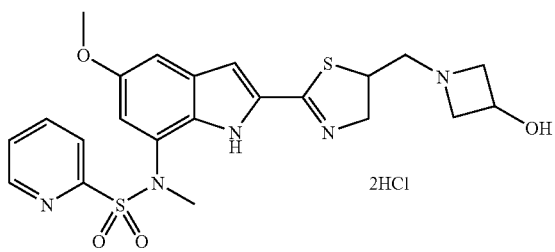

In the same manner as in Example 456, the title compound (106 mg, yield 50%) was obtained as yellow crystals from N-[2-(5-formyl-4,5-dihydro-1,3-thiazol-2-yl)-5-methoxy-1H-indol-7-yl]-N-methylpyridine-2-sulfonamide (165 mg) and 3-hydroxyazetidine (110 mg). melting point 146° C.

Example 492

N-(5-methoxy-2-{5-[(3-oxopyrazolidin-1-yl)methyl]-4,5-dihydro-1,3-thiazol-2-yl}-1H-indol-7-yl)-N-methylpyridine-2-sulfonamide dihydrochloride

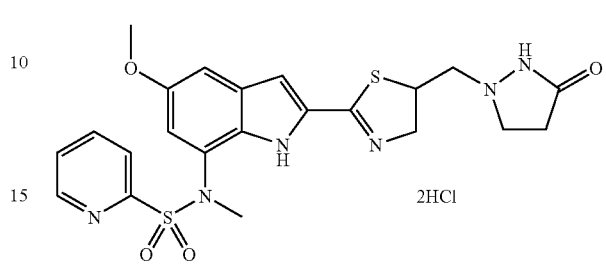

In the same manner as in Example 456, the title compound (77 mg, yield 35%) was obtained as yellow crystals from N-[2-(5-formyl-4,5-dihydro-1,3-thiazol-2-yl)-5-methoxy-1H-indol-7-yl]-N-methylpyridine-2-sulfonamide (165 mg) and pyrazolidin-3-one (123 mg). melting point 168° C.

Example 493

N-{5-(2-methoxyethoxy)-2-[5-(thiomorpholinomethyl)-4,5-dihydro-1,3-thiazol-2-yl]-1H-indol-7-yl}-N-methylpyridine-2-sulfonamide

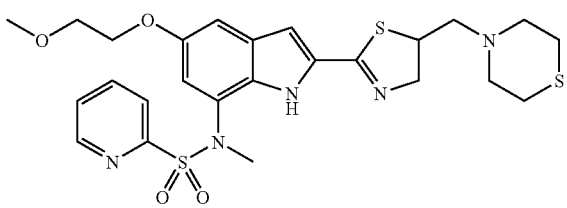

In the same manner as in Example 404, the title compound (52 mg, yield 33%) was obtained as white crystals from N-[2-(5-formyl-4,5-dihydro-1,3-thiazol-2-yl)-5-(2-methoxyethoxy)-1H-indol-7-yl]-N-methylpyridine-2-sulfonamide (200 mg) and thiomorpholine (62 mg). melting point 138° C.

Example 494

(2-{3-fluoro-7-[methyl(2-thienylsulfonyl)amino]-1H-indol-2-yl}-4,5-dihydro-1,3-thiazol-5-yl)acetic acid

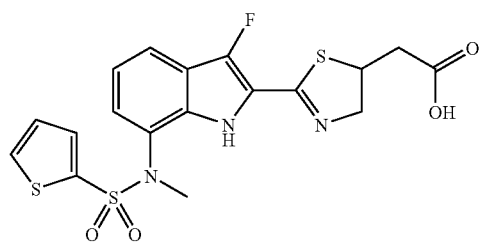

To a solution of ethyl (2-{3-fluoro-7-[methyl(2-thienylsulfonyl)amino]-1H-indol-2-yl}-4,5-dihydro-1,3-thiazol-5-yl)acetate (0.1 g) in tetrahydrofuran (1 mL) and ethanol (1 mL) was added 2N aqueous sodium hydroxide solution (0.15 mL), and the mixture was stirred at room temperature for 1 hr, and then at 50° C. for 1 hr. The mixture was acidified with 1N hydrochloric acid, and extracted with ethyl acetate. The organic layer was washed with water and saturated brine, dried (MgSO$_4$), and concentrated. The obtained residue was recrystallized from ethyl acetate to give the title compound (0.080 g, yield 85%) as colorless crystals. melting point 213-214° C.

Example 495

2-(2-{3-fluoro-7-[methyl(2-thienylsulfonyl)amino]-1H-indol-2-yl}-4,5-dihydro-1,3-thiazol-5-yl)acetamide

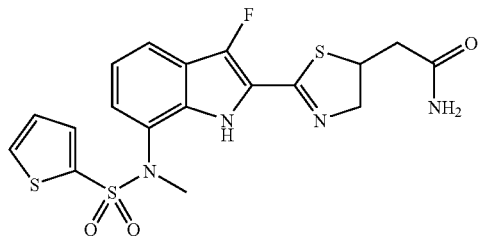

To a solution of (2-{3-fluoro-7-[methyl(2-thienylsulfonyl)amino]-1H-indol-2-yl}-4,5-dihydro-1,3-thiazol-5-yl)acetic acid (97.2 mg) in tetrahydrofuran (2 mL) and acetonitrile (2 mL) were added 1-ethyl-3-(3-dimethylaminopropyl)carbodiimide hydrochloride (48 mg) and 1-hydroxybenzotriazole monohydrate (39 mg), and the mixture was stirred at room temperature for 1 hr. Aqueous ammonia (28%, 2 mL) was added, and the mixture was stirred at room temperature for 30 min, and diluted with ethyl acetate. The organic layer was washed with saturated aqueous sodium hydrogencarbonate, water and saturated brine, dried over anhydrous magnesium sulfate, and filtrated, and the filtrate was concentrated under reduced pressure. The residue was subjected to silica gel column chromatography (eluate: ethyl acetate), and the obtained solid was recrystallized (ethyl acetate-diisopropyl ether) to give the title compound (50.1 mg, yield 53%) as a colorless solid. melting point 204-205° C.

Example 496

N-(5-[(1S)-2-methoxy-1-methylethoxy]-2-{5-[(1-oxidothiomorpholino)methyl]-4,5-dihydro-1,3-thiazol-2-yl}-1H-indol-7-yl)-N-methylpyridine-2-sulfonamide

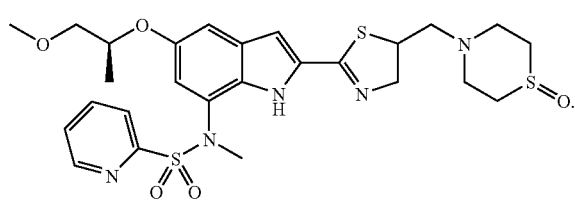

To a solution of N-{5-[(1S)-2-methoxy-1-methylethoxy]-2-[5-(thiomorpholinomethyl)-4,5-dihydro-1,3-thiazol-2-yl]-1H-indol-7-yl}-N-methylpyridine-2-sulfonamide (80 mg) in dichloromethane (2 mL) was added m-chloroperbenzoic acid (16 mg) under ice-cooling, and the mixture was stirred for 30 min. Aqueous sodium thiosulfate solution was added, and the mixture was diluted with ethyl acetate. The organic layer was washed with water and saturated brine, dried over anhydrous magnesium sulfate, and concentrated under reduced pressure. The residue was recrystallized (acetone-hexane-diisopropyl ether) to give the title compound (37.5 mg, yield 46%) as a colorless solid. melting point 175-176° C.

Example 497

N-{5-(2-hydroxyethoxy)-2-[5-(thiomorpholinomethyl)-4,5-dihydro-1,3-thiazol-2-yl]-1H-indol-7-yl}-N-methylpyridine-2-sulfonamide

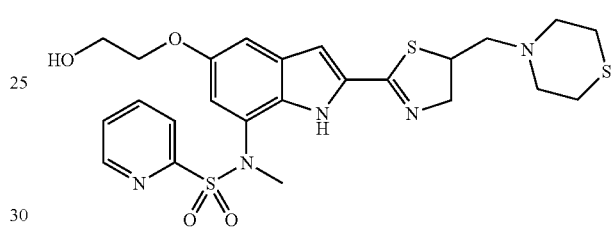

To a solution of ethyl ({7-[methyl(pyridin-2-ylsulfonyl)amino]-2-[5-(thiomorpholinomethyl)-4,5-dihydro-1,3-thiazol-2-yl]-1H-indol-5-yl}oxy)acetate (400 mg) in tetrahydrofuran (5 mL) was added lithium borohydride (18 mg) under ice-cooling, and the mixture was stirred at room temperature for 3 days. 1N Hydrochloric acid was added under ice-cooling, and the mixture was basified with saturated aqueous sodium hydrogencarbonate, and extracted with ethyl acetate. The organic layer was washed with water and saturated brine, dried over anhydrous magnesium sulfate, and concentrated under reduced pressure. The residue was crystallized from ethyl acetate to give the title compound (205 mg, yield 55%) as a colorless solid. melting point 160-162° C.

Example 498

N-(5-(2-hydroxyethoxy)-2-{5-[(1-oxidothiomorpholino)methyl]-4,5-dihydro-1,3-thiazol-2-yl}-1H-indol-7-yl)-N-methylpyridine-2-sulfonamide

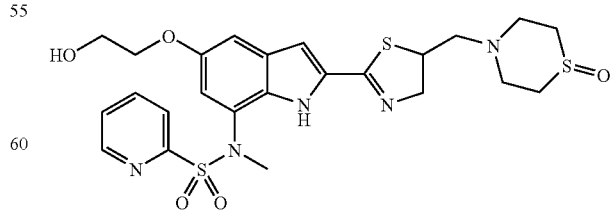

In the same manner as in Example 496, the title compound (59 mg, yield 45%) was obtained as yellow crystals from N-{5-(2-hydroxyethoxy)-2-[5-(thiomorpholinomethyl)-4,5- dihydro-1,3-thiazol-2-yl]-1H-indol-7-yl}-N-methylpyridine-2-sulfonamide (102 mg). melting point 160-162° C.

Example 499

N-methyl-N-[2-{5-[(1-oxidothiomorpholino)methyl]-4,5-dihydro-1,3-thiazol-2-yl}-5-(2-oxopropoxy)-1H-indol-7-yl]pyridine-2-sulfonamide

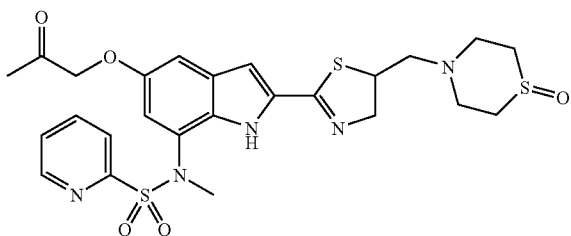

In the same manner as in Example 496, the title compound (81 mg, yield 62%) was obtained as yellow crystals from N-methyl-N-{5-(2-oxopropoxy)-2-[5-(thiomorpholinomethyl)-4,5-dihydro-1,3-thiazol-2-yl]-1H-indol-7-yl}pyridine-2-sulfonamide (127 mg). melting point 110-112° C.

Example 500 ethyl ({7-[methyl(pyridin-2-ylsulfonyl)amino]-2-[5-(thiomorpholinomethyl)-4,5-dihydro-1,3-thiazol-2-yl]-1H-indol-5-yl}oxy)acetate

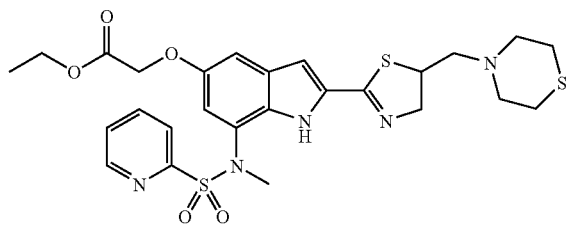

To a solution of N-{5-hydroxy-2-[5-(thiomorpholinomethyl)-4,5-dihydro-1,3-thiazol-2-yl]-1H-indol-7-yl}-N-methylpyridine-2-sulfonamide (800 mg) in N,N-dimethylformamide (10 mL) were added potassium carbonate (264 mg) and ethyl bromoacetate (0.18 mL), and the mixture was stirred at 50° C. for 6 hr. The mixture was diluted with ethyl acetate, washed with water and saturated brine, dried over anhydrous magnesium sulfate, and concentrated under reduced pressure. The residue was purified by silica gel column chromatography (hexane:ethyl acetate=85:15-0:1) to give the title compound (724 mg, yield 76%) as a pale-yellow powder.

MS: 590 (MH$^+$).

Example 501

N-methyl-N-{5-(2-oxopropoxy)-2-[5-(thiomorpholinomethyl)-4,5-dihydro-1,3-thiazol-2-yl]-1H-indol-7-yl}pyridine-2-sulfonamide

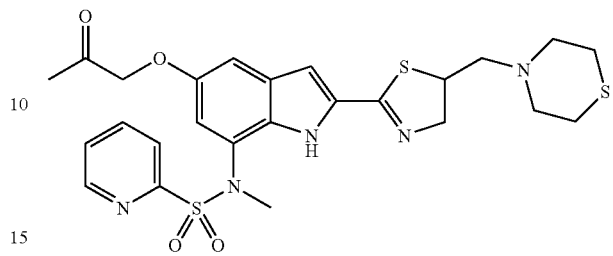

In the same manner as in Example 500, the title compound (456 mg, yield 79%) was obtained as a pale-yellow powder from N-{5-hydroxy-2-[5-(thiomorpholinomethyl)-4,5-dihydro-1,3-thiazol-2-yl]-1H-indol-7-yl}-N-methylpyridine-2-sulfonamide (517 mg) and bromoacetone (205 mg). MS: 560 (MH$^+$).

Example 502

({7-[methyl(pyridin-2-ylsulfonyl)amino]-2-[5-(thiomorpholinomethyl)-4,5-dihydro-1,3-thiazol-2-yl]-1H-indol-5-yl}oxy)acetic acid

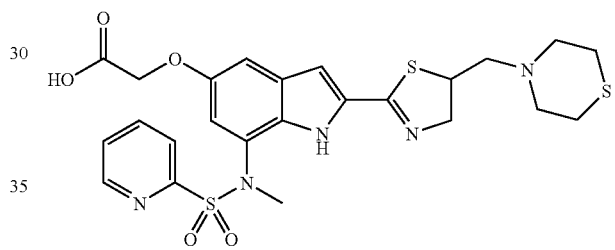

To a solution of ethyl ({7-[methyl(pyridin-2-ylsulfonyl)amino]-2-[5-(thiomorpholinomethyl)-4,5-dihydro-1,3-thiazol-2-yl]-1H-indol-5-yl}oxy)acetate (275 mg) in tetrahydrofuran (2 mL) and ethanol (2 mL) was added 1N aqueous sodium hydroxide solution (0.70 mL), and the mixture was stirred overnight at room temperature. The organic solvent was evaporated under reduced pressure, and the residue was neutralized with 1N hydrochloric acid. The mixture was extracted with a mixed solvent of tetrahydrofuran-ethyl acetate, and the combined organic layers were washed with saturated brine, dried over anhydrous magnesium sulfate, and concentrated under reduced pressure. The residue was crystallized from ethyl acetate to give the title compound (137 mg, yield 53%) as colorless crystals. melting point 132-134° C.

Example 503

2-({7-[methyl(pyridin-2-ylsulfonyl)amino]-2-[5-(thiomorpholinomethyl)-4,5-dihydro-1,3-thiazol-2-yl]-1H-indol-5-yl}oxy)acetamide

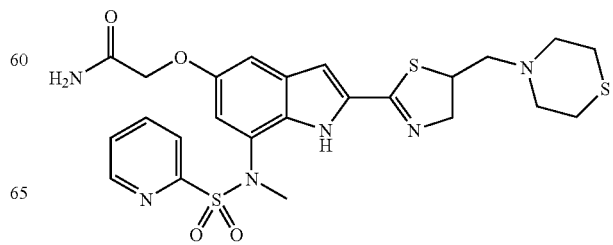

In the same manner as in Example 495, the title compound (31.7 mg, yield 30%) was obtained as colorless crystals from ({7-[methyl(pyridin-2-ylsulfonyl)amino]-2-[5-(thiomorpholinomethyl)-4,5-dihydro-1,3-thiazol-2-yl]-1H-indol-5-yl}oxy)acetic acid (100 mg). melting point 192-193° C.

Example 504

2-[(7-[methyl(pyridin-2-ylsulfonyl)amino]-2-{5-[(1-oxidothiomorpholino)methyl]-4,5-dihydro-1,3-thiazol-2-yl}-1H-indol-5-yl)oxy]acetamide

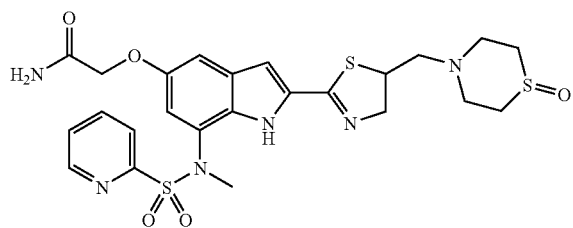

To a solution of 2-({7-[methyl(pyridin-2-ylsulfonyl)amino]-2-[5-(thiomorpholinomethyl)-4,5-dihydro-1,3-thiazol-2-yl]-1H-indol-5-yl}oxy)acetamide (31.7 mg) in tetrahydrofuran (1 mL) and ethanol (1 mL) were added water (1 mL) and OXONE (registered trade mark, 20 mg), and the mixture was stirred at room temperature for 3 hr. Aqueous sodium thiosulfate solution was added, and the mixture diluted with ethyl acetate. The organic layer was washed with water and saturated brine, dried over anhydrous magnesium sulfate, and concentrated under reduced pressure. The residue was crystallized from ethyl acetate-diisopropyl ether to give the title compound (15.7 mg, yield 48%) as colorless crystals. melting point 160-161° C.

Example 505

N-{5-[(1S)-2-methoxy-1-methylethoxy]-2-[5-(thiomorpholinomethyl)-4,5-dihydro-1,3-thiazol-2-yl]-1H-indol-7-yl}-N-methylpyridine-2-sulfonamide

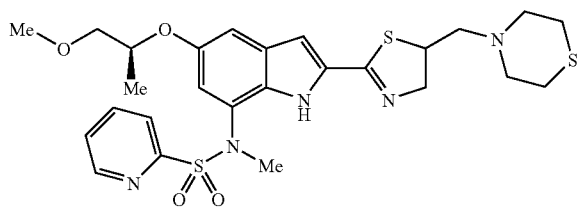

To a solution of N-{5-hydroxy-2-[5-(thiomorpholinomethyl)-4,5-dihydro-1,3-thiazol-2-yl]-1H-indol-7-yl}-N-methylpyridine-2-sulfonamide (145 mg) in toluene (2 mL) and tetrahydrofuran (1 mL) were added tributylphosphine (0.22 mL), (2R)-1-methoxypropan-2-ol (0.057 mL) and 1,1'-(azodicarbonyl)dipiperidine (220 mg), and the mixture was stirred at 80° C. for 3 hr, and concentrated. The residue was diluted with ethyl acetate, and subjected to basic silica gel column chromatography (eluate: ethyl acetate), and the obtained crude product was purified by silica gel column chromatography (hexane:ethyl acetate=3:1-1:2) to give the title compound (80 mg, yield 48%) as a colorless powder.
MS: 576 (MH$^+$).

Example 506 ethyl 1-[(2-{7-[methyl(pyridin-2-ylsulfonyl)amino]-1H-indol-2-yl}-4,5-dihydro-1,3-thiazol-5-yl)methyl]-1H-imidazole-2-carboxylate

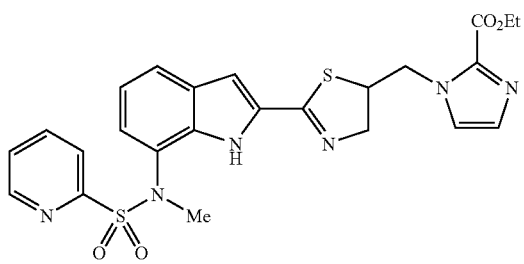

A mixture of (2-{7-[methyl(pyridin-2-ylsulfonyl)amino]-1H-indol-2-yl}-4,5-dihydro-1,3-thiazol-5-yl)methyl methanesulfonate (250 mg), ethyl 1H-imidazole-2-carboxylate (146 mg), potassium carbonate (144 mg) and N,N-dimethylformamide (5 mL) was stirred at 60° C. for 4.5 hr. Water was added to the reaction mixture, and the mixture was extracted with ethyl acetate. The organic layer was washed successively with water and saturated brine, dried over magnesium sulfate, and filtrated, and the filtrate was concentrated under reduced pressure. The residue was silica gel column chromatography (ethyl acetate:hexane=15:85-100:0) to give the title compound (227 mg, yield 83%) as a orange oil.
MS: 525 (MH$^+$).
$^1$H-NMR (CDCl$_3$) δ: 1.46 (3H, t, J=7.2 Hz), 3.33 (3H, s), 4.25-4.39 (2H, m), 4.38-4.52 (4H, m), 4.64 (1H, dd, J=13.1 Hz, 5.9 Hz), 6.96 (1H, d, J=2.3 Hz), 7.08 (1H, t, J=7.8 Hz), 7.12-7.23 (3H, m), 7.56-7.67 (2H, m), 7.92-8.03 (1H, m), 8.04-8.13 (1H, m), 9.08 (1H, d, J=4.2 Hz), 12.07 (1H, brs).

Example 507

N-[2-[5-(dimethoxymethyl)-4,5-dihydro-1,3-thiazol-2-yl]-5-(2-methoxyethoxy)-1H-indol-7-yl]-N,1-dimethyl-1H-imidazole-2-sulfonamide

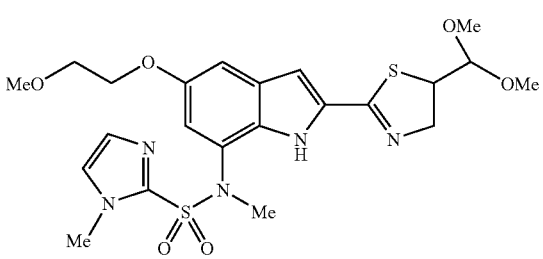

Triphenylphosphine oxide (0.9 g) was dissolved in dichloromethane (10 mL), trifluoromethanesulfonic anhydride (0.55 mL) was added under ice-cooling, and the mixture was stirred for 10 min. A solution of N-[2-(benzylthio)-3,3-dimethoxypropyl]-5-(2-methoxyethoxy)-7-{methyl[(1-methyl-1H-imidazol-2-yl)sulfonyl]amino}-1H-indole-2-carboxamide (1.9 g) and thioanisole (0.7 mL) in dichloromethane (10 mL) was added dropwise under ice-cooling, and the mixture was stirred for 25 min, and then at room temperature for 1 hr. Water was added to the reaction solution, and the mixture was extracted with ethyl acetate. The organic layer was washed with saturated brine, dried over magnesium sulfate, and filtrated, and the filtrate was concentrated under reduced pressure. The residue was silica gel column chromatography (ethyl acetate:hexane=10:90-80:20) to give the title compound (620 mg, yield 39%) as a colorless oil.

$^1$H-NMR (CDCl$_3$) δ: 3.41 (3H, s), 3.43 (3H, s), 3.46 (3H, s), 3.48 (3H, s), 3.74-3.77 (2H, m), 3.80 (3H, s), 4.10-4.15 (3H, m), 4.32-4.40 (2H, m), 4.50-4.57 (1H, m), 6.82 (1H, d, J=2.1 Hz), 6.95 (1H, s), 6.99 (1H, d, J=2.1 Hz), 7.10 (1H, d, J=2.1 Hz), 7.23 (1H, d, J=0.9 Hz), 12.1 (1H, brs).

Example 508

N-[2-(5-{[2-(hydroxymethyl)-1H-imidazol-1-yl]methyl}-4,5-dihydro-1,3-thiazol-2-yl)-1H-indol-7-yl]-N-methylpyridine-2-sulfonamide

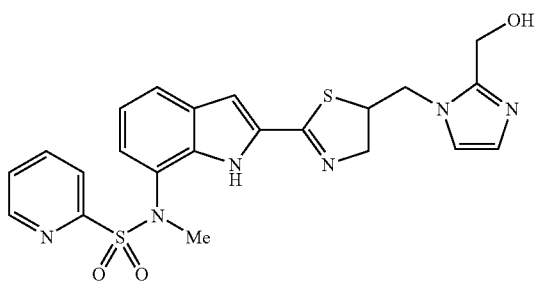

Ethyl 1-[(2-{7-[methyl(pyridin-2-ylsulfonyl)amino]-1H-indol-2-yl}-4,5-dihydro-1,3-thiazol-5-yl)methyl]-1H-imidazole-2-carboxylate (220 mg) was dissolved in a mixed solvent of tetrahydrofuran (8 mL) and methanol (4 mL), lithium borohydride (27 mg) was added, and the mixture was stirred at room temperature for 1 hr. Lithium borohydride (20 mg) was added, and the mixture was stirred at room temperature for 24 hr. Saturated aqueous sodium hydrogencarbonate solution was added to the reaction solution, and the mixture was extracted with ethyl acetate. The organic layer was washed with saturated brine, dried over magnesium sulfate, and filtrated, and the filtrate was concentrated under reduced pressure. The residue was silica gel column chromatography (methanol:ethyl acetate=0:100-15:85) to give the title compound (38 mg, yield 19%) as a white solid. MS: 482 (MH$^+$).

$^1$H-NMR (CDCl$_3$) δ: 3.33 (3H, s), 4.13 (2H, t, J=6.6 Hz), 4.22-4.44 (2H, m), 4.52 (1H, d, J=15.1 Hz), 4.74 (2H, s), 6.90-7.04 (3H, m), 7.09 (1H, t, J=7.8 Hz), 7.14-7.22 (1H, m), 7.62 (2H, d, J=8.3 Hz), 7.91-8.03 (1H, m), 8.04-8.14 (1H, m), 9.07 (1H, d, J=4.2 Hz), 12.10 (1H, s).

Example 509

N-(5-(2-methoxyethoxy)-2-{5-[(1-oxidothiomorpholino)methyl]-4,5-dihydro-1,3-thiazol-2-yl}-1H-indol-7-yl)-N,1-dimethyl-1H-imidazole-2-sulfonamide

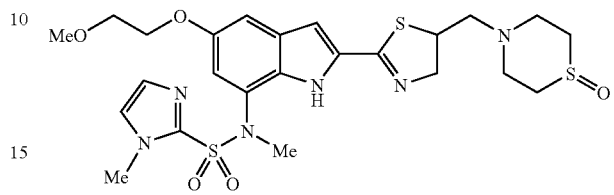

To a mixture of N-[2-[5-(dimethoxymethyl)-4,5-dihydro-1,3-thiazol-2-yl]-5-(2-methoxyethoxy)-1H-indol-7-yl]-N,1-dimethyl-1H-imidazole-2-sulfonamide (280 mg), trifluoroacetic acid (3.5 mL) and water (10.5 mL) was added concentrated sulfuric acid (3.5 mL), and the mixture was stirred at 60° C. for 3.5 hr. The excess trifluoroacetic acid was evaporated under reduced pressure, and the residue was neutralized with sodium hydrogencarbonate. The reaction mixture was extracted with ethyl acetate. The organic layer was washed with saturated brine, dried over magnesium sulfate, and filtrated, and the filtrate was concentrated under reduced pressure. The obtained crude product was dissolved in tetrahydrofuran (10 mL), thiomorpholine 1-oxide hydrochloride (103 mg) and triethylamine (0.1 mL) were added, and the mixture was stirred at room temperature for 15 min. Sodium triacetoxyborohydride (233 mg) was added, and the mixture was stirred at room temperature for 16 hr. Water was added to the reaction solution, and the mixture was extracted with ethyl acetate. The organic layer was washed with saturated brine, dried over magnesium sulfate, and filtrated, and the filtrate was concentrated under reduced pressure. The residue was purified by silica gel column chromatography (methanol:ethyl acetate=0:100-10:90), and the obtained crude product was further purified by preparative HPLC to give the title compound (56 mg, yield 18%) as a white solid. MS: 581 (MH$^+$).

$^1$H-NMR (CDCl$_3$) δ: 2.62-2.65 (2H, m), 2.71-2.94 (6H, m), 3.10-3.22 (2H, m), 3.46 (3H, s), 3.48 (3H, s), 3.52-3.77 (2H, m), 3.80 (3H, s), 4.06-4.15 (3H, m), 4.29-4.46 (2H, m), 6.82 (1H, d, J=2.1 Hz), 6.96 (1H, d, J=0.9 Hz), 6.99 (1H, d, J=2.1 Hz), 7.10 (1H, d, J=2.4 Hz), 7.23 (1H, d, J=0.9 Hz), 12.10 (1H, s).

Example 510

N-[2-[5-(hydroxymethyl)-4,5-dihydro-1,3-thiazol-2-yl]-5-(2-methoxyethoxy)-1H-indol-7-yl]-N,1-dimethyl-1H-imidazole-2-sulfonamide

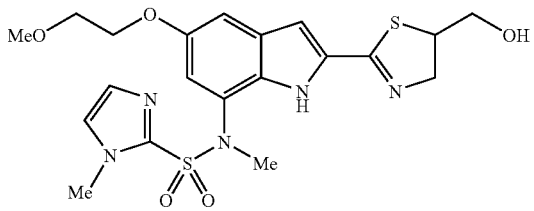

To a mixture of N-[2-[5-(dimethoxymethyl)-4,5-dihydro-1,3-thiazol-2-yl]-5-(2-methoxyethoxy)-1H-indol-7-yl]-N,1-dimethyl-1H-imidazole-2-sulfonamide (335 mg), trifluoroacetic acid (4 mL) and water (12 mL) was added concentrated sulfuric acid (4 mL), and the mixture was stirred at 60° C. for 2 hr. The excess trifluoroacetic acid was evaporated under reduced pressure, and the residue was neutralized with sodium hydrogencarbonate. The reaction mixture was extracted with ethyl acetate. The organic layer was washed with saturated brine, dried over magnesium sulfate, and filtrated, and the filtrate was concentrated under reduced pressure. The obtained crude product was dissolved in a mixed solvent of tetrahydrofuran (3 mL) and ethanol (2 mL), and sodium borohydride (26.5 mg) was added under ice-cooling. The reaction solution was stirred at room temperature for 2 hr, water was added, and the mixture was extracted with ethyl acetate. The organic layer was washed successively with 1N hydrochloric acid, saturated aqueous sodium hydrogencarbonate solution and saturated brine, dried over magnesium sulfate, and filtrated, and the filtrate was concentrated under reduced pressure. The residue was silica gel column chromatography (ethyl acetate:hexane=20:80-90:10), and the obtained crude product was further purified by preparative HPLC to give the title compound (30.8 mg, yield 10%) as a white solid.

MS: 480 (MH+).

¹H-NMR (CDCl₃) δ: 3.47 (3H, s), 3.49 (3H, s), 3.61-3.73 (2H, m), 3.74-3.80 (2H, m), 3.81 (3H, s), 4.11-4.18 (3H, m), 4.32-4.43 (1H, m), 4.49-4.58 (1H, m), 6.84 (1H, d, J=2.1 Hz), 6.97 (1H, s), 7.01 (1H, d, J=2.3 Hz), 7.12 (1H, d, J=2.3 Hz), 7.24 (1H, s), 12.19 (1H, s).

Example 511

N-{5-(2-methoxyethoxy)-2-[5-(morpholinomethyl)-4,5-dihydro-1,3-thiazol-2-yl]-1H-indol-7-yl}-N,1-dimethyl-1H-imidazole-2-sulfonamide

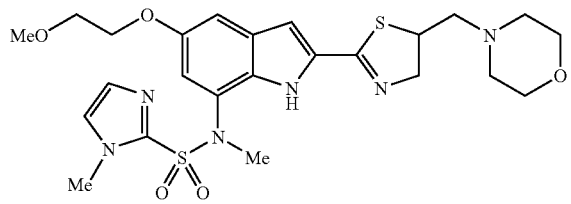

To a mixture of N-[2-[5-(dimethoxymethyl)-4,5-dihydro-1,3-thiazol-2-yl]-5-(2-methoxyethoxy)-1H-indol-7-yl]-N,1-dimethyl-1H-imidazole-2-sulfonamide (580 mg), trifluoroacetic acid (7 mL) and water (14 mL) was added concentrated sulfuric acid (7 mL), and the mixture was stirred at 60° C. for 3 hr. The excess trifluoroacetic acid was evaporated under reduced pressure, and the residue was neutralized with sodium hydrogencarbonate. The reaction mixture was extracted with ethyl acetate. The organic layer was washed with saturated brine, dried over magnesium sulfate, and filtrated, and the filtrate was concentrated under reduced pressure. The obtained crude product was dissolved in tetrahydrofuran (15 mL), morpholine (0.1 mL) was added, and the mixture was stirred at room temperature for 15 min. Sodium triacetoxyborohydride (466 mg) was added, and the mixture was stirred for 1 hr. Water was added to the reaction solution, and the mixture was extracted with ethyl acetate. The organic layer was washed with saturated brine, dried over magnesium sulfate, and filtrated, and the filtrate was concentrated under reduced pressure. The residue was subjected to basic silica gel column chromatography (ethyl acetate:hexane=10:90-80:20) to give the title compound (183.5 mg, yield 30%) as a white solid.

¹H-NMR (CDCl₃) δ: 2.47-2.54 (4H, m), 2.54-2.59 (2H, m), 3.46 (3H, s), 3.49 (3H, s), 3.68-3.79 (6H, m), 3.80 (3H, s), 4.08-4.17 (3H, m), 4.29-4.50 (2H, m), 6.83 (1H, d, J=1.9 Hz), 6.96 (1H, s), 6.99 (1H, d, J=2.3 Hz), 7.11 (1H, d, J=2.3 Hz), 7.24-7.26 (1H, m).

Example 512

N-[5-(2-methoxyethoxy)-2-(8-oxa-1-thia-3-azaspiro[4.5]dec-2-en-2-yl)-1H-indol-7-yl]-N-methylpyridine-2-sulfonamide

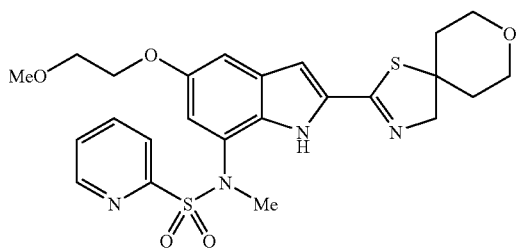

Triphenylphosphine oxide (0.63 g) was dissolved in dichloromethane (2 mL), trifluoromethanesulfonic anhydride (0.38 mL) was added under ice-cooling, and the mixture was stirred for 10 min. A solution of N-{[4-(benzylthio)tetrahydro-2H-pyran-4-yl]methyl}-5-(2-methoxyethoxy)-7-[methyl(pyridin-2-ylsulfonyl)amino]-1H-indole-2-carboxamide (0.71 g) and thioanisole (0.27 mL) in dichloromethane (8 mL) was added dropwise, and the mixture was stirred for 1 hr under ice-cooling. Water was added to the reaction solution, and the mixture was extracted with ethyl acetate. The organic layer was washed with saturated brine, dried over magnesium sulfate, and filtrated, and the filtrate was concentrated under reduced pressure. The residue was subjected to basic silica gel column chromatography (ethyl acetate:hexane=10:90-80:20), and the obtained crude product was purified by preparative HPLC to give a white solid (108.6 mg) as a crude product. The white solid was dissolved in a small amount of ethyl acetate, and an excess amount of 4N hydrogen chloride-ethyl acetate solution was added. The mixture was concentrated under reduced pressure, and the obtained white solid was washed with a small amount of ethyl acetate, and collected by filtration. The obtained solid was suspended in ethyl acetate, and the mixture was neutralized with saturated aqueous sodium hydrogencarbonate solution. The aqueous layer was extracted with ethyl acetate, and the combined organic layer was dried over magnesium sulfate, and filtrated, and the filtrate was concentrated under reduced pressure to give the title compound (85 mg, yield 15%) as a white solid. MS: 517 (MH+).

¹H-NMR (CDCl₃) δ: 1.94-2.04 (4H, m), 3.30-3.32 (3H, m), 3.45-3.47 (3H, m), 3.55-3.68 (2H, m), 3.72-3.79 (2H, m), 3.94-4.05 (2H, m), 4.09-4.14 (2H, m), 4.22-4.23 (2H, m), 6.82 (1H, d, J=2.1 Hz), 6.90 (1H, d, J=2.3 Hz), 7.06 (1H, d, J=2.1 Hz), 7.57-7.63 (1H, m), 7.89-8.00 (1H, m), 8.00-8.08 (1H, m), 9.02-9.09 (1H, m), 11.72 (1H, brs).

Example 513

N-[5-(2-methoxyethoxy)-2-(8-oxido-1,8-dithia-3-azaspiro[4.5]dec-2-en-2-yl)-1H-indol-7-yl]-N-methylpyridine-2-sulfonamide

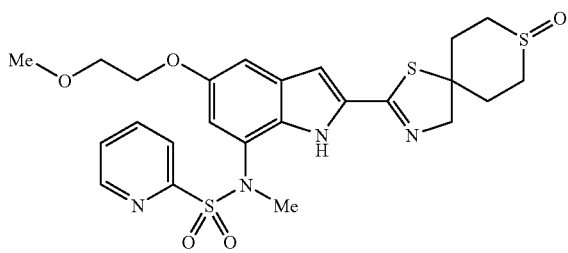

To a solution of N-[2-(1,8-dithia-3-azaspiro[4.5]dec-2-en-2-yl)-5-(2-methoxyethoxy)-1H-indol-7-yl]-N-methylpyridine-2-sulfonamide (50.7 mg) in methanol (2 mL), water (1 mL) and dichloromethane (1 mL) was added OXONE (registered trade mark, 29 mg) at room temperature, and the mixture was stirred for 18 hr. Aqueous sodium sulfite solution was added to the reaction mixture, and the mixture was stirred for 30 min. The organic solvent was evaporated under reduced pressure. The residue was extracted with ethyl acetate, and the organic layer was washed with water and saturated brine, dried (MgSO₄), and concentrated. The residue was subjected to basic silica gel column chromatography, and eluted with ethyl acetate to give two steric isomers (10.3 mg, yield 20% (retention time: shorter), and 1.7 mg, yield 3% (retention time: longer)) of the title compound as a colorless amorphous solid, respectively.

(retention time: shorter) ¹H-NMR (CDCl₃) δ: 2.08-2.17 (2H, m), 2.68-2.81 (4H, m), 3.05-3.21 (2H, m), 3.28 (3H, s), 3.46 (3H, s), 3.65-3.82 (2H, m), 4.06-4.18 (2H, m), 4.28 (2H, s), 6.79 (1H, d, J=1.9 Hz), 6.95 (1H, d, J=2.3 Hz), 7.07 (1H, d, J=1.9 Hz), 7.60-7.65 (1H, m), 7.98 (1H, td, J=7.8, 1.9 Hz), 8.06-8.11 (1H, m), 9.06 (1H, d, J=4.9 Hz), 11.98 (1H, d, J=1.5 Hz).

(retention time: longer) ¹H-NMR (CDCl₃) δ: 1.98-2.25 (2H, m), 2.53-2.64 (2H, m), 2.96 (2H, t, J=10.6 Hz), 3.14-3.28 (2H, m), 3.31 (3H, s), 3.46 (3H, s), 3.74-3.78 (2H, m), 4.06-4.16 (2H, m), 4.26 (2H, s), 6.84 (1H, d, J=1.9 Hz), 6.90 (1H, d, J=2.3 Hz), 7.07 (1H, d, J=2.3 Hz), 7.60 (1H, dd, J=8.3, 5.3 Hz), 7.95 (1H, t, J=6.8 Hz), 8.00-8.17 (1H, m), 9.02 (1H, d, J=3.8 Hz), 11.66 (1H, brs).

Example 514

N-[2-{5-[(1,1-dioxidothiomorpholino)methyl]-4,5-dihydro-1,3-thiazol-2-yl}-5-(2-methoxyethoxy)-1H-indol-7-yl]-N-methylpyridine-2-sulfonamide

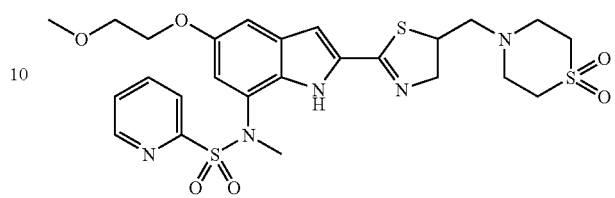

To a solution of N-[2-(5-formyl-4,5-dihydro-1,3-thiazol-2-yl)-5-(2-methoxyethoxy)-1H-indol-7-yl]-N-methylpyridine-2-sulfonamide (200 mg) and thiomorpholine 1,1-oxide (81 mg) in acetic acid (5 mL) was added sodium triacetoxyborohydride (212 mg) at room temperature, and the mixture was stirred for 10 min. The reaction mixture was neutralized with saturated aqueous sodium hydrogencarbonate solution, and extracted with ethyl acetate. The ethyl acetate layer was washed with saturated brine, dried (MgSO₄), and concentrated. The obtained residue was subjected to basic silica gel column chromatography to give the title compound (128 mg, yield 50%) as white crystals from a fraction eluted with ethyl acetate. melting point 115° C. MS: 594 (MH⁺).

Example 515

N-{5-(2-methoxyethoxy)-2-[5-(morpholinomethyl)-4,5-dihydro-1,3-thiazol-2-yl]-1H-indol-7-yl}-N-methylpyridine-2-sulfonamide dihydrochloride

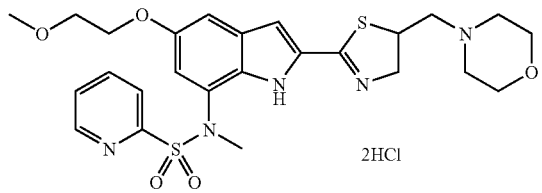

In the same manner as in Example 456, the title compound (130 mg, yield 50%) was obtained as yellow crystals from N-[2-(5-formyl-4,5-dihydro-1,3-thiazol-2-yl)-5-(2-methoxyethoxy)-1H-indol-7-yl]-N-methylpyridine-2-sulfonamide (200 mg) and morpholine (80 mg). melting point 165° C.

Example 516

N-[2-{5-[(3-hydroxyazetidin-1-yl)methyl]-4,5-dihydro-1,3-thiazol-2-yl}-5-(2-methoxyethoxy)-1H-indol-7-yl]-N-methylpyridine-2-sulfonamide dihydrochloride

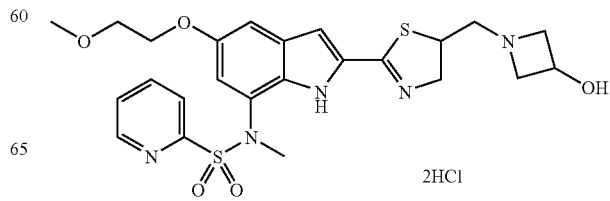

In the same manner as in Example 456, the title compound (60 mg, yield 28%) was obtained as yellow crystals from N-[2-(5-formyl-4,5-dihydro-1,3-thiazol-2-yl)-5-(2-methoxyethoxy)-1H-indol-7-yl]-N-methylpyridine-2-sulfonamide (200 mg) and 3-hydroxyazetidine (100 mg). melting point 160° C.

Example 517

N-[2-(5-{[(2-hydroxyethyl)(methyl)amino]methyl}-4,5-dihydro-1,3-thiazol-2-yl)-5-(2-methoxyethoxy)-1H-indol-7-yl]-N-methylpyridine-2-sulfonamide dihydrochloride

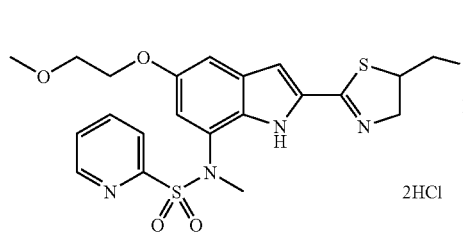

In the same manner as in Example 438, the title compound (110 mg, yield 28%) was obtained as yellow crystals from (2-{5-(2-methoxyethoxy)-7-[methyl(pyridin-2-ylsulfonyl)amino]-1H-indol-2-yl}-4,5-dihydro-1,3-thiazol-5-yl)methyl methanesulfonate (200 mg) and 2-(methylamino)ethanol (60 mg). MS: 534 (MH$^+$).

Example 518

N-methyl-N-(2-{5-[(3-oxopyrrolidin-1-yl)methyl]-4,5-dihydro-1,3-thiazol-2-yl}-1H-indol-7-yl)pyridine-2-sulfonamide dihydrochloride

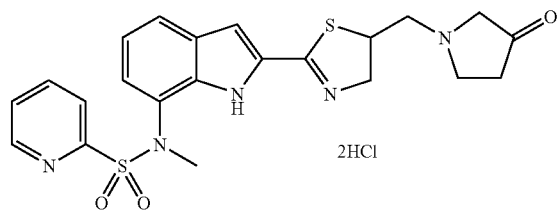

To a mixture of N-[2-(5-formyl-4,5-dihydro-1,3-thiazol-2-yl)-1H-indol-7-yl]-N-methylpyridine-2-sulfonamide (200 mg), pyrrolidin-3-one hydrochloride (120 mg), triethylamine (150 µL) and tetrahydrofuran (5 mL) was added sodium triacetoxyborohydride (210 mg), and the mixture was stirred at room temperature for 10 min. Saturated aqueous ammonium chloride solution was added to the reaction mixture, and the mixture was extracted with ethyl acetate. The ethyl acetate layer was washed with saturated brine, dried (MgSO$_4$), and concentrated. The obtained residue was subjected to silica gel column chromatography to give a colorless oil from a fraction eluted with ethyl acetate. The colorless oil was dissolved in ethyl acetate (3 mL), and 4N hydrogen chloride-ethyl acetate solution (1 mL) was added. The precipitated solid was collected by filtration, washed with diethyl ether, and dried to give the title compound (110 mg, yield 40%) as a yellow amorphous solid. MS: 470 (MH$^+$).

Example 519

N-{5-bromo-2-[5-(morpholinomethyl)-4,5-dihydro-1,3-thiazol-2-yl]-1H-indol-7-yl}-N-methylpyridine-2-sulfonamide

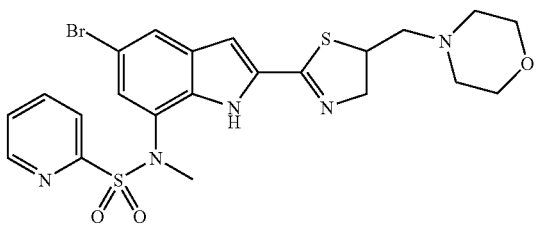

In the same manners as in Reference Example 178 and Reference Example 179, the title compound (128 mg, yield 46%) was obtained as white crystals from 5-bromo-2-[5-(morpholinomethyl)-4,5-dihydro-1,3-thiazol-2-yl]-1H-indol-7-amine (200 mg). melting point 232° C.

Example 520

2-{2-[7-[methyl(2-thienylsulfonyl)amino]-5-(trifluoromethoxy)-1H-indol-2-yl]-4,5-dihydro-1,3-thiazol-5-yl}acetamide

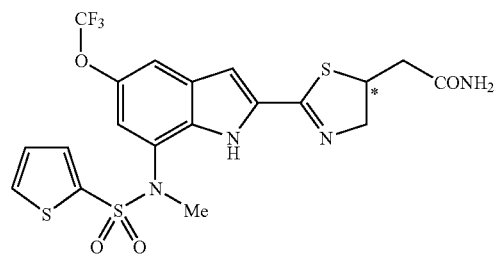

2-{2-[7-[Methyl(2-thienylsulfonyl)amino]-5-(trifluoromethoxy)-1H-indol-2-yl]-4,5-dihydro-1,3-thiazol-5-yl}acetamide (140 mg) was dissolved in hexane-ethanol (850:150, volume ratio, 700 mL). This solution was subjected to HPLC using CHIRALPAK AD (50 mmID×500 mmL, manufactured by DAICEL CHEMICAL INDUSTRIES, LTD.), and eluted with hexane-ethanol (850:150, volume ratio) as a mobile phase at 35° C. at flow rate of 75 mL/min. A fraction with the retention time of 1 hr and 39 min was separated, and concentrated. The obtained solid was crystallized from ethyl acetate-hexane to give the title compound (67 mg) as colorless crystals. melting point 202-203° C.

Example 521 ethyl {2-[7-[(2-thienylsulfonyl)amino]-5-(trifluoromethoxy)-1H-indol-2-yl]-4,5-dihydro-1,3-thiazol-5-yl}acetate

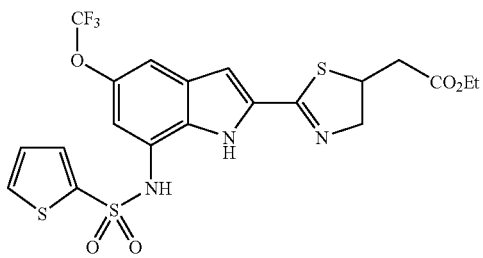

A mixture of 7-[(2-thienylsulfonyl)amino]-5-(trifluoromethoxy)-1H-indole-2-carboxamide (2.14 g), Lawesson's reagent (2.14 g) and tetrahydrofuran (50 mL) was stirred at 50° C. for 1.5 hr, and heated under reflux for 1.5 hr. The reaction mixture was concentrated, and the residue was washed with diisopropyl ether to give pale-yellow crystals. The obtained crystals were subjected to silica gel column chromatography, and eluted with hexane-ethyl acetate (4:1-1:2, volume ratio) to give yellow crystals. A mixture of the obtained crystals, ethyl but-2-ynoate (1.49 g), tributylphosphine (1.07 g), toluene (30 mL) and tetrahydrofuran (10 mL) was stirred at 70° C. for 5 hr. ethyl but-2-ynoate (900 mg) and tributylphosphine (1.07 g) were added to the mixture, and the mixture was further stirred at room temperature for 2.5 days. The reaction mixture was concentrated, and the residue was subjected to silica gel column chromatography, and eluted with hexane-ethyl acetate (4:1-1:3, volume ratio) to give the title compound (780 mg, yield 28%) as a brown oil.

$^1$H-NMR (CDCl$_3$) δ: 1.28 (3H, t, J=6.44 Hz), 2.73 (2H, d, J=6.82 Hz), 4.15-4.26 (2H, m), 4.27-4.49 (3H, m), 6.68 (1H, s), 6.89 (1H, s), 6.91-6.99 (1H, m), 7.32-7.43 (2H, m), 7.52 (1H, d, J=4.92 Hz), 10.05 (1H, brs).

Example 522 ethyl (2-{5-(2-methoxyethoxy)-7-[methyl(2-thienylsulfonyl)amino]-1H-indol-2-yl}-4,5-dihydro-1,3-thiazol-5-yl)acetate

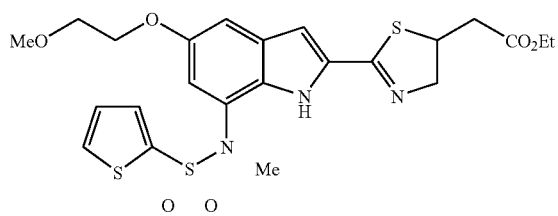

A mixture of 5-(2-methoxyethoxy)-7-[methyl(2-thienylsulfonyl)amino]-1H-indole-2-carboxamide (920 mg), Lawesson's reagent (690 mg) and tetrahydrofuran (20 mL) was stirred at 50° C. for 2 hr. The reaction mixture was concentrated, and the residue was subjected to silica gel column chromatography, and eluted with hexane-ethyl acetate (2:1-1:9, volume ratio) to give a yellow amorphous solid. A mixture of the obtained amorphous solid, ethyl but-2-ynoate (620 mg), tributylphosphine (450 mg), toluene (30 mL) and tetrahydrofuran (15 mL) was stirred at 50° C. for 1 hr. The reaction mixture was concentrated, and the residue was subjected to silica gel column chromatography, and eluted with hexane-ethyl acetate (4:1-1:1, volume ratio). The obtained compound was further subjected to silica gel column chromatography, and eluted with hexane-ethyl acetate (1:1, volume ratio) to give the title compound (500 mg, yield 42%) as a yellow oil $^1$H-NMR (CDCl$_3$) δ: 1.28 (3H, t, J=7.16 Hz), 2.65-2.77 (2H, m), 3.27 (3H, s), 3.43 (3H, s), 3.66-3.74 (2H, m), 4.01-4.09 (2H, m), 4.14-4.49 (5H, m), 6.35 (1H, d, J=2.26 Hz), 6.81 (1H, d, J=2.07 Hz), 7.03 (1H, d, J=2.07 Hz), 7.11 (1H, dd, J=4.99, 3.86 Hz), 7.40 (1H, dd, J=3.77, 1.13 Hz), 7.62 (1H, dd, J=5.09, 1.32 Hz), 9.39 (1H, brs).

Example 523 ethyl (2-{5-(2-methoxyethoxy)-7-[methyl(pyridin-2-ylsulfonyl)amino]-1H-indol-2-yl}-4,5-dihydro-1,3-thiazol-5-yl)acetate

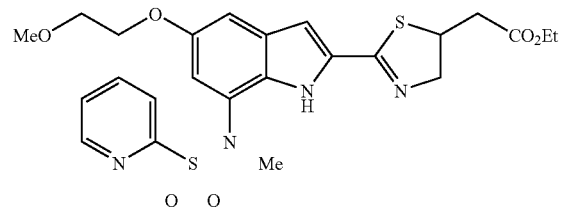

A mixture of 5-(2-methoxyethoxy)-7-[methyl(pyridin-2-ylsulfonyl)amino]-1H-indole-2-carboxamide (2.28 g), Lawesson's reagent (1.70 g) and tetrahydrofuran (50 mL) was stirred at 50° C. for 2 hr. The reaction mixture was concentrated, the residue was crystallized from diisopropyl ether-toluene, and the crystals were collected by filtration. A mixture of the obtained crystals, ethyl but-2-ynoate (1.57 g), tributylphosphine (1.13 g), toluene (100 mL) and tetrahydrofuran (100 mL) was stirred at 50° C. for 4 hr. The reaction mixture was concentrated, and the residue was subjected to basic silica gel column chromatography, and eluted with hexane-ethyl acetate (1:1-1:9, volume ratio). The obtained compound was further subjected to silica gel column chromatography, and eluted with hexane-ethyl acetate (1:1-1:9, volume ratio) to give the title compound (1.57 g, yield 53%) as a brown oil.

$^1$H-NMR (CDCl$_3$) δ: 1.28 (3H, t, J=7.16 Hz), 2.67-2.77 (2H, m), 3.31 (3H, s), 3.46 (3H, s), 3.71-3.78 (2H, m), 4.04-4.24 (4H, m), 4.27-4.55 (3H, m), 6.83 (1H, d, J=2.07 Hz), 6.91 (1H, d, J=2.07 Hz), 7.06 (1H, d, J=2.07 Hz), 7.54-7.66 (1H, m), 7.86-8.00 (1H, m), 8.01-8.09 (1H, m), 9.00-9.09 (1H, m), 11.75 (1H, brs).

Example 524

N-{2-[5-(dimethoxymethyl)-4,5-dihydro-1,3-thiazol-2-yl]-5-[3-(methylsulfonyl)propoxy]-1H-indol-7-yl}-N-methylpyridine-2-sulfonamide

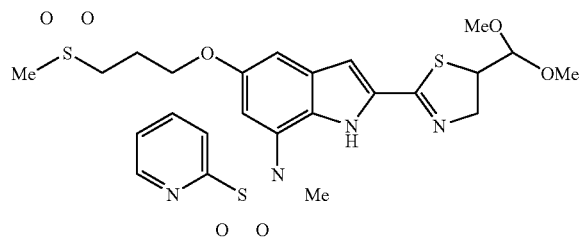

A mixture of triphenylphosphine oxide (1.17 g), trifluoromethanesulfonic anhydride (1.18 g) and dichloromethane (30 mL) was stirred for 15 min under ice-cooling. A solution of N-[2-(benzylthio)-3,3-dimethoxypropyl]-7-[methyl(pyridin-2-ylsulfonyl)amino]-5-[3-(methylsulfonyl)propoxy]-1H-indole-2-carboxamide (2.65 g) and thioanisole (940 mg) in dichloromethane (10 mL) was added dropwise to the reaction mixture under ice-cooling, and the mixture was stirred for 30 min under ice-cooling. The reaction mixture was diluted with ethyl acetate, and extracted with 3N hydrochloric acid. The aqueous layer was alkalified with 2N aqueous sodium hydroxide solution, and extracted with ethyl acetate. The ethyl acetate layer was washed with saturated brine, dried (MgSO$_4$), and concentrated. The obtained residue was subjected to silica gel column chromatography, and eluted with hexane-ethyl acetate (2:8-1:9, volume ratio) to give the title compound (840 mg, yield 38%) as a colorless amorphous solid.

$^1$H-NMR (CDCl$_3$) δ: 2.25-2.44 (2H, m), 2.96 (3H, s), 3.18-3.33 (2H, m), 3.29 (3H, s), 3.43 (3H, s), 3.45 (3H, s), 4.07-4.22 (3H, m), 4.33-4.46 (2H, m), 4.52-4.64 (1H, m), 6.83 (1H, d, J=1.89 Hz), 6.89 (1H, d, J=2.27 Hz), 7.05 (1H, d, J=2.27 Hz), 7.62 (1H, dd, J=6.44, 4.92 Hz), 7.93-8.03 (1H, m), 8.06-8.13 (1H, m), 9.09 (1H, d, J=3.79 Hz), 11.98 (1H, brs).

Example 525

N-{5-(3-methoxypropoxy)-2-[5-(thiomorpholinomethyl)-4,5-dihydro-1,3-thiazol-2-yl]-1H-indol-7-yl}-N-methylpyridine-2-sulfonamide

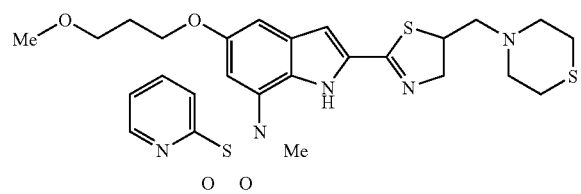

To a mixture of triphenylphosphine oxide (610 mg) and acetonitrile (10 mL) was added trifluoromethanesulfonic anhydride (310 mg) at 2° C., and the mixture was stirred at 0-5° C. for 30 min. A solution of N-[2-(benzylthio)-3-thiomorpholinopropyl]-5-(3-methoxypropoxy)-7-[methyl(pyridin-2-ylsulfonyl)amino]-1H-indole-2-carboxamide (380 mg) and thioanisole (140 mg) in acetonitrile (10 mL) was added dropwise to the reaction mixture at 0-5° C., and the mixture was stirred at 0-5° C. for 30 min. The reaction mixture was poured into saturated aqueous sodium hydrogencarbonate, and the mixture was extracted with ethyl acetate. The ethyl acetate layer was extracted with concentrated hydrochloric acid (10 mL×3), and the hydrochloric acid layers were combined, and washed with ethyl acetate. The aqueous layer was basified with potassium carbonate, and extracted with ethyl acetate. The ethyl acetate layer was washed with saturated brine, dried (MgSO$_4$), and concentrated. The obtained residue was subjected to basic silica gel column chromatography, and eluted with hexane-ethyl acetate (9:1-1:2, volume ratio) to give the title compound (110 mg, yield 34%) as a colorless oil.

$^1$H-NMR (CDCl$_3$) δ: 1.96-2.12 (2H, m), 2.50-2.86 (10H, m), 3.31 (3H, s), 3.36 (3H, s), 3.56 (2H, t, J=6.25 Hz), 3.97-4.18 (3H, m), 4.27-4.50 (2H, m), 6.83 (2H, dd, J=7.76, 2.08 Hz), 7.06 (1H, d, J=1.89 Hz), 7.54-7.64 (1H, m), 7.89-7.99 (1H, m), 8.01-8.09 (1H, m), 9.07 (1H, d, J=4.16 Hz), 11.72 (1H, brs).

Example 526

N-(5-(3-methoxypropoxy)-2-{5-[(1-oxidothiomorpholino)methyl]-4,5-dihydro-1,3-thiazol-2-yl}-1H-indol-7-yl)-N-methylpyridine-2-sulfonamide

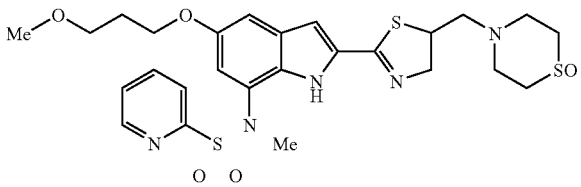

To a mixture of N-{5-(3-methoxypropoxy)-2-[5-(thiomorpholinomethyl)-4,5-dihydro-1,3-thiazol-2-yl]-1H-indol-7-yl}-N-methylpyridine-2-sulfonamide (110 mg), methanol (3 mL), water (3 mL) and tetrahydrofuran (3 mL) was added OXONE (registered trade mark, 60 mg) at room temperature, and the mixture was stirred at room temperature for 1 hr. Aqueous sodium sulfite solution was added to the reaction mixture, and the mixture was stirred for 30 min, and extracted with ethyl acetate. The ethyl acetate layer was washed with saturated brine, dried (MgSO$_4$), and concentrated. The residue was subjected to silica gel column chromatography, and eluted with ethyl acetate-methanol (100:0-90:10, volume ratio). The obtained crystals were washed with diisopropyl ether to give the title compound (35 mg, yield 32%) as colorless crystals. The crystals were recrystallized from acetone-hexane to give colorless prism crystals. melting point 176-177° C.

Example 527

N-[2-{5-[(1,1-dioxidothiomorpholino)methyl]-4,5-dihydro-1,3-thiazol-2-yl}-5-(2-methoxyethoxy)-1H-indol-7-yl]-N-methylpyridine-2-sulfonamide

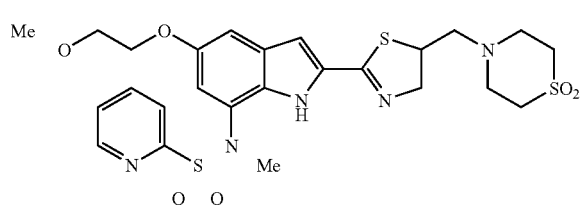

N-[2-{5-[(1,1-Dioxidothiomorpholino)methyl]-4,5-dihydro-1,3-thiazol-2-yl}-5-(2-methoxyethoxy)-1H-indol-7-yl]-N-methylpyridine-2-sulfonamide (48 mg) was dissolved in methanol (48 mL). This solution was subjected to supercritical fluid chromatography using CHIRALPAK AS-H (manufactured by DAICEL CHEMICAL INDUSTRIES, LTD.), and eluted with carbon dioxide-methanol (550:450, volume ratio) as a mobile phase at 100 bar at 35° C. at flow rate of 50 mL/min. A fraction with the retention time of 7.5 min was separated, and concentrated. The obtained solid was crystallized from ethyl acetate-hexane, and the obtained crystals were washed with hexane to give the title compound (13 mg) as pale-yellow crystals. melting point 113-116° C.

Example 528

N-[2-{5-[(1,1-dioxidothiomorpholino)methyl]-4,5-dihydro-1,3-thiazol-2-yl}-5-(2-methoxyethoxy)-1H-indol-7-yl]-N-methylpyridine-2-sulfonamide

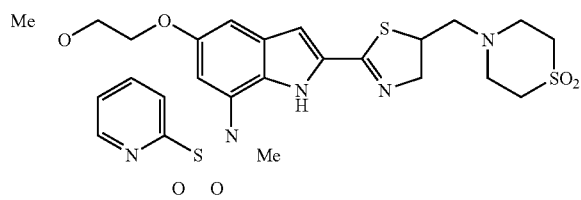

N-[2-{5-[(1,1-Dioxidothiomorpholino)methyl]-4,5-dihydro-1,3-thiazol-2-yl}-5-(2-methoxyethoxy)-1H-indol-7-yl]-N-methylpyridine-2-sulfonamide (48 mg) was dissolved in methanol (48 mL). This solution was subjected to supercritical fluid chromatography using CHIRALPAK AS-H (manufactured by DAICEL CHEMICAL INDUSTRIES, LTD.), and eluted with carbon dioxide-methanol (550:450, volume ratio) as a mobile phase at 100 bar at 35° C. at flow rate of 50 mL/min. A fraction with the retention time of 8.5 min was separated, and concentrated. The obtained solid was crystallized from diethyl ether-ethyl acetate to give the title compound (15.7 mg) as colorless crystals. melting point 164.6-166.7° C.

Example 529

N-{5-(2-methoxyethoxy)-2-[5-methyl-5-(thiomorpholinomethyl)-4,5-dihydro-1,3-thiazol-2-yl]-1H-indol-7-yl}-N-methylpyridine-2-sulfonamide

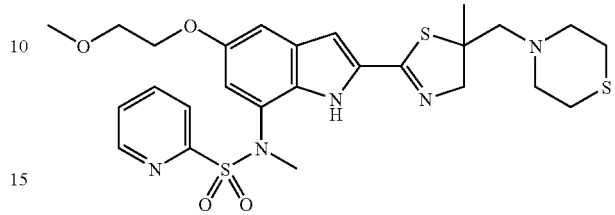

To a mixture of triphenylphosphine oxide (178 mg) and dichloromethane (8 mL) was added trifluoromethanesulfonic anhydride (0.11 mL) at 0° C., the mixture was stirred at 0° C. for 15 min, and dichloromethane (4 mL) was added. A mixture of N-[2-(benzylthio)-2-methyl-3-thiomorpholinopropyl]-5-(2-methoxyethoxy)-7-[methyl(pyridin-2-ylsulfonyl)amino]-1H-indole-2-carboxamide (220 mg), thioanisole (0.075 mL) and dichloromethane (3 mL) was added to the reaction solution at −78° C., and the mixture was stirred at −78° C. for 10 min. Aqueous sodium bicarbonate was added, and the mixture was extracted with dichloromethane. The extract was washed with saturated brine, dried over sodium sulfate, and filtrated, and the filtrate was concentrated. The residue was subjected to silica gel column chromatography, and eluted with ethyl acetate. The obtained amorphous solid was purified by preparative HPLC to give the title compound (28 mg, yield 15%) as a colorless amorphous solid.

$^1$H-NMR (CDCl$_3$) δ: 1.56 (3H, s), 2.60-2.75 (6H, m), 2.82-2.98 (4H, m), 3.32 (3H, s), 3.45 (3H, s), 3.73-3.80 (2H, m), 4.01 (1H, d, J=15.9 Hz), 4.07-4.15 (2H, m), 4.19 (1H, d, J=15.9 Hz), 6.78 (1H, d, J=1.9 Hz), 6.86 (1H, d, J=2.3 Hz), 7.05 (1H, d, J=2.3 Hz), 7.58 (1H, dd, J=6.2, 4.7 Hz), 7.85-7.98 (1H, m), 7.98-8.07 (1H, m), 9.03 (1H, d, J=4.2 Hz), 11.54 (1H, brs).

Example 530

N-[5-(2-methoxyethoxy)-2-{5-methyl-5-[(1-oxidothiomorpholino)methyl]-4,5-dihydro-1,3-thiazol-2-yl}-1H-indol-7-yl]-N-methylpyridine-2-sulfonamide

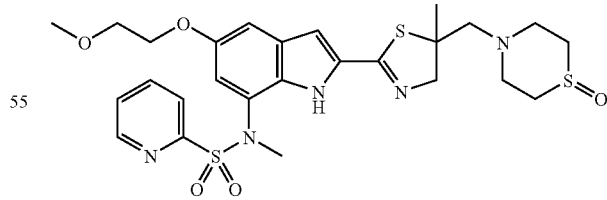

To a mixture of N-{5-(2-methoxyethoxy)-2-[5-methyl-5-(thiomorpholinomethyl)-4,5-dihydro-1,3-thiazol-2-yl]-1H-indol-7-yl}-N-methylpyridine-2-sulfonamide (253 mg), tetrahydrofuran (5 mL), ethanol (5 mL) and water (5 mL) was added OXONE (registered trade mark, 160 mg) at room temperature, and the mixture was added at room temperature for 2 hr. 10% Aqueous sodium sulfite solution was added, and the mixture was concentrated to dryness. The residue was diluted with ethyl acetate, tetrahydrofuran and water, and the organic layer was washed with saturated brine, dried over sodium sulfate, and filtrated. The filtrate was concentrated, and the residue was purified by preparative HPLC to give the title compound (605 mg, yield 99%) as a colorless amorphous solid.

$^1$H-NMR (CDCl$_3$) δ: 1.59 (3H, s), 2.62-2.98 (8H, m), 3.24-3.41 (5H, m), 3.45 (3H, s), 3.68-3.79 (2H, m), 4.00-4.17 (3H, m), 4.17-4.27 (1H, m), 6.78 (1H, d, J=1.9 Hz), 6.87 (1H, d, J=2.3 Hz), 7.05 (1H, d, J=2.1 Hz), 7.59 (1H, ddd, J=7.5, 4.7, 1.1 Hz), 7.87-7.99 (1H, m), 7.98-8.08 (1H, m), 9.02 (1H, d, J=4.5 Hz), 11.57 (1H, brs).

Example 531 ethyl (2-{7-[(2-thienylsulfonyl)amino]-1H-indol-2-yl}-4,5-dihydro-1,3-thiazol-5-yl)acetate

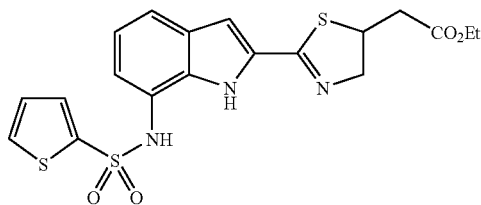

A solution of 7-[(2-thienylsulfonyl)amino]-1H-indole-2-carbothioamide (4.3 g), ethyl but-2-ynoate (3.2 mL) and tributylphosphine (3.2 mL) in tetrahydrofuran (40 mL)-toluene (40 mL) was stirred at room temperature for 2 days. ethyl but-2-ynoate (1.6 mL) was added to the reaction solution again, and the mixture was stirred at 60° C. for 2 hr. The reaction solution was concentrated under reduced pressure, and the obtained residue was subjected to silica gel column chromatography (ethyl acetate:hexane=2:8-4:6) to give the title compound (1.6 g, yield: 28%) as a pale-brown oil.

MS: 450 (MH$^+$).

Example 532

(4R)-2-{5-(2-methoxyethoxy)-7-[methyl(pyridin-2-ylsulfonyl)amino]-1H-indol-2-yl}-4,5-dihydro-1,3-thiazole-4-carboxylic acid

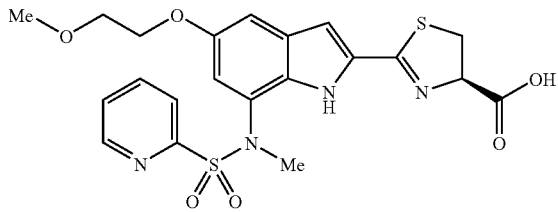

To a solution of triphenylphosphine oxide (8.9 g) in dichloromethane (12 mL) was added dropwise trifluoromethanesulfonic anhydride (3.9 mL) at 0° C., and the mixture was stirred for 30 min at 0° C. The obtained suspension was diluted with dichloromethane (38 mL), and a solution of S-benzyl-N-({5-(2-methoxyethoxy)-7-[methyl(pyridin-2-ylsulfonyl)amino]-1H-indol-2-yl}carbonyl)-L-cysteine methyl ester (3.2 g) and thioanisole (5.0 mL) in dichloromethane (50 mL) was added. The reaction mixture was stirred at 0° C. for 2 hr, and saturated aqueous sodium hydrogencarbonate solution was added. The mixture was concentrated, and the residue was extracted with ethyl acetate. The ethyl acetate layer was washed with water and saturated brine, dried (MgSO$_4$), and concentrated. The obtained residue was subjected to silica gel column chromatography, and eluted with hexane-ethyl acetate (4:1-1:1, volume ratio) to give a mixture (2.3 g) of methyl (4R)-2-{5-(2-methoxyethoxy)-7-[methyl(pyridin-2-ylsulfonyl)amino]-1H-indol-2-yl}-4,5-dihydro-1,3-thiazole-4-carboxylate and triphenylphosphine oxide. A mixture of the obtained mixture (1.3 g), 2N aqueous sodium hydroxide solution (2.0 mL), tetrahydrofuran (2.0 mL) and methanol (2.0 mL) was stirred at room temperature for 2 hr. Diethyl ether was added to the reaction mixture, and the aqueous layer was separated, and acidified with 1N hydrochloric acid. The mixture was extracted with ethyl acetate. The ethyl acetate layer was washed with water and saturated brine, dried (MgSO$_4$), and concentrated to give the title compound (1.1 g, yield 43%).

$^1$H-NMR (CDCl$_3$) δ: 3.31 (3H, s), 3.46 (3H, s), 3.68-3.85 (4H, m), 4.05-4.17 (2H, m), 5.38 (1H, t, J=9.3 Hz), 6.92 (1H, d, J=2.1 Hz), 6.94 (1H, d, J=2.3 Hz), 7.05 (1H, d, J=2.3 Hz), 7.50-7.64 (1H, m), 7.83-7.97 (1H, m), 7.96-8.06 (1H, m), 9.10 (1H, d, J=4.0 Hz), 11.90 (1H, brs).

Example 533

(4R)-2-{5-(2-methoxyethoxy)-7-[methyl(pyridin-2-ylsulfonyl)amino]-1H-indol-2-yl}-4,5-dihydro-1,3-thiazole-4-carboxamide

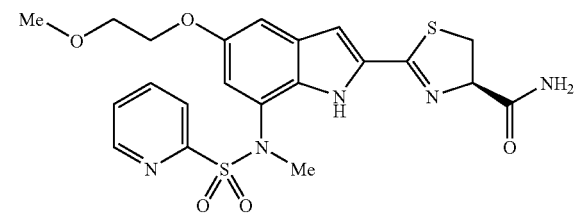

A solution of (4R)-2-{5-(2-methoxyethoxy)-7-[methyl(pyridin-2-ylsulfonyl)amino]-1H-indol-2-yl}-4,5-dihydro-1,3-thiazole-4-carboxylic acid (0.15 g), 1H-1,2,3-benzotriazol-1-ol ammonium salt (0.072 g), N-[3-(dimethylamino)propyl]-N'-ethylcarbodiimide hydrochloride (0.090 g) and triethylamine (0.086 mL) in N,N-dimethylformamide (5 mL) was stirred at room temperature for 3 hr. The reaction mixture was concentrated, water was added, and the mixture was extracted with ethyl acetate. The ethyl acetate layer was washed with 1N hydrochloric acid, saturated aqueous sodium hydrogencarbonate solution and saturated brine, dried (MgSO$_4$), and concentrated. The obtained residue was subjected to silica gel column chromatography, and eluted with ethyl acetate to give the title compound (0.056 g, yield 37%) as colorless crystals.

$^1$H-NMR (CDCl$_3$) δ: 3.35 (3H, s), 3.45 (3H, s), 3.70-3.86 (4H, m), 4.05-4.17 (2H, m), 5.25 (1H, t, J=9.1 Hz), 5.50 (1H, brs), 6.75 (1H, brs), 6.86 (1H, d, J=2.3 Hz), 6.93 (1H, d, J=2.1

Hz), 7.06 (1H, d, J=2.1 Hz), 7.53-7.70 (1H, m), 7.91-8.00 (1H, m), 8.01-8.07 (1H, m), 8.99 (1H, dd, J=4.7, 0.8 Hz), 11.43 (1H, brs).

Example 534

N-(cyclopropylmethyl)-N-(5-(2-methoxyethoxy)-2-{5-[(1-oxidothiomorpholino)methyl]-4,5-dihydro-1,3-thiazol-2-yl}-1H-indol-7-yl)pyridine-2-sulfonamide

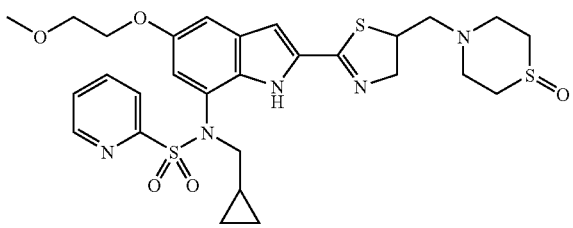

To a mixture of triphenylphosphine oxide (557 mg) and dichloromethane (1 mL) was added trifluoromethanesulfonic anhydride (0.17 mL) at 0° C., and the mixture was stirred at 0° C. for 15 min, followed by an addition of dichloromethane (3 mL). A mixture of N-[2-(benzylthio)-3-thiomorpholinopropyl]-7-[(cyclopropylmethyl)(pyridin-2-ylsulfonyl)amino]-5-(2-methoxyethoxy)-1H-indole-2-carboxamide (355 mg), thioanisole (0.12 mL) and dichloromethane (3 mL) was added thereto at 0° C., and the mixture was stirring at 0° C. for 10 min. Aqueous sodium bicarbonate solution was added to the reaction mixture, and the organic layer was separated. The organic layer was extracted with concentrated hydrochloric acid, and after basified with the aqueous layer with potassium carbonate, the whole mixture was extracted with ethyl acetate. The extract was washed with saturated brine, dried over anhydrous sodium sulfate, and filtered, and the filtrate was concentrated under reduced pressure. The residue was subjected to silica gel column chromatography to give the amorphous solid from a fraction eluted with ethyl acetate. To the mixture of the obtained amorphous solid, tetrahydrofurane (5 mL), ethanol (5 mL) and water (5 mL) was added OXONE (registered trade mark, 369 mg) at room temperature, and the mixture was stirred at room temperature for 1 hr. To the resulting mixture was added 10% aqueous sodium sulfite solution, and the mixture was extracted with a mixed solvent of ethyl acetate and tetrahydrofuran. The organic layer was washed with saturated brine, dried over anhydrous sodium sulfate, and filtered, and the filtrate was concentrated under reduced pressure. The residue was purified by preparative HPLC to give amorphous solid, which was crystallized from diisopropyl ether to give the title compound (146 mg, yield 47%) as colorless crystals.

$^1$H-NMR (CDCl$_3$) δ: −0.07 (2H, q, J=4.8 Hz), 0.27 (2H, d, J=7.0 Hz), 0.76-0.91 (1H, m), 2.56-2.69 (2H, m), 2.71-2.99 (6H, m), 3.10-3.26 (2H, m), 3.46 (3H, s), 3.55 (2H, d, J=7.2 Hz), 3.74-3.86 (2H, m), 4.00-4.22 (3H, m), 4.34-4.48 (2H, m), 6.83 (1H, d, J=2.1 Hz), 6.94 (1H, d, J=2.1 Hz), 7.10 (1H, d, J=2.1 Hz), 7.59 (1H, dd, J=4.8, 1.0 Hz), 7.93 (1H, td, J=7.8, 1.6 Hz), 7.99-8.13 (1H, m), 9.05 (1H, d, J=4.0 Hz), 11.70 (1H, brs).

Example 535

N-(2,2-difluoroethyl)-N-(5-(2-methoxyethoxy)-2-{5-[(1-oxidothiomorpholino)methyl]-4,5-dihydro-1,3-thiazol-2-yl}-1H-indol-7-yl)pyridine-2-sulfonamide

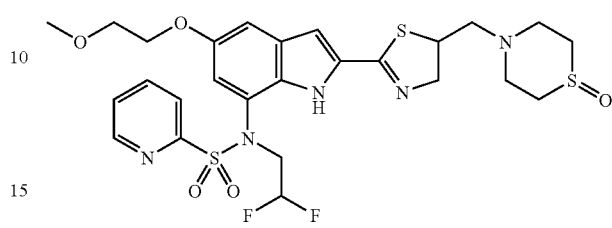

In the same manner as in Example 534, the title compound (45 mg, yield 14%) was obtained as colorless crystals from N-[2-(benzylthio)-3-(thiomorpholino)propyl]-7-[(2,2-difluoroethyl)(pyridin-2-ylsulfonyl)amino]-5-(2-methoxyethoxy)-1H-indole-2-carboxamide (360 mg).

$^1$H-NMR (CDCl$_3$) δ: 2.59-2.69 (2H, m), 2.71-2.98 (6H, m), 3.08-3.25 (2H, m), 3.45 (3H, s), 3.67-3.82 (3H, m), 4.05-4.22 (4H, m), 4.31-4.44 (2H, m), 5.60-6.10 (1H, m), 6.77-6.87 (2H, m), 7.09 (1H, d, J=1.9 Hz), 7.59 (1H, ddd, J=6.8, 4.8, 1.8 Hz), 7.86-8.02 (2H, m), 9.01 (1H, d, J=4.5 Hz), 11.01 (1H, brs).

Example 536

N-cyclopropyl-N-(5-(2-methoxyethoxy)-2-{5-[(1-oxidothiomorpholino) methyl]-4,5-dihydro-1,3-thiazol-2-yl}-1H-indol-7-yl)pyridine-2-sulfonamide

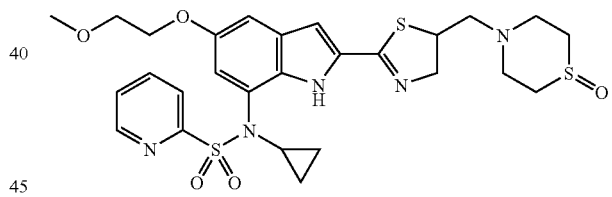

In the same manner as in Example 534, the title compound (140 mg, yield 46%) was obtained as colorless crystals from N-[2-(benzylthio)-3-thiomorpholinopropyl]-7-[cyclopropyl(pyridin-2-ylsulfonyl)amino]-5-(2-methoxyethoxy)-1H-indole-2-carboxamide (350 mg).

$^1$H-NMR (CDCl$_3$) δ: 0.34 (2H, brs), 0.61 (2H, d, J=6.0 Hz), 2.64 (2H, dd, J=7.6, 1.6 Hz), 2.71-2.96 (6H, m), 3.12-3.28 (3H, m), 3.47 (3H, s), 3.68-3.85 (2H, m), 4.05-4.21 (3H, m), 4.33-4.49 (2H, m), 6.82 (1H, d, J=2.1 Hz), 6.97-7.12 (2H, m), 7.63 (1H, ddd, J=7.6, 4.7, 1.0 Hz), 8.00 (1H, td, J=7.8, 1.8 Hz), 8.16 (1H, d, J=7.9 Hz), 9.09 (1H, dd, J=4.7, 0.9 Hz), 12.18 (1H, brs).

Reference Example 1A Construction of Glucokinase (GK) Expression Vector

Plasmid DNA to be used for the expression of a protein (GST-hLGK1) containing GST (Glutathione S-transferase) added to the amino terminal of human liver GK in *Escherichia coli* was prepared as follows.

First, PCR was performed using human liver cDNA (Marathon Ready cDNA, Clontech Laboratories, Inc.) as a template and two kinds of synthetic DNAs (5'-CAGCTCTCCATC-CAAGCAGCCGTTGCT-3' (SEQ ID NO: 1) and 5'-GGCG-GCCTGGGTCCTGACAAG-3' (SEQ ID NO: 2)), and the obtained DNA fragment was closed using a TOPO TA Cloning Kit (Invitrogen Corporation). PCR was performed using the obtained plasmid DNA as a template and a synthetic DNA (5'-GGATCCATGCCCAGACCAAGATC-CCAACTCCCACAACCCAACTCCCAGGTA-GAGCAGATCCTGGCAGAG-3' (SEQ ID NO: 3)) with a BamHI site added to immediately before the initiation codon, and a synthetic DNA (5'-GAATTCCTGGCCCAGCATA-CAGGC-3' (SEQ ID NO: 4)) with an EcoRI site added to immediately after the stop codon. The obtained DNA fragment was subcloned to pGEX6P-2 (Amersham Biosciences K.K.) cleaved with BamHI and EcoRI to give a plasmid (pGEX6P-2/hLGK1) for expression of human liver GK.

Reference Example 2A Expression and Purification of GST-hLGK1

BL21 strain (Stratagene) transformed with pGEX6P-2/hLGK1 obtained in Reference Example 1A was cultured with shaking at 37° C. for 14 hr in a 200 ml Erlenmeyer flask containing 50 ml of 100 μg/ml ampicillin-containing LB medium. The culture medium (25 ml) was diluted with 225 ml of 100 μg/ml ampicillin-containing LB medium, and further cultured with shaking at 37° C. for 1 hr in a 1 L Erlenmeyer flask. After culture, the Erlenmeyer flask was cooled on ice, 125 μL of 100 mM isopropyl-thio-β-D-galactopyranoside (IPTG) was added (final concentration 50 μM), and cultured at 17° C. for 20 hr. The culture medium was centrifuged, and the obtained fungus was disrupted by ultrasonication. The object protein (GST-hLGK1) was purified from the supernatant using Glutathione Sepharose 4B (Amersham Biosciences K.K.).

Experimental Example 1

Determination of GK Activity Value

A solution (5 μL) of test compound in 50% dimethyl sulfoxide was added to each well of 384 well black plate (Nalge Nunc International K.K.). Then, a solution (35 mL) obtained by diluting GST-hLGK1 obtained in Reference Example 2A with measurement buffer (containing 50 mM HEPES (pH 7.4), 200 mM KCl, 5 mM $MgCl_2$, 2.5 mM DTT and 50 μM 2'-(or-3')-O—(N-methylanthraniloyl)adenosine 5'-triphosphate (Mant-ATP) (Jena Bioscience GmbH)) to 6 μg/mL was added to each well.

Each well was stood at 37° C. for 10 min, and 25 mM D-glucose solution (10 μL) was added to start the reaction.

Each well after the reaction was stood at 37° C. for 60 min, and the reaction was quenched by adding 25 μL of a quenching solution (containing 200 mM HEPES (pH 7.4), 20 mM $MgCl_2$, 200 mM EDTA, 0.03% Triton-X 100, 0.3% Coating 3 reagent (Caliper Life Sciences, Inc.)).

2'-(or-3')-O—(N-methylanthraniloyl)adenosine 5'-triphosphate (Mant-ATP, substrate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

As a control group, the reaction rate was calculated in the same manner as above except that "solution in 50% dimethyl sulfoxide (without test compound)" was used instead of "solution of test compound in 50% dimethyl sulfoxide".

A concentration dependency curve of the test compound was drawn with the percentage obtained by dividing the reaction rate of the well added with the test compound (test compound addition group) by the reaction rate of the control group was taken as the GK activity value of the test compound, and the concentration of the test compound at the midpoint between the maximum activity value of the test compound addition group and the control group activity value is shown as $EC_{50}$ value. The results are shown in Table 1.

TABLE 1

| Test compound (Example No.) | $EC_{50}$ value (μM) |
|---|---|
| 10 | 0.21 |
| 191 | 0.031 |
| 198 | 0.53 |
| 200 | 0.061 |
| 218 | 0.18 |
| 226 | 0.053 |
| 229 | 0.12 |
| 236 | 0.25 |
| 243 | 0.024 |
| 253 | 0.21 |
| 254 | 0.20 |
| 274 | 0.081 |
| 337 | 0.082 |
| 348 | 0.044 |
| 398 | 0.21 |
| 414 | 0.037 |
| 520 | 0.19 |
| 528 | 0.26 |

As is clear from Table 1, the compound of the present invention has a superior glucokinase activation action.

Formulation Example 1

Production of Capsule

| | | |
|---|---|---|
| 1) | compound of Example 1 | 30 mg |
| 2) | finely divided powder cellulose | 10 mg |
| 3) | lactose | 19 mg |
| 4) | magnesium stearate | 1 mg |
| | total | 60 mg |

1), 2), 3) and 4) are mixed and filled in a gelatin capsule.

Formulation Example 2

Production of Tablet

| | | |
|---|---|---|
| 1) | compound of Example 1 | 30 g |
| 2) | lactose | 50 g |

-continued

| 3) | cornstarch | 15 g |
| 4) | calcium carboxymethylcellulose | 44 g |
| 5) | magnesium stearate | 1 g |
| | 1000 tablets total | 140 g |

The total amount of 1), 2) and 3), and 30 g of 4) are kneaded with water, vacuum dried and sized. The sized powder is mixed with 14 g of 4) and 1 g of 5), and the mixture is punched by a tabletting machine. In this way, 1000 tablets containing 30 mg of the compound of Example 1 per tablet are obtained.

INDUSTRIAL APPLICABILITY

The compound of the present invention has a superior glucokinase activating action, and is useful as a pharmaceutical agent such as an agent for the prophylaxis or treatment of diabetes, obesity and the like, and the like.

This application is based on patent application No. 2006-285551 filed in Japan, the contents of which are incorporated in full herein by this reference.

The invention claimed is:

1. N-(5-(2-Methoxyethoxy)-2-{5-[(1-oxidothiomorpholino)methyl]-4,5-dihydro-1,3-thiazol-2-yl}-1H-indol-7-yl)-N-methylpyridine-2-sulfonamide or a salt thereof.

* * * * *

SEQUENCE LISTING

<160> NUMBER OF SEQ ID NOS: 4

<210> SEQ ID NO 1
<211> LENGTH: 27
<212> TYPE: DNA
<213> ORGANISM: Artificial
<220> FEATURE:
<223> OTHER INFORMATION: primer for cloning glucokinase

<400> SEQUENCE: 1
cagctctcca tccaagcagc cgttgct                                        27

<210> SEQ ID NO 2
<211> LENGTH: 21
<212> TYPE: DNA
<213> ORGANISM: Artificial
<220> FEATURE:
<223> OTHER INFORMATION: primer for cloning glucokinase

<400> SEQUENCE: 2
ggcggcctgg gtcctgacaa g                                              21

<210> SEQ ID NO 3
<211> LENGTH: 69
<212> TYPE: DNA
<213> ORGANISM: Artificial
<220> FEATURE:
<223> OTHER INFORMATION: primer for cloning glucokinase

<400> SEQUENCE: 3
ggatccatgc ccagaccaag atcccaactc ccacaaccca actcccaggt agagcagatc    60
ctggcagag                                                            69

<210> SEQ ID NO 4
<211> LENGTH: 24
<212> TYPE: DNA
<213> ORGANISM: Artificial
<220> FEATURE:
<223> OTHER INFORMATION: primer for cloning glucokinase

<400> SEQUENCE: 4
gaattcctgg cccagcatac aggc                                           24